US009874570B2

(12) United States Patent
Charretier et al.

(10) Patent No.: US 9,874,570 B2
(45) Date of Patent: Jan. 23, 2018

(54) METHOD OF DETECTING AT LEAST ONE MECHANISM OF RESISTANCE TO CEPHALOSPORINS BY MASS SPECTROMETRY

(71) Applicant: BIOMERIEUX, INC., Durham, NC (US)

(72) Inventors: Yannick Charretier, Courzieu (FR); Jean-Philippe Charrier, Tassin la demi-lune (FR); Christine Franceschi, Meximieux (FR); Gilles Zambardi, Chezeneuve (FR); Tiphaine Cecchini, Saint-Genis les Ollieres (FR); Elodie Degout-Charmette, Tossieux (FR)

(73) Assignee: BIOMERIEUX, INC., Durham, NC (US)

( * ) Notice: Subject to any disclaimer, the term of this patent is extended or adjusted under 35 U.S.C. 154(b) by 0 days.

(21) Appl. No.: 15/295,061

(22) Filed: Oct. 17, 2016

(65) Prior Publication Data
US 2017/0052198 A1 Feb. 23, 2017

Related U.S. Application Data

(62) Division of application No. 14/111,118, filed as application No. PCT/EP2012/057322 on Apr. 20, 2012, now Pat. No. 9,506,932.

(60) Provisional application No. 61/477,907, filed on Apr. 21, 2011.

(51) Int. Cl.
*A61K 38/00* (2006.01)
*G01N 33/68* (2006.01)

(52) U.S. Cl.
CPC ... *G01N 33/6851* (2013.01); *G01N 2333/986* (2013.01)

(58) Field of Classification Search
CPC .... A61K 38/00; C07K 14/47; C07K 14/4702; C07K 14/4746; C07K 2319/00
See application file for complete search history.

(56) References Cited

U.S. PATENT DOCUMENTS

| 2004/0229283 A1 | 11/2004 | Gygi et al. |
| 2007/0006950 A1 | 1/2007 | Okada et al. |
| 2007/0269895 A1 | 11/2007 | Aebersold et al. |
| 2011/0245105 A1 | 10/2011 | Citri |
| 2012/0245128 A1 | 9/2012 | Haag et al. |
| 2012/0264156 A1 | 10/2012 | Beaulieu et al. |

FOREIGN PATENT DOCUMENTS

| WO | 2005/098071 A1 | 10/2005 |
| WO | 2006/128492 A1 | 12/2006 |
| WO | 2008/066629 A2 | 6/2008 |
| WO | 2008/145763 A1 | 12/2008 |
| WO | 2011/045544 A2 | 4/2011 |

OTHER PUBLICATIONS

Kruger et al. Infections with Nontyphoidal *Salmonella* Species Producing TEM-63 or a Novel TEM Enzyme, TEM-131, in South Africa. Antimicrobial Agents and Chemotherapy, Nov. 2004. vol. 48, No. 11. pp. 4263-4270.*
Sep. 4, 2014 Office Action issued in U.S. Appl. No. 14/111,118.
Jan. 3, 2014 Office Action issued in U.S. Appl. No. 13/502,020.
May 15, 2014 Office Action issued in U.S. Appl. No. 13/502,020.
Sauer, Sascha, et al., "Classification and Identification of Bacteria by Mass Spectrometry and Computational Analysis," vol. 3, Issue 7, Jul. 2008, pp. 1-10.
Dec. 5, 2014 Office Action issued in U.S. Appl. No. 14/111,083.
Apr. 24, 2015 Office Action issued in U.S. Appl. No. 14/111,118.
Ahmet et al., "Pyrolysis Mass Spectrometry of Cephalosporin-Resistant Enterobacter Cloacae," Journal Hospital Infection, 1995, vol. 31, pp. 99-104.
Bush, Extended-Spectrum Beta-Lactamases in North America, 1987-2006, Clin Microbial Infect 2008, vol. 14 (Suppl 1), pp. 134-143.
Hope et al., Efficacy of Practised Screening Methods for Detection of Cephalosporin-Resistant Enterobacteriaceae. J Antimicrob Chemotherapy 2007, vol. 59, pp. 110-113.
Moosdeen, "The Evolution of Resistance to Cephalosporins," CID 1997, pp. 487-493.
ExPaSy Peptidecutter for KPC-1—http://web.expasy.org/cgi-bin/peptide_cutter/peptidecutter.pl, 2 pgs., Jun. 8, 2015.
Savini et al., "Bacillus Cereus Heteroresistance to Carbapenems in a Cancer Patient," J. Hospital Infection, pp. 288-289, 2009.
Yigit et al., "Novel Carbapenem-Hydrolyzing Beta-Lactamase, KPC-1, from a Carbapenem-Resistant Strain of Klebsiella Pneumoniae," Antimicrobial Agents and Chemotherapy, vol. 45, No. 4, pp. 1151-1161, 2001.
Yigit et al., "Novel Carbapenem-Hydrolyzing Beta-Lactamase, KPC-1, from a Carbapenem-Resistant Strain of Klebisella Pneumoniae," Author's Correction, Antimicrobial Agents and Chemotherapy, vol. 52, No. 2, p. 809, 2008.
Kulkarni et al., "Use of Impipenem to Detect KPC, NDM, OXA, IMP, and VIM Carbapenemase Activity from Gram-Negative Rods in 75 Minutes Using Liquid Chromatography-Tandem Mass Spectrometry," JCM, vol. 52, No. 7, pp. 2500-2505, Jul. 2014.
Jun. 11, 2015 Office Action issued in U.S. Appl. No. 14/111,083.
Beccerril et al., "Combination of Analytical and Microbiological Techniques to Study the Antimicrobial Activity of a New Active Food Packaging Containing Cinnamon or Oregano Against *E. Coli* and *S. Aureus*," Anal Bioanal Chem, vol. 388, pp. 1003-1011, 2007.

(Continued)

*Primary Examiner* — Marcela M Cordero Garcia
(74) *Attorney, Agent, or Firm* — Oliff PLC

(57) ABSTRACT

The present invention pertains to a method of detection, by mass spectrometry, of at least one marker of at least one mechanism of resistance to at least one antimicrobial, resistance of at least one microorganism contained in a sample, characterised in that the antimicrobial is a cephalosporin, and said resistance markers are proteins or peptides. Preferably, said proteins or peptides are proteins from said microorganism.

5 Claims, No Drawings

(56) References Cited

OTHER PUBLICATIONS

Kuhn et al., "Quantification of C-Reactive Protein in the Serum of Patients with Rheumatoid Arthritis Using Multiple Reaction Monitoring Mass Spectrometry and 13C-Labeled Peptide Standards," Proteomics, vol. 4, pp. 1175-1186, 2004.
Keller et al., "A Uniform Proteomics MS/MS Analysis Platform Utilizing Open XML File Formats," Molecular Systems Biology, vol. 1, pp. 1-8, 2005.
Sep. 23, 2015 Office Action issued in U.S. Appl. No. 13/502,020.
Jan. 4, 2016 Office Action issued in U.S. Appl. No. 14/111,118.
Mar. 11, 2016 Office Action issued in U.S. Appl. No. 14/111,083.
U.S. Appl. No. 13/502,020, filed Jun. 29, 2012 in the name of Beaulieu et al.
Jul. 15, 2016 Notice of Allowance issued in U.S. Appl. No. 14/111,118.
Anhalt, J. et al. "Identification of Bacteria Using Mass Spectrometry." Analytical Chemistry, Feb. 1975, pp. 219-225, vol. 47, No. 2.
Oct. 11, 2012 International Search Report issued in International Patent Application No. PCT/EP2012/057323.
Jun. 14, 2011 International Search Report issued in International Patent Application No. PCT/FR2010/052181.
May 6, 2013 International Search Report issued in International Patent Application No. PCT/EP2012/057322.
Oct. 11, 2012 Written Opinion issued in International Application No. PCT/EP2012/057323.
May 6, 2013 Written Opinion issued in International Application No. PCT/EP2012/057322.
Jun. 14, 2011 Written Opinion issued in International Application No. PCT/FR2010/1052181.
U.S. Appl. No. 14/111,083, filed Oct. 10, 2013 in the name of Charretier et al.
Savinova, T.A. et al. Abstract of "A mass-spectrometric analysis of genetic markers of S. pneumonia resistance to β-lactam antibiotics." XP00268431, Database accession No. NLM20882772, Database Medline, 2010, US National Library of Medicine, Bethesda, MD.
Seng, P. et al. "Ongoing Revolution in Bacteriology: Routine Identification of Bacteria by Matrix-Assisted Laser Desorption Ionization Time-of-Flight Mass Spectrometry." Clinical Infectious Diseases, Aug. 2009, pp. 543-551, vol. 49, Infectious Diseases Society of America.
Stahl-Zeng, J. et al. "High Sensitivity Detection of Plasma Proteins by Multiple Reaction Monitoring of N-Glycosites." Molecular & Cellular Proteomics, Jul. 2007, pp. 1809-1817, vol. 6, No. 10, The American Society for Biochemistry and Molecular Biology, Inc.
Takao, T., et al. "Identity of molecular structure of Shiga-like toxin I (VTI) from *Escherichia coli* 0157 : H7 with that of Shiga toxin." Microbial Pathogenesis, 1988, pp. 357-369, 5(5).
Teng, C.H. et al. "Gold Nanoparticles as Selective and Concentrating Probes for Samples in MALDI MS Analysis." Analytical Chemistry, Aug. 2004, pp. 4337-4342, vol. 76, No. 15, American Chemical Society.
Vaidyanathan, S. et al. "Discrimination of Aerobic Endospore-forming Bacteria via Electrospray-Ionization Mass Spectrometry of Whole Cell Suspensions." Analytical Chemistry, Sep. 2001, pp. 4134-4144, vol. 73, No. 17, American Chemical Society.
Wang, K.Y. et al. "Multiplexed Immunoassay: Quantitation and Profiling of Serum Biomarkers Using Magnetic Nanoprobes and MALDI-TOF MS." Analytical Chemistry, Aug. 2008, pp. 6159-6167, vol. 80, No. 16, American Chemical Society.
Wybo, I. et al. "Differentiation of cfiA-Negative and cfiA-Positive Bacteroides fragilis Isolates by Matrix-Assisted Laser Desorption Ionization-Time of Flight Mass Spectrometry." Journal of Clinical Microbiology, May 2011, pp. 1961-1964, vol. 49, No. 5, American Society for Microbiology.
Zheng, K. "Elucidation of peptide metabolism by on-line immunoaffinity liquid chromatography mass spectrometry." Rapid Communications in Mass Spectrometry, 2000, pp. 261-269, vol. 14, John Wiley & Sons, Ltd.

Majcherczyk P., et al. "The discriminatory power of MALDI-TOF mass spectrometry to differentiate between isogenic teicoplanin-susceptible and teicoplanin-resistant strains of methicillin-resistant *Staphylococcus aureus*", Fems Microbiol Letters, 2006, pp. 233-239, 255(2).
Manes, N. et al. "Targeted Protein Degradation by *Salmonella* under Phagosome-mimicking Culture conditions Investigated Using Comparative Peptidomics." Molecular & Cellular Proteomics, Jan. 2007, pp. 717-727, vol. 6, No. 4, MCP Papers in Press.
Marinach, C. et al. "MALDI-TOF MS-based drug susceptibility testing of pathogens: The example of Candida albicans and fluconazole." Proteomics, 2009, pp. 4627-4631, 9(20).
Mazzeo, M., et al. "Matrix-assisted laser desorption ionization-time of flight mass spectrometry for the discrimination of food-borne microorganisms", Applied and Env. Microbio., 2006, pp. 1180-1189, 72(2).
Mead, J. et al. "MRMaid, the Web-based Tool for Designing Multiple Reaction Monitoring (MRM) Transitions." Molecular & Cellular Proteomics, 2009, pp. 696-705, vol. 8, No. 4, The American Society for Biochemistry and Molecular Biology, Inc.
Melanson, J., et al. "Targeted comparative proteomics by liquid chromatography/matrix-assisted laser desorption/ionization triple-quadruple mass spectrometry." Rapid Communications in Mass Spectrometry, 2006, pp. 904-910, 20(5).
Nandakumar, R. et al. "Proteomic analysis of endodontic infections by liquid chromatography-tandem mass spectrometry." Oral Microbiology and Immunology, 2009, pp. 347-352, vol. 24, John Wiley & Sons, Ltd.
Pratt, J. et al. "Multiplexed absolute quantification for proteomics using concatenated signature peptides encoded by QconCAT genes." Nature Protocols, 2006, pp. 1029-1043, vol. 1, No. 2, Nature Publishing Group.
Qian, J., et al, "MALDI-TOF mass signatures for differentiation of yeast species, strain grouping and monitoring of morphogenesis markers", Analytical and Bioanal. Chemistry, 2008, pp. 439-449, 392(3).
Keshishian, H. et al. "Quantitative, Multiplexed Assays for Low Abundance Proteins in Plasma by Targeted Mass Spectrometry and Stable Isotope Dilution." Molecular & Cellular Proteomics, 2007, pp. 2212-2229, vol. 6, No. 12, The American Society for Biochemistry and Molecular Biology, Inc.
Kondo, F., et al. "Identification of Shiga toxins in Shiga toxin-producing *Escherichia coli* using immunoprecipitation and high-performance liquid chromatography-electrospray ionization mass spectrometry." The Analyst, 2003, pp. 1360-1364, 128(11).
Krishnamurthy, T. et al. "Rapid Identification of Bacteria by Direct Matrix-assisted Laser Desorption/Ionization Mass Spectrometric Analysis of Whole Cells." Rapid Communications in Mass Spectrometry, 1996, pp. 1992-1996, vol. 18, John Wiley & Sons, Ltd.
Li, M., et al. "Comparative proteomic analysis to identification of extracellular virulence factors of enterohemorrhagic *Escherichia coli* (EHEC) and enteropathogenic *Escherichia coli* (EPEC)." Faseb Journal, 2005, A1388, 19(5).
Lin, Y.C. et al. "Differences in carbapenem resistance genes among Acinetobacter baumannii, Acinetobacter genospecies 3 and Acinetobacter genospecies 13TU in Taiwan." International Journal of Antimicrobial Agents, 2010, pp. 439-443, vol. 35.
Lin, Y.S. et al. "Affinity Capture Using Vancomycin-Bound Magnetic Nanoparticles for the MALDI-MS Analysis of Bacteria." Analytical Chemistry, Mar. 2005, pp. 1753-1760, vol. 77, No. 6, American Chemical Society.
López-Ferrer, D. et al. "Ultra Fast Trypsin Digestion of Proteins by High Intensity Focused Ultrasound." Journal of Proteome Research, 2005, pp. 1569-1574, vol. 4, American Chemical Society.
López-Ferrer, D. et al. "On-line Digestion System for Protein Characterization and Proteome Analysis." Analytical Chemistry, Dec. 2008, pp. 8930-8936, vol. 80, No. 23, American Chemical Society.
Mainardi, J. et al. "Resistance to cefotaxime and peptidoglycan composition in Enterococcus faecalis are influenced by exogenous sodium chloride." Microbiology, 1998, pp. 2679-2685, vol. 144, SGM.

(56) References Cited

OTHER PUBLICATIONS

Fortin, T. et al. "Clinical Quantitation of Prostate-specific Antigen Biomarker in the Low Nanogram/Milliliter Range by Conventional Bore Liquid Chromatography-Tandem Mass Spectrometry (Multiple Reaction Monitoring) Coupling and Correlation with ELISA Tests." Molecular & Cellular Proteomics, pp. 1006-1015, vol. 8, No. 5, The American Society for Biochemistry and Molecular Biology, Inc.

Fox, A. et al. ed., "Analytical Microbiology Methods: Chromatography and Mass Spectrometry." 1990, Plenum Press, New York, NY.

Fusaro, V. et al. "Prediction of high-responding peptides for targeted protein assays by mass spectrometry." Nature Biotechnology, Feb. 2009, pp. 190-198, vol. 27, No. 2, Nature America, Inc.

Gaskell, S. "Electrospray: Principles and Practice." Journal of Mass Spectrometry, 1997, pp. 677-688, vol. 32, John Wiley & Sons, Ltd.

Gröbner, S. et al. "Emergence of carbapenem-non-susceptible extended-spectrum β-lactamase-producing Klebsiella pneumonia isolates at the university hospital of Tübingen, Germany." Journal of Medical Microbiology, 2009, pp. 912-922, vol. 58, SGM.

Han, B. et al. "Proteomics: from hypothesis to quantitative assay on a single platform. Guidelines for developing MRM assays using ion trap mass spectrometers." Briefings in Functional Genomics and Proteomics, Jun. 2008, pp. 340-354, vol. 7, No. 5, Oxford University Press, Oxford, UK.

Hernychova, L. et al. "Detection and Identification of Coxiella bumetii Based on the Mass Spectrometric Analyses of the Extracted Proteins." Analytical Chemistry, Sep. 2008, pp. 7097-7104, vol. 80, No. 18, American Chemical Society.

Ho, K., et al. "Using Biofunctionalized Nanoparticles to Probe Pathogenic Bacteria", Anal. Chem., 2004,pp. 7162-7168, 76.

Hofstadler, S. et al. "TIGER: the universal biosensor." International Journal of Mass Spectrometry, 2005, pp. 23-41, vol. 242.

Ding, D. et al "Identification of protein components and quantitative immunoassay for SEC2 in Staphylococciinjection." Journal of Pharmaceutical and Biomedical Analysis, 2009, pp. 79-85, vol. 50.

Ecker, D. et al. "Ibis T5000: a universal biosensor approach for microbiology." Nature Reviews Microbiology, Jun. 2008, pp. 553-558, vol. 6, No. 7, Nature Publishing Group.

Everley, R. et al. "Characterization of Clostridium species utilizing liquid chromatography/mass spectrometry of intact proteins." Journal of Microbiological Methods, pp. 152-158, Feb. 2009, vol. 77.

Camara et al, "Discrimination between wild-type and ampicillin-resistant *Escherichia coli* by matrix-assisted laser desorption/ionization time-of-flight mass spectrometry." Analytical and Bioanal. Chemistry, 2007, pp. 1633-1638,389 (5).

Carbonnelle et al, "Rapid identification of *Staphylococci* isolated in clinical microbiology laboratories by matrix-assisted laser desorption ionization-time of flight mass spectrometry", Journal of Clinical Microbio., 2007, pp. 2156-2161, 45(7).

Chen, W. et al. "Functional Nanoparticle-Based Proteomic Strategies for Characterization of Pathogenic Bacteria." Analytical Chemistry, Dec. 2008, pp. 9612-9621, vol. 80, No. 24, American Chemical Society.

Claydon, M. et al. "The rapid identification of intact microorganisms using mass spectrometry." Nature Biotechnology, Nov. 1996, pp. 1584-1586, vol. 14.

Dare et al. "*Staphylococci* speciation and Panton-Valentine leukocidin detection by matrix assisted laser desorption ionisation time-of-flight mass spectrometry", Intern. Journal of Antimicrobial Agents, 2007, pp. 103-104, 29(2).

Desiere, F. et al. "The PeptideAtlas project." Nucleic Acids Research, 2006, pp. D655-D658, vol. 34, Database Issue, Oxford University Press, Oxford, UK.

Bundy,J. et al. "Lectin-Based Affinity Capture for MALDI-MS Analysis of Bacteria." Analytical Chemistry, Apr. 1999, pp. 1460-1463, vol. 71, No. 7, American Chemical Society.

Bush, K. et al. "Updated Classification of β-Lactamases." Antimicrobial Agents and Chemotherapy, Mar. 2010, pp. 969-976, vol. 54, No. 3, American Society for Microbiology.

Bernardo et al. "Identification of *Staphylococcus aureus* exotoxins by combined sodium dodecyl sulfate gel electrophoresis and matrix-assisted laser desorption/ionization-time of flight mass spectrometry." Proteomics, 2002, pp. 740-746, 2(6).

Anderson, L. et al. "Quantitative Mass Spectrometric Multiple Reaction Monitoring Assays for Major Plasma Proteins." Molecular & Cellular Proteomics, 2006, pp. 573-588, vol. 5, No. 4. The American Society for Biochemistry and Molecular Biology, Inc.

Brun, V. et al. "Isotope-labeled Protein Standards Toward Absolute Quantitative Proteomics." Molecular & Cellular Proteomics, 2007, pp. 2139-2149, vol. 6, No. 12, The American Society for Biochemistry and Molecular Biology, Inc.

Bernardo et al, "Identification and discrimination of *Staphylococcus aureus* strains using matrix-assisted laser desorption/ionization-time of flight mass spectrometry." Proteomics, 2002, pp. 747-753,2 (6).

Fenselau, C. et al. "Identification of β-Lactamase in Antibiotic-Resistant Bacillus cereus Spores." Applied and Environmental Microbiology. Feb. 2008, pp. 904-906, vol. 74, No. 3, American Society for Microbiology.

\* cited by examiner

US 9,874,570 B2

METHOD OF DETECTING AT LEAST ONE MECHANISM OF RESISTANCE TO CEPHALOSPORINS BY MASS SPECTROMETRY

This application is a divisional application of U.S. patent application Ser. No. 14/111,118, filed Dec. 23, 2013, which is in turn a U.S. National Stage of International Application No. PCT/EP2012/057322, filed Apr. 20, 2012, which claims priority from U.S. Provisional Application No. 61/477,907, filed Apr. 21, 2011. The disclosure of the prior applications is hereby incorporated by reference herein in their entirety.

The present invention relates to the field of microbiology. More precisely, the invention relates to the detection of at least one mechanism of resistance to cephalosporins of at least one microorganism from a sample by using mass spectrometry.

Since Pasteur's discovery of microbes, microorganisms have been studied by microscopy and biochemical analyses. These conventional methods are often long and tedious, and analytical alternatives were sought very early on. This is why the analysis of bacteria by mass spectrometry was initiated from 1975 by J. Anhalt and C. Fenselau [1].

This preliminary work was followed by the study of fatty acids from the wall of the microorganisms using gas chromatography combined with mass spectrometry (GC-MS) [2]. This method was popularised under the English term FAME, standing for Fatty Acid Methyl Ester. It currently constitutes a reference method for taxonomic studies. However, its use remains limited to certain specialised laboratories dealing with the treatment of the sample by saponification, hydrolysis and derivation. In 1996, the works by M. Claydon et al. [3] as well as by T. Krishnamurthy and P. Ross [4] demonstrated the possibility of identifying different bacterial species with a MALDI-TOF mass spectrometer (English acronym for Matrix Assisted Laser Desorption Ionization—Time Of Flight). The analysis combines the acquisition of a mass spectrum and the interpretation of expert software. It is extremely simple and can be carried out in a few minutes. However it has only been making it into medical analysis laboratories fairly recently [5]. Its clinical use is currently limited to the identification of bacteria and yeast species. It is not routinely used to identify resistances to antimicrobials.

Yet the identification of resistances to antimicrobials such as antibiotics is an essential element in ensuring optimal patient care.

Other mass spectrometry methods, particularly in tandem, have been proposed to meet these needs. By way of example, it is possible to cite the work of C. Fenselau et al. for identifying β-Lactamase with a quadripole-TOF (Q-TOF) [6].

However these research results are not applicable to routine clinical use. They were obtained with research instruments requiring highly qualified personnel. The analysis times, often greater than one hour per sample, are incompatible with the workload of a microbiological analysis laboratory.

More recently, S. Hofstadler et al. [7] proposed a method combining a microbial genome amplification by PCR to a detection of the PCR products by electrospray-TOF (ESI-TOF). This method is now fully automated [8]. However, it requires a PCR amplification with the flaws inherent in molecular biology, namely extraction yield, cost of the probes, etc.

In this context, the objective of the present invention is to propose a method of detecting mechanisms of resistance to cephalosporins which makes it possible to overcome the disadvantages of the prior art methods, namely providing an inexpensive method, without reagents specific to each species, particularly compared to molecular biology methods, which gives a result in a short amount of time, less than one hour, and which can be used in routine clinical work, without requiring highly qualified personnel.

To this end, the invention proposes a new method of detecting, by mass spectrometry, at least one mechanism of resistance to at least one antimicrobial of at least one microorganism from a sample, characterised in that the antimicrobial is a cephalosporin and in that proteins and/or peptides are detected as markers of said mechanism of resistance to at least one cephalosporin-class antibiotic.

Advantageously, markers of resistance to several different antimicrobials can be detected simultaneously.

As indicated in application PCT/FR2010/052181, markers of type and/or virulence of said microorganisms can be detected in the same way by mass spectrometry prior to or at the same time as the detection of the resistance mechanism markers.

Markers of resistance to at least one cephalosporin-class antimicrobial is understood to mean molecules of protein origin which are characteristic of said properties.

Cephalosporins are antibiotics belonging to the beta-lactam family. They are usually classified in several subclasses:
  first-generation cephalosporins, such as cefazolin, cephalothin, cefaclor, cephalexin, which are broken down by the beta-lactamases of groups 1 and 2b, 2br, 2be, 2ber
  second-generation cephalosporins, such as cefamandole, cefpodoxime, cefuroxime, which are broken down by the beta-lactamases of groups 1, 2be, 2ber
  third-generation cephalosporins, such as cefotaxime, ceftazidime, ceftriaxone, cefixime, which are broken down by the beta-lactamases of groups 1, 2be, 2ber, even though they are more stable than the first-generation and second-generation cephalosporins
  fourth-generation cephalosporins, such as cefepime and cefpirome, which are broken down by the beta-lactamases of groups 2be and 2ber
  cephalosporins exhibiting anti-MRSA activity such as ceftaroline and ceftobiprole, which are broken down by the beta-lactamases of groups 2be and 2ber
  cephamycins, such as cefoxitin, cefotetan, cefmetazole, which are broken down by the beta-lactamases of group 1

Determination of the resistance to at least one antimicrobial is understood to mean determining the susceptibility of a microorganism to being destroyed by an antimicrobial. The proteins involved in the resistance mechanisms will differ depending on the family and the species.

The nomenclature of the beta-lactamases, beta-lactam-resistant bacterial enzymes, is not standardised. They are either classified in four molecular classes (A to D) on the basis of their primary structure, or in functional groups on the basis of the target substrates and their resistance to inhibitors (for an overview, see [9] Bush and Jacoby, Antimicrobial Agents and Chemotherapy, 2010; 54 (3): 969-976). For molecular classification, sequencing techniques have made more precise classification possible: for example, 183 variants of the TEM protein have been described (labelled TEM-i, with i being between 1 and 183). For the functional classification, Bush and Jacoby (supra) have proposed new functional subgroups:

the group 1 enzymes are cephalosporinases belonging to the molecular class C. ACC, ACT, MIR, MOX, DHA, CMY and FOX are plasmid-borne enzymes, belonging to this subgroup.

the group 2 enzymes belong to molecular classes A and D. This group is itself subdivided into subgroups: 2a, 2b, 2be, 2br, 2ber, 2c, 2ce, 2d, 2de, 2df, 2f, etc. CTX-M (2be), SHV (2b, 2be or 2br), PER (2be), VEB (2be) and TEM (2b, 2be, 2br or 2ber) are enzymes belonging to this group.

The subgroup 2a corresponds to beta-lactamases which hydrolyse benzylpenicillin and penicillin derivatives, but which do not hydrolyse cephalosporins, carbapenems or monobactams.

The subgroup 2b corresponds to broad-spectrum beta-lactamases which hydrolyse first-generation penicillins and cephalosporins such as cephaloridine and cephalothin, and which are inhibited by clavulanic acid, sulfobactam, or tazobactam. The variants TEM-1, TEM-2 and SHV-1 belong to this subgroup.

The subgroup 2b corresponds to extended-spectrum beta-lactamases (ESBL) which are also inhibited by clavulanic acid, sulfobactam, or tazobactam. These enzymes, in addition to the properties of subgroup 2b, hydrolyse at least one oxyimino-beta-lactam such as cefotaxime or ceftazidime, and monobactams such as aztreonam. This subgroup contains numerous variants of TEM and SHV, variants of PER and VEB, as well as CTX-M, BEL-1, BES-1, SFO-1, TAL-1 and TAL-2.

The subgroup 2br corresponds to beta-lactamases from the subgroup 2b which are insensitive to inhibition by clavulanic acid, sulfobactam or tazobactam. This subgroup contains variants of the enzymes TEM and SHV.

The subgroup 2ber corresponds to beta-lactamases from the subgroup 2be which are insensitive to inhibition by clavulanic acid, sulfobactam or tazobactam. This subgroup contains TEM variants.

The subgroup 2ce is characterised by its ability to hydrolyse carbenicillin or ticarcillin, as well as cefepime and cefpirome. CARB-10 is part of this subgroup.

The subgroup 2d includes the OXA beta-lactamases capable of hydrolysing cloxacillin or oxacillin. The OXAs (or oxacillinases) correspond to class-D beta-lactamases, according to their primary sequence, and they can confer resistances to cephalosporins or to cephalosporins and to carbapenems (Poirel et al., 2010, Antimicrobio. Agents Chemother., 54:24-38).

The subgroup 2de includes OXAs having an extended spectrum extended to oxy-imino-beta-lactams, but not to carbapenems.

The subgroup 2df includes OXAs having a spectrum extended to carbapenems.

The subgroup 2e corresponds to extended-spectrum cephalosporinases, which are inhibited by clavulanic acid or tazobactam.

The subgroup 2f corresponds to carbapenemases such as SME, KPC or certain variants of GES. The first GES beta-lactamase was isolated in 1998 in French Guiana (Poirel et al., 2000, Antimicrobio. Agents Chemother., 43:622-632). This enzyme (GES-1) conferred an ESBL resistance (subgroup 2be). The second isolate from a bacterium bearing a GES beta-lactamase was achieved in 2000 in South Africa (Poirel et al., 2001, Antimicrobio. Agents Chemother., 45: 2598-2603). This enzyme (GES-2) conferred a resistance to cephalosporins and to carbapenems such as imipenem (subgroup 2f).

The group 3 enzymes are metallo-beta-lactamases known for hydrolysing carbapenem-class antibiotics. The enzymes IMP, VIM, CAU, GOB or FEZ are part of this group.

The method of the invention can be employed to detect mechanisms of resistance to cephalosporins in bacteria. Thus, for example, as bacteria in which it is possible to seek a mechanism of resistance to cephalosporins according to the method of the invention, non-exhaustive mention may be made of:

the Enterobacteriaceae, using group 1 and group 2 proteins and peptides as a resistance marker;

non-fermenting bacteria (*Pseudomonas aeruginosa, Acinetobacter baumannii*)

etc.

It should further be noted that the strains known to be resistant to carbapenems are also resistant to cephalosporins and to penicillins. Therefore, a method of detecting a mechanism of resistance to carbapenems also makes it possible to detect a mechanism of resistance to cephalosporins and to penicillins.

The sample on which the method of the invention can be employed is any sample susceptible of containing a target microorganism. The sample can be of biological origin, either animal, vegetable or human. In this case it may correspond to a specimen of biological fluid (whole blood, serum, plasma, urine, cerebrospinal fluid, organic secretion, for example), a tissue specimen or isolated cells. This specimen can be used such as it is insofar as the markers of mechanisms of bacterial resistance to beta-lactams are available in the sample tested, or it can, prior to the analysis, undergo preparation by enrichment, extraction, concentration, purification, culturing, in accordance with methods known to the person skilled in the art.

The sample can be of industrial origin, or, according to a non-exhaustive list, can be an air specimen, a water specimen, a surface specimen, a part or a manufactured product, or a food product. Amongst the food samples, non-exhaustive mention can be made of a sample of a dairy product (yogurts, cheeses), of meat, of fish, of egg, of fruit, of vegetable, of water, of a beverage (milk, fruit juice, soda, etc.). These food samples can also come from sauces or ready meals. Finally, a food sample can come from an animal feed, such as animal meals.

Upstream of the detection by mass spectrometry, the sample to be analysed is preferably pre-treated to produce peptides from the entirety of the proteins present in the sample to fragment these proteins into peptides, for example by digestion with a proteolytic enzyme (protease), or by the action of a chemical reagent. In fact, the cleaving of the protein can be performed by a physico-chemical treatment, by a biological treatment or by a combination of the two treatments. Amongst the useable treatments, mention can be made of treatment by hydroxyl radicals, in particular with $H_2O_2$. Treatment by hydroxyl radicals results in a cutting of the peptide bonds which takes place randomly on any of the protein's peptide bonds. The hydroxyl radical concentration determines the number of cleavages performed, and therefore the length of the peptide fragments obtained. Other chemical treatments can also be used such as, for example, cyanogen bromide (CNBr) treatment which specifically splits the peptide bonds at the carboxyl group of the methionyl residues. It is also possible to perform partial acid cleaving at the aspartyl residues by heating a solution of proteins in trifluoroacetic acid to 1000° C.

Treatment of the proteins by enzymatic digestion is nevertheless preferred over physico-chemical treatment because it preserves more of the structure of the protein, and is easier to control. "Enzymatic digestion" is understood to mean the single or combined action of one or more enzymes under appropriate reaction conditions. The enzymes carrying out the proteolysis, which are called proteases, cut the proteins at specific locations. Each protease generally recognises a sequence of amino acids within which it always makes the same cut. Certain proteases recognise a single amino acid or a sequence of two amino acids between which they perform a cleavage, whereas other proteases only recognise longer sequences. These proteases can be endoproteases or exoproteases. Amongst the known proteases, mention may be made of the following as described in WO2005/098071:

specific enzymes such as trypsin which splits the peptide bond at the carboxyl group of the Arg and Lys residues, endolysin which cleaves the peptide bond of the —CO group of the lysines, chymotrypsin which hydrolyses the peptide bond at the carboxylic group of the aromatic residues (Phe, Tyr and Trp), pepsin which makes a cut at the $NH_2$ group of the aromatic residues (Phe, Tyr and Trp), the protease V8 from the V8 strain of *Staphylococcus aureus* which cleaves the peptide bond at the carboxylic group of the Glu residue;

the non-specific enzymes such as thermolysin from the bacteria *Bacillus thermoproteolyticus* which hydrolyses the peptide bond of the $NH_2$ group of hydrophobic amino acids (Xaa-The, Xaa-Ile, Xaa-Phe), subtilisin and pronase which are bacterial proteases which hydrolyse practically all the bonds and can transform the proteins into oligopeptides under controlled reaction conditions (enzyme concentration and duration of reaction).

Several proteases may be used simultaneously, if their modes of action are compatible, or they may be used successively. Within the framework of the invention, the digestion of the sample is preferably performed by the action of a protease enzyme, for example trypsin.

The generation of peptides using a chemical reagent or a protease can be obtained by means of a simple reaction in solution. It can also be performed with a microwave oven [10], or under pressure [11], or even with an ultrasound device [12]. In these three latter cases, the protocol will be much faster.

Amongst the peptides thus obtained, the peptides specific to the protein are referred to as proteotypic peptides. It is these which will be assayed by mass spectrometry. According to the invention, the markers of the mechanisms of bacterial resistance to cephalosporins are proteins from the bacterium in which the mechanisms of resistance to cephalosporins are to be sought. In particular, said proteins are digested into peptides, preferably by an enzyme, and more preferably by trypsin. Similarly, the sample containing protein markers characterising mechanisms of bacterial resistance to cephalosporins can also be pre-treated for the purposes of purification. This purification pretreatment can be employed before or after the peptide production step as described above.

The sample purification pretreatment is widely known to the person skilled in the art and may in particular employ the techniques of centrifugation, filtration, electrophoresis or chromatography. These separating techniques can be used alone or in combination with one another to obtain a multidimensional separation. For example, multidimensional chromatography can be used by combining separation by ion exchange chromatography with reversed-phase chromatography, as described by T. Fortin et al. [13], or H. Keshishian et al. [14]. In these publications, the chromatography medium can be in a column or in a cartridge (solid-phase extraction).

The electrophoretic or chromatographic fraction (or the retention time in monodimensional or multidimensional chromatography) of the proteotypic peptides is characteristic of each peptide, and employing these techniques therefore makes it possible to select the proteotypic peptide or peptides to be assayed. Such a fractionation of the produced peptides makes it possible to increase the specificity of the subsequent assay by mass spectrometry.

An alternative to the electrophoresis or chromatography techniques for the fractionation of the peptides consists in specifically purifying the N-glycopeptides ([15] and patent application WO 2008/066629). However, such a purification only makes it possible to quantify the peptides which have undergone an N-glycosylation post-translational modification. Not all proteins are glycosylated though, which therefore limits its use.

The mass spectrometry to be employed in the method of the invention is widely known to the person skilled in the art as a powerful tool for analysing and detecting different types of molecules. Generally, any type of molecule able to be ionised can be detected according to its molecular mass with the aid of a mass spectrometer. According to the nature of the molecule to be detected, whether of protein or metabolic origin, certain mass spectrometry technologies can be more suitable. Nevertheless, whatever mass spectrometry method is used for the detection, this latter includes a step of ionising the target molecule into so-called molecular ions, in the present case a step of ionising the characterising markers, and a step of separating the molecular ions obtained according to their mass.

All mass spectrometers therefore comprise:

an ionising source intended to ionise the markers present in the sample to be analysed, i.e. to confer a positive or negative charge upon these markers;

a mass analyser intended to separate the ionised markers, or molecular ions, according to their mass-to-charge ratio (m/z);

a detector intended to measure the signal produced either directly by the molecular ions, or by ions produced from molecular ions as detailed hereafter.

The ionisation step necessary for employing mass spectrometry can be performed via any method known to the person skilled in the art. The ionising source makes it possible to transform the molecules to be assayed into a gaseous and ionised state. An ionising source can be used either in positive mode to study the positive ions, or in negative mode to study the negative ions. Several types of sources exist and will be used depending on the result sought and the molecules analysed. In particular, mention may be made of:

electron ionisation (EI), chemical ionisation (CI) and desorption chemical ionisation (DCI)

fast atom bombardment (FAB), metastable atom bombardment (MAB) or ion bombardment (SIMS, LSIMS)

inductively coupled plasma (ICP)

atmospheric-pressure chemical ionisation (APCI) and atmospheric-pressure photoionisation (APPI)

electronebulisation or electrospray (ESI)

matrix-assisted laser desorption/ionisation (MALDI), surface-activated laser desorption/ionisation (SELDI) or desorption/ionisation on silicon (DIOS)

ionisation/desorption by interaction with metastable species (DART)

In particular, ionisation can be employed as follows: the sample containing the target molecules is introduced into an ionisation source, where the molecules are ionised in gaseous state and thus transformed into molecular ions which correspond to the initial molecules. An electrospray ionisation (ESI) source makes it possible to ionise a molecule by making it pass from a liquid state into a gaseous state. The molecular ions obtained therefore correspond to the molecules present in liquid state, with, in positive mode, one, two, or even three or more additional protons and therefore carry one, two, or even three or more charges. For example, when the target molecule is a protein, an ionisation of the proteotypic peptides obtained after fractionation of the target protein, by means of an electrospray source functioning in positive mode, leads to polypeptide ions in gaseous state, with one, two, or even three or more additional protons and which therefore carry one, two, or even three or more charges, and makes it possible to move from a liquid state to a gaseous state [16]. This type of source is particularly well suited when the target molecules or proteotypic peptides obtained are separated beforehand by reversed-phase liquid chromatography. Nevertheless, the ionisation yield of the molecules present in the sample may vary depending on the concentration and the nature of the different species present. This phenomenon leads to a matrix effect well known to the person skilled in the art.

A MALDI ionisation source will allow ionisation of the molecules from a solid-state sample.

The mass analyser in which the step of separating the ionised markers according to their mass-to-charge ratio (m/z) is performed is any mass analyser known to the person skilled in the art. Mention can be made of low-resolution analysers, quadripole or quadrupole (Q), 3D ion trap (IT) or linear ion trap (LIT), also called ion trap, and high-resolution analysers which make it possible to measure the exact mass of the analytes and which in particular use the magnetic sector linked to an electric sector, the time of flight (TOF), Fourier transform ion cyclotron resonance (FT-ICR), orbitrap.

The separation of the molecular ions depending upon their m/z ratio can be employed just once (single mass spectrometry or MS), or several successive MS separations can be conducted. When two successive MS separations are carried out, the analysis is called MS/MS or $MS^2$. When three successive MS separations are carried out, the analysis is called MS/MS/MS or $MS^3$, and more generally, when n successive MS separations are carried out, the analysis is called $MS^n$.

Amongst the techniques which employ several successive separations, SRM (Selected Reaction Monitoring) mode when detecting or assaying a single target molecule, or MRM (Multiple Reaction Monitoring) mode when detecting or assaying several target molecules are particular uses of $MS^2$ separation. Similarly the $MRM^3$ mode is a particular use of MS/MS/MS separation. This is referred to as targeted mass spectrometry.

In the case of a detection in single MS mode, it is the mass-to-charge ratio of the molecular ions obtained which is correlated to the target molecule to be detected.

In the case of detection in MS/MS mode, essentially two steps are added, compared to an MS assay, which are:
 a fragmentation of the molecular ions, then called precursor ions, to give ions called $1^{st}$ generation fragment ions, and
 a separation of the ions called $1^{st}$ generation fragment ions according to their mass $(m/z)_2$, the ratio $(m/z)_1$ corresponding to the ratio (m/z) of the precursor ions.

It is therefore the mass-to-charge ratio of the $1^{st}$ generation fragment ions thus obtained which is correlated to the target molecule to be detected. First-generation fragment ion is understood to be an ion derived from the precursor ion, following a fragmentation step and of which the mass-to-charge ratio m/z is different from the precursor ion.

The $(m/z)_1$ and $(m/z)_2$ pairs are called transitions and are representative of the characteristic ions to be detected.

The choice of the characteristic ions which are detected to be correlated to the target molecule is made by the person skilled in the art in accordance with the standard methods. Their selection will advantageously lead to the most sensitive, specific and robust assays possible, in terms of reproducibility and reliability. In the methods developed for the selection of proteotypic peptides $(m/z)_1$, and of the first-generation fragment $(m/z)_2$, the choice is essentially based on the intensity of the response. For more details, it is possible to refer to V. Fusaro et al. [17]. Commercially available software, such as the MIDAS and MRM Pilot software from Applied Biosystems or MRMaid [18] can be used by the person skilled in the art to allow him to predict all the possible transition pairs. He can also make use of a database called PeptideAtlas constructed by F Desiere et al. [19] to compile all of the MRM transitions of peptides described by the scientific community. This database PeptideAtlas is freely available on the internet. For non-protein molecules, it is also possible to use databases, such as, for example, the one accessible through the Cliquid software from the company Applied Biosystems (United States of America).

An alternative approach to selecting the proteotypic peptides $(m/z)_1$ and $(m/z)_2$ consists in using MS/MS fragmentation spectra obtained during other work. This work can be, for example, the phases of biomarker discovery and identification by proteomic analysis. This approach was proposed by Thermo Scientific during user conferences [18]. It makes it possible to generate a list of candidate transitions from the peptides identified through testing by the SIEVE (Thermo Scientific) software. Certain criteria were detailed by J. Mead et al. [18] for the choice of the ions $(m/z)_1$ and $(m/z)_2$ and are detailed hereafter:
 peptides with internal cleavage sites, i.e. with internal Lysine or Arginine, must be avoided, unless the Lysine or Arginine is followed by Proline,
 peptides with Aspargine or Glutamine must be avoided because they may deaminate,
 peptides with Glutamine or Glutamic Acid at the N-terminal must be avoided because they may cyclise spontaneously,
 peptides with Methionine must be avoided because they may be oxidised,
 peptides with Cysteine must be avoided because they may be non-reproducibly modified during a potential step of denaturation, reduction and blocking of the thiol functions,
 peptides with Proline may be considered to be favourable because they generally produce intense fragments in MS/MS with a very strong single peak. However, a very strong single fragment does not make it possible to validate the identity of the transition in a complex mixture. Indeed, only the simultaneous presence of several characteristic fragments makes it possible to verify that the precursor ion sought has actually been detected, the peptides having a Proline adjacent to the C-terminal (Position n−1) or in second position relative to the C-terminal (position n−2) should be avoided because, in this case, the size of the first-generation peptide fragment is generally considered to be too small to be sufficiently specific, the selection of fragments having a mass greater than the precursor should be given preference in order to promote specificity. To this end, it is necessary to select a dicharged precursor ion and select the most intense first-generation ion fragment having a mass greater than the precursor, i.e. a monocharged first-generation fragment ion.

The fragmentation of the selected precursor ions is performed in a fragmentation cell such as the triple quadripole model [20], ion trap model [21], or time-of-flight (TOF) model [22], which also make it possible to separate ions. The fragmentation or fragmentations will be conventionally performed by collision with an inert gas such as argon or nitrogen, within an electrical field, by photo-excitation or photo-dissociation using an intense light source, collision with electrons or radical species, by applying a potential difference, for example in a time-of-flight tube, or by any other activation mode. The characteristics of the electrical field determine the intensity and nature of the fragmentation. Thus, the electrical field applied in the presence of an inert gas, for example in a quadripole, determines the collision energy provided to the ions. This collision energy will be optimised, by the person skilled in the art, to increase the sensitivity of the transition to be assayed. By way of example, it is possible to vary the collision energy between 5 and 180 e$^-$V in q2 in an AB SCIEX QTRAP® 5500 mass spectrometer from the company Applied Biosystems (Foster City, United States of America). Similarly, the duration of the collision step and the excitation energy within, for example, an ion trap will be optimised by the person skilled in the art to lead to the most sensitive assay. By way of example, it is possible to vary this duration, called excitation time, between 0.010 and 50 ms and the excitation energy between 0 and 1 (arbitrary unit) in Q3 in an AB SCIEX QTRAP® 5500 mass spectrometer by the company Applied Biosystems.

Finally, the detection of the selected characteristic ions takes place in the conventional manner, particularly by means of a detector and a processing system. The detector collects the ions and produces an electrical signal whose intensity depends on the amount of ions collected. The signal obtained is then amplified such that it can be processed by computer. A computer data processing assembly makes it possible to transform the information received by the mass spectrum detector.

The principle of the SRM mode, or even of the MRM mode, is to specifically select a precursor ion, fragment it, and then specifically select one of its fragment ions. For such applications, triple quadripole or hybrid triple quadripole/ion trap devices are generally used.

In the case of a triple quadripole device (Q1q2Q3) used in MS$^2$ mode, with a view to assaying or detecting a target protein, the first quadripole (Q1) makes it possible to filter the molecular ions corresponding to the proteotypic peptides characteristic of the protein to be assayed and obtained during an earlier digestion step, depending on their mass-to-charge ratio (m/z). Only the peptides having the mass-to-charge ratio of the proteotypic peptide sought, which ratio is called $(m/z)_1$, are transmitted into the second quadripole (q2) and act as precursor ions for the subsequent fragmentation. The analyser q2 can fragment the peptides of mass-to-charge ratio $(m/z)_1$ into first-generation fragment ions. Fragmentation is generally obtained through collision of the precursor peptides with an inert gas, such as nitrogen or argon in q2. The first-generation fragment ions are transmitted into a third quadripole (Q3) which filters the first-generation fragment ions depending on a specific mass-to-charge ratio, called $(m/z)_2$. Only the first-generation fragment ions having the mass-to-charge ratio of a fragment characteristic of the sought proteotypic peptide $(m/z)_2$ are transmitted into the detector in order to be detected, or even quantified.

This mode of operation exhibits a double selectivity, with regard to the selection of the precursor ion on the one hand, and the selection of the first-generation fragment ion on the other hand. Mass spectrometry in SRM or MRM mode is therefore advantageous for quantification.

When the mass spectrometry employed in the method according to invention is tandem mass spectrometry (MS$^2$, MS$^3$, MS$^4$ or MS$^5$), several mass analysers can be linked to one another. For example, a first analyser separates the ions, a collision cell makes it possible to fragment the ions, and a second analyser separates the fragment ions. Certain analysers, such as the ion traps or the FT-ICR, constitute several analysers in one and make it possible to fragment the ions and analyse the fragments directly.

According to preferred embodiments of the invention, the method of the invention comprises one or more of the following characteristics:

the mass spectrometry employed for the properties of potential resistance to at least one antimicrobial is MS/MS spectrometry, which has the advantage of producing a fragment which is specific to the molecule to be detected or quantified, and thus of providing great specificity to the assaying method;

the MS/MS spectrometry is MRM which has the advantage of using an analysis cycle time in the mass spectrometer of several tens of milliseconds, which makes it possible to detect or quantify, with a high degree of sensitivity, a large number of different molecules in a multiplexed manner;

where applicable, the determination of the type properties and of the virulence factor is performed in the same mass spectrometry apparatus as the determination of the markers of resistance to at least one antimicrobial, preferably simultaneously, which has the advantage of reducing the analysis time and the cost of the instrument, which also facilitates the processing and the yielding of the results.

In addition to determining the resistance to an antibiotic, it is necessary to identify the microorganism or microorganisms present in the sample to be tested.

The methods of identifying microorganisms are widely known to the person skilled in the art, as described for example by Murray P. R. et al. in Manual of Clinical Microbiology, 2007, 9$^{th}$ edition, and especially in Vol. I, Section III, chapters 15 and 16 for bacteria and yeasts, Vol. II, Section VI, chapter 82 for viruses, and Vol. II, Section X, chapter 135 for protozoa. As an example of conventional identification methods, mention can be made of the determination of the biological profile, by using the Vitek 2 (bioMérieux) identification cards, for example, or even by using molecular biology techniques with identification criteria based on the study of the presence of certain genes, and on the study of their sequence.

Identification can be performed directly from the sample in which the identification is made, or the microorganisms contained in the sample can be cultured using methods well known to the person skilled in the art with optimal culture media and culturing conditions tailored to the species of microorganisms to be sought, as described by Murray P. R. et al. in Manual of Clinical Microbiology, 2007, 9$^{th}$ edition, Vol. I, Section III, chapter 14, and in particular in Vol. I, Section IV, chapter 21 for bacteria, and Vol. II, Section VI, chapter 81 for viruses, Vol. II, Section VIII, chapter 117 for yeasts, and Vol. II, Section X, chapter 134 for protozoa.

Thus, generally, in the case of an identification using a biochemical method of a bacterium in a specimen, it is first necessary to obtain it in a pure culture, for example after seeding on agar. Molecular biology (PCR) can in certain cases be applied directly to the sample to be analysed.

Instead of cultivating the microorganisms, they can be concentrated by capture directly in the sample by means of active surfaces. Such a method was described by W.-J. Chen et al. [11] who captured different bacterial species with the aid of magnetic beads with an $Fe_3O_4/TiO_2$-activated surface. Capture by other means is also possible, such as a capture by lectins [23], or by antibodies [24], or by Vancomycin [25]. The capture makes it possible to concentrate the microorganisms and thus to reduce or even eliminate the culture step. This results in a considerable timesaving.

The identification may also be performed by mass spectrometry, in accordance with the techniques described previously, preferably by MS, by MS/MS, or even by MS followed by MS/MS spectrometry, which constitutes one embodiment of the invention. In this case too, the sample can be subjected to a culture step beforehand, such as seeding on agar.

The use of an MS identification method is advantageous in that it may be carried out in a few minutes, and in that it requires a mass spectrometer with a single analyser, i.e. a less complex instrument than a tandem mass spectrometer used in MS/MS.

The use of a method of identification by MS followed by MS/MS spectrometry is also advantageous. It makes it possible to check the identity of the ions observed by MS, which increases the specificity of the analysis.

The use of an MRM-type MS/MS identification method has the advantage of being more sensitive and simpler than the conventional MS followed by MS/MS approaches. This method requires neither a high-performance software to process the information between the acquisition of the MS spectrum and of the MS/MS spectrum, nor a change in the setting of the machine parameters for linking up MS then MS/MS spectra.

The method of identification by MS may be employed with an electrospray source on a raw sample, as described by S. Vaidyanathan et al. [26] or by R. Everley et al. [27] after chromatographic separation. Different m/z ranges thus make it possible to identify the microorganisms. S. Vaidyanathan et al. used a window of between 200 and 2000 Th, and R. Everley et al. used a window of between 620 and 2450 Th. The mass spectra may also be deconvoluted to access the mass of the proteins independently of their charge state. R. Everley et al. therefore used masses of between about 5,000 and 50,000 Da. Alternatively, the method of identification by MS can also be employed with the aid of a MALDI-TOF, as described by Claydon et al. [3] and T. Krishnamurthy and P. Ross [4]. The analysis combines acquisition of a mass spectrum and interpretation of expert software. It is extremely simple and can be carried out in a few minutes. This method of identification is currently becoming more widespread in medical analysis laboratories [28].

The identification of bacteria by MS followed by MS/MS via their proteins present in the sample has been applied widely by a number of teams. By way of example, mention can be made of the recent work of Manes N. et al. [29], who studied the peptidome of *Salmonella enterica*, or the work of R. Nandakumar et al. [30] or of L. Hernychova et al. [31] who have studied the proteome of bacteria after digestion of the proteins with trypsin. The conventional approach consists in i) acquiring an MS spectrum, ii) successively selecting each precursor ion observed on the MS spectrum with an intense signal, iii) successively fragmenting each precursor ion and acquiring its MS/MS spectrum, iv) interrogating protein databases such as SWISS-PROT or NCBI, through software such as Mascot (Matrix Science, London, United Kingdom) or SEQUEST (Thermo Scientific, Waltham, United States of America), to identify the peptide which has a strong probability of matching the MS/MS spectrum observed. This method may lead to the identification of a microorganism if a protein or a peptide characteristic of the species is identified.

One of the advantages of the use of the mass spectrometry lies in that it is particularly useful for quantifying molecules, in the present case the markers of the mechanisms of bacterial resistance to beta-lactams. To this end, the current intensity detected is used, which is proportional to the quantity of target molecule. The current intensity thus measured may serve as a quantitative measurement making it possible to determine the quantity of target molecule present, which is characterised by its expression in International System (SI) mol/m$^3$ or kg/m$^3$ units, or by multiples or sub-multiples of these units, or by the usual derivatives of the SI units, including multiples or sub-multiples thereof. As a non-limiting example, the units such as ng/ml or fmol/l are units characterising a quantitative measurement.

A calibration is nevertheless necessary in order to be able to correlate the measured area of the peak, which corresponds to the current intensity induced by the detected ions, to the quantity of target molecule to be assayed. For this purpose, the calibrations conventionally used in mass spectrometry may be employed, within the framework of the invention. MRM assays are conventionally calibrated with the aid of external standards or, preferably, with the aid of internal standards such as described by T. Fortin et al. [13]. If the target molecule is a proteotypic peptide which permits the assaying of a protein of interest, the correlation between the quantitative measurement and the quantity of target proteotypic peptide, and subsequently of protein of interest, is obtained by calibrating the measured signal relative to a standard signal for which the quantity to be assayed is known. The calibration may be performed using a calibration curve, for example obtained by successive injections of standard proteotypic peptide at different concentrations (external calibration), or preferably by internal calibration using a heavy peptide as an internal standard, for example in accordance with the AQUA, QconCAT or PSAQ methods detailed below. "Heavy peptide" is understood to mean a peptide corresponding to the proteotypic peptide, but in which one or more atoms of carbon 12 ($^{12}$C) is (are) replaced by carbon 13 ($^{13}$C), and/or one or more atoms of nitrogen 14 ($^{14}$N) is (are) replaced by nitrogen 15 ($^{15}$N).

The use of heavy peptides as internal standards (AQUA) was also proposed in US patent application 2004/0229283. The principle is to artificially synthesise proteotypic peptides with amino acids containing isotopes which are heavier than the usual natural isotopes. Such amino acids are obtained, for example, by replacing some of the atoms of carbon 12 ($^{12}$C) with carbon 13 ($^{13}$C), or by replacing some of the atoms of nitrogen 14 ($^{14}$N) with nitrogen 15 ($^{15}$N). The artificial peptide (AQUA) thus synthesised has strictly the same physicochemical properties as the natural peptide (with the exception of a higher mass). It is generally added, at a given concentration, to the sample, upstream of assaying by mass spectroscopy, for example between the treatment entailing the cleaving of the proteins in the sample of interest and the fractionation of the peptides obtained after the treatment step. Thus, the AQUA peptide is co-purified with the natural peptide to be assayed, during fractionation of the peptides. The two peptides are therefore injected simultaneously into the mass spectrometer, for assaying. They then undergo the same ionisation yield in the source. The comparison of the peak areas of the natural and AQUA peptides, whose concentration is known, makes it possible to calculate the concentration of the natural peptide and thus trace back the concentration of the protein to be assayed. A variation of the AQUA technique was proposed by J.-M. Pratt et al. [32] under the name QconCat. This variant is also described in patent application WO 2006/128492. It consists in concatenating various AQUA peptides and producing the artificial polypeptide in the form of a heavy recombinant protein. The recombinant protein is synthesised with amino acids comprising heavy isotopes. In this way, it is possible to obtain a standard to calibrate the simultaneous assay of several proteins at lower cost. The QconCAT standard is added from the start, upstream of the treatment entailing the cleaving of the proteins and prior to the steps of protein fractionation, denaturation, reduction and blocking of the protein thiol functions, if these are present. The QconCAT standard therefore undergoes the same treatment cycle entailing the cleaving of the proteins as the natural protein, which makes it possible to take account of the yield from the treatment step which entails the cleaving of the proteins. In fact, the treatment, particularly by digestion, of the natural protein may not be complete. In this case, the use of an AQUA standard would lead to underestimating the quantity of natural protein. For full assaying, it may therefore be important to take into account the yields from treatment which entails the cleaving of the proteins. However, V. Brun et al. [33] have shown that the QconQAT standards sometimes do not exactly reproduce the treatment yield, particularly by digestion of the natural protein, undoubtedly due to a three-dimensional conformation different from the QconCAT protein.

V. Brun et al. [33] then proposed the use of a method dubbed PSAQ, and described in patent application WO 2008/145763. In this case, the internal standard is a recombinant protein having the same sequence as the natural protein but synthesised with heavy amino acids. The synthesis is performed ex-vivo with heavy amino acids. This standard has strictly the same physicochemical properties as the natural protein (with the exception of a higher mass). It is added from the start, before the protein fractionation step, when the latter is present. It is therefore co-purified with the native protein, during the protein fractionation step. It exhibits the same treatment yield, particularly by digestion, as the native protein. The heavy peptide obtained after cleaving is also co-purified with the natural peptide, if a peptide fractionation step is performed. The two peptides are therefore injected simultaneously into the mass spectrometer, to be quantitatively assayed. They then undergo the same ionisation yield in the source. Comparison of the peak areas of the natural and the reference peptides in the PSAQ method make it possible to calculate the concentration of the protein to be assayed taking into account all of the steps of the assay method.

All of these techniques, namely AQUA, QconCAT or PSAQ or any other calibration technique, used in the mass spectrometry assays and in particular in MRM or MS assays, may be employed to carry out calibration, within the framework of the invention.

Preferably, the mass spectrometry used in the detection method according to the invention is MS/MS. More preferably, the mass spectrometry is MRM.

The method of the invention makes it possible to detect resistances to cephalosporin, characterised by the detection of at least one peptide as a resistance marker. Said resistance marker peptide preferably belongs to the proteins TEM, CMY, CTX-M, SHV, FOX, ACC, ACT, CARB, DHA, MIR, MOX, PER, VEB, OXA or GES.

In particular, the detection of a mechanism of resistance to cephalosporins induced by the expression of the TEM protein is characterised by the detection of at least one peptide belonging to the TEM protein and its different sequence variants SEQ ID No. 1 to SEQ ID No. 165 and SEQ ID No. 1836 to SEQ ID No. 1843.

SEQ ID No. 1:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 2:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 3:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

-continued
```
MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 4:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYMTGSQATMDERNRQIAEIGASLIKHW

SEQ ID No. 5:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGTGKRGSRGIIAALGPDGKPSRIVVIYTTGSQATMDERNRQIAEIGASLIKHW

SEQ ID No. 6:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 7:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 8:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 9:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYMTGSQATMDERNRQIAEIGASLIKHW

SEQ ID No. 10:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI
```

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 11:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 12:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 13:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYMTGSQATMDERNRQIAEIGASLIKHW

SEQ ID No. 14:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 15:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 16:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 17:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

-continued

SEQ ID No. 18:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 19:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 20:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLRNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 21:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGGSERGSRGIIAALGPDGKPSRIVVIYTTGSQATMDERNRQIAEIGASLIKH

SEQ ID No. 22:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGTGKRGSRGIIAALGPDGKPSRIVVIYTTGSQATMDERNRQIAEIGASLIKHW

SEQ ID No. 23:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYMTGSQATMDERNRQIAEIGASLIKHW

SEQ ID No. 24:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 25:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

-continued

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGKRGSRGIIAALGPDGKPSRIVVIYMTGSQATMDERNRQIAEIGASLIKHW

SEQ ID No. 26:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 27:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 28:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

HADKSGAGERGSSGIIAALGPDGKPSRIVVIYTTGSQATMDERNRQIAEIGASLIKHW

SEQ ID No. 29:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSCGIIAALGPDGKPSRIVVIYTTGSQATMDERNRQIAEIGASLIKHW

SEQ ID No. 30:
MSIQHFRVALIPFFAAFCLPVFAHPETLVKVKDAEDQLGARVGYIELDLNSGKILESF

RPEERFPMISTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 31:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 32:
MSIQHFRVALIPFFAAFCLPVFAHPETLVKVKDAEDQLGARVGYIELDLNSGKILESF

RPEERFPMVSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 33:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERDRQIAEIGASLIKHW

SEQ ID No. 34:
MSIQHFRVALIPFFAAFCLPVFAHPETLVKVKDAEDQLGARVGYIELDLNSGKILESF

RPEERFPMVSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERDRQIAEIGASLIKHW

SEQ ID No. 35:
MSIQHFRVALIPFFAAFCLPVFAHPETLVKVKDAEDQLGARVGYIELDLNSGKILESF

RPEERFPMISTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERDRQIAEIGASLIKHW

SEQ ID No. 36:
MSIQHFRVALIPFFAAFCLPVFAHPETLVKVKDAEDQLGARVGYIELDLNSGKILESF

RPEERFPMVSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDELNRQIAEIGASLIKHW

SEQ ID No. 37:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRREPELNEAIP

NDERDTTMPAAMATTLRKLLTGELLTLASRQQLIDWMEADKVAGPLLRSALPAGWF

IADKSGAGERGSRGIIAALGPDGKPSRIVVIYTTGSQATMDERDRQIAEIGASLIKHW

SEQ ID No. 38:
MSIQHFRVALIPFFAAFCLPVFAHPETLVKVKDAEDQLGARVGYIELDLNSGKILESF

RPEERFPMISTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 39:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSTGIIAALGPDGKPSRIVVIYTTGSQATMDERNRQIAEIGASLIKHW

SEQ ID No. 40:
MSIQHFRVALIPFFAAFCLPVFAHPETLVKVKDAEDKLGVRVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGSQATMDERNRQIAEIGASLIKHW

SEQ ID No. 41:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDHWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 42:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSSGIIAALGPDGKPSRIVVIYTTGSQATMDERNRQIAEIGASLIKHW

SEQ ID No. 43:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDEQNRQIAEIGASLIKHW

SEQ ID No. 44:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 45:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGSQATMDERNRQIAEIGASLIKHW

SEQ ID No. 46:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGSQATMDERNRQIAEIGASLIKHW

SEQ ID No. 47:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGGQATMDERNRQIAEIGASLIKHW

SEQ ID No. 48:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERDRQIAEIGASLIKHW

SEQ ID No. 49:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSHGIIAALGPDGKPSRIVVIYTTGSQATMDERNRQIAEIGASLIKHW

SEQ ID No. 50:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 51:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 52:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSLGIIAALGPDGKPSRIVVIYTTGSQATMDERNRQIAEIGASLIKHW

SEQ ID No. 53:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAEPLLRSALPAGW

FIADKSGAGERGSRGIIAALGPDGKPSRIVVIYTTGSQATMDERNRQIAEIGASLIKHW

SEQ ID No. 54:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLRNMGDHVTRLDRWEPELNEAI

-continued

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 55:
MSIQHFRVALIPFFAAFCLPVFAHPETLVKVKDAEDQLGARVGYIELDLNSGKILESF

RPEERFPMMSTFKVLLCGAVLSRVDAGQEQLDRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 56:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSSGIIAALGPDGKPSRIVIIYTTGSQATMDERNRQIAEIGASLIKHW

SEQ ID No. 57:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMGDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 58:
MSIQHFRVALIPFFAAFCLPVFAHPETLVKVKDAEDKLGARVGYIELDPNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 59:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 60:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 61:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSCGIIAALGPDGKPSRIVVIYTTGSQATMDERNRQIAEIGASLIKHW

SEQ ID No. 62:
MSIQHFRVALIPFFAAFCLPVFAHPETLVKVKDAEDKLGARVGYIELDLNSGKILESFR

PEERFPMMSTFKVLLCGAVLSRVDAGQEQLDRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 63:
MSIQHFRVALIPFFAAFCIPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSCGIIAALGPDGKPSRIVVIYTTGSQATMDERNRQIAEIGASLIKHW

SEQ ID No. 64:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGSQATMDELNRQIAEIGASLIKHW

SEQ ID No. 65:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASQQQLIDWMEADKVAGPLLRSALPAGW

FIADKSGAGERGSRGIIAALGPDGKPSRIVVIYTTGSQATMDERNRQIAEIGASLIKHW

SEQ ID No. 66:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYTTGSQATMDERNRQIAEIGASLIKHW

SEQ ID No. 67:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGASKRGSRGIIAALGPDGKPSRIVVIYTTGSQATMDERNRQIAEIGASLIKHW

SEQ ID No. 68:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSCGIIAALGPDGKPSRIVVIYMTGSQATMDERNRQIAEIGASLIKHW

SEQ ID No. 69:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSSGIIAALGPDGKPSRAIVVIYMTGSQATMDERNRQIAEIGASLIKHW

SEQ ID No. 70:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYMTGSQATMDERNRQIAEIGASLIKHW

SEQ ID No. 71:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMGDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 72:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSSGIIAALGPDGKPSRIVVIYTTGSQATMDERNRQIAEIGASLIKHW

SEQ ID No. 73:
MSIQHFRVALIPFFAAFCLPVFAHPETLVKVKDAEDQLGARVGYIELDLNSGKILESF

RPEERFPMVSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRREPELNEAIP

NDERDTTMPAAMATTLRKLLTGELLTLASRQQLIDWMEADKVAGPLLRSALPAGWF

IADKSGAGERGSRGIIAALGPDGKPSRIVVIYTTGSQATMDERDRQIAEIGASLIKHW

SEQ ID No. 74:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSGGIIAALGPDGKPSRIVVIYTTGSQATMDERNRQIAEIGASLIKHW

SEQ ID No. 75:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAVTMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERDRQIAEIGASLIKHW

SEQ ID No. 76:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAVTMSDNTAANLLLTTIGGPKELTAFLHNMGDHVTRLDRWEPELNEAI

-continued

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 77:
MSIQHFRVALIPFFAAFCLPVFAHPETLVKVKDAEDQLGARVGYIELDLNSGKILESF

RPEERFPMVSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDEQNRQIAEIGASLIKHW

SEQ ID No. 78:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRCEPELNEAIP

NDERDTTMPAAMATTLRKLLTGELLTLASRQQLIDWMEADKVAGPLLRSALPAGWF

IADKSGAGERGSRGIIAALGPDGKPSRIVVIYTTGSQATMDEQNRQIAEIGASLIKHW

SEQ ID No. 79:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERDRQIAEIGASLIKHW

SEQ ID No. 80:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGKRGSRGIIAALGPDGKPSRIVVIYMTGSQATMDERNRQIAEIGASLIKHW

SEQ ID No. 81:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGTGKRGSRGIIAALGPDGKPSRIVVIYMTGSQATMDERNRQIAEIGASLIKHW

SEQ ID No. 82:
MSIKHFRVALIPFFAAFCLPVFAHPETLVKVKDAEDQLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLHCWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 83:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTTPAAMATTLRKLLTDELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 84:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMGDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 85:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTG

GMTVRELCSAAITMSDNTAANLLLTTIGGPKELTAFLHNMGDHVTRLDRWEPELNE

AIPNDERDTTMPAAMATTLRKLLTGELLTLASRQQLIDWMEADKVAGPLLRSALPAG

WFIADKSGAGERGSRGIIAALGPDGKPSRIVVIYTTGSQATMDERNRQIAEIGASLIK

HW

SEQ ID No. 86:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDCWEPELNEAI

PNDERDTTTPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 87:
MSIKHFRVALIPFFAAFCLPVFAHPETLVKVKDAEDQLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 88:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGASKRGSRGIIAALGPDGKPSRIVVIYTTGSQATMDERNRQIAEIGASLIKHW

SEQ ID No. 89:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGASERGSRGIIAALGPDGKPSRIVVIYMTGSQATMDERNRQIAEIGASLIKHW

SEQ ID No. 90:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGAKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

-continued

SEQ ID No. 91:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLGRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 92:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYTTGSQATMDERNRQIVEIGASLIKHW

SEQ ID No. 93:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYMTGSQATMDERNRQIAEIGASLIKHW

SEQ ID No. 94:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDELNRQIAEIGASLIKHW

SEQ ID No. 95:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIVEIGASLIKHW

SEQ ID No. 96:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCNAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 97:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 98:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDHWEPELNEAI

PNDERDTTTPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 99:
MSIQHFRVALIPFFAAFCLPVFAHPETLVKVKDAEDQLGARVGYIELDLNSGKILESF

RPEERFPMMSTFKVLLCGAELSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTSELLTLASRQQLIDWMEADKVAGPLLRSALPAGW

FIADKSGAGERGSRGIIAALGPDGKPSRIVVIYTTGSQATMDERSRQIAEIGASLIKHW

SEQ ID No. 100:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 101:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYMTGSQATMDERNRQIAEIGASLIKHW

SEQ ID No. 102:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGADERGSRGIIAALGPDGKPSRIVVIYMTGSQATMDERNRQIAEIGASLIKHW

SEQ ID No. 103:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLRNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 104:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 105:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGTGKRGSRGIIAALGPDGKPSRIVVIYTTGSQATMDERNRQIAEIGASLIKHW

SEQ ID No. 106:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 107:
MSIQHFRVALIPFFAAFCLPVFAHPETLVKVKDAEDQLGARVGYIELDLNSGKILESF

RPEERFPMMSTFKVLLCGAVLSRIDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPVAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 108:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 109:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYMTGSQATMDERNRQIAEIGASLIKHW

SEQ ID No. 110:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 111:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGTGKRGSSGIIAALGPDGKPSRIVVIYTTGSQATMDERNRQIAEIGASLIKHW

SEQ ID No. 112:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDEQNRQIAEIGASLIKHW

SEQ ID No. 113:
MSIKHFRVALIPFFAAFCLPVFAHPETLVKVKDAEDQLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 114:
MSIKHFRVALIPFFAAFCLPVFAHPETLVKVKDAEDQLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 115:
MSIQHFRVALIPFLAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSREPELNEAIP

NDERDTTMPAAMATTLRKLLTGELLTLASRQQLIDWMEADKVAGPLLRSALPAGWF

IADKSGAGERGSRGIIAALGPDGKPSRIVVIYTTGSQATMDERDRQIAEIGASLIKHW

SEQ ID No. 116:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERETTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 117:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDNVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 118:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGEHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 119:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 120:
MSIQHFRVALIPFFAAFCLPVFAHPETLVKVKPAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGTGERGSRGIIAALGPDGKPSRIVVIYTTGSQATMDERNRQIAEIGASLIKHW

SEQ ID No. 121:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTTPAAMATTLRKLLTGELLTLASRQQLIDWMEADKVAGPLLRSALPAGW

FIADKSGTGERGSRGIIAALGPDGKPSRIVVIYTTGSQATMDERNRQIAEIGASLIKHW

SEQ ID No. 122:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAV

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 123:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 124:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 125:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 126:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGTGKRGSRGIIAALGPDGKPSRIVVIYTTGGQATMDERNRQIAEIGASLIKHW

SEQ ID No. 127:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

SEQ ID No. 128:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PIDERDTTMPAAMATTLRKLLTGELLTLASRQQLIDWMEADKVAGPLLRSALPAGWF

IADKSGASERGSRGIIAALGPDGKPSRIVVIYTTGSQATMDERNRQIAEIGASLIKHW

SEQ ID No. 129:
MSIQHFRVALIPFFAAFCLPVFAHPETLVKVKDAEDKLGARVGYIEMDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASERGSRGIIAALGPDGKPSRIVVIYTTGSQATMDERNRQIAEIGASLIKHW

SEQ ID No. 130:
MSIQHFRVALIPFFAAFCLPVFAHPETLVKVEDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 131:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGANERGSRGIIAALGPDGKPSRIVVIYMTGSQATMDERNRQIAEIGASLIKHW

SEQ ID No. 132:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDCWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 133:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDCWEPELNEAI

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 134:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLMRSALPAG

-continued
```
WFIADKSGAGERGSHGIIAALGPDGKPSRIVVIYTTGSQATMDERNRQIAEIGASLIK

HW

SEQ ID No. 135:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLPD

GMTVRELCSAAITMSDNTAANLLLTTIGGPKELTAFLHNMGDHVTRLDRWEPELNE

AIPNDERDTTMPAAMATTLRKLLTGELLTLASRQQLIDWMEADKVAGPLLRSALPAG

WFIADKSGAGERGSHGIIAALGPDGKPSRIVVIYTTGSQATMDERNRQIAEIGASLIK

HW

SEQ ID No. 136:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSVLPAGW

FIADKSGAGERGSRGIIAALGPDGKPSRIVVIYTTGSQATMDERNRQIAEIGASLIKHW

SEQ ID No. 137:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATKLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 138:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTTPAAMATTLRKLLTGELLTLASRQQLIDWMEADKVAGPLLRSALPAGW

FIADKSGAGVRGSRGIIAALGPDGKPSRIVVIYTTGSQATMDERNRQIAEIGASLIKHW

SEQ ID No. 139:
MSIQHFRVALIPFFAAFCLPVFAHPDTLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 140:
MSIQHFRVALIPFFAAFCLPVFAHPETLVKVKDAEDQLGARVGYIELDLNSGKILESF

RPEERFPMVSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERDRQIAEIGGSLIKHW

SEQ ID No. 141:
MSIQHFRVALIPFFAAFCLPVFAHPETLVKVKDAEDQLGARVGYIELDLNSGKILESF

RPEERFPMVSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI
```

-continued

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERDRQIAEIGASLIKHW

SEQ ID No. 142:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 143:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGKRGSRGIIAALGPDGKPSRIVVIYTTGSQATMDERNRQIAEIGASLIKHW

SEQ ID No. 144:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNIGDHVTRLDRWEPELNEAIP

NDERDTTMPAAMATTLRKLLTGELLTLASRQQLIDWMEADKVAGPLLRSALPAGWF

IADKSGAGERGSRGIIAALGPDGKPSRIVVIYTTGSQATMDERNRQIAEIGASLIKHW

SEQ ID No. 145:
MSIQHFRVALIPFFAAFCLPVFAHPETLVKVKDAEDQLGARVGYIELDLNSGKILESF

RPEERFPMMSTFKVLLCGAVLSRIDAGQEQLGRRIHYSQSDLVEYSPVTEKHLTDG

MTVRELCSAAITMSDNTAANLLLTTIGGPKELTAFLHNMGDHVTRLDRWEPELNEAI

PNDERDTTMPVAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 146:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERDRQIAEIGASLIKHW

SEQ ID No. 147:
MSIQHFRVALIPFFAAFCFPVFAHPETLVKVKDAEDQLGARVGYIELDLNSGKILESF

RPEERFPMISTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 148:
MSIQHFRVALIPFFAAFCLPVFAHPETLVKVKDAEDKLGARVGYIELDLNSGKILESFR

PEERFPMVSTFKVLLCGAVLSRVDAGQEQLGRRIHYSQNDLVEYSPVTEKHLTDGM

TVRELCSAAITMSDNTAANLLLTTIGGPKELTAFLHNMGDHVTRLDRWEPELNEAIP

NDERDTTMPAAMATTLRKLLTGELLTLASRQQLIDWMEADKVAGPLLRSALPAGWF

IADKSGAGERGSRGIIAALGPDGKPSRIVVIYTTGSQATMDERNRQIAEIGASLIKHW

SEQ ID No. 149:
MSIKHFRVALIPFFAAFCLPVFAHPETLVKVKDAEDQLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDHWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 150:
MSIQHFRVALIPFFAAFCLPVFAHPKTLVKVKDAENQLGARVGYIELDLNSGKILESF

RPEKRFPMMSTFKVLLCGAVLSRIDAGQEQLGRRIHYSQSDVVEYSPVTEKHLTDG

MTVRELCSAAITMSDNTAANLLLTTIGGPKELTAFLHNMGDHVTRLDRWEPELNEAI

PNDERDTTMPVAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 151:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDEQNRQIAEIGASLIKLW

SEQ ID No. 152:
MSIQHFRVALIPFFAAFCLPVFAHPETLVKVKDAEDQVGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQTAEIGASLIKHW

SEQ ID No. 153:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDSWEPELNEAI

PNDERDTTTPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 154:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVGELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 155:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSVLPAGW

FIADKSGASERGSRGIIAALGPDGKPSRIVVIYMTGSQATMDERNRQIAEIGASLIKHW

SEQ ID No. 156:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYMTGSQATMDERNRQIAEIGASLIKHW

SEQ ID No. 157:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRGEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 158:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEICASLIKHW

SEQ ID No. 159:
MSIQHFRVALIPFFAAFCLPVFAHPETLVKVKDAEDQLGARVGYIELDLNSGKILESF

RPEERFPMMSTFKVLLCGAVLSRIDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 160:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEVDKVAGPLLRSALPAGW

FIADKSGAGERGSSGIIAALGPDGKPSRIVIIYTTGSQATMDERNRQIAEIGASLIKHW

SEQ ID No. 161:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEVDKVAGPLLRSALPAGW

FIADKSGAGERGSSGIIAALGPDGKPSRIVVIYTTGSQATMDERKRQIAEIGASLIKHW

SEQ ID No. 162:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEVDKVAGPLLRSALPAGW

FIADKSGAGERGSRGIIAALGPDGKPSRIVVIYTTGSQATMDERNRQIAEIGASLIKHW

SEQ ID No. 163:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

-continued

PNDERDTTMPAAMATTLRKLLTGELLTLASRQQLIDWMEADKVAGPLLRSVLPAGW

FIADKSGAGERGSRGIIAALGPDGKPSRIVVIYTTGSQATMDERNRQIAEIGASLIKHW

SEQ ID No. 164:
MSIKHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVKYSPVTEKHLTDG

MTVRELCSAAITMSDNTAANLLLTTIGGPKELTAFLHNMGDHVTRLDSWEPELNEAI

PNDERDTTTPAAMATTLRKLLTGELLTLASRQQLIDWMEADKVAGPLLRSALPAGW

FIADKSGTGKRGSRGIIAALGPDGKPSRIVVIYTTGSQATMDERNRQIAEIGASLIKHW

SEQ ID No. 165:
MSIQHFRVALIPFFAAFCLPVFAHPETLVKVKDAEDQLGSTSGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGSQELTAFLHNMGDHVTRLDRWEPELNEAI

PNDEADTTMPAAMATTLRKLLTGELLTLASRQQLIDWMADKVAGPLLRSALPAGWFI

ADKSGARERGSRGIIAALGPDGKPSRIVVIYTTGSQATMDERNRQIAEIGASLIKHW

SEQ ID No. 1836:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 1837:
MSIQHFRVALIPFFAAFCLPVFAHPETLVKVKDAEDQLGARVGYIELDLNSGKILESF

RPEERFPMLSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 1838:
MSIQHFRVALIPFFAAFCLPVFAHPETLVKVKDAEDKLGARVGYIELDLNSGKILESFR

PEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 1839:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGSQATMDERNRQIAEIGASLIKHW

SEQ ID No. 1840:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGSQATMDERNRQIAEIGASLIKHW

-continued

SEQ ID No. 1841:
MSIQHFRVALIPFFAAFCFPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGASKRGSRGIIAALGPDGKPSRIVVIYMTGGQATMDERNRQIAEIGASLIKHW

SEQ ID No. 1842:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDHWEPELNEAI

PNDERDTTMPAAMATTLRKLLTGELLTLASRQQLIDWMEADKVAGPLLRSALPAGW

FIADKSGAGERGSRGIIAALGPDGKPSRIVVIYTTGSQATMDERNRQIAEIGASLIKHW

SEQ ID No. 1843:
MSIQHFRVALIPFFAAFCLPVFAHPETLVKVKDAEDQLGARVGYIELDLNSGKILESF

RPEERFPMMSTFKVLLCGAVLSRVDAGQEQLGRRIHYSQNDLVEYSPVTEKHLTDG

MTVRELCSAAITMSDNTAANLLLTTIGGPKELTAFLHNMGDHVTRLDRWEPELNEAI

PNDERDTTMPAAMATTLRKLLTGELLTLASRQQLIDWMEADKVAGPLLRSALPAGW

FIADKSGAGERGSSGIIAALGPDGKPSRIVVIYTTGSQATMDERNRQIAEIGASLIKHW said peptides being chosen, preferably, from the peptides of sequence SEQ ID No. 166 to SEQ ID 261 and SEQ ID No. 1923 to SEQ ID 1928 as defined hereafter:

| Peptide SEQ ID No. | Amino acid sequence | Position of the peptide in the TEM protein(s) | Clinical interest |
|---|---|---|---|
| SEQ ID No. 166 | CEPELNEAIPNDER | 163-176 for the protein of SEQ No. 78 | 2br |
| SEQ ID No. 167 | DAEDQLGAR | 33-41 for the proteins of SEQ No. 1, 4, 5, 6, 9, 10, 12, 14, 16, 18, 19, 23, 24, 25, 26, 27, 28, 29, 30, 31, 32, 33, 34, 35, 36, 37, 38, 39, 41, 43, 45, 46, 47, 48, 49, 50, 51, 52, 53, 55, 56, 60, 64, 65, 66, 68, 69, 70, 71, 72, 73, 74, 75, 76, 77, 78, 79, 80, 81, 82, 83, 85, 86, 87, 88, 89, 90, 91, 93, 94, 95, 96, 97, 98, 99, 100, 101, 102, 103, 106, 107, 108, 109, 110, 112, 113, 114, 115, 116, 117, 118, 121, 122, 123, 125, 126, 127, 128, 130, 131, 132, 133, 134, 135, 136, 137, 138, 139, 140, 141, 142, 144, 145, 146, 147, 149, 151, 153, 154, 155, 156, 157, 158, 159, 160, 161, 162, 163, 1837, 1838, 1840, 1841, 1842, 1843, 1844 | TEM |
| SEQ ID No. 168 | DAEDQLGSTSGYIELDLNSGK | 33-53 for the protein of SEQ No. 165 | 2be |
| SEQ ID No. 169 | DAEDQVGAR | 33-41 for the protein of SEQ No. 152 | 2be |
| SEQ ID No. 170 | DAENQLGAR | 33-41 for the protein of SEQ No. 150 | TEM |
| SEQ ID No. 171 | DTTMPAAMATK | 177-187 for the protein of SEQ No. 137 | TEM |
| SEQ ID No. 172 | DTTMPAAMATTLR | 177-189 for the proteins of SEQ No. 1, 2, 3, 4, 5, 6, 7, 8, 9, 10, 11, 12, 13, 14, 15, 16, 17, 18, 20, 21, 22, 23, 24, 25, 26, 27, 28, 29, 31, 32, 33, 34, 35, 36, 37, 38, 39, 40, 42, 43, 44, 45, 46, 47, 48, 49, 51, 52, | TEM |

-continued

| Peptide SEQ ID No. | Amino acid sequence | Position of the peptide in the TEM protein(s) | Clinical interest |
|---|---|---|---|
| | | 53, 54, 55, 56, 57, 58, 59, 61, 62, 63, 64, 65, 66, 68, 69, 70, 71, 72, 73, 74, 75, 76, 77, 78, 79, 80, 81, 84, 85, 90, 91, 92, 93, 94, 95, 96, 99, 100, 101, 102, 103, 105, 106, 108, 109, 110, 111, 112, 113, 115, 117, 118, 119, 120, 122, 123, 124, 126, 127, 128, 129, 130, 131, 132, 133, 134, 135, 136, 139, 140, 141, 142, 143, 144, 146, 148, 151, 152, 154, 155, 156, 157, 158, 159, 160, 161, 162, 163, 165, 1837, 1838, 1839, 1840, 1841, 1842, 1843, 1844 | |
| SEQ ID No. 173 | DTTMPVAMATTLR | 177-189 for the proteins of SEQ No. 107, 145, 150 | TEM |
| SEQ ID No. 174 | DTTTPAAMATTLR | 177-189 for the proteins of SEQ No. 19, 30, 41, 50, 60, 67, 82, 83, 86, 87, 88, 89, 97, 98, 104, 114, 121, 125, 138, 147, 149, 153, 164 | TEM |
| SEQ ID No. 175 | ELTAFLHNIGDHVTR | 145-159 for the protein of SEQ No. 144 | TEM |
| SEQ ID No. 176 | ELTAFLHNMGDHVTR | 145-159 for the proteins of SEQ No. 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 104, 105, 106, 107, 108, 109, 110, 111, 112, 113, 114, 115, 116, 119, 120, 121, 122, 123, 124, 125, 126, 127, 128, 129, 130, 131, 132, 133, 134, 135, 136, 137, 138, 139, 140, 141, 142, 143, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 177 | ELTAFLHNMGDNVTR | 145-159 for the protein of SEQ No. 117 | 2b |
| SEQ ID No. 178 | ELTAFLHNMGEHVTR | 145-159 for the protein of SEQ No. 118 | 2b |
| SEQ ID No. 179 | ELTAFLR | 145-151 for the proteins of SEQ No. 20, 54, 103 | 2be |
| SEQ ID No. 180 | EPELNEAIPNDER | 164-176 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 123, 124, 125, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844 | TEM |
| SEQ ID No. 181 | ETTTPAAMATTLR | 177-189 for the protein of SEQ No. 116 | 2be |

-continued

| Peptide SEQ ID No. | Amino acid sequence | Position of the peptide in the TEM protein(s) | Clinical interest |
|---|---|---|---|
| SEQ ID No. 182 | FPMISTFK | 64-71 for the proteins of SEQ No. 30, 35, 38, 147 | 2br |
| SEQ ID No. 183 | FPMLSTFK | 64-71 for the proteins of SEQ No. 31, 33, 37, 43, 48, 72, 76, 78, 100, 115, 142, 146, 157, 1838 | TEM |
| SEQ ID No. 184 | FPMMSTFK | 64-71 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 39, 40, 41, 42, 44, 45, 46, 47, 49, 50, 51, 52, 53, 54, 55, 56, 57, 58, 59, 60, 61, 62, 63, 64, 65, 66, 67, 68, 69, 70, 71, 74, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 116, 117, 118, 119, 120, 121, 122, 123, 124, 125, 126, 127, 128, 129, 130, 131, 132, 133, 134, 135, 136, 137, 138, 139, 143, 144, 145, 149, 150, 151, 152, 153, 154, 155, 156, 158, 159, 160, 161, 162, 163, 164, 165, 1837, 1839, 1840, 1841, 1842, 1843, 1844 | TEM |
| SEQ ID No. 185 | FPMVSTFK | 64-71 for the proteins of SEQ No. 32, 34, 36, 73, 77, 140, 141, 148 | TEM |
| SEQ ID No. 186 | GEPELNEAIPNDER | 163-176 for the protein of SEQ No. 157 | 2be |
| SEQ ID No. 187 | GIIAALGPDGKPSR | 242-255 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844; 241-254 for the protein of sequence SEQ ID No. 165 | TEM |
| SEQ ID No. 188 | GSCGIIAALGPDGKPSR | 239-255 for the proteins of SEQ No. 29, 61, 63, 68 | 2br |
| SEQ ID No. 189 | GSGGIIAALGPDGKPSR | 239-255 for the protein of SEQ No. 74 | 2br |
| SEQ ID No. 190 | GSHGIIAALGPDGKPSR | 239-255 for the proteins of SEQ No. 49, 134, 135 | 2br |
| SEQ ID No. 191 | GSLGIIAALGPDGKPSR | 239-255 for the protein of SEQ No. 52 | 2br |
| SEQ ID No. 192 | GSSGIIAALGPDGKPSR | 239-255 for the proteins of SEQ No. 28, 42, 56, 69, 72, 111, 160, 161, 1844 | TEM |
| SEQ ID No. 193 | GSTGIIAALGPDGKPSR | 239-255 for the protein of SEQ No. 39 | TEM |
| SEQ ID No. 194 | HLPDGMTVR | 110-118 for the protein of SEQ No. 135 | TEM |

-continued

| Peptide SEQ ID No. | Amino acid sequence | Position of the peptide in the TEM protein(s) | Clinical interest |
|---|---|---|---|
| SEQ ID No. 195 | HLTDGMTVR | 110-118 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 136, 137, 138, 139, 140, 141, 142, 143, 144, 145, 146, 147, 148, 149, 150, 151, 152, 153, 155, 156, 157, 158, 159, 160, 161, 162, 163, 164, 165, 1837, 1838, 1839, 1840, 1841, 1842, 1843, 1844 | TEM |
| SEQ ID No. 196 | HLTGGMTVR | 110-118 for the protein of SEQ No. 85 | 2b |
| SEQ ID No. 197 | IDAGQEQLGR | 82-91 for the proteins of SEQ No. 107, 145, 150, 159 | TEM |
| SEQ ID No. 198 | IHYSQNDLVEYSPVTEK | 93-109 for the proteins of SEQ No. 1, 2, 5, 7, 10, 11, 12, 13, 18, 19, 23, 25, 26, 27, 28, 29, 30, 31, 32, 33, 34, 35, 36, 37, 38, 39, 40, 42, 43, 45, 46, 47, 49, 51, 52, 53, 55, 56, 57, 59, 61, 63, 64, 65, 66, 67, 68, 69, 70, 71, 72, 73, 74, 75, 76, 77, 78, 79, 80, 81, 85, 86, 88, 90, 91, 92, 93, 94, 95, 96, 99, 101, 103, 105, 106, 107, 108, 109, 110, 112, 115, 116, 117, 118, 122, 125, 126, 127, 130, 132, 133, 134, 135, 136, 137, 139, 140, 141, 142, 143, 144, 146, 147, 148, 151, 152, 153, 154, 156, 157, 158, 159, 160, 161, 162, 163, 165, 1837, 1838, 1839, 1840, 1841, 1842, 1843, 1844 | TEM |
| SEQ ID No. 199 | IHYSQNDLVK | 93-102 for the proteins of SEQ No. 3, 4, 6, 8, 9, 14, 15, 16, 17, 20, 21, 22, 24, 41, 44, 48, 50, 54, 58, 60, 62, 82, 83, 84, 87, 89, 97, 98, 100, 102, 104, 111, 113, 114, 119, 120, 121, 123, 124, 128, 129, 131, 138, 149, 155, 164 | 2be |
| SEQ ID No. 200 | IHYSQSDLVEYSPVTEK | 93-109 for the protein of SEQ No. 145 | 2be |
| SEQ ID No. 201 | IHYSQSDVVEYSPVTEK | 93-109 for the protein of SEQ No. 150 | TEM |
| SEQ ID No. 202 | ILESFRPEER | 54-63 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 151, 152, 153, 154, 155, 156, 157, 158, 159, 160, 161, 162, 163, 164, 165, 1837, 1838, 1839, 1840, 1841, 1842, 1843, 1844 | TEM |

-continued

| Peptide SEQ ID No. | Amino acid sequence | Position of the peptide in the TEM protein(s) | Clinical interest |
|---|---|---|---|
| SEQ ID No. 203 | ILESFRPEK | 54-62 for the protein of SEQ No. 150 | TEM |
| SEQ ID No. 204 | IVIIYTTGSQATMDER | 256-271 for the proteins of SEQ No. 56, 160 | 2br |
| SEQ ID No. 205 | IVVIYMTGGQATMDER | 256-271 for the proteins of SEQ No. 47, 1842 | 2be |
| SEQ ID No. 206 | IVVIYMTGSQATMDELNR | 256-273 for the protein of SEQ No. 64 | 2be |
| SEQ ID No. 207 | IVVIYMTGSQATMDER | 256-271 for the proteins of SEQ No. 4, 9, 13, 23, 25, 40, 45, 46, 68, 69, 70, 80, 81, 89, 93, 101, 102, 109, 131, 155, 156, 1840, 1841 | TEM |
| SEQ ID No. 208 | IVVIYTTGGQATMDER | 256-271 for the protein of SEQ No. 126 | 2be |
| SEQ ID No. 209 | IVVIYTTGSQATMDELNR | 256-273 for the proteins of SEQ No. 36, 94 | 2br |
| SEQ ID No. 210 | IVVIYTTGSQATMDEQNR | 256-273 for the proteins of SEQ No. 43, 77, 78, 112, 151 | 2br |
| SEQ ID No. 211 | IVVIYTTGSQATMDER | 256-271 for the proteins of SEQ No. 1, 2, 3, 5, 6, 7, 8, 10, 11, 12, 14, 15, 16, 17, 18, 19, 20, 21, 22, 24, 26, 27, 28, 29, 30, 31, 32, 33, 34, 35, 37, 38, 39, 41, 42, 44, 48, 49, 50, 51, 52, 53, 54, 55, 57, 58, 59, 60, 61, 62, 63, 65, 66, 67, 71, 72, 73, 74, 75, 76, 79, 82, 83, 84, 85, 86, 87, 88, 90, 91, 92, 95, 96, 97, 98, 99, 100, 103, 104, 105, 106, 107, 108, 110, 111, 113, 114, 115, 116, 117, 118, 119, 120, 121, 122, 123, 124, 125, 127, 128, 129, 130, 132, 133, 134, 135, 136, 137, 138, 139, 140, 141, 142, 143, 144, 145, 146, 147, 148, 149, 150, 152, 153, 154, 157, 158, 159, 161, 162, 163, 164, 1837, 1838, 1839, 1843, 1844 | TEM |
| SEQ ID No. 212 | LDCWEPELNEAIPNDER | 160-176 for the proteins of SEQ No. 86, 132, 133 | 2be |
| SEQ ID No. 213 | LDHWEPELNEAIPNDER | 160-176 for the proteins of SEQ No. 6, 11, 15, 25, 26, 27, 41, 59, 70, 98, 100, 106, 109, 124, 136, 140, 141, 149, 1843 | 2be |
| SEQ ID No. 214 | LDHWEPELNEAVPNDER | 160-176 for the protein of SEQ No. 122 | 2be |
| SEQ ID No. 215 | LDSWEPELNEAIPNDER | 160-176 for the proteins of SEQ No. 5, 7, 8, 9, 10, 12, 22, 24, 44, 51, 58, 60, 80, 81, 93, 105, 111, 119, 120, 121, 123, 126, 127, 138, 142, 143, 146, 153, 164 | 2be |
| SEQ ID No. 216 | LHCWEPELNEAIPNDER | 160-176 for the protein of SEQ No. 82 | 2be |
| SEQ ID No. 217 | LLTDELLTLASR | 191-202 for the protein of SEQ No. 83 | 2be |
| SEQ ID No. 218 | LLTGELLTLASQQQLIDWMEADK | 191-213 for the protein of SEQ No. 65 | TEM |
| SEQ ID No. 219 | LLTGELLTLASR | 191-202 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, | TEM |

-continued

| Peptide SEQ ID No. | Amino acid sequence | Position of the peptide in the TEM protein(s) | Clinical interest |
|---|---|---|---|
| | | 84, 85, 86, 87, 88, 89, 90, 91, 92, 93, 94, 95, 96, 97, 98, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | |
| SEQ ID No. 220 | LLTSELLTLASR | 191-202 for the protein of SEQ No. 99 | TEM |
| SEQ ID No. 221 | MSIQHFR | 1-7 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 83, 84, 85, 86, 88, 89, 90, 91, 92, 93, 94, 95, 96, 97, 98, 99, 100, 101, 102, 103, 104, 105, 106, 107, 108, 109, 110, 111, 112, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 150, 151, 152, 153, 154, 155, 156, 157, 158, 159, 160, 161, 162, 163, 165, 1837, 1838, 1839, 1840, 1841, 1842, 1843, 1844 | TEM |
| SEQ ID No. 222 | NMGDHVTR | 152-159 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 119, 120, 121, 122, 123, 124, 125, 126, 127, 128, 129, 130, 131, 132, 133, 134, 135, 136, 137, 138, 139, 140, 141, 142, 143, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | 2be |
| SEQ ID No. 223 | QIAEICASLIK | 274-284 for the protein of SEQ No. 158 | TEM |
| SEQ ID No. 224 | QIAEIGASLIK | 274-284 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 93, 94, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 141, 142, 143, 144, 145, 146, 147, 148, 149, 150, 151, 153, 154, 155, 156, 157, 159, 160, 161, 162, | TEM |

-continued

| Peptide SEQ ID No. | Amino acid sequence | Position of the peptide in the TEM protein(s) | Clinical interest |
|---|---|---|---|
| | | 163, 164, 1837, 1838, 1839, 1840, 1841, 1842, 1843, 1844; 273-283 for the protein of sequence SEQ ID No. 165 | |
| SEQ ID No. 225 | QIAEIGGSLIK | 274-284 for the protein of SEQ No. 140 | 2be |
| SEQ ID No. 226 | QIVEIGASLIK | 274-284 for the proteins of SEQ No. 92, 95 | 2be |
| SEQ ID No. 227 | QQLIDWMADK | 203-212 for the protein of SEQ No. 165 | 2be |
| SEQ ID No. 228 | QQLIDWMEADK | 203-213 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 163, 164, 1837, 1838, 1839, 1840, 1841, 1842, 1843, 1844 | TEM |
| SEQ ID No. 229 | QQLIDWMEVDK | 203-213 for the proteins of SEQ No. 160, 161, 162 | TEM |
| SEQ ID No. 230 | QTAEIGASLIK | 274-284 for the protein of SEQ No. 152 | 2be |
| SEQ ID No. 231 | SALPAGWFIADK | 221-232 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 137, 138, 139, 140, 141, 142, 143, 144, 145, 146, 147, 148, 149, 150, 151, 152, 153, 154, 156, 157, 158, 159, 160, 161, 162, 164, 1837, 1838, 1839, 1840, 1841, 1842, 1843, 1844; 220-231 for the protein of sequence SEQ ID No. 165 | TEM |
| SEQ ID No. 232 | SGADER | 233-238 for the protein of SEQ No. 102 | TEM |
| SEQ ID No. 233 | SGAGER | 233-238 for the proteins of SEQ No. 1, 2, 6, 7, 9, 11, 12, 13, 15, 16, 17, 24, 27, 28, 29, 30, 31, 32, 33, 34, 35, 36, 37, 38, 39, 41, 42, 43, 49, 51, 52, 53, 54, 55, 56, 57, 58, 60, 61, 63, 65, 68, 69, 70, 71, 72, 73, 74, 75, 76, 77, 78, 79, 82, 85, 90, 91, 93, 94, 95, 96, 97, 99, 100, 101, 106, 107, 108, 109, 112, 114, 115, 116, 117, 118, 119, 123, 125, 130, 132, 134, 135, 136, 137, 139, 140, 142, 144, 145, 146, 147, | TEM |

-continued

| Peptide SEQ ID No. | Amino acid sequence | Position of the peptide in the TEM protein(s) | Clinical interest |
|---|---|---|---|
| | | 148, 149, 150, 151, 152, 153, 154, 156, 157, 158, 159, 160, 161, 162, 163, 1837, 1838, 1839, 1843, 1844 | |
| SEQ ID No. 234 | SGAGVR | 233-238 for the protein of SEQ No. 138 | 2be |
| SEQ ID No. 235 | SGANER | 233-238 for the protein of SEQ No. 131 | TEM |
| SEQ ID No. 236 | SGASER | 233-238 for the proteins of SEQ No. 3, 4, 8, 14, 18, 19, 20, 23, 48, 50, 62, 83, 84, 87, 89, 98, 103, 104, 110, 113, 124, 128, 129, 155 | 2be |
| SEQ ID No. 237 | SGASK | 233-237 for the proteins of SEQ No. 40, 45, 46, 47, 64, 66, 67, 88, 92, 1840, 1841, 1842 | 2be |
| SEQ ID No. 238 | SGGSER | 233-238 for the protein of SEQ No. 21 | 2be |
| SEQ ID No. 239 | SGTGER | 233-238 for the proteins of SEQ No. 120, 121 | 2be |
| SEQ ID No. 240 | SVLPAGWFIADK | 221-232 for the proteins of SEQ No. 136, 155, 163 | 2be |
| SEQ ID No. 241 | VAEPLLR | 214-220 for the protein of SEQ No. 53 | 2b |
| SEQ ID No. 242 | VAGPLLR | 214-220 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844; 213-219 for the protein of sequence SEQ ID No. 165 | TEM |
| SEQ ID No. 243 | VAGPLMR | 214-220 for the protein of SEQ No. 134 | 2br |
| SEQ ID No. 244 | VALIPFFAAFCFPVFAHPETLVK | 8-30 for the proteins of SEQ No. 4, 9, 23, 46, 47, 51, 60, 68, 69, 70, 80, 81, 89, 93, 101, 106, 108, 110, 121, 123, 147, 155, 1841, 1842 | TEM |
| SEQ ID No. 245 | VALIPFFAAFCIPVFAHPETLVK | 8-30 for the protein of SEQ No. 63 | 2br |
| SEQ ID No. 246 | VALIPFFAAFCLPVFAHPDTLVK | 8-30 for the protein of SEQ No. 139 | TEM |
| SEQ ID No. 247 | VALIPFFAAFCLPVFAHPETLVK | 8-30 for the proteins of SEQ No. 1, 2, 3, 5, 6, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 48, 49, 50, 52, 53, 54, 55, 56, 57, 58, 59, 61, 62, 64, 65, 66, 67, 71, 72, 73, 74, 75, 76, 77, 78, 79, 82, 83, 84, 85, 86, 87, 88, 90, 91, 92, 94, 95, 96, | TEM |

-continued

| Peptide SEQ ID No. | Amino acid sequence | Position of the peptide in the TEM protein(s) | Clinical interest |
|---|---|---|---|
| | | 97, 98, 99, 100, 102, 103, 104, 105, 107, 109, 111, 112, 113, 114, 116, 117, 118, 119, 120, 122, 124, 125, 126, 127, 128, 129, 130, 131, 132, 133, 134, 135, 136, 137, 138, 140, 141, 142, 143, 144, 145, 146, 148, 149, 151, 152, 153, 154, 156, 157, 158, 159, 160, 161, 162, 163, 164, 165, 1837, 1838, 1839, 1840, 1843, 1844 | |
| SEQ ID No. 248 | VALIPFFAAFCLPVFAHPK | 8-26 for the protein of SEQ No. 150 | TEM |
| SEQ ID No. 249 | VALIPFLAAFCLPVFAHPETLVK | 8-30 for the protein of SEQ No. 115 | 2be |
| SEQ ID No. 250 | VDAGQEQLDR | 82-91 for the proteins of SEQ No. 55, 62 | TEM |
| SEQ ID No. 251 | VDAGQEQLGR | 82-91 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 146, 147, 148, 149, 151, 152, 153, 154, 155, 156, 157, 158, 160, 161, 162, 163, 164, 165, 1837, 1838, 1839, 1840, 1841, 1842, 1843, 1844 | TEM |
| SEQ ID No. 252 | VEDAEDQLGAR | 31-41 for the protein of SEQ No. 130 | 2b |
| SEQ ID No. 253 | VGYIELDLNSGK | 42-53 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844 | TEM |
| SEQ ID No. 254 | VGYIELDPNSGK | 42-53 for the protein of SEQ No. 58 | 2be |
| SEQ ID No. 255 | VGYIEMDLNSGK | 42-53 for the protein of SEQ No. 129 | 2be |
| SEQ ID No. 256 | VKPAEDK | 31-37 for the protein of SEQ No. 120 | 2be |
| SEQ ID No. 257 | VLLCGAELSR | 72-81 for the protein of SEQ No. 99 | TEM |

-continued

| Peptide SEQ ID No. | Amino acid sequence | Position of the peptide in the TEM protein(s) | Clinical interest |
|---|---|---|---|
| SEQ ID No. 258 | VLLCGAVLSR | 72-81 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 259 | WEPELNEAIPIDER | 163-176 for the protein of SEQ No. 128 | 2be |
| SEQ ID No. 260 | WEPELNEAIPNDER | 163-176 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 74, 75, 76, 77, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 116, 117, 118, 119, 120, 121, 123, 124, 125, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 160, 161, 162, 163, 164, 1837, 1838, 1839, 1840, 1841, 1842, 1843, 1844 | TEM |
| SEQ ID No. 261 | YSPVTEK | 103-109 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | 2be |
| SEQ ID No. 1923 | DAEDK | 33-37 for the proteins of SEQ No. 2, 3, 7, 8, 11, 13, 15, 17, 20, 21, 22, 40, 42, 44, 54, 57, 58, 59, 61, 62, 63, 67, 84, 92, 104, 105, 111, 119, 124, 129, 143, 148, 164, 1839 | TEM |

-continued

| Peptide SEQ ID No. | Amino acid sequence | Position of the peptide in the TEM protein(s) | Clinical interest |
|---|---|---|---|
| SEQ ID No. 1924 | GIIAALGPDGK | 242-252 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 1837, 1838, 1839, 1840, 1841, 1842, 1843, 1844; 241-251 for the protein of sequence SEQ ID No. 165 | TEM |
| SEQ ID No. 1925 | GSSGIIAALGPDGK | 239-252 for the proteins of SEQ No. 28, 42, 56, 69, 72, 111, 160, 161, 1844 | TEM |
| SEQ ID No. 1926 | ILESFR | 54-59 for the proteins of SEQ No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 1837, 1838, 1839, 1840, 1841, 1842, 1843, 1844 | TEM |
| SEQ ID No. 1927 | SGAGK | 233-237 for the proteins of SEQ No. 10, 25, 26, 44, 59, 80, 86, 122, 133, 141, 143 | 2be |
| SEQ ID No. 1928 | SGTGK | 233-237 for the proteins of SEQ No. 5, 22, 81, 105, 111, 126, 164 | 2be |

In the clinical interest column, the entries 2b, 2br, 2be and 2ber correspond to the functional subgroups of TEM beta-lactamases which the corresponding peptide makes it possible to detect. Thus, the detection of a 2be peptide indicates the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The entry TEM indicates a common peptide between at least two of the subgroups 2b, 2br and 2be or 2ber. The corresponding peptide indicates the presence of a TEM beta-lactamase and the presence of a mechanism of resistance to at least penicillins and first-generation cephalosporins.

The detection of a mechanism of resistance to ESBL (extended-spectrum beta-lactamase) cephalosporins, induced by the TEM protein, is characterised by the detection of at least one resistance-marking 2be peptide, chosen from the sequences SEQ ID No. 168, SEQ ID No. 169, SEQ ID No. 179, SEQ ID No. 181, SEQ ID No. 186, SEQ ID No. 199, SEQ ID No. 200, SEQ ID No. 205, SEQ ID No. 206, SEQ ID No. 208, SEQ ID No. 212, SEQ ID No. 213, SEQ ID No. 214, SEQ ID No. 215, SEQ ID No. 216, SEQ ID No. 217, SEQ ID No. 222, SEQ ID No. 225, SEQ ID No. 226, SEQ ID No. 227, SEQ ID No. 230, SEQ ID No. 234, SEQ ID No. 236, SEQ ID No. 237, SEQ ID No. 238, SEQ ID No. 239, SEQ ID No. 240, SEQ ID No. 249, SEQ ID No. 254, SEQ ID No. 255, SEQ ID No. 256, SEQ ID No. 259, SEQ ID No. 261, SEQ ID No. 1927, SEQ ID No. 1928.

The detection of a mechanism of resistance to cephalosporins induced by the expression of the CMY protein is characterised by the detection of at least one peptide belonging to the CMY protein and to its different sequence variants SEQ ID No. 262 to SEQ ID No. 311 and SEQ ID No. 1844 to SEQ ID No. 1870.

```
SEQ ID No. 262:
MQQRQSILWGAVATLMWAGLAHAGEASPVDPLRPVVDASIQPLLKEHRIPGMAVAV

LKDGKAHYFNYGVANRESGASVSEQTLFEIGSVSKTLTATLGAYAVVKGAMQLDDK

ASRHAPWLKGSVFDSITMGELATYSAGGLPLQFPEEVDSSEKMRAYYRQWAPVYS

PGSHRQYSNPSIGLFGHLAASSLKQPFAQLMEQTLLPGLGMHHTYVNVPKQAMAS

YAYGYSKEDKPIRVNPGMLADEAYGIKTSSADLLAFVKANIGGVDDKALQQAISLTH

KGHYSVGGMTQGLGWESYAYPVTEQTLLAGNSAKVILEANPTAAPRESGSQVLFN

KTGSTNGFGAYVAFVPARGIGIVMLANRNYPIPARVKAAHAILAQLAG

SEQ ID No. 263:
MQQRQSILWGAVATLMWAGLAHAGEASPVDPLRPVVDASIQPLLKEHRIPGMAVAV

LKDGKAHYFNYGVANRESGAGVSEQTLFEIGSVSKTLTATLGAYAVVKGAMQLDDK

ASRHAPWLKGSAFDSITMGELATYSAGGLPLQFPEEVDSSEKMRAYYRQWAPVYS

PGSHRQYSNPSIGLFGHLAASSLKQPFAPLMEQTLLPGLGMHHTYVNVPKQAMAS

YAYGYSKEDKPIRVNPGMLADEAYGIKTSSADLLRFVKANIGGVDDKALQQAISLTH

QGHYSVGGMTQGLGWESYAYPVTEQTLLAGNSAKVILEANPTAAPRESGSQVLFN

KTGSTNGFGAYVAFVPARGIGIVMLANRNYPIEARIKAAHAILAQLAG

SEQ ID No. 264:
MQQRQSILWGAVATLMWAGLAHAGEASPVDPLRPVVDASIQPLLKEHRIPGMAVAV

LKDGKAHYFNYGVANRESGAGVSEQTLFEIGSVSKTLTATLGAYAVVKGAMQLDDK

ASRHAPWLKGSAFDSITMGELATYSAGGLPLQFPEEVDSSEKMRAYYRQWAPVYS

PGSHRQYSNPSIGLFGHLAASSLKQPFAPLMEQTLLPGLGMHHTYVNVPKQAMAS

YAYGYSKEDKPIRVNPGMLADEAYGIKTSSADLLRFVKANIGGVDDKALQQAISLTH

QGHYSVGGMTQGLGWESYAYPVTEQTLLAGNSAKVSLEANPTAAPRESGSQVLFN

KTGSTNGFGAYVAFVPARGIGIVMLANRNYPIEARIKAAHAILAQLAG

SEQ ID No. 265:
MMKKSLCCALLLTASFSTFASAKTEQQIADIVNRTITPLMQEQAIPGMAVAIIYQGKPY

YFTWGKADIANNHPVTQQTLFELGSVSKTFNGVLGGDAIARGEIKLSDPVTKYWPEL

TGKQWQGISLLHLATYTAGGLPLQIPDDVTDKAALLRFYQNWQPQWAPGAKRLYA

NSSIGLFGALAVKPSGMSYEEAMTRRVLQPLKLAHTWITVPQNEQKDYAWGYREG

KPVHVSPGQLDAEAYGVKSNVTDMARWVQVNMDASRVQEKTLQQGIALAQSRYW

RIGDMYQGLGWEMLNWPLKADSIINGSDSKVALAALPAVEVNPPAPAVKASWVHKT

GSTGGFGSYVAFVPEKNLGIVMLANKSYPNPVRVEAAWRILEKLQ

SEQ ID No. 266:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVAFAALPAVEVNPPAPAVKASWVH

KTGSTGGFGSYVAFVPEKNLGIVMLANKSYPNPVRVEAAWRILEKLQ
```

-continued

SEQ ID No. 267:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGNGSDSKVALAALPAVEVNPPAPAVKASW

VHKTGSTGGFGSYVAFVPEKNLGIVMLANKSYPNPVRVEAAWRILEKLQ

SEQ ID No. 268:
MKKSLCCALLLTASFSTFAAAKTEQQIADIVNRTITPLMQEQAIPGMAVAVIYQGKPY

YFTWGKADIANNHPVTQQTLFELGSVSKTFNGVLGGDAIARGEIKLSDPVTKYWPEL

TGKQWQGISLLHLATYTAGGLPLQIPDDVTDKAALLHFYQNWQPQWTPGAKRLYA

NSSIGLFGALAVKPSGMSYEEAMTRRVLQPLKLAHTWITVPQNEQKDYAWGYREG

KPVHVSPGQLDAEAYGVKSSVIDMARWVQANMDASHVQEKTLQQGIALAQSRYW

RIGDMYQGLGWEMLNWPLKADSIINGSDNKVALAALPAVEVNPPAPAVKASWVHKT

GSTGGFGSYVAFVPEKNLGIVMLANKSYPNPVRVEAAWRILEKLQ

SEQ ID No. 269:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGELAVKPSGMSYEEAMTRRVLQPLKLAHTWITVPQNEQKDYAWGYR

EGKPVHVSPGKLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 270:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAYWRILEKLQ

SEQ ID No. 271:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAGAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 272:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGISLLHLATYTAGGLPLQIPDDVTDKAALLHFYQNWQPQWTPGAKRLY

ANSSIGLFGALAVKPSGMSYEEAMTRRVLQPLKLAHTWITVPQNEQKDYAWGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 273:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKAVHVSPGQLDAEAYGVKSSVIDMARWVQVNMDASRVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 274:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVYVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 275:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGELAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDNKVALAALPAVEVNPPAPAVKASWVH

KTGSTGGFGSYVAFVPEKNLGIVMLANKSYPNPVRVEAAWRILEKLQ

SEQ ID No. 276:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGRLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 277:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQFPDDVRDKAALLHFYQNWQPQWTPGAKRL

YANSSIGLFGELAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

-continued

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 278:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHGSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 279:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDCIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPENEQKDYAWGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 280:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVTDKAALLHFYQNWQPQWTPGAKRLY

ANSSIGLFGALAVKPSGMSYEEAMTRRVLQPLKLAHTWITVPQNEQKDYAWGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 281:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYACGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 282:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGISLLHLATYTAGGLPLQIPDDVTDKAALLRFYQNWQPQWTPGAKRLY

ANSSIGLFGTLAVKPSGMSYEEAMTRRVLQPLKLAHTWITVPQSEQKDYAWGYRE

GKPVHVSPGQLDAEAYGVKSSVIDMAHWVQANMDASHVQEKTLQQGIELAQSRY

WRIGDMYQGLGWEMLNWPLKADSIINGSDSKVALAALPAVEVNPPAPAVKASWVH

KTGYTGGFGSYVAFVPEKNLGIVMLANKSYPNPVRVEAAWRILEKLQ

SEQ ID No. 283:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPEQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 284:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVAALPAVEVNPPAPAVKASWVHKT

GSTGGFGSYVAFVPEKNLGIVMLANKSYPNPVRVEAAWRILEKLQ

SEQ ID No. 285:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFAALAVKPSGMSYEEAMTRRVLQPLKLAHTWITVPQNEQKDYAWGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 286:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVAPAVEVNPPAPAVKASWVHKTGS

TGGFGSYVAFVPEKNLGIVMLANKSYPNPVRVEAAWRILEKLQ

SEQ ID No. 287:
MMKKSLCCALLLTASFSTFAAAKTEQQIADIVNRTITPLMQEQAIPGMAVAIIYQGKPY

YFTWGKADIANNHPVTQQTLFELGSVSKTFNGVLGGDAIARGEIKLSDPVTKYWPEL

TGKQWQGISLLHLATYTAGGLPLQIPDDVTDKAALLRFYQNWQPQWTPGAKRLYA

NSSIGLFGALAVKPSGMSYEEAMTRRVLQPLKLAHTWITVPQNEQKDYAWGYREG

KPVHVTPGQLDAEAYGVKSNVTDMARWIQVNMDASRVQEKTLQQGIALAQSRYW

RIGDMYQGLGWEMLNWPLKADSIINGSDSKVALAALHTVEVNPPAPAVKASWVHKT

GSTGGFGSYVAFIPEKNLGIVMLANKSYPNPVRVEAAWRILEKLQ

SEQ ID No. 288:
MMKKSICCALLLTASFSTFAAAKTEQQIADIVNRTITPLMQEQAIPGMAVAIIYEGKPY

YFTWGKADIANNHPVTQQTLFELGSVSKTFNGVLGGDAIARGEIKLSDPVTKYWPEL

TGKQWRGISLLHLATYTAGGLPLQIPDEVTDKAELLRFYQNWQPQWTPGAKRLYAN

SSIGLFGALVVKPSGMSYEEAMTRRVLQPLKLAHTWITVPQSEQKNYAWGYREGK

PVHVSPGQLDAEAYGVKSSVIDMARWVQANMDASHVQEKTLQQGIELAQSRYWRI

GDMYQGLGWEMLNWPLKADSIINGSDSKVALAALPAVEVNPPAPAVKASWVHKTG

STGGFGSYVAFVPEKNLGIVMLANKSYPNPARVEAAWRILEKLQ

SEQ ID No. 289:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLELDAEAYGVKSSVIDMARWVQANMDASHVQEKTLQQGIALAQS

RYWRIGDMYQGLGWEMLNWPLKADSIINGSDSKVALAALPAVEVNPPAPAVKASW

VHKTGSTGGFGSYVAFVPEKNLGIVMLANKSYPNPVRVEAAWRILEKLQ

SEQ ID No. 290:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGEAIARGEIKLSDPVTKYWPE

LTGKQWQGIRLLHLATYTAGGLPLQIPDDVRDKAALLHFYQNWQPQWTPGAKRLY

ANSSIGLFGALAVKPSGMSYEEAMTRRVLQPLKLAHTWITVPQNEQKDYAWGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 291:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQFDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 292:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKTDSIINGSDSKVALAALPAVEVNPPAPAVKASWVH

KTGSTGGFGSYVAFVPEKNLGIVMLANKSYPNPVRVEAAWRILEKLQ

SEQ ID No. 293:
MQQRQSILWGAVATLMWAGLAHAGEASPVDPLRPVVDASIQPLLKEHRIPGMAVAV

LKDGKAHYFNYGVANRESGASVSEQTLFDIGSVSKTLTATLGAYAVVKGAMQLDDK

ASRHAPWLKGSVFDSITMGELATYSAGGLPLQFPEEVDSSEKMRAYYRQWAPVYS

PGSHRQYSNPSIGLFGHLAASSLKQPFAQLMEQTLLPGLGMHHTYVNVPKQAMAS

YAYGYSKEDKPIRVNPGMLADEAYGIKTSSADLLAFVKANIGGVDDKALQQAISLTH

-continued

KGHYSVGGMTQGLGWESYAYPVTEQTLLAGNSAKVILEANPTAAPRESGSQVLFN

KTGSTNGFGAYVAFVPARGIGIVMLANRNYPIPARVKAAHAILAQLAG

SEQ ID No. 294:
MQQRQSILWGAVATLMWAGLAHAGEASPVDPLRPVVDASIQPLLKEHRIPGMAVAV

LKDGKAHYFNYGVANRESGASVSEQTLFDIGSVSKTLTATLGAYAVVKGAMQLDDK

ASRHAPWLKGSVFDSITMGELATYSAGGLPLQFPEEVDSSEKMRAYYRQWAPVYS

PGSHRQYSNPSIGLFGHLAASSLKQPFAQLMEQTLLPGLGMHHTYVNVPKQAMAS

YAYGYSKEDKPIRVNPGMLADEAYGIKTSSADLLAFVKANIGGVDDKALQQAISLTH

KGHYSVGGMTQGLGWESYAYPVTEQTLLAGNSAKVSLEANPTAAPRESGSQVLFN

KTGSTNGFGAYVAFVPARGIGIVMLANRNYPIPARVKAAHAILAQLAG

SEQ ID No. 295:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWS

ELTGKQWQGISLLHLATYTAGGLPLQIPDDVTDKTALLHFYQNWQPQWAPGAKRLY

ANSSIGLFGALAVKPSGMSYEEAMTRRVLQPLKLAHTWITVPQSEQKDYAWGYRE

GKPVHVSPGQLDAEAYGVKSSVIDMARWVQANMDASRVQEKTLQQGIALAQSRY

WRIGDMYQGLGWEMLNWPLKADSIINGSDSKVALAAIPAVEVNPPAPAVKASWVHK

TGSTGGFGSYVAFVPEKNLGIVMLANKSYPNPIRVEAAWRILEKLQ

SEQ ID No. 296:
MMKKSLCCALLLTASFSTFASAKTEQQIADIVNRTITPLMQEQAIPGMAVAVIYQGKT

YYFTWGKADIANNHPVTQQTLFELGSVSKTFNGVLGGDAIARGEIKLSDPVTKYWP

ELTGKQWQDISLLHLATYTAGGLPLQIPDDVTDKTALLHFYQNWQPQWAPGAKRLY

ANSSIGLFGALAVKPSGMSYEEAMTRRVLQPLKLAHTWITVPQSEQKDYAWGYRE

GKPVHVSPGQLDAEAYGVKSNVTDMARWVQVNMDASRVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 297:
MMKKSLCCALLLTAPLSTFAAAKTEQQIADIVNRTITPLMQEQAIPGMAVAVIYQGKP

YYFTWGKADITNNHPVTQQTLFELGSVSKTFNGVLGGDAIARGEIKLSDPVTKYWPE

LTGKQWQGISLLHLATYTAGGLPLQIPDDVTDKAALLRFYQNWQPQWAPGAKRLYA

NSSIGLFGALAVKPSGMSYEEAMTRRVLQPLKLAHTWIKVPQSEQKDYAWGYREG

KAVHVSPGQLDAEAYGVKSSVIDMARWVQVNMDASRVQEKTLQQGIALAQSRYW

RIGDMYQGLGWEMLNWPLKADSIINGSDSKVALAALPAVEVNPPAPAVKASWVHKT

GSTGGFGSYVAFVPEKNLGIVMLANKSYPNPVRVEAAWRILEKLQ

SEQ ID No. 298:
MMKKSICCALLLTASFSTFAATKTEQQIADIVNRTITPLMQEQAIPGMAVAIIYEEKPY

YFTWGKADIANNHPVTQQTLFELGSVSKTFNGVLGGDAIARGEIKLSDPVTKYWPEL

TGKQWRGISLLHLATYTAGGLPLQIPDEVTDKAALLRFYQNWQPQWTPGAKRLYAN

SSIGLFGALAVKPSGMSYEEAMTRRVLQPLKLAHTWITVPQSEQKNYAWGYREGK

PVHVSPGQLDAEAYGVKSSVIDMARWVQANMDASHVQEKTLQQGIELAQSRYWRI

GDMYQGLGWEMLNWPLKADSIINGSDSKVALAALPAVEVNPPAPAVKASWVHKTG

STGGFGSYVAFVPEKNLGIVMLANKSYPNPARVEAAWRILEKLQ

SEQ ID No. 299:
GPGHLFAFNYGTDFMMKKSLCCALLLTASFSTFAAAKTEQQIADIVNRTITPLMQEQ

AIPGMAVAVIYQGKPYYFTWGKADIANNHPVTQQTLFELGSVSKTFNGVLGGDAIAR

GEIKLSDPVTKYWPELTGKQWQGIRLLHLATYTAGGLPLQIPDDVRDKAALLHFYQN

WQPQWTPGAKRLYANSSIGLFGALAVKPSGMSYEEAMTRRVLQPLKLAHTWITVP

QNEQKDYAWGYREGKPVHASPGQLDAEAYGVKSSVIDMARWVQANMDASHVQE

KTLQQGIALAQSRYWRIGDMYQGLGWEMLNWPLKADSIINGSDSKVALAALPAVEV

NPPAPAVKASWVHKTGSTGGFGSYVAFVPEKNLGIVMLANKSYPNPVRVEAAWRIL

EKLQ

SEQ ID No. 300:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 301:
MQQRQSILWGAVATLMWAGLAHAGEASPVDPLRPVVDASIQPLLKEHRIPGMAVAV

LKDGKAHYFNYGVANRESGAGVSEQTLFEIGSVSKTLTATLGAYAVVKGAMQLDDK

ASRHAPWLKGSAFDSITMGELATYSAGGLPLQFPEEVDSSEKMRAYYRQWAPVYS

PGSHRQYSNPSIGLFGHLAASSLKQPFAPLMEQTLLPGLGMHHTYVNVPKQAMAS

YAYGYSKEDKPIRVNPGMLADEAYGIKTSSADLLRFVKANIGGVDDKALQQAISLTH

QGHYSVGGMTQGLGWESYAYPVTEQTLLAGNSAKVILEANPTAAPRESGSQVLFN

KTGSTNGFGAYVAFVPARGIGIVMLANRNYPNEARIKAAHAILAQLAG

SEQ ID No. 302:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 303:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 304:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YSNSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKNYPNPVRVEAAWRILEKLQ

SEQ ID No. 305:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGELAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 306:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYALGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 307:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKFSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 308:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKNYPNPVRVEAAWRILEKLQ

SEQ ID No. 309:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

-continued

WRIGDMYQGLGWEMLNWPLKADSIINGSDSKVALAALPAVEINPPAPAVKASWVHK

TGSTGGFGSYVAFVPEKNLGIVMLANKSYPNPVRVEAAWRILEKLQ

SEQ ID No. 310:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YSNSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 311:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYARGYRE

GKPVHVSPGQLNAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKNYPNPVRVEAAWRILEKLQ

SEQ ID No. 1844:
MQQRQSILWGAVATLMWAGLAHAGEASPVDPLRPVVDASIQPLLKEHRIPGMAVAV

LKDGKAHYFNYGVANRESGAGVSEQTLFEIGSVSKTLTATLGAYAVVKGAMQLDDK

ASRHAPWLKGSAFDSITMGELATYSAGGLPLQFPEEVDSSEKMRAYYRQWAPVYS

PGSHRQYSNPSIGLFGHLAASSLKQPFAPLMEQTLLPGLGMHHTYVNVPKQAMAS

YAYGYSKEDKPIRVNPGMLADEAYGIKTSSADLLRFVKANIGGVDDKALQQAISLTH

QGHYSVGGMTQGLGWESYAYPVTEQTLLAGNSAKVILEANPTAAPRESGSQVLFN

KTGSTNGFGAYVAFVPARGIGIVMLANRNYPIEARIKAAHAILAQLAG

SEQ ID No. 1845:
MQQRQSILWGAVATLMWAGLAHAGEASPVDPLRPVVDASIQPLLKEHRIPGMAVAV

LKDGKAHYFNYGVANRESGAGVSEQTLFEIGSVSKTLTATLGAYAVVKGAMQLDDK

ASRHAPWLKGSAFDSITMGELATYSAGGLPLQFPEEVDSSEKMRAYYRQWAPVYS

PGSHRQYSNPSIGLFGHLAASSLKQPFAPLMEQTLLPGLGMHHTYVNVPKQAMAS

YAYGYSKEDKPIRVNPGMLADEAYGIKTSSADLLRFVKANIGGVDDKALQQAISLTH

QGHYSVGGMTQGLGWESYAYPVTEQTLLAGNSAKVSLEANPTAAPRESGSQVLFN

KTGSTNGFGAYVAFVPARGIGIVMLANRNYPIEARIKAAHAILAQLAG

SEQ ID No. 1846:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVAFAALPAVEVNPPAPAVKASWVH

KTGSTGGFGSYVAFVPEKNLGIVMLANKSYPNPVRVEAAWRILEKLQ

SEQ ID No. 1847:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGNGSDSKVALAALPAVEVNPPAPAVKASW

VHKTGSTGGFGSYVAFVPEKNLGIVMLANKSYPNPVRVEAAWRILEKLQ

SEQ ID No. 1848:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAYWRILEKLQ

SEQ ID No. 1849:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGELAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDNKVALAALPAVEVNPPAPAVKASWVH

KTGSTGGFGSYVAFVPEKNLGIVMLANKSYPNPVRVEAAWRILEKLQ

SEQ ID No. 1850:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVAALPAVEVNPPAPAVKASWVHKT

GSTGGFGSYVAFVPEKNLGIVMLANKSYPNPVRVEAAWRILEKLQ

SEQ ID No. 1851:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVAPAVEVNPPAPAVKASWVHKTGS

TGGFGSYVAFVPEKNLGIVMLANKSYPNPVRVEAAWRILEKLQ

SEQ ID No. 1852:
MMKKSLCCALLLTASFSTFAAAKTEQQIADIVNRTITPLMQEQAIPGMAVAVLYQGKP

YYFTWGKADIANNHPVTQQTLFELGSVSKTFNGVLGGDAIARGEIKLSDPVTKYLPE

LTGKQWQGISLLHLATYTAGGLPLQIPDDVTDKAALLRFYQNWQPQWTPGAKRLYA

NSSIGLFGALAVKPSGMSYEEAMTRRVLQPLKLAHTWITVPQNEQKDYAWGYREG

KPVHVTPGQLDAEAYGVKSNVTDMARWIQVNMDASRVQEKTLQQGIALAQSRYW

RIGDMYQGLGWEMLNWPLKADSIINGSDSKVALAALPTVEVNPPAPAVKASWVHKT

GSTGGFGSYVAFVPEKNLGIVMLANKSYPNPVRVEAAWRILEKLQ

SEQ ID No. 1853:
MMKKSICCALLLTASFSTFAAAKTEQQIADIVNRTITPLMQEQAIPGMAVAIIYEGKPY

YFTWGKADIANNHPVTQQTLFELGSVSKTFNGVLGGDAIARGEIKLSDPVTKYWPEL

TGKQWRGISLLHLATYTAGGLPLQIPDDVTDKAALLRFYQNWQPQWTPGAKRLYAN

SSIGLFGALAVKPSGMSYEEAMTRRVLQPLKLAHTWITVPQSEQKNYAWGYREGK

PVHVSPGQLDAEAYGVKSSVIDMARWVQANMDASHVQEKTLQQGIELAQSRYWRI

GDMYQGLGWEMLNWPLKADSIINGSDSKVALAALPAVEVNPPAPAVKASWVHKTG

STGGFGSYVAFVPEKNLGIVMLANKSYPNPARVEAAWRILEKLQ

SEQ ID No. 1854:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKTDSIINGSDSKVALAALPAVEVNPPAPAVKASWVH

KTGSTGGFGSYVAFVPEKNLGIVMLANKSYPNPVRVEAAWRILEKLQ

SEQ ID No. 1855:
MMKKSLCCALLLTASLSTFAAAKTEQQIADIVNRTITPLMQEQAIPGMAIAVIYQGKPY

YFTWGKADITNNHPVTQQTLFELGSVSKTFNGVLGGDAIARGEIKLSDPVTKYWPEL

TGKQWQGISLLHLATYTAGGLPLQIPDDVTDKAALLRFYQNWQPQWAPGAKRLYA

NSSIGLFGALAVKPSGMSYEEAMTRRVLQPLKLAHTWITVPQNEQKDYAWGYREG

KAVHVSPGQLDAEAYGVKSSVIDMARWVQVNMDASRVQEKTLQQGIALAQSRYW

RIGDMYQGLGWEMLNWPLKADSIINGSDSKVALAALPAVEVNPPAPAVKASWVHKT

GSTGGFGSYVAFVPEKNLGIVMLANKSYPNPVRVEAAWRILEKLQ

SEQ ID No. 1856:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYCVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 1857:
MMKKSLCCALLLTASFSTFAAAKTEQQIADIVNRTITPLMQEQAIPGMAVAVIYQGKP

YYFTWGKADIANNHPVTQQTLFELGSVSKTFIGVLGGDAIARGEIKLSDPVTKYWPE

LTGKQWQGIRLLHLATYTAGGLPLQIPDDVRDKAALLHFYQNWQPQWTPGAKRLY

ANSSIGLFGALAVKPSGMSYEEAMTRRVLQPLKLAHTWITVPQNEQKDYAWGYRE

GKPVHVSPGQLDAEAYGVKSSVIDMARWVQANMDASHVQEKTLQQGIALAQSRY

-continued

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 1858:
MMNRYAAALLLTASFSTFAAAKTEQQIADIVNRTITPLMQEQAIPGMAVAVIYQGKPY

YFTWGKADIANNHPVTQQTLFELGSVSKTFNGVLGGDAIARGEIKLSDPVTKYWPEL

TGKQWQGIRLLHLATYTAGGLPLQIPDDVRDKAALLHFYQNWQPQWTPGAKRLYA

NSSIGLFGALAVKPSGMSYEEAMTRRVLQPLKLAHTWITVPQNEQKDYAWGYREG

KPVHVSPGQLDAEAYGVKSSVIDMARWVQANMDASHVQEKTLQQGIALAQSRYW

RIGDMYQGLGWEMLNWPLKADSIINGSDSKVALAALPAVEVNPPAPAVKASWVHKT

GSTGGFGSYVAFVPEKNLGIVMLANKSYPNPVRVEAAWRILEKLQ

SEQ ID No. 1859:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFSALAVKPSGMSYEEAMTRRVLQPLKLAHTWITVPQNEQKDYAWGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 1860:
MQQRQSILWGAVATLMWAGLAHAGEASPVDPLRPVVDASIQPLLKEHRIPGMAVAV

LKDGKAHYFNYGVANRESGASVSEQTLFDIGSVSKTLTATLGAYAVVKGAMQLDDK

ASRHAPWLKGSVFDSITMGELATYSAGGLPLQFPEEVDSSEKMRAYYRQWAPVYS

PGSHRQYSNPSIGLFGHLAASSLKQPFAQLMEQTLLPGLGMHHTYVNVPKQAMAS

YAYGYSKEDKPIRVNPGMLADEAYGIKTSSADLLAFVKANIGGVDDKALQQAISLTH

KGHYSVGGMTQGLGWESYAYPVTEQTLLAGNSAKVILEANPTAAPRESGSQVLFN

KTGSTNGFGAYVAFVPARGIGIVMLANRNYPIPARVKAAHAILAQLAG

SEQ ID No. 1861:
MQQRQSILWGAVATLMWAGLAHAGEASPVDPLRPVVDASIQPLLKEHRIPGMAVAV

LKDGKAHYFNYGVANRESGASVSEQTLFDIGSVSKTLTATLGAYAVVKGAMQLDDK

ASRHAPWLKGSVFDSITMGELATYSAGGLPLQFPEEVDSSEKMRAYYRQWAPVYS

PGSHRQYSNPSIGLFGHLAASSLKQPFAQLMEQTLLPGLGMHHTYVNVPKQAMAS

YAYGYSKEDKPIRVNPGMLADEAYGIKTSSADLLAFVKANIGGVDDKALQQAISLTH

KGHYSVGGMTQGLGWESYAYPVTEQTLLAGNSAKVSLEANPTAAPRESGSQVLFN

KTGSTNGFGAYVAFVPARGIGIVMLANRNYPIPARVKAAHAILAQLAG

SEQ ID No. 1862:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 1863:
MQQRQSILWGAVATLMWAGLAHAGEASPVDPLRPVVDASIQPLLKEHRIPGMAVAV

LKDGKAHYFNYGVANRESGAGVSEQTLFEIGSVSKTLTATLGAYAVVKGAMQLDDK

ASRHAPWLKGSAFDSITMGELATYSAGGLPLQFPEEVDSSEKMRAYYRQWAPVYS

PGSHRQYSNPSIGLFGHLAASSLKQPFAPLMEQTLLPGLGMHHTYVNVPKQAMAS

YAYGYSKEDKPIRVNPGMLADEAYGIKTSSADLLRFVKANIGGVDDKALQQAISLTH

QGHYSVGGMTQGLGWESYAYPVTEQTLLAGNSAKVILEANPTAAPRESGSQVLFN

KTGSTNGFGAYVAFVPARGIGIVMLANRNYPNEARIKAAHAILAQLAG

SEQ ID No. 1864:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 1865:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YSNSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKNYPNPVRVEAAWRILEKLQ

SEQ ID No. 1866:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGELAVKPSGMSYEEAMTRRVLQPLKLAHTWITVPQNEQKDYAWGYR

EGKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 1867:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

YANSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKNYPNPVRVEAAWRILEKLQ

SEQ ID No. 1868:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIPDDVRDKAALLHFYQNWQPQWTPGAKRL

-continued

```
YANSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEINPPAPAVKASWVHK

TGSTGGFGSYVAFVPEKNLGIVMLANKSYPNPVRVEAAWRILEKLQ

SEQ ID No. 1869:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLQIIDDDVRDKAALLHFYQNWQPQWTPGAKRL

YSNSSIGLFGALAVKPSGMSYEEAMTRRVLQPLKLAHTWITVPQNEQKDYARGYRE

GKPVHVSPGQLDAEAYGVKSSVIDMARWVQANMDASHVQEKTLQQGIALAQSRY

WRIGDMYQGLGWEMLNWPLKADSIINGSDSKVALAALPAVEVNPPAPAVKASWVH

KTGSTGGFGSYVAFVPEKNLGIVMLANKSYPNPVRVEAAWRILEKLQ

SEQ ID No. 1870:
MMKKSLCCALLLTASFSTFAAAKTEQQIADIVNRTITPLMQEQAIPGMAVAVIYQGKP

YYFTWGKADIANNHPVTQQTLFELGSVSKTFNGVLGGDAIARGEIKLSDPVTKYWP

ELTGKQWQGIRLLHLATYTAGGLPLKIPDDVRDKAALLHFYQNWQPQWTPGAKRLY

SNSSIGLFGALAVKPSGMSYEEAMTRRVLQPLKLAHTWITVPQNEQKDYARGYREG

KPVHVSPGQLDAEAYGVKSSVIDMARWVQANMDASHVQEKTLQQGIALAQSRYW

RIGDMYQGLGWEMLNWPLKADSIINGSDSKVALAALPAVEVNPPAPAVKASWVHKT

GSTVGFGSYVAFVPEKNLGIVMLANKSYPNPVRVEAAWRILEKLQ
``` said peptides being chosen, preferably, from the peptides of sequence SEQ ID No. 312 to SEQ ID No. 350, SEQ ID No. 734, SEQ ID No. 735 and SEQ ID No. 1929 to SEQ ID No. 2007, as defined hereafter:

| Peptide SEQ ID No. | Amino acid sequence | Position of the peptide in the CMY protein |
|---|---|---|
| SEQ ID No. 312 | AALLHFYQNWQPQWTPGAK | 149-167 for the proteins of SEQ No. 266, 267, 269, 270, 271, 272, 273, 274, 275, 276, 277, 278, 279, 280, 281, 283, 284, 285, 286, 289, 290, 291, 292, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 148-166 for the protein of sequence SEQ ID No. 268; 163-181 for the protein of sequence SEQ ID No. 299; 148-166 for the protein of sequence SEQ ID No. 1858 |
| SEQ ID No. 313 | ADIANNHPVTQQTLFELGSVSK | 66-87 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 298, 300, 302, 303, 304, 305, 306, 307, 308, 309, 310, 311, 1846, 1847, 1848, 1849, 1850, 1851, 1852, 1853, 1854, 1856, 1857, 1859, 1862, 1864, 1865, 1866, 1867, 1868, 1869, 1870; 65-86 for the protein of sequence SEQ ID No. 268; 80-101 for the protein of sequence SEQ ID No. 299; 65-86 for the protein of sequence SEQ ID No. 1858 |
| SEQ ID No. 314 | ADSIINGSDSK | 300-310 for the proteins of SEQ No. 265, 266, 269, 270, 271, 272, 273, 274, 276, 277, 278, 279, 280, 281, 282, 283, 284, 285, 286, 287, 288, 290, 291, 295, 296, 297, 298, 300, 302, 303, 304, 305, 306, 307, 308, 309, 310, 311, 1846, 1848, 1850, 1851, 1852, 1853, 1855, 1856, 1857, 1859, 1862, 1864, 1865, 1866, 1867, 1868, 1869, 1870; 302-312 for the protein of sequence SEQ ID No. 289; 314-324 for the protein of sequence SEQ ID No. 299; 299-309 for the protein of sequence SEQ ID No. 1858 |
| SEQ ID No. 315 | ASWVHK | 330-335 for the proteins of SEQ No. 265, 266, 269, 270, 271, 272, 273, 274, 275, 276, 277, 278, 279, 280, 281, 282, 283, 285, 287, 288, 290, 291, 292, 295, 296, 297, 298, 300, 302, 303, 304, 305, 306, 307, 308, 309, 310, 311, 1846, 1848, 1849, 1852, 1853, 1854, 1855, 1856, 1857, 1859, 1862, 1864, 1865, 1866, |

-continued

| Peptide SEQ ID No. | Amino acid sequence | Position of the peptide in the CMY protein |
|---|---|---|
| | | 1867, 1868, 1869, 1870; 332-337 for the protein of sequence SEQ ID No. 267; 329-334 for the protein of sequence SEQ ID No. 268; 328-333 for the protein of sequence SEQ ID No. 284; 326-331 for the protein of sequence SEQ ID No. 286; 332-337 for the protein of sequence SEQ ID No. 289; 344-349 for the protein of sequence SEQ ID No. 299; 332-337 for the protein of sequence SEQ ID No. 1847; 328-333 for the protein of sequence SEQ ID No. 1850; 326-331 for the protein of sequence SEQ ID No. 1851; 329-334 for the protein of sequence SEQ ID No. 1858 |
| SEQ ID No. 316 | DYAWGYR | 218-224 for the proteins of SEQ No. 265, 266, 267, 269, 270, 271, 272, 273, 274, 275, 276, 277, 278, 279, 280, 282, 283, 284, 285, 286, 287, 289, 290, 291, 292, 295, 296, 297, 300, 305, 307, 1846, 1847, 1848, 1849, 1850, 1851, 1852, 1854, 1855, 1856, 1857, 1859, 1862, 1866; 217-223 for the protein of sequence SEQ ID No. 268; 232-238 for the protein of sequence SEQ ID No. 299; 217-223 for the protein of sequence SEQ ID No. 1858 |
| SEQ ID No. 317 | IGDMYQGLGWEMLNWPLK | 282-299 for the proteins of SEQ ID No. 265, 266, 267, 269, 270, 271, 272, 273, 274, 275, 276, 277, 278, 279, 280, 281, 282, 283, 284, 285, 286, 287, 288, 290, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 281-298 for the protein of sequence SEQ ID No. 268; 284-301 for the protein of sequence SEQ ID No. 289; 296-313 for the protein of sequence SEQ ID No. 299; 281-298 for the protein of sequence SEQ ID No. 1858 |
| SEQ ID No. 318 | LAHTWITVPQNEQK | 204-217 for the proteins of SEQ ID No. 265, 266, 267, 269, 270, 271, 272, 273, 274, 275, 276, 277, 278, 280, 281, 283, 284, 285, 286, 287, 289, 290, 291, 292, 300, 302, 303, 304, 305, 306, 307, 308, 309, 310, 311, 1846, 1847, 1848, 1849, 1850, 1851, 1852, 1854, 1855, 1856, 1857, 1859, 1862, 1864, 1865, 1866, 1867, 1868, 1869, 1870; 203-216 for the protein of sequence SEQ ID No. 268; 218-231 for the protein of sequence SEQ ID No. 299; 203-216 for the protein of sequence SEQ ID No. 1858 |
| SEQ ID No. 319 | LLHLATYTAGGLPLQIPDDVR | 126-146 for the proteins of SEQ ID No. 266, 267, 269, 270, 271, 273, 274, 275, 276, 278, 279, 281, 283, 284, 285, 286, 289, 290, 291, 292, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869; 140-160 for the protein of sequence SEQ ID No. 299; 125-145 for the protein of sequence SEQ ID No. 1858 |
| SEQ ID No. 320 | LSDPVTK | 105-111 for the proteins of SEQ ID No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 297, 298, 300, 302, 303, 304, 305, 306, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 104-110 for the protein of sequence SEQ ID No. 268; 119-125 for the protein of sequence SEQ ID No. 299; 104-110 for the protein of sequence SEQ ID No. 1858 |
| SEQ ID No. 321 | LYANSSIGLFGALAVK | 169-184 for the proteins of SEQ ID No. 265, 266, 267, 270, 271, 272, 273, 274, 276, 278, 279, 280, 281, 283, 284, 286, 287, 289, 290, 291, 292, 295, 296, 297, 298, 300, 302, 303, 306, 307, 308, 309, 311, 1846, 1847, 1848, 1850, 1851, 1852, 1853, 1854, 1855, 1856, 1857, 1862, 1864, 1867, 1868; 168-183 for the protein of sequence SEQ ID No. 268; 183-198 for the protein of sequence SEQ ID No. 299; 168-183 for the protein of sequence SEQ ID No. 1858 |
| SEQ ID No. 322 | NLGIVMLANK | 353-362 for the proteins of SEQ ID No. 265, 266, 269, 270, 271, 272, 273, 274, 275, 276, 277, 278, 279, 280, 281, 282, 283, 285, 287, 288, 290, 291, 292, 295, 296, 297, 298, 300, 302, 303, 304, 305, 306, 307, 308, 309, 310, 311, 1846, 1848, 1849, 1852, 1853, 1854, 1855, 1856, 1857, 1859, 1862, 1864, 1865, 1866, 1867, 1868, 1869, 1870; 355-364 for the protein of sequence SEQ ID No. 267; 352-361 for the protein of sequence SEQ ID No. 268; 351-360 for the protein of sequence SEQ ID No. 284; 349-358 for the protein of sequence SEQ ID No. 286; 355-364 |

-continued

| Peptide SEQ ID No. | Amino acid sequence | Position of the peptide in the CMY protein |
|---|---|---|
| | | for the protein of sequence SEQ ID No. 289; 367-376 for the protein of sequence SEQ ID No. 299; 355-364 for the protein of sequence SEQ ID No. 1847; 351-360 for the protein of sequence SEQ ID No. 1850; 349-358 for the protein of sequence SEQ ID No. 1851; 352-361 for the protein of sequence SEQ ID No. 1858 |
| SEQ ID No. 323 | QWQGIR | 120-125 for the proteins of SEQ No. 266, 267, 269, 270, 271, 273, 274, 275, 276, 277, 278, 279, 280, 281, 283, 284, 285, 286, 289, 290, 291, 292, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 134-139 for the protein of sequence SEQ ID No. 299; 119-124 for the protein of sequence SEQ ID No. 1858 |
| SEQ ID No. 324 | SLCCALLLTASFSTFAAAK | 5-23 for the proteins of SEQ No. 266, 267, 269, 270, 271, 272, 273, 274, 275, 276, 277, 278, 279, 280, 281, 282, 283, 284, 285, 286, 287, 289, 290, 291, 292, 295, 300, 302, 303, 304, 305, 306, 307, 308, 309, 310, 311, 1846, 1847, 1848, 1849, 1850, 1851, 1852, 1854, 1856, 1857, 1859, 1862, 1864, 1865, 1866, 1867, 1868, 1869, 1870; 4-22 for the protein of sequence SEQ ID No. 268; 19-37 for the protein of sequence SEQ ID No. 299 |
| SEQ ID No. 325 | SSVIDMAR | 245-252 for the proteins of SEQ No. 266, 267, 269, 270, 271, 272, 273, 274, 275, 276, 277, 278, 279, 280, 281, 283, 284, 285, 286, 288, 290, 291, 292, 295, 297, 298, 300, 302, 303, 304, 305, 306, 307, 308, 309, 310, 311, 1846, 1847, 1848, 1849, 1850, 1851, 1853, 1854, 1855, 1856, 1857, 1859, 1862, 1864, 1865, 1866, 1867, 1868, 1869, 1870; 244-251 for the protein of sequence SEQ ID No. 268; 247-254 for the protein of sequence SEQ ID No. 289; 259-266 for the protein of sequence SEQ ID No. 299; 244-251 for the protein of sequence SEQ ID No. 1858 |
| SEQ ID No. 326 | SYPNPVR | 363-369 for the proteins of SEQ No. 265, 266, 269, 270, 271, 272, 273, 274, 275, 276, 277, 278, 279, 280, 281, 282, 283, 285, 287, 290, 291, 292, 296, 297, 300, 302, 303, 305, 306, 307, 309, 310, 1846, 1848, 1849, 1852, 1854, 1855, 1856, 1857, 1859, 1862, 1864, 1866, 1868, 1869, 1870; 365-371 for the protein of sequence SEQ ID No. 267; 362-368 for the protein of sequence SEQ ID No. 268; 361-367 for the protein of sequence SEQ ID No. 284; 359-365 for the protein of sequence SEQ ID No. 286; 365-371 for the protein of sequence SEQ ID No. 289; 377-383 for the protein of sequence SEQ ID No. 299; 365-371 for the protein of sequence SEQ ID No. 1847; 361-367 for the protein of sequence SEQ ID No. 1850; 359-365 for the protein of sequence SEQ ID No. 1851; 362-368 for the protein of sequence SEQ ID No. 1858 |
| SEQ ID No. 327 | TEQQIADIVNR | 24-34 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 23-33 for the protein of sequence SEQ ID No. 268; 38-48 for the protein of sequence SEQ ID No. 299; 23-33 for the protein of sequence SEQ ID No. 1858 |
| SEQ ID No. 328 | TFNGVLGGDAIAR | 88-100 for the proteins of SEQ No. 265, 266, 267, 269, 270, 271, 272, 273, 274, 275, 276, 277, 278, 280, 281, 282, 283, 284, 285, 286, 287, 288, 289, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1859, 1862, 1864, 1865, 1866, 1867, 1868, 1869, 1870; 87-99 for the protein of sequence SEQ ID No. 268; 102-114 for the protein of sequence SEQ ID No. 299; 87-99 for the protein of sequence SEQ ID No. 1858 |
| SEQ ID No. 329 | TGSTGGFGSYVAFVPEK | 336-352 for the proteins of SEQ No. 265, 266, 269, 270, 271, 272, 273, 274, 275, 276, 277, 278, 279, 280, 281, 283, 285, 288, 290, 291, 292, 295, 296, 297, 298, 300, 302, 303, 304, 305, 306, 307, 308, 309, 310, 311, 1846, 1848, 1849, 1852, 1853, 1854, 1855, 1856, 1857, 1859, 1862, 1864, 1865, 1866, 1867, 1868, 1869; 338-354 for the protein of sequence SEQ ID No. 267; 335-351 for the protein of sequence SEQ ID No. 268; 334-350 |

-continued

| Peptide SEQ ID No. | Amino acid sequence | Position of the peptide in the CMY protein |
|---|---|---|
| | | for the protein of sequence SEQ ID No. 284; 332-348 for the protein of sequence SEQ ID No. 286; 338-354 for the protein of sequence SEQ ID No. 289; 350-366 for the protein of sequence SEQ ID No. 299; 338-354 for the protein of sequence SEQ ID No. 1847; 334-350 for the protein of sequence SEQ ID No. 1850; 332-348 for the protein of sequence SEQ ID No. 1851; 335-351 for the protein of sequence SEQ ID No. 1858 |
| SEQ ID No. 330 | TITPLMQEQAIPGMAVAVIYQGK | 35-57 for the proteins of SEQ No. 266, 267, 269, 270, 271, 272, 273, 274, 275, 276, 277, 278, 279, 280, 281, 282, 283, 284, 285, 286, 289, 290, 291, 292, 295, 296, 297, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 34-56 for the protein of sequence SEQ ID No. 268; 49-71 for the protein of sequence SEQ ID No. 299; 34-56 for the protein of sequence SEQ ID No. 1858 |
| SEQ ID No. 331 | TLQQGIALAQSR | 267-278 for the proteins of SEQ No. 265, 266, 267, 269, 270, 271, 272, 273, 274, 275, 276, 277, 278, 279, 280, 281, 283, 284, 285, 286, 287, 290, 291, 292, 295, 296, 297, 300, 302, 303, 304, 305, 306, 307, 308, 309, 310, 311, 1846, 1847, 1848, 1849, 1850, 1851, 1852, 1854, 1855, 1856, 1857, 1859, 1862, 1864, 1865, 1866, 1867, 1868, 1869, 1870; 266-277 for the protein of sequence SEQ ID No. 268; 269-280 for the protein of sequence SEQ ID No. 289; 281-292 for the protein of sequence SEQ ID No. 299; 266-277 for the protein of sequence SEQ ID No. 1858 |
| SEQ ID No. 332 | VALAALPAVEVNPPAPAVK | 311-329 for the proteins of SEQ No. 265, 269, 270, 271, 272, 273, 274, 275, 276, 277, 278, 279, 280, 281, 282, 283, 285, 288, 290, 291, 292, 296, 297, 298, 300, 302, 303, 304, 305, 306, 307, 308, 310, 311, 1848, 1849, 1853, 1854, 1855, 1856, 1857, 1859, 1862, 1864, 1865, 1866, 1867, 1869, 1870; 313-331 for the protein of sequence SEQ ID No. 267; 310-328 for the protein of sequence SEQ ID No. 268; 313-331 for the protein of sequence SEQ ID No. 289; 325-343 for the protein of sequence SEQ ID No. 299; 313-331 for the protein of sequence SEQ ID No. 1847; 310-328 for the protein of sequence SEQ ID No. 1858 |
| SEQ ID No. 333 | VEAAWR | 370-375 for the proteins of SEQ No. 265, 266, 269, 271, 272, 273, 274, 275, 276, 277, 278, 279, 280, 281, 282, 283, 285, 287, 288, 290, 291, 292, 295, 296, 297, 298, 300, 302, 303, 304, 305, 306, 307, 308, 309, 310, 311, 1846, 1849, 1852, 1853, 1854, 1855, 1856, 1857, 1859, 1862, 1864, 1865, 1866, 1867, 1868, 1869, 1870; 372-377 for the protein of sequence SEQ ID No. 267; 369-374 for the protein of sequence SEQ ID No. 268; 368-373 for the protein of sequence SEQ ID No. 284; 366-371 for the protein of sequence SEQ ID No. 286; 372-377 for the protein of sequence SEQ ID No. 289; 384-389 for the protein of sequence SEQ ID No. 299; 372-377 for the protein of sequence SEQ ID No. 1847; 368-373 for the protein of sequence SEQ ID No. 1850; 366-371 for the protein of sequence SEQ ID No. 1851; 369-374 for the protein of sequence SEQ ID No. 1858 |
| SEQ ID No. 334 | VLQPLK | 198-203 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 197-202 for the protein of sequence SEQ ID No. 268; 212-217 for the protein of sequence SEQ ID No. 299; 197-202 for the protein of sequence SEQ ID No. 1858 |
| SEQ ID No. 335 | WVQANMDASHVQEK | 253-266 for the proteins of SEQ No. 266, 267, 269, 270, 271, 272, 274, 275, 276, 277, 278, 279, 280, 281, 282, 283, 284, 285, 286, 288, 290, 291, 292, 298, 300, 302, 303, 304, 305, 306, 307, 308, 309, 310, 311, 1846, 1847, 1848, 1849, 1850, 1851, 1853, 1854, 1856, 1857, 1859, 1862, 1864, 1865, 1867, 1868, 1869, 1870; 252-265 for the protein of sequence SEQ ID No. 268; 255-268 for the protein of sequence SEQ ID No. 289; 267-280 for the protein of sequence SEQ ID No. 299; 252-265 for the protein of sequence SEQ ID No. 1858 |

-continued

| Peptide SEQ ID No. | Amino acid sequence | Position of the peptide in the CMY protein |
|---|---|---|
| SEQ ID No. 336 | YWPELTGK | 112-119 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 296, 297, 298, 300, 302, 303, 304, 305, 306, 307, 308, 309, 310, 311, 1846, 1847, 1848, 1849, 1850, 1851, 1853, 1854, 1855, 1856, 1857, 1859, 1862, 1864, 1865, 1866, 1867, 1868, 1869, 1870; 111-118 for the protein of sequence SEQ ID No. 268; 126-133 for the protein of sequence SEQ ID No. 299; 111-118 for the protein of sequence SEQ ID No. 1858 |
| SEQ ID No. 337 | AHYFNYGVANR | 62-72 for the proteins of SEQ No. 262, 263, 264, 293, 294, 301, 1844, 1845, 1860, 1861, 1863 |
| SEQ ID No. 338 | ANIGGVDDK | 261-269 for the proteins of SEQ No. 262, 263, 264, 293, 294, 301, 1844, 1845, 1860, 1861, 1863 |
| SEQ ID No. 339 | ESGSQVLFNK | 326-335 for the proteins of SEQ No. 262, 263, 264, 293, 294, 301, 1844, 1845, 1860, 1861, 1863 |
| SEQ ID No. 340 | GAMQLDDK | 105-112 for the proteins of SEQ No. 262, 263, 264, 293, 294, 301, 1844, 1845, 1860, 1861, 1863 |
| SEQ ID No. 341 | GIGIVMLANR | 353-362 for the proteins of SEQ No. 262, 263, 264, 293, 294, 301, 1844, 1845, 1860, 1861, 1863 |
| SEQ ID No. 342 | HAPWLK | 116-121 for the proteins of SEQ No. 262, 263, 264, 293, 294, 301, 1844, 1845, 1860, 1861, 1863 |
| SEQ ID No. 343 | IPGMAVAVLK | 49-58 for the proteins of SEQ No. 262, 263, 264, 293, 294, 301, 1844, 1845, 1860, 1861, 1863 |
| SEQ ID No. 344 | PVVDASIQPLLK | 34-45 for the proteins of SEQ No. 262, 263, 264, 293, 294, 301, 1844, 1845, 1860, 1861, 1863 |
| SEQ ID No. 345 | QAMASYAYGYSK | 218-229 for the proteins of SEQ No. 262, 263, 264, 293, 294, 301, 1844, 1845, 1860, 1861, 1863 |
| SEQ ID No. 346 | QWAPVYSPGSHR | 161-172 for the proteins of SEQ No. 262, 263, 264, 293, 294, 301, 1844, 1845, 1860, 1861, 1863 |
| SEQ ID No. 347 | QYSNPSIGLFGHLAASSLK | 173-191 for the proteins of SEQ No. 262, 263, 264, 293, 294, 301, 1844, 1845, 1860, 1861, 1863 |
| SEQ ID No. 348 | TGSTNGFGAYVAFVPAR | 336-352 for the proteins of SEQ No. 262, 263, 264, 293, 294, 301, 1844, 1845, 1860, 1861, 1863 |
| SEQ ID No. 349 | TLTATLGAYAVVK | 92-104 for the proteins of SEQ No. 262, 263, 264, 293, 294, 301, 1844, 1845, 1860, 1861, 1863 |
| SEQ ID No. 350 | VNPGMLADEAYGIK | 236-249 for the proteins of SEQ No. 262, 263, 264, 293, 294, 301, 1844, 1845, 1860, 1861, 1863 |
| SEQ ID No. 734 | PSGMSYEEAMTR | 185-196 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 296, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 184-195 for the protein of sequence SEQ ID No. 268; 199-210 for the protein of sequence SEQ ID No. 299; 184-195 for the protein of sequence SEQ ID No. 1858 |
| SEQ ID No. 735 | PYYFTWGK | 58-65 for the proteins of SEQ No. 265, 266, 267, 269, 270, 271, 272, 273, 274, 275, 276, 277, 278, 279, 280, 281, 282, 283, 284, 285, 286, 287, 288, 289, 290, 291, 292, 295, 297, 298, 300, 302, 303, 304, 305, 306, 307, 308, 309, 310, 311, 1846, 1847, 1848, 1849, 1850, 1851, 1852, 1853, 1854, 1855, 1856, 1857, 1859, 1862, 1864, 1865, 1866, 1867, 1868, 1869, 1870; 57-64 for the protein of sequence SEQ ID No. 268; 72-79 for the protein of sequence SEQ ID No. 299; 57-64 for the protein of sequence SEQ ID No. 1858 |
| SEQ ID No. 1929 | AALLR | 149-153 for the proteins of SEQ No. 265, 282, 287, 297, 298, 1852, 1853, 1855 |

| Peptide SEQ ID No. | Amino acid sequence | Position of the peptide in the CMY protein |
|---|---|---|
| SEQ ID No. 1930 | ADSIINGNGSDSK | 300-312 for the proteins of SEQ No. 267, 1847 |
| SEQ ID No. 1931 | ADSIINGSDNK | 300-310 for the proteins of SEQ No. 275, 1849; 299-309 for the protein of sequence SEQ ID No. 268 |
| SEQ ID No. 1932 | AELLR | 149-153 for the protein of SEQ No. 288 |
| SEQ ID No. 1933 | ALQQAISLTHK | 270-280 for the proteins of SEQ No. 262, 293, 294, 1860, 1861 |
| SEQ ID No. 1934 | AVHVSPGQLDAEAYGVK | 228-244 for the proteins of SEQ No. 273, 297, 1855 |
| SEQ ID No. 1935 | DYACGYR | 218-224 for the protein of SEQ No. 281 |
| SEQ ID No. 1936 | DYALGYR | 218-224 for the protein of SEQ No. 306 |
| SEQ ID No. 1937 | EDKPIR | 230-235 for the proteins of SEQ No. 262, 263, 264, 293, 294, 301, 1844, 1845, 1860, 1861, 1863 |
| SEQ ID No. 1938 | EGKPVHASPGQLDAEAYGVK | 239-258 for the protein of SEQ No. 299 |
| SEQ ID No. 1939 | EGKPVHGSPGQLDAEAYGVK | 225-244 for the protein of SEQ No. 278 |
| SEQ ID No. 1940 | EGKPVHVSPEQLDAEAYGVK | 225-244 for the protein of SEQ No. 283 |
| SEQ ID No. 1941 | EGKPVHVSPGK | 225-235 for the protein of SEQ No. 269 |
| SEQ ID No. 1942 | EGKPVHVSPGQFDAEAYGVK | 225-244 for the protein of SEQ No. 291 |
| SEQ ID No. 1943 | EGKPVHVSPGQLDAEAYCVK | 225-244 for the proteins of SEQ No. 1856 |
| SEQ ID No. 1944 | EGKPVHVSPGQLDAEAYGVK | 225-244 for the proteins of SEQ No. 265, 266, 267, 270, 272, 275, 277, 279, 280, 281, 282, 284, 285, 286, 288, 290, 292, 295, 296, 298, 300, 302, 303, 304, 305, 306, 307, 308, 309, 310, 1846, 1847, 1848, 1849, 1850, 1851, 1854, 1857, 1859, 1862, 1864, 1865, 1866, 1867, 1868, 1869, 1870; 224-243 for the protein of sequence SEQ ID No. 268; 224-243 for the protein of sequence SEQ ID No. 1858 |
| SEQ ID No. 1945 | EGKPVHVSPGQLDAGAYGVK | 225-244 for the protein of SEQ No. 271 |
| SEQ ID No. 1946 | EGKPVHVSPGQLNAEAYGVK | 225-244 for the protein of SEQ No. 311 |
| SEQ ID No. 1947 | EGKPVHVSPGR | 225-235 for the protein of SEQ No. 276 |

-continued

| Peptide SEQ ID No. | Amino acid sequence | Position of the peptide in the CMY protein |
|---|---|---|
| SEQ ID No. 1948 | EGKPVHVTPGQLDAEAYGVK | 225-244 for the proteins of SEQ No. 287, 1852 |
| SEQ ID No. 1949 | EGKPVYVSPGQLDAEAYGVK | 225-244 for the protein of SEQ No. 274 |
| SEQ ID No. 1950 | ESGAGVSEQTLFEIGSVSK | 73-91 for the proteins of SEQ No. 263, 264, 301, 1844, 1845, 1863 |
| SEQ ID No. 1951 | ESGASVSEQTLFDIGSVSK | 73-91 for the proteins of SEQ No. 293, 294, 1860, 1861 |
| SEQ ID No. 1952 | ESGASVSEQTLFEIGSVSK | 73-91 for the protein of SEQ No. 262 |
| SEQ ID No. 1953 | FSDPVTK | 105-111 for the protein of SEQ No. 307 |
| SEQ ID No. 1954 | FYQNWQPQWAPGAK | 154-167 for the proteins of SEQ No. 265, 295, 296, 297, 1855 |
| SEQ ID No. 1955 | FYQNWQPQWTPGAK | 154-167 for the proteins of SEQ No. 266, 267, 269, 270, 271, 272, 273, 274, 275, 276, 277, 278, 279, 280, 281, 282, 283, 284, 285, 286, 287, 288, 289, 290, 291, 292, 298, 300, 302, 303, 304, 305, 306, 307, 308, 309, 310, 311, 1846, 1847, 1848, 1849, 1850, 1851, 1852, 1853, 1854, 1856, 1857, 1859, 1862, 1864, 1865, 1866, 1867, 1868, 1869, 1870; 153-166 for the protein of sequence SEQ ID No. 268; 168-181 for the protein of sequence SEQ ID No. 299; 153-166 for the protein of sequence SEQ ID No. 1858 |
| SEQ ID No. 1956 | IPDDVR | 141-146 for the proteins of SEQ No. 266, 267, 269, 270, 271, 273, 274, 275, 276, 278, 279, 281, 283, 284, 285, 286, 289, 290, 291, 292, 300, 302, 303, 304, 305, 306, 307, 308, 309, 310, 311, 1846, 1847, 1848, 1849, 1850, 1851, 1854, 1856, 1857, 1859, 1862, 1864, 1865, 1866, 1867, 1868, 1869, 1870; 155-160 for the protein of sequence SEQ ID No. 299; 140-145 for the protein of sequence SEQ ID No. 1858 |
| SEQ ID No. 1957 | LAHTWIK | 204-210 for the protein of SEQ No. 297 |
| SEQ ID No. 1958 | LAHTWITVPENEQK | 204-217 for the protein of SEQ No. 279 |
| SEQ ID No. 1959 | LAHTWITVPQSEQK | 204-217 for the proteins of SEQ No. 282, 288, 295, 296, 298, 1853 |
| SEQ ID No. 1960 | LDAEAYGVK | 236-244 for the proteins of SEQ No. 265, 266, 267, 269, 270, 272, 273, 274, 275, 276, 277, 278, 279, 280, 281, 282, 283, 284, 285, 286, 287, 288, 290, 292, 295, 296, 297, 298, 300, 302, 303, 304, 305, 306, 307, 308, 309, 310, 1846, 1847, 1848, 1849, 1850, 1851, 1852, 1853, 1854, 1855, 1857, 1859, 1862, 1864, 1865, 1866, 1867, 1868, 1869, 1870; 235-243 for the protein of sequence SEQ ID No. 268; 238-246 for the protein of sequence SEQ ID No. 289; 250-258 for the protein of sequence SEQ ID No. 299; 235-243 for the protein of sequence SEQ ID No. 1858 |
| SEQ ID No. 1961 | LLHLATYTAGGLPLK | 126-140 for the proteins of SEQ No. 1870 |
| SEQ ID No. 1962 | LLHLATYTAGGLPLQFPDDVR | 126-146 for the protein of SEQ No. 277 |

| Peptide SEQ ID No. | Amino acid sequence | Position of the peptide in the CMY protein |
|---|---|---|
| SEQ ID No. 1963 | LYANSSIGLFAALAVK | 169-184 for the protein of SEQ No. 285 |
| SEQ ID No. 1964 | LYANSSIGLFGALVVK | 169-184 for the protein of SEQ No. 288 |
| SEQ ID No. 1965 | LYANSSIGLFGELAVK | 169-184 for the proteins of SEQ No. 269, 275, 277, 305, 1849, 1866 |
| SEQ ID No. 1966 | LYANSSIGLFGTLAVK | 169-184 for the protein of SEQ No. 282 |
| SEQ ID No. 1967 | LYANSSIGLFSALAVK | 169-184 for the proteins of SEQ No. 1859 |
| SEQ ID No. 1968 | LYSNSSIGLFGALAVK | 169-184 for the proteins of SEQ No. 304, 310, 1865, 1869, 1870 |
| SEQ ID No. 1969 | NYAWGYR | 218-224 for the proteins of SEQ No. 288, 298, 1853 |
| SEQ ID No. 1970 | NYPIPAR | 363-369 for the proteins of SEQ No. 262, 293, 294, 1860, 1861 |
| SEQ ID No. 1971 | NYPNEAR | 363-369 for the proteins of SEQ No. 301, 1863 |
| SEQ ID No. 1972 | NYPNPVR | 363-369 for the proteins of SEQ No. 304, 308, 311, 1865, 1867 |
| SEQ ID No. 1973 | SICCALLLTASFSTFAAAK | 5-23 for the proteins of SEQ No. 288, 1853 |
| SEQ ID No. 1974 | SICCALLLTASFSTFAATK | 5-23 for the protein of SEQ No. 298 |
| SEQ ID No. 1975 | SLCCALLLTAPLSTFAAAK | 5-23 for the protein of SEQ No. 297 |
| SEQ ID No. 1976 | SLCCALLLTASFSTFASAK | 5-23 for the proteins of SEQ No. 265, 296 |
| SEQ ID No. 1977 | SLCCALLLTASLSTFAAAK | 5-23 for the proteins of SEQ No. 1855 |
| SEQ ID No. 1978 | SNVTDMAR | 245-252 for the proteins of SEQ No. 265, 287, 296, 1852 |
| SEQ ID No. 1979 | SYPNPIR | 363-369 for the protein of SEQ No. 295 |
| SEQ ID No. 1980 | TALLHFYQNWQPQWAPGAK | 149-167 for the proteins of SEQ No. 295, 296 |
| SEQ ID No. 1981 | TDSIINGSDSK | 300-310 for the proteins of SEQ No. 292, 1854 |

-continued

| Peptide SEQ ID No. | Amino acid sequence | Position of the peptide in the CMY protein |
|---|---|---|
| SEQ ID No. 1982 | TFIGVLGGDAIAR | 88-100 for the proteins of SEQ No. 1857 |
| SEQ ID No. 1983 | TFNGVLGGDCIAR | 88-100 for the protein of SEQ No. 279 |
| SEQ ID No. 1984 | TFNGVLGGEAIAR | 88-100 for the protein of SEQ No. 290 |
| SEQ ID No. 1985 | TGSTVGFGSYVAFVPEK | 336-352 for the proteins of SEQ No. 1870 |
| SEQ ID No. 1986 | TGYTGGFGSYVAFVPEK | 336-352 for the protein of SEQ No. 282 |
| SEQ ID No. 1987 | TLQQGIELAQSR | 267-278 for the proteins of SEQ No. 282, 288, 298, 1853 |
| SEQ ID No. 1988 | TSSADLLAFVK | 250-260 for the proteins of SEQ No. 262, 293, 294, 1860, 1861 |
| SEQ ID No. 1989 | TSSADLLR | 250-257 for the proteins of SEQ No. 263, 264, 301, 1844, 1845, 1863 |
| SEQ ID No. 1990 | TYYFTWGK | 58-65 for the protein of SEQ No. 296 |
| SEQ ID No. 1991 | VAALPAVEVNPPAPAVK | 311-327 for the proteins of SEQ No. 284, 1850 |
| SEQ ID No. 1992 | VAFAALPAVEVNPPAPAVK | 311-329 for the proteins of SEQ No. 266, 1846 |
| SEQ ID No. 1993 | VALAAIPAVEVNPPAPAVK | 311-329 for the protein of SEQ No. 295 |
| SEQ ID No. 1994 | VALAALHTVEVNPPAPAVK | 311-329 for the protein of SEQ No. 287 |
| SEQ ID No. 1995 | VALAALPAVEINPPAPAVK | 311-329 for the proteins of SEQ No. 309, 1868 |
| SEQ ID No. 1996 | VALAALPTVEVNPPAPAVK | 311-329 for the proteins of SEQ No. 1852 |
| SEQ ID No. 1997 | VAPAVEVNPPAPAVK | 311-325 for the proteins of SEQ No. 286, 1851 |
| SEQ ID No. 1998 | VEAYWR | 370-375 for the proteins of SEQ No. 270, 1848 |
| SEQ ID No. 1999 | VILEANPTAAPR | 314-325 for the proteins of SEQ No. 262, 263, 293, 301, 1844, 1860, 1863 |
| SEQ ID No. 2000 | VPQSEQK | 211-217 for the proteins of SEQ No. 282, 288, 295, 296, 297, 298, 1853 |

| Peptide SEQ ID No. | Amino acid sequence | Position of the peptide in the CMY protein |
|---|---|---|
| SEQ ID No. 2001 | VSLEANPTAAPR | 314-325 for the proteins of SEQ No. 264, 294, 1845, 1861 |
| SEQ ID No. 2002 | WIQVNMDASR | 253-262 for the proteins of SEQ No. 287, 1852 |
| SEQ ID No. 2003 | WVQANMDASR | 253-262 for the protein of SEQ No. 295 |
| SEQ ID No. 2004 | WVQVNMDASR | 253-262 for the proteins of SEQ No. 265, 273, 296, 297, 1855 |
| SEQ ID No. 2005 | YAAALLLTASFSTFAAAK | 5-22 for the proteins of SEQ No. 1858 |
| SEQ ID No. 2006 | YLPELTGK | 112-119 for the proteins of SEQ No. 1852 |
| SEQ ID No. 2007 | YWSELTGK | 112-119 for the protein of SEQ No. 295 |

The detection of a mechanism of resistance to cephalosporins induced by the expression of the CTX-M protein is characterised by the detection of at least one peptide belonging to the CTX-M protein and to its different sequence variants SEQ ID No. 351 to SEQ ID No. 445 and SEQ ID No. 1871 to SEQ ID No. 1908.

SEQ ID No. 351:
MMTQSIRRSMLTVMATLPLLFSSATLHAQTNSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWGVGDKTGSGDYGTTNDIA
VIWPANHAPLVLVTYFTQPEQKAESRRDVLAAAAKIVTHGF

SEQ ID No. 352:
MMRHRVKRMMLMTTACISLLLGSAPLYAQANDVQQKLAALEKSSGGRLGV
ALIDTADNAQTLYRADERFAMCSTSKVMAAAAVLKQSETQKKVLSQKVEI
KSSDLINYNPITEKHVNGTMTLAELSAAALQYSDNTAMNKLIAHLGGPDK
VTAFARAIGDNTFRLDRTEPTLNTAIPGDPRDTTTPLAMAQTLRNLTLGS
ALGETQRAQLVTWLKGNTTGAASIQAGLPTSWVVGDKTGSGDYGTTNDIA
VIWPEGRAPLILVTYFTQPEQKAESRRDVLAAAAKIVTDGY

SEQ ID No. 353:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTAGDKTGSGDYGTTNDIA
VIWPQGRAPLVLVTYFTQPQQNAESRRDVLASAARIIAEGL

SEQ ID No. 354:
MVKKSLRQFTLMATATVTLLLGSVPLYAQTVDVQQKLAELEQQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 355:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 356:
MVTKRMQRMMFAAAACIPLLLGSAPLYAQTSAVQQKLAALEKSSGGRLGV
ALIDTKDNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFAREIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 357:
MVKKSLRQFTLMATATVTLLLGSVPLYAQTADVQQKLAGLERQSGGRLGV
ALINTADNSQILYRADERFAMCSTSKVMAAAAVLKKSESEPNLLNQRVEI
KKSDLVNYNPIAEKHVNGTMSPAELSAAALQYSDNVAMNKLIAHVGGPAS
VTAFARQLGDETFRLDRTEPTLNTAIPGDPRDTTSPRAMAQTLRNLTLGK
ALGDSQRAQLVTVVMKGNTTGAASIQAGLPASWVVGDKTGSGDYGTTNDI
AVIWPKDRAPLILVTYFTQPQPKAESRRHVLAS

SEQ ID No. 358:
MVKKSLRQFTLMATAAVTLLLGSVPLYAQTADVQQKLAELERQSGGRLGV
ALINTADNSQILYRADERFAMCSTSKVMAAAAVLKKSESEPSLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDILASAAKIVTDGL

SEQ ID No. 359:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTAGDKTGSGGYGTTNDIA
VIWPQGRAPLVLVTYFTQPQQNAESRRDVLASAARIIAEGL

SEQ ID No. 360:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 361:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTESTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 362:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAKGL

SEQ ID No. 363:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 364:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTNGL

SEQ ID No. 365:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTETTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTNGL

SEQ ID No. 366:
MMRKSVRRAMLMTTACVSLLLASVPLCAQANDVQQKLAALEKSSGGRLGV
ALINTADNTQTLYRADERFAMCSTSKVMAVAAVLKQSETQKGLLSQRVEI
KPSDLINYNPIAEKHVNGTMTFGELSAAALQYSDNTAMNKLIAHLGGPDK
VTAFARTIGDDTFRLDRTEPTLNTAIPGDPRDTTTPLAMAQALRNLTLGN
ALGDTQRAQLVMWLKGNTTGAASIQAGLPTSWVVGDKTGSGGYGTTNDIA
VIWPEGRAPLVLVTYFTQSEPKAESRRDVLAAAARIVTDGY

SEQ ID No. 367:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAERRRDVLASAARIIAEGL

SEQ ID No. 368:
MMRKSVRRAMLMTTACVSLLLASVPLCAQANDVQQKLAALEKSSGGRLGV
ALINTADNTQTLYRADERFAMCSTSKVMAAAAVLKQSETQKGLLSQRVEI
KPSDLINYNPIAEKHVNGTMTFGELSAAALQYSDNTAMNKLIAHLGGPDK
VTAFARTIGDDTFRLDRTEPTLNTAIPGDPRDTTTPLAMAQALRNLTLGN
ALGDTQRAQLVMWLKGNTTGAASIRAGLPTSWVVGDKTGSGDYGTTNDIA
VIWPEGRAPLVLVTYFTQSEPKAESRRDVLAAAARIVTDGY

SEQ ID No. 369:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGGYGTTNDIA
VIWPQGRAPLVLVTYFTQPQQNAESRRDVLASAARIIAEGL

SEQ ID No. 370:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYSPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 371:
MVKKSLRQFTLMATAAVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVDGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTNGL

SEQ ID No. 372:
MVKKSLRQFTLMATAAVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVDGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 373:
MVKKSLRQFTLMATATVTLLLGSVPLYAQTDVQQKLAELEQQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSCDYGTTNDIA
VIWPKDRAPLILVTYFTQPQPKAESRRDVLASAAKIVTDGL

SEQ ID No. 374:
MVKKSLRQFTLMATATVTLLLGSVPLHAQTADVQQKLAELEQQSGGRLGV
ALINTADNSQILYRADERFAMCSTSKVMAAAAVLKKSESEPNLLNQRVEI
KKSDLVNYNPIAEKHVDGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 375:
MRHRVKRMMLMTTACISLLLGSAPLYAQANDVQQKLAALEKSSGGRLGVA
LIDTADNAQTLYRADERFAMCSTSKVMAAAAVLKQSETQKNVLSQKVEIK
SSDLINYNPIAEKHVNGTMTLAELSAAALQYSDNTAMNKLIAHLGGPDKV
TAFARAIGDDTFRLDRTEPTLNTAIPGDPRDTTTPLAMAQTLRHLTLGSA
LGETQRAQLVTWLKGNTTGAASIQAGLPTSWVVGDKTGSGDYGTTNDIAV
IWPEGRAPLILVTYFTQPEQKAESRRDVLAAAAKIVTDGY

SEQ ID No. 376:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAARIRAGLPTSWTVGDKTGSGDYGTTNDIA
VIWPQGRAPLVLVTYFTQPQQNAESRRDVLASAARIIAEGL

SEQ ID No. 377:
MVTKRVQRMMFAAAACIPLLLGSAPLYAQTSAVQQKLAALEKSSGRRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 378:
MVTKRVQRMMFAAAACIPLLLGSAPLYAQTNAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 379:
MVTKRVQRMMFAAAACIPLLLGSAPLYAQTSAVQQKLAALEKSSGRRLGV
PLIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 380:
MVTKRVQRMMFAAAACIPLLLGSAPLYAQTSAVQQKLAALEKSSGGRLGV
PLIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 381:
MVTKRVQRMMFAAAACIPLLLGSAPLYAQTNAVQQKLAALEKSSGGRLGV
PLIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 382:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDGTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 383:
MMRKSVRRAMLMTTACVSLLLASVPLCAQANDVQQKLAALEKSSGGRLGV
ALINTADNTQTLYRADERFAMCSTSKVMAAAAVLKQSETQKGLLSQRVEI
KPSDLINYNPIAEKHVNGTMTFGELSAAALQYSDNTAMNKLIAHLGGPDK
VTAFARTIGDDTFRLDRTEPTLNTAIPGDPRDTTTPLAMAQALRNLTLGN
ALGDTQRAQLVMWLKGNTTGAASIQAGLPTSWVVGDKTGSGDYGTTNDIA
VIWPEGRAPLVLVTYFTQSEPKAESRRDVLAAAARIVTDGY

SEQ ID No. 384:
MMRKSVRRAMLMTTACVSLLLASVPLCAQANDVQQKLAALEKSSGGRLGV
ALINTADNTQTLYRADERFAMCSTSKVMAAAAVLKQSETQKGLLSQRVEI
KPSDLVNYNPIAEKHVNGTMTFGELIAAALQYSDNTAMNKLIAHLGGPDK
VTAFARTIGDDTFRLDRTEPTLNTAIPGDPRDTTTPLAMAQALRNLTLGN
ALGDTQRAQLVMWLKGNTTGAASIQAGLPTSWVVGDKTGSGDYGTTNDIA
VIWPEGRAPLVLVTYFTQSEPKAESRRDVLAAAARIVTDGY

SEQ ID No. 385:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTETTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 386:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGGYGTTNDIA
VIWPENHAPLVLVTYFTQPEQKAERRRDILAAAAKIVTHGF

SEQ ID No. 387:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTAGDKTGSGDYGTTNDIA
VIWPQGRAPLVLVTYFTQPQQNAESRRDVLASAARIIAEGL

SEQ ID No. 388:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTESTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 389:
MVKKSLRQFTLMATATVTLLLGSVPLYAQTADVQQKLAELERQSGGRLGV
ALINTADNSQILYRADERFPMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 390:
MVKKSLRQFTLMATATVTLLLGSVPLYAQTVDVQQKLAELEQQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVIYFTQPQPKAESRRDVLASAAKIVTDGL

SEQ ID No. 391:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEQTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 392:
MMTQSIRRSMLTVMATLPLLFSSATLHAQANSVQQQLEALEKSSGGRLGV
ALINTADNSQILYRADERFAMCSTSKVMAAAAVLKQSESDKLLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAESRRDILAAAAKIVTHGF

SEQ ID No. 393:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 394:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 395:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVDGTMSLAELSAAALQYSDNVAMNKLISHVGGPAS
VTAFARQLGDETFRLDRTETTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTNGL

SEQ ID No. 396:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVDGTMSLAELSAAALQYSDNVAMNKLISHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 397:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAENRRDILAAAAKIVTHGF

SEQ ID No. 398:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAERRRDVLASAARIIAEGL

SEQ ID No. 399:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTNGL

SEQ ID No. 400:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTESTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 401:
MVKKSLRQFTLMATATVTLLLGNVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 402:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYSPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 403:
MVTKRVQRMMFAAAACIPLLLGSAPLYAQTSAVQQKLAALEKSSGGRLGV
ALIDTADNTQVLYRGDERFPMCSTSKVMAAAAVLEQSETQKQLLNQPVEI
QPADLVNYNPIAEKHVNGTMTLAELSAAALQYSDHTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 404:
MVKKSLRQFTLMATATVTLLLGSVPLHAQTVDVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDDTFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 405:
MVKKSLRQFTLMATATVTLLLGSVPLYAQTVDVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 406:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPNAESRRDVLASAAKIVTNGL

SEQ ID No. 407:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTELTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 408:
MVTKRVQRMMFAAAACIPLLLGSAPLYAQTSAVQQKLAALEKSSGGRLGV
ALIDTADNTHVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 409:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVAWLKGNTTGAASIRAGLPTSWTVGDKTGSGDYGTTNDIA
VIWPQGRAPLVLVTYFTQPQQNAESRRDVLASAARIIAEGL

SEQ ID No. 410:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTPAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 411:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPFAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 412:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRHDVLASAAKIVTDGL

SEQ ID No. 413:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 414:
MMRKSVRRAMLMTTACVSLLLASVPLCAQANDVQQKLAALEKSSGGRLGV
ALIDTADNTQTLYRADERFAMCSTSKVMAVAAVLKQSETQKGLLSQRVEI
KPSDLINYNPIAEKHVNGTMTFGELSAAALQYSDNTAMNKLIAHLGGPDK
VTAFARTIGDDTFRLDRTEPTLNTAIPGDPRDTTTPLAMAQALRNLTLGN
ALGDTQRAQLVMWLKGNTTGAASIQAGLPTSWVVGDKTGSGDYGTTNDIA
VIWPEGRAPLVLVTYFTQSEPKAESRRDVLAAAARIVTDGY

SEQ ID No. 415:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTETTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAESRRDILAAAAKIVTHGF

SEQ ID No. 416:
MMTQSIRRSMLTVMATLSLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAESRRDILAAAAKIVTHGF

SEQ ID No. 417:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSCGYGTTNDIA
VIWPKDRAPLILVTYFTQPQPKAESRRDVLASAAKIVTDGL

SEQ ID No. 418:
MMRKSVRRAMLMTTACVSLLLASVPLCAQANDVQQKLAALEKSSGGRLGV
ALINTADNTQTLYRADERFAMCSTSKVMAVAAVLKQSETQKGLLSQRVEI
KPSDLINYNPIAEKHVNGTMTFGELSAAALQYSDNTAMNKLIAHLGGPDK
VTAFARTIGDDTFRLDRTEPTLNTAIPGDPRDTTTPLAMAQSLRNLTLGN
ALGDTQRAQLVMWLKGNTTGAASIQAGLPTSWVVGDKTGSGDYGTTNDIA
VIWPEGRAPLVLVTYFTQSEPKAESRRDVLAAAARIVTDGY

SEQ ID No. 419:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRTQLVTWLKGNTTGSASIRAGLPKSWVVGDKTGSGDYGTTNDIA
VIWPENHAPLVLVTYFTQPEQKAESRRDILAAAAKIVTHGF

SEQ ID No. 420:
MMRKSVRRAMLMTTACVSLLLASVPLCAQANDVQQKLAALEKSSGGRLGV
ALINTADNTQTLYRADERFAMCSTSKVMAAAAVLKQSETQKGLLSQRVEI
KPSDLINYNPIAEKHVNGTMTLGELSAAALQYSDNTAMNKLIAHLGGPDK
VTAFARTIGDDTFRLDRTEPTLNTAIPGDPRDTTTPLAMAQALRNLTLGN
ALGDTQRAQLVMWLKGNTTGAASIQAGLPTSWVVGDKTGSGDYGTTNDIA
VIWPEGRAPLVLVTYFTQSEPKAESRRDVLAAAARIVTDGY

SEQ ID No. 421:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTESTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAERRRDVLASAARIIAEGL

SEQ ID No. 422:
MMTQSIGRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAESRRDILAAAAKIVTHGF

SEQ ID No. 423:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGGYGTTNDIA
VIWPQGRAPLVLVTYFTQPQQNAESRRDVLASAARIIAEGL

SEQ ID No. 424:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAERRRDILAAAAKIVTHGF

SEQ ID No. 425:
MVTKRVQRMMSAAAACIPLLLGSPTLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTARAGADVASLRWVMR
WAKPSGAVGDVAQRQYDRAAGIRAGLPTSWTVGDKTGSGDYGTTNDIAVI
WPQGRAPLVLVTYFTQPQQNAESRRDVLASAARIIAEGL

SEQ ID No. 426:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVDGTMSLAELSAAALQYSDNVAMNKLISHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTNGL

SEQ ID No. 427:
MRHRVKRMMLMTTACISLLLGSAPLYAQANDVQQKLAALEKSSGGRLGVA
LIDTADNAQTLYRADERFAMCSTSKVMAAAAVLKQSETQKNVLSQKVEIK
SSDLINYNPIAEKHVNGTMTLAELSAAALQYSDNTAMNKLIAHLGGPDKV
TAFARAIGDDTFRLDRTEPTLNTAIPGDPRDTTTPLAMAQTLRHLTLGSA
LGETQRAQLVTWLKGNTTGAASIQAGLPTSWVVGDKTGSGDYGTTNDIAV
IWPEGRAPLILVTYFTQPEQKAENRRDVLAAAAKIVTDGY

SEQ ID No. 428:
MVKKSLRQFTLMATATVTLLLGSVPLYAQTADVQQKLAELERQSGGRLGV
ALINTADNSQILYRADERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPASWVGDKTGSGGYGTTNDIA
VIWPKDRAPLILVTYFTQPQPKAESRRDVLASAAKIVTDGL

SEQ ID No. 429:
MMTQSIRRSMLTVMATLPLLFSSATLHAQANSVQQQLEALEKSSGGRLGV
ALINTADNSQILYLADERFAMCSTSKVMAAAAVLKQSESDKHLLNQRVEI
KASDLVNYNPIAEKHVNGTMTLAELGAGALQYSDNTAMNKLIAHLGGPDK
VTAFARSLGDETFRLDRTEPTLNSAIPGDPRDTTTPLAMAQTLKNLTLGK
ALAETQRAQLVTWLKGNTTGSASIRAGLPKCWVVGDKTGSGDYGTTNDIA
VIWPENHAPLVLVTYFTQPEQKAESRRDVLAAAAKIVTHGF

SEQ ID No. 430:
MMTQSIRRSMLTVMATLPLLFSSATLHAQANSVQQQLEALEKSSGGRLGV
ALINTADNSQILYVADERFAMCSTSKVMAAAAVLKQSESDKHLLNQRVEI
RASDLVNYNPIAEKHVNGTMTLAQLGAGALQYSDNTAMNKLIAHLGGPDK
VTAFARSLGDETFRLDRTEPTLNSAIPGDPRDTTTPLAMAQTLKNLTLGK
ALAETQRAQLVTWLKGNTTGSASIRAGLPKSWGVGDKTGSGDYGTTNDIA
VIWPENHAPLVLVTYFTQPEQKAESRRDVLAAAAKIVTHGF

SEQ ID No. 431:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVDGTMSLAELSAAALQYSDNVAMNKLISHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTNGL

SEQ ID No. 432:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAESRRDILAAAAKIVTHGF

SEQ ID No. 433:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 434:
MMTQSIRRSMLTVMATLPLLFSSATLHAQANSVQQQLEALEKSSGGRLGV
AQINTADNSQILYVADERFAMCSTSKVMAAAAVLKQSESDKHLLNQRVEI
RASDLVNYNPIAEKHVNGTMTLAELGAGALQYSDNTAMNKLIAHLGGPDK
VTAFARSLGDETFRLDRTEPTLNSAIPGDPRDTTTPLAMAQTLKNLTLGK
ALAETQRAQLVTWLKGNTTGSASIRAGMPKSWGVGDKTGSGDYGTTNDIA
VIWPENHAPLVLVTYFTQPEQKAESRRDILAAAAKIVTHGF

SEQ ID No. 435:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAESRRDFLAAAAKIVTHGF

SEQ ID No. 436:
MVTKRVQRMMFAGGAGIPLLLGSAPFYAQTSAGQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 437:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTNGL

SEQ ID No. 438:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVDGTMSLAELSAAALQYSDNVAMNKLISHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTNGL

SEQ ID No. 439:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDESFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAESRRDILAAAAKIVTHGF

SEQ ID No. 440:
MVKKSLRQFTLMATAAVTLLLGSVPLYAQTADVQQKLAELERQSGGRLGV
ALINTADNSQILYRADERFAMCSTSKVMAAAAVLKKSESEPSLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDILASAAKIVTDGL

SEQ ID No. 441:
MVKKSLRQFTLMATAAVTLLLGSVPLYAQTADVQQKLAELERQSGGRLGV
ALINTADNSQILYRADERFAMCSTSKVMAVAAVLKKSESEPSLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDILASAAKIVTDGL

SEQ ID No. 442:
MMTQSIRRSMLTVMATLPLLFSSATLHAQTNSVQQQLKALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIQAGLPKSWVVGDKTGSGDYGTTNDIA
IIWPENHAPLVLVTYFTQPEQKAESRRDVLAAAAKIVTRGF

SEQ ID No. 443:
MMRKSVRRAILMTTACVSLLLASVPLYAQANDIQQKLAALEKSSGGRLGV
ALINTADNTQTLYRADERFAMCSTSKVMAAAAVLKQSETQKDLLSQRVEI
KSSDLINYNPIAEKHVNGTMTLGELSAAALQYSDNTAMNKLIAHLGGPGK
VTAFARVIGDDTFRLDRTEPTLNTAIPGDPRDTTTPLAMAQTLRNLTLGN
ALGDTQRAQLVTWLKGNTTGAASIQAGLPTSWVVGDKTGSGDYGTTNDIA
VIWPEGRAPLVLVTYFTQPEPKAESRRDVLAAAARIVTDGY

SEQ ID No. 444:
MMTQSIRRSMLTVMATLPLLFSSATLHAQTNSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWGVGDKTGSGDYGTTNDIA
VIWPENHAPLVLVTYFTQPEQKAESRRDVLAAAAKIVTHGF

SEQ ID No. 445:
MMTQSIRRSMLTVMATLPLLFSSATLHAQTNSVQQQLEALEKSSGGRLGV
ALINTADNSQILYRADERFAMCSTSKVMAAAALLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIQAGLPKSWVVGDKTGSGDYGTTNDIA
VIWPENHAPLVLVTYFTQPEQKAESRRDVLAAAAKIVTHGF

SEQ ID No. 1871:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 1872:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTESTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 1873:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAKGL

SEQ ID No. 1874:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 1875:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTNGL

SEQ ID No. 1876:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAERRRDVLASAARIIAEGL

SEQ ID No. 1877:
MRHRVKRMMLMTTACISLLLGSAPLYAQANDVQQKLAALEKSSGGRLGVA
LIDTADNAQTLYRADERFAMCSTSKVMAAAAVLKQSETQKNVLSQKVEIK
SSDLINYNPIAEKHVNGTMTLAELSAAALQYSDNTAMNKLIAHLGGPDKV
TAFARAIGDDTFRLDRTEPTLNTAIPGDPRDTTTPLAMAQTLRHLTLGSA
LGETQRAQLVTWLKGNTTGAASIQAGLPTSWVVGDKTGSGDYGTTNDIAV
IWPEGRAPLILVTYFTQPEQKAESRRDVLAAAAKIVTDGY

SEQ ID No. 1878:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 1879:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVDGTMSLAELSAAALQYSDNVAMNKLISHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGDYGTTNDIA
VIWPKDRAPLILVTYFTQPQPKAESRRDVLASAAKIVTDGL

SEQ ID No. 1880:
MMTQSIRRSMLTVMATLPLLFSSATLHAQANSVQQQLEALEKSSGGRLGV
ALINTADNSQILYRADERFAMCSTSKVMAAAAVLKQSESDKHLLNQRVEI
KKSDLVNYNPIAEKHVNGTMTLAELGAAALQYSDNTAMNKLIAHLGGPDK
VTAFARSLGDETFRLDRTEPTLNTAIPGDPRDTTTPLAMAQTLKNLTLGK
ALAETQRAQLVTWLKGNTTGSASIRAGLPKSWVVGDKTGSGDYGTTNDIA
VIWPENHAPLVLVTYFTQPEQKAENRRDILAAAAKIVTHGF

SEQ ID No. 1881:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAERRRDVLASAARIIAEGL

SEQ ID No. 1882:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTNGL

SEQ ID No. 1883:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPNAESRRDVLASAAKIVTNGL

SEQ ID No. 1884:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRHDVLASAAKIVTDGL

SEQ ID No. 1885:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 1886:
MVKKSLRQFTLMATATVTLLLGSVPLYAQTADVQQKLAELERQSGGRLGV
ALINTADNSQILYRADERFAMCSTSKAMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 1887:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTESTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAERRRDVLASAARIIAEGL

SEQ ID No. 1888:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTQNTAIPGDPRDTTTPRAMAQTLRQLTLGH
ALGETQRAQLVTWLKGNTTGAASIRAGLPTSWTVGDKTGSGGYGTTNDIA
VIWPQGRAPLVLVTYFTQPQQNAESRRDVLASAARIIAEGL

SEQ ID No. 1889:
MVKKSLRQFTLMATATVTLLLGSVPLYAQTADVQQKLAELERQSGGRLGV
ALINTADNSQILYRADERFAMCSTSKVMAAAAVLKKSESEPNLLNQRVEI
KKSDLVNYNPIAEKHVNGTMSLAELIAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTDGL

SEQ ID No. 1890:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQREQLVTWLKGNTTGAASIRAGLPTSWTVGDKTGSGGYGTTNDIA
VIWPQGRAPLVLVTYFTQPQQNAESRRDVLASAARIIAEGL

SEQ ID No. 1891:
MVTKRVQRMMFAAAACIPLLLGSAPLYAQTSAVQQKLAALEKSSGGRLGV
ALIDTADNTQVLYRGDERFPMCSTSKVMAVAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQREQLVTWLKGNTTGAASIRAGLPTSWTVGDKTGSGGYGTTNDIA
VIWPQGRAPLVLVTYFTQPQQNAESRRDVLASAARIIAEGL

SEQ ID No. 1892:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAENRRDVLASAARIIAEGL

SEQ ID No. 1893:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDRTGSGDYGTTNDIA
VIWPQGRAPLVLVTYFTQPQQNAESRHDVLASAARIIAEG

SEQ ID No. 1894:
MVKKSLRQFTLMATATVTLLLGSVPLYAQTADVQQKLAELERQSGGRLGV
ALINTADNSQILYRADERFAMCSTSKVMAVAAVLKKSESEPNLLNQRVEI
KKSDLVNYNPIAEKHVNGTMSLAELSAAALQYSDNVAMNKLIAHVGGPAS
VTAFARQLGDETFRLDRTEPTLNTAIPGDPRDTTSPRAMAQTLRNLTLGK
ALGDSQRAQLVTWMKGNTTGAASIQAGLPASWVVGDKTGSGGYGTTNDIA
VIWPKDRAPLILVTYFTQPQPKAESRRDVLASAAKIVTNGL

SEQ ID No. 1895:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEEHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGNL

SEQ ID No. 1896:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELSAAALQYSDNTAMNKLIAQLGGQGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 1897:
VKKSLRQFTLMATATVTLLLGSVPLYAQTADVQQKLAELERQSGGRLGVA
LINTADNSQILYRADERFAMCSTSKVMAAAAVLKKSESEPNLLNQRVEIK
KSDLVNYNPIAEKHVNGTMSLAELSAAALQYSDNVAMNKLIAHVGGPASV
TAFARQLGDETFRLDRTEPTLNTAIPGDPRDTTSPRAMAQTLRNLTLGKA
LGDSQRAQLVTWMKGNTTGAASIQAGLPASWVVGDRTGSGGYGTTNDIAV
IWPKDRAPLILVTYFTQPQPKAESRRDVLASAAKIVT

SEQ ID No. 1898:
VKKSLRQFTLMATATVTLLLGSVPLYAQTADVQQKLAELERQSGGRLGVA
LINTADNSQILYRADERFAMCSTSKVMAAAAVLKKSESEPNLLNQRAEIK
KSDLVNYNPIAEKHVNGTMSLAELSAAALQYSDNVAMNKLIAHVGGPASV
TAFARQLGDETFRLDRTEPTLNTAIPGDPRDTTSPRAMAQTLRNLTLGKA
LGDSQRAQLVTWMKGNTTGAASIQAGLPASWVVGDKTGSGGYGTTNDIAV
IWPKDRAPLILVTYFTQPQPKAESRRDVLASAAKIVT

SEQ ID No. 1899:
MVTKRVQRMMFAAAACIPLLLGSAPLYAQTSAVQQKLAALEKSSGGRLGV
ALIDTADNTQVLYRGDERFPMCSTSKVMAAAAVLKQSETQKQLLNQPVEI
KPADLVNYNPIAEKHVNGTMTLAELGAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 1900:
MVTKRVQRMMFAAAACIPLLLGSAPLYAQTSAVQQKLAALEKSSGGRLGV
ALIDTADNTQVLYRGDERFPMCSTSKVMAAAAVLKRSETQKQLLNQPVEI
KPADLVNYNPIAEKHVNGTMTLAELSAAALQYSDNTAMNKLIAQLGGPGG
VTAFARAIGDETFRLDRTEPTLNTAIPGDPRDTTTPRAMAQTLRQLTLGH
ALGETQRAQLVTWLKGNTTGAASIRAGLPTSWTVGDKTGSGDYGTTNDIA
VIWPQGRAPLVLVTYFTQPQQNAESRRDVLASAARIIAEGL

SEQ ID No. 1901:
VKKSLRQFTLMATATVTLLLGSVPLYAQTADVQQKLAELERQSGGRLGVA
LINTADNSRILYRADERFAMCSTSKVMAAAAVLKKSESEPNLLNQRVEIK
KSDLVNYNPIAEKHVNGTMSLAELSAAALQYSDNVAMNKLIAHVGGPASV
TAFARQLGDETFRLDRTEPTLNTAIPGDPRDTTSPRAMAQTLRNLTLGKA
LGDSQRAQLVTWMKGNTTGAASIQAGLPASWVVGDKTGSGGYGTTNDIAV
IWPKDRAPLILVTYFTQPQPKAESRRDVLASAAKIVTK

SEQ ID No. 1902:
MMTQSIRRSMLTVMATLPLLFSSATLHAQANSVQQQLEALEKSSGGRLGV

ALINTADNSQILYRADERFAMCSTSKVMAAAAVLKQSESDKHLLNQRVEI

KKSDLVNYNPIAEKHVNGTMTLAELGAAALQYSDNTAMNKLIAHLGGPDK

VTAFARSLGDETFRLDRTEPTLNTAIPGDPRDTTTPLAMAQTLKNLTLGK

ALAETQRAQLVTWLKGNTTGSASIRAGLPKSWVVGDKTGSGDYGTTNDIA

VIWPENHAPLVLVTYFTQPEQKAERRRDILAAAAKIVTHGF

SEQ ID No. 1903:
MRHRVKRMMLMTTACISLLLGSAPLYAQANDVQQKLAALEKSSGGRLGVA

LIDTADNAQTLYRADERFAMCSTSKVMAAAAVLKQSETQKNVLSQKVEIK

SSDLINYNPIAEKHVNGTMTLAELSAAALQYSDNTAMNKLIAHLGGPDKV

TAFARAIGDDTFRLDRTEPTLNTAIPGDPRDTTTPLAMAQTLRHLTLGSA

LGETQRAQLVTWLKGNTTGAASIQAGLPTSWVVGDKTGSGDYGTTNDIAV

IWPEGRAPLILVTYFTQPEQKAENRRDVLAAAAKIVTDGY

SEQ ID No. 1904:
MVKKSLRQFTLMATATVTLLLGSVPLYAQTADVQQKLAELERQSGGRLGV

ALINTADNSQILYRADERFAMCSTSKVMAVAAVLKKSESEPNLLNQRVEI

KKSDLVNYNPIAEKHVDGTMSLAELSAAALQYSDNVAMNKLISHVGGPAS

VTAFARQLGDETFRLDRTEPTLNTAIPGDPRDTTSPRAMAQTLRNLTLGK

ALGDSQRAQLVTWMKGNTTGAASIQAGLPASWVVGDKTGSGDYGTTNDIA

VIWPKDRAPLILVTYFTQPQPKAESRRDVLASAAKIVTNGL

SEQ ID No. 1905:
MMTQSIRRSMLTVMATLPLLFSSATLHAQANSVQQQLEALEKSSGGRLGV

ALINTADNSQILYRADERFAMCSTSKVMAAAAVLKQSESDKHLLNQRVEI

KKSDLVNYNPIAEKHVNGTMTLAELGAAALQYSDNTAMNKLIAHLGGPDK

VTAFARSLGDETFRLDRTEPTLNTAIPGDPRDTTTPLAMAQTLKNLTLGK

ALAETQRAQLVTWLKGNTTGSASIRAGLPKSWVVGDKTGSGDYGTTNDIA

VIWPENHAPLVLVTYFTQPEQKAESRRDILAAAAKIVTHGF

SEQ ID No. 1906:
MVKKSLRQFTLMATATVTLLLGSVPLYAQTADVQQKLAELERQSGGRLGV

ALINTADNSQILYRADERFAMCSTSKVMAAAAVLKKSESEPNLLNQRVEI

KKSDLVNYNPIAEKHVNGTMSLAELSAAALQYSDNVAMNKLIAHVGGPAS

VTAFARQLGDETFRLDRTEPTLNTAIPGDPRDTTSPRAMAQTLRNLTLGK

ALGDSQRAQLVTWMKGNTTGAASIQAGLPASWVVGDKTGSGDYGTTNDIA

VIWPKDRAPLILVTYFTQPQPKAESRRDVLASAAKIVTDGL

SEQ ID No. 1907:
MMTQSIRRSMLTVMATLPLLFSSATLHAQANSVQQQLEALEKSSGGRLGV

ALINTADNSQILYRADERFAMCSTSKVMAAAAVLKQSESDKHLLNQRVEI

KKSDLVNYNPIAEKHVNGTMTLAELGAAALQYSDNTAMNKLIAHLGGPDK

VTAFARSLGDETFRLDRTEPTLNTAIPGDPRDTTTPLAMAQTLKNLTLGK

ALAETQRAQLVTWLKGNTTGSASIRAGLPKSWVVGDKTGSGDYGTTNDIA

VIWPENHAPLVLVTYFTQPEQKAESRRDFLAAAAKIVTHGF

SEQ ID No. 1908:
MVKKSLRQFTLMATATVTLLLGSVPLYAQTADVQQKLAELERQSGGRLGV

ALINTADNSQILYRADERFAMCSTSKVMAAAAVLKKSESEPNLLNQRVEI

KKSDLVNYNPIAEKHVNGTMSLAELSAAALQYSDNVAMNKLIAHVGGPAS

VTAFARQLGDETFRLDRTEPTLNTAIPGDPRDTTSPRAMAQTLRNLTLGK

ALGDSQRAQLVTWMKGNTTGAASIQAGLPASWVVGDKTGSGGYGTTNDIA

VIWPKDRAPLILVTYFTQPQPKAESRRDVLASAAKIVTNGL said peptides being chosen, preferably, from the peptides of sequence SEQ ID No. 446 to SEQ ID 495 and SEQ ID No. 2008 to SEQ ID No. 2092 as defined hereafter:

| Peptide SEQ ID No. | Amino acid sequence | Position of the peptide in the CTX-M protein | Clinical interest |
|---|---|---|---|
| SEQ ID No. 446 | AGLPK | 226-230 for the proteins of SEQ No. 351, 386, 392, 397, 415, 416, 419, 422, 424, 429, 430, 432, 435, 439, 442, 444, 445, 1881, 1903, 1906, 1908 | 2be |
| SEQ ID No. 447 | AGLPTSWTVGDK | 226-237 for the proteins of SEQ No. 355, 356, 360, 361, 362, 367, 369, 376, 377, 378, 379, 380, 381, 398, 402, 403, 407, 408, 409, 410, 411, 413, 421, 423, 436, 1872, 1873, 1874, 1877, 1882, 1886, 1888, 1889, 1891, 1892, 1893, 1896, 1897, 1900, 1901; 224-235 for the protein of sequence SEQ ID No. 425 | 2be |
| SEQ ID No. 448 | AIGDETFR | 157-164 for the proteins of SEQ No. 353, 355, 359, 360, 361, 362, 367, 369, 376, 377, 378, 379, 380, 381, 387, 398, 402, 403, 407, 408, 409, 410, 411, 413, 421, 423, 425, 428, 436, 1872, 1873, 1874, 1877, 1882, 1886, 1888, 1889, 1891, 1892, 1893, 1894, 1896, 1897, 1900, 1901 | 2be |
| SEQ ID No. 449 | ALAETQR | 201-207 for the proteins of SEQ No. 351, 386, 392, 397, 415, 416, 419, 422, 424, 429, 430, 432, 434, 435, 439, 442, 444, 445, 1881, 1903, 1906, 1908 | 2be |
| SEQ ID No. 450 | ALGDSQR | 201-207 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 440, 441, 1875, 1876, 1879, 1880, 1883, 1884, 1885, 1887, 1890, 1895, | 2be |

-continued

| Peptide SEQ ID No. | Amino acid sequence | Position of the peptide in the CTX-M protein | Clinical interest |
|---|---|---|---|
| | | 1905, 1907, 1909; 200-206 for the protein of sequence SEQ ID No. 1898; 200-206 for the protein of sequence SEQ ID No. 1899; 200-206 for the protein of sequence SEQ ID No. 1902 | |
| SEQ ID No. 451 | AMAQTLR | 188-194 for the proteins of SEQ No. 352, 353, 354, 355, 356, 357, 358, 359, 360, 361, 362, 363, 364, 365, 367, 369, 370, 371, 372, 373, 374, 376, 377, 378, 379, 380, 381, 382, 385, 387, 388, 389, 390, 391, 393, 394, 395, 396, 398, 399, 400, 401, 402, 403, 404, 405, 406, 407, 408, 409, 410, 411, 412, 413, 417, 421, 423, 426, 428, 431, 433, 436, 437, 438, 440, 441, 443, 1872, 1873, 1874, 1875, 1876, 1877, 1879, 1880, 1882, 1883, 1884, 1885, 1886, 1887, 1888, 1889, 1890, 1891, 1892, 1893, 1894, 1895, 1896, 1897, 1900, 1901, 1905, 1907, 1909; 187-193 for the protein of sequence SEQ ID No. 375; 187-193 for the protein of sequence SEQ ID No. 427; 187-193 for the protein of sequence SEQ ID No. 1878; 187-193 for the protein of sequence SEQ ID No. 1898; 187-193 for the protein of sequence SEQ ID No. 1899; 187-193 for the protein of sequence SEQ ID No. 1902; 187-193 for the protein of sequence SEQ ID No. 1904 | 2be |
| SEQ ID No. 452 | APLILVTYFTQPQPK | 258-272 for the proteins of SEQ No. 354, 357, 358, 363, 364, 365, 370, 371, 372, 373, 374, 382, 385, 388, 389, 391, 393, 394, 395, 396, 399, 400, 401, 404, 405, 412, 417, 426, 428, 431, 433, 437, 438, 440, 441, 1875, 1876, 1879, 1880, 1883, 1885, 1887, 1890, 1895, 1905, 1907, 1909; 257-271 for the protein of sequence SEQ ID No. 1898; 257-271 for the protein of sequence SEQ ID No. 1899; 257-271 for the protein of sequence SEQ ID No. 1902 | 2be |
| SEQ ID No. 453 | APLVLVTYFTQPQQNAESR | 258-276 for the proteins of SEQ No. 353, 355, 356, 359, 360, 361, 362, 369, 376, 377, 378, 379, 380, 381, 387, 402, 403, 407, 408, 409, 410, 411, 413, 423, 436, 1872, 1873, 1874, 1886, 1889, 1891, 1892, 1894, 1896, 1897, 1900, 1901; 256-274 for the protein of sequence SEQ ID No. 425 | 2be |
| SEQ ID No. 454 | AQLVTWLK | 208-215 for the proteins of SEQ No. 351, 352, 353, 355, 356, 359, 360, 361, 362, 367, 369, 376, 377, 378, 379, 380, 381, 386, 387, 392, 397, 398, 402, 403, 407, 408, 410, 411, 413, 415, 416, 421, 422, 423, 424, 428, 429, 430, 432, 434, 435, 436, 439, 442, 443, 444, 445, 1872, 1873, 1874, 1877, 1881, 1882, 1886, 1888, 1889, 1893, 1894, 1896, 1897, 1900, 1901, 1903, 1906, 1908; 207-214 for the protein of SEQ ID No. 375; 207-214 for the protein of sequence SEQ ID No. 427; 207-214 for the protein of sequence SEQ ID No. 1878; 207-214 for the protein of sequence SEQ ID No. 1904 | 2be |
| SEQ ID No. 455 | AQLVTWMK | 208-215 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 440, 441, 1875, 1876, 1879, 1880, 1883, 1884, 1885, 1887, 1890, 1895, 1905, 1907, 1909; 207-214 for the protein of sequence SEQ ID No. 1898; 207-214 for the protein of sequence SEQ ID No. 1899; 207-214 for the protein of sequence SEQ ID No. 1902 | 2be |
| SEQ ID No. 456 | DILAAAAK | 278-285 for the proteins of SEQ No. 386, 392, 397, 415, 416, 419, 422, 424, 432, 434, 439, 1881, 1903, 1906 | 2be |
| SEQ ID No. 457 | DTTSPR | 182-187 for the proteins of SEQ No. 354, 357, 358, 363, 364, 365, 370, 371, 372, 373, 374, 382, 385, 388, 389, 390, 391, 393, 394, 395, 396, 399, 400, 401, 405, 406, 412, 417, 426, 431, 433, 437, 438, 440, 441, 1875, 1876, 1879, 1880, 1883, 1884, 1885, 1887, 1890, 1895, 1905, 1907, 1909; 181-186 for the protein of sequence SEQ ID No. 1898; 181-186 for the protein of sequence SEQ ID No. 1899; 181-186 for the protein of sequence SEQ ID No. 1902 | 2be |

-continued

| Peptide SEQ ID No. | Amino acid sequence | Position of the peptide in the CTX-M protein | Clinical interest |
|---|---|---|---|
| SEQ ID No. 458 | DTTTPLAMAQTLK | 182-194 for the proteins of SEQ No. 351, 386, 392, 397, 415, 416, 419, 422, 424, 429, 430, 432, 434, 435, 439, 442, 444, 445, 1881, 1903, 1906, 1908 | 2be |
| SEQ ID No. 459 | DTTTPR | 182-187 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 428, 436, 1872, 1873, 1874, 1877, 1882, 1886, 1888, 1889, 1891, 1892, 1893, 1894, 1896, 1897, 1900, 1901 | 2be |
| SEQ ID No. 460 | DVLAAAAK | 277-284 for the proteins of SEQ No. 375, 427, 1878, 1904; 278-285 for the protein of sequence SEQ ID No. 351; 278-285 for the protein of sequence SEQ ID No. 352; 278-285 for the protein of sequence SEQ ID No. 429; 278-285 for the protein of sequence SEQ ID No. 430; 278-285 for the protein of sequence SEQ ID No. 442; 278-285 for the protein of sequence SEQ ID No. 444; 278-285 for the protein of sequence SEQ ID No. 445 | 2be |
| SEQ ID No. 461 | DVLASAAK | 278-285 for the proteins of SEQ No. 354, 363, 364, 365, 370, 371, 372, 373, 374, 382, 385, 388, 389, 390, 391, 393, 394, 395, 396, 399, 400, 401, 404, 405, 406, 412, 417, 426, 428, 431, 433, 437, 438, 1875, 1876, 1879, 1880, 1883, 1884, 1885, 1887, 1890, 1895, 1905, 1907, 1909; 277-284 for the protein of sequence SEQ ID No. 1898; 277-284 for the protein of sequence SEQ ID No. 1899; 277-284 for the protein of sequence SEQ ID No. 1902 | 2be |
| SEQ ID No. 462 | DVLASAAR | 278-285 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 436, 1872, 1873, 1874, 1877, 1882, 1886, 1888, 1889, 1891, 1892, 1893, 1894, 1896, 1897, 1900, 1901; 276-283 for the protein of sequence SEQ ID No. 425 | 2be |
| SEQ ID No. 463 | FAMCSTSK | 69-76 for the proteins of SEQ No. 351, 352, 354, 357, 358, 363, 364, 365, 366, 368, 370, 371, 372, 373, 374, 382, 383, 384, 385, 386, 388, 390, 391, 392, 393, 394, 395, 396, 397, 399, 400, 401, 404, 405, 406, 412, 414, 415, 416, 417, 418, 419, 420, 422, 424, 426, 429, 430, 431, 432, 433, 434, 435, 437, 438, 439, 440, 441, 442, 443, 444, 445, 1875, 1876, 1879, 1880, 1881, 1883, 1884, 1885, 1887, 1890, 1895, 1903, 1905, 1906, 1907, 1908, 1909; 68-75 for the protein of sequence SEQ ID No. 375; 68-75 for the protein of sequence SEQ ID No. 427; 68-75 for the protein of sequence SEQ ID No. 1878; 68-75 for the protein of sequence SEQ ID No. 1898; 68-75 for the protein of sequence SEQ ID No. 1899; 68-75 for the protein of sequence SEQ ID No. 1902; 68-75 for the protein of sequence SEQ ID No. 1904 | 2be |
| SEQ ID No. 464 | FPMCSTSK | 69-76 for the proteins of SEQ No. 353, 355, 356, 359, 360, 361, 362, 367, 369, 376, 377, 378, 379, 380, 381, 387, 389, 398, 402, 403, 407, 408, 409, 410, 411, 413, 421, 423, 425, 428, 436, 1872, 1873, 1874, 1877, 1882, 1886, 1888, 1889, 1891, 1892, 1893, 1894, 1896, 1897, 1900, 1901 | 2be |
| SEQ ID No. 465 | GNTTGAASIQAGLPASWVVGDK | 216-237 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 440, 441, 1875, 1876, 1879, 1880, 1883, 1884, 1885, 1887, 1890, 1895, 1905, 1907, 1909; 215-236 for the protein of sequence SEQ ID No. 1899; 215-236 for the protein of sequence SEQ ID No. 1902 | 2be |
| SEQ ID No. 466 | GNTTGAASIQAGLPTSWVVGDK | 215-236 for the proteins of SEQ No. 375, 427, 1878, 1904; 216-237 for the protein of sequence SEQ ID No. 352; 216-237 for the protein of sequence SEQ ID No. 366; 216-237 for the protein of sequence SEQ ID No. 383; 216-237 for the protein of sequence SEQ ID No. 384; 216-237 for the protein of sequence SEQ ID No. 414; 216-237 for the protein of sequence SEQ ID No. | 2be |

-continued

| Peptide SEQ ID No. | Amino acid sequence | Position of the peptide in the CTX-M protein | Clinical interest |
|---|---|---|---|
| | | 418; 216-237 for the protein of sequence SEQ ID No. 420; 216-237 for the protein of sequence SEQ ID No. 443 | |
| SEQ ID No. 467 | GNTTGAASIR | 216-225 for the proteins of SEQ No. 353, 355, 356, 359, 360, 361, 362, 367, 368, 369, 377, 378, 379, 380, 381, 387, 398, 402, 403, 407, 408, 409, 410, 411, 413, 421, 423, 428, 436, 1872, 1873, 1874, 1877, 1882, 1886, 1888, 1889, 1891, 1892, 1893, 1894, 1896, 1897, 1900, 1901 | 2be |
| SEQ ID No. 468 | GNTTGSASIR | 216-225 for the proteins of SEQ No. 351, 386, 392, 397, 415, 416, 419, 422, 424, 429, 430, 432, 434, 435, 439, 444, 1881, 1903, 1906, 1908 | 2be |
| SEQ ID No. 469 | HLLNQR | 92-97 for the proteins of SEQ No. 351, 386, 397, 415, 416, 419, 422, 424, 429, 430, 432, 434, 435, 439, 442, 444, 445, 1881, 1903, 1906, 1908 | 2be |
| SEQ ID No. 470 | LAALEK | 36-41 for the proteins of SEQ No. 375, 427, 1878, 1904; 37-42 for the proteins of sequence SEQ ID No. 352, 353, 355, 356, 359, 360, 361, 362, 366, 367, 368, 369, 376, 377, 378, 379, 380, 381, 383, 384, 387, 398, 402, 403, 407, 408, 409, 410, 411, 413, 414, 418, 420, 421, 423, 425, 436, 443, 1872, 1873, 1874, 1877, 1882, 1886, 1888, 1889, 1891, 1892, 1893, 1894, 1896, 1897, 1900, 1901 | 2be |
| SEQ ID No. 471 | LAELER | 37-42 for the proteins of SEQ No. 358, 363, 364, 365, 370, 371, 372, 382, 385, 388, 389, 391, 393, 394, 395, 396, 399, 400, 401, 404, 405, 406, 412, 417, 426, 428, 431, 433, 437, 438, 440, 441, 1875, 1876, 1879, 1880, 1883, 1884, 1885, 1887, 1890, 1895, 1905, 1907, 1909; 36-41 for the protein of sequence SEQ ID No. 1898; 36-41 for the protein of sequence SEQ ID No. 1899; 36-41 for the protein of sequence SEQ ID No. 1902 | 2be |
| SEQ ID No. 472 | LGVALIDTADNTQVLYR | 48-64 for the proteins of SEQ No. 353, 355, 359, 360, 361, 362, 367, 369, 376, 377, 378, 387, 398, 402, 403, 407, 409, 410, 411, 413, 421, 423, 425, 436, 1872, 1873, 1874, 1877, 1882, 1886, 1888, 1889, 1891, 1892, 1893, 1894, 1896, 1897, 1900, 1901 | 2be |
| SEQ ID No. 473 | LGVALINTADNSQILYR | 48-64 for the proteins of SEQ No. 351, 354, 357, 358, 363, 364, 365, 370, 371, 372, 373, 374, 382, 385, 386, 388, 389, 390, 391, 392, 393, 394, 395, 396, 397, 399, 400, 401, 404, 405, 406, 412, 415, 416, 417, 419, 422, 424, 426, 428, 431, 432, 433, 435, 437, 438, 439, 440, 441, 442, 444, 445, 1875, 1876, 1879, 1880, 1881, 1883, 1884, 1885, 1887, 1890, 1895, 1903, 1905, 1906, 1907, 1908, 1909; 47-63 for the protein of sequence SEQ ID No. 1898; 47-63 for the protein of sequence SEQ ID No. 1899 | 2be |
| SEQ ID No. 474 | LIAHLGGPDK | 141-150 for the proteins of SEQ No. 351, 352, 366, 368, 383, 384, 386, 392, 397, 414, 415, 416, 418, 419, 420, 422, 424, 429, 430, 432, 434, 435, 439, 442, 444, 445, 1881, 1903, 1906, 1908; 140-149 for the protein of sequence SEQ ID No. 375; 140-149 for the protein of sequence SEQ ID No. 427; 140-149 for the protein of sequence SEQ ID No. 1878; 140-149 for the protein of sequence SEQ ID No. 1904 | 2be |
| SEQ ID No. 475 | LIAHVGGPASVTAFAR | 141-156 for the proteins of SEQ No. 354, 357, 358, 363, 364, 365, 370, 371, 372, 373, 374, 382, 385, 388, 389, 390, 391, 393, 394, 399, 400, 401, 404, 405, 406, 412, 417, 433, 437, 440, 441, 1875, 1876, 1879, 1883, 1884, 1885, 1887, 1890, 1895, 1907, 1909; 140-155 for the protein of sequence SEQ ID No. 1898; 140-155 for the protein of sequence SEQ ID No. 1899; 140-155 for the protein of sequence SEQ ID No. 1902 | 2be |
| SEQ ID No. 476 | LIAQLGGPGGVTAFAR | 141-156 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 425, 428, 436, 1872, 1873, 1874, 1877, 1882, 1886, 1888, 1889, 1891, 1892, 1893, 1894, 1896, 1900, 1901 | 2be |

-continued

| Peptide SEQ ID No. | Amino acid sequence | Position of the peptide in the CTX-M protein | Clinical interest |
|---|---|---|---|
| SEQ ID No. 477 | NLTLGK | 195-200 for the proteins of SEQ No. 351, 354, 357, 358, 363, 364, 365, 370, 371, 372, 373, 374, 382, 385, 386, 388, 389, 390, 391, 392, 393, 394, 395, 396, 397, 399, 400, 401, 404, 405, 406, 412, 415, 416, 417, 419, 422, 424, 426, 429, 430, 431, 432, 433, 434, 435, 437, 438, 439, 440, 441, 442, 444, 445, 1875, 1876, 1879, 1880, 1881, 1883, 1884, 1885, 1887, 1890, 1895, 1903, 1905, 1906, 1907, 1908, 1909; 194-199 for the protein of sequence SEQ ID No. 1898; 194-199 for the protein of sequence SEQ ID No. 1899; 194-199 for the protein of sequence SEQ ID No. 1902 | 2be |
| SEQ ID No. 478 | QLGDETFR | 157-164 for the proteins of SEQ No. 354, 357, 358, 363, 364, 365, 370, 371, 372, 373, 374, 382, 385, 388, 389, 390, 391, 393, 394, 395, 396, 399, 400, 401, 405, 406, 412, 417, 426, 431, 433, 437, 438, 440, 441, 1875, 1876, 1879, 1880, 1883, 1884, 1885, 1887, 1890, 1895, 1905, 1907, 1909; 156-163 for the protein of sequence SEQ ID No. 1898; 156-163 for the protein of sequence SEQ ID No. 1899; 156-163 for the protein of sequence SEQ ID No. 1902 | 2be |
| SEQ ID No. 479 | QLLNQPVEIK | 92-101 for the proteins of SEQ No. 353, 355, 356, 359, 360, 361, 362, 367, 369, 376, 377, 378, 379, 380, 381, 387, 398, 402, 407, 408, 409, 410, 411, 413, 421, 423, 425, 428, 436, 1872, 1873, 1874, 1877, 1882, 1886, 1888, 1889, 1891, 1892, 1893, 1894, 1896, 1897, 1900, 1901 | 2be |
| SEQ ID No. 480 | QLTLGHALGETQR | 195-207 for the proteins of SEQ No. 353, 355, 356, 359, 360, 361, 362, 367, 369, 376, 377, 378, 379, 380, 381, 387, 398, 402, 403, 407, 408, 409, 410, 411, 413, 421, 423, 428, 436, 1872, 1873, 1874, 1877, 1882, 1886, 1888, 1889, 1891, 1892, 1893, 1894, 1896, 1897, 1900, 1901 | 2be |
| SEQ ID No. 481 | QSESDK | 86-91 for the proteins of SEQ No. 351, 386, 392, 397, 415, 416, 419, 422, 424, 429, 430, 432, 434, 435, 439, 442, 444, 445, 1881, 1903, 1906, 1908 | 2be |
| SEQ ID No. 482 | QSETQK | 85-90 for the proteins of SEQ No. 375, 427, 1878, 1904; 86-91 for the protein of sequence SEQ ID No. 352; 86-91 for the protein of sequence SEQ ID No. 353; 86-91 for the protein of sequence SEQ ID No. 355; 86-91 for the protein of sequence SEQ ID No. 356; 86-91 for the protein of sequence SEQ ID No. 359; 86-91 for the protein of sequence SEQ ID No. 360; 86-91 for the protein of sequence SEQ ID No. 361; 86-91 for the protein of sequence SEQ ID No. 362; 86-91 for the protein of sequence SEQ ID No. 366; 86-91 for the protein of sequence SEQ ID No. 367; 86-91 for the protein of sequence SEQ ID No. 368; 86-91 for the protein of sequence SEQ ID No. 369; 86-91 for the protein of sequence SEQ ID No. 376; 86-91 for the protein of sequence SEQ ID No. 377; 86-91 for the protein of sequence SEQ ID No. 378; 86-91 for the protein of sequence SEQ ID No. 379; 86-91 for the protein of sequence SEQ ID No. 380; 86-91 for the protein of sequence SEQ ID No. 381; 86-91 for the protein of sequence SEQ ID No. 383; 86-91 for the protein of sequence SEQ ID No. 384; 86-91 for the protein of sequence SEQ ID No. 387; 86-91 for the protein of sequence SEQ ID No. 398; 86-91 for the protein of sequence SEQ ID No. 402; 86-91 for the protein of sequence SEQ ID No. 403; 86-91 for the protein of sequence SEQ ID No. 407; 86-91 for the protein of sequence SEQ ID No. 408; 86-91 for the protein of sequence SEQ ID No. 409; 86-91 for the protein of sequence SEQ ID No. 410; 86-91 for the protein of sequence SEQ ID No. 411; 86-91 for the protein of sequence SEQ ID No. 413; 86-91 for the protein of sequence SEQ ID No. 414; 86-91 for the protein of sequence SEQ ID No. 418; 86-91 for the protein of sequence SEQ ID No. 420; 86-91 for the protein of sequence SEQ ID No. 421; 86-91 for the protein of sequence SEQ ID No. 423; 86-91 for the protein of sequence SEQ ID No. 425; 86-91 for the | 2be |

-continued

| Peptide SEQ ID No. | Amino acid sequence | Position of the peptide in the CTX-M protein | Clinical interest |
|---|---|---|---|
| | | protein of sequence SEQ ID No. 428; 86-91 for the protein of sequence SEQ ID No. 436; 86-91 for the protein of sequence SEQ ID No. 443; 86-91 for the protein of sequence SEQ ID No. 1872; 86-91 for the protein of sequence SEQ ID No. 1873; 86-91 for the protein of sequence SEQ ID No. 1874; 86-91 for the protein of sequence SEQ ID No. 1877; 86-91 for the protein of sequence SEQ ID No. 1882; 86-91 for the protein of sequence SEQ ID No. 1886; 86-91 for the protein of sequence SEQ ID No. 1888; 86-91 for the protein of sequence SEQ ID No. 1889; 86-91 for the protein of sequence SEQ ID No. 1891; 86-91 for the protein of sequence SEQ ID No. 1892; 86-91 for the protein of sequence SEQ ID No. 1893; 86-91 for the protein of sequence SEQ ID No. 1894; 86-91 for the protein of sequence SEQ ID No. 1896; 86-91 for the protein of sequence SEQ ID No. 1897; 86-91 for the protein of sequence SEQ ID No. 1900 | |
| SEQ ID No. 483 | QSGGR | 43-47 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 428, 431, 433, 437, 438, 440, 441, 1875, 1876, 1879, 1880, 1883, 1884, 1885, 1887, 1890, 1895, 1905, 1907, 1909; 42-46 for the protein of sequence SEQ ID No. 1898; 42-46 for the protein of sequence SEQ ID No. 1899; 42-46 for the protein of sequence SEQ ID No. 1902 | 2be |
| SEQ ID No. 484 | SDLVNYNPIAEK | 103-114 for the proteins of SEQ No. 351, 354, 357, 358, 363, 364, 365, 371, 372, 373, 374, 382, 384, 385, 386, 388, 389, 390, 391, 392, 393, 394, 395, 396, 397, 399, 400, 401, 404, 405, 406, 412, 415, 416, 417, 419, 422, 424, 426, 429, 430, 431, 432, 433, 434, 435, 437, 438, 439, 440, 441, 442, 444, 445, 1875, 1876, 1879, 1880, 1881, 1883, 1884, 1885, 1887, 1890, 1895, 1903, 1905, 1906, 1907, 1908, 1909; 102-113 for the protein of sequence SEQ ID No. 1898; 102-113 for the protein of sequence SEQ ID No. 1899; 102-113 for the protein of sequence SEQ ID No. 1902 | 2be |
| SEQ ID No. 485 | SESEPNLLNQR | 87-97 for the proteins of SEQ No. 354, 357, 363, 364, 365, 370, 371, 372, 373, 374, 382, 385, 388, 389, 390, 391, 393, 394, 395, 396, 399, 400, 401, 404, 405, 406, 412, 417, 426, 431, 433, 437, 438, 1875, 1876, 1879, 1880, 1883, 1884, 1885, 1887, 1890, 1895, 1905, 1907, 1909; 86-96 for the protein of sequence SEQ ID No. 1898; 86-96 for the protein of sequence SEQ ID No. 1899; 86-96 for the protein of sequence SEQ ID No. 1902 | 2be |
| SEQ ID No. 486 | SLGDETFR | 157-164 for the proteins of SEQ No. 351, 386, 392, 397, 415, 416, 419, 422, 424, 429, 430, 432, 434, 435, 442, 444, 445, 1881, 1903, 1906, 1908 | 2be |
| SEQ ID No. 487 | SSGGR | 43-47 for the proteins of SEQ No. 351, 352, 353, 355, 356, 359, 360, 361, 362, 366, 367, 368, 369, 376, 378, 380, 381, 383, 384, 386, 387, 392, 397, 398, 402, 403, 407, 408, 409, 410, 411, 413, 414, 415, 416, 418, 419, 420, 421, 422, 423, 424, 425, 429, 430, 432, 434, 435, 436, 439, 442, 443, 444, 445, 1872, 1873, 1874, 1877, 1881, 1882, 1886, 1888, 1889, 1891, 1892, 1893, 1894, 1896, 1897, 1900, 1901, 1903, 1906, 1908; 42-46 for the protein of sequence SEQ ID No. 375; 42-46 for the protein of sequence SEQ ID No. 427; 42-46 for the protein of sequence SEQ ID No. 1878; 42-46 for the protein of sequence SEQ ID No. 1904 | 2be |
| SEQ ID No. 488 | SWVVGDK | 231-237 for the proteins of SEQ No. 352, 354, 357, 358, 363, 364, 365, 366, 368, 370, 371, 372, 373, 374, 382, 383, 384, 385, 386, 388, 389, 390, 391, 392, 393, 394, 395, 396, 397, 399, 400, 401, 404, 405, 406, 412, 414, 415, 416, 417, 418, 419, 420, 422, 424, 426, 428, 431, 432, 433, 435, 437, 438, 439, 440, 441, 442, 443, 445, 1875, 1876, 1879, 1880, 1881, 1883, 1884, 1885, 1887, 1890, 1895, 1903, 1905, 1906, 1907, 1908, 1909; 230-236 | 2be |

| Peptide SEQ ID No. | Amino acid sequence | Position of the peptide in the CTX-M protein | Clinical interest |
|---|---|---|---|
| | | for the protein of sequence SEQ ID No. 375; 230-236 for the protein of sequence SEQ ID No. 427; 230-236 for the protein of sequence SEQ ID No. 1878; 230-236 for the protein of sequence SEQ ID No. 1899; 230-236 for the protein of sequence SEQ ID No. 1902; 230-236 for the protein of sequence SEQ ID No. 1904 | |
| SEQ ID No. 489 | TEPTLNTAIPGDPR | 168-181 for the proteins of SEQ No. 351, 352, 353, 354, 355, 356, 357, 358, 359, 360, 362, 363, 364, 366, 367, 368, 369, 370, 371, 372, 373, 374, 376, 377, 378, 379, 380, 381, 382, 383, 384, 386, 387, 389, 390, 392, 393, 394, 396, 397, 398, 399, 401, 402, 403, 404, 405, 406, 408, 409, 410, 411, 412, 413, 414, 416, 417, 418, 419, 420, 422, 423, 424, 425, 426, 428, 431, 432, 433, 435, 436, 437, 438, 439, 440, 441, 442, 443, 444, 445, 1872, 1874, 1875, 1876, 1877, 1879, 1880, 1881, 1882, 1883, 1884, 1885, 1886, 1887, 1890, 1891, 1892, 1893, 1894, 1895, 1896, 1897, 1900, 1901, 1903, 1905, 1906, 1907, 1908, 1909; 167-180 for the protein of sequence SEQ ID No. 375; 167-180 for the protein of sequence SEQ ID No. 427; 167-180 for the protein of sequence SEQ ID No. 1878; 167-180 for the protein of sequence SEQ ID No. 1898; 167-180 for the protein of sequence SEQ ID No. 1899; 167-180 for the protein of sequence SEQ ID No. 1902; 167-180 for the protein of sequence SEQ ID No. 1904 | 2be |
| SEQ ID No. 490 | TGSGDYGTTNDIAVIWPK | 238-255 for the proteins of SEQ No. 354, 357, 358, 364, 365, 372, 374, 382, 385, 388, 391, 395, 396, 400, 401, 404, 405, 426, 431, 433, 441, 1876, 1880, 1895, 1905, 1907 | 2be |
| SEQ ID No. 491 | TGSGDYGTTNDIAVIWPQGR | 238-257 for the proteins of SEQ No. 353, 355, 356, 360, 361, 362, 367, 376, 377, 378, 379, 380, 381, 387, 398, 402, 403, 407, 408, 409, 410, 411, 413, 421, 436, 1872, 1873, 1874, 1877, 1882, 1886, 1888, 1893, 1894, 1896, 1897, 1900, 1901; 236-255 for the protein of sequence SEQ ID No. 425 | 2be |
| SEQ ID No. 492 | TGSGGYGTTNDIAVIWPK | 238-255 for the proteins of SEQ No. 363, 370, 371, 389, 390, 393, 394, 399, 406, 412, 428, 437, 438, 440, 1875, 1879, 1883, 1884, 1885, 1887, 1890, 1909; 237-254 for the protein of sequence SEQ ID No. 1898; 237-254 for the protein of sequence SEQ ID No. 1899; 237-254 for the protein of sequence SEQ ID No. 1902 | 2be |
| SEQ ID No. 493 | VMAAAAVLK | 77-85 for the proteins of SEQ No. 351, 352, 353, 354, 355, 356, 357, 358, 359, 360, 361, 362, 363, 364, 367, 368, 369, 370, 371, 372, 373, 374, 376, 377, 378, 379, 380, 381, 382, 383, 384, 385, 386, 389, 391, 392, 397, 400, 401, 402, 404, 405, 408, 409, 410, 411, 412, 415, 416, 417, 419, 420, 421, 422, 424, 425, 426, 428, 429, 430, 432, 433, 434, 435, 436, 437, 439, 440, 442, 443, 444, 1872, 1873, 1874, 1875, 1876, 1877, 1881, 1885, 1888, 1889, 1890, 1891, 1893, 1894, 1896, 1897, 1900, 1901, 1903, 1906, 1907, 1908, 1909; 76-84 for the protein of sequence SEQ ID No. 375; 76-84 for the protein of sequence SEQ ID No. 427; 76-84 for the protein of sequence SEQ ID No. 1878; 76-84 for the protein of sequence SEQ ID No. 1898; 76-84 for the protein of sequence SEQ ID No. 1899; 76-84 for the protein of sequence SEQ ID No. 1902; 76-84 for the protein of sequence SEQ ID No. 1904 | 2be |
| SEQ ID No. 494 | VMAVAAVLK | 77-85 for the proteins of SEQ No. 365, 366, 387, 388, 390, 393, 394, 395, 396, 398, 399, 406, 407, 413, 414, 418, 423, 431, 438, 441, 1879, 1880, 1882, 1883, 1884, 1886, 1892, 1895, 1905 | 2be |
| SEQ ID No. 495 | VTAFAR | 151-156 for the proteins of SEQ No. 351, 352, 353, 354, 355, 356, 357, 358, 359, 360, 361, 362, 363, 364, 365, 366, 367, 368, 369, 370, 371, 372, 373, 374, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, | 2be |

| Peptide SEQ ID No. | Amino acid sequence | Position of the peptide in the CTX-M protein | Clinical interest |
|---|---|---|---|
| | | 411, 412, 413, 414, 415, 416, 417, 418, 419, 420, 421, 422, 423, 424, 425, 426, 428, 429, 430, 431, 432, 433, 434, 435, 436, 437, 438, 439, 440, 441, 442, 443, 444, 445, 1872, 1873, 1874, 1875, 1876, 1877, 1879, 1880, 1881, 1882, 1883, 1884, 1885, 1886, 1887, 1888, 1889, 1890, 1891, 1892, 1893, 1894, 1895, 1896, 1897, 1900, 1901, 1903, 1905, 1906, 1907, 1908, 1909; 150-155 for the protein of sequence SEQ ID No. 375; 150-155 for the protein of sequence SEQ ID No. 427; 150-155 for the protein of sequence SEQ ID No. 1878; 150-155 for the protein of sequence SEQ ID No. 1898; 150-155 for the protein of sequence SEQ ID No. 1899; 150-155 for the protein of sequence SEQ ID No. 1902; 150-155 for the protein of sequence SEQ ID No. 1904 | |
| SEQ ID No. 2008 | AAGIR | 219-223 for the protein of SEQ No. 425 | 2be |
| SEQ ID No. 2009 | AGADVASLR | 188-196 for the protein of SEQ No. 425 | 2be |
| SEQ ID No. 2010 | AGLPASWVVGDK | 226-237 for the proteins of SEQ No. 354, 357, 358, 363, 364, 365, 370, 371, 372, 373, 374, 382, 385, 388, 389, 390, 391, 393, 394, 395, 396, 399, 400, 401, 404, 405, 406, 412, 417, 426, 428, 431, 433, 437, 438, 440, 441, 1875, 1876, 1879, 1880, 1883, 1884, 1885, 1887, 1890, 1895, 1905, 1907, 1909; 225-236 for the protein of sequence SEQ ID No. 1899; 225-236 for the protein of sequence SEQ ID No. 1902 | 2be |
| SEQ ID No. 2011 | AGLPTSWTAGDK | 226-237 for the proteins of SEQ No. 353, 359, 387 | 2be |
| SEQ ID No. 2012 | AGLPTSWTVGDR | 226-237 for the proteins of SEQ No. 1894 | 2be |
| SEQ ID No. 2013 | AGLPTSWVVGDK | 225-236 for the proteins of SEQ No. 375, 427, 1878, 1904; 226-237 for the protein of sequence SEQ ID No. 352; 226-237 for the protein of sequence SEQ ID No. 366; 226-237 for the protein of sequence SEQ ID No. 368; 226-237 for the protein of sequence SEQ ID No. 383; 226-237 for the protein of sequence SEQ ID No. 384; 226-237 for the protein of sequence SEQ ID No. 414; 226-237 for the protein of sequence SEQ ID No. 418; 226-237 for the protein of sequence SEQ ID No. 420; 226-237 for the protein of sequence SEQ ID No. 443 | 2be |
| SEQ ID No. 2014 | AGMPK | 226-230 for the protein of SEQ No. 434 | 2be |
| SEQ ID No. 2015 | AIGDDTFR | 156-163 for the proteins of SEQ No. 375, 427, 1878, 1904 | 2be |
| SEQ ID No. 2016 | AIGDNTFR | 157-164 for the protein of SEQ No. 352 | 2be |
| SEQ ID No. 2017 | AMAVAAVLK | 77-85 for the proteins of SEQ No. 1887 | 2be |
| SEQ ID No. 2018 | APLILVIYFTQPQPK | 258-272 for the protein of SEQ No. 390 | 2be |
| SEQ ID No. 2019 | APLILVTYFTQPEQK | 257-271 for the proteins of SEQ No. 375, 427, 1878, 1904; 258-272 for the protein of sequence SEQ ID No. 352 | 2be |
| SEQ ID No. 2020 | APLILVTYFTQPQPNAESR | 258-276 for the proteins of SEQ No. 406, 1884 | 2be |
| SEQ ID No. 2021 | APLVLVTYFTQPEPK | 258-272 for the protein of SEQ No. 443 | 2be |
| SEQ ID No. 2022 | APLVLVTYFTQPQQNAENR | 258-276 for the proteins of SEQ No. 1893 | 2be |

| Peptide SEQ ID No. | Amino acid sequence | Position of the peptide in the CTX-M protein | Clinical interest |
|---|---|---|---|
| SEQ ID No. 2023 | APLVLVTYFTQPQQNAER | 258-275 for the proteins of SEQ No. 367, 398, 421, 1877, 1882, 1888 | 2be |
| SEQ ID No. 2024 | APLVLVTYFTQSEPK | 258-272 for the proteins of SEQ No. 366, 368, 383, 384, 414, 418, 420 | 2be |
| SEQ ID No. 2025 | AQLVAWLK | 208-215 for the protein of SEQ No. 409 | 2be |
| SEQ ID No. 2026 | AQLVMWLK | 208-215 for the proteins of SEQ No. 366, 368, 383, 384, 414, 418, 420 | 2be |
| SEQ ID No. 2027 | ASDLVNYNPIAEK | 102-114 for the proteins of SEQ No. 429, 430, 434 | 2be |
| SEQ ID No. 2028 | CWVVGDK | 231-237 for the protein of SEQ No. 429 | 2be |
| SEQ ID No. 2029 | DFLAAAAK | 278-285 for the proteins of SEQ No. 435, 1908 | 2be |
| SEQ ID No. 2030 | DILASAAK | 278-285 for the proteins of SEQ No. 358, 440, 441 | 2be |
| SEQ ID No. 2031 | DLLSQR | 92-97 for the protein of SEQ No. 443 | 2be |
| SEQ ID No. 2032 | DNTQVLYR | 57-64 for the proteins of SEQ No. 353, 355, 356, 359, 360, 361, 362, 367, 369, 376, 377, 378, 379, 380, 381, 387, 398, 402, 403, 407, 409, 410, 411, 413, 421, 423, 425, 436, 1872, 1873, 1874, 1877, 1882, 1886, 1888, 1889, 1891, 1892, 1893, 1894, 1896, 1897, 1900, 1901 | 2be |
| SEQ ID No. 2033 | DTTTAR | 182-187 for the protein of SEQ No. 425 | 2be |
| SEQ ID No. 2034 | DTTTPLAMAQALR | 182-194 for the proteins of SEQ No. 366, 368, 383, 384, 414, 420 | 2be |
| SEQ ID No. 2035 | DTTTPLAMAQSLR | 182-194 for the protein of SEQ No. 418 | 2be |
| SEQ ID No. 2036 | DTTTPLAMAQTLR | 181-193 for the proteins of SEQ No. 375, 427, 1878, 1904; 182-194 for the protein of sequence SEQ ID No. 352; 182-194 for the protein of sequence SEQ ID No. 443 | 2be |
| SEQ ID No. 2037 | DVLAAAAR | 278-285 for the proteins of SEQ No. 366, 368, 383, 384, 414, 418, 420, 443 | 2be |
| SEQ ID No. 2038 | EIGDETFR | 157-164 for the protein of SEQ No. 356 | 2be |
| SEQ ID No. 2039 | EQLVTWLK | 208-215 for the proteins of SEQ No. 1891, 1892 | 2be |
| SEQ ID No. 2040 | GLLSQR | 92-97 for the proteins of SEQ No. 366, 368, 383, 384, 414, 418, 420 | 2be |
| SEQ ID No. 2041 | GNTTGAAR | 216-223 for the protein of SEQ No. 376 | 2be |
| SEQ ID No. 2042 | GNTTGSASIQAGLPK | 216-230 for the proteins of SEQ No. 442, 445 | 2be |
| SEQ ID No. 2043 | HDVLASAAK | 277-285 for the proteins of SEQ No. 412, 1885 | 2be |
| SEQ ID No. 2044 | HDVLASAAR | 277-285 for the proteins of SEQ No. 1894 | 2be |
| SEQ ID No. 2045 | HLTLGSALGETQR | 194-206 for the proteins of SEQ No. 375, 427, 1878, 1904 | 2be |
| SEQ ID No. 2046 | LAELEQQSGGR | 37-47 for the proteins of SEQ No. 354, 373, 374, 390 | 2be |

-continued

| Peptide SEQ ID No. | Amino acid sequence | Position of the peptide in the CTX-M protein | Clinical interest |
|---|---|---|---|
| SEQ ID No. 2047 | LAGLER | 37-42 for the protein of SEQ No. 357 | 2be |
| SEQ ID No. 2048 | LDGTEPTLNTAIPGDPR | 165-181 for the protein of SEQ No. 382 | 2be |
| SEQ ID No. 2049 | LGVALIDTADNAQTLYR | 47-63 for the proteins of SEQ No. 375, 427, 1878, 1904; 48-64 for the protein of sequence SEQ ID No. 352 | 2be |
| SEQ ID No. 2050 | LGVALIDTADNTHVLYR | 48-64 for the protein of SEQ No. 408 | 2be |
| SEQ ID No. 2051 | LGVALIDTK | 48-56 for the protein of SEQ No. 356 | 2be |
| SEQ ID No. 2052 | LGVALINTADNSQILYLADER | 48-68 for the protein of SEQ No. 429 | 2be |
| SEQ ID No. 2053 | LGVALINTADNSQILYVADER | 48-68 for the protein of SEQ No. 430 | 2be |
| SEQ ID No. 2054 | LGVALINTADNSR | 47-59 for the proteins of SEQ No. 1902 | 2be |
| SEQ ID No. 2055 | LGVALINTADNTQTLYR | 48-64 for the proteins of SEQ No. 366, 368, 383, 384, 414, 418, 420, 443 | 2be |
| SEQ ID No. 2056 | LGVAQINTADNSQILYVADER | 48-68 for the protein of SEQ No. 434 | 2be |
| SEQ ID No. 2057 | LGVPLIDTADNTQVLYR | 48-64 for the proteins of SEQ No. 379, 380, 381 | 2be |
| SEQ ID No. 2058 | LIAHLGGPGK | 141-150 for the protein of SEQ No. 443 | 2be |
| SEQ ID No. 2059 | LIAQLGGQGGVTAFAR | 141-156 for the proteins of SEQ No. 1897 | 2be |
| SEQ ID No. 2060 | LISHVGGPASVTAFAR | 141-156 for the proteins of SEQ No. 395, 396, 426, 431, 438, 1880, 1905 | 2be |
| SEQ ID No. 2061 | LLLNQR | 92-97 for the protein of SEQ No. 392 | 2be |
| SEQ ID No. 2062 | NLTLGNALGDTQR | 195-207 for the proteins of SEQ No. 366, 368, 383, 384, 414, 418, 420, 443 | 2be |
| SEQ ID No. 2063 | NLTLGSALGETQR | 195-207 for the protein of SEQ No. 352 | 2be |
| SEQ ID No. 2064 | NVLSQK | 91-96 for the proteins of SEQ No. 375, 427, 1878, 1904 | 2be |
| SEQ ID No. 2065 | QLGDDTFR | 157-164 for the protein of SEQ No. 404 | 2be |
| SEQ ID No. 2066 | SDLVNYSPIAEK | 103-114 for the protein of SEQ No. 370 | 2be |
| SEQ ID No. 2067 | SESEPSLLNQR | 87-97 for the proteins of SEQ No. 358, 440, 441 | 2be |
| SEQ ID No. 2068 | SETQK | 86-90 for the proteins of SEQ No. 375, 427, 1878, 1904; 87-91 for the protein of sequence SEQ ID No. 352; 87-91 for the protein of sequence SEQ ID No. 353; 87-91 for the protein of sequence SEQ ID No. 355; 87-91 for the protein of sequence SEQ ID No. 356; 87-91 for the protein of sequence SEQ ID No. 359; 87-91 for the protein of sequence SEQ ID No. 360; 87-91 for the protein of sequence SEQ ID No. 361; 87-91 for the protein of sequence SEQ ID No. 362; 87-91 for the protein of sequence SEQ ID No. 366; 87-91 for the protein of sequence SEQ ID No. 367; 87-91 for the protein of sequence SEQ ID No. 368; 87-91 for the | 2be |

-continued

| Peptide SEQ ID No. | Amino acid sequence | Position of the peptide in the CTX-M protein | Clinical interest |
|---|---|---|---|
| | | protein of sequence SEQ ID No. 369; 87-91 for the protein of sequence SEQ ID No. 376; 87-91 for the protein of sequence SEQ ID No. 377; 87-91 for the protein of sequence SEQ ID No. 378; 87-91 for the protein of sequence SEQ ID No. 379; 87-91 for the protein of sequence SEQ ID No. 380; 87-91 for the protein of sequence SEQ ID No. 381; 87-91 for the protein of sequence SEQ ID No. 383; 87-91 for the protein of sequence SEQ ID No. 384; 87-91 for the protein of sequence SEQ ID No. 387; 87-91 for the protein of sequence SEQ ID No. 398; 87-91 for the protein of sequence SEQ ID No. 402; 87-91 for the protein of sequence SEQ ID No. 403; 87-91 for the protein of sequence SEQ ID No. 407; 87-91 for the protein of sequence SEQ ID No. 408; 87-91 for the protein of sequence SEQ ID No. 409; 87-91 for the protein of sequence SEQ ID No. 410; 87-91 for the protein of sequence SEQ ID No. 411; 87-91 for the protein of sequence SEQ ID No. 413; 87-91 for the protein of sequence SEQ ID No. 414; 87-91 for the protein of sequence SEQ ID No. 418; 87-91 for the protein of sequence SEQ ID No. 420; 87-91 for the protein of sequence SEQ ID No. 421; 87-91 for the protein of sequence SEQ ID No. 423; 87-91 for the protein of sequence SEQ ID No. 425; 87-91 for the protein of sequence SEQ ID No. 428; 87-91 for the protein of sequence SEQ ID No. 436; 87-91 for the protein of sequence SEQ ID No. 443; 87-91 for the protein of sequence SEQ ID No. 1872; 87-91 for the protein of sequence SEQ ID No. 1873; 87-91 for the protein of sequence SEQ ID No. 1874; 87-91 for the protein of sequence SEQ ID No. 1877; 87-91 for the protein of sequence SEQ ID No. 1882; 87-91 for the protein of sequence SEQ ID No. 1886; 87-91 for the protein of sequence SEQ ID No. 1888; 87-91 for the protein of sequence SEQ ID No. 1889; 87-91 for the protein of sequence SEQ ID No. 1891; 87-91 for the protein of sequence SEQ ID No. 1892; 87-91 for the protein of sequence SEQ ID No. 1893; 87-91 for the protein of sequence SEQ ID No. 1894; 87-91 for the protein of sequence SEQ ID No. 1896; 87-91 for the protein of sequence SEQ ID No. 1897; 87-91 for the protein of sequence SEQ ID No. 1900; 87-91 for the protein of sequence SEQ ID No. 1901 | |
| SEQ ID No. 2069 | SLGDESFR | 157-164 for the protein of SEQ No. 439 | 2be |
| SEQ ID No. 2070 | SSDLINYNPIAEK | 101-113 for the proteins of SEQ No. 375, 427, 1878, 1904; 102-114 for the protein of sequence SEQ ID No. 443 | 2be |
| SEQ ID No. 2071 | SSDLINYNPITEK | 102-114 for the protein of SEQ No. 352 | 2be |
| SEQ ID No. 2072 | SWGVGDK | 231-237 for the proteins of SEQ No. 351, 430, 434, 444 | 2be |
| SEQ ID No. 2073 | TELTLNTAIPGDPR | 168-181 for the protein of SEQ No. 407 | 2be |
| SEQ ID No. 2074 | TEPTLNSAIPGDPR | 168-181 for the proteins of SEQ No. 429, 430, 434 | 2be |
| SEQ ID No. 2075 | TEPTQNTAIPGDPR | 168-181 for the protein of SEQ No. 1889 | 2be |
| SEQ ID No. 2076 | TEQTLNTAIPGDPR | 168-181 for the protein of SEQ No. 391 | 2be |
| SEQ ID No. 2077 | TESTLNTAIPGDPR | 168-181 for the proteins of SEQ No. 361, 388, 400, 421, 1873, 1888 | 2be |
| SEQ ID No. 2078 | TETTLNTAIPGDPR | 168-181 for the proteins of SEQ No. 365, 385, 395, 415 | 2be |

-continued

| Peptide SEQ ID No. | Amino acid sequence | Position of the peptide in the CTX-M protein | Clinical interest |
|---|---|---|---|
| SEQ ID No. 2079 | TGSCDYGTTNDIAVIWPK | 238-255 for the protein of SEQ No. 373 | 2be |
| SEQ ID No. 2080 | TGSCGYGTTNDIAVIWPK | 238-255 for the protein of SEQ No. 417 | 2be |
| SEQ ID No. 2081 | TGSGDYGTTNDIAVIWPEGR | 237-256 for the proteins of SEQ No. 375, 427, 1878, 1904; 238-257 for the protein of sequence SEQ ID No. 352; 238-257 for the protein of sequence SEQ ID No. 368; 238-257 for the protein of sequence SEQ ID No. 383; 238-257 for the protein of sequence SEQ ID No. 414; 238-257 for the protein of sequence SEQ ID No. 418; 238-257 for the protein of sequence SEQ ID No. 443 | 2be |
| SEQ ID No. 2082 | TGSGGYGTTNDIAVIWPEGR | 238-257 for the proteins of SEQ No. 366, 384, 420 | 2be |
| SEQ ID No. 2083 | TGSGGYGTTNDIAVIWPQGR | 238-257 for the proteins of SEQ No. 359, 369, 423, 1889, 1891, 1892 | 2be |
| SEQ ID No. 2084 | TIGDDTFR | 157-164 for the proteins of SEQ No. 366, 368, 383, 384, 414, 418, 420 | 2be |
| SEQ ID No. 2085 | TQLVTWLK | 208-215 for the protein of SEQ No. 419 | 2be |
| SEQ ID No. 2086 | VEIKPSDLINYNPIAEK | 98-114 for the proteins of SEQ No. 366, 368, 383, 414, 418, 420 | 2be |
| SEQ ID No. 2087 | VEIKPSDLVNYNPIAEK | 98-114 for the protein of SEQ No. 384 | 2be |
| SEQ ID No. 2088 | VIGDDTFR | 157-164 for the protein of SEQ No. 443 | 2be |
| SEQ ID No. 2089 | VLSQK | 92-96 for the proteins of SEQ No. 375, 427, 1878, 1904; 93-97 for the protein of sequence SEQ ID No. 352 | 2be |
| SEQ ID No. 2090 | VMAAAALLK | 77-85 for the protein of SEQ No. 445 | 2be |
| SEQ ID No. 2091 | VMAAAAVLEQSETQK | 77-91 for the protein of SEQ No. 403 | 2be |
| SEQ ID No. 2092 | WAKPSGAVGDVAQR | 201-214 for the protein of SEQ No. 425 | 2be |

In the clinical interest column, the entry 2be indicates that all of the CTX-M peptides indicates the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The detection of a mechanism of resistance to ESBL (extended-spectrum beta-lactamase) cephalosporins, induced by the CTX-M protein is characterised by the detection of at least one resistance-marking 2be peptide chosen from the sequences SEQ ID No. 446 to SEQ ID No. 478, SEQ ID No. 480 to SEQ ID No. 495 and SEQ ID No. 2008 to SEQ ID No. 2092.

The detection of a mechanism of resistance to cephalosporins induced by the expression of the SHV protein is characterised by the detection of at least one peptide belonging to the SHV protein and to its different sequence variants SEQ ID No. 496 to SEQ ID No. 613 and SEQ ID No. 1909 to SEQ ID No. 1919.

SEQ ID No. 496:
KRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 497:
LRYIRLCIISLLATLPLAVHASPQPLEQIKLSESQLSGRVGMIEMDLASGRTLTAWRAD

ERFPMMSTFKVVLCGAVLARVDAGDEQLERKIHYRQQDLVDYSPVSEKHLADGMT

VGELCAAAITMSDNSAANLLLATVGGPAGLTAFLRQIGDNVTRLDRWETELNEALPG

DARDTTTPASMAATLRKLLTSQRLSASSQRQLLQWMVDDRVAGPLIRSVLPAGWFI

ADKTGAGERGARGIVALLGPNNKAERIVVIYLRDTPASMAERNQQIAGIGAALIEHW

QR

SEQ ID No. 498:
MRFIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 499:
MRFIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNNAERMVVIYLRDTPASMAERNQQIAGIGAALIEH

WQR

SEQ ID No. 500:
MRFIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 501:
MRIRLCIISLLATLPLAVHASPQPLEQIKLSESQLSGRVGMIEMDLASGRTLTAWRAD

ERFPMMSTFKVVLCGAVLARVDAGDEQLERKIHYRQQDLVDYSPVSEKHLADGMT

VGELCAAAITMSDNSAANLLLATVGGPVGLTAFLRQIGDNVTRLDRWETELNEALPG

DARDTTTPASMAATLRKLLTSQRLSARSQRQLLQWMVDDRVAGPLIRSVLPAGWFI

ADRTGAGERGARGIVALLGPNNKAERIVVIYLRDTPASMAERNQQIAGIGAALIEHW

QR

SEQ ID No. 502:
MRYARLCIISLLATLPLVVHASPQPLEQIKQSESQLSGRVGMIEMDLASGRTLTAWR

ADERFPMMSTFKVVLCGAVLARVDAGDEQLERKIHYRQQDLVDYSPVSEKHLADG

MTVGELCAAAITVSDNSAANLLLATVGGPAGLTAFLRQIGDNVTRLDRWETELNEAL

PGDARDTTTPASMAATLRKLLTSQRLSARSQRQLLQWMVDDRVAGPLIRSVLPAG

WFIADKTGAGERGARGIVALLGPNNKAERIVVIYLRDTPASMAERNQQIAGIGAALIE

HWQR

SEQ ID No. 503:
MRYFRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASERGARGIVALLGPNNKAERIVVIYLRDTPASMAERNQQIAGIGAALIEH

WQR

SEQ ID No. 504:
MRYFRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPVGLTAFLRQIGDNVTRLDRWETELNEALP

GDARDTTTPASMAATLRKLLTSQRLSARSQRQLLQWMVDDRVAGPLIRSVLPAGW

FIADRTGAGERGARGIVALLGPNNKAERIVVIYLRDTPASMAERNQQIAGIGAALIEH

WQR

SEQ ID No. 505:
MRYFRLCIISLLATLPLAVHASPQPLEQIKLSESQLSGSVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIDDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 506:
MRYFRLCIISLLATLPLAVHASPQPLEQIKLSESQLSGSVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAAKRGARGIVALLGPNNKAERIVVIYLRDTPASMAERNQQIAGIGAALIEH

WQR

SEQ ID No. 507:
MRYFRLCIISLLATLPLAVHASPQPLEQIKLSESQLSGSVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 508:
MRYFRLCIISLLATLPLAVHASPQPLEQIKLSESQLSGSVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASERGARGIVALLGPNNKAERIVVIYLRDTPASMAERNQQIAGIGAALIEH

WQR

-continued

SEQ ID No. 509:
MRYFRLCIISLLATLPLAVHASPQPLEQIKLSESQLSGSVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 510:
MRYFRLCIISLLATLPLAVHASPQPLEQIKLSESQLSGSVGMIEMDLASGRTLTAWRA

DGRFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASERGARGIVALLGPNNKAERIVVIYLRDTPASMAERNQQIAGIGAALIEH

WQR

SEQ ID No. 511:
MRYIRLCIISLLAALPLAVHASPQPLEQIKQSESQLSGRVGMIEMDLASGRTLTAWRA

DERFPMISTFKVVLCGAVLARVDAGDEQLERKIHYRQQDLVDYSPVSEKHLADGMT

VGELCAAAITMSDNSAANLLLAIVGGPAGLTAFLRQIGDNVTRLDRWETELNEALPG

DARDTTTPASMAATLRKLLTSQRLSARSQRQLLQWMVDDRVAGPLIRSVLPAGWFI

ADKTGAGERGARGIVALLGPNNKAERIVVIYLRDTPASMAERNQQIAGIGAALIEHW

QR

SEQ ID No. 512:
MRYIRLCIISLLAALPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVEDRVAGPLIRSVLPAGW

FIADKTGAGERGARGIVALLGPNNKAERIVVIYLRDTPASMAERNQQIAGIGAALIEH

WQR

SEQ ID No. 513:
MRYIRLCIISLLAALPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITVSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQHIAGIGAALIEH

WQR

SEQ ID No. 514:
MRYIRLCIISLLAALPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITVSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 515:
MRYIRLCIISLLATLPLAVHASPQPLDQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 516:
MRYIRLCIISLLATLPLAVHASPQPLEQIKLSESQLSGRVGMIEMDLASGRTLTAWHA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 517:
MRYIRLCIISLLATLPLAVHASPQPLEQIKLSESQLSGRVGMIEMDLASGRTLTAWHA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGKRGARGIVALLGPNNKAERIVVIYLRDTPASMAKRNQQIAGIGAALIEH

WQR

SEQ ID No. 518:
MRYIRLCIISLLATLPLAVHASPQPLEQIKLSESQLSGRVGMIEMDLASGRTLTAWRA

DERFPMISTFKVVLCGAVLARVDAGDEQLERKIHYRQQDLVDYSPVSEKHLADGMT

VGELCAAAITMSDNSAANLLLATVGGPAGLTAFLRQIGDNVTRLDRWETELNEALPG

DARDTTTPASMAATLRKLLTSQRLSARSQRQLLQWMVDDRVAGPLIRSVLPAGWFI

ADKTGAGERGARGIVALLGPNNKAERIVVIYLRDTPASMAERNQQIAGIGAALIEHW

QR

SEQ ID No. 519:
MRYIRLCIISLLATLPLAVHASPQPLEQIKLSESQLSGRVGMIEMDLASGRTLTAWRA

DERFPMMSTFKVVLCGAVLARVDAGDEQLERKIHYLQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 520:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHFADGM

TVGELCAAAITMSDNSAANLLLATVGGPAGLSAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 521:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TIGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 522:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGEFCAAAITMSDNSAANLLLATVGGPAGLTAFLRQIGDNVTRLDRWETELNEAFP

GDARDTTTPASMAATLRKLLTSQRLSARSQRQLLQWMVDDRVAGPLIRSVLPAGW

FIADKTGASERGARGIVALLGPNNKAERIVVIYLRDTPASMAERNQQIAGIGAALIEH

WQR

SEQ ID No. 523:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGEFCAAAITMSDNSAANLLLATVGGPAGLTAFLRQIGDNVTRLDRWETELNEALP

GDARDTTTPASMAGTLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 524:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAAKLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 525:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATFGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 526:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGLAGLTAFLRQIGDNVTRLDRWETELNEALP

ADARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 527:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIDDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 528:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIDDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 529:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDKVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 530:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETDRWETE

LNEALPGDARDTTTPASMAATLRKLLTSQRLSARSQRQLLQWMVDDRVAGPLIRSV

LPAGWFIADKTGAGERGARGIVALLGPNNKAERIVVIYLRDTPASMAERNQQIAGIG

AALIEHWQR

SEQ ID No. 531:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEAFP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 532:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEAFP

GDARDTTTPASMAATLRKLLTSQRLSARSQRQLLQWMVDDRVAGPLIRSVLPAGW

FIADKTGASERGARGIVALLGPNNKAERIVVIYLRDTPASMAERNQQIAGIGAALIEH

WQR

SEQ ID No. 533:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARATTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 534:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLNSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 535:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARLQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 536:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQLQLLQWMVDDRVAGPLIRSVLPAGW

FIADKTGAGERGARGIVALLGPNNKAERIVVIYLRDTPASMAERNQQIAGIGAALIEH

WQR

SEQ ID No. 537:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQLQLLQWMVDDRVAGPLIRSVLPAGW

FIADKTGASERGARGIVALLGPNNKAERIVVIYLRDTPASMAERNQQIAGIGAALIEH

WQR

SEQ ID No. 538:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQLQLLQWMVDDRVAGPLIRSVLPAGW

FIADKTGASKRGARGIVALLGPNNKAERIVVIYLRDTPASMAERNQQIAGIGAALIEH

WQR

SEQ ID No. 539:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDGVAGPLIRSVLPAGW

FIADKTGAGERGARGIVALLGPNNKAERIVVIYLRDTPASMAERNQQIAGIGAALIEH

WQR

SEQ ID No. 540:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAAERGARGIVALLGPNNKAERIVVIYLRDTPASMAERNQQIAGIGAALIEH

WQR

SEQ ID No. 541:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPDNKAERIVVIYLRDTPASMAERNQQIAGIGAALIEH

WQR

SEQ ID No. 542:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNHKAERIVVIYLRDTPASMAERNQQIAGIGAALIEH

WQR

SEQ ID No. 543:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 544:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALRGPNNKAERIVVIYLRDTPASMAERNQQIAGIGAALIEH

WQR

SEQ ID No. 545:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGKRGARGIVALLGPNNKAERIVVIYLRDSPASMAERNQQIAGIGAALIEH

WQR

SEQ ID No. 546:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGKRGARGIVALLGPNNKAERTVVIYLRDTPASMAERNQQIAGIGAALIEH

WQR

SEQ ID No. 547:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASERGARGIVALLGPNNKAERIVVIYLRDSPASMAERNQQIAGIGAALIEH

WQR

SEQ ID No. 548:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASERGARGIVALLGPNNKAERIVVIYLRDTPASMAERNQQIAGIGAALIEH

WQR

SEQ ID No. 549:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 550:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGLGAALIEH

WQR

SEQ ID No. 551:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADRTGAGERGARGIVALLGPNNKAERIVVIYLRDTPASMAERNQQIAGIGAALIEH

WQR

SEQ ID No. 552:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLSAGW

FIADKTGAGERGARGIVALLGPNNKAERIVVIYLRDTPASMAERNQQIAGIGAALIEH

WQR

SEQ ID No. 553:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDGRVAGPLIRSVLPAGW

FIADKTGAGERGARGIVALLGPNNKAERIVVIYLRDTPASMAERNQQIAGIGAALIEH

WQR

SEQ ID No. 554:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMTATLRKLLTSQRLSARSQRHLLQWMVDDRVAGPLIRSVLPAGW

FIADKTGAGERGARGIVALLGPNNKAERIVVIYLRDTPASMAERNQQIAGIGAALIEH

WQR

SEQ ID No. 555:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMTATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 556:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMTATLRKLLTSQRLSARSQRQLLQWMVDDRVAGPLIRSVLPAGW

FIADKTGAGKRGARGIVALLGPNNKAERIVVIYLRDTPASMAERNQQIAGIGAALIEH

WQR

SEQ ID No. 557:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMTATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 558:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARGTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 559:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARNTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 560:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALS

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 561:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETERNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 562:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGENVTRLDRWETELNEALP

GDARDTTTPASMAATLRKLLTNQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 563:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPVGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 564:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSVANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTLASMAERNQQIAGIGAALIEH

WQR

SEQ ID No. 565:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAVITMSDNSAANLLLATVGGPAGLTAFLRQIDDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 566:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCTAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 567:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKYLADGM

TVGELCAAAITMSDNSAANLLLATVGGPVGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 568:
MRYIRLCIISLLATLPLAVHASPQPLEQIKLSESQLSGRVGMIEMDLASRTLTAWRAD

ERFPMMSTFKVVLCGAVLARVDAGDEQLERKIHYRQQDLVDYSPVSEKHLADGMT

VGELCAAAITMGDNSAANLLLRTVGGPAGLTAFLRQIGDNVTRLDRWETELNEALP

GDARDTTTPASMAATLRNVLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 569:
MRYIRLCIISLLATLPLAVHASPQPLEQIKLSESQLSGRVGMIEMDLASRTLTAWRAD
ERFPMMSTFKVVLCGAVLARVDAGDEQLERKIHYRQQDLVDYSPVSEKHLADGMT
VGELCAAAITMSDNSAANLLLRTVGGPAGLTAFLRQIGDNVTRLDRWETELNEALPG
DARDTTTPASMAATLRNVLTSQRLSARSQRQLLQWMVDDRVAGPLIRSVLPAGWFI
ADKTGASKRGARGIVALLGPNNKAERIVVIYLRDTPASMAERNQQIAGIGAALIEHW
QR

SEQ ID No. 570:
MRYIRLCIISLLATLPLAVHASPQPLEQIKLSESQLSGRVGMIEMDLASSRTLTAWRA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 571:
MRYIRLCIISLLATLPLAVHASPQPLEQIKQSESQLSGRVGMIEMDLASGRTLTAWCA
DERFPMMSTFKVVLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 572:
MRYIRLCIISLLATLPLAVHASPQPLEQIKQSESQLSGRVGMIEMDLASGRTLTAWRA
DERFPMISTFKVVLCGAVLARVDAGDEQLERKIHYRQQDLVDYSPVSEKHLADGMT
VGELCAAAITMSDNSAANLLLAIVGGPAGLTAFLRQIGDNVTRLDRWETELNEALPG
DARDTTTPASMAATLRKLLTSQRLSARSQRQLLQWMVDDRVAGPLIRSVLPAGWFI
ADKTGAGERGARGIVALLGPNNKAERIVVIYLRDTPASMAERNQQIAGIGAALIEHW
QR

SEQ ID No. 573:
MRYIRLCIISLLATLPLAVHASPQPLEQIKQSESQLSGRVGMIEMDLASGRTLTAWRA
DERFPMMSTFKVALCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGAGERGARGIVALLGPNNKAERIVVIYLRDTPASMAERNQQIAGIGAALIEH
WQR

SEQ ID No. 574:
MRYIRLCIISLLATLPLAVHASPQPLEQIKQSESQLSGRVGMIEMDLASGRTLTAWRA
DERFPMMSTFKVLLCGAVLARVDAGDEQLERKIHYRQQDLVDYSPVSEKHLADGM
TVGELCAAAITMSDNSAANLLLATVGGPAGLTAFLRQIGDNVTRLDRWETELNEALP
GDARDTTTPASMAATLRKLLTSQRLSARSQRQLLQWMVDDRVAGPLIRSVLPAGW
FIADKTGASKRGARGIVALLGPNNKAERIVVIYLRDTPASMAERNQQIAGIGAALIEH
WQR

SEQ ID No. 575:
MRYIRLCIISLLATLPLAVHASPQPLEQIKQSESQLSGRVGMIEMDLASGRTLTAWRA

DERFPMMSTFKVVLCGAMLARVDAGDKQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 576:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLAIVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 577:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIDDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 578:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLISQRLSARSQRQLLQWMVDDRVAGPLIRSVLPAGWF

IADKTGAGERGARGIVALLGPNNKAERIVVIYLRDTPASMAERNQQIAGIGAALIEHW

QR

SEQ ID No. 579:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDARVAGPLIRSVLPAGW

FIADKTGAGERGARGIVALLGPNNKAERIVVIYLRDTPASMAERNQQIAGIGAALIEH

WQR

SEQ ID No. 580:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKAGAGERGARGIVALLGPNNKAERIVVIYLRDTPASMAERNQQIAGIGAALIEH

WQR

SEQ ID No. 581:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAAERGARGIVALLGPNNKAERIVVIYLRDTPASMAERNQQIAGIGAALIEH

WQR

SEQ ID No. 582:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 583:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGGRGIVALLGPNNKAERIVVIYLRDTPASMAERNQQIAGIGAALIEH

WQR

SEQ ID No. 584:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGKRGARGIVALLGPNNKAERIVVIYLRDTPASMAERNQQIAGIGAALIEH

WQR

SEQ ID No. 585:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASERGARGIVALLGPNNKAERIVVIYLRDTPASMAERNQQIAGIGAALIEH

WQR

SEQ ID No. 586:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGGNIKAERIVVIYLRDTPASMAERNQQIAGIGAALIEHW

QR

SEQ ID No. 587:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAELDQQIAGIGAALIEHW

QR

SEQ ID No. 588:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 589:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASRRGARGIVALLGPNNKAERIVVIYLRDTPASMAERNQQIAGIGAALIEH

WQR

SEQ ID No. 590:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADRTGAGERGARGIVALLGPNNKAERIVVIYLRDTPASMAERNQQIAGIGAALIEH

WQR

SEQ ID No. 591:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMTATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 592:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEVLP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 593:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGVTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 594:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPTGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 595:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGSPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 596:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITVSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 597:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLTDGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 598:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKYLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

-continued

SEQ ID No. 599:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQHLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 600:
MRYIRLCIISLLATLPLAVHASPQPLEQIKQSESQLSGRVGMIEMDLASGRTLTAWRA

DERFPMMSTFKVVLCGAVLARVDAGDKQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGGRGIVALLGPNNKAERIVVIYLRDTPASMAERNQQIAGIGAALIEH

WQR

SEQ ID No. 601:
MRYIRLCIISLLATLPLAVHASPQPLEQIKQSESQLSGRVGMIEMDLASGRTLTAWRA

DERFPMMSTFKVVLCGTVLARVDAGDEQLERKIHYRQQDLVDYSPVSEKHLADGM

TVGELCAAAITMSDNSAANLLLATVGGPAGLTAFLRQIDDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 602:
MRYIRLCIISLLATLPLAVHASPQPLEQIKQSESQLSGRVGMIEMDLASGRTLTAWRA

DQRFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 603:
MRYIRLCIISLLATLPLAVHASPQPLEQIKQSESQLSGSVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAAERGARGIVALLGPNNKAERIVVIYLRDTPASMAERNQQIAGIGAALIEH

WQR

SEQ ID No. 604:
MRYIRLCIISLLATLPLAVHSSPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITVSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 605:
MRYIRLCIISLLATLPLTVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 606:
MRYIRLCIISLLATLSLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGKRGARGIVALLGPNNKAERIVVIYLRDTPASMAERNQQIAGIGAALIEH

WQR

SEQ ID No. 607:
MRYIRLCIISLLATMPLAVHASPQPLEQIKQSESQLSGRVGMIEMDLASGRTLTAWR

ADERFPMMSTFKVVLCGAVLARVDAGDEQLERKIHYRQQDLVDYSPVSEKHLADG

MTVGELCAAAITMSDNSAANLLLATVGGPAGLTAFLRQIGDNVTRLDRWETELNEAL

PGDARDTTTPASMAATLRKLLTSQRLSARSQRQLLQWMVDDRVAGPLIRSVLPAG

WFIADKTGAGERGARGIVALLGPNNKAERIVVIYLRDTPASMAERNQQIAGIGAALIE

HWQR

SEQ ID No. 608:
MRYIRLCIISLLAVLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITVSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 609:
MRYIRLNIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 610:
MRYIRRCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDMPASMAERNQQIAGIGAALIEH

WQR

-continued

SEQ ID No. 611:
MRYIRRCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 612:
MRYVRLCIISLLATLPLAVHASPQPLEQIKQSESQLSGRVGMIEMDLASGRTLTAWR

ADERFPMMSTFKVVLCGAVLARVDAGDEQLERKIHYRQQDLVDYSPVSEKHLADG

MTVGELCAAAITMSDNSAANLLLATVGGPAGLTAFLRQIGDNVTRLDRWETELNEAL

PGDARDTTTPASMAATLRKLLTSQRLSARSQRQLLQWMVDDRVAGPLIRSVLPAG

WFIADKTGAGERGARGIVALLGPNNKAERIVVIYLRDTPASMAERNQQIAGIGAALIE

HWQR

SEQ ID No. 613:
MRYVRLCIISLLATLPLAVHTSPQPLEQIKQSESQLSGRVGMIEMDLASGRTLTAWR

ADERFPMMSTFKVVLCGAVLARVDAGDEQLERKIHYRQQDLVDYSPVSEKHLADG

MTVGELCAAAITMSDNSAANLLLATVGGPAGLTAFLRQIGDNVTRLDRWETELNEAL

PGDARDTTTPASMAATLRKLLTSQRLSARSQRQLLQWMVDDRVAGPLIRSVLPAG

WFIADKTGAGERGARGIVALLGPNNKAERIVVIYLRDTPASMAERNQQIAGIGAALIE

HWQR

SEQ ID No. 1909:
MRYIRLCIISLLAALPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITVSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQHIAGIGAALIEH

WQR

SEQ ID No. 1910:
ALPGDARDTTTPASMAATLRKLLTSQRLSARSQRQLLQWMVDDRVAGPLIRSVLPA

GWFIADKTGASERGARGIVALLGPNNKAERIVVIYLRDS

SEQ ID No. 1911:
MRYIRLCIISLLAALPLVVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITVSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 1912:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

-continued

FIADKTGASKRGARGIVALLGPNNKAERIVVIYLRDTPASMAELDQQIAGIGAALIEHW

QR

SEQ ID No. 1913:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELRAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGTGAAPIEH

WQR

SEQ ID No. 1914:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLREIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

SEQ ID No. 1915:
MRYIRLCIISLLATLPLAVHASPQPLKQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMTATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 1916:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAALTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPHNKAERIVVIYLRDTPASMAERNQQIAGIGAALIEH

WQR

SEQ ID No. 1917:
KRYIRLCIISLLATLPLAVHASPQPLEQIKLSESQLSGRVGMIEMDLASGRTLTAWRA

DERFPMMSTFKVVLCGAVLARVDAGDEQLERKIHYSQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGAGERGARGIVALLGPNNKAERIVVIYLRDTPASMAERNQQIAGIGAALIEH

WQR

SEQ ID No. 1918:
MRYIRLCIISLLATLPLAVHASPQPLEQIKLSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAALIEH

WQR

-continued

SEQ ID No. 1919:
MRYIRLCIISLLATLPLAVHASPQPLEQIKQSESQLSGRVGMIEMDLASGRTLTAWRA

DERFPMMSTFKVVLCGAVLARVDAGDEQLERKIHYRQQDLVDYSPVSEKHLADGM

TVGELCAAAITMSDNSAANLLLATVGGPAGLTAFLRQIGDNVTRLDRWETELNEALP

GDARDTTTPASMAATLRKLLTSQRLSARSQRQLLQWMVDDRVAGPLIRSVLPAGW

FIADKTGASKRGARGIVALLGPNNKAERIVVIYLRDTPASMAERNQQIAGIGAA said peptides being chosen, preferably, from the peptides of sequence SEQ ID No. 614 to SEQ ID No. 711 and SEQ ID No. 2093 to SEQ ID No. 2096 as defined hereafter:

| Peptide SEQ ID No. | Amino acid sequence | Position of the peptide in the SHV protein | Clinical interest |
|---|---|---|---|
| SEQ ID No. 614 | AGAGER | 231-236 for the protein of SEQ No. 580 | SHV |
| SEQ ID No. 615 | ATTTPASMAATLR | 175-187 for the protein of SEQ No. 533 | 2be |
| SEQ ID No. 616 | CIISLLATLPLAVH ASPQPLEQIK | 7-30 for the proteins of SEQ No. 496, 497, 498, 499, 500, 503, 504, 505, 506, 507, 508, 509, 510, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 610, 611, 612, 1913, 1914, 1915, 1917, 1918, 1919, 1920; 6-29 for the protein of sequence SEQ ID No. 501 | SHV |
| SEQ ID No. 617 | DMPASMAER | 261-269 for the protein of SEQ No. 610 | 2b |
| SEQ ID No. 618 | DSPASMAER | 261-269 for the proteins of SEQ No. 545, 547 | SHV |
| SEQ ID No. 619 | DTLASMAER | 261-269 for the protein of SEQ No. 564 | SHV |
| SEQ ID No. 620 | DTPASMAER | 261-269 for the proteins of SEQ No. 496, 497, 498, 499, 500, 502, 503, 504, 505, 506, 507, 508, 509, 510, 511, 512, 513, 514, 515, 516, 518, 519, 520, 521, 522, 523, 524, 525, 526, 527, 528, 529, 531, 532, 533, 534, 535, 536, 537, 538, 539, 540, 541, 542, 543, 544, 546, 548, 549, 550, 551, 552, 553, 554, 555, 556, 557, 558, 559, 560, 561, 562, 563, 565, 566, 567, 570, 571, 572, 573, 574, 575, 576, 577, 578, 579, 580, 581, 582, 583, 584, 585, 586, 588, 589, 590, 591, 592, 593, 594, 595, 596, 597, 598, 599, 600, 601, 602, 603, 604, 605, 606, 607, 608, 609, 611, 612, 613, 1910, 1912, 1914, 1915, 1916, 1917, 1918, 1919, 1920; 260-268 for the protein of sequence SEQ ID No. 501; 266-274 for the protein of sequence SEQ ID No. 530; 260-268 for the protein of sequence SEQ ID No. 568; 260-268 for the protein of sequence SEQ ID No. 569 | SHV |
| SEQ ID No. 621 | DTPASMAK | 261-268 for the protein of SEQ No. 517 | SHV |
| SEQ ID No. 622 | DTTTPASMAATLR | 175-187 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 524, 525, 526, 527, 528, 529, 531, 532, 534, 535, 536, 537, 538, 539, 540, 541, 542, 543, 544, 545, 546, 547, 548, 549, 550, 551, 552, 553, 560, 561, 562, 563, 564, 565, 566, 567, 570, 571, 572, 573, 574, 575, 576, 577, 578, 579, 580, 581, 582, 583, 584, 585, 586, 587, 588, 589, 590, 592, 593, 594, 595, 596, 597, 598, 599, 600, 601, 602, 603, 604, 605, 606, 607, 608, 609, 610, 611, 612, 613, 1910, 1912, 1913, 1914, 1915, 1917, 1918, | SHV |

| Peptide SEQ ID No. | Amino acid sequence | Position of the peptide in the SHV protein | Clinical interest |
|---|---|---|---|
| | | 1919, 1920; 174-186 for the protein of sequence SEQ ID No. 501; 180-192 for the protein of SEQ ID No. 530; 174-186 for the protein of sequence SEQ ID No. 568; 174-186 for the protein of sequence SEQ ID No. 569; 8-20 for the protein of sequence SEQ ID No. 1911 | |
| SEQ ID No. 623 | DTTTPASMAGTLR | 175-187 for the protein of SEQ No. 523 | 2b |
| SEQ ID No. 624 | DTTTPASMTATLR | 175-187 for the proteins of SEQ No. 554, 555, 556, 557, 591, 1916 | SHV |
| SEQ ID No. 625 | FPMISTFK | 62-69 for the proteins of SEQ No. 511, 518, 572 | 2br |
| SEQ ID No. 626 | FPMMSTFK | 62-69 for the proteins of SEQ No. 496, 497, 498, 499, 500, 502, 503, 504, 505, 506, 507, 508, 509, 510, 512, 513, 514, 515, 516, 517, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 61-68 for the protein of sequence SEQ ID No. 501; 61-68 for the protein of sequence SEQ ID No. 568; 61-68 for the protein of sequence SEQ ID No. 569 | SHV |
| SEQ ID No. 627 | GIVALLGGNIK | 240-250 for the protein of SEQ No. 586 | 2b |
| SEQ ID No. 628 | GIVALLGPDNK | 240-250 for the protein of SEQ No. 541 | SHV |
| SEQ ID No. 629 | GIVALLGPNHK | 240-250 for the protein of SEQ No. 542 | SHV |
| SEQ ID No. 630 | GIVALLGPNNK | 240-250 for the proteins of SEQ No. 496, 497, 498, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 543, 545, 546, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1918, 1919, 1920; 239-249 for the protein of sequence SEQ ID No. 501; 245-255 for the protein of sequence SEQ ID No. 530; 239-249 for the protein of sequence SEQ ID No. 568; 239-249 for the protein of sequence SEQ ID No. 569; 73-83 for the protein of sequence SEQ ID No. 1911 | SHV |
| SEQ ID No. 631 | GIVALLGPNNNAER | 240-253 for the protein of SEQ No. 499 | 2b |
| SEQ ID No. 632 | GIVALR | 240-245 for the protein of SEQ No. 544 | SHV |
| SEQ ID No. 633 | GPNNK | 246-250 for the proteins of SEQ No. 496, 497, 498, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 543, 544, 545, 546, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, | SHV |

-continued

| Peptide SEQ ID No. | Amino acid sequence | Position of the peptide in the SHV protein | Clinical interest |
|---|---|---|---|
| | | 1914, 1915, 1916, 1918, 1919, 1920; 245-249 for the protein of sequence SEQ ID No. 501; 251-255 for the protein of sequence SEQ ID No. 530; 245-249 for the protein of sequence SEQ ID No. 568; 245-249 for the protein of sequence SEQ ID No. 569; 79-83 for the protein of sequence SEQ ID No. 1911 | |
| SEQ ID No. 634 | GTTTPASMAATLR | 175-187 for the protein of SEQ No. 558 | 2be |
| SEQ ID No. 635 | HLADGMTVGELCAAAITMSDNSAAK | 108-132 for the protein of SEQ No. 524 | SHV |
| SEQ ID No. 636 | HLLQWMVDDR | 202-211 for the protein of SEQ No. 554 | SHV |
| SEQ ID No. 637 | IHYLQQDLVDYSPVSEK | 91-107 for the protein of SEQ No. 519 | SHV |
| SEQ ID No. 638 | IVVIYLR | 254-260 for the proteins of SEQ No. 496, 497, 498, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 253-259 for the protein of sequence SEQ ID No. 501; 259-265 for the protein of sequence SEQ ID No. 530; 253-259 for the protein of sequence SEQ ID No. 568; 253-259 for the protein of sequence SEQ ID No. 569; 87-93 for the protein of sequence SEQ ID No. 1911 | SHV |
| SEQ ID No. 639 | LCIISLLAALPLAVHASPQPLEQIK | 6-30 for the proteins of SEQ No. 511, 512, 513, 514, 1910 | 2b |
| SEQ ID No. 640 | LCIISLLATLPLAVHASPQPLDQIK | 6-30 for the protein of SEQ No. 515 | 2b |
| SEQ ID No. 641 | LCIISLLATLPLAVHASPQPLEQIK | 6-30 for the proteins of SEQ No. 496, 497, 498, 499, 500, 503, 504, 505, 506, 507, 508, 509, 510, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 612, 1913, 1914, 1915, 1917, 1918, 1919, 1920; 5-29 for the protein of sequence SEQ ID No. 501 | SHV |
| SEQ ID No. 642 | LCIISLLATLPLAVHSSPQPLEQIK | 6-30 for the protein of SEQ No. 604 | SHV |
| SEQ ID No. 643 | LCIISLLATLPLAVHTSPQPLEQIK | 6-30 for the protein of SEQ No. 613 | SHV |
| SEQ ID No. 644 | LCIISLLATLPLTVHASPQPLEQIK | 6-30 for the protein of SEQ No. 605 | 2b |
| SEQ ID No. 645 | LCIISLLATLPLVVHASPQPLEQIK | 6-30 for the protein of SEQ No. 502 | 2b |
| SEQ ID No. 646 | LCIISLLATLSLAVHASPQPLEQIK | 6-30 for the protein of SEQ No. 606 | 2be |
| SEQ ID No. 647 | LCIISLLATMPLAVHASPQPLEQIK | 6-30 for the protein of SEQ No. 607 | SHV |
| SEQ ID No. 648 | LCIISLLAVLPLAVHASPQPLEQIK | 6-30 for the protein of SEQ No. 608 | 2b |

| Peptide SEQ ID No. | Amino acid sequence | Position of the peptide in the SHV protein | Clinical interest |
|---|---|---|---|
| SEQ ID No. 649 | LLISQR | 189-194 for the protein of SEQ No. 578 | SHV |
| SEQ ID No. 650 | LLLATVGGPAGLTAFLR | 133-149 for the proteins of SEQ No. 496, 497, 498, 499, 500, 502, 503, 505, 506, 507, 508, 509, 510, 512, 513, 514, 515, 516, 517, 518, 519, 521, 522, 523, 524, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 564, 565, 566, 570, 571, 573, 574, 575, 577, 578, 579, 580, 581, 582, 583, 584, 585, 586, 587, 588, 589, 590, 591, 592, 596, 597, 598, 599, 600, 601, 602, 603, 604, 605, 606, 607, 608, 609, 610, 611, 612, 613, 1910, 1912, 1913, 1914, 1915, 1916, 1918, 1919, 1920 | SHV |
| SEQ ID No. 651 | LLNSQR | 189-194 for the protein of SEQ No. 534 | 2be |
| SEQ ID No. 652 | LLTNQR | 189-194 for the protein of SEQ No. 562 | SHV |
| SEQ ID No. 653 | LLTSQR | 189-194 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 535, 536, 537, 538, 539, 540, 541, 542, 543, 544, 545, 546, 547, 548, 549, 550, 551, 552, 553, 554, 555, 556, 557, 558, 559, 560, 561, 563, 564, 565, 566, 567, 570, 571, 572, 573, 574, 575, 576, 577, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 188-193 for the protein of sequence SEQ ID No. 501; 194-199 for the protein of sequence SEQ ID No. 530; 22-27 for the protein of sequence SEQ ID No. 1911 | SHV |
| SEQ ID No. 654 | LNIISLLATLPLAVHASPQPLEQIK | 6-30 for the protein of SEQ No. 609 | 2b |
| SEQ ID No. 655 | LSASSQR | 195-201 for the protein of SEQ No. 497 | SHV |
| SEQ ID No. 656 | LSESQLSGR | 31-39 for the proteins of SEQ No. 496, 497, 498, 499, 500, 503, 504, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 604, 606, 609, 1917, 1918, 1919; 30-38 for the protein of sequence SEQ ID No. 501 | SHV |
| SEQ ID No. 657 | LSESQLSGSVGMIEMDLASGR | 31-51 for the proteins of SEQ No. 505, 506, 507, 508, 509, 510 | SHV |
| SEQ ID No. 658 | MVVIYLR | 254-260 for the protein of SEQ No. 499 | 2b |
| SEQ ID No. 659 | NEALPGDAR | 166-174 for the proteins of SEQ No. 496, 497, 498, 499, 500, 502, 503, 504, 505, 506, 507, 508, 509, 510, 511, 512, 513, 514, 515, 516, 517, 518, 519, 520, 521, 523, 524, 525, 527, 528, 529, 533, 534, 535, 536, 537, 538, 539, 540, 541, 542, 543, 544, 545, 546, 547, 548, 549, 550, 551, 552, 553, 554, 555, 556, 557, 558, 559, 561, 562, 563, 564, 565, 566, 567, 570, 571, 572, 573, 574, 575, 576, 577, 578, 579, 580, 581, 582, 583, 584, 585, 586, 587, 588, 589, 590, 591, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 165-173 for the protein of sequence SEQ ID No. 501; 171-179 for the protein of sequence SEQ ID No. 530; 165-173 for the protein of sequence SEQ ID No. 568; 165-173 for the protein of sequence SEQ ID No. 569 | 2be |
| SEQ ID No. 660 | NQHIAGIGAALIEHWQR | 270-286 for the proteins of SEQ No. 513, 1910 | SHV |

-continued

| Peptide SEQ ID No. | Amino acid sequence | Position of the peptide in the SHV protein | Clinical interest |
|---|---|---|---|
| SEQ ID No. 661 | NQQIAGIGAALIE HWQR | 270-286 for the proteins of SEQ No. 496, 497, 498, 499, 500, 502, 503, 504, 505, 506, 507, 508, 509, 510, 511, 512, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 546, 547, 548, 549, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 588, 589, 590, 591, 592, 593, 594, 595, 596, 597, 598, 599, 600, 601, 602, 603, 604, 605, 606, 607, 608, 609, 610, 611, 612, 613, 1912, 1915, 1916, 1917, 1918, 1919; 269-285 for the protein of sequence SEQ ID No. 501; 275-291 for the protein of sequence SEQ ID No. 530; 269-285 for the protein of sequence SEQ ID No. 568; 269-285 for the protein of sequence SEQ ID No. 569 | SHV |
| SEQ ID No. 662 | NQQIAGLGAALIE HWQR | 270-286 for the protein of SEQ No. 550 | SHV |
| SEQ ID No. 663 | NTTTPASMAATLR | 175-187 for the protein of SEQ No. 559 | 2be |
| SEQ ID No. 664 | NVLTSQR | 187-193 for the proteins of SEQ No. 568, 569 | SHV |
| SEQ ID No. 665 | QIDDNVTR | 150-157 for the proteins of SEQ No. 505, 527, 528, 565, 577, 601 | 2be |
| SEQ ID No. 666 | QIGDK | 150-154 for the protein of SEQ No. 529 | 2b |
| SEQ ID No. 667 | QIGDNVTR | 150-157 for the proteins of SEQ No. 496, 497, 498, 499, 500, 502, 503, 504, 506, 507, 508, 509, 510, 511, 512, 513, 514, 515, 516, 517, 518, 519, 520, 521, 522, 523, 524, 525, 526, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 563, 564, 566, 567, 570, 571, 572, 573, 574, 575, 576, 578, 579, 580, 581, 582, 583, 584, 585, 586, 587, 588, 589, 590, 591, 592, 593, 594, 595, 596, 597, 598, 599, 600, 602, 603, 604, 605, 606, 607, 608, 609, 610, 611, 612, 613, 1910, 1912, 1913, 1914, 1916, 1917, 1918, 1919, 1920; 149-156 for the protein of sequence SEQ ID No. 501; 149-156 for the protein of sequence SEQ ID No. 568; 149-156 for the protein of sequence SEQ ID No. 569 | SHV |
| SEQ ID No. 668 | QIGENVTR | 150-157 for the protein of SEQ No. 562 | 2b |
| SEQ ID No. 669 | QLLQWMVDAR | 202-211 for the protein of SEQ No. 579 | SHV |
| SEQ ID No. 670 | QLLQWMVDDGV AGPLIR | 202-218 for the protein of SEQ No. 539 | SHV |
| SEQ ID No. 671 | QLLQWMVDDR | 202-211 for the proteins of SEQ No. 496, 497, 498, 499, 500, 502, 503, 504, 505, 506, 507, 508, 509, 510, 511, 513, 514, 515, 516, 517, 518, 519, 520, 521, 522, 523, 524, 525, 526, 527, 528, 529, 531, 532, 533, 534, 535, 536, 537, 538, 540, 541, 542, 543, 544, 545, 546, 547, 548, 549, 550, 551, 552, 555, 556, 557, 558, 559, 560, 561, 562, 563, 564, 565, 566, 567, 570, 571, 572, 573, 574, 575, 576, 577, 578, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 201-210 for the protein of sequence SEQ ID No. 501; 207-216 for the protein of sequence SEQ ID No. 530; 201-210 for the protein of sequence SEQ ID No. 568; 201-210 for the protein of sequence SEQ ID No. 569; 35-44 for the protein of sequence SEQ ID No. 1911 | SHV |
| SEQ ID No. 672 | QLLQWMVDGR | 202-211 for the protein of SEQ No. 553 | 2b |
| SEQ ID No. 673 | QLLQWMVEDR | 202-211 for the protein of SEQ No. 512 | SHV |

-continued

| Peptide SEQ ID No. | Amino acid sequence | Position of the peptide in the SHV protein | Clinical interest |
|---|---|---|---|
| SEQ ID No. 674 | QQDLVDYSPVSEK | 95-107 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 587, 588, 589, 590, 591, 592, 593, 594, 595, 596, 597, 598, 600, 601, 602, 603, 604, 605, 606, 607, 608, 609, 610, 611, 612, 613, 1910, 1912, 1913, 1914, 1915, 1916, 1917, 1918, 1919, 1920; 94-106 for the protein of sequence SEQ ID No. 501; 94-106 for the protein of sequence SEQ ID No. 568; 94-106 for the protein of sequence SEQ ID No. 569 | SHV |
| SEQ ID No. 675 | QQHLVDYSPVSEK | 95-107 for the protein of SEQ No. 599 | 2b |
| SEQ ID No. 676 | QSESQLSGR | 31-39 for the proteins of SEQ No. 502, 511, 512, 513, 514, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 605, 607, 608, 610, 611, 612, 613, 1910, 1912, 1913, 1914, 1915, 1916, 1920 | SHV |
| SEQ ID No. 677 | QSESQLSGSVGMIEMDLASGR | 31-51 for the protein of SEQ No. 603 | 2b |
| SEQ ID No. 678 | SQLQLLQWMVDDR | 199-211 for the proteins of SEQ No. 536, 537, 538 | 2be |
| SEQ ID No. 679 | SVLPAGWFIADK | 219-230 for the proteins of SEQ No. 496, 497, 498, 499, 500, 502, 503, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 546, 547, 548, 549, 550, 553, 554, 555, 556, 557, 558, 559, 560, 561, 562, 563, 564, 565, 566, 567, 570, 571, 572, 573, 574, 575, 576, 577, 578, 579, 580, 581, 582, 583, 584, 585, 586, 587, 588, 589, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 224-235 for the protein of sequence SEQ ID No. 530; 218-229 for the protein of sequence SEQ ID No. 568; 218-229 for the protein of sequence SEQ ID No. 569; 52-63 for the protein of sequence SEQ ID No. 1911 | SHV |
| SEQ ID No. 680 | SVLPAGWFIADR | 219-230 for the proteins of SEQ No. 504, 551, 590; 218-229 for the protein of sequence SEQ ID No. 501 | SHV |
| SEQ ID No. 681 | SVLSAGWFIADK | 219-230 for the protein of SEQ No. 552 | 2b |
| SEQ ID No. 682 | TGAAER | 231-236 for the proteins of SEQ No. 540, 581, 603 | SHV |
| SEQ ID No. 683 | TGAAK | 231-235 for the protein of SEQ No. 506 | 2be |
| SEQ ID No. 684 | TGAGER | 231-236 for the proteins of SEQ No. 496, 497, 498, 499, 502, 504, 507, 511, 512, 513, 514, 516, 518, 519, 520, 521, 524, 525, 526, 527, 531, 533, 535, 536, 539, 541, 542, 543, 544, 551, 552, 553, 554, 555, 558, 559, 560, 561, 562, 563, 564, 565, 566, 567, 570, 571, 572, 573, 576, 577, 578, 579, 582, 583, 590, 591, 592, 593, 594, 595, 596, 597, 598, 599, 600, 601, 604, 605, 607, 608, 609, 610, 611, 612, 613, 1910, 1912, 1916, 1917, 1918; 230-235 for the protein of sequence SEQ ID No. 501; 236-241 for the protein of sequence SEQ ID No. 530 | SHV |
| SEQ ID No. 685 | TGAGK | 231-235 for the proteins of SEQ No. 517, 545, 546, 556, 584, 606 | SHV |
| SEQ ID No. 686 | TGASER | 64-69 for the proteins of SEQ No. 1911; 231-236 for the protein of sequence SEQ ID No. 503; 231-236 for the protein of sequence SEQ ID No. 508; 231-236 for the protein of sequence | 2be |

| Peptide SEQ ID No. | Amino acid sequence | Position of the peptide in the SHV protein | Clinical interest |
|---|---|---|---|
| | | SEQ ID No. 522; 231-236 for the protein of sequence SEQ ID No. 532; 231-236 for the protein of sequence SEQ ID No. 537; 231-236 for the protein of sequence SEQ ID No. 547; 231-236 for the protein of sequence SEQ ID No. 548; 231-236 for the protein of sequence SEQ ID No. 585 | |
| SEQ ID No. 687 | TGASK | 231-235 for the proteins of SEQ No. 500, 505, 509, 515, 523, 528, 529, 534, 538, 549, 550, 557, 574, 575, 586, 587, 588, 602, 1913, 1914, 1915, 1919, 1920; 230-234 for the protein of sequence SEQ ID No. 568; 230-234 for the protein of sequence SEQ ID No. 569 | SHV |
| SEQ ID No. 688 | TGASR | 231-235 for the protein of SEQ No. 589 | SHV |
| SEQ ID No. 689 | TLTAWCADER | 52-61 for the protein of SEQ No. 571 | SHV |
| SEQ ID No. 690 | TLTAWHADER | 52-61 for the proteins of SEQ No. 516, 517 | 2be |
| SEQ ID No. 691 | TLTAWR | 52-57 for the proteins of SEQ No. 496, 497, 498, 499, 500, 502, 503, 504, 505, 506, 507, 508, 509, 510, 511, 512, 513, 514, 515, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 51-56 for the protein of sequence SEQ ID No. 501; 51-56 for the protein of sequence SEQ ID No. 568; 51-56 for the protein of sequence SEQ ID No. 569 | SHV |
| SEQ ID No. 692 | TVGGPAGLTAFLR | 137-149 for the proteins of SEQ No. 496, 497, 498, 499, 500, 502, 503, 505, 506, 507, 508, 509, 510, 512, 513, 514, 515, 516, 517, 518, 519, 521, 522, 523, 524, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 564, 565, 566, 570, 571, 573, 574, 575, 577, 578, 579, 580, 581, 582, 583, 584, 585, 586, 587, 588, 589, 590, 591, 592, 596, 597, 598, 599, 600, 601, 602, 603, 604, 605, 606, 607, 608, 609, 610, 611, 612, 613, 1910, 1912, 1913, 1914, 1915, 1916, 1918, 1919, 1920; 136-148 for the protein of sequence SEQ ID No. 568; 136-148 for the protein of sequence SEQ ID No. 569 | SHV |
| SEQ ID No. 693 | TVVIYLR | 254-260 for the protein of SEQ No. 546 | SHV |
| SEQ ID No. 694 | VAGPLIR | 212-218 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 211-217 for the protein of sequence SEQ ID No. 501; 217-223 for the protein of sequence SEQ ID No. 530; 211-217 for the protein of sequence SEQ ID No. 568; 211-217 for the protein of sequence SEQ ID No. 569; 45-51 for the protein of sequence SEQ ID No. 1911 | SHV |
| SEQ ID No. 695 | VALCGAVLAR | 70-79 for the protein of SEQ No. 573 | 2b |
| SEQ ID No. 696 | VDAGDEQLER | 80-89 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, | SHV |

-continued

| Peptide SEQ ID No. | Amino acid sequence | Position of the peptide in the SHV protein | Clinical interest |
|---|---|---|---|
| | | 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 572, 573, 574, 576, 577, 578, 579, 580, 581, 582, 583, 584, 585, 586, 587, 588, 589, 590, 591, 592, 593, 594, 595, 596, 597, 598, 599, 601, 602, 603, 604, 605, 606, 607, 608, 609, 610, 611, 612, 613, 1910, 1912, 1913, 1914, 1915, 1916, 1917, 1918, 1919, 1920; 79-88 for the protein of sequence SEQ ID No. 501; 79-88 for the protein of sequence SEQ ID No. 568; 79-88 for the protein of sequence SEQ ID No. 569 | |
| SEQ ID No. 697 | VDAGDK | 80-85 for the proteins of SEQ No. 575, 600 | SHV |
| SEQ ID No. 698 | VGMIEMDLASGR | 40-51 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 39-50 for the protein of sequence SEQ ID No. 501 | SHV |
| SEQ ID No. 699 | VGMIEMDLASR | 40-50 for the proteins of SEQ No. 568, 569 | SHV |
| SEQ ID No. 700 | VGMIEMDLASSR | 40-51 for the protein of SEQ No. 570 | SHV |
| SEQ ID No. 701 | VLLCGAVLAR | 70-79 for the protein of SEQ No. 574 | SHV |
| SEQ ID No. 702 | VVLCGAMLAR | 70-79 for the protein of SEQ No. 575 | 2be |
| SEQ ID No. 703 | VVLCGAVLAR | 70-79 for the proteins of SEQ No. 496, 497, 498, 499, 500, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 570, 571, 572, 576, 577, 578, 579, 580, 581, 582, 583, 584, 585, 586, 587, 588, 589, 590, 591, 592, 593, 594, 595, 596, 597, 598, 599, 600, 602, 603, 604, 605, 606, 607, 608, 609, 610, 611, 612, 613, 1910, 1912, 1913, 1914, 1915, 1916, 1917, 1918, 1919, 1920; 69-78 for the protein of sequence SEQ ID No. 501; 69-78 for the protein of sequence SEQ ID No. 568; 69-78 for the protein of sequence SEQ ID No. 569 | SHV |
| SEQ ID No. 704 | VVLCGTVLAR | 70-79 for the protein of SEQ No. 601 | 2b |
| SEQ ID No. 705 | WETDR | 161-165 for the protein of SEQ No. 530 | 2be |
| SEQ ID No. 706 | WETELNEAFPGDAR | 161-174 for the proteins of SEQ No. 522, 531, 532 | SHV |
| SEQ ID No. 707 | WETELNEALPADAR | 161-174 for the protein of SEQ No. 526 | 2b |
| SEQ ID No. 708 | WETELNEALPGDAR | 161-174 for the proteins of SEQ No. 496, 497, 498, 499, 500, 502, 503, 504, 505, 506, 507, 508, 509, 510, 511, 512, 513, 514, 515, 516, 517, 518, 519, 520, 521, 523, 524, 525, 527, 528, 529, 533, 534, 535, 536, 537, 538, 539, 540, 541, 542, 543, 544, 545, 546, 547, 548, 549, 550, 551, 552, 553, 554, 555, 556, 557, 558, 559, 562, 563, 564, 565, 566, 567, 570, 571, 572, 573, 574, 575, 576, 577, 578, 579, 580, 581, 582, 583, 584, 585, 586, 587, 588, 589, 590, 591, 593, 594, 595, | SHV |

| Peptide SEQ ID No. | Amino acid sequence | Position of the peptide in the SHV protein | Clinical interest |
|---|---|---|---|
| | | 596, 597, 598, 599, 600, 601, 602, 603, 604, 605, 606, 607, 608, 609, 610, 611, 612, 613, 1910, 1912, 1913, 1914, 1915, 1916, 1917, 1918, 1919, 1920; 160-173 for the protein of sequence SEQ ID No. 501; 166-179 for the protein of sequence SEQ ID No. 530; 160-173 for the protein of sequence SEQ ID No. 568; 160-173 for the protein of sequence SEQ ID No. 569 | |
| SEQ ID No. 709 | WETELNEALSGDAR | 161-174 for the protein of SEQ No. 560 | 2b |
| SEQ ID No. 710 | WETELNEVLPGDAR | 161-174 for the protein of SEQ No. 592 | SHV |
| SEQ ID No. 711 | WETER | 161-165 for the protein of SEQ No. 561 | SHV |
| SEQ ID No. 2093 | EIGDNVTR | 150-157 for the proteins of SEQ No. 1915 | SHV |
| SEQ ID No. 2094 | GIVALLGPHNK | 240-250 for the proteins of SEQ No. 1917 | SHV |
| SEQ ID No. 2095 | HLADGMTVGELR | 108-119 for the proteins of SEQ No. 1914 | 2be |
| SEQ ID No. 2096 | IHYSQQDLVDYSPVSEK | 91-107 for the proteins of SEQ No. 1918 | SHV |

In the clinical interest column, the entries 2b, 2br, 2be and 2ber correspond to the functional subgroups of the SHV beta-lactamases which the corresponding peptide makes it possible to detect. Thus, the detection of a 2be peptide will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The entry SHV indicates a common peptide between at least two of the subgroups 2b, 2br and 2be or 2ber. The corresponding peptide indicates the presence of an SHV beta-lactamase and the presence of a mechanism of resistance at least to penicillins and to first-generation cephalosporins.

The detection of a mechanism of resistance to ESBL (extended-spectrum beta-lactamase) cephalosporins, induced by the SHV protein, is characterised by the detection of at least one resistance-marking 2be peptide, chosen from the sequences SEQ ID No. 616, SEQ ID No. 617, SEQ ID No. 627, SEQ ID No. 629, SEQ ID No. 634, SEQ ID No. 647, SEQ ID No. 648, SEQ ID No. 653, SEQ ID No. 654, SEQ ID No. 656, SEQ ID No. 660, SEQ ID No. 661, SEQ ID No. 662, SEQ ID No. 663, SEQ ID No. 664, SEQ ID No. 665, SEQ ID No. 670, SEQ ID No. 673, SEQ ID No. 674, SEQ ID No. 675, SEQ ID No. 678, SEQ ID No. 682, SEQ ID No. 684, SEQ ID No. 685, SEQ ID No. 686, SEQ ID No. 687, SEQ ID No. 688, SEQ ID No. 697, SEQ ID No. 702, SEQ ID No. 703, SEQ ID No. 704, SEQ ID No. 707, SEQ ID No. 708, SEQ ID No. 709, SEQ ID No. 711, SEQ ID No. 2095.

The detection of a mechanism of resistance to cephalosporins induced by the expression of the FOX protein is characterised by the detection of at least one peptide belonging to the FOX protein and to its different sequence variants SEQ ID No. 712 to SEQ ID No. 718 and SEQ ID No. 1920 to SEQ ID No. 1922.

SEQ ID No. 712:
MQQRRAFALLTLGSLLLAPCTYASGEAPLTAAVDGIIQPMLKAYRIPGMA

VAVLKDGKAHYFNYGVANRESGQRVSEQTLFEIGSVSKTLTATLGAYAAV

KGGFELDDKVSQHAPWLKGSALDGVTMAELATYSAGGLPLQFPDEVDSND

KMRTYYRSWSPVYPAGTHRQYSNPSIGLFGHLAANSLGQPFEQLMSQTLL

PKLGLHHTYIQVPESAMVNYAYGYSKEDKPVRVTPGVLAAEAYGIKTGSA

DLLKFAEANMGYQGDAAVKSAIALTHTGFYSVGDMTQGLGWESYAYPVTE

QTLLAGNAPAVSFQANPVTRFAVPKAMGEQRLYNKTGSTGGFGAYVAFVP

ARGIAIVMLANRNYPIEARVKAAHAILSQLAE

SEQ ID No. 713:
MQQRRAFALLTLGSLLLAPCTYASGEAPLTAAVDGIIQPMLKAYRIPGMA

VAVLKDGKAHYFNYGVANRESGQRVSEQTLFEIGSVSKTLTATLGAYAAV

KGGFELDDKVSQHAPWLKGSALDGVTMAELATYSAGGLPLQFPDEVDSND

KMRTYYRSWSPVYPAGTHRQYSNPSIGLFGHLAANSLGQPFEQLMSQTLL

PKLGLHHTYIQVPESAMVNYAYGYSKEDKPVRVTPGVLAAEAYGIKTGSA

DLLKFAEANMGYQGDAAVKSAIALTHTGFYSVGDMTQGLGWESYAYPVTE

QTLLAGNAPAVSFQANPVTRFAVPKAMGEQRLYNKTGSTGGFGAYVAFVP

ARGIAIVMLANRNYPIEARVKAAHAILSQLAE

SEQ ID No. 14:
MQQRRAFALLTLGSLLLAPCTYARGEAPLTAAVDGIIQPMLKEYRIPGMA

VAVLKDGKAHYFNYGVANRESGQRVSEQTLFEIGSVSKTLTATLGAYAAV

KGGFELDDKVSQHAPWLKGSAFDGVTMAELATYSAGGLPLQFPDEVDSND

KMRTYYRHWSPVYPAGTHRQYSNPSIGLFGHLAANSLGQPFEQLMSQTLL

PKLGLHHTYIQVPESAIANYAYGYSKEDKPVRVTPGVLAAEAYGIKTGSA

-continued
DLLKFTEANMGYQGDAALKTRIALTHTGFYSVGDMTQGLGWESYAYPLTE

QALLAGNSPAVSFQANPVTRFAVPKAMGEQRLYNKTGSTGGFGAYVAFVP

ARGIAIVMLANRNYPIEARVKAAHAILSQLAE

SEQ ID No. 715:
MQQRRALALLTLGSLLLAPCTYASGEAPLTAAVDGIIQPMLKEYRIPGMA

VAVLKDGKAHYFNYGVANRESGQRVSEQTLFEIGSVSKTLTATLGAYAAV

KGGFELDDKVSHHAPWLKGSAFDGVTMAELATYSAGGLPLQFPDEVDSND

KMQTYYRSWSPVYPAGTHRQYSNPSIGLFGHLAANSLGQPFEKLMSQTLL

PKLGLHHTYIQVPESAMANYAYGYSKEDKPIRVTPGVLAAEAYGIKTGSA

DLLKFVEANMGYQGDAALKSAIALTHTGFYSVGDMTQGLGWESYAYPVTE

QALLAGNSPAVSFQANPVTRFAVPKAMGEQRLYNKTGSTGGFGAYVAFVP

ARGIAIVMLANRNYPIEARVKAAHAILSQLAE

SEQ ID No. 716:
MQQRRAFALLTLGSLLLAPCTYASGEAPLTATVDGIIQPMLKEYRIPGIA

VAVLKDGKAHYFNYGVANRESGQRVSEQTLFEIGSVSKTLTATLGAYAAV

KGGFVLDDKVSQHAPWLKGSALDGVTMAELATYSAGGLPLQFPDKVDSND

KMQTYYRSWSPVYPAGTHRQYSNPSIGLFGHLAANSLGQPFEQLMSQTLL

PKLGLHHTYIQVPESAMANYAYGYSKEDKPIRVTPGVLAAEAYGIKTGSA

DLLKFAEANMGYQGDALVKSAIALTHTGFYSVGEMTQGLGWESYDYPVTE

QVLLAGNSPAVSFQANPVTRFAVPKAMGEQRLYNKTGSTGGFGAYVAFVP

ARGIAIVMLANRNYPIEARVKAAHAILSQLAE

SEQ ID No. 717:
MQQRRALALLMLGSLLLAPCTYASGEAPLTATVDGIIQPMLKAYRIPGMA

VAVLKDGKAHYFNYGVANRESGQRVSEQTLFEIGSVSKTLTATLGAYAAV

KGGFELDDKVSQHAPWLKGSAFDGVTMAELATYSAGGLPLQFPDEVDSND

KMQTYYRSWSPVYPAGTHRQYSNPSIGLFGHLAANSLGQPFEQLMSQTLL

PKLGLHHTYIQVPESAMANYAYGYSKEDKPIRATPGVLAAEAYGIKTGSA

DLLKFVEANMGYQGDAALKSAIALTHTGFHSVGEMTQGLGWESYDYPVTE

QVLLAGNSPAVSFQANPVTRFAVPKAMGEQRLYNKTGSTGGFGAYVAFVP

ARGIAIVMLANRNYPIEARVKAAHAILSQLAE

SEQ ID No. 718:
MQQRRAFALLTLGSLLLAPCTYARGEAPLTAAVDGIIQPMLKEYRIPGMA

VAVLKDGKAHYFNYGVANRESGQRVSEQTLFEIGSVSKTLTATLGAYAAV

KGGFELDDKVSQHAPWLKGSAFDGVTMAELATYSAGGLPLQFPDEVDSND

KMRTYYRHWSPVYPAGTHRQYSNPSIGLFGHLAANSLGQPFEQLMSQTLL

PKLGLHHTYIQVPESAIANYAYGYSKEDKPVRATPGVLAAEAYGIKTGSA

DLLKFTEANMGYQGDAALKSAIALTHTGFYSVGDMTQGLGWESYAYPLTE

QALLAGNSPAVSFQANPVTRFAVPKAMGEQRLYNKTGSTGGFGAYVAFVP

ARGIAIVMLANRNYPIEARVKAAHAILSQLAE

SEQ ID No. 1920:
MQQRRAFALLTLGSLLLAPCTYASGEAPLTATVDGIIQPMLKEYRIPGIA

VAVLKDGKAHYFNYGVANRESGQRVSEQTLFEIGSVSKTLTATLGAYAAV

KGGFVLDDKVSQHAPWLKGSALDGVTMAELATYSAGGLPLQFPDKVDSND

KMQTYYRSWSPVYPAGTHRQYSNPSIGLFGHLAANSLGQPFEQLMSQTLL

PKLGLHHTYIQVPESAMANYAYGYSKEDKPIRVTPGVLAAEAYGIKTGSA

DLLKFAEANMGYQGDALVKSAIALTHTGFYSVGEMTQGLGWESYDYPVTE

QVLLAGNSPAVSLQANPVTRFAVPKAMGEQRLYNKTGSTGGFGAYVAFVP

ARGIAIVMLANRNYPIEARVKAAHAILSQLAE

SEQ ID No. 1921:
MQQRRAFALLTLGSLLLAPCTYASGEAPLTVTVDGIIQPMLKAYRIPGMA

VAVLKDGKAHYFNYGVANRESGQRVSEQTLFEIGSVSKTLTATLGAYAAV

KGGFELDDKVSQHAPWLKGSAFDGVTMAELATYSAGGLPLQFPEEVDSND

KMRTYYRSWSPVYPAGTHRQYANTSIGLFGYLAANSLGQSFEQLMSQTLL

PKLGLHHTYIQVPESAMANYAYGYSKEEKPIRVTPGMLAAEAYGIKTGSA

DLLKFAEANMGYQGDAAVKSAIALTHTGFYSVGDMTQGLGWESYDYPVTE

QVLLADNSPAVSFQANPVTRFAVPKAMGEQRLYNKTGSTGGFGAYVAFVP

ARGIAIVMLANRNYPIEARVKAAHAILSQLAE

SEQ ID No. 1922:
MQQRRAFALLTLGSLLLAPCTYASGEAPLTATVDGIIQPMLKEYRIPGIA

VAVLKDGKAHYFNYGVANRESGQRVSEQTLFEIGSVSKTLTATLGAYAAV

KGGFVLDDKVSQHAPWLKGSALDGVTMAELATYSAGGLPLQFPDKVDSND

KMQTYYRSWSPVYPAGTHRQYSNPSIGLFGHLAANSLGQPFEQLMSQTLL

PKLGLHHTYIQVPESAMANYAYGYSKEDKPIRVTPGVLAAEAYGIKTGSA

DLLKFAEANMGYQGDALVKSAIALTHTGFYSVGEMTQGLGWESYDYPVTE

QVLLAGNSPAVSFQANPVTRFAVPKAMGEQRLYNKTGSTGGFGAYVAFVP

ARGIAIVMLANRNYPIEARVKAAHAILSQLAE said peptides being chosen, preferably, from the peptides of sequence SEQ ID No. 719 to SEQ ID No. 733 and SEQ ID No. 2097 to SEQ ID No. 2113 as defined hereafter:

| Peptide SEQ ID No. | Amino acid sequence | Position of the peptide in the FOX protein |
|---|---|---|
| SEQ ID No. 719 | AHYFNYGVANR | 59-69 for the proteins of SEQ No. 712, 713, 714, 715, 716, 717, 718, 1920, 1921, 1922 |
| SEQ ID No. 720 | AMGEQR | 326-331 for the proteins of SEQ No. 712, 713, 714, 715, 716, 717, 718, 1920, 1921, 1922 |
| SEQ ID No. 721 | ESGQR | 70-74 for the proteins of SEQ No. 712, 713, 714, 715, 716, 717, 718, 1920, 1921, 1922 |

-continued

| Peptide SEQ ID No. | Amino acid sequence | Position of the peptide in the FOX protein |
|---|---|---|
| SEQ ID No. 722 | FAVPK | 321-325 for the proteins of SEQ No. 712, 713, 714, 715, 716, 717, 718, 1920, 1921, 1922 |
| SEQ ID No. 723 | GGFELDDK | 102-109 for the proteins of SEQ No. 712, 713, 714, 715, 717, 718, 1921 |
| SEQ ID No. 724 | GIAIVMLANR | 353-362 for the proteins of SEQ No. 712, 713, 714, 715, 716, 717, 718, 1920, 1921, 1922 |
| SEQ ID No. 725 | IPGMAVAVLK | 46-55 for the proteins of SEQ No. 712, 713, 714, 715, 717, 718, 1921 |
| SEQ ID No. 726 | NYPIEAR | 363-369 for the proteins of SEQ No. 712, 713, 714, 715, 716, 717, 718, 1920, 1921, 1922 |
| SEQ ID No. 727 | SWSPVYPAGTHR | 158-169 for the proteins of SEQ No. 712, 713, 715, 716, 717, 1920, 1921, 1922 |
| SEQ ID No. 728 | TGSADLLK | 247-254 for the proteins of SEQ No. 712, 713, 714, 715, 716, 717, 718, 1920, 1921, 1922 |
| SEQ ID No. 729 | TGSTGGFGAYVAFVPAR | 336-352 for the proteins of SEQ No. 712, 713, 714, 715, 716, 717, 718, 1920, 1921, 1922 |
| SEQ ID No. 730 | TLTATLGAYAAVK | 89-101 for the proteins of SEQ No. 712, 713, 714, 715, 716, 717, 718, 1920, 1921, 1922 |
| SEQ ID No. 731 | VSEQTLFEIGSVSK | 75-88 for the proteins of SEQ No. 712, 713, 714, 715, 716, 717, 718, 1920, 1921, 1922 |
| SEQ ID No. 732 | VSQHAPWLK | 110-118 for the proteins of SEQ No. 712, 713, 714, 716, 717, 718, 1920, 1921, 1922 |
| SEQ ID No. 733 | VTPGVLAAEAYGIK | 233-246 for the proteins of SEQ No. 712, 713, 714, 715, 716, 1920, 1922 |
| SEQ ID No. 2097 | AFALLTLGSLLLAPCTYAR | 6-24 for the proteins of SEQ No. 714, 718 |
| SEQ ID No. 2098 | ATPGVLAAEAYGIK | 233-246 for the proteins of SEQ No. 717, 718 |
| SEQ ID No. 2099 | EDKPVR | 227-232 for the proteins of SEQ No. 712, 713, 714, 718 |
| SEQ ID No. 2100 | EEKPIR | 227-232 for the proteins of SEQ No. 1921 |
| SEQ ID No. 2101 | FAEANMGYQGDAAVK | 255-269 for the proteins of SEQ No. 712, 713, 1921 |
| SEQ ID No. 2102 | FAEANMGYQGDALVK | 255-269 for the proteins of SEQ No. 716, 1920, 1922 |
| SEQ ID No. 2103 | FTEANMGYQGDAALK | 255-269 for the proteins of SEQ No. 714, 718 |
| SEQ ID No. 2104 | FVEANMGYQGDAALK | 255-269 for the proteins of SEQ No. 715, 717 |
| SEQ ID No. 2105 | GEAPLTAAVDGIIQPMLK | 25-42 for the proteins of SEQ No. 712, 713, 714, 715, 718 |
| SEQ ID No. 2106 | GGFVLDDK | 102-109 for the proteins of SEQ No. 716, 1920, 1922 |
| SEQ ID No. 2107 | HWSPVYPAGTHR | 158-169 for the proteins of SEQ No. 714, 718 |
| SEQ ID No. 2108 | IPGIAVAVLK | 46-55 for the proteins of SEQ No. 716, 1920, 1922 |
| SEQ ID No. 2109 | LMSQTLLPK | 194-202 for the proteins of SEQ No. 712, 713, 714, 715, 716, 717, 718, 1920, 1921, 1922 |

-continued

| Peptide SEQ ID No. | Amino acid sequence | Position of the peptide in the FOX protein |
|---|---|---|
| SEQ ID No. 2110 | MQTYYR | 152-157 for the proteins of SEQ No. 715, 716, 717, 1920, 1922 |
| SEQ ID No. 2111 | VDSNDK | 146-151 for the proteins of SEQ No. 712, 713, 714, 715, 716, 717, 718, 1920, 1921, 1922 |
| SEQ ID No. 2112 | VSHHAPWLK | 110-118 for the protein of SEQ No. 715 |
| SEQ ID No. 2113 | VTPGMLAAEAYGIK | 233-246 for the proteins of SEQ No. 1921 |

The detection of a mechanism of resistance to cephalosporins induced by the expression of the ACC protein is characterised by the detection of at least one peptide belonging to the ACC protein and to its different sequence variants SEQ ID No. 736 to SEQ ID No. 739.

SEQ ID No. 736:
MRKKMQNTLKLLSVITCLAATAQGAMAANIDESKIKDTVDGLIQPLMQKN

NIPGMSVAVTIRGRNYIYNYGLAAKQPQQPVTENTLFEVGSLSKTFAAIL

ASYAQASGKLSLEQSVSHYVPELRGSSFDHVSVLNVGTHTSGLQLFMPED

IKNTTQLMTYLKAWKPADAAGTHRVYSNIGTGLLGMIAAKSLGVSYEDAI

EQTILPLLGMNQTYLKVPADQMENYAWGYNKKDEPVHVNMEILGNEAYGI

KTTSSDLLRYVQANMGQLKLDGNAKIQHALTATHTGYFKSGEITQDLMWE

QLPYPVSLPNLLTGNDMAMTKSVATPIVPPLPPQENVWINKTGSTNGFGA

YIAFVPAKKMGIVMLANKNYSIDQRVTVAYKILSSLEVNK

SEQ ID No. 737:
MRKKMQNTLKMLSVITCLALTAQGAMASEMDQAKIKDTVDSLIQPLMQKN

NIPGMSVAVTLNGKNYIYNYGLASKQPQQPVTDNTLFEVGSLSKTFAATL

ASYAQVSGKLSLDKSISHYVPELRGSSFDHISVLNAGTHTTGLALFMPEE

VKNTDQLMAYLKAWKPADPAGTHRVYSNIGTGLLGMIAAQSMGMTYEDAI

EKTLLPKLGMTHTYLNVPADQAENYAWGYNKKNEPIHVNMEVLGNEAYGI

RTNASDLIRYVQANMGQLKLDGNSTLQKALTDTHIGYFKSGKITQDLMWE

QLPYPVSLPDLLTGNDMAMTKSVATPIVPPLPPQENVWINKTGSTNGFGA

YIAFVPAKKMGIVMLANKNYSIDQRVT

SEQ ID No. 738:
MQNTLKLLSVITCLAATVQGALAANIDESKIKDTVDDLIQPLMQKNNIPG

MSVAVTVNGKNYIYNYGLAAKQPQQPVTENTLFEVGSLSKTFAATLASYA

QVSGKLSLDQSVSHYVPELRGSSFDHVSVLNVGTHTSGLQLFMPEDIKNT

TQLMAYLKAWKPADAAGTHRVYSNIGTGLLGMIAAKSLGVSYEDAIEKTL

LPQLGMHHSYLKVPADQMENYAWGYNKKDEPVHGNMEILGNEAYGIKTTS

SDLLRYVQANMGQLKLDANAKMQQALTATHTGYFKSGEITQDLMWEQLPY

PVSLPNLLTGNDMAMTKSVATPIVPPLPPQENVWINKTGSTNGFGAYIAF

VPAKKMGIVMLANKNYSIDQRVTVAYKILSSLEGNK

SEQ ID No. 739:
MQNTLKLLSVITCLAATVQGALAANIDESKIKDTVDDLIQPLMQKNNIPG

MSVAVTVNGKNYIYNYGLAAKQPQQPVTENTLFEVGSLSKTFAATLASYA

QVSGKLSLDQSVSHYVPELRGSSFDHVSVLNVGTHTSGLQLFMPEDIKNT

TQLMAYLKAWKPADAAGTHRVYSNIGTGLLGMIAAKSLGVSYEDAIEKTL

LPQLGMHHSYLKVPADQMENYAWGYNKKDEPVHVNMEILGNEAYGIKTTS

SDLLRYVQANMGQLKLDANAKMQQALTATHTGYFKSGEITQDLMWEQLPY

PVSLPNLLTGNDMAMTKSVATPIVPPLPPQENVWINKTGSTNGFGAYIAF

VPAKKMGIVMLANKNYSIDQRVTVAYKILSSLEGNK said peptides being chosen, preferably, from the peptides of sequence SEQ ID No. 740 to SEQ ID No. 787 as defined hereafter:

| Peptide SEQ ID No. | Amino acid sequence | Position of the peptide in the ACC protein(s) |
|---|---|---|
| SEQ ID No. 740 | ALTDTHIGYFK | 279-289 for the protein of SEQ No. 737 |
| SEQ ID No. 741 | AWKPADAAGTHR | 159-170 for the proteins of SEQ No. 738, 739; 163-174 for the protein of sequence SEQ ID No. 736 |
| SEQ ID No. 742 | AWKPADPAGTHR | 163-174 for the protein of SEQ No. 737 |
| SEQ ID No. 743 | DEPVHGNMEILGNEAYGIK | 229-247 for the protein of SEQ No. 738 |

-continued

| Peptide SEQ ID No. | Amino acid sequence | Position of the peptide in the ACC protein(s) |
|---|---|---|
| SEQ ID No. 744 | DEPVHVNMEILGNEAYGIK | 229-247 for the protein of SEQ No. 739; 233-251 for the protein of sequence SEQ ID No. 736 |
| SEQ ID No. 745 | DTVDDLIQPLMQK | 33-45 for the proteins of SEQ No. 738, 739 |
| SEQ ID No. 746 | DTVDGLIQPLMQK | 37-49 for the protein of SEQ No. 736 |
| SEQ ID No. 747 | DTVDSLIQPLMQK | 37-49 for the protein of SEQ No. 737 |
| SEQ ID No. 748 | IQHALTATHTGYFK | 276-289 for the protein of SEQ No. 736 |
| SEQ ID No. 749 | LDANAK | 266-271 for the proteins of SEQ No. 738, 739 |
| SEQ ID No. 750 | LDGNAK | 270-275 for the protein of SEQ No. 736 |
| SEQ ID No. 751 | LDGNSTLQK | 270-278 for the protein of SEQ No. 737 |
| SEQ ID No. 752 | LGMTHTYLNVPADQAENYAWGYNK | 208-231 for the protein of SEQ No. 737 |
| SEQ ID No. 753 | LLSVITCLAATAQGAMAANIDESK | 11-34 for the protein of SEQ No. 736 |
| SEQ ID No. 754 | LLSVITCLAATVQGALAANIDESK | 7-30 for the proteins of SEQ No. 738, 739 |
| SEQ ID No. 755 | LSLDK | 110-114 for the protein of SEQ No. 737 |
| SEQ ID No. 756 | LSLDQSVSHYVPELR | 106-120 for the proteins of SEQ No. 738, 739 |
| SEQ ID No. 757 | LSLEQSVSHYVPELR | 110-124 for the protein of SEQ No. 736 |
| SEQ ID No. 758 | MGIVMLANK | 356-364 for the proteins of SEQ No. 738, 739; 360-368 for the proteins of sequence SEQ ID No. 736, 737 |
| SEQ ID No. 759 | MLSVITCLALTAQGAMASEMDQAK | 11-34 for the protein of SEQ No. 737 |
| SEQ ID No. 760 | MQNTLK | 1-6 for the proteins of SEQ No. 738, 739; 5-10 10 for the proteins of sequence SEQ ID No. 736, 737 |
| SEQ ID No. 761 | MQQALTATHTGYFK | 272-285 for the proteins of SEQ No. 738, 739 |
| SEQ ID No. 762 | NEPIHVNMEVLGNEAYGIR | 233-251 for the protein of SEQ No. 737 |
| SEQ ID No. 763 | NNIPGMSVAVTIR | 50-62 for the protein of SEQ No. 736 |
| SEQ ID No. 764 | NNIPGMSVAVTLNGK | 50-64 for the protein of SEQ No. 737 |
| SEQ ID No. 765 | NNIPGMSVAVTVNGK | 46-60 for the proteins of SEQ No. 738, 739 |
| SEQ ID No. 766 | NTDQLMAYLK | 153-162 for the protein of SEQ No. 737 |
| SEQ ID No. 767 | NTTQLMAYLK | 149-158 for the proteins of SEQ No. 738, 739 |

-continued

| Peptide SEQ ID No. | Amino acid sequence | Position of the peptide in the ACC protein(s) |
|---|---|---|
| SEQ ID No. 768 | NTTQLMTYLK | 153-162 for the protein of SEQ No. 736 |
| SEQ ID No. 769 | NYIYNYGLAAK | 61-71 for the proteins of SEQ No. 738, 739; 65-75 for the protein of sequence SEQ ID No. 736 |
| SEQ ID No. 770 | NYIYNYGLASK | 65-75 for the protein of SEQ No. 737 |
| SEQ ID No. 771 | NYSIDQR | 365-371 for the proteins of SEQ No. 738, 739; 369-375 for the protein of sequence SEQ ID No. 736, 737 |
| SEQ ID No. 772 | QPQQPVTDNTLFEVGSLSK | 76-94 for the protein of SEQ No. 737 |
| SEQ ID No. 773 | QPQQPVTENTLFEVGSLSK | 72-90 for the proteins of SEQ No. 738, 739; 76-94 for the protein of sequence SEQ ID No. 736 |
| SEQ ID No. 774 | SISHYVPELR | 115-124 for the protein of SEQ No. 737 |
| SEQ ID No. 775 | SLGVSYEDAIEK | 187-198 for the proteins of SEQ No. 738, 739 |
| SEQ ID No. 776 | SVATPIVPPLPPQENVWINK | 318-337 for the proteins of SEQ No. 738, 739; 322-341 for the protein of sequence SEQ ID No. 736, 737 |
| SEQ ID No. 777 | TFAAILASYAQASGK | 95-109 for the protein of SEQ No. 736 |
| SEQ ID No. 778 | TFAATLASYAQVSGK | 91-105 for the proteins of SEQ No. 738, 739; 95-109 for the protein of sequence SEQ ID No. 737 |
| SEQ ID No. 779 | TGSTNGFGAYIAFVPAK | 338-354 for the proteins of SEQ No. 738, 739; 342-358 for the protein of sequence SEQ ID No. 736, 737 |
| SEQ ID No. 780 | TLLPK | 203-207 for the protein of SEQ No. 737 |
| SEQ ID No. 781 | TLLPQLGMHHSYLK | 199-212 for the proteins of SEQ No. 738, 739 |
| SEQ ID No. 782 | TNASDLIR | 252-259 for the protein of SEQ No. 737 |
| SEQ ID No. 783 | TTSSDLLR | 248-255 for the proteins of SEQ No. 738, 739; 252-259 for the protein of sequence SEQ ID No. 736 |
| SEQ ID No. 784 | VPADQMENYAWGYNK | 213-227 for the proteins of SEQ No. 738, 739; 217-231 for the protein of sequence SEQ ID No. 736 |
| SEQ ID No. 785 | VTVAYK | 372-377 for the proteins of SEQ No. 738, 739; 376-381 for the protein of sequence SEQ ID No. 736 |
| SEQ ID No. 786 | VYSNIGTGLLGMIAAK | 171-186 for the proteins of SEQ No. 738, 739; 175-190 for the protein of sequence SEQ ID No. 736 |
| SEQ ID No. 787 | YVQANMGQLK | 256-265 for the proteins of SEQ No. 738, 739; 260-269 for the protein of sequence SEQ ID No. 736, 737 |

The detection of a mechanism of resistance to cephalosporins induced by the expression of the ACT protein is characterised by the detection of at least one peptide belonging to the ACT protein and to its different sequence variants SEQ ID No. 788 to SEQ ID No. 794.

SEQ ID No. 788:
MMMTKSLCCALLLSTSCSVLATPMSEKQLAEVVERTVTPLMKAQAIPGMA

VAVIYEGQPHYFTFGKADVAANKPVTPQTLFELGSISKTFTGVLGGDAIA

RGEISLGDPVTKYWPELTGKQWQGIRMLDLATYTAGGLPLQVPDEVKDNA

SLLRFYQNWQPQWKPGTTRLYANASIGLFGALAVKPSGMSYEQAITTRVF

KPLKLDHTWINVPKAEEAHYAWGYRDGKAVHVSPGMLDAEAYGVKTNVQD

MASWVMVNMKPDSLQDNSLRKGLTLAQSRYWRVGAMYQGLGWEMLNWPVD

AKTVVEGSDNKVALAPLPAREVNPPAPPVNASWVHKTGSTGGFGSYVAFI

PEKQLGIVMLANKSYPNPARVEAAYRILSAL

SEQ ID No. 789:
MMMTKSLCCALLLSTSCSVLATPMSEKQLAEVVERTVTPLMKAQAIPGMA

VAVIYEGQPHYFTFGKADVAANKPVTPQTLFELGSISKTFTGVLGGDAIA

RGEISLGDPVTKYWPELTGKQWQGIRMLDLATYTAGGLPLQVPDEVTDNA

SLLRFYQNWQPQWKPGTTRLYANASIGLFGALAVKPSGMSYEQAITTRVF

KPLKLDHTWINVPKAEEAHYAWGYRDGKAIHVSPGMLDAEAYGVKTNVQD

MASWVMVNMKPDSLQDNSLRKGLTLAQSRYWRVGAMYQGLGWEMLNWPVD

AKTVVEGSDNKVALAPLPAREVNPPAPPVNASWVHKTGSTGGFGSYVAFI

PEKQLGIVMLANKSYPNPARVEAAYRILSAL

SEQ ID No. 790:
MMTKSLCCALLLSTSCSVLAAPMSEKQLAEVVERTVTPLMKAQAIPGMAV

AVIYQGQPHYFTFGKADVAANKPVTPQTLFELGSISKTFTGVLGGDAIAR

GEISLGDPVTKYWPELTGKQWQGIRMLDLATYTAGGLPLQVPDEVADNAS

LLRFYQNWQPQWKPGTTRLYANTSIGLFGALAVKPSGMSYEQAITTRVFK

PLKLDHTWINVPKAEEAHYAWGYRDGKAVHVSPGMLDAEAYGVKTNVQDM

ASWVMVNMKPDSLQDNSLRQGIALAQSRYWRVGAMYQGLGWEMLNWPVDA

KTVVEGSDNKVALAPLPAREVNPPAPPVNASWVHKTGSTGGFGSYVAFIP

EKQLGIVMLANKSYPNPARVEAAYRILSAL

SEQ ID No. 791:
MMTKSLCCALLLSTSCSVLAAPMSEKQLAEVVERTVTPLMKAQAIPGMAV

AVIYQGQPHYFTFGKADVAANKPVTPQTLFELGSISKTFTGVLGGDAIAR

GEISLGDPVTKYWPELTGKQWQGIRMLDLATYTAGGLPLQVPDEVTDNAS

LLRFYQNWQPQWKPGTTRLYANASIGLFGALAVKPSGMSYEQAITTRVFK

PLKLDHTWINVPKAEEAHYAWGYRDGKAVHVSPGMLDAEAYGVKTNVKDM

ANWVMVNMKPDSLQDSSLKEGITLAQSRYWRVGAMYQGLGWEMLNWPVDA

KTVVEGSDNKVALAPLPAREVNPPAPPVNASWVHKTGSTGGFGSYVAFIP

EKQLGIVMLANKSYPNPARVEAAYRILDALQ

SEQ ID No. 792:
MMRKSLCCALLLGISCSALATPVSEKQLAEVVANTVTPLMKAQSVPGMAV

AVIYQGKPHYYTFGKADIAANKPVTPQTLFELGSISKTFTGVLGGDAIAR

GEISLDDPVTRYWPQLTGKQWQGIRMLDLATYTAGGLPLQVPDEVTDNAS

LLRFYQNWQPQWKPGTTRLYANASIGLFGALAVKPSGMPYEQAMTTRVLK

PLKLDHTWINVPKAEEAHYAWGYRDGKAVRVSPGMLDAQAYGVKTNVQDM

ANWVMANMAPENVADASLKQGIALAQSRYWRIGSMYQGLGWEMLNWPVEA

NTVVEGSDSKVALAPLPVAEVNPPAPPVKASWVHKTGSTGGFGSYVAFIP

EKQIGIVMLANTSYPNPARVEAAYHILEALQ

SEQ ID No. 793:
MMKKSLCCALLLGISCSALAAPVSEKQLAEVVANTVTPLMKAQSIPGMAV

AVIYQGKPHYYTFGKADIAASKPVTPQTLFELGSISKTFTGVLGGDAIAR

GEISLDDPVTRYWPQLTGKQWQGIRMLDLATYTAGGLPLQVPDEVTDNAA

LLRFYQNWQPQWKPGTTRLYANASIGLFGALAVKPSGMPFEQAMTTRVLK

PLKLDHTWINVPKAEEAHYAWGYRDGKAVRVSPGMLDAQAYGMKTNVQDM

ANWVMANMAPENVADASLKQGISLAQSRYWRIGSMYQGLGWEMLNWPVEA

NTVIEGSDSKVALAPLPVAEVNPPAPPVKASWVHKTGSTGGFGSYVAFIP

EKQIGIVMLANKSYPNPARVEAAYPILDALQ

SEQ ID No. 794:
MMMTKSLCCALLLSTSCSVLATPMSEKQLAEVVERTVTPLMKAQAIPGMA

VAVIYEGQPHYFTFGKADVAANKPVTPQTLFELGSISKTFTGVLGGDAIA

RGEISLGDPVTKYWPELTGKQWQGIRMLDLATYTAGGLPLQVPDEVTDNA

SLLRFYQNWQPQWKPGTTRLYANASIGLFGALAVKPSGMSYEQAITTRVF

KPLKLDHTWINVPKAEEAHYAWGYRDGKAVHVSPGMLDAEAYGVKTNVQD

MASWVMVNMKPDSLQDNSLRKGLTLAQSRYWRVGAMYQGLGWEMLNWPVD

AKTVVEGSDNKVALAPLPAREVNPPAPPVNASWVHKTGSTGGFGSYVAFI

PEKQLGIVMLANKSYPNPARVEAAYRILSAL said peptides being chosen, preferably, from the peptides of sequence SEQ ID No. 795 to SEQ ID No. 841 as defined hereafter:

| Peptide SEQ ID No. | Amino acid sequence | Position of the peptide in the ACT protein(s) |
|---|---|---|
| SEQ ID No. 795 | ADIAANK | 66-72 for the protein of SEQ No. 792 |
| SEQ ID No. 796 | ADIAASK | 66-72 for the protein of SEQ No. 793 |
| SEQ ID No. 797 | ADVAANK | 67-73 for the proteins of SEQ No. 788, 789, 794; 66-72 for the protein of sequence SEQ ID No. 790, 791 |

-continued

| Peptide SEQ ID No. | Amino acid sequence | Position of the peptide in the ACT protein(s) |
|---|---|---|
| SEQ ID No. 798 | AEEAHYAWGYR | 215-225 for the proteins of SEQ No. 788, 789, 794; 214-224 for the proteins of sequence SEQ ID No. 790, 791, 792, 793 |
| SEQ ID No. 799 | AIHVSPGMLDAEAYGVK | 229-245 for the protein of SEQ No. 789 |
| SEQ ID No. 800 | AQSIPGMAVAVIYQGK | 42-57 for the protein of SEQ No. 793 |
| SEQ ID No. 801 | AQSVPGMAVAVIYQGK | 42-57 for the protein of SEQ No. 792 |
| SEQ ID No. 802 | AVHVSPGMLDAEAYGVK | 229-245 for the proteins of SEQ No. 788, 794; 228-244 for the proteins of sequence SEQ ID No. 790, 791 |
| SEQ ID No. 803 | DMANWVMVNMK | 249-259 for the protein of SEQ No. 791 |
| SEQ ID No. 804 | DMANWVMVNMKPDSLQDSSLK | 249-269 for the protein of SEQ No. 791 |
| SEQ ID No. 805 | DNASLLR | 148-154 for the proteins of SEQ No. 788, 789, 794; 147-153 for the proteins of sequence SEQ ID No. 790, 791, 792 |
| SEQ ID No. 806 | EGITLAQSR | 270-278 for the protein of SEQ No. 791 |
| SEQ ID No. 807 | EVNPPAPPVNASWVHK | 321-336 for the proteins of SEQ No. 788, 789, 794; 320-335 for the proteins of sequence SEQ ID No. 790, 791 |
| SEQ ID No. 808 | FYQNWQPQWK | 155-164 for the proteins of SEQ No. 788, 789, 794; 154-163 for the proteins of sequence SEQ ID No. 790, 791, 792, 793 |
| SEQ ID No. 809 | FYQNWQPQWKPGTTR | 155-169 for the proteins of SEQ No. 788, 789, 794; 154-168 for the proteins of sequence SEQ ID No. 790, 791, 792, 793 |
| SEQ ID No. 810 | GEISLDDPVTR | 101-111 for the proteins of SEQ No. 792, 793 |
| SEQ ID No. 811 | GEISLGDPVTK | 102-112 for the proteins of SEQ No. 788, 789, 794; 101-111 for the proteins of sequence SEQ ID No. 790, 791 |
| SEQ ID No. 812 | GLTLAQSR | 272-279 for the proteins of SEQ No. 788, 789, 794 |
| SEQ ID No. 813 | LDHTWINVPK | 205-214 for the proteins of SEQ No. 788, 789, 794; 204-213 the proteins of sequence SEQ ID No. 791, 792, 793 |
| SEQ ID No. 814 | LYANASIGLFGALAVK | 170-185 for the proteins of SEQ No. 788, 789, 794; 169-184 for the proteins of sequence SEQ ID No. 791, 792, 793 |
| SEQ ID No. 815 | LYANTSIGLFGALAVK | 169-184 for the protein of SEQ No. 790 |
| SEQ ID No. 816 | MLDLATYTAGGLPLQVPDEVK | 127-147 for the protein of SEQ No. 788 |
| SEQ ID No. 817 | QGIALAQSR | 270-278 for the proteins of SEQ No. 790, 792 |
| SEQ ID No. 818 | QGISLAQSR | 270-278 for the protein of SEQ No. 793 |
| SEQ ID No. 819 | QIGIVMLANK | 353-362 for the protein of SEQ No. 793 |

-continued

| Peptide SEQ ID No. | Amino acid sequence | Position of the peptide in the ACT protein(s) |
|---|---|---|
| SEQ ID No. 820 | QIGIVMLANTSYPNPAR | 353-369 for the protein of SEQ No. 792 |
| SEQ ID No. 821 | QLAEVVANTVTPLMK | 27-41 for the proteins of SEQ No. 792, 793 |
| SEQ ID No. 822 | QLAEVVER | 28-35 for the proteins of SEQ No. 788, 789, 794; 27-34 for the proteins of sequence SEQ ID No. 790, 791 |
| SEQ ID No. 823 | QLGIVMLANK | 354-363 for the proteins of SEQ No. 788, 789, 794; 353-362 for the proteins of sequence SEQ ID No. 790, 791 |
| SEQ ID No. 824 | SYPNPAR | 364-370 for the proteins of SEQ No. 788, 789, 794; 363-369 for the proteins of sequence SEQ ID No. 790, 791, 792, 793 |
| SEQ ID No. 825 | TFTGVLGGDAIAR | 89-101 for the proteins of SEQ No. 788, 789, 794; 88-100 for the proteins of sequence SEQ ID No. 790, 791, 792, 793 |
| SEQ ID No. 826 | TGSTGGFGSYVAFIPEK | 337-353 for the proteins of SEQ No. 788, 789, 794; 336-352 for the proteins of sequence SEQ ID No. 790, 791, 792, 793 |
| SEQ ID No. 827 | TNVQDMASWVMVNMK | 246-260 for the proteins of SEQ No. 788, 789, 794; 245-259 for the protein of sequence SEQ ID No. 790 |
| SEQ ID No. 828 | TVTPLMK | 36-42 for the proteins of SEQ No. 788, 789, 794; 35-41 for the proteins of sequence SEQ ID No. 790, 791, 792, 793 |
| SEQ ID No. 829 | TVVEGSDNK | 303-311 for the proteins of SEQ No. 788, 789, 794; 302-310 for the proteins of sequence SEQ ID No. 790, 791 |
| SEQ ID No. 830 | VALAPLPAR | 312-320 for the proteins of SEQ No. 788, 789, 794; 311-319 for the proteins of sequence SEQ ID No. 790, 791 |
| SEQ ID No. 831 | VALAPLPVAEVNPPAPPVK | 311-329 for the proteins of SEQ No. 792, 793 |
| SEQ ID No. 832 | VEAAYR | 371-376 for the proteins of SEQ No. 788, 789, 794; 370-375 for the proteins of sequence SEQ ID No. 790, 791 |
| SEQ ID No. 833 | VFKPLK | 199-204 for the proteins of SEQ No. 788, 789, 794; 198-203 for the proteins of sequence SEQ ID No. 790, 791 |
| SEQ ID No. 834 | VGAMYQGLGWEMLNWPVDAK | 283-302 for the proteins of SEQ No. 788, 789, 794; 282-301 for the proteins of sequence SEQ ID No. 790, 791 |
| SEQ ID No. 835 | VLKPLK | 198-203 for the proteins of SEQ No. 792, 793 |
| SEQ ID No. 836 | VSPGMLDAQAYGMK | 231-244 for the protein of SEQ No. 793 |
| SEQ ID No. 837 | VSPGMLDAQAYGVK | 231-244 for the protein of SEQ No. 792 |
| SEQ ID No. 838 | YWPQLTGK | 112-119 for the proteins of SEQ No. 792, 793 |
| SEQ ID No. 839 | ASWVHK | 331-336 for the proteins of SEQ No. 788, 789, 794; 330-335 for the proteins of sequence SEQ ID No. 790, 791, 792, 793 |

| Peptide SEQ ID No. | Amino acid sequence | Position of the peptide in the ACT protein(s) |
|---|---|---|
| SEQ ID No. 840 | QWQGIR | 121-126 for the proteins of SEQ No. 788, 789, 794; 120-125 for the proteins of sequence SEQ ID No. 790, 791, 792, 793 |
| SEQ ID No. 841 | YWPELTGK | 113-120 for the proteins of SEQ No. 788, 789, 794; 112-119 for the proteins of sequence SEQ ID No. 790, 791 |

The detection of a mechanism of resistance to cephalosporins induced by the expression of the CARB protein is characterised by the detection of at least one peptide belonging to the CARB protein and to its different sequence variants SEQ ID No. 842 to SEQ ID No. 852.

SEQ ID No. 842:
MLLYKMCDNQNYGVTYMKFLLAFSLLIPSVVFASSSKFQQVEQDVKAIEVSLSARIGVSVLDTQNGEYWDYNGNQRFPLTSTFKTIACAKLLYDAEQGKVNPNSTVEIKKADLVTYSPVIEKQVGQAITLDDACFATMTTSDNTAANIILSAVGGPKGVTDFLRQIGDKETRLDRIEPDLNEGKLGDLRDTTTPKAIASTLNKFLFGSALSEMNQKKLESWMVNNQVTGNLLRSVLPAGWNIADRSGAGGFGARSITAVVWSEHQAPIIVSIYLAQTQASMAERNDAIVKIGHSIFDVYTSQSR

SEQ ID No. 843:
MLLYKMCDNQNYGVTYMKFLLAFSLLIPSVVFASSSKFQQVEQDVKAIEVSLSARIGVSVLDTQNGEYWDYNGNQRFPLTSTFKTIACAKLLYDAEQGKVNPNSTVEIKKADLVTYSPVIEKQVGQAITLDDACFATMTTSDNTAANIILSAVGGPKGVTDFLRQIGDKETRLDRIEPDLNEGKLGDLRDTTTPKAIASTLNKLLFGSALSEMNQKKLESWMVNNQVTGNLLRSVLPAGWNIADRSGAGGFGARSITAVVWSEHQAPIIVSIYLAQTQASMAERNDAIVKIGHSIFDVYTSQSR

SEQ ID No. 844:
MKLLLVFSLLIPSMVFANSSKFQQVEQDAKVIEASLSAHIGISVLDTQTGEYWDYNGNQRFPLTSTFKTIACAKLLYDAEQGEINPKSTIEIKKADLVTYSPVIEKQVGQAITLDDACFATMTTSDNAAANIILNALGGPESVTDFLRQIGDKETRLDRIEPELNEGKLGDLRDTTTPNAIVNTLNELLFGSTLSQDGQKKLEYWMVNNQVTGNLLRSVLPEGWNIADRSGAGGFGARSITAVVWSEAQSPIIVSIYLAQTEASIADRNDAIVKIGRSIFEVYSSQSR

SEQ ID No. 845:
MKFLLAFSLLIPSVVFASSSKFQQVEQDVKAIEVSLSARIGVSVLDTQNGEYWDYNGNQRFPLTSTEKTIACAKLLYDAEQGKVNPNSTVEIKKADLVTYSPVIEKQVGQAITLDDACFATMTTSDNTAANIILSAVGGPKGVTDFLRQIGDKETRLDRIEPDLNEGKLGDLRDTTTPKAIASTLNQLLFGSTLSEASQKKLESWMVNNQVTGNLLRSVLPVKWSIADRSGAGGFGARSITAIVWSEEKKTIIVSIYLAQTEASMAERNDAIVKIGRSIFEVYTSQSR

SEQ ID No. 846:
MNVRKHKASFFSVVITFLCLTLSLNANATDSVLEAVTNAETELGARIGLAVHDLETGKRWEHKSNERFPLSSTFKTLACANVLQRVDLGKERIDRVVRFSESNLVTYSPVTEKHVGKKGMSLAELCQATLSTSDNSAANFILQAIGGPKALTKFLRSIGDDTTRLDRWETELNEAVPGDKRDTTTPIAMVTTLEKLLIDETLSIKSRQQLESWLKGNEVGDALFRKGVPSDWIVADRTGAGGYGSRAITAVMWPPNRKPIVAALYITETDASFEERNAVIAKIGEQIAKTVLMENSRN

SEQ ID No. 847:
MKFLLAFSLLIPSVVFASSSKFQQVEQDVKAIEVSLSARIGVSVLDTQNGEYWDYNGNQRFPLTSTFKTIACAKLLYDAEQGKVNSNSTVEIKKADLVTYSPVIEKQVGQAITLDDACFATMTTSDNTAANIILSAVGGPKGVTDFLRQIGDKETRLDRIEPDLNEGKLGDLRDTTTPKAIASTLNKFLFGSALSEMNQKKLESWMVNNQVTGNLLRSVLPAGWNIADRSGAGGFGARSITAVVWSEHQAPIIVSIYLAQTQASMAERNDAIVKIGHSIFDVYTSQSR

SEQ ID No. 848:
MKFLLAFSLLIPSVVFASSSKFQQVEQDVKAIEVSLSARIGVSVLDTQNGEYWDYNGNQRFPLTSTFKTIACAKLLYDAEQGKVNPNSTVEIKKADLVTYSPVIEKQVGQAITLDDACFATMTTSDNTAANIILSAVGGPKGVTDFLRQIGDKETRLDRIEPDLNEGKLGDLRDTTTPKAIASTLNKFLFGSALSEMNQKKLESWMVNNQVTGNLLRSVLPAGWNIADRSGAGGFGARSITAVVWSEHQAPIIVSIYLAQTQASMEERNDAIVKIGHSIFDVYTSQSR

SEQ ID No. 849:
MKSLLVFALLMPSVVFASSSKFQSVEQEIKGIESSLSARIGVAILDTQNGESWDYNGDQRFPLTSTFKTIACAKLLYDAEHGKVNLNSTVEIKKADLVTYSPVLEKQVGKPITLSDACLATMTTSDNTAANIVINAVGDPKSITDFLRQIGDKETRLDRVEPELNEGKLGDLRDTTTPNAITSTLNQLLFGSTLSEASQKKLESWMVNNQVTGNLLRSVLPVKWSIADRSGAGGFGARSITAIVWSEEKKPIIVSIYLAQTEASMAERNDAIVKIGRSIFEVYTSQSR

SEQ ID No. 850:
MDVRKHKASFFSWITFLCLTLSLNANATDSVLEAVTNAETELGARIGLAVHDLETGKRWEHKSNERFPLSSTFKTLACANVLQRVDLGKERIDRVVRFSESNLVTYSPVTEKHVGKKGMSLAELCQATLSTSDNSAANFILQAIGGPKALTKFLRSIGDDTTRLDRWETELNEAVPGDKRDTTTPIAMVTTLEKLLIDETLSIKSRQQLESWLKGNEVGDALFRKGVPSDWIVADRTGAGGYGSRAITAVMWPPNRKPIVAALYITETDASFEERNAVIAKIGEQIAKTILMENSRN

-continued

SEQ ID No. 851:
MKSLLVFALLMPSVVFASSSKFQSVEQEIKGIESSLSARIGVAILDTQNG

ESWDYNGDQRFPLTSTFKTIACAKLLYDAEHGKVNLNSTVEVKKADLVTY

SPVLEKQVGKPITLSDACFATMTTSDNTAANIVINAVGDPKSITDFLRQI

GDKETRLDRVEPELNEGKLGDLRDTTTPNAITSTLNQLLFGSTLSEASQK

KLESWMVNNQVTGNLLRSVLPVTWSIADRSGAGGFGARSITAIVWSEEKK

PIIVSIYLAQTEASMAERNDAIVKIGRSIFEVYTSQSR

-continued

SEQ ID No. 852:
MKFLLVFSLLIPSVVFASSSKFRQVEQDVKAIEVSLSARIGVSVLDTQNG

EYWDYNGNQRFPLTSTFKTIACAKLLYDAEQGKVNPNSTVEIKKADLVTY

SPVIEKQVGQAITLDDACFATMTTSDNTAANIILSAVGGSKGVTDFLRQI

GDKETRLDRIEPDLNEGKLGDLRDTTTPKAIASTLNKFLFGSALSEMNKK

KLESWMVNNQVTGNLLRSVLPAGWNIADRSGAGGFGARSITAVVWSEHQA

PIIVSIYLAQTQASMAERNDAIVKIGRSIFDVYTSQSR said peptides being chosen, preferably, from the peptides of sequence SEQ ID No. 853 to SEQ ID No. 921 as defined hereafter:

| Peptide SEQ ID No. | Amino acid sequence | Position of the peptide in the CARB protein(s) |
|---|---|---|
| SEQ ID No. 853 | ADLVTYSPVIEK | 95-106 for the proteins of SEQ No. 844, 845, 847, 848, 852; 111-122 for the protein of sequence SEQ ID No. 842; 111-122 for the protein of sequence SEQ ID No. 843 |
| SEQ ID No. 854 | ADLVTYSPVLEK | 95-106 for the proteins of SEQ No. 849, 851 |
| SEQ ID No. 855 | AIASTLNK | 180-187 for the proteins of SEQ No. 847, 848, 852; 196-203 for the protein of sequence SEQ ID No. 842; 196-203 for the protein of sequence SEQ ID No. 843 |
| SEQ ID No. 856 | AIASTLNQLLFGSTLSEASQK | 180-200 for the protein of SEQ No. 845 |
| SEQ ID No. 857 | AIEVSLSAR | 31-39 for the proteins of SEQ No. 845, 847, 848, 852; 47-55 for the protein of sequence SEQ ID No. 842; 47-55 for the protein of sequence SEQ ID No. 843 |
| SEQ ID No. 858 | AITAVMWPPNR | 247-257 for the proteins of SEQ No. 846, 850 |
| SEQ ID No. 859 | DTTTPIAMVTTLEK | 182-195 for the proteins of SEQ No. 846, 850 |
| SEQ ID No. 860 | DTTTPK | 174-179 for the proteins of SEQ No. 845, 847, 848, 852; 190-195 for the protein of sequence SEQ ID No. 842; 190-195 for the protein of sequence SEQ ID No. 843 |
| SEQ ID No. 861 | FLFGSALSEMNK | 188-199 for the proteins of SEQ No. 852 |
| SEQ ID No. 862 | FLFGSALSEMNQK | 188-200 for the proteins of SEQ No. 847, 848; 204-216 for the protein of sequence SEQ ID No. 842 |
| SEQ ID No. 863 | FLLAFSLLIPSVVFASSSK | 3-21 for the proteins of SEQ No. 845, 847, 848; 19-37 for the protein of sequence SEQ ID No. 842; 19-37 for the protein of sequence SEQ ID No. 843 |
| SEQ ID No. 864 | FLLVFSLLIPSVVFASSSK | 3-21 for the protein of SEQ No. 852 |
| SEQ ID No. 865 | FPLSSTFK | 68-75 for the proteins of SEQ No. 846, 850 |
| SEQ ID No. 866 | FPLTSTFK | 61-68 for the proteins of SEQ No. 844, 845, 847, 848, 849, 851, 852; 77-84 for the protein of sequence SEQ ID No. 842; 77-84 for the protein of sequence SEQ ID No. 843 |
| SEQ ID No. 867 | FQQVEQDAK | 22-30 for the protein of SEQ No. 844 |

-continued

| Peptide SEQ ID No. | Amino acid sequence | Position of the peptide in the CARB protein(s) |
|---|---|---|
| SEQ ID No. 868 | FQQVEQDAK | 22-30 for the proteins of SEQ No. 845, 847, 848; 38-46 for the protein of sequence SEQ ID No. 842; 38-46 for the protein of sequence SEQ ID No. 843 |
| SEQ ID No. 869 | FQSVEQEIK | 22-30 for the proteins of SEQ No. 849, 851 |
| SEQ ID No. 870 | FSESNLVTYSPVTEK | 99-113 for the proteins of SEQ No. 846, 850 |
| SEQ ID No. 871 | GIESSLSAR | 31-39 for the proteins of SEQ No. 849, 851 |
| SEQ ID No. 872 | GNEVGDALFR | 216-225 for the proteins of SEQ No. 846, 850 |
| SEQ ID No. 873 | GVPSDWIVADR | 227-237 for the proteins of SEQ No. 846, 850 |
| SEQ ID No. 874 | GVTDFLR | 142-148 for the proteins of SEQ No. 845, 847, 848, 852; 158-164 for the protein of sequence SEQ ID No. 842; 158-164 for the protein of sequence SEQ ID No. 843 |
| SEQ ID No. 875 | IEPDLNEGK | 160-168 for the proteins of SEQ No. 845, 847, 848, 852; 176-184 for the protein of sequence SEQ ID No. 842; 176-184 for the protein of sequence SEQ ID No. 843 |
| SEQ ID No. 876 | IEPELNEGK | 160-168 for the protein of SEQ No. 844 |
| SEQ ID No. 877 | IGEQIAK | 283-289 for the proteins of SEQ No. 846, 850 |
| SEQ ID No. 878 | IGLAVHDLETGK | 47-58 for the proteins of SEQ No. 846, 850 |
| SEQ ID No. 879 | IGVAILDTQNGESWDYNGDQR | 40-60 for the proteins of SEQ No. 849, 851 |
| SEQ ID No. 880 | IGVSVLDTQNGEYWDYNGNQR | 40-60 for the proteins of SEQ No. 845, 847, 848, 852; 56-76 for the protein of sequence SEQ ID No. 842; 56-76 for the protein of sequence SEQ ID No. 843 |
| SEQ ID No. 881 | KPIIVSIYLAQTEASMAER | 250-268 for the proteins of SEQ No. 849, 851 |
| SEQ ID No. 882 | KPIVAALYITETDASFEER | 258-276 for the proteins of SEQ No. 846, 850 |
| SEQ ID No. 883 | LESWMVNNQVTGNLLR | 202-217 for the proteins of SEQ No. 845, 847, 848, 849, 851, 852; 218-233 for the protein of sequence SEQ ID No. 842; 218-233 for the protein of sequence SEQ ID No. 843 |
| SEQ ID No. 884 | LEYWMVNNQVTGNLLR | 202-217 for the protein of SEQ No. 844 |
| SEQ ID No. 885 | LGDLR | 169-173 for the proteins of SEQ No. 844, 845, 847, 848, 849, 851, 852; 185-189 for the protein of sequence SEQ ID No. 842; 185-189 for the protein of sequence SEQ ID No. 843 |
| SEQ ID No. 886 | LLFGSALSEMNQK | 204-216 for the protein of SEQ No. 843 |
| SEQ ID No. 887 | LLIDETLSIK | 196-205 for the proteins of SEQ No. 846, 850 |

-continued

| Peptide SEQ ID No. | Amino acid sequence | Position of the peptide in the CARB protein(s) |
|---|---|---|
| SEQ ID No. 888 | LLLVFSLLIPSMVFANSSK | 3-21 for the protein of SEQ No. 844 |
| SEQ ID No. 889 | LLYDAEHGK | 75-83 for the proteins of SEQ No. 849, 851 |
| SEQ ID No. 890 | LLYDAEQGEINPK | 75-87 for the protein of SEQ No. 844 |
| SEQ ID No. 891 | LLYDAEQGK | 75-83 for the proteins of SEQ No. 845, 847, 848, 852; 91-99 for the protein of sequence SEQ ID No. 842; 91-99 for the protein of sequence SEQ ID No. 843 |
| SEQ ID No. 892 | MCDNQNYGVTYMK | 6-18 for the proteins of SEQ No. 842, 843 |
| SEQ ID No. 893 | NAVIAK | 277-282 for the proteins of SEQ No. 846, 850 |
| SEQ ID No. 894 | NDAIVK | 269-274 for the proteins of SEQ No. 844, 845, 847, 848, 849, 851, 852; 285-290 for the protein of sequence SEQ ID No. 842; 285-290 for the protein of sequence SEQ ID No. 843 |
| SEQ ID No. 895 | QIGDK | 149-153 for the proteins of SEQ No. 844, 845, 847, 848, 849, 851, 852; 165-169 for the protein of sequence SEQ ID No. 842; 165-169 for the protein of sequence SEQ ID No. 843 |
| SEQ ID No. 896 | QQLESWLK | 208-215 for the proteins of SEQ No. 846, 850 |
| SEQ ID No. 897 | QVEQDVK | 24-30 for the proteins of SEQ No. 845, 847, 848, 852; 40-46 for the protein of sequence SEQ ID No. 842; 40-46 for the protein of sequence SEQ ID No. 843 |
| SEQ ID No. 898 | SGAGGFGAR | 230-238 for the proteins of SEQ No. 844, 845, 847, 848, 849, 851, 852; 246-254 for the protein of sequence SEQ ID No. 842; 246-254 for the protein of sequence SEQ ID No. 843 |
| SEQ ID No. 899 | SIGDDTTR | 157-164 for the proteins of SEQ No. 846, 850 |
| SEQ ID No. 900 | SITAIVWSEEK | 239-249 for the proteins of SEQ No. 845, 849, 851 |
| SEQ ID No. 901 | SITDFLR | 142-148 for the proteins of SEQ No. 849, 851 |
| SEQ ID No. 902 | SLLVFALLMPSVVFASSSK | 3-21 for the proteins of SEQ No. 849, 851 |
| SEQ ID No. 903 | STIEIK | 88-93 for the protein of SEQ No. 844 |
| SEQ ID No. 904 | SVLPAGWNIADR | 218-229 for the proteins of SEQ No. 847, 848, 852; 234-245 for the protein of sequence SEQ ID No. 842; 234-245 for the protein of sequence SEQ ID No. 843 |
| SEQ ID No. 905 | SVLPEGWNIADR | 218-229 for the protein of SEQ No. 844 |
| SEQ ID No. 906 | SVLPVK | 218-223 for the proteins of SEQ No. 845, 849 |
| SEQ ID No. 907 | SVLPVTWSIADR | 218-229 for the protein of SEQ No. 851 |

| Peptide SEQ ID No. | Amino acid sequence | Position of the peptide in the CARB protein(s) |
|---|---|---|
| SEQ ID No. 908 | TGAGGYGSR | 238-246 for the proteins of SEQ No. 846, 850 |
| SEQ ID No. 909 | TIACAK | 69-74 for the proteins of SEQ No. 844, 845, 847, 848, 849, 851, 852; 85-90 for the protein of sequence SEQ ID No. 842; 85-90 for the protein of sequence SEQ ID No. 843 |
| SEQ ID No. 910 | TIIVSIYLAQTEASMAER | 251-268 for the protein of SEQ No. 845 |
| SEQ ID No. 911 | TILMENSR | 290-297 for the protein of SEQ No. 850 |
| SEQ ID No. 912 | TLACANVLQR | 76-85 for the proteins of SEQ No. 846, 850 |
| SEQ ID No. 913 | TVLMENSR | 290-297 for the protein of SEQ No. 846 |
| SEQ ID No. 914 | VDLGK | 86-90 for the proteins of SEQ No. 846, 850 |
| SEQ ID No. 915 | VEPELNEGK | 160-168 for the proteins of SEQ No. 849, 851 |
| SEQ ID No. 916 | VNLNSTVEIK | 84-93 for the protein of SEQ No. 849 |
| SEQ ID No. 917 | VNLNSTVEVK | 84-93 for the protein of SEQ No. 851 |
| SEQ ID No. 918 | VNPNSTVEIK | 84-93 for the proteins of SEQ No. 845, 848, 852; 100-109 for the protein of sequence SEQ ID No. 842; 100-109 for the protein of sequence SEQ ID No. 843 |
| SEQ ID No. 919 | VNSNSTVEIK | 84-93 for the protein of SEQ No. 847 |
| SEQ ID No. 920 | WETELNEAVPGDK | 168-180 for the proteins of SEQ No. 846, 850 |
| SEQ ID No. 921 | WSIADR | 224-229 for the proteins of SEQ No. 845, 849, 851 |

The detection of a mechanism of resistance to cephalosporins induced by the expression of the DHA protein is characterised by the detection of at least one peptide belonging to the DHA protein and to its different sequence variants SEQ ID No. 922 to SEQ ID No. 927.

SEQ ID No. 922:
MKKSLSATLISALLAFSAPGFSAADNVAAVVDSTIKPLMAQQDIPGMAVA

VSVKGKPYYFNYGFADVQAKQPVTENTLFELGSVSKTFTGVLGAVSVAKK

EMMLNDPAEKYQPELALPQWKGITLLDLATYTTGGLPLQVPDAVKNRAEL

LHFYQQWQPSRKPGDMRLYANSSIGLFGALTANAAGMPYEQLLTARILAP

LGLSHTFITVPESAQSQYAYGYKNKKPVRVSPGQLDAESYGVKSASKDML

RWAEMNMEPSRAGNADLEMAMYLAQTRYYKTAAINQGLGWEMYDWPQQKD

MIINGVTNEVALQPHPVTDNQVQPYNRASWVHKTGATTGFGAYVAFIPEK

QVAIVILANKNYPNTERVKAAQAILSALE

SEQ ID No. 923:
MKKSLSATLISALLAFSAPGFSAADNVAAVVDSTIKPLMAQQDIPGMAVA

VSVKGKPYYFNYGFADIQAKQPVTENTLFELGSVSKTFTGVLGAVSVAKK

EMALNDPAAKYQPELALPQWKGITLLDLATYTAGGLPLQVPDAVKSRADL

LNFYQQWQPSRKPGDMRLYANSSIGLFGALTANAAGMPYEQLLTARILAP

LGLSHTFITVPDSAQSQYAYGYKNKKPVRVSPGQLDAESYGVKSASKDML

RWAEMNIEPSRAGNADLEMAMYLAQTRYYKTAAINQGLGWEMYDWPQQKD

MIINGVTNEVALQPHPVTDNQVQPYNRASWVHKTGATTGFGAYVAFIPEK

QVAIVILANKNYPNTERVKAAQAILSALE

SEQ ID No. 924:
MKKSLSATLISALLAFSAPGFSAADNVAAVVDSTIKPLMAQQDIPGMAVA

VSVKGKPYYFNYGFADIQAKQPVTENTLFELGSVSKTFTGVLGAVSVAKK

EMALNDPAAKYQPELALPQWKGITLLDLATYTAGGLPLQVPDAVKSRADL

LNFYQQWQPSRKPGDMRLYANSSIGLFGALTANAAGMPYEQLLTARILAP

-continued
LGLSHTFITVPESAQSQYAYGYKNKKPVRVSPGQLDAESYGVKSASKDML

RWAEMNMEPSRAGNADLEMAMYLAQTRYYKTAAINQGLGWEMYDWPQQKD

MIINGVTNEVALQPHPVTDNQVQPYNRASWVHKTGATTGSGAYVAFIPEK

QVAIVILANKNYPNTERVKAAQAILSALE

SEQ ID No. 925:
MKKSLSATLISALLAFSAPGFSAADNVAAVVDSTIKPLMAQQDIPGMAVA

VSVKGKPYYFNYGFADIQAKQPVTENTLFELGSVSKTFTGVLGAVSVAKK

EMALNDPAAKYQPELALPQWKGITLLDLATYTAGGLPLQVPDAVKSRADL

LNFYQQWQPSRKPGDMRLYANSSIGLFGALTANAAGMPYEQLLTARILAP

LGLSHTFITVPESAQSQYAYGYKNKKPVRVSPGQLDAESYGVKSTSKDML

RWAEMNMEPSRAGNADLEMAMYLAQTRYYKTAAINQGLGWEMYDWPQQKD

MIINGVTNEVALQPHPVTDNQVQPYNRASWVHKTGATTGFGAYVAFIPEK

QVAIVILANKNYPNTERVKAAQAILSALE

SEQ ID No. 926:
MKKSLSATLISALLAFSAPGFSAADNVAAVVDSTIKPLMAQQDIPGMAVA

VSVKGRPYYFNYGFADVQAKQPVTENTLFELGSVSKTFTGVLGAVSVAKK

EMALNDPAAKYQPELALPQWKGITLLDLATYTAGGLPLQVPDAVKSRADL

-continued
LHFYQQWQPSRKPGDMRLYANSSIGLFGALTANAAGMPYEQLLTARILAP

LGLSHTFITVPESAQSQYAYGYKNKKPVRVSPGQLDAESYGVKSASKDML

RWAEMNMEPSRAGNADLEMAMYLAQTRYYKTAAINQGLGWEMYDWPQQKD

MIINGVTNEVALQPHPVTDNQVQPYNRASWVHKTGATTGFGAYVAFIPEK

QVAIVILANKNYPNTERVKAAQAILSALE

SEQ ID No. 927:
MKKSLSATLISALLAFSAPGFSAADNVAAVVDSTIKPLMAQQDIPGMAVA

VSVKGKPYYFNYGFADIQAKQPVTENTLFELGSVSKTFTGVLGAVSVAKK

EMALNDPAAKYQPELALPQWKGITLLDLATYTAGGLPLQVPDAVKSRADL

LNFYQQWQPSRKPGDMRLYANSSIGLFGALTANAAGMPYEQLLTARILAP

LGLSHTFITVPESAQSQYAYGYKNKKPVRVSPGQLDAESYGVKSASKDML

RWAEMNMEPSRAGNADLEMAMYLAQTRYYKTAAINQGLGWEMYDWPQQKD

MIINGVTNEVALQPHPVTDNQVQPYNRASWVHKTGATTGFGAYVAFIPEK

QVAIVILANKNYPNTERVKAAQAILSALE said peptides being chosen, preferably, from the peptides of sequence SEQ ID No. 928 to SEQ ID No. 948 as defined hereafter:

| Peptide SEQ ID No. | Amino acid sequence | Position of the peptide in the DHA protein(s) |
|---|---|---|
| SEQ ID No. 928 | ADLLHFYQQWQPSR | 148-161 for the protein of SEQ No. 926 |
| SEQ ID No. 929 | ADLLNFYQQWQPSR | 148-161 for the proteins of SEQ No. 923, 924, 925, 927 |
| SEQ ID No. 930 | AELLHFYQQWQPSR | 148-161 for the protein of SEQ No. 922 |
| SEQ ID No. 931 | AGNADLEMAMYLAQTR | 262-277 for the proteins of SEQ No. 922, 923, 924, 925, 926, 927 |
| SEQ ID No. 932 | EMALNDPAAK | 101-110 for the proteins of SEQ No. 923, 924, 925, 926, 927 |
| SEQ ID No. 933 | EMMLNDPAEK | 101-110 for the protein of SEQ No. 922 |
| SEQ ID No. 934 | GKPYYFNYGFADIQAK | 55-70 for the proteins of SEQ No. 923, 924, 925, 927 |
| SEQ ID No. 935 | GKPYYFNYGFADVQAK | 55-70 for the protein of SEQ No. 922 |
| SEQ ID No. 936 | KPGDMR | 162-167 for the proteins of SEQ No. 922, 923, 924, 925, 926, 927 |
| SEQ ID No. 937 | NYPNTER | 361-367 for the proteins of SEQ No. 922, 923, 924, 925, 926, 927 |
| SEQ ID No. 938 | QPVTENTLFELGSVSK | 71-86 for the proteins of SEQ No. 922, 923, 924, 925, 926, 927 |
| SEQ ID No. 939 | QVAIVILANK | 351-360 for the proteins of SEQ No. 922, 923, 924, 925, 926, 927 |
| SEQ ID No. 940 | TAAINQGLGWEMYDWPQQK | 281-299 for the proteins of SEQ No. 922, 923, 924, 925, 926, 927 |
| SEQ ID No. 941 | TFTGVLGAVSVAK | 87-99 for the proteins of SEQ No. 922, 923, 924, 925, 926, 927 |

| Peptide SEQ ID No. | Amino acid sequence | Position of the peptide in the DHA protein(s) |
|---|---|---|
| SEQ ID No. 942 | TGATTGFGAYVAFIPEK | 334-350 for the proteins of SEQ No. 922, 923, 925, 926, 927 |
| SEQ ID No. 943 | TGATTGSGAYVAFIPEK | 334-350 for the protein of SEQ No. 924 |
| SEQ ID No. 944 | VSPGQLDAESYGVK | 230-243 for the proteins of SEQ No. 922, 923, 924, 925, 926, 927 |
| SEQ ID No. 945 | WAEMNIEPSR | 252-261 for the protein of SEQ No. 923 |
| SEQ ID No. 946 | WAEMNMEPSR | 252-261 for the proteins of SEQ No. 922, 924, 925, 926, 927 |
| SEQ ID No. 947 | YQPELALPQWK | 111-121 for the proteins of SEQ No. 922, 923, 924, 925, 926, 927 |
| SEQ ID No. 948 | ASWVHK | 328-333 for the proteins of SEQ No. 922, 923, 924, 925, 926, 927 |

The detection of a mechanism of resistance to cephalosporins induced by the expression of the MIR protein is characterised by the detection of at least one peptide belonging to the MIR protein and to its different sequence variants SEQ ID No. 949 to SEQ ID No. 953.

SEQ ID No. 949:
MMTKSLSCALLLSVASSAFAAPMSEKQLAEVVERTVTPLMNAQAIPGMAV

AVIYQGQPHYFTFGKADVAANKPVTPQTLFELGSISKTFTGVLGGDAIAR

GEIALGDPVAKYWPELTGKQWQGIRMLDLATYTAGGLPLQVPDEVTDTAS

LLRFYQNWQPQWKPGTTRLYANASIGLFGALAVKPSGMSYEQAMTTRVFK

PLKLDHTWINVPKAEEAHFAWGYREGKAVHVSPGMLDAEAYGVKTNVKDM

ASWLIANMKPDSLQAPSLKQGIALAQSRYWRVGAMYQGLGWEMLNWPVDA

KTVVGGSDNKVALAPLPVAEVNPPAPPVKASWVHKTGSTGGFGSYVAFIP

EKQLGIVMLANKSYPNPARVEAAYRILDALQ

SEQ ID No. 950:
MMTKSLSCALLLSVASAAFAAPMSETQLAEVVERTVTPLMNAQAIPGMAV

AVIYQGQPHYFTFGKADVAANKPVTPQTLFELGSISKTFTGVLGGDAIAR

GEIALGDPVAKYWPELTGKQWQGIRMLDLATYTAGGLPLQVPDEVTDTAS

LLRFYQNWQPQWKPGTTRLYANASIGLFGALAVKPSGMSYEQAMTTRVFK

PLKLDHTWINVPKAEEAHYAWGYREGKAVHVSPGMLDAEAYGVKTNVKDM

ASWVIANMKPDSLQAPSLKQGIALAQSRYWRVGAMYQGLGWEMLNWPVDA

KTVVGGSDNKVALAPLPVAEVNPPAPPVKASWVHKTGSTGGFGSYVAFIP

EKQLGIVMLANKSYPNPARVEAAYHILDALQ

SEQ ID No. 951:
MMTKSLSCALLLSVASAAFAAPMSEKQLAEVVERTVTPLMNAQAIPGMAV

AVIYQGQPHYFTFGKADVAANKPVTPQTLFELGSISKTFTGVLGGDAIAR

GEIALGDPVAKYWPELTGKQWQGIRMLDLATYTAGGLPLQVPDEVTDTAS

LLRFYQNWQPQWKPGTTRLYANASIGLFGALAVKPSGMSYEQAMTTRVFK

PLKLDHTWINVPKAEEAHYAWGYREGKAVHVSPGMLDAEAYGVKTNVKDM

ASWLIANMKPDSLHAPSLKQGIALAQSRYWRVGAMYQGLGWEMLNWPVDA

KTVVGGSDNKVALAPLPVAEVNPPAPPVKASWVHKTGSTGGFGSYVAFIP

EKQLGIVMLANKSYPNPARVEAAYRILDALQ

SEQ ID No. 952:
MMTKSLSCALLLSVASAAFAAPMFEKQLAEVVERTVTPLMNAQAIPGMAV

AVIYQGQPHYFTFGKADVAANKPVTPQTLFELGSISKTFTGVLGGDAIAR

GEIALGDPVAKYWPELTGKQWQGIRMLDLATYTAGGLPLQVPDEVTDTAS

LLRFYQNWQPQWKPGTTRLYANASIGLFGALAVKPSGMSYEQAMTTRVFK

PLKLDHTWINVPKAEEAHYAWGYREGKAVHVSPGMLDAEAYGVKTNVKDM

ASWLIANMKPDSLHAPSLKQGIALAQSRYWRVGAMYQGLGWEMLNWPVDA

KTVVGGSDNKVALAPLPVAEVNPPAPPVKASWVHKTGSTGGFGSYVAFIP

EKQLGIVMLANKSYPNPARVEAAYRILDALQ

SEQ ID No. 953:
MMTKSLSCALLLSVASAAFAAPMSEKQLAEVVERTVTPLMNAQAIPGMAV

AVIYQGQPHYFTFGKADVAANKPVTPQTLFELGSISKTFTGVLGGDAIAR

GEIALGDPVAKYWPELTGKQWQGIRMLDLATYTAGGLPLQVPDEVTDTAS

LLRFYQNWQPQWKPGTTRLYANASIGLFGALAVKPSGMSYEQAMTTRVFK

PLKLDHTWINVPKAEEAHYAWGYREGKAVHVSPGMLDAEAYGVKTNVKDM

ASWLIANMKPDSLQAPSLKQGIALAQSRYWRVGAMYQGLGWEMLNWPVDA

KTVVGGSDNKVALAPLPVAEVNPPAPPVKASWVHKTGSTGGFGSYVAFIP

EKQLGIVMLANKSYPNPARVEAAYRILDALQ said peptides being chosen, preferably, from the peptides of sequence SEQ ID No. 954 to SEQ ID No. 981 as defined hereafter:

| Peptide SEQ ID No. | Amino acid sequence | Position of the peptide in the MIR protein(s) |
|---|---|---|
| SEQ ID No. 954 | AEEAHFAWGYR | 214-224 for the protein of SEQ No. 949 |
| SEQ ID No. 955 | DMASWLIANMK | 249-259 for the proteins of SEQ No. 949, 951, 952, 953 |
| SEQ ID No. 956 | DMASWLIANMKPDSLHAPSLK | 249-269 for the proteins of SEQ No. 951, 952 |
| SEQ ID No. 957 | DMASWLIANMKPDSLQAPSLK | 249-269 for the proteins of SEQ No. 949, 953 |
| SEQ ID No. 958 | DMASWVIANMK | 249-259 for the protein of SEQ No. 950 |
| SEQ ID No. 959 | DMASWVIANMKPDSLQAPSLK | 249-269 for the protein of SEQ No. 950 |
| SEQ ID No. 960 | GEIALGDPVAK | 101-111 for the proteins of SEQ No. 949, 950, 951, 952, 953 |
| SEQ ID No. 961 | TVVGGSDNK | 302-310 for the proteins of SEQ No. 949, 950, 951, 952, 953 |
| SEQ ID No. 962 | ADVAANK | 66-72 for the proteins of SEQ No. 949, 950, 951, 952, 953 |
| SEQ ID No. 963 | AEEAHYAWGYR | 214-224 for the proteins of SEQ No. 950, 951, 952, 953 |
| SEQ ID No. 964 | AVHVSPGMLDAEAYGVK | 228-244 for the proteins of SEQ No. 949, 950, 951, 952, 953 |
| SEQ ID No. 965 | FYQNWQPQWK | 154-163 for the proteins of SEQ No. 949, 950, 951, 952, 953 |
| SEQ ID No. 966 | FYQNWQPQWKPGTTR | 154-168 for the proteins of SEQ No. 949, 950, 951, 952, 953 |
| SEQ ID No. 967 | LDHTWINVPK | 204-213 for the proteins of SEQ No. 949, 950, 951, 952, 953 |
| SEQ ID No. 968 | LYANASIGLFGALAVK | 169-184 for the proteins of SEQ No. 949, 950, 951, 952, 953 |
| SEQ ID No. 969 | QGIALAQSR | 270-278 for the proteins of SEQ No. 949, 950, 951, 952, 953 |
| SEQ ID No. 970 | QLAEVVER | 27-34 for the proteins of SEQ No. 949, 950, 951, 952, 953 |
| SEQ ID No. 971 | QLGIVMLANK | 353-362 for the proteins of SEQ No. 949, 950, 951, 952, 953 |
| SEQ ID No. 972 | SYPNPAR | 363-369 for the proteins of SEQ No. 949, 950, 951, 952, 953 |
| SEQ ID No. 973 | TFTGVLGGDAIAR | 88-100 for the proteins of SEQ No. 949, 950, 951, 952, 953 |
| SEQ ID No. 974 | TGSTGGFGSYVAFIPEK | 336-352 for the proteins of SEQ No. 949, 950, 951, 952, 953 |
| SEQ ID No. 975 | VALAPLPVAEVNPPAPPVK | 311-329 for the proteins of SEQ No. 949, 950, 951, 952, 953 |
| SEQ ID No. 976 | VEAAYR | 370-375 for the proteins of SEQ No. 949, 951, 952, 953 |
| SEQ ID No. 977 | VFKPLK | 198-203 for the proteins of SEQ No. 949, 950, 951, 952, 953 |
| SEQ ID No. 978 | VGAMYQGLGWEMLNWPVDAK | 282-301 for the proteins of SEQ No. 949, 950, 951, 952, 953 |
| SEQ ID No. 979 | ASWVHK | 330-335 for the proteins of SEQ No. 949, 950, 951, 952, 953 |

| Peptide SEQ ID No. | Amino acid sequence | Position of the peptide in the MIR protein(s) |
|---|---|---|
| SEQ ID No. 980 | QWQGIR | 120-125 for the proteins of SEQ No. 949, 950, 951, 952, 953 |
| SEQ ID No. 981 | YWPELTGK | 112-119 for the proteins of SEQ No. 949, 950, 951, 952, 953 |

The detection of a mechanism of resistance to cephalosporins induced by the expression of the MOX protein is characterised by the detection of at least one peptide belonging to the MOX protein and to its different sequence variants SEQ ID No. 982 to SEQ ID No. 988.

SEQ ID No. 982:
MQQRQSILWGAVATLMWAGLAHAGETSPVDPLRPVVDASIQPLLKEHRIP
GMAVAVLKDGKAHYFNYGVADRERAVGVSEQTLFEIGSVSKPLTATLGAY
AVVKGAMQLDDKASRHAPWLKGSAFDSITMGELATYSAGGLPLQFPEEVD
SLEKMQAYYRQWTPAYSPGSHRQYSNPSIGLFGHLAASSLKQPFAQLMEQ
TLLPGLGLHHTYVNVPKQAMASYAYGYSKEDKPIRVSPGMLADEAYGIKT
SSADLLRFVKANISGVDDKALQQAISLTHKGHYSVGGMTQGLGWERYAYP
VSEQTLLAGNSAKVILEANPTAAPRESGSQMLFNKTGSTSGFGAYVAFVP
AKGIGIVMLANRNYPIPARVKAAHAILTQLAR

SEQ ID No. 983:
MQQRQSILWGALATLMWAGLAHAGDTSAVDPLRPVVDASIRPLLKEHRIP
GMAVAVLKDGKAHYFNYGVADRERAVGVSEQTLFEIGSVSKPLTATLGAY
AVVKGAMQLDDKASRHAPWLKGSAFDSITMGELATYSAGGLPLQFPEEVD
SLEKMQAYYRQWTPAYSPGSHRQYSNPSIGLFGHLAASSMKQPFAQLMEQ
TLLPGLGLHHTYVNVPKQAMASYAYGYSKEDKPIRVSPGMLADEAYGIKT
SSADLLRFVKANISGVDDKALQQAISLTHKGHYSVGGMTQGLGWESYAYP
VSEQTLLAGNSAEVILEANPTAAPRESGNLMLFNKTGSTSGFGAYVAFVP
AKGIGIVMLANRNYPIPARVKAAHAILTQLAR

SEQ ID No. 984:
MQQRQSILWGALATLMWAGLAHAGDKAATDPLRPVVDASIRPLLKEHRIP
GMAVAVLKDGKAHYFNYGVADRERAVGVSEQTLFEIGSVSKTLTATLGAY
AVVQGGFELDDKASLFAPWLKGSAFDNITMGELATYSAGGLPLQFPEEVD
SLEKMQAYYRQWTPAYSRGSHRQYANPSIGLFGYLAASSMKQPFDRLMEQ
TMLPGLGLYHTYLNVPEQPMGHYAYGYWKEDKPFRVTPAMLAEEPYGIKT
SSADLLRFVKANISGVDNAAMQQAIDLTHQGQYAVGEMTQGLGWERYPYP
VSEQTLLAGNSPAMIYNANPAAPAPAAAGHPVLFKKTGSTNGFGAYVAFV
PAKGIGVVMLANRNYPNEGTLKAGHAILTQLAR

SEQ ID No. 985:
MQQRQSILWGVLPTLMWAGLAHAGDRAATDPLRPVVDASIRPLLKEHRIP
GMAVAVLKDGKAHYFNYGVADRERAVGVSEQTLFEIGSVSKTLTATLGAY
AVVQGSFELDDKASLFAPWLKGSVFDNITMGELATYSAGGLPLQFPEEVD
SLEKMQAYYRQWTPAYSPGSHRQYANPSIGLFGYLAASSMKQPFDRLMEQ
TILPGLGLYHTYLNVPEQAMGHYAYGYSKEDKPIRVTPGMLADEAYGIKT
SSADLLRFVKANISGVDNAAMQQAIDLTHQGQYAVGEMTQGLGWERYAYP
VSEQTLLAGNSAAMIYNANPAAPAPAARGHPVLFNKTGSTNGFGAYVAFV
PAKGIGIVMLANRNSPIEGTLKAGHAILTQLAR

SEQ ID No. 986:
MQQRQSILWGALATLMWAGLVHAGDKAATDPLRPVVDASIRPLLKEHRIP
GMAVAVLKDGKAHYFNYGVADRERAVGVSEQTLFEIGSVSKTLTATLGAY
AVVQGSFELDDKASLFAPWLKGSVFDNITMGELATYSAGGLPLQFPEEVD
SLEKMQAYYRQWTPAYSPGSHRQYANPSIGLFGYLAASSMKQPFDRLMEQ
TMLPGLGLYHTYLTVPEQAMGHYAYGYSKEDKPIRVTPGMLADEAYGIKT
SSADLLRFVKANIGGVDNAAMQQAIDLTHQGQYAVGEMTQGLGWERYAYP
VSEQTLLAGNSPAMIYNAIPAVPAPAAAGHPVLFNKTGSTNGFGAYVAFV
PAKGIGIVMLANRNSPIEARIKAAHAILTQLAR

SEQ ID No. 987:
MQQRQSILWGAVATLMWAGLAHAGEASPVDPLRPVVDASIQPLLKEHRIP
GMAVAVLKDGKAHYFNYGVANRESGASVSEQTLFEIGSVSKTLTATLGAY
AVVKGAMQLDDKASRHAPWLKGSVFDSITMGELATYSAGGLPLQFPEEVD
SSEKMRAYYRQWAPVYSPGSHRQYSNPSIGLFGHLAASSLKQPFAQLMEQ
TLLPGLGMHHTYVNVPKQAMASYAYGYSKEDKPIRVNPGMLADEAYGIKT
SSADLLAFVKANIGGVDDKALQQAISLTHKGHYSVGGMTQGLGWESYAYP
VTEQTLLAGNSAKVILEANPTAAPRESGSQVLFNKTGSSNGFGAYVAFVP
ARGIGIVMLANRNYPIPARVKAAHAILAQLAG

SEQ ID No. 988:
MQQRQSILWGALATLMWAGLAHAGETSPVDPLRPVVDASIRPLLKEHRIP
GMAVAVLKDGKAHYFNYGVADRERAVGVSEQTLFEIGSVSKPLTATLGAY
AVVKGAMQLDDKASRHAPWLKGSAFDSITMGELATYSAGGLPLQFPEEVD
SLEKMQAYYRQWTPAYSPGSHRQYSNPSIGLFGHLAASSMKQPFAQLMEQ
TLLPGLGLHHTYVNVPKQAMASYAYGYSKEDKPIRVSPGMLADEAYGIKT
SSADLLRFVKANISGVHDKALQQAISLTHKGHYSVGGMTQGLGWESYAYP
VSEQTLLAGNSAKVILEANPTAAPRESGSQMLFNKTGSTSGFGAYVAFVP
AKGIGIVMLANRNYPIPARVKAAHAILTQLAR said peptides being chosen, preferably, from the peptides of sequence SEQ ID No. 989 to SEQ ID No. 1037 as defined hereafter:

| Peptide SEQ ID No. | Amino acid sequence | Position of the peptide in the MOX protein(s) |
| --- | --- | --- |
| SEQ ID No. 989 | AATDPLR | 27-33 for the proteins of SEQ No. 984, 985, 986 |
| SEQ ID No. 990 | AHYFNYGVADR | 62-72 for the proteins of SEQ No. 982, 983, 984, 985, 986, 988 |
| SEQ ID No. 991 | ANISGVDDK | 261-269 for the proteins of SEQ No. 982, 983 |
| SEQ ID No. 992 | ANISGVHDK | 261-269 for the protein of SEQ No. 988 |
| SEQ ID No. 993 | ASLFAPWLK | 113-121 for the proteins of SEQ No. 984, 985, 986 |
| SEQ ID No. 994 | AVGVSEQTLFEIGSVSK | 75-91 for the proteins of SEQ No. 982, 983, 984, 985, 986, 988 |
| SEQ ID No. 995 | EDKPFR | 230-235 for the protein of SEQ No. 984 |
| SEQ ID No. 996 | ESGNLMLFNK | 326-335 for the protein of SEQ No. 983 |
| SEQ ID No. 997 | ESGSQMLFNK | 326-335 for the proteins of SEQ No. 982, 988 |
| SEQ ID No. 998 | GHPVLFNK | 329-336 for the proteins of SEQ No. 985, 986 |
| SEQ ID No. 999 | GHYSVGGMTQGLGWER | 281-296 for the protein of SEQ No. 982 |
| SEQ ID No. 1000 | GIGVVMLANR | 354-363 for the protein of SEQ No. 984 |
| SEQ ID No. 1001 | MQAYYR | 155-160 for the proteins of SEQ No. 982, 983, 984, 985, 986, 988 |
| SEQ ID No. 1002 | NSPIEAR | 364-370 for the protein of SEQ No. 986 |
| SEQ ID No. 1003 | NSPIEGTLK | 364-372 for the protein of SEQ No. 985 |
| SEQ ID No. 1004 | NYPNEGTLK | 364-372 for the protein of SEQ No. 984 |
| SEQ ID No. 1005 | QPFDR | 192-196 for the proteins of SEQ No. 984, 985, 986 |
| SEQ ID No. 1006 | QWTPAYSPGSHR | 161-172 for the proteins of SEQ No. 982, 983, 985, 986, 988 |
| SEQ ID No. 1007 | QWTPAYSR | 161-168 for the protein of SEQ No. 984 |
| SEQ ID No. 1008 | QYANPSIGLFGYLAASSMK | 173-191 for the proteins of SEQ No. 984, 985, 986 |
| SEQ ID No. 1009 | QYSNPSIGLFGHLAASSMK | 173-191 for the proteins of SEQ No. 983, 988 |
| SEQ ID No. 1010 | TGSSNGFGAYVAFVPAR | 336-352 for the protein of SEQ No. 987 |

-continued

| Peptide SEQ ID No. | Amino acid sequence | Position of the peptide in the MOX protein(s) |
|---|---|---|
| SEQ ID No. 1011 | TGSTNGFGAYVAFVPAK | 337-353 for the proteins of SEQ No. 984, 985, 986 |
| SEQ ID No. 1012 | TGSTSGFGAYVAFVPAK | 336-352 for the proteins of SEQ No. 982, 983, 988 |
| SEQ ID No. 1013 | TLTATLGAYAVVQGGFELDDK | 92-112 for the protein of SEQ No. 984 |
| SEQ ID No. 1014 | TLTATLGAYAVVQGSFELDDK | 92-112 for the proteins of SEQ No. 985, 986 |
| SEQ ID No. 1015 | VSPGMLADEAYGIK | 236-249 for the proteins of SEQ No. 982, 983, 988 |
| SEQ ID No. 1016 | VTPAMLAEEPYGIK | 236-249 for the protein of SEQ No. 984 |
| SEQ ID No. 1017 | VTPGMLADEAYGIK | 236-249 for the proteins of SEQ No. 985, 986 |
| SEQ ID No. 1018 | YAYPVSEQTLLAGNSAK | 297-313 for the proteins of SEQ No. 982, 988 |
| SEQ ID No. 1019 | ALQQAISLTHK | 270-280 for the proteins of SEQ No. 982, 983, 987, 988 |
| SEQ ID No. 1020 | ANIGGVDDK | 261-269 for the protein of SEQ No. 987 |
| SEQ ID No. 1021 | EDKPIR | 230-235 for the proteins of SEQ No. 982, 983, 985, 986, 987, 988 |
| SEQ ID No. 1022 | ESGASVSEQTLFEIGSVSK | 73-91 for the protein of SEQ No. 987 |
| SEQ ID No. 1023 | ESGSQVLFNK | 326-335 for the protein of SEQ No. 987 |
| SEQ ID No. 1024 | GAMQLDDK | 105-112 for the proteins of SEQ No. 982, 983, 987, 988 |
| SEQ ID No. 1025 | GIGIVMLANR | 353-362 for the proteins of SEQ No. 982, 983, 987, 988; 354-363 for the proteins of sequence SEQ ID No. 985, 986 |
| SEQ ID No. 1026 | HAPWLK | 116-121 for the proteins of SEQ No. 982, 983, 987, 988 |
| SEQ ID No. 1027 | NYPIPAR | 363-369 for the proteins of SEQ No. 982, 983, 987, 988 |
| SEQ ID No. 1028 | QAMASYAYGYSK | 218-229 for the proteins of SEQ No. 982, 983, 987, 988 |
| SEQ ID No. 1029 | QWAPVYSPGSHR | 161-172 for the protein of SEQ No. 987 |

| Peptide SEQ ID No. | Amino acid sequence | Position of the peptide in the MOX protein(s) |
|---|---|---|
| SEQ ID No. 1030 | QYSNPSIGLFGHLAASSLK | 173-191 for the proteins of SEQ No. 982, 987 |
| SEQ ID No. 1031 | TLTATLGAYAVVK | 92-104 for the protein of SEQ No. 987 |
| SEQ ID No. 1032 | TSSADLLAFVK | 250-260 for the protein of SEQ No. 987 |
| SEQ ID No. 1033 | TSSADLLR | 250-257 for the proteins of SEQ No. 982, 983, 984, 985, 986, 988 |
| SEQ ID No. 1034 | VILEANPTAAPR | 314-325 for the proteins of SEQ No. 982, 983, 987, 988 |
| SEQ ID No. 1035 | VNPGMLADEAYGIK | 236-249 for the protein of SEQ No. 987 |
| SEQ ID No. 1036 | AHYFNYGVANR | 62-72 for the protein of SEQ No. 987 |
| SEQ ID No. 1037 | IPGMAVAVLK | 49-58 for the proteins of SEQ No. 982, 983, 984, 985, 986, 987, 988 |

The detection of a mechanism of resistance to cephalosporins induced by the expression of the PER protein is characterised by the detection of at least one peptide belonging to the PER protein and to its different sequence variants SEQ ID No. 1038 to SEQ ID No. 1044.

SEQ ID No. 1038:
MNVIIKAVVTASTLLMVSFSSFETSAQSPLLKEQIESIVIGKKATVGVAV
WGPDDLEPLLINPFEKFPMQSVFKLHLAMLVLHQVDQGKLDLNQTVIVNR
AKVLQNTWAPIMKAYQGDEFSVPVQQLLQYSVSLSDNVACDLLFELVGGP
AALHDYIQSMGIKETAVVANEAQMHADDQVQYQNWTSMKGAAEILKKFEQ
KTQLSETSQALLWKWMVETTTGPERLKGLLPAGTVVAHKTGTSGIKAGKT
AATNDLGIILLPDGRPLLVAVFVKDSAESSRTNEAIIAQVAQTAYQFELK
KLSALSPN

SEQ ID No. 1039:
MNVIIKAVVTASTLLMVSFSSFETSAQSPLLKEQIESIVIGKKATVGVAV
WGPDDLEPLLINPFEKFPMQSVFKLHLAMLVLHQVDQGKLDLNQTVIVNR
AKVLQNTWAPIMKAYQGDEFSVPVQQLLQYSVSHTDNVACDLLFELVGGP
AALHDYIQSMGIKETAVVANEAQMHADDQVQYQNWTSMKGAAEILKKFEQ
KTQLSETSQALLWKWMVETTTGPERLKGLLPAGTVVAHKTGTSGIKAGKT
AATNDLGIILLPDGRPLLVAVFVKDSAESSRTNEAIIAQVAQTAYQFELK
KLSALSPN

SEQ ID No. 1040:
MNVIIKAVVTASTLLMVSFSSFETSAQSPLLKGQIESIVIGKKATVGVAV
WGPDDLEPLLINPFEKFPMQSVFKLHLAMLVLHQVDQGKLDLNQTVIVNR
AKVLQNTWAPIMKAYQGDEFSVPVQQLLQYSVSHSDNVACDLLFELVGGP
AALHDYIQSMGIKETAVVANEAQMHADDQVQYQNWTSMKGAAEILKKFEQ
KTQLSETSQALLWKWMVETTTGPERLKGLLPAGTVVAHKTGTSGIKAGKT
AATNDLGIILLPDGRPLLVAVFVKDSAESSRTNEAIIAQVAQTAYQFELK
KLSALSPN

SEQ ID No. 1041:
MNVIAKGVFTTTALLMLSLSSWVVSAQSPLLKEQIETIVTGKKATVGVAV
WGPDDLEPLLVNPFEKFPMQSVFKMHLAMLVLHQVDQGKLDLNKTVAVNR
AAVLQNTWSPMMKDHQGDEFTVTVQQLLQYSVSHSDNVACDLLFELVGGP
AALHAYIQSLGIKETEVVANEAQMHADDQVQYKNWTSMKAAAQLLRKFEQ
KKQLSETSQALLWKWMVETTTGPQRLKGLLPAGTVVAHKTGTSGVRAGKT
AATNDIGVIMLPDGRPLLVAVFVKDSAESARTNEAIIAQVAQAAYQFELK
KLSAVSPD

SEQ ID No. 1042:
MNVIIKAVVTASTLLMVSFSSFETSAQSPLLKEQIESIVIGKKATVGVAV
WGPDDLEPLLINPFEKFPMQSVFKLHLAMLVLHQVDQGKLDLNQTVIVNR
AKVLQNTWAPIMKAYQGDQFSVPVQQLLQYSVSHSDNVACDLLFELVGGP
AALHDYIQSMGIKETAVVANEAQMHADDQVQYQNWTSMKGAAEILKKFEQ
KTQLSETSQALLWKWMVETTTGPERLKGLLPAGTVVAHKTGTSGVRAGKT

-continued

```
AATNDLGIILLPDGRPLLVAVFVKDSAESSRTNEAIIAQVAQAAYQFELK

KLSALSPN

SEQ ID No. 1043:
MNVITKCVFTASALLMLGLSSFVVSAQSPLLKEQIETIVTGKKATVGVAV

WGPDDLEPLLLNPFEKFPMQSVFKLHLAMLVLHQVDQGKLDLNQSVTVNR

AAVLQNTWSPMMKDHQGDEFTVAVQQLLQYSVSHSDNVACDLLFELVGGP

QALHAYIQSLGVKEAAVVANEAQMHADDQVQYQNWTSMKAAAQVLQKFEQ

KKQLSETSQALLWKWMVETTTGPQRLKGLLPAGTIVAHKTGTSGVRAGKT

AATNDAGVIMLPDGRPLLVAVFVKDSAESERTNEAIIAQVAQAAYQFELK

KLSAVSPD
```

-continued

```
SEQ ID No. 1044:
MNVIIKAVVTASTLLMVSFSSFETSAQSPLLKEQIESIVIGKKATVGVAV

WGPDDLEPLLINPFEKFPMQSVFKLHLAMLVLHQVDQGKLDLNQTVIVNR

AKVLQNTWAPIMKAYQGDEFSVPVQQLLQYSVSHSDNVACDLLFELVGGP

AALHDYIQSMGIKETAVVANEAQMHADDQVQYQNWTSMKGAAEILKKFEQ

KTQLSETSQALLWKWMVETTTGPERLKGLLPAGTVVAHKTGTSGIKAGKT

AATNDLGIILLPDGRPLLVAVFVKDSAESSRTNEAIIAQVAQTAYQFELK

KLSALSPN
``` said peptides being chosen, preferably, from the peptides of sequence SEQ ID No. 1045 to SEQ ID No. 1077 as defined hereafter:

| Peptide SEQ ID No. | Amino acid sequence | Position of the peptide in the PER protein(s) |
|---|---|---|
| SEQ ID No. 1045 | AAAQLLR | 190-196 for the proteins of SEQ No. 1041 |
| SEQ ID No. 1046 | AAAQVLQK | 190-197 for the proteins of SEQ No. 1043 |
| SEQ ID No. 1047 | AAVLQNTWSPMMK | 101-113 for the proteins of SEQ No. 1041, 1043 |
| SEQ ID No. 1048 | DSAESAR | 275-281 for the proteins of SEQ No. 1041 |
| SEQ ID No. 1049 | DSAESER | 275-281 for the proteins of SEQ No. 1043 |
| SEQ ID No. 1050 | DSAESSR | 275-281 for the proteins of SEQ No. 1038, 1039, 1040, 1042, 1044 |
| SEQ ID No. 1051 | EQIESIVIGK | 33-42 for the proteins of SEQ No. 1038, 1039, 1042, 1044 |
| SEQ ID No. 1052 | EQIETIVTGK | 33-42 for the proteins of SEQ No. 1041, 1043 |
| SEQ ID No. 1053 | ETEVVANEAQMHADDQVQYK | 164-183 for the proteins of SEQ No. 1041 |
| SEQ ID No. 1054 | FPMQSVFK | 67-74 for the proteins of SEQ No. 1038, 1039, 1040, 1041, 1042, 1043, 1044 |
| SEQ ID No. 1055 | GAAEILK | 190-196 for the proteins of SEQ No. 1038, 1039, 1040, 1042, 1044 |
| SEQ ID No. 1056 | GLLPAGTIVAHK | 228-239 for the proteins of SEQ No. 1043 |
| SEQ ID No. 1057 | GLLPAGTVVAHK | 228-239 for the proteins of SEQ No. 1038, 1039, 1040, 1041, 1042, 1044 |
| SEQ ID No. 1058 | GQIESIVIGK | 33-42 for the proteins of SEQ No. 1040 |

-continued

| Peptide SEQ ID No. | Amino acid sequence | Position of the peptide in the PER protein(s) |
|---|---|---|
| SEQ ID No. 1059 | LDLNK | 90-94 for the proteins of SEQ No. 1041 |
| SEQ ID No. 1060 | LDLNQSVTVNR | 90-100 for the proteins of SEQ No. 1043 |
| SEQ ID No. 1061 | LDLNQTVIVNR | 90-100 for the proteins of SEQ No. 1038, 1039, 1040, 1042, 1044 |
| SEQ ID No. 1062 | LHLAMLVLHQVDQGK | 75-89 for the proteins of SEQ No. 1038, 1039, 1040, 1042, 1043, 1044 |
| SEQ ID No. 1063 | MHLAMLVLHQVDQGK | 75-89 for the proteins of SEQ No. 1041 |
| SEQ ID No. 1064 | NWTSMK | 184-189 for the proteins of SEQ No. 1038, 1039, 1040, 1041, 1042, 1043, 1044 |
| SEQ ID No. 1065 | QLSETSQALLWK | 203-214 for the proteins of SEQ No. 1038, 1039, 1040, 1041, 1042, 1043, 1044 |
| SEQ ID No. 1066 | TAATNDAGVIMLPDGR | 250-265 for the proteins of SEQ No. 1043 |
| SEQ ID No. 1067 | TAATNDIGVIMLPDGR | 250-265 for the proteins of SEQ No. 1041 |
| SEQ ID No. 1068 | TAATNDLGIILLPDGR | 250-265 for the proteins of SEQ No. 1038, 1039, 1040, 1042, 1044 |
| SEQ ID No. 1069 | TGTSGIK | 240-246 for the proteins of SEQ No. 1038, 1039, 1040, 1044 |
| SEQ ID No. 1070 | TGTSGVR | 240-246 for the proteins of SEQ No. 1041, 1042, 1043 |
| SEQ ID No. 1071 | TNEAIIAQVAQAAYQFELK | 282-300 for the proteins of SEQ No. 1041, 1042, 1043 |
| SEQ ID No. 1072 | TNEAIIAQVAQTAYQFELK | 282-300 for the proteins of SEQ No. 1038, 1039, 1040, 1044 |
| SEQ ID No. 1073 | TQLSETSQALLWK | 202-214 for the proteins of SEQ No. 1038, 1039, 1040, 1042, 1044 |
| SEQ ID No. 1074 | TVAVNR | 95-100 for the proteins of SEQ No. 1041 |
| SEQ ID No. 1075 | VLQNTWAPIMK | 103-113 for the proteins of SEQ No. 1038, 1039, 1040, 1042, 1044 |
| SEQ ID No. 1076 | WMVETTTGPER | 215-225 for the proteins of SEQ No. 1038, 1039, 1040, 1042, 1044 |

| Peptide SEQ ID No. | Amino acid sequence | Position of the peptide in the PER protein(s) |
|---|---|---|
| SEQ ID No. 1077 | WMVETTTGPQR | 215-225 for the proteins of SEQ No. 1041, 1043 |

The detection of a mechanism of resistance to cephalosporins induced by the expression of the PER protein indicates an ESBL resistance. It is preferably detected with the aid of SEQ ID No. 1045 to SEQ ID No. 1065 and SEQ ID No. 1069 to SEQ ID No. 1077.

The detection of a mechanism of resistance to cephalosporins induced by the expression of the VEB protein is characterised by the detection of at least one peptide belonging to the VEB protein and to its different sequence variants SEQ ID No. 1078 to SEQ ID No. 1084.

SEQ ID No. 1078:
MKIVKRILLVLLSLFFTIVYSNAQTDNLTLKIENVLKAKNARIGVAIFNS
NEKDTLKINNDFHFPMQSVMKFPIALAVLSEIDKGNLSFEQKIEITPQDL
LPKTWSPIKEEFPNGTTLTIEQILNYTVSESDNIGCDILLKLIGGTDSVQ
KFLNANHFTDISIKANEEQMHKDWNTQYQNWATPTAMNKLLIDTYNNKNQ
LLSKKSYDFIWKIMRETTTGSNRLKGQLPKNTIVAHKTGTSGINNGIAAA
TNDVGVITLPNGQLIFISVFVAESKETSEINEKIISDIAKITWNYY
LNK

SEQ ID No. 1079:
MKIVKRILLVLLSLFFTIVYSNAQADNLTLKIENVLKAKNARIGVAIFNS
NEKDTLKINNDFHFPMQSVMKFPIALAVLSEIDKGNLSFEQKIEITPQDL
LPKTWSPIKEEFPNGTTLTIEQILNYTVSESDNIGCDILLKLIGGTDSVQ
KFLNANHFTDISIKANEEQMHKDWNTQYQNWATPTAMNKLLIDTYNNKNQ
LLSKKSYDFIWKIMRETTTGSNRLKGQLPKNTIVAHKTGTSGINNGIAAA
TNDVGVITLPNGQLIFISVFVAESKETSEINEKIISDIAKITWNYYLNK

SEQ ID No. 1080:
MKIVKRILLVLLSLFFTVVYSNAQTDNLTLKIENVLKAKNARIGVAIFNS
NEKDTFKINNDFHFPMQSVMKFPIALAVLSEIDKGNLSFEQKIEITPQDL
LPKTWSPIKEEFPNGTTLTIEQILNYTVSESDNIGCDILLKLIGGTDSVQ
KFLNANHFTDISIKANEEQMHKDWNTQYQNWATPTAMNKLLIDTYNNKNQ
LLSKKSYDFIWKIMRETTTGSNRLKGQLPKNTIVAHKTGTSGINNGIAAA
TNDVGVITLPNGQLIFISVFVAESKETSEINEKIISDIAKITWNYYLNK

SEQ ID No. 1081:
MKIVKRILLVLLSLFFTIVYSNAQADNLTLKIENVLKAKNARIGVAIFNS
NEKDTLKINNDFHFPMQSVMKFPIALAVLSEIDKGNLSFEQKIEITPQDL
LPKMWSPIKEEFPNGTTLTIEQILNYTVSESDNIGCDILLKLIGGTDSVQ
KFLNANHFTDISIKANEEQMHKDWNTQYQNWATPTAMNKLLIDTYNNKNQ
LLSKKSYDFIWKIMRETTTGSNRLKGQLPKNTIVAHKTGTSGINNGIAAA
TNDVGVITLPNGQLIFISVFVAESKETSEINEKIISDIAKITWNYYLNK

SEQ ID No. 1082:
MKIVKRILLVLLSLFFTVEYSNAQTDNLTLKIENVLKAKNARIGVAIFNS
NEKDTLKINNDFHFPMQSVMKFPIALAVLSEIDKGNLSFEQKIEITPQDL
LPKMWSPIKEEFPNGTTLTIEQILNYTVSESDNIGCDILLKLIGGTDSVQ
KFLNANHFTDISIKANEEQMHKDWNTQYQNWATPTAMNKLLIDTYNNKNQ
LLSKKSYDFIWKIMRETTTGSNRLKGQLPKNTIVAHKTGTSGINNGIAAA
TNDVGVITLPNGQLIFISVFVAESKETSEINEKIISDIAKITWNYYLNK

SEQ ID No. 1083:
MKIVKRILLVLLSLFFTVVYSNAQADNLTLKIENVLKAKNARIGVAIFNS
NEKDTLKINNDFHFPMQSVMKFPIALAVLSEIDKGNLSFEQKIEITPQDL
LPKMWSPIKEEFPNGTTLTIEQILNYTVSESDNIGCDILLKLIGGTDSVQ
KFLNANHFTDISIKANEEQMHKDWNTQYQNWATPTAMNKLLIDTYNNKNQ
LLSKKSYDFIWKIMRETTTGSNRLKGQLPKNTIVAHKTGTSGINNGIAAA
TNDVGVITLPNGQLIFISVFVAESKETSEINEKIISDIAKITWNYYLNK

SEQ ID No. 1084:
MKIVKRILLVLLSLFFTVEYSNAQTDNLTLKIENVLKAKNARIGVAIFNS
NEKDTLKINNDFHFPMQSVMKFPIALAVLSEIDKGNLSFEQKIEITPQDL
LPKTWSPIKEEFPNGTTLTIEQILNYTVSESDNIGCDILLKLIGGTDSVQ
KFLNANHFTDISIKANEEQMHKDWNTQYQNWATPTAMNKLLIDTYNNKNQ
LLSKKSYDFIWKIMRETTTGSNRLKGQLPKNTIVAHKTGTSGINNGITAA
TNDVGVITLPNGQLIFISVFVAESKETSEINEKIISDIAKITWNYYLNK said peptides being chosen, preferably, from the peptides of sequence SEQ ID No. 1085 to SEQ ID No. 1104 as defined hereafter:

| Peptide SEQ ID No. | Amino acid sequence | Position of the peptide in the VEB protein(s) |
|---|---|---|
| SEQ ID No. 1085 | ANEEQMHK | 165-172 for the proteins of SEQ No. 1078, 1079, 1080, 1081, 1082, 1083, 1084 |
| SEQ ID No. 1086 | DWNTQYQNWATPTAMNK | 173-189 for the proteins of SEQ No. 1078, 1079, 1080, 1081, 1082, 1083, 1084 |

-continued

| Peptide SEQ ID No. | Amino acid sequence | Position of the peptide in the VEB protein(s) |
|---|---|---|
| SEQ ID No. 1087 | ETSEINEK | 276-283 for the proteins of SEQ No. 1078, 1079, 1080, 1081, 1082, 1083, 1084 |
| SEQ ID No. 1088 | ETTTGSNR | 216-223 for the proteins of SEQ No. 1078, 1079, 1080, 1081, 1082, 1083, 1084 |
| SEQ ID No. 1089 | FLNANHFTDISIK | 152-164 for the proteins of SEQ No. 1078, 1079, 1080, 1081, 1082, 1083, 1084 |
| SEQ ID No. 1090 | FPIALAVLSEIDK | 72-84 for the proteins of SEQ No. 1078, 1079, 1080, 1081, 1082, 1083, 1084 |
| SEQ ID No. 1091 | GNLSFEQK | 85-92 for the proteins of SEQ No. 1078, 1079, 1080, 1081, 1082, 1083, 1084 |
| SEQ ID No. 1092 | GQLPK | 226-230 for the proteins of SEQ No. 1078, 1079, 1080, 1081, 1082, 1083, 1084 |
| SEQ ID No. 1093 | IEITPQDLLPK | 93-103 for the proteins of SEQ No. 1078, 1079, 1080, 1081, 1082, 1083, 1084 |
| SEQ ID No. 1094 | IENVLK | 32-37 for the proteins of SEQ No. 1078, 1079, 1080, 1081, 1082, 1083, 1084 |
| SEQ ID No. 1095 | IGVAIFNSNEK | 43-53 for the proteins of SEQ No. 1078, 1079, 1080, 1081, 1082, 1083, 1084 |
| SEQ ID No. 1096 | IISDIAK | 284-290 for the proteins of SEQ No. 1078, 1079, 1080, 1081, 1082, 1083, 1084 |
| SEQ ID No. 1097 | INNDFHFPMQSVMK | 58-71 for the proteins of SEQ No. 1078, 1079, 1080, 1081, 1082, 1083, 1084 |
| SEQ ID No. 1098 | LIGGTDSVQK | 142-151 for the proteins of SEQ No. 1078, 1079, 1080, 1081, 1082, 1083, 1084 |
| SEQ ID No. 1099 | LLIDTYNNK | 190-198 for the proteins of SEQ No. 1078, 1079, 1080, 1081, 1082, 1083, 1084 |
| SEQ ID No. 1100 | MWSPIK | 104-109 for the proteins of SEQ No. 1081, 1082, 1083 |
| SEQ ID No. 1101 | NQLLSK | 199-204 for the proteins of SEQ No. 1078, 1079, 1080, 1081, 1082, 1083, 1084 |
| SEQ ID No. 1102 | NTIVAHK | 231-237 for the proteins of SEQ No. 1078, 1079, 1080, 1081, 1082, 1083, 1084 |
| SEQ ID No. 1103 | SYDFIWK | 206-212 for the proteins of SEQ No. 1078, 1079, 1080, 1081, 1082, 1083, 1084 |
| SEQ ID No. 1104 | TWSPIK | 104-109 for the proteins of SEQ No. 1078, 1079, 1080, 1084 |

The detection of a mechanism of resistance to cephalosporins induced by the expression of the VEB protein indicates an ESBL resistance.

The detection of a mechanism of resistance to cephalosporins or to carbapenems induced by the expression of the OXA protein is characterised by the detection of at least one peptide belonging to the OXA protein and to its different sequence variants SEQ ID No. 1105 to SEQ ID No. 1266:

SEQ. ID. No. 1105:
MSRLLLSGLLATGLLCAVPASAASGCFLYADGNGQTLSSEGDCSSQLPPASTFKIPL

ALMGYDSGFLVNEEHPALPYKPSYDGWLPAWRETTTPRRWETYSVVWFSQQITE

WLGMERFQQYVDRFDYGNRDLSGNPGKHDGLTQAWLSSSLAISPEEQARFLGKM

VSGKLPVSAQTLQYTANILKVSEVEGWQIHGKTGMGYPKKLDGSLNRDQQIGWFV

GWASKPGKQLIFVHTVVQKPGKQFASIKAKEEVLAALPAQLKKL

SEQ ID No. 1106:
IACLSSTALAGSITENTSWNKEFSAEAVNGVFVLCKSSSKSCATNDLARASKEYLPA

STFKIPNAIIGLETGVIKNEHQVFKWDGKPRAMKQWERDLTLRGAIQVSAVPVFQQI

AREVGEVRMQKYLKKFSYGNQNISGGIDKFWLEDQLRISAVNQVEFLESLYLNKLSA

SKENQLIVKEALVTEAAPEYLVHSKTGFSGVGTESNPGVAWWVGWVEKETEVYFF

AFNMDIDNESKLPLRKSIPTKIMESEGIIGG

SEQ ID No. 1107:
MKKILLLHMLVFVSATLPISSVASDEVETLKCTIIADAITGNTLYETGECARRVSPCSS

FKLPLAIMGFDSGILQSPKSPTWELKPEYNPSPRDRTYKQVYPALWQSDSVVWFSQ

QLTSRLGVDRFTEYVKKFEYGNQDVSGDSGKHNGLTQSWLMSSLTISPKEQIQFLL

RFVAHKLPVSEAAYDMAYATIPQYQAAEGWAVHGKSGSGWLRDNNGKINESRPQ

GWFVGWAEKNGRQVVFARLEIGKEKSDIPGGSKAREDILVELPVLMGNK

SEQ ID No. 1108:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNAGPSTSNGDYWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 1109:
MQRSLSMSGKRHFIFAVSFVISTVCLTFSPANAAQKLSCTLVIDEASGDLLHREGSC

DKAFAPMSTFKLPLAIMGYDADILLDATTPRWDYKPEFNGYKSQQKPTDPTIWLKDS

IVWYSQELTRRLGESRFSDYVQRFDYGNKDVSGDPGKHNGLTHAWLASSLKISPEE

QVRFLRRFLRGELPVSEDALEMTKAVVPHFEAGDWDVQGKTGTGSLSDAKGGKAP

IGWFIGWATRDDRRVVFARLTVGARKGEQPAGPAARDEFLNTLPALSENF

SEQ ID No. 1110:
MKTFAAYVIIACLSSTALAGSITENTSWNKEFSAEAVNGVFVLCKSSSKSCATNDLAR

ASKEYLPASTFKIPNAIIGLETGVIKNEHQVFKWDGKPRAMKQWERDLTLRGAIQVS

AVPVFQQIAREVGEVRMQKYLKKFSYGNQNISGGIDKFWLEGQLRISAVNQVEFLE

SLYLNKLSASKENQLIVKEALVTEAAPEYLVHSKTGFSGVGTESNPGVAWWVGWVE

KETEVYFFAFNMDIDNESKLPLRKSIPTKIMESEGIIGG

SEQ ID No. 1111:
IACLSSTALAGSITENTSWNKEFSAEAVNGVFVLCKSSSKSCATNDLARASKEYLPA

STFKIPNAIIGLETGVIKNEHQVFKWDGKPRAMKQWERDLTLRGAIQVSAVPVFQQIT

REVGEVRMQKYLKKFSYGNQNISGGIDKFWLEDQLRISAVNQVEFLESLYLNKLSAS

-continued

KENQLIVKEALVTEAAPEYLVHSKTGFSGVGTESNPGVAWWVGWVEKETEVYFFA

FNMDIDNESKLPLRKSIPTKIMESEGIIGG

SEQ ID No. 1112:
IACLSSTALAGSITENTSWNKEFSAEAVNGVFVLCKSSSKSCATNDLARASKEYLPA

STFKIPSAIIGLETGVIKNEHQVFKWDGKPRAMKQWERDLTLRGAIQVSAVPVFQQIA

REVGEVRMQKYLKKFSYGNQNISGGIDKFWLEGQLRISAVNQVEFLESLYLNKLSAS

KENQLIVKEALVTEAAPEYLVHSKTGFSGVGTESNPGVAWWVGWVEKETEVYFFA

FNMDIDNESKLPLRKSIPTKIMESEGIIGG

SEQ ID No. 1113:
MIIRFLALLFSAVVLVSLGHAQEKTHESSNWGKYFSDFNAKGTIVVVDERTNGNSTS

VYNESRAQQRYSPASTFKIPHTLFALDAGAVRDEFHVFRWDGAKRSFAGHNQDQN

LRSAMRNSTVWVYQLFAKEIGENKARSYLEKLNYGNADPSTKSGDYWIDGNLAISA

NEQISILKKLYRNELPFRVEHQRLVKDLMIVEAKRDWILRAKTGWDGQMGWWVGW

VEWPTGPVFFALNIDTPNRMEDLHKREAIARAILQSVNALPPN

SEQ ID No. 1114:
MAIRIFAILFSTFVFGTFAHAQEGMRERSDWRKFFSEFQAKGTIVVADERQTDRVILV

FDQVRSEKRYSPASTFKIPHTLFALDAGAARDEFQVFRWDGIKRSFAAHNQDQDLR

SAMRNSTVWIYELFAKEIGEDKARRYLKQIDYGNADPSTSNGDYWIDGNLAIAAQEQ

IAFLRKLYHNELPFRVEHQRLVKDLMIVEAGRNWILRAKTGWEGRIGWWVGWVEW

PTGPVFFALNIDTPNRMDDLFKREAIVRAILRSIEALPPNPAVNSDAAR

SEQ ID No. 1115:
MKTFAAYVITACLSSTALASSITENTSWNKEFSAEAVNGVFVLCKSSSKSCATNNLA

RASKEYLPASTFKIPSAIIGLETGVIKNEHQVFKWDGKPRAMKQWERDLSLRGAIQV

SAVPVFQQIAREVGEVRMQKYLKKFSYGNQNISGGIDKFWLEGQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

SEQ ID No. 1116:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFWLEDQLRISAVNQVEFLE

SLFLNKLSASKENQLIVKEALVTEAAPEYLVHSKTGFSGVGTESNPGVAWWVGWVE

KGTEVYFFAFNMDIDNENKLPLRKSIPTKIMASEGIIGG

SEQ ID No. 1117:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFGLEGQLRISAVNQVEFLE

SLFLNKLSASKENQLIVKEALVTEAAPEYLVHSKTGFSGVGTESNPGVAWWVGWVE

KGTEVYFFAFNMDIDNENKLPLRKSIPTKIMASEGIIGG

SEQ ID No. 1118:
MKNTIHINFAIFLIIANIIYSSASASTDISTVASPLFEGTEGCFLLYDASTNAEIAQFNKA

KCATQMAPDSTFKIALSLMAFDAEIIDQKTIFKWDKTPKGMEIWNSNHTPKTWMQFS

VVWVSQEITQKIGLNKIKNYLKDFDYGNQDFSGDKERNNGLTEAWLESSLKISPEEQ

IQFLRKIINHNLPVKNSAIENTIENMYLQDLDNSTKLYGKTGAGFTANRTLQNGWFEG

FIISKSGHKYVFVSALTGNLGSNLTSSIKAKKNAITILNTLNL

-continued

SEQ ID No. 1119:
ANIIYSSASASTDISTVASPLFEGTEGCFLLYDVSTNAEIAQFNKAKCATQMAPDSTF

KIALSLMAFDAEIIDQKTIFKWDKTPKGMEIWNSNHTPKTWMQFSVVWVSQEITQKI

GLNKIKNYLKDFDYGNQDFSGDKERNNGLTEAWLESSLKISPEEQIQFLRKIINHNLP

VKNSAIENTIENMYLQDLENSTKLYGKTGAGFTANRTLQNGWFEGFIISKSGHKYVF

VSALTGNLGSNLTSSIKAKKNAITIL

SEQ ID No. 1120:
IFSLATFAHAQEGTLERSDWRKFFSEFQAKGTIVVADERQADRAMLVFDPVRSKKR

YSPASTFKIPHTLFALDAGAVRDEFQIFRWDGVNRGFAGHNQDQDLRSAMRNSTV

WVYELFAKEIGDDKARRYLKKIDYGNAYPSTSNGDYWIEGSLAISAQEQIAFLRKLYR

NELPFRVEHQRLVKDLMIVEAGRNWILRAKTGWEGRMGWWVGWVEWPTGSVFFA

LNIDTPNRMDDLFKREAIVRAIL

SEQ ID No. 1121:
MIIRFLALLFSAVVLVSLGHAQDKTHESSNWGKYFSDFNAKGTIVVVDERTNGNSTS

VYNESRAQQRYSPASTFKIPHTLFALDAGAVRDEFHVFRWDGAKRSFAGHNQDQN

LRSAMRNSTVWVYQLFAKEIGENKARSYLEKLNYGNADPSTKSGDYWIDGNLAISA

NEQISILKKLYRNELPFRVEHQRLVKDLMIVEAKRDWILRAKTGWDGQMGWVGW

VEWPTGPVFFALNIDTPNRMEDLHKREAIARAILQSVNALPPN

SEQ ID No. 1122:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVEKMLLIKEVNGSKIYAKSGWGMGVTPQV

GWLTGWVEQANGKKIPFSLNLEMKEGMSGSIRNEITYKLLENLGII

SEQ ID No. 1123:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMGVTPQV

GWLTGWVEQANGKKIPFSLNLEMKEGMTGSIRNEITYKSLENLGII

SEQ ID No. 1124:
MNKYFTCYVVASLFLSGCTVQHNLINETPSQIVQGHNQVIHQYFDEKNTSGVLVIQT

DKKINLYGNALSRANTEYVPASTFKMLNALIGLENQKADINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALKMEMRSEMPASIRNELLMKSLKQLNII

SEQ ID No. 1125:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYCIEGSLAISAQEQ

IAFLRKLYRNELPFRVEHQRLVKDLMIVEAGRNWILRAKTGWEGRMGWWVGWVE

WPTGSVFFALNIDTPNRMDDLFKREAIVRAIL

SEQ ID No. 1126:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

```
SAVPVFQQIAREVGEVRMQKYLKKFSYGNQNISGGIDKFWLEGQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

SEQ ID No. 1127:
MAIRFLTILLSTFFLTSFVHAQEHVLERSDWKKFFSDLRAEGAIVISDERQAEHALLVF

GQERAAKRYSPASTFKLPHTLFALDADAVRDEFQVFRWDGVKRSFAGHNQDQDLR

SAMRNSAVWVYELFAKEIGKDKARHYLKQIDYGNADPSTIKGDYWIDGNLEISAHEQ

ISFLRKLYRNQLPFQVEHQRLVKDLMITEAGRNWILRAKTGWEGRFGWWVGWVE

WPTGPVFFALNIDTPNRTDDLFKREAIARAILRSIDALPPN

SEQ ID No. 1128:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYWIEGSIAISAQEQ

IAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 1129:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMGVTPQV

GWLTGWVEQANGKKIPFSLNLEMKEGMSGSIRNEITYKSLENLGII

SEQ ID No. 1130:
MAIRFLTILLSTFFLTSFVHAQEHVLERSDWKKFFSDLRAEGAIVISDERQAEHALLVF

GQERAAKRYSPASTFKLPHTLFALDADAVRDEFQVFRWDGVKRSFAGHNQDQDLR

SAMRNSAVWVYELFAKEIGEDKARRYLKQIDYGNADPSTIKGDYWIDGNLEISAHEQ

ISFLRKLYRNQLPFQVEHQRLVKDLMITEAGRNWILRAKTGWEGRFGWWVGWVE

WPTGPVFFALNIDTPNRTDDLFKREAIARAILRSIDALPPN

SEQ ID No. 1131:
MAIRFFTILLSTFFLTSFVYAQEHVVIRSDWKKFFSDLQAEGAIVIADERQAKHTLSVF

DQERAAKRYSPASTFKIPHTLFALDADAVRDEFQVFRWDGVNRSFAGHNQDQDLR

SAMRNSTVWVYELFAKDIGEDKARRYLKQIDYGNVDPSTIKGDYWIDGNLKISAHEQ

ILFLRKLYRNQLPFKVEHQRLVKDLMITEAGRSWILRAKTGWEGRFGWWVGWIEW

PTGPVFFALNIDTPNRTDDLFKREAIARAILRSIDALPPN

SEQ ID No. 1132:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVERIGFGNAEIGQQVDNFWLVGPL

KVTPIQEVEFVSQLAHTQLPFSEKVQANVKNMLLLEESNGYKIFGKTGWAAMDIKPQ

VGWLTGWVEQPDGKIVAFALNMEMRSEMPASIRNELLMKSLKQLNII

SEQ ID No. 1133:
MAIQIFAILFSTFVLATFAHAQDGTLERSDWGKFFSDFQAKGTIVVADERQADHAILV

FDQARSMKRYSPASTFKIPHTLFALDAGAVRDEFQIFRWDGVKRSFAGHNKDQDLR

SAMRNSTVWVYELFAKEIGDGKARRYLKQIGYGNADPSTHGDYWIEGSLAISAQE
```

QIAFLRKLYQNDLPFRVEHQRLVKDLMIVEAGRNWILRAKTGWEGSMGWWVGWV

EWPTGPVFFALNIDTPNRMDDLFKREAIARAILLSIEALPPNPAVHSDAAR

SEQ ID No. 1134:
MKNTIHINFAIFLIIANIIYSSASASTDISTVASQLFEGTEGCFLLYDASTNAEIAQFNKA

KCAAQMAPDSTFKIALSLMAFDAEIIDQKTIFKWDKIPKGMEIWNSNHTPKTWMQFS

VVWVSQEITQKIGLNKIKNYLKDFDYGNQDFSGDKERNNGLTEAWLESSLKISPEEQ

IQFLRKIINHNLPVRNSAIENTIDNMYLQDLENSTKLYGKTGAGFTANRTLQNGWFEG

FIISKSGHKYVFVSALTGSLGSNLTSSIKAKKNAITILNTLNL

SEQ ID No. 1135:
MLLFMFSIISFGNENQFMKEIFERKGLNGTFVVYDLKNDKIDYYNLDRANERFYPASS

FKIFNTLIGLENGIVKNVDEMFYYYDGSKVFLDSWAKDSNLRYAIKVSQVPAYKKLAR

ELGKERMQEGLNKLNYGNKEIGSEIDKFWLEGPLKISAMEQVKLLNLLSQSKLPFKL

ENQEQVKDITILEKKDDFILHGKTGWATDNIVVPIGWFVGWIETSDNIYSFAINLDISD

SKFLPKREEIVREYFKNINVIK

SEQ ID No. 1136:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIATWNRDHNLI

TAMKYSVVPVYQEFARQIGEARMSKMLHAFDYGNEDISGNVDSFWLDGGIRISATE

QISFLRKLYHNKLHVSERSQRIVKQAMLTEANGDYIIRAKTGYSTRIEPKIGWWVGW

VELDDNVWFFAMNMDMPTSDGLGLRQAITKEVLKQEKIIP

SEQ ID No. 1137:
MLSRYSKTLAFAVVACTLAISTATAHAELVVRNDLKRVFDDAGVSGTFVLMDITADR

TYVVDPARAARSIHPASTFKIPNSLIAFDTGAVRDDQEVLPYGGKPQPYEQWEHDM

ALPEAIRLSAVPIYQEVARRVGFERMQAYVDAFDYGNRQLGSAIDQFWLRGPLEISA

FEEARFTSRMALKQLPVKPRTWDMVQRMLLIEQQGDAALYAKTGVATEYQPEIGW

WAGWVERAGHVYAFALNIDMPREGDMAKRIPLGKQLMRALEVWPAP

SEQ ID No. 1138:
MRPLLFSALLLLSGHTQASEWNDSQAVDKLFGAAGVKGTFVLYDVQRQRYVGHDR

ERAETRFVPASTYKVANSLIGLSTGAVRSADEVLPYGGKPQRFKAWEHDMSLRDAI

KASNVPVYQELARRIGLERMRANVSRLGYGNAEIGQVVDNFWLVGPLKISAMEQTR

FLLRLAQGELPFPAPVQSTVRAMTLLESGPGWELHGKTGWCFDCTPELGWWVGW

VKRNERLYGFALNIDMPGGEADIGKRVELGKASLKALGILP

SEQ ID No. 1139:
MNKGLHRKRLSKRLLLPMLLCLLAQQTQAVAAEQTKVSDVCSEVTAEGWQEVRRW

DKLFESAGVKGSLLLWDQKRSLGLSNNLSRAAEGFIPASTFKLPSSLIALETGAVRD

ETSRFSWDGKVREIAVWNRDQSFRTAMKYSVVPVYQQLAREIGPKVMAAMVRQLE

YGNQDIGGQADSFWLDGQLRITAFQQVDFLRQLHDNKLPVSERSQRIVKQMMLTE

ASTDYIIRAKTGYGVRRTPAIGWWVGWLELDDNTVYFAVNLDLASASQLPLRQQLV

KQVLKQEQLLP

SEQ ID No. 1140:
MNTIISRRWRAGLWRRLVGAVVLPATLAATPAAYAADVPKAALGRITERADWGKLF

AAEGVKGTIVVLDARTQTYQAYDAARAEKRMSPASTYKIFNSLLALDSGALDNERAII

PWDGKPRRIKNWNAAMDLRTAFRVSCLPCYQVVSHKIGRRYAQAKLNEVGYGNRT

IGGAPDAYWVDDSLQISAREQVDFVQRLARGTLPFSARSQDIVRQMSIVEATPDYVL

-continued

HGKTGWFVDKKPDIGWWVGWIERDGNITSVAINIDMLSEADAPKRARIVKAVLKDLK

LI

SEQ ID No. 1141:
MKTFAAYVITACLSSTALASSITENTFWNKEFSAEAVNGVFVLCKSSSKSCATNNLA

RASKEYLPASTFKIPNAIIGLETGVIKNEHQIFKWDGKPRAMKQWERDLSLRGAIQVS

AVPVFQQIAREVGEVRMQKYLKKFSYGNQNISGGIDKFWLEGQLRISAVNQVEFLE

SLFLNKLSASKENQLIVKEALVTEAAPEYLVHSKTGFSGVGTESNPGVAWWVGWVE

KGAEVYFFAFNMDIDNENKLPLRKSIPTKIMASEGIIGG

SEQ ID No. 1142:
MRVLALSAVLVVASIVGMPAMANEWQEKPSWNTHFSEHKAQGVIVLWNENKQQGF

TNNLKRANQAFLPASTFKIPNSLIALDLGVVKDEHQVFKWDGQTRDIAAWNRDHDLI

TAMKYSVVPVYQEFARQIGQARMSKMLHAFDYGNEDISGNLDSFWLDGGIRISATE

QVAFLRKLYHNKLHVSERSQRIVKQAMLTEANSDYIIRAKTGYSTRIEPQIGWWVGW

VELDDNVWFFAMNMDMPTADGLGLRQAITKEVLKQEKIIP

SEQ ID No. 1143:
MKKITLFLLFLNLVFGQDKILNNWFKEYNTSGTFVFYDGKTWASNDFSRAMETFSPA

STFKIFNALIALDSGVIKTKKEIFYHYRGEKVFLSSWAQDMNLSSAIKYSNVLAFKEVA

RRIGIKTMQEYLNKLHYGNAKISKIDTFWLDNSLKISAKEQAILLFRLSQNSLPFSQEA

MNSVKEMIYLKNMENLELFGKTGFNDGQKIAWIVGFVYLKDENKYKAFALNLDIDKF

EDLYKREKILEKYLDELVKKVKNDG

SEQ ID No. 1144:
MSKKNFILIFIFVILISCKNTEKISNETTLIDNIFTNSNAEGTLVIYNLNDDKYIIHNKERAE

QRFYPASTFKIYNSLIGLNEKAVKDVDEVFYKLMAKSFLESWAKDSNLRYAIKNSQV

PAYKELARRIGIKKMKENIEKLDFGNKSIGDSVDTFWLEGPLEISAMEQVKLLTKLAQ

NELQYPIEIQKAISDITITRANLHITLHGKTGLADSKNMTTEPIGWFVGWLEENDNIYV

FALNIDNINSDDLAKRINIVKESLKALNLLK

SEQ ID No. 1145:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALKMEMRSEMPASIRNELLMKSLKQLNII

SEQ ID No. 1146:
MNIQALLLITSAIFISACSPYIVTANPNYSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRIGYGNADIGTQVDNFWLVGPLKI

TPQQEAQFAYKLANKTLPFSQKVQDEVQSMLFIEEKNGNKIYAKSGWGWDVNPQV

GWVVQPQGNIVAFSLNLEMKKGISSSVRKEITYRGLEQLGIL

SEQ ID No. 1147:
MNIKALLLITSAIFISACSPYIVTANPNHSASKSDEKGEKIKNLFNEAHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1148:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1149:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1150:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQEVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1151:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1152:
MNIKALLLITSAIFISACSPYIVTANPNHSASKSDKKAEKIKNLFNEAHTTGVLVIQQGQ

TQQSYGNDLARASTEYVPASTFKMLNALIGLEHHKATTTEVFKWNGQKRLFPEWEK

DMTLGDAMKASAIPVYQDLARRIGLELMSNEVKRVGYGNADIGTQVDNFWLVGPLK

ITPQQEAQFAYKLANKTLPFSQKVQHEVQSMLFIEEKNGNKIYAKSGWGWDVDPQV

GWLTGWVVQPQGNIVAFSLNLEMKKGIPSSVRKEITYKSLEQLGIL

SEQ ID No. 1153:
MNIKALLLITSAIFISACSPYIVTANPNHSASKSDEKAEKIKNLFNEAHTTGVLVIQQGQ

TQQSYGNDLARASTEYVPASTFKMLNALIGLEHHKTTTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1154:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTAVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGTPSSVRKEITYKSLEQLGIL

SEQ ID No. 1155:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

```
SEQ ID No. 1156:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEKLGIL

SEQ ID No. 1157:
MNIKTLLLITSTIFISACSPYIVTANPNHSTSKSDEKAEKIKNLFNEAHTTGVLVIQQGQ

TQQSYGNDLARASIEYVPASTFKMLNALIGLEHHKATTTEIFKWDGQKRLFPEWEKD

MTLGDAMKASAIPVYQDLARRIGLELMSKEVKRVGYGNADIGTQVDNFWLVGPLKIT

PQQEAQFAYKLANKTLPFSLKVQDEVQSMLFIEEKNGNKIYAKSGWGWDVDPQVG

WLTGWVVQPQGNIVAFSLNLEMKKGIPSSVRKEITYKSLEQLGIL

SEQ ID No. 1158:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAISVYQDLARRIGLELMSKEVKRVGYGNADIGTQVDNFWLAGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1159:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASALPVYQDLARRIGLELMSKEVKRVGYGNADIGTQVDNFWLVGPL

KITPQQEAQFAYKLANKTLPFSQKVQDEVQSMLFIEEKNGNKIYAKSGWGWDVNPQ

VGWLTGWVVQPQGNIVAFSLNLEMKKGIPSSVRKEITYKSLEQLGIL

SEQ ID No. 1160:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGSVVQPQGNIVAFSLNLEMKKGIPSSVRKEITYKSLEQLGIL

SEQ ID No. 1161:
MNIKTLLLITSTIFISACSPYIVTANPNHSTSKSDEKAEKIKNLFNEAHTTGVLVIQQGQ

TQQSYGNDLARASIEYVPASTFKMLNALIGLEHHKATTTEIFKWDGQKRLFPEWEKD

MTLGDAMKASAIPVYQDLARRIGLELMSKEVKRVGYGNADIGTQVDNFWLVGPLKIT

PQQEAQFAYKLANKTLPFSLKAQDEVQSMLFIEEKNGNKIYAKSGWGWDVDPQVG

WLTGWVVQPQGNIVAFSLNLEMKKGIPSSVRKEITYKSLEQLGIL

SEQ ID No. 1162:
MNIKALLLITSAIFISACSPYIVTANPNHSASKSDKKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK
```

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1163:
MNIKTLLLITSAIFISACSHYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFTYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1164:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1165:
MNIKALLLITSTIFISACSPYIVTANPNHSASKSDEKAEKIKNLFNEAHTTGVLVIQQGQ

TQQSYGNDLARASTEYVPASTFKMLNALISLEHHKATTTEVFKWDGQKRLFPEWEK

DMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1166:
MNIQALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPHGNIVAFSLNLEMKKGIPSSVRKEITYKSLEQLGIL

SEQ ID No. 1167:
MNIKALFLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1168:
MKLLKILSLVCLSISIGACAEHSMSRAKTSTIPQVNNSIIDQNVQALFNEISADAVFVTY

DGQNIKKYGTHLDRAKTAYIPASTFKIANALIGLENHKATSTEIFKWDGKPRFFKAWD

KDFTLGEAMQASTVPVYQELARRIGPSLMQSELQRIGYGNMQMGTEVDQFWLKGP

LTITPIQEVKFVYDLAQGQLPFKPEVQQQVKEMLYVERRGENRLYAKSGWGMAVD

PQVGWYVGFVEKADGQVVAFALNMQMKAGDDIALRKQLSLDVLDKLGVFHYL

SEQ ID No. 1169:
MNIKALLLITSTIFISACSPYIVTANPNHSTSKSDEKAEKIKNLFNEAHTTGVLVIQQGQ

TQQSYGNDLARASTEYVPASTFKMLNALIGLEHHKATTTEIFKWDGQKRLFPEWEK

DMTLGDAMKASAIPVYQDLARRIGLELMSKEVKRVGYGNADIGTQVDNFWLVGPLK

ITPQQEAQFAYKLANKTLPFSLKVQDEVQSMLFIEEKNGNKIYAKSGWGWDVDPQV

GWLTGWVVQPQGNIVAFSLNLEMKKGIPSSVRKEITYKSLEQLGIL

-continued

SEQ ID No. 1170:
MNIKTLLLITSAIFISACSPYIVTANPNHSASKSDEKAEKIKNLFNEVHTTGVLVIRQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEMNGNKIYAKSGWGWDVDPQV

GWLTGWVVQPQGNIVAFSLNLEMKKGIPSSVRKEITYKSLEQLGIL

SEQ ID No. 1171:
MKLLKILSLVCLSISIGACAEHSMSRAKTSTIPQVNNSIIDQNVQALFNEISGDAVFVTY

DGQNIKKYGTHLDRAKTAYIPASTFKIANALIGLENHKATSTEIFKWDGKPRFFKAWD

KDFTLGEAMQASTVPVYQELARRIGPSLMQSELQRIGYGNMQIGTEVDQFWLKGPL

TITPIQEVKFVYDLAQGQLPFKPEVQQQVKEMLYVERRGENRLYAKSGWGMAVDP

QVGWYVGFVEKADGQVVAFALNMQMKAGDDIALRKQLSLDVLDKLGVFHYL

SEQ ID No. 1172:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMDVTPQV

GWLTGWVEQANGKKIPFSLNLEMKEGMSGSIRNEITYKSLENLGII

SEQ ID No. 1173:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYWIESSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 1174:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1175:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAILVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1176:
MNIKALLLITSAIFISACSPYIVTANPNHSASKSDKKAEKIKNLFNEAHTTGVLVIQQGQ

TQQSYGNDLARASTEYVPASTFKMLNALIGLEHHKATTTEVFKWNGQKRLFPEWEK

DMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1177:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

-continued

NMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1178:
MNIKALLLITSAIFISACSPYIVTTNPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNTDIGTQVDNFWVVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1179:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIQVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1180:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASALPVYQDLARRIGLELMSKEVKRVGYGNADIGTQVDNFWLVGPL

KITPQQEAQFAYKLANKTLPFSQKVQDEVQSMLFIEEKNGNKIYAKSGWGWDVNPQ

VGWLTGWVVQPQGNIVAFSLNLEMKKGIPSSVRKEITYKSLEQLGIL

SEQ ID No. 1181:
MNIKTLLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEMNGNKIYAKSGWGWDVDPQV

GWLTGWVVQPQGNIVAFSLNLEMKKGIPSSVRKEITYKSLEQLGIL

SEQ ID No. 1182:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFPLNLEMKKGIPSSVRKEITYKSLEQLGIL

SEQ ID No. 1183:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGGDVNPQV

GWLTGWVVQPQGNIVAFSLNLEMKKGIPSSVRKEITYKSLEQLGIL

SEQ ID No. 1184:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAILVYQDLARRIGLELMSKEVKRVGYGNADIGTQVDNFWLVGPLKI

-continued

TPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1185:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1186:
MNIKALLLITSAIFISACSPYIVTANPNHSASKSDEKAEKIKNLFNEAHTTGVLVIQQGQ

TQQSYGNDLARASTEYVPASTFKMLNALIGLEHHKTTTTEVFKWDGQKRLFPEWEK

DMTLGDAMKASAIPVYQDLARRIGLELMSKEVKRVGYGNADIGTQVDNFWVVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1187:
MSKKNFILIFIFVILISCKNTEKISNETTLIDNIFTNSNAEGTLVIYNLNDDKYIIHNKERAE

QRFYPASTFKIYNSLIGLNEKAVKDVDEVFYKYNGEKVFLESWAKDSNLRYAIKNSQ

VPAYKELARRIGLKKMKENIEKLDFGNKSIGDSVDTFWLEGPLEISAMEQVKLLTKLA

QNELPYPIEIQKAVSDITILEQTYNYTLHGKTGLADSKNMTTEPIGWFVGWLEENDNI

YVFALNIDNINSDDLAKRINIVKESLKALNLLK

SEQ ID No. 1188:
MSKKNFILIFIFVILTSCKNTEKISNETTLIDNIFTNSNAEGTLVIYNLNDDKYIIHNKERA

EQRFYPASTFKIYNSLIGLNEKAVKDVDEVFYKYNGEKVFLESWAKDSNLRYAIKNS

QVPAYKELARRIGLKKMKENIEKLDFGNKSIGDSVDTFWLEGPLEISAMEQIKLLTKL

AQNELPYPIEIQKAVSDITILEQTYNYTLHGKTGLADSKNMTTEPIGWFVGWLEENDN

IYVFALNIDNINSDDLAKRINIVKESLKALNLLK

SEQ ID No. 1189:
LLITSAIFISACSPYIVSANPNHSASKSDDKAEKIKNLFNEAHTTGVLVIQQGQTQQSY

GNDLARASTEYVPASTFKMLNALIGLEHHKATTTEVFKWDGQKRLFPEWEKNMTLG

DAMKASAIPVYQDLARRIGLELMSNEVKRVGYGNADIGTQVDNFWLVGPLKITPQQ

EAQFAYKLANKTLPFSQKVQDEVQSMLFIEEKNGNKIYAKSGWGWDVDPQVGWLT

GWVVQPQGNIVAFSLNLEMKKGIPSSVRKEITYKSL

SEQ ID No. 1190:
LLITSAIFISACSPYIVSANPNHSASKSDEKAEKIKNLFNEAHTTGVLVIQQGQTQQSY

GNDLARASTEYVPASTFKMLNALIGLEHHKATTTEVFKWDGQKRLFPEWEKNMTLG

DAMKASAIPVYQDLARRIGLELMSNEVKRVGYGNADIGTQVDNFWLVGPLKITPQQ

EAQFAYKLANKTLPFSQKVQDEVQSMLFIEEKNGNKIYAKSGWGWDVNPQVGWLT

EWVVQPQGNIVAFSLNLEMKKGIPSSVRKEITYKSL

SEQ ID No. 1191:
MTVRRLSCALGAALSLSALGGGPVQAAVLCTVVADAADGRILFQQGTQQACAERYT

PASTFKLAIALMGADAGILQGPHEPVWNYQPAYPDWGGDAWRQPTDPARWIKYSV

VWYSQLTAKALGQDRFQRYTSAFGYGNADVSGEPGKHNGTDGAWIISSLRISPLEQ

LAFLRKLVNRQLPVKAAAYELAENLFEAGQADGWRLYGKTGTGSPGSNGVYTAAN

AYGWFVGWARKDGRQLVYARLLQDERATRPNAGLRARDELVRDWPAMAGAWRP

-continued

SEQ ID No. 1192:
MNIKALLLITSAIFISACSPYIVSANPNHSASKSDEKAEKIKNLFNEAHTTGVLVIQQGQ

TQQSYGNVLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQEVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1193:
MKTFAAYVIIACLSSTALAGSITENTSWNKEFSAEAVNGVFVLCKSSSKSCATNDLAR

ASKEYLPASTFKIPSAIIGLETGVIKNEHQVFKWDGKPRAMKQWERDLTLRGAIQVS

AVPVFQQIAREVGEVRMQKYLKKFSYGNQNISGGIDKFWLEDQLRISAVNQVEFLES

LYLNKLSASKENQLIVKEALVTEAAPEYLVHSKTGFSGVGTESNPGVAWWVGWVEK

ETEVYFFAFNMDIDNESKLPLRKSIPTKIMESEGIIGG

SEQ ID No. 1194:
MNIKTLLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1195:
MNIKALLLITSAIFISACSPYIVTTNPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNTDIGTQVDNFWLVGPLKI

TPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1196:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAVPVYQDLARRIGLELMSKEVKRVGYGNADIGTQVDNFWLVGPL

KITPQQEAQFAYKLANKTLPFSQKVQDEVQSMLFIEEKNGNKIYAKSGWGWDVNQ

QVGWLTGWVVQPQGNIVAFSLNLEMKKGIPSSVRKEITYKSLEQLGIL

SEQ ID No. 1197:
MNIKTLLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEMTYKSLEQLGIL

SEQ ID No. 1198:
MNKYFTCYVVASLFFSGCTVQHNLINETQSQIVQGHNQVIHQYFDEKNTSGVLVIQT

DKKINLYGNALSRANTEYVPASTFKMLNALIGLENQKTDINEIFKWKGEKRSFTTWE

KDMTLGEAMKLSAVPVYQELARRIGLDLMQKEVERIDFGNAEIGQQVDNFWLIGPLK

VTPIQEVEFVSQLAHTQLPFSEKVQANVKNMLLLEENNGYKIFGKTGWAMDIKPQV

GWLTGWVEQPDGKIVAFALNMEMRSEMPASIRNELLMKSLKQLNII

SEQ ID No. 1199:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

-continued

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAAMDIKPQ

VGWLTGWVEQPDGKIVAFALNMEMRSEMPASIRNELLMKSLKQLNII

SEQ ID No. 1200:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFLLEGQLRISAVNQVEFLE

SLFLNKLSASKENQLIVKEALVTEAAPEYLVHSKTGFSGVGTESNPGVAWWVGWVE

KGTEVYFFAFNMDIDNENKLPLRKSIPTKIMASEGIIGG

SEQ ID No. 1201:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGDADPSTSNGDYWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 1202:
MNIKALLLITSAIFISACSPYIVTANPNHSASKSDKKAEKIKNLFNEAHTTGVLVIQQGQ

TQQSYGNDLARASTEYVPASTFKMLNALIGLEHHKASTTEVFKWNGQKRLFPEWEK

DMTLGDAMKASAIPVYQDLARRIGLELMSNEVKRVGYGNADIGTQVDNFWLVGPLK

ITPQQEAQFAYKLANKTLPFSQKVQDEVKSMLFIEEKNGNKIYAKSGWGWDVDPQV

GWLTGWVVQPQGNIVAFSLNLEMKKGIPSSVRKEITYKSLEQLGIL

SEQ ID No. 1203:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKHVGYGNADIGTQVDNFWLVGPLK

ITPQQEAQFAYKLANKTLPFSPKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1204:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKHVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1205:
MKKFILPILSISTLLSVSACSSIQTKFEDTFHTSNQQHEKAIKSYFDEAQTQGVIIIKKG

KNISTYGNNLTRAHTEYVPASTFKMLNALIGLENHKATTTEIFKWDGKKRSYPMWEK

DMTLGDAMALSAVPVYQELARRTGLDLMQKEVKRVGFGNMNIGTQVDNFWLVGPL

KITPIQEVNFADDFANNRLPFKLETQEEVKKMLLIKEFNGSKIYAKSGWGMDVTPQV

GWLTGWVEKSNGEKVAFSLNIEMKQGMPGSIRNEITYKSLENLGII

SEQ ID No. 1206:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

-continued

ITPQQEAQFAYKLANKTLPFSQEVQDEVQSILFIEEKNGNKIYAKSGWGWDVNPQV

GWLTGWVVQPQGNIVAFSLNLEMKKGIPSSVRKEITYKSLEQLGIL

SEQ ID No. 1207:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMGVTSQV

GWLTGWVEQANGKKIPFSLNLEMKEGMSGSIRNEITYKSLENLGII

SEQ ID No. 1208:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIATWNRDHNLI

TAMKYSVVPVYQEFARQIGEARMSKMLHAFDYGNEDISGNVDSFWLDGGIRISATE

QISFLRKLYHNKLHVSERSQRIVKQAMLTEANGDYIIRAKTGYSARIEPKIGWWVGW

VELDDNVWFFAMNMDMPTSDGLGLRQAITKEVLKQEKIIP

SEQ ID No. 1209:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAVPVYQDLARRIGLELMSKEVKRVGYGNADIGTQVDNFWLVGPL

KITPQQEAQFAYKLANKTLPFSQKVQDEVQSMLFIEEKNGNKIYAKSGWGLDVNPQ

VGWLTGWVVQPQGNIVAFSLNLEMKKGIPSSVRKEITYKSLEQLGIL

SEQ ID No. 1210:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAVPVYQDLARRIGLELMSKEVKRVGYGNADIGTQVDNFWLVGPL

KITPQQEAQFAYKLANKTLPFSQKVQDEVQSMLFIEEKNGNKIYAKSGWGLDVNLQ

VGWLTGWVVQPQGNIVAFSLNLEMKKGIPSSVRKEITYKSLEQLGIL

SEQ ID No. 1211:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEKLGIL

SEQ ID No. 1212:
MNIKALLLITSAIFISACSPYIVTANPNHSASKSDVKAEKIRNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1213:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDSKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

-continued

SEQ ID No. 1214:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDGVQSMLFIEEKNGNKIYAKSGWGWDVNPQ

VGWLTGWVVQPQGNIVAFSLNLEMKKGIPSSVRKEITYKSLEQLGIL

SEQ ID No. 1215:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDSKKRLFPEWEK

DMTLGDAMKASAILVYQDLARRIGLELMSKEVKRVGYGNADIGTQVDNFWLVGPLKI

TPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1216:
MKLLKILSLVCLSISIGACAEHSMSRAKTSTIPQVNNSIIDQNVQALFNEISADAVFVTY

DGQNIKKYGTHLDRAKTAYIPASTFKIANALIGLENHKATSTEIFKWDGKPRFLKAWD

KDFTLGEAMQASTVPVYQELARRIGPSLMQSELQRIGYGNMQIGTEVDQFWLKGPL

TITPIQEVKFVYDLAQGQLPFKPEVQQQVKEMLYVERRGENRLYAKSGWGMAVDP

QVGWYVGFVEKADGQVVAFALNMQMKAGDDIALRKQLSLDVLDKLGVFHYL

SEQ ID No. 1217:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDVKPQ

VGWLTGWVEQPDGKIVAFALNMEMRSEMPASIRNELLMKSLKQLNII

SEQ ID No. 1218:
MNKYFTCYVVASLFLSGCTVQHNLINETPSQIVQGHNQVIHQYFDEKNTSGALVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASIRNELLMKSLKQLNII

SEQ ID No. 1219:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASIRNELMMKSLKQLNII

SEQ ID No. 1220:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLAGWVEQPDGKIVAFALNMEMRSEMPASIRNELLMKSLKQLNII

SEQ ID No. 1221:
MNKYFTCYVVASLFLSGCTVQHNLINETPSQIVQGHNQVIHQYFDERNTSGVLVIQT

DKKINLYGNALSRANTEYVPASTFKMLNALIGLENQKTDINEIFKWKGEKRSFTAWE

-continued

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASIRNELLMKSLKQLNII

SEQ ID No. 1222:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEKSNGYKIFGKTGWAMDIKPQV

GWLTGWVEQPDGKIVAFALNMEMRSEMPASIRNELLMKSLKQLNII

SEQ ID No. 1223:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASTRNELLMKSLKQLNII

SEQ ID No. 1224:
MKKFILPIFSISILLSLSACSSIQTKFEDTFHISNQKHEKAIKSYFDEAQTQGVIIIKEGKN

ISSYGNNLVRAHTEYVPASTFKMLNALIGLENHKATTNEIFKWDGKKRSYPMWEKD

MTLGEAMALSAVPVYQDLARRIGLNLMQKEVKRVGFGNMNIGTQVDNFWLIGPLKI

TPIQEVNFADDLANNRLPFKLETQEEVKKMLLIKEVNGSKIYAKSGWGMDVSPQVG

WLTGWVEKSNGEKVSFSLNIEMKQGMSGSIRNEITYKSLENLGII

SEQ ID No. 1225:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAMKASAIAVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1226:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAIKASAIPVYQDLARRIGLELMSKEVKRVGYGNADIGTQVDNFWLVGPLKI

TPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1227:
MKILIFLPLLSCLGLTACSLPVSSLPSQSISTQAIASLFDQAQSSGVLVIQRDQQVQVY

GNDLNRANTEYVPASTFKMLNALIGLQHGKATTNEIFKWDGKKRSFTAWEKDMTLG

QAMQASAVPVYQELARRIGLELMQQEVQRIQFGNQQIGQQVDNFWLVGPLKVTPK

QEVQFVSALAREQLAFDPQVQQQVKAMLFLQERKAYRLYVKSGWGMDVEPQVGW

LTGWVETPQAEIVAFSLNMQMQNGIDPAIRLEILQQALAELGLYPKAEG

SEQ ID No. 1228:
MHKHMSKLFIAFLAFLLSVPAAAEDQTLAELFAQQGIDGTIVISSLHNGKTFIHNDPRA

KQRFSTASTFKILNTLISLEEKAISGKDDVLKWDGHIYDFPDWNRDQTLESAFKVSCV

WCYQALARQVGAEKYRNYLRKSVYGELREPFEETTFWLDGSLQISAIEQVNFLKKV

-continued

HLRTLPFSASSYETLRQIMLIEQTPAFTLRAKTGWATRVKPQVGWYVGHVETPTDV

WFFATNIEVRDEKDLPLRQKLTRKALQAKGIIE

SEQ ID No. 1229:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGTDKFWLEDQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

SEQ ID No. 1230:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAILVYQDLARRIGLELMSKEVKRVGYGNADIGTQVDNFWLVGPLKI

TPQQEAQFAYKLANKTLPFSQKVQDEVQSMLFIEEKNGNKIYAKSGWGLDVDPQV

GWLTGWVVQPQGNIVAFSLNLEMKKGIPSSVRKEITYKSLEQLGIL

SEQ ID No. 1231:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIQVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1232:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAMPVYQDLARRIGLELMSKEVKRVGYGNADIGTQVDNFWLVGPL

KITPQQEAQFAYKLANKTLPFSQKVQDEVQSMLFIEEKNGNKIYAKSGWGWDVNPQ

VGWLTGWVVQPQGNIVAFSLNLEMKKGIPSSVRKEITYKSLEQLGIL

SEQ ID No. 1233:
MNIKALLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGKKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1234:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIATWNRDHNLI

TAMKYSVVPVYQEFARQIGEARMSKMLHAFDYGNEDISGNVDSFWLDGGIRISATE

QISFLRKLYHNKLHVSERSQRIVKQAMLTEANGDYIIRAKTGYDTKIGWWVGWVELD

DNVWFFAMNMDMPTSDGLGLRQAITKEVLKQEKIIP

SEQ ID No. 1235:
MSKKNFILIFIFVILISCKNTEKTSNETTLIDNIFTNSNAEGTLVIYNLNDDKYIIHNKERA

EQRFYPASTFKIYNSLIGLNEKAVKDVDEVFYKYNGEKVFLESWAKDSNLRYAIKNS

QVPAYKELARRIGLEKMKENIEKLDFGNKNIGDSVDTFWLEGPLEISAMEQVKLLTKL

AQNELPYPIEIQKAVSDITILEQTDNYTLHGKTGLADSENMTTEPIGWLVGWLEENNN

IYVFALNIDNINSDDLAKRINIVKESLKALNLLK

-continued

SEQ ID No. 1236:
MNIKALFLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1237:
MNIKALFLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPSSQKVQDEVQSMLFIEEKNGNKMYAKSGWGWDVNPQ

VGWLTGWVVQPQGNIVAFSLNLEMKKGIPSSVRKEITYKSLEQLGIL

SEQ ID No. 1238:
MNIKALFLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEIAYKSLEQLGIL

SEQ ID No. 1239:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDCWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 1240:
MNIKTLLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWVVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1241:
MNIKTLLLITSAIFISACSPYIVTANPNHSASKSDEKAEKIKNLFNEVHTTGVLVIQQGQ

TQQSYGNDLARASTEYVPASTFKMLNALIGLEYHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1242:
MAIRFLTILLSTFFLTSFVHAQEHVVVRSDWKKFFSDLQAEGAIVIADERQAEHALLV

FGQERAAKRYSPASTFKLPHTLFALDAGAVRDEFQVFRWDGVKRSFAGHNQDQDL

RSAMRNSAVWVYELFAKEIGEDNARRYLKQIDYGNADPSTIKGNYWIDGNLEISAHE

QISFLRKLYRNQLPFQVEHQRLVKYLMITEAGRNWILRAKTGWEGRFGWWIGWVE

WPTGPVFFALNIDTPNRTDDLFKREAIARAILRSIDALPPN

SEQ ID No. 1243:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIAAWNRDHDLI

-continued
TAMKYSVVPVYQEFARQIGEARMSKMLHAFDYGNEDISGNVDSFWLDGGIRISATQ

QIAFLRKLYHNKLHVSERSQRIVKQAMLTEANGDYIIRAKTGYSTRIEPKIGWWVGW

VELDDNVWFFAMNMDMPTSDGLGLRQAITKEVLKQEKIIP

SEQ ID No. 1244:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKSQV

GWLTGWVEQPDGKIVAFALNMEMRSEMPASIRNELLMKSLKQLNII

SEQ ID No. 1245:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAISVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1246:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 1247:
MKTIAAYLVLVFYASTALSESISENLAWNKEFSSESVHGVFVLCKSSSNSCTTNNAA

RASTAYIPASTFKIPNALIGLETGAIKDERQVFKWDGKPRAMKQWEKDLKLRGAIQV

SAVPVFQQIAREVGEIRMQKYLNLFSYGNANIGGGIDKFWLEGQLRISAFNQVKFLE

SLYLNNLPASKANQLIVKEAIVTEATPEYIVHSKTGYSGVGTESSPGVAWWVGWVE

KGTEVYFFAFNMDIDNESKLPSRKSISTKIMASEGIIIGG

SEQ ID No. 1248:
MKTFAAYVITACLSSTALASSITENTFWNKEFSAEAVNGVFVLCKSSSKLACATNNLA

RASKEYLPASTFKIPNAIIGLETGVIKNEHQIFKWDGKPRAMKQWERDLSLRGAIQVS

AVPVFQQIAREVGEVRMQKYLKKFSYGNQNISGGIDKFWLEGQLRISAVNQVEFLE

SLFLNKLSASKENQLIVKEALVTEAPEYLVHSKTGFSGVGTESNPGVAWWVGWVEK

GAEVYFFAFNMDIDNENKLPLRKSIPTKIMASEGIIGG

SEQ ID No. 1249:
MAIRIFAILFSTFVFGTFAHAQEGMRERSDWRKFFSEFQAKGTIVVADERQTDRVILV

FDQVRSEKRYSPASTFKIPHTLFALDAGAARDEFQVFRWDGIKRSFAAHNQDQDLR

SAMRNSTVWIYELFAKEIGEDKARRYLKQIDYGNADPSTSNGDYWIDGNLAIAAQEQ

IAFLRKLYHNELPFRVEHQRLVKDLMIVEAGRNWILRAKTGWEGRMGWWVGWVE

WPTGPVFFALNIDTPNRMDDLFKREAIVRAILRSIEALPPNPAVNSDAAR

SEQ ID No. 1250:
MKTFAAYVIIACLSSTALAGSITENTSWNKEFSAEAVNGVFVLCKSSSKSCATNDLAR

ASKEYLPASTFKIPNAIIGLETGVIKNEHQVFKWDGKPRAMKQWERDLTLRGAIQVS

AVPVFQQIAREVGEVRMQKYLKKFSYGSQNISGGIDKFWLEDQLRISAVNQVEFLES

-continued

LYLNKLSASKENQLIVKEALVTEAAPEYLVHSKTGFSGVGTESNPGVAWWVGWVEK

ETEVYFFAFNMDIDNESKLPLRKSIPTKIMESEGIIGG

SEQ ID No. 1251:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASIRNELLMKSLKQLNII

SEQ ID No. 1252:
MKKLSVLLWLTLFYCGTIWAQSTCFLVQENQTVLKHEGKDCNKRFAPESTFKIALSL

MGFDSGILKDTLNPEWPYKKEYELYLNVWKYPHNPRTWIRDSCVWYSQVLTQQLG

MTRFKNYVDAFHYGNQDISGDKGQNNGLTHSWLSSSLAISPSEQIQFLQKIVNKKLS

VNPKAFTMTKDILYIQELAGGWKLYGKTGNGRQLTKDKSQKLSLQHGWFIGWIEKD

GRVITFTKHIADSKKHVTFASFRAKNETLNQLFYLINELEK

SEQ ID No. 1253:
MNIKTLLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1254:
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYSVVWYSQQV

AHHLGAQRFAQYAKAFGYGNADVSGDPGQNNGLDRAWIGSSLQISPLEQLEFLGK

MLNRKLPVSPTAVDMTERIVESTTLADGTVVHGKTGVSYPLLADGTRDWARGSGW

FVGWIVRGNQTLVFARLTQDERKQPVSAGIRTREAFLRDLPRLLAAR

SEQ ID No. 1255:
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYPVVWYSQQV

AHHLGAQRFAQYAKAFGYGNADVSGDPGQNNGLDRAWIGSSLQISPLEQLEFLGK

MLNRKLPVSPTAVDMTERIVESTTLADGTVVHGKTGVSYPLLADGTRDWARGSGW

FVGWIVRGKQTLVFARLTQDERKQPVSAGIRTREAFLRDLPRLLAAR

SEQ ID No. 1256:
MRGKHTVILGAALSALFAGAAGAQMLECTLVADAASGQELYRKGACDKAFAPMSTF

KVPLAVMGYDAGILVDAHNPRWDYKPEFNGYKFQQKTTDPTIWEKDSIVWYSQQLT

RKMGQKRFAAYVAGFGYGNGDISGEPGKSNGLTHSWLGSSLKISPEGQVRFVRDL

LSAKLPASKDAQQMTVSILPHFAAGDWAVQGKTGTGSFIDARGAKAPLGWFIGWAT

HEERRVVFARMTAGGKKGEQPAGPAARDAFLKALPDLAKRF

SEQ ID No. 1257:
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYSVVWYSQQV

AHHLGAQRFAQYAKAFGYGNADVSGDPGQNNGLDRAWIGSSLQISPLEQLEFLGK

MLDRKLPVSPTAVDMTERIVESTTLADGTVVHGKTGVSYPLLADGTRDWARGSGW

FVGWIVRGKQTLVFARLTQDERKQPVSAGIRTREAFLRDLPRLLAAR

-continued

SEQ ID No. 1258:
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYSVVWYSQQV

AHHLGAQRFAQYAKAFGYGNADVSGDPGQNNGLDRAWIGSSLQISPLEQLEFLGK

MLNRKLPVSPTAVDMTERIVESTTLADGTVVHGKTGVSYPLLADGTRDWARGSGW

FVGWIVRGKQTLVFARLTQDERKQPVSAGIRTREAFLRDLPRLLAAR

SEQ ID No. 1259:
MKTFAAYVIIACLSSTALAGSITENTSWNKEFSAEAVNGVFVLCKSSSKSCATNDLAR

ASKEYLPVSTFKIPSAIIGLETGVIKNEHQVFKWDGKPRAMKQWERDLTLRGAIQVS

AVPVFQQIAREVGEVRMQKYLKKFSYGNQNISGGIDKFWLEGQLRISAVNQVEFLE

SLYLNKLSASKENQLIVKEALVTEAAPEYLVHSKTGFSGVGTESNPGVAWWVGWVE

KETEVYFFAFNMDIDNESKLPLRKSIPTKIMESEGIIGG

SEQ ID No. 1260:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1261:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 1262:
MKTFAAYVITACLSSTALASSITENTFWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFWLEGQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

SEQ ID No. 1263:
MKTIAAYLVLVFFAGTALSESISENLAWNKEFSSESVHGVFVLCKSSSNSCTTNNAT

RASTAYIPASTFKIPNALIGLETGAIKDARQVFKWDGKPRAMKQWEKDLTLRGAIQV

SAVPVFQQIARDIGKKRMQKYLNLFSYGNANIGGGIDKFWLEGQLRISAVNQVKFLE

SLYLNNLPASKANQLIVKEAIVTEATPEYIVHSKTGYSGVGTESNPGVAWWVGWVE

KGTEVYFFAFNMDIDNESKLPSRKSIPTKIMASEGIIIGG

SEQ ID No. 1264:
MKKFILPIFSISILVSLSACSSIKTKSEDNFHISSQQHEKAIKSYFDEAQTQGVIIIKEGK

NLSTYGNALARANKEYVPASTFKMLIALIGLENHKATTNEIFKWDGKKRTYPMWEKD

MTLGEAMALSAVPVYQELARRTGLELMQKEVKRVNFGNTNIGTQVDNFWLVGPLKI

TPVQEVNFADDLAHNRLPFKLETQEEVKKMLLIKEVNGSKIYAKSGWGMGVTPQVG

WLTGWVEQANGKKIPFSLNLEMKEGMSGSIRNEITYKSLENLGII

SEQ ID No. 1265:
MNIKALLLITSAIFISACSPYIVTANPNHSASKSDDKAEKIKNLFNEAHTTGVLVIHGQ

TQQSYGNDLARASTEYVPASTFKMLNALIGLEHHKATTTEVFKWNGQKRLFPEWEK

-continued

```
DMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 1266:
MNIKALLLITSAISISACSPYIVTANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAIKASAIPVYQDLARRIGLELMSKEVKRVGYGNADIGTQVDNFWLVGPLKI

TPQQEAQFAYKLANKTLPFSQKVQDEVQSMLFIEEKNGNKIYAKSGWGWDVDPQV
``` said peptides being chosen, preferably, from the peptides of sequence SEQ ID No. 1267 to SEQ ID No. 1835 and SEQ ID No. 2160 to SEQ ID No. 2171 as defined hereafter:

| Peptide SEQ ID No. | Amino acid sequence | Position of the peptide in the OXA protein(s) | Clinical interest |
|---|---|---|---|
| SEQ ID No. 1267 | AAAYELAENLFEAGQADGWR | 183-202 for the proteins of SEQ No. 1191 | 2d |
| SEQ ID No. 1268 | AAEGFIPASTFK | 86-97 for the proteins of SEQ No. 1139 | 2df |
| SEQ ID No. 1269 | AALGR | 41-45 for the proteins of SEQ No. 1140 | 2df |
| SEQ ID No. 1270 | ADGQVVAFALNMQMK | 241-255 for the proteins of SEQ No. 1168, 1171, 1216 | 2df |
| SEQ ID No. 1271 | ADINEIFK | 95-102 for the proteins of SEQ No. 1124 | 2df |
| SEQ ID No. 1272 | ADWGK | 50-54 for the proteins of SEQ No. 1140 | 2df |
| SEQ ID No. 1273 | AEGAIVISDER | 40-50 for the proteins of SEQ No. 1127, 1130 | OXA |
| SEQ ID No. 1274 | AFALNLDIDK | 222-231 for the proteins of SEQ No. 1143 | 2d |
| SEQ ID No. 1275 | AFAPMSTFK | 49-57 for the proteins of SEQ No. 1256; 60-68 for the protein of sequence SEQ ID No. 1109 | OXA |
| SEQ ID No. 1276 | AFGYGNADVSGDPGQNNGLDR | 127-147 for the proteins of SEQ No. 1254, 1255, 1257, 1258 | 2d |
| SEQ ID No. 1277 | AFTMTK | 174-179 for the proteins of SEQ No. 1252 | 2de |
| SEQ ID No. 1278 | AGDDIALR | 256-263 for the proteins of SEQ No. 1168, 1171, 1216 | 2df |
| SEQ ID No. 1279 | AGHVYAFALNIDMPR | 233-247 for the proteins of SEQ No. 1137 | 2df |
| SEQ ID No. 1280 | AGLWR | 11-15 for the proteins of SEQ No. 1140 | 2df |
| SEQ ID No. 1281 | AHTEYVPASTFK | 73-84 for the proteins of SEQ No. 1205, 1224 | 2df |
| SEQ ID No. 1282 | AIIPWDGK | 112-119 for the proteins of SEQ No. 1140 | 2df |
| SEQ ID No. 1283 | AIIPWDGKPR | 112-121 for the proteins of SEQ No. 1140 | 2df |
| SEQ ID No. 1284 | AISDITITR | 190-198 for the proteins of SEQ No. 1144 | 2d |

-continued

| Peptide SEQ ID No. | Amino acid sequence | Position of the peptide in the OXA protein(s) | Clinical interest |
|---|---|---|---|
| SEQ ID No. 1285 | AISGK | 82-86 for the proteins of SEQ No. 1228 | 2df |
| SEQ ID No. 1286 | ALGQDR | 121-126 for the proteins of SEQ No. 1191 | 2d |
| SEQ ID No. 1287 | ALPDLAK | 256-262 for the proteins of SEQ No. 1256 | 2d |
| SEQ ID No. 1288 | ALQAK | 254-258 for the proteins of SEQ No. 1228 | 2df |
| SEQ ID No. 1289 | AMETFSPASTFK | 50-61 for the proteins of SEQ No. 1143 | 2d |
| SEQ ID No. 1290 | AMLFLQER | 196-203 for the proteins of SEQ No. 1227 | 2df |
| SEQ ID No. 1291 | AMLVFDPVR | 55-63 for the proteins of SEQ No. 1108, 1125, 1128, 1173, 1201, 1239, 1246; 44-52 for the protein of sequence SEQ ID No. 1120 | OXA |
| SEQ ID No. 1292 | AMTLLESGPGWELHGK | 189-204 for the proteins of SEQ No. 1138 | 2d |
| SEQ ID No. 1293 | ANLHITLHGK | 199-208 for the proteins of SEQ No. 1144 | 2d |
| SEQ ID No. 1294 | ANQLIVK | 183-189 for the proteins of SEQ No. 1247, 1263 | OXA |
| SEQ ID No. 1295 | ANTEYVPASTFK | 71-82 for the proteins of SEQ No. 1124, 1132, 1145, 1198, 1199, 1217, 1218, 1219, 1220, 1221, 1222, 1223, 1244, 1251; 66-77 for the protein of sequence SEQ ID No. 1227 | 2df |
| SEQ ID No. 1296 | ANVSR | 133-137 for the proteins of SEQ No. 1138 | 2d |
| SEQ ID No. 1297 | APIGWFIGWATR | 224-235 for the proteins of SEQ No. 1109 | 2de |
| SEQ ID No. 1298 | APLGWFIGWATHEER | 213-227 for the proteins of SEQ No. 1256 | 2d |
| SEQ ID No. 1299 | AQDEVQSMLFIEEK | 196-209 for the proteins of SEQ No. 1161 | 2df |
| SEQ ID No. 1300 | AQGVIVLWNENK | 40-51 for the proteins of SEQ No. 1142 | 2df |
| SEQ ID No. 1301 | ASAIAVYQDLAR | 126-137 for the proteins of SEQ No. 1225 | 2df |
| SEQ ID No. 1302 | ASAILVYQDLAR | 126-137 for the proteins of SEQ No. 1175, 1184, 1215, 1230 | 2df |
| SEQ ID No. 1303 | ASAIPVYQDLAR | 126-137 for the proteins of SEQ No. 1146, 1147, 1148, 1149, 1150, 1151, 1152, 1153, 1154, 1156, 1157, 1160, 1161, 1162, 1163, 1164, 1165, 1166, 1167, 1169, 1170, 1174, 1176, 1177, 1178, 1181, 1182, 1183, 1185, 1186, 1192, 1194, 1195, 1197, 1202, 1203, 1204, 1206, 1211, 1212, 1213, 1214, 1226, 1233, 1236, 1237, 1238, 1240, 1241, 1253, 1260, 1261, 1265, 1266; 120-131 for the protein of sequence SEQ ID No. 1189; 120-131 for the protein of sequence SEQ ID No. 1190 | 2df |
| SEQ ID No. 1304 | ASAIPVYQDLPR | 126-137 for the proteins of SEQ No. 1155 | 2df |
| SEQ ID No. 1305 | ASAIQVYQDLAR | 126-137 for the proteins of SEQ No. 1179, 1231 | 2df |

-continued

| Peptide SEQ ID No. | Amino acid sequence | Position of the peptide in the OXA protein(s) | Clinical interest |
|---|---|---|---|
| SEQ ID No. 1306 | ASAISVYQDLAR | 126-137 for the proteins of SEQ No. 1158, 1245 | 2df |
| SEQ ID No. 1307 | ASALPVYQDLAR | 126-137 for the proteins of SEQ No. 1159, 1180 | 2df |
| SEQ ID No. 1308 | ASAMPVYQDLAR | 126-137 for the proteins of SEQ No. 1232 | 2df |
| SEQ ID No. 1309 | ASAVPVYQDLAR | 126-137 for the proteins of SEQ No. 1196, 1209, 1210 | 2df |
| SEQ ID No. 1310 | ASIEYVPASTFK | 72-83 for the proteins of SEQ No. 1157, 1161 | 2df |
| SEQ ID No. 1311 | ASNVPVYQELAR | 113-124 for the proteins of SEQ No. 1138 | 2d |
| SEQ ID No. 1312 | ASPASTFK | 49-56 for the proteins of SEQ No. 1254, 1255, 1257, 1258 | 2d |
| SEQ ID No. 1313 | ASTAYIPASTFK | 59-70 for the proteins of SEQ No. 1247, 1263 | OXA |
| SEQ ID No. 1314 | ASTEYVPASTFK | 72-83 for the proteins of SEQ No. 1146, 1147, 1148, 1149, 1150, 1151, 1152, 1153, 1154, 1155, 1156, 1158, 1159, 1160, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 66-77 for the protein of sequence SEQ ID No. 1189; 66-77 for the protein of sequence SEQ ID No. 1190 | 2df |
| SEQ ID No. 1315 | ASTTEVFK | 96-103 for the proteins of SEQ No. 1202 | 2df |
| SEQ ID No. 1316 | ATSTEIFK | 99-106 for the proteins of SEQ No. 1168, 1171, 1216 | 2df |
| SEQ ID No. 1317 | ATTNEIFK | 97-104 for the proteins of SEQ No. 1122, 1123, 1129, 1172, 1207, 1224, 1264; 90-97 for the protein of sequence SEQ ID No. 1227 | 2df |
| SEQ ID No. 1318 | ATTTAVFK | 96-103 for the proteins of SEQ No. 1154 | 2df |
| SEQ ID No. 1319 | ATTTEIFK | 97-104 for the proteins of SEQ No. 1205; 96-103 for the protein of sequence SEQ ID No. 1157; 96-103 for the protein of sequence SEQ ID No. 1161; 96-103 for the protein of sequence SEQ ID No. 1169 | 2df |
| SEQ ID No. 1320 | ATTTEVFK | 96-103 for the proteins of SEQ No. 1146, 1147, 1148, 1149, 1150, 1151, 1152, 1155, 1156, 1158, 1159, 1160, 1162, 1163, 1165, 1166, 1167, 1170, 1174, 1175, 1176, 1177, 1178, 1179, 1180, 1181, 1182, 1183, 1184, 1185, 1192, 1194, 1195, 1196, 1197, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 90-97 for the protein of sequence SEQ ID No. 1189; 90-97 for the protein of sequence SEQ ID No. 1190 | 2df |
| SEQ ID No. 1321 | AVSDITILEQTDNYTLHGK | 191-209 for the proteins of SEQ No. 1235 | OXA |
| SEQ ID No. 1322 | AVSDITILEQTYNYTLHGK | 191-209 for the proteins of SEQ No. 1187, 1188 | 2d |

-continued

| Peptide SEQ ID No. | Amino acid sequence | Position of the peptide in the OXA protein(s) | Clinical interest |
|---|---|---|---|
| SEQ ID No. 1323 | AVVPHFEAGDWDVQGK | 195-210 for the proteins of SEQ No. 1109 | 2de |
| SEQ ID No. 1324 | AWEHDMSLR | 100-108 for the proteins of SEQ No. 1138 | 2d |
| SEQ ID No. 1325 | AWIGSSLQISPLEQLEFLGK | 148-167 for the proteins of SEQ No. 1254, 1255, 1257, 1258 | 2d |
| SEQ ID No. 1326 | CAAQMAPDSTFK | 63-74 for the proteins of SEQ No. 1134 | 2d |
| SEQ ID No. 1327 | CATQMAPDSTFK | 48-59 for the proteins of SEQ No. 1119; 63-74 for the protein of sequence SEQ ID No. 1118 | 2d |
| SEQ ID No. 1328 | CTIIADAITGNTLYETGECAR | 32-52 for the proteins of SEQ No. 1107 | 2d |
| SEQ ID No. 1329 | DAFLK | 251-255 for the proteins of SEQ No. 1256 | 2d |
| SEQ ID No. 1330 | DDFILHGK | 189-196 for the proteins of SEQ No. 1135 | 2d |
| SEQ ID No. 1331 | DDQEVLPYGGK | 92-102 for the proteins of SEQ No. 1137 | 2df |
| SEQ ID No. 1332 | DDVLK | 87-91 for the proteins of SEQ No. 1228 | 2df |
| SEQ ID No. 1333 | DEFHVFR | 90-96 for the proteins of SEQ No. 1113, 1121 | 2d |
| SEQ ID No. 1334 | DEFQIFR | 90-96 for the proteins of SEQ No. 1108, 1125, 1128, 1133, 1173, 1201, 1239, 1246; 79-85 for the protein of sequence SEQ ID No. 1120 | OXA |
| SEQ ID No. 1335 | DEFQVFR | 90-96 for the proteins of SEQ No. 1114, 1127, 1130, 1131, 1242, 1249 | 2d |
| SEQ ID No. 1336 | DELVR | 260-264 for the proteins of SEQ No. 1191 | 2d |
| SEQ ID No. 1337 | DETSR | 112-116 for the proteins of SEQ No. 1139 | 2df |
| SEQ ID No. 1338 | DFDYGNQDFSGDK | 141-153 for the proteins of SEQ No. 1118, 1134; 126-138 for the protein of sequence SEQ ID No. 1119 | 2d |
| SEQ ID No. 1339 | DFTLGEAMQASTVPVYQELAR | 120-140 for the proteins of SEQ No. 1168, 1171, 1216 | 2df |
| SEQ ID No. 1340 | DGNITSVAINIDMLSEADAPK | 250-270 for the proteins of SEQ No. 1140 | 2df |
| SEQ ID No. 1341 | DHDLITAMK | 108-116 for the proteins of SEQ No. 1142, 1243 | 2df |
| SEQ ID No. 1342 | DIAAWNR | 101-107 for the proteins of SEQ No. 1142, 1243 | 2df |
| SEQ ID No. 1343 | DIGEDK | 131-136 for the proteins of SEQ No. 1131 | 2d |
| SEQ ID No. 1344 | DILYIQELAGGWK | 180-192 for the proteins of SEQ No. 1252 | 2de |
| SEQ ID No. 1345 | DITILEK | 181-187 for the proteins of SEQ No. 1135 | 2d |
| SEQ ID No. 1346 | DLLSAK | 166-171 for the proteins of SEQ No. 1256 | 2d |

-continued

| Peptide SEQ ID No. | Amino acid sequence | Position of the peptide in the OXA protein(s) | Clinical interest |
|---|---|---|---|
| SEQ ID No. 1347 | DLMITEAGR | 195-203 for the proteins of SEQ No. 1127, 1130, 1131 | 2d |
| SEQ ID No. 1348 | DLMIVEAGR | 195-203 for the proteins of SEQ No. 1108, 1114, 1125, 1128, 1133, 1173, 1201, 1239, 1246, 1249; 184-192 for the protein of sequence SEQ ID No. 1120 | OXA |
| SEQ ID No. 1349 | DLMIVEAK | 195-202 for the proteins of SEQ No. 1113, 1121 | 2d |
| SEQ ID No. 1350 | DLPLR | 243-247 for the proteins of SEQ No. 1228 | 2df |
| SEQ ID No. 1351 | DLSGNPGK | 131-138 for the proteins of SEQ No. 1105 | 2d |
| SEQ ID No. 1352 | DLSLR | 105-109 for the proteins of SEQ No. 1115, 1116, 1117, 1126, 1141, 1200, 1229, 1262; 106-110 for the protein of sequence SEQ ID No. 1248 | OXA |
| SEQ ID No. 1353 | DLTLR | 105-109 for the proteins of SEQ No. 1110, 1193, 1250, 1259, 1263; 96-100 for the protein of sequence SEQ ID No. 1106; 96-100 for the protein of sequence SEQ ID No. 1111; 96-100 for the protein of sequence SEQ ID No. 1112 | OXA |
| SEQ ID No. 1354 | DMTLGDAIK | 117-125 for the proteins of SEQ No. 1226, 1266 | 2df |
| SEQ ID No. 1355 | DMTLGDAMALSAVPVYQELAR | 118-138 for the proteins of SEQ No. 1205 | 2df |
| SEQ ID No. 1356 | DMTLGDAMK | 117-125 for the proteins of SEQ No. 1147, 1148, 1149, 1152, 1153, 1156, 1157, 1158, 1159, 1161, 1162, 1165, 1166, 1167, 1169, 1170, 1175, 1176, 1178, 1179, 1181, 1183, 1184, 1185, 1186, 1194, 1195, 1196, 1197, 1202, 1209, 1210, 1211, 1212, 1213, 1214, 1215, 1225, 1230, 1231, 1232, 1236, 1237, 1238, 1240, 1241, 1245, 1253, 1260, 1265 | 2df |
| SEQ ID No. 1357 | DMTLGEAMALSAVPVYQDLAR | 118-138 for the proteins of SEQ No. 1224 | 2df |
| SEQ ID No. 1358 | DMTLGEAMALSAVPVYQELAR | 118-138 for the proteins of SEQ No. 1122, 1123, 1129, 1172, 1207, 1264 | 2df |
| SEQ ID No. 1359 | DMTLGEAMK | 116-124 for the proteins of SEQ No. 1124, 1132, 1145, 1198, 1199, 1217, 1218, 1219, 1220, 1221, 1222, 1223, 1244, 1251 | 2df |
| SEQ ID No. 1360 | DMTLGQAMQASAVPVYQELAR | 111-131 for the proteins of SEQ No. 1227 | 2df |
| SEQ ID No. 1361 | DNNGK | 214-218 for the proteins of SEQ No. 1107 | 2d |
| SEQ ID No. 1362 | DQDLR | 110-114 for the proteins of SEQ No. 1108, 1114, 1125, 1127, 1128, 1130, 1131, 1133, 1173, 1201, 1239, 1242, 1246, 1249; 99-103 for the protein of sequence SEQ ID No. 1120 | 2d |
| SEQ ID No. 1363 | DQQIGWFVGWASK | 213-225 for the proteins of SEQ No. 1105 | 2d |
| SEQ ID No. 1364 | DQQIGWFVGWASKPGK | 213-228 for the proteins of SEQ No. 1105 | 2d |
| SEQ ID No. 1365 | DQQVQVYGNDLNR | 53-65 for the proteins of SEQ No. 1227 | 2df |
| SEQ ID No. 1366 | DQSFR | 132-136 for the proteins of SEQ No. 1139 | 2df |

| Peptide SEQ ID No. | Amino acid sequence | Position of the peptide in the OXA protein(s) | Clinical interest |
|---|---|---|---|
| SEQ ID No. 1367 | DQTLESAFK | 105-113 for the proteins of SEQ No. 1228 | 2df |
| SEQ ID No. 1368 | DSCVWYSQVLTQQLGMTR | 98-115 for the proteins of SEQ No. 1252 | 2de |
| SEQ ID No. 1369 | DSIVWYSQELTR | 113-124 for the proteins of SEQ No. 1109 | 2de |
| SEQ ID No. 1370 | DSIVWYSQQLTR | 102-113 for the proteins of SEQ No. 1256 | 2d |
| SEQ ID No. 1371 | DSNLR | 109-113 for the proteins of SEQ No. 1187, 1188, 1235; 96-100 for the protein of sequence SEQ ID No. 1135; 108-112 for the protein of sequence SEQ ID No. 1144 | 2d |
| SEQ ID No. 1372 | DSYIAWGGEAWK | 81-92 for the proteins of SEQ No. 1254, 1255, 1257, 1258 | 2d |
| SEQ ID No. 1373 | DTLNPEWPYK | 67-76 for the proteins of SEQ No. 1252 | 2de |
| SEQ ID No. 1374 | DVDEVFYK | 88-95 for the proteins of SEQ No. 1144, 1187, 1188, 1235 | 2d |
| SEQ ID No. 1375 | DVSGDPGK | 144-151 for the proteins of SEQ No. 1109 | 2de |
| SEQ ID No. 1376 | DWILR | 204-208 for the proteins of SEQ No. 1113, 1121 | 2d |
| SEQ ID No. 1377 | DWPAMAGAWR | 265-274 for the proteins of SEQ No. 1191 | 2d |
| SEQ ID No. 1378 | EAFLR | 256-260 for the proteins of SEQ No. 1254, 1255, 1257, 1258 | 2d |
| SEQ ID No. 1379 | EAIAR | 250-254 for the proteins of SEQ No. 1113, 1121, 1127, 1130, 1131, 1133, 1242 | 2d |
| SEQ ID No. 1380 | EAIVR | 250-254 for the proteins of SEQ No. 1108, 1114, 1125, 1128, 1173, 1201, 1239, 1246, 1249; 239-243 for the protein of sequence SEQ ID No. 1120 | OXA |
| SEQ ID No. 1381 | EAIVTEATPEYIVHSK | 190-205 for the proteins of SEQ No. 1247, 1263 | OXA |
| SEQ ID No. 1382 | EALVTEAAPEYLVHSK | 190-205 for the proteins of SEQ No. 1110, 1115, 1116, 1117, 1126, 1141, 1193, 1200, 1229, 1250, 1259, 1262; 181-196 for the protein of sequence SEQ ID No. 1106; 181-196 for the protein of sequence SEQ ID No. 1111; 181-196 for the protein of sequence SEQ ID No. 1112 | OXA |
| SEQ ID No. 1383 | EALVTEAPEYLVHSK | 191-205 for the proteins of SEQ No. 1248 | 2d |
| SEQ ID No. 1384 | EEIVR | 240-244 for the proteins of SEQ No. 1135 | 2d |
| SEQ ID No. 1385 | EEVLAALPAQLK | 251-262 for the proteins of SEQ No. 1105 | 2d |
| SEQ ID No. 1386 | EFNGSK | 209-214 for the proteins of SEQ No. 1205 | 2df |
| SEQ ID No. 1387 | EFSAEAVNGVFVLCK | 31-45 for the proteins of SEQ No. 1110, 1115, 1116, 1117, 1126, 1141, 1193, 1200, 1229, 1248, 1250, 1259, 1262; 22-36 for the protein of sequence SEQ ID No. 1106; 22-36 for the protein of sequence SEQ ID No. 1111; 22-36 for the protein of sequence SEQ ID No. 1112 | OXA |

-continued

| Peptide SEQ ID No. | Amino acid sequence | Position of the peptide in the OXA protein(s) | Clinical interest |
|---|---|---|---|
| SEQ ID No. 1388 | EFSSESVHGVFVLCK | 31-45 for the proteins of SEQ No. 1247, 1263 | OXA |
| SEQ ID No. 1389 | EGDMAK | 248-253 for the proteins of SEQ No. 1137 | 2df |
| SEQ ID No. 1390 | EGMSGSIR | 254-261 for the proteins of SEQ No. 1122, 1129, 1172, 1207, 1264 | 2df |
| SEQ ID No. 1391 | EGMTGSIR | 254-261 for the proteins of SEQ No. 1123 | 2df |
| SEQ ID No. 1392 | EGSCDK | 54-59 for the proteins of SEQ No. 1109 | 2de |
| SEQ ID No. 1393 | EIAVWNR | 125-131 for the proteins of SEQ No. 1139 | 2df |
| SEQ ID No. 1394 | EIAYK | 262-266 for the proteins of SEQ No. 1238 | 2df |
| SEQ ID No. 1395 | EIFER | 20-24 for the proteins of SEQ No. 1135 | 2d |
| SEQ ID No. 1396 | EIFYHYR | 79-85 for the proteins of SEQ No. 1143 | 2d |
| SEQ ID No. 1397 | EIGDDK | 131-136 for the proteins of SEQ No. 1108, 1125, 1128, 1173, 1201, 1239, 1246; 120-125 for the protein of sequence SEQ ID No. 1120 | OXA |
| SEQ ID No. 1398 | EIGDGK | 131-136 for the proteins of SEQ No. 1133 | 2d |
| SEQ ID No. 1399 | EIGEDK | 131-136 for the proteins of SEQ No. 1114, 1130, 1249 | 2d |
| SEQ ID No. 1400 | EIGEDNAR | 131-138 for the proteins of SEQ No. 1242 | OXA |
| SEQ ID No. 1401 | EIGENK | 131-136 for the proteins of SEQ No. 1113, 1121 | 2d |
| SEQ ID No. 1402 | EIGPK | 153-157 for the proteins of SEQ No. 1139 | 2df |
| SEQ ID No. 1403 | EIGSEIDK | 136-143 for the proteins of SEQ No. 1135 | 2d |
| SEQ ID No. 1404 | EITYK | 262-266 for the proteins of SEQ No. 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1202, 1203, 1204, 1206, 1209, 1210, 1211, 1212, 1213, 1214, 1215, 1225, 1226, 1230, 1231, 1232, 1233, 1236, 1237, 1240, 1241, 1245, 1253, 1260, 1261, 1265, 1266; 263-267 for the protein of sequence SEQ ID No. 1122; 263-267 for the protein of sequence SEQ ID No. 1123; 263-267 for the protein of sequence SEQ ID No. 1129; 263-267 for the protein of sequence SEQ ID No. 1172; 256-260 for the protein of sequence SEQ ID No. 1189; 256-260 for the protein of sequence SEQ ID No. 1190; 263-267 for the protein of sequence SEQ ID No. 1205; 263-267 for the protein of sequence SEQ ID No. 1207; 263-267 for the protein of sequence SEQ ID No. 1224; 263-267 for the protein of sequence SEQ ID No. 1264 | 2df |
| SEQ ID No. 1405 | EITYR | 262-266 for the proteins of SEQ No. 1146 | 2df |

-continued

| Peptide SEQ ID No. | Amino acid sequence | Position of the peptide in the OXA protein(s) | Clinical interest |
|---|---|---|---|
| SEQ ID No. 1406 | EMIYLK | 181-186 for the proteins of SEQ No. 1143 | 2d |
| SEQ ID No. 1407 | EMLYVER | 205-211 for the proteins of SEQ No. 1168, 1171, 1216 | 2df |
| SEQ ID No. 1408 | EMTYK | 262-266 for the proteins of SEQ No. 1197 | 2df |
| SEQ ID No. 1409 | ENIEK | 138-142 for the proteins of SEQ No. 1187, 1188, 1235; 137-141 for the protein of sequence SEQ ID No. 1144 | 2d |
| SEQ ID No. 1410 | ENQLIVK | 183-189 for the proteins of SEQ No. 1110, 1115, 1116, 1117, 1126, 1141, 1193, 1200, 1229, 1250, 1259, 1262; 174-180 for the protein of sequence SEQ ID No. 1106; 174-180 for the protein of sequence SEQ ID No. 1111; 174-180 for the protein of sequence SEQ ID No. 1112; 184-190 for the protein of sequence SEQ ID No. 1248 | OXA |
| SEQ ID No. 1411 | EQAILLFR | 156-163 for the proteins of SEQ No. 1143 | 2d |
| SEQ ID No. 1412 | EQIQFLLR | 165-172 for the proteins of SEQ No. 1107 | 2d |
| SEQ ID No. 1413 | EQLAPDPQVQQQVK | 182-195 for the proteins of SEQ No. 1227 | 2df |
| SEQ ID No. 1414 | EQVDFVQR | 189-196 for the proteins of SEQ No. 1140 | 2df |
| SEQ ID No. 1415 | ETEVYFFAFNMDIDNESK | 229-246 for the proteins of SEQ No. 1110, 1193, 1250, 1259; 220-237 for the protein of sequence SEQ ID No. 1106; 220-237 for the protein of sequence SEQ ID No. 1111; 220-237 for the protein of sequence SEQ ID No. 1112 | OXA |
| SEQ ID No. 1416 | ETTTPR | 90-95 for the proteins of SEQ No. 1105 | 2d |
| SEQ ID No. 1417 | EVGEIR | 126-131 for the proteins of SEQ No. 1247 | 2d |
| SEQ ID No. 1418 | EVGEVR | 126-131 for the proteins of SEQ No. 1110, 1115, 1116, 1117, 1126, 1141, 1193, 1200, 1229, 1250, 1259, 1262; 117-122 for the protein of sequence SEQ ID No. 1106; 117-122 for the protein of sequence SEQ ID No. 1111; 117-122 for the protein of sequence SEQ ID No. 1112; 127-132 for the protein of sequence SEQ ID No. 1248 | OXA |
| SEQ ID No. 1419 | EVNGSK | 209-214 for the proteins of SEQ No. 1122, 1123, 1129, 1172, 1207, 1224, 1264 | 2df |
| SEQ ID No. 1420 | EWQENK | 24-29 for the proteins of SEQ No. 1136, 1208, 1234, 1243 | 2df |
| SEQ ID No. 1421 | EYELYLNVWK | 78-87 for the proteins of SEQ No. 1252 | 2de |
| SEQ ID No. 1422 | EYVPASTFK | 62-70 for the proteins of SEQ No. 1110, 1115, 1116, 1117, 1126, 1141, 1193, 1200, 1229, 1250, 1262; 53-61 for the protein of sequence SEQ ID No. 1106; 53-61 for the protein of sequence SEQ ID No. 1111; 53-61 for the protein of sequence SEQ ID No. 1112; 63-71 for the protein of sequence SEQ ID No. 1248 | OXA |
| SEQ ID No. 1423 | EYLPVSTFK | 62-70 for the proteins of SEQ No. 1259 | 2de |

-continued

| Peptide SEQ ID No. | Amino acid sequence | Position of the peptide in the OXA protein(s) | Clinical interest |
|---|---|---|---|
| SEQ ID No. 1424 | EYNTSGTFVFYDGK | 27-40 for the proteins of SEQ No. 1143 | 2d |
| SEQ ID No. 1425 | EYVPASTFK | 75-83 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 76-84 for the protein of sequence SEQ ID No. 1122; 76-84 for the protein of sequence SEQ ID No. 1123; 74-82 for the protein of sequence SEQ ID No. 1124; 76-84 for the protein of sequence SEQ ID No. 1129; 74-82 for the protein of sequence SEQ ID No. 1132; 74-82 for the protein of sequence SEQ ID No. 1145; 76-84 for the protein of sequence SEQ ID No. 1172; 69-77 for the protein of sequence SEQ ID No. 1189; 69-77 for the protein of sequence SEQ ID No. 1190; 74-82 for the protein of sequence SEQ ID No. 1198; 74-82 for the protein of sequence SEQ ID No. 1199; 76-84 for the protein of sequence SEQ ID No. 1205; 76-84 for the protein of sequence SEQ ID No. 1207; 74-82 for the protein of sequence SEQ ID No. 1217; 74-82 for the protein of sequence SEQ ID No. 1218; 74-82 for the protein of sequence SEQ ID No. 1219; 74-82 for the protein of sequence SEQ ID No. 1220; 74-82 for the protein of sequence SEQ ID No. 1221; 74-82 for the protein of sequence SEQ ID No. 1222; 74-82 for the protein of sequence SEQ ID No. 1223; 76-84 for the protein of sequence SEQ ID No. 1224; 69-77 for the protein of sequence SEQ ID No. 1227; 74-82 for the protein of sequence SEQ ID No. 1244; 74-82 for the protein of sequence SEQ ID No. 1251; 76-84 for the protein of sequence SEQ ID No. 1264 | 2df |
| SEQ ID No. 1426 | FAAYVAGFGYGNGDISGEPGK | 120-140 for the proteins of SEQ No. 1256 | 2d |
| SEQ ID No. 1427 | FAPESTFK | 45-52 for the proteins of SEQ No. 1252 | 2de |
| SEQ ID No. 1428 | FAQYAK | 121-126 for the proteins of SEQ No. 1254, 1255, 1257, 1258 | 2d |
| SEQ ID No. 1429 | FDYGNK | 138-143 for the proteins of SEQ No. 1109 | 2de |
| SEQ ID No. 1430 | FDYGNR | 146-151 for the proteins of SEQ No. 1137; 125-130 for the protein of sequence SEQ ID No. 1105 | 2d |
| SEQ ID No. 1431 | FEDLYK | 232-237 for the proteins of SEQ No. 1143 | 2d |
| SEQ ID No. 1432 | FEDTFHISNQK | 27-37 for the proteins of SEQ No. 1224 | 2df |
| SEQ ID No. 1433 | FEDTFHTSNQQHEK | 27-40 for the proteins of SEQ No. 1205 | 2df |
| SEQ ID No. 1434 | FEYGNQDVSGDSGK | 133-146 for the proteins of SEQ No. 1107 | 2d |
| SEQ ID No. 1435 | FFSDFQAK | 34-41 for the proteins of SEQ No. 1133 | 2d |

-continued

| Peptide SEQ ID No. | Amino acid sequence | Position of the peptide in the OXA protein(s) | Clinical interest |
|---|---|---|---|
| SEQ ID No. 1436 | FFSDLQAEGAIVIADER | 34-50 for the proteins of SEQ No. 1131, 1242 | 2d |
| SEQ ID No. 1437 | FFSDLR | 34-39 for the proteins of SEQ No. 1127, 1130 | OXA |
| SEQ ID No. 1438 | FFSEFQAK | 34-41 for the proteins of SEQ No. 1108, 1114, 1125, 1128, 1173, 1201, 1239, 1246, 1249; 23-30 for the protein of sequence SEQ ID No. 1120 | OXA |
| SEQ ID No. 1439 | FGLEGQLR | 153-160 for the proteins of SEQ No. 1117 | 2de |
| SEQ ID No. 1440 | FILPIFSISILVSLSACSSIK | 4-24 for the proteins of SEQ No. 1122, 1123, 1129, 1172, 1207, 1264 | 2df |
| SEQ ID No. 1441 | FLALLFSAVVLVSLGHAQDK | 5-24 for the proteins of SEQ No. 1121 | 2d |
| SEQ ID No. 1442 | FLALLFSAVVLVSLGHAQEK | 5-24 for the proteins of SEQ No. 1113 | 2d |
| SEQ ID No. 1443 | FLESLYLNNLPASK | 169-182 for the proteins of SEQ No. 1247, 1263 | OXA |
| SEQ ID No. 1444 | FLLEGQLR | 153-160 for the proteins of SEQ No. 1200 | 2de |
| SEQ ID No. 1445 | FQQYVDR | 118-124 for the proteins of SEQ No. 1105 | 2d |
| SEQ ID No. 1446 | FSDYVQR | 131-137 for the proteins of SEQ No. 1109 | 2de |
| SEQ ID No. 1447 | FSTASTFK | 63-70 for the proteins of SEQ No. 1228 | 2df |
| SEQ ID No. 1448 | FSWDGK | 117-122 for the proteins of SEQ No. 1139 | 2df |
| SEQ ID No. 1449 | FSYGNQNISGGIDK | 139-152 for the proteins of SEQ No. 1110, 1115, 1116, 1117, 1126, 1141, 1193, 1200, 1259, 1262; 130-143 for the protein of sequence SEQ ID No. 1106; 130-143 for the protein of sequence SEQ ID No. 1111; 130-143 for the protein of sequence SEQ ID No. 1112; 140-153 for the protein of sequence SEQ ID No. 1248 | OXA |
| SEQ ID No. 1450 | FSYGNQNISGGTDK | 139-152 for the proteins of SEQ No. 1229 | 2de |
| SEQ ID No. 1451 | FSYGSQNISGGIDK | 139-152 for the proteins of SEQ No. 1250 | 2de |
| SEQ ID No. 1452 | FTEYVK | 126-131 for the proteins of SEQ No. 1107 | 2d |
| SEQ ID No. 1453 | FVAHK | 173-177 for the proteins of SEQ No. 1107 | 2d |
| SEQ ID No. 1454 | FVPASTYK | 62-69 for the proteins of SEQ No. 1138 | 2d |
| SEQ ID No. 1455 | FVYDLAQGQLPFK | 184-196 for the proteins of SEQ No. 1168, 1171, 1216 | 2df |
| SEQ ID No. 1456 | FVYDLAQGQLPFKPEVQQQVK | 184-204 for the proteins of SEQ No. 1168, 1171, 1216 | 2df |
| SEQ ID No. 1457 | FWLEDQLR | 153-160 for the proteins of SEQ No. 1116, 1193, 1229, 1250; 144-151 for the protein of sequence SEQ ID No. 1106; 144-151 for the protein of sequence SEQ ID No. 1111 | 2de |

-continued

| Peptide SEQ ID No. | Amino acid sequence | Position of the peptide in the OXA protein(s) | Clinical interest |
|---|---|---|---|
| SEQ ID No. 1458 | FWLEGPLK | 144-151 for the proteins of SEQ No. 1135 | 2d |
| SEQ ID No. 1459 | FWLEGQLR | 153-160 for the proteins of SEQ No. 1110, 1115, 1126, 1141, 1247, 1259, 1262, 1263; 144-151 for the protein of sequence SEQ ID No. 1112; 154-161 for the protein of sequence SEQ ID No. 1248 | OXA |
| SEQ ID No. 1460 | FYPASSFK | 53-60 for the proteins of SEQ No. 1135 | 2d |
| SEQ ID No. 1461 | FYPASTFK | 66-73 for the proteins of SEQ No. 1144, 1187, 1188, 1235 | 2d |
| SEQ ID No. 1462 | GACDK | 44-48 for the proteins of SEQ No. 1256 | 2d |
| SEQ ID No. 1463 | GAEVYFFAFNMDIDNENK | 229-246 for the proteins of SEQ No. 1141, 1248 | 2d |
| SEQ ID No. 1464 | GAIQVSAVPVFQQIAR | 110-125 for the proteins of SEQ No. 1110, 1115, 1116, 1117, 1126, 1141, 1193, 1200, 1229, 1247, 1250, 1259, 1262, 1263; 101-116 for the protein of sequence SEQ ID No. 1106; 101-116 for the protein of sequence SEQ ID No. 1112; 111-126 for the protein of sequence SEQ ID No. 1248 | OXA |
| SEQ ID No. 1465 | GAIQVSAVPVFQQITR | 101-116 for the proteins of SEQ No. 1111 | 2de |
| SEQ ID No. 1466 | GDYWIDGNLEISAHEQISFLR | 156-176 for the proteins of SEQ No. 1127, 1130 | OXA |
| SEQ ID No. 1467 | GDYWIDGNLK | 156-165 for the proteins of SEQ No. 1131 | 2d |
| SEQ ID No. 1468 | GELPVSEDALEMTK | 181-194 for the proteins of SEQ No. 1109 | 2de |
| SEQ ID No. 1469 | GEQPAGPAAR | 241-250 for the proteins of SEQ No. 1256; 252-261 for the protein of sequence SEQ ID No. 1109 | OXA |
| SEQ ID No. 1470 | GFAGHNQDQDLR | 103-114 for the proteins of SEQ No. 1108, 1125, 1128, 1173, 1201, 1239, 1246; 92-103 for the protein of sequence SEQ ID No. 1120 | OXA |
| SEQ ID No. 1471 | GIPSSVR | 254-260 for the proteins of SEQ No. 1147, 1148, 1149, 1150, 1151, 1152, 1153, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 248-254 for the protein of sequence SEQ ID No. 1189; 248-254 for the protein of sequence SEQ ID No. 1190 | 2df |
| SEQ ID No. 1472 | GISSSVR | 254-260 for the proteins of SEQ No. 1146 | 2df |
| SEQ ID No. 1473 | GLNGTFVVYDLK | 26-37 for the proteins of SEQ No. 1135 | 2d |
| SEQ ID No. 1474 | GMEIWNSNHTPK | 101-112 for the proteins of SEQ No. 1118, 1134; 86-97 for the protein of sequence SEQ ID No. 1119 | 2d |
| SEQ ID No. 1475 | GNQTLVFAR | 230-238 for the proteins of SEQ No. 1254 | 2d |

-continued

| Peptide SEQ ID No. | Amino acid sequence | Position of the peptide in the OXA protein(s) | Clinical interest |
|---|---|---|---|
| SEQ ID No. 1476 | GNYWIDGNLEISAHEQISFLR | 156-176 for the proteins of SEQ No. 1242 | OXA |
| SEQ ID No. 1477 | GPLEISAFEEAR | 164-175 for the proteins of SEQ No. 1137 | 2df |
| SEQ ID No. 1478 | GPLTITPIQEVK | 172-183 for the proteins of SEQ No. 1168, 1171, 1216 | 2df |
| SEQ ID No. 1479 | GSGWFVGWIVR | 219-229 for the proteins of SEQ No. 1254, 1255, 1257, 1258 | 2d |
| SEQ ID No. 1480 | GSLLLWDQK | 66-74 for the proteins of SEQ No. 1139 | 2df |
| SEQ ID No. 1481 | GTEVYFFAFNMDIDNENK | 229-246 for the proteins of SEQ No. 1115, 1116, 1117, 1126, 1200, 1229, 1262 | OXA |
| SEQ ID No. 1482 | GTEVYFFAFNMDIDNESK | 229-246 for the proteins of SEQ No. 1247, 1263 | OXA |
| SEQ ID No. 1483 | GTFVLYDVQR | 38-47 for the proteins of SEQ No. 1138 | 2d |
| SEQ ID No. 1484 | GTIVVADER | 42-50 for the proteins of SEQ No. 1108, 1114, 1125, 1128, 1133, 1173, 1201, 1239, 1246, 1249; 31-39 for the protein of sequence SEQ ID No. 1120 | OXA |
| SEQ ID No. 1485 | GTIVVLDAR | 63-71 for the proteins of SEQ No. 1140 | 2df |
| SEQ ID No. 1486 | GTIVVVDER | 42-50 for the proteins of SEQ No. 1113, 1121 | 2d |
| SEQ ID No. 1487 | GTLPFSAR | 200-207 for the proteins of SEQ No. 1140 | 2df |
| SEQ ID No. 1488 | GTPSSVR | 254-260 for the proteins of SEQ No. 1154 | 2df |
| SEQ ID No. 1489 | HALSSAFVLLGCIAASAHAK | 5-24 for the proteins of SEQ No. 1254, 1255, 1257, 1258 | 2d |
| SEQ ID No. 1490 | HIADSK | 234-239 for the proteins of SEQ No. 1252 | 2de |
| SEQ ID No. 1491 | HNGLTHAWLASSLK | 152-165 for the proteins of SEQ No. 1109 | 2de |
| SEQ ID No. 1492 | HNGLTQSWLMSSLTISPK | 147-164 for the proteins of SEQ No. 1107 | 2d |
| SEQ ID No. 1493 | HNGTDGAWIISSLR | 148-161 for the proteins of SEQ No. 1191 | 2d |
| SEQ ID No. 1494 | HTLSVFDQER | 54-63 for the proteins of SEQ No. 1131 | 2d |
| SEQ ID No. 1495 | HVTFASFR | 241-248 for the proteins of SEQ No. 1252 | 2de |
| SEQ ID No. 1496 | IAISLMGYDAGFLR | 57-70 for the proteins of SEQ No. 1254, 1255, 1257, 1258 | 2d |
| SEQ ID No. 1497 | IALSLMAFDAEIIDQK | 75-90 for the proteins of SEQ No. 1118, 1134; 60-75 for the protein of sequence SEQ ID No. 1119 | 2d |
| SEQ ID No. 1498 | IALSLMGFDSGILK | 53-66 for the proteins of SEQ No. 1252 | 2de |
| SEQ ID No. 1499 | IANALIGLENHK | 87-98 for the proteins of SEQ No. 1168, 1171, 1216 | 2df |

-continued

| Peptide SEQ ID No. | Amino acid sequence | Position of the peptide in the OXA protein(s) | Clinical interest |
|---|---|---|---|
| SEQ ID No. 1500 | IAWIVGFVYLK | 205-215 for the proteins of SEQ No. 1143 | 2d |
| SEQ ID No. 1501 | IDTFWLDNSLK | 141-151 for the proteins of SEQ No. 1143 | 2d |
| SEQ ID No. 1502 | IDYYNLDR | 41-48 for the proteins of SEQ No. 1135 | 2d |
| SEQ ID No. 1503 | IFNALIALDSGVIK | 62-75 for the proteins of SEQ No. 1143 | 2d |
| SEQ ID No. 1504 | IFNSLLALDSGALDNER | 95-111 for the proteins of SEQ No. 1140 | 2df |
| SEQ ID No. 1505 | IFNTLIGLENGIVK | 61-74 for the proteins of SEQ No. 1135 | 2d |
| SEQ ID No. 1506 | IGLDLMQK | 138-145 for the proteins of SEQ No. 1124, 1132, 1145, 1198, 1199, 1217, 1218, 1219, 1220, 1221, 1222, 1223, 1244, 1251 | 2df |
| SEQ ID No. 1507 | IGLEK | 131-135 for the proteins of SEQ No. 1235 | OXA |
| SEQ ID No. 1508 | IGLELMQQEVQR | 133-144 for the proteins of SEQ No. 1227 | 2df |
| SEQ ID No. 1509 | IGLELMSK | 139-146 for the proteins of SEQ No. 1147, 1148, 1149, 1151, 1153, 1156, 1157, 1158, 1159, 1160, 1161, 1162, 1166, 1167, 1169, 1170, 1175, 1177, 1178, 1179, 1180, 1181, 1182, 1183, 1184, 1185, 1186, 1194, 1195, 1196, 1197, 1209, 1210, 1211, 1212, 1213, 1214, 1215, 1225, 1226, 1230, 1231, 1232, 1236, 1237, 1238, 1240, 1241, 1245, 1253, 1260, 1266 | 2df |
| SEQ ID No. 1510 | IGLELMSNEVK | 139-149 for the proteins of SEQ No. 1146, 1150, 1152, 1154, 1155, 1163, 1164, 1165, 1174, 1176, 1192, 1202, 1203, 1204, 1206, 1233, 1261, 1265; 133-143 for the protein of sequence SEQ ID No. 1189; 133-143 for the protein of sequence SEQ ID No. 1190 | 2df |
| SEQ ID No. 1511 | IGLER | 126-130 for the proteins of SEQ No. 1138 | 2d |
| SEQ ID No. 1512 | IGLNK | 130-134 for the proteins of SEQ No. 1118, 1134; 115-119 for the protein of sequence SEQ ID No. 1119 | 2d |
| SEQ ID No. 1513 | IGLNLMQK | 140-147 for the proteins of SEQ No. 1224 | 2df |
| SEQ ID No. 1514 | IGPSLMQSELQR | 142-153 for the proteins of SEQ No. 1168, 1171, 1216 | 2df |
| SEQ ID No. 1515 | IGYGNMQIGTEVDQFWLK | 154-171 for the proteins of SEQ No. 1171, 1216 | 2df |
| SEQ ID No. 1516 | IGYGNMQMGTEVDQFWLK | 154-171 for the proteins of SEQ No. 1168 | 2df |
| SEQ ID No. 1517 | IINHNLPVK | 167-175 for the proteins of SEQ No. 1119; 182-190 for the protein of sequence SEQ ID No. 1118 | 2d |
| SEQ ID No. 1518 | IINHNLPVR | 182-190 for the proteins of SEQ No. 1134 | 2d |
| SEQ ID No. 1519 | ILFQQGTQQACAER | 41-54 for the proteins of SEQ No. 1191 | 2d |

-continued

| Peptide SEQ ID No. | Amino acid sequence | Position of the peptide in the OXA protein(s) | Clinical interest |
|---|---|---|---|
| SEQ ID No. 1520 | ILNNWFK | 20-26 for the proteins of SEQ No. 1143 | 2d |
| SEQ ID No. 1521 | ILNTLISLEEK | 71-81 for the proteins of SEQ No. 1228 | 2df |
| SEQ ID No. 1522 | ILSLVCLSISIGACAEHSMSR | 6-26 for the proteins of SEQ No. 1168, 1171, 1216 | 2df |
| SEQ ID No. 1523 | INESR | 219-223 for the proteins of SEQ No. 1107 | 2d |
| SEQ ID No. 1524 | INIVK | 255-259 for the proteins of SEQ No. 1187, 1188, 1235; 254-258 for the protein of sequence SEQ ID No. 1144 | 2d |
| SEQ ID No. 1525 | INLYGNALSR | 61-70 for the proteins of SEQ No. 1124, 1132, 1145, 1198, 1199, 1217, 1218, 1219, 1220, 1221, 1222, 1223, 1244, 1251 | 2df |
| SEQ ID No. 1526 | IPFSLNLEMK | 244-253 for the proteins of SEQ No. 1122, 1123, 1129, 1172, 1207, 1264 | 2df |
| SEQ ID No. 1527 | IPHTLFALDADAVR | 76-89 for the proteins of SEQ No. 1131 | 2d |
| SEQ ID No. 1528 | IPHTLFALDAGAAR | 76-89 for the proteins of SEQ No. 1114, 1249 | 2d |
| SEQ ID No. 1529 | IPHTLFALDAGAVR | 76-89 for the proteins of SEQ No. 1108, 1113, 1121, 1125, 1128, 1133, 1173, 1201, 1239, 1246; 65-78 for the protein of sequence SEQ ID No. 1120 | OXA |
| SEQ ID No. 1530 | IPLGK | 255-259 for the proteins of SEQ No. 1137 | 2df |
| SEQ ID No. 1531 | IPNAIIGLETGVIK | 71-84 for the proteins of SEQ No. 1110, 1116, 1117, 1126, 1141, 1200, 1229, 1250, 1262; 62-75 for the protein of sequence SEQ ID No. 1106; 62-75 for the protein of sequence SEQ ID No. 1111; 72-85 for the protein of sequence SEQ ID No. 1248 | OXA |
| SEQ ID No. 1532 | IPNALIGLETGAIK | 71-84 for the proteins of SEQ No. 1247, 1263 | OXA |
| SEQ ID No. 1533 | IPNSLIAFDTGAVR | 78-91 for the proteins of SEQ No. 1137 | 2df |
| SEQ ID No. 1534 | IPSAIIGLETGVIK | 71-84 for the proteins of SEQ No. 1115, 1193, 1259; 62-75 for the protein of sequence SEQ ID No. 1112 | 2de |
| SEQ ID No. 1535 | ISAFNQVK | 161-168 for the proteins of SEQ No. 1247 | 2d |
| SEQ ID No. 1536 | ISAHEQILFLR | 166-176 for the proteins of SEQ No. 1131 | 2d |
| SEQ ID No. 1537 | ISAMEQTR | 160-167 for the proteins of SEQ No. 1138 | 2d |
| SEQ ID No. 1538 | ISAMEQVK | 165-172 for the proteins of SEQ No. 1187, 1235; 152-159 for the protein of sequence SEQ ID No. 1135; 164-171 for the protein of sequence SEQ ID No. 1144 | 2d |
| SEQ ID No. 1539 | ISATEQVAFLR | 164-174 for the proteins of SEQ No. 1142 | 2df |
| SEQ ID No. 1540 | ISATQQIAFLR | 164-174 for the proteins of SEQ No. 1243 | 2df |

-continued

| Peptide SEQ ID No. | Amino acid sequence | Position of the peptide in the OXA protein(s) | Clinical interest |
|---|---|---|---|
| SEQ ID No. 1541 | ISAVNQVEFLESLFLNK | 161-177 for the proteins of SEQ No. 1115, 1116, 1117, 1126, 1141, 1200, 1229, 1262; 162-178 for the protein of sequence SEQ ID No. 1248 | OXA |
| SEQ ID No. 1542 | ISAVNQVEFLESLYLNK | 161-177 for the proteins of SEQ No. 1110, 1193, 1250, 1259; 152-168 for the protein of sequence SEQ ID No. 1106; 152-168 for the protein of sequence SEQ ID No. 1111; 152-168 for the protein of sequence SEQ ID No. 1112 | OXA |
| SEQ ID No. 1543 | ISAVNQVK | 161-168 for the proteins of SEQ No. 1263 | 2de |
| SEQ ID No. 1544 | ISPEEQIQFLR | 170-180 for the proteins of SEQ No. 1118, 1134; 155-165 for the protein of sequence SEQ ID No. 1119 | 2d |
| SEQ ID No. 1545 | ISPEEQVR | 166-173 for the proteins of SEQ No. 1109 | 2de |
| SEQ ID No. 1546 | ISPEGQVR | 155-162 for the proteins of SEQ No. 1256 | 2d |
| SEQ ID No. 1547 | ISPLEQLAFLR | 162-172 for the proteins of SEQ No. 1191 | 2d |
| SEQ ID No. 1548 | ITAFQQVDFLR | 188-198 for the proteins of SEQ No. 1139 | 2df |
| SEQ ID No. 1549 | ITLFLLFLNLVFGQDK | 4-19 for the proteins of SEQ No. 1143 | 2d |
| SEQ ID No. 1550 | ITPIQEVNFADDFANNR | 174-190 for the proteins of SEQ No. 1205 | 2df |
| SEQ ID No. 1551 | ITPIQEVNFADDLANNR | 174-190 for the proteins of SEQ No. 1224 | 2df |
| SEQ ID No. 1552 | ITPQQEAQFAYK | 173-184 for the proteins of SEQ No. 1146, 1147, 1148, 1149, 1150, 1151, 1152, 1153, 1154, 1155, 1156, 1157, 1158, 1159, 1160, 1161, 1162, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 167-178 for the protein of sequence SEQ ID No. 1189; 167-178 for the protein of sequence SEQ ID No. 1190 | 2df |
| SEQ ID No. 1553 | ITPQQEAQFTYK | 173-184 for the proteins of SEQ No. 1163 | 2df |
| SEQ ID No. 1554 | ITPVQEVNFADDLAHNR | 174-190 for the proteins of SEQ No. 1122, 1123, 1129, 1172, 1207, 1264 | 2df |
| SEQ ID No. 1555 | IVAFALK | 241-247 for the proteins of SEQ No. 1124, 1145 | 2df |
| SEQ ID No. 1556 | IVAFALNMEMR | 241-251 for the proteins of SEQ No. 1198, 1217, 1218, 1219, 1220, 1221, 1222, 1223, 1244, 1251; 242-252 for the protein of sequence SEQ ID No. 1132; 242-252 for the protein of sequence SEQ ID No. 1199 | 2df |
| SEQ ID No. 1557 | IVESTTLADGTVVHGK | 186-201 for the proteins of SEQ No. 1254, 1255, 1257, 1258 | 2d |
| SEQ ID No. 1558 | IYNSLIGLNEK | 74-84 for the proteins of SEQ No. 1144, 1187, 1188, 1235 | 2d |

-continued

| Peptide SEQ ID No. | Amino acid sequence | Position of the peptide in the OXA protein(s) | Clinical interest |
|---|---|---|---|
| SEQ ID No. 1559 | KPDIGWWVGWIER | 237-249 for the proteins of SEQ No. 1140 | 2df |
| SEQ ID No. 1560 | LACATNNLAR | 50-59 for the proteins of SEQ No. 1248 | 2d |
| SEQ ID No. 1561 | LAQGELPFPAPVQSTVR | 172-188 for the proteins of SEQ No. 1138 | 2d |
| SEQ ID No. 1562 | LAQNELPYPIEIQK | 177-190 for the proteins of SEQ No. 1187, 1188, 1235 | 2d |
| SEQ ID No. 1563 | LAQNELQYPIEIQK | 176-189 for the proteins of SEQ No. 1144 | 2d |
| SEQ ID No. 1564 | LDFGNK | 143-148 for the proteins of SEQ No. 1187, 1188, 1235; 142-147 for the protein of sequence SEQ ID No. 1144 | 2d |
| SEQ ID No. 1565 | LDGSLNR | 206-212 for the proteins of SEQ No. 1105 | 2d |
| SEQ ID No. 1566 | LEIGK | 244-248 for the proteins of SEQ No. 1107 | 2d |
| SEQ ID No. 1567 | LEILQQALAELGLYPK | 255-270 for the proteins of SEQ No. 1227 | 2df |
| SEQ ID No. 1568 | LENQEQVK | 173-180 for the proteins of SEQ No. 1135 | 2d |
| SEQ ID No. 1569 | LETQEEVEK | 195-203 for the proteins of SEQ No. 1122 | 2df |
| SEQ ID No. 1570 | LETQEEVK | 195-202 for the proteins of SEQ No. 1123, 1129, 1172, 1205, 1207, 1224, 1264 | 2df |
| SEQ ID No. 1571 | LFAAEGVK | 55-62 for the proteins of SEQ No. 1140 | 2df |
| SEQ ID No. 1572 | LFESAGVK | 58-65 for the proteins of SEQ No. 1139 | 2df |
| SEQ ID No. 1573 | LFGAAGVK | 30-37 for the proteins of SEQ No. 1138 | 2d |
| SEQ ID No. 1574 | LFPEWEK | 110-116 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 104-110 for the protein of sequence SEQ ID No. 1189; 104-110 for the protein of sequence SEQ ID No. 1190 | 2df |
| SEQ ID No. 1575 | LGESR | 126-130 for the proteins of SEQ No. 1109 | 2de |
| SEQ ID No. 1576 | LGVDR | 121-125 for the proteins of SEQ No. 1107 | 2d |
| SEQ ID No. 1577 | LHVSER | 181-186 for the proteins of SEQ No. 1136, 1142, 1208, 1234, 1243 | 2df |
| SEQ ID No. 1578 | LHYGNAK | 131-137 for the proteins of SEQ No. 1143 | 2d |
| SEQ ID No. 1579 | LLNLLSQSK | 160-168 for the proteins of SEQ No. 1135 | 2d |

-continued

| Peptide SEQ ID No. | Amino acid sequence | Position of the peptide in the OXA protein(s) | Clinical interest |
|---|---|---|---|
| SEQ ID No. 1580 | LLQDER | 243-248 for the proteins of SEQ No. 1191 | 2d |
| SEQ ID No. 1581 | LLVQDGDCGR | 38-47 for the proteins of SEQ No. 1254, 1255, 1257, 1258 | 2d |
| SEQ ID No. 1582 | LNEVGYGNR | 160-168 for the proteins of SEQ No. 1140 | 2df |
| SEQ ID No. 1583 | LNYGNADPSTK | 144-154 for the proteins of SEQ No. 1113, 1121 | 2d |
| SEQ ID No. 1584 | LNYGNK | 130-135 for the proteins of SEQ No. 1135 | 2d |
| SEQ ID No. 1585 | LPASK | 178-182 for the proteins of SEQ No. 1247, 1263; 172-176 for the protein of sequence SEQ ID No. 1256 | 2d |
| SEQ ID No. 1586 | LPHTLFALDADAVR | 76-89 for the proteins of SEQ No. 1127, 1130 | OXA |
| SEQ ID No. 1587 | LPHTLFALDAGAVR | 76-89 for the proteins of SEQ No. 1242 | OXA |
| SEQ ID No. 1588 | LPLAIMGFDSGILQSPK | 62-78 for the proteins of SEQ No. 1107 | 2d |
| SEQ ID No. 1589 | LPLAIMGYDADILLDATTPR | 69-88 for the proteins of SEQ No. 1109 | 2de |
| SEQ ID No. 1590 | LPSSLIALETGAVR | 98-111 for the proteins of SEQ No. 1139 | 2df |
| SEQ ID No. 1591 | LPVSAQTLQYTANILK | 170-185 for the proteins of SEQ No. 1105 | 2d |
| SEQ ID No. 1592 | LPVSER | 205-210 for the proteins of SEQ No. 1139 | 2df |
| SEQ ID No. 1593 | LPVSPTAVDMTER | 173-185 for the proteins of SEQ No. 1254, 1255, 1257, 1258 | 2d |
| SEQ ID No. 1594 | LSASK | 178-182 for the proteins of SEQ No. 1110, 1115, 1116, 1117, 1126, 1141, 1193, 1200, 1229, 1250, 1259, 1262; 169-173 for the protein of sequence SEQ ID No. 1106; 169-173 for the protein of sequence SEQ ID No. 1111; 169-173 for the protein of sequence SEQ ID No. 1112; 179-183 for the protein of sequence SEQ ID No. 1248 | OXA |
| SEQ ID No. 1595 | LSAVPIYQEVAR | 121-132 for the proteins of SEQ No. 1137 | 2df |
| SEQ ID No. 1596 | LSAVPVYQELAR | 127-138 for the proteins of SEQ No. 1122, 1123, 1129, 1172, 1205, 1207, 1264; 125-136 for the protein of sequence SEQ ID No. 1124; 125-136 for the protein of sequence SEQ ID No. 1132; 125-136 for the protein of sequence SEQ ID No. 1145; 125-136 for the protein of sequence SEQ ID No. 1198; 125-136 for the protein of sequence SEQ ID No. 1199; 125-136 for the protein of sequence SEQ ID No. 1217; 125-136 for the protein of sequence SEQ ID No. 1218; 125-136 for the protein of sequence SEQ ID No. 1219; 125-136 for the protein of sequence SEQ ID No. 1220; 125-136 for the protein of sequence SEQ ID No. 1221; 125-136 for the protein of sequence SEQ ID No. 1222; 125-136 for the protein of sequence SEQ ID No. 1223; 125-136 for the protein of sequence SEQ ID No. 1244; 125-136 for the protein of sequence SEQ ID No. 1251 | 2df |

-continued

| Peptide SEQ ID No. | Amino acid sequence | Position of the peptide in the OXA protein(s) | Clinical interest |
|---|---|---|---|
| SEQ ID No. 1597 | LSCTLVIDEASGDLLHR | 37-53 for the proteins of SEQ No. 1109 | 2de |
| SEQ ID No. 1598 | LSLQHGWFIGWIEK | 211-224 for the proteins of SEQ No. 1252 | 2de |
| SEQ ID No. 1599 | LSQNSLPFSQEAMNSVK | 164-180 for the proteins of SEQ No. 1143 | 2d |
| SEQ ID No. 1600 | LSVNPK | 168-173 for the proteins of SEQ No. 1252 | 2de |
| SEQ ID No. 1601 | LTQDER | 239-244 for the proteins of SEQ No. 1254, 1255, 1257, 1258 | 2d |
| SEQ ID No. 1602 | LTVGAR | 245-250 for the proteins of SEQ No. 1109 | 2de |
| SEQ ID No. 1603 | LYGFALNIDMPGGEADIGK | 228-246 for the proteins of SEQ No. 1138 | 2d |
| SEQ ID No. 1604 | LYHNELPFR | 178-186 for the proteins of SEQ No. 1114, 1249 | 2d |
| SEQ ID No. 1605 | LYHNK | 176-180 for the proteins of SEQ No. 1136, 1142, 1208, 1234, 1243 | 2df |
| SEQ ID No. 1606 | LYQNDLPFR | 178-186 for the proteins of SEQ No. 1133 | 2d |
| SEQ ID No. 1607 | MDDLFK | 243-248 for the proteins of SEQ No. 1108, 1114, 1125, 1128, 1133, 1173, 1201, 1239, 1246, 1249; 232-237 for the protein of sequence SEQ ID No. 1120 | OXA |
| SEQ ID No. 1608 | MEDLHK | 243-248 for the proteins of SEQ No. 1113, 1121 | 2d |
| SEQ ID No. 1609 | MLIALIGLENHK | 85-96 for the proteins of SEQ No. 1264 | 2df |
| SEQ ID No. 1610 | MLLIEQQGDAALYAK | 198-212 for the proteins of SEQ No. 1137 | 2df |
| SEQ ID No. 1611 | MLLIK | 204-208 for the proteins of SEQ No. 1122, 1123, 1129, 1172, 1205, 1207, 1224, 1264 | 2df |
| SEQ ID No. 1612 | MLNALIGLEHHK | 84-95 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1166, 1167, 1169, 1170, 1174, 1175, 1176, 1177, 1178, 1179, 1180, 1181, 1182, 1183, 1184, 1185, 1186, 1192, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1245, 1253, 1260, 1261, 1265, 1266; 78-89 for the protein of sequence SEQ ID No. 1189; 78-89 for the protein of sequence SEQ ID No. 1190 | 2df |
| SEQ ID No. 1613 | MLNALIGLENHK | 85-96 for the proteins of SEQ No. 1122, 1123, 1129, 1172, 1205, 1207, 1224 | 2df |
| SEQ ID No. 1614 | MLNALIGLENQK | 83-94 for the proteins of SEQ No. 1124, 1132, 1145, 1198, 1199, 1217, 1218, 1219, 1220, 1221, 1222, 1223, 1244, 1251 | 2df |
| SEQ ID No. 1615 | MLNALIGLEYHK | 84-95 for the proteins of SEQ No. 1241 | 2df |
| SEQ ID No. 1616 | MLNALIGLQHGK | 78-89 for the proteins of SEQ No. 1227 | 2df |

-continued

| Peptide SEQ ID No. | Amino acid sequence | Position of the peptide in the OXA protein(s) | Clinical interest |
|---|---|---|---|
| SEQ ID No. 1617 | MLNALISLEHHK | 84-95 for the proteins of SEQ No. 1165 | 2df |
| SEQ ID No. 1618 | MQAYVDAFDYGNR | 139-151 for the proteins of SEQ No. 1137 | 2df |
| SEQ ID No. 1619 | MQEGLNK | 123-129 for the proteins of SEQ No. 1135 | 2d |
| SEQ ID No. 1620 | MSPASTYK | 87-94 for the proteins of SEQ No. 1140 | 2df |
| SEQ ID No. 1621 | MTAGGK | 234-239 for the proteins of SEQ No. 1256 | 2d |
| SEQ ID No. 1622 | MVSGK | 165-169 for the proteins of SEQ No. 1105 | 2d |
| SEQ ID No. 1623 | NEHDPVLPYR | 71-80 for the proteins of SEQ No. 1254, 1255, 1257, 1258 | 2d |
| SEQ ID No. 1624 | NEHQIFK | 86-92 for the proteins of SEQ No. 1248; 85-91 for the protein of sequence SEQ ID No. 1141 | 2d |
| SEQ ID No. 1625 | NEHQVFK | 85-91 for the proteins of SEQ No. 1110, 1115, 1116, 1117, 1126, 1193, 1200, 1229, 1250, 1259, 1262; 76-82 for the protein of sequence SEQ ID No. 1106; 76-82 for the protein of sequence SEQ ID No. 1111; 76-82 for the protein of sequence SEQ ID No. 1112 | OXA |
| SEQ ID No. 1626 | NEITYK | 262-267 for the proteins of SEQ No. 1122, 1123, 1129, 1172, 1205, 1207, 1224, 1264 | 2df |
| SEQ ID No. 1627 | NELLMK | 260-265 for the proteins of SEQ No. 1124, 1145, 1198, 1217, 1218, 1220, 1221, 1222, 1223, 1244, 1251; 261-266 for the protein of sequence SEQ ID No. 1132; 261-266 for the protein of sequence SEQ ID No. 1199 | 2df |
| SEQ ID No. 1628 | NELMMK | 260-265 for the proteins of SEQ No. 1219 | 2df |
| SEQ ID No. 1629 | NELPFR | 181-186 for the proteins of SEQ No. 1108, 1113, 1114, 1121, 1125, 1128, 1173, 1201, 1239, 1246, 1249; 170-175 for the protein of sequence SEQ ID No. 1120 | OXA |
| SEQ ID No. 1630 | NFILIFIFVILISCK | 5-19 for the proteins of SEQ No. 1144, 1187, 1235 | 2d |
| SEQ ID No. 1631 | NFILIFIFVILTSCK | 5-19 for the proteins of SEQ No. 1188 | 2d |
| SEQ ID No. 1632 | NISSYGNNLVR | 62-72 for the proteins of SEQ No. 1224 | 2df |
| SEQ ID No. 1633 | NISTYGNNLTR | 62-72 for the proteins of SEQ No. 1205 | 2df |
| SEQ ID No. 1634 | NLFNEVHTTGVLVIR | 43-57 for the proteins of SEQ No. 1170 | 2df |
| SEQ ID No. 1635 | NLSTYGNALAR | 62-72 for the proteins of SEQ No. 1122, 1123, 1129, 1172, 1207, 1264 | 2df |
| SEQ ID No. 1636 | NMENLELFGK | 187-196 for the proteins of SEQ No. 1143 | 2d |
| SEQ ID No. 1637 | NMLLLEENNGYK | 201-212 for the proteins of SEQ No. 1198 | 2df |
| SEQ ID No. 1638 | NMLLLEESNGYK | 201-212 for the proteins of SEQ No. 1124, 1132, 1145, 1199, 1217, 1218, 1219, 1220, 1221, 1223, 1244, 1251 | 2df |

-continued

| Peptide SEQ ID No. | Amino acid sequence | Position of the peptide in the OXA protein(s) | Clinical interest |
|---|---|---|---|
| SEQ ID No. 1639 | NMLLLEK | 201-207 for the proteins of SEQ No. 1222 | 2df |
| SEQ ID No. 1640 | NMTLGDAMK | 117-125 for the proteins of SEQ No. 1146, 1150, 1151, 1154, 1155, 1160, 1163, 1164, 1174, 1177, 1180, 1182, 1192, 1203, 1204, 1206, 1233, 1261; 111-119 for the protein of sequence SEQ ID No. 1189; 111-119 for the protein of sequence SEQ ID No. 1190 | 2df |
| SEQ ID No. 1641 | NNGLTEAWLESSLK | 156-169 for the proteins of SEQ No. 1118, 1134; 141-154 for the protein of sequence SEQ ID No. 1119 | 2d |
| SEQ ID No. 1642 | NQLPFK | 181-186 for the proteins of SEQ No. 1131 | 2d |
| SEQ ID No. 1643 | NQLPFQVEHQR | 181-191 for the proteins of SEQ No. 1127, 1130, 1242 | OXA |
| SEQ ID No. 1644 | NSAIENTIDNMYLQDLENSTK | 191-211 for the proteins of SEQ No. 1134 | 2d |
| SEQ ID No. 1645 | NSAIENTIENMYLQDLDNSTK | 191-211 for the proteins of SEQ No. 1118 | 2d |
| SEQ ID No. 1646 | NSAIENTIENMYLQDLENSTK | 176-196 for the proteins of SEQ No. 1119 | 2d |
| SEQ ID No. 1647 | NSAVWVYELFAK | 119-130 for the proteins of SEQ No. 1127, 1130, 1242 | OXA |
| SEQ ID No. 1648 | NSQVPAYK | 118-125 for the proteins of SEQ No. 1187, 1188, 1235; 117-124 for the protein of sequence SEQ ID No. 1144 | 2d |
| SEQ ID No. 1649 | NSTVWIYELFAK | 119-130 for the proteins of SEQ No. 1114, 1249 | 2d |
| SEQ ID No. 1650 | NSTVWVYELFAK | 119-130 for the proteins of SEQ No. 1108, 1125, 1128, 1131, 1133, 1173, 1201, 1239, 1246; 108-119 for the protein of sequence SEQ ID No. 1120 | OXA |
| SEQ ID No. 1651 | NSTVWVYQLFAK | 119-130 for the proteins of SEQ No. 1113, 1121 | 2d |
| SEQ ID No. 1652 | NTSGALVIQTDK | 48-59 for the proteins of SEQ No. 1218 | 2df |
| SEQ ID No. 1653 | NTSGVLVIQTDK | 48-59 for the proteins of SEQ No. 1124, 1132, 1145, 1198, 1199, 1217, 1219, 1220, 1221, 1222, 1223, 1244, 1251 | 2df |
| SEQ ID No. 1654 | NVDEMFYYYDGSK | 75-87 for the proteins of SEQ No. 1135 | 2d |
| SEQ ID No. 1655 | NWILR | 204-208 for the proteins of SEQ No. 1108, 1114, 1125, 1127, 1128, 1130, 1133, 1173, 1201, 1239, 1242, 1246, 1249; 193-197 for the protein of sequence SEQ ID No. 1120 | OXA |
| SEQ ID No. 1656 | NWNAAMDLR | 125-133 for the proteins of SEQ No. 1140 | 2df |
| SEQ ID No. 1657 | NYVDAFHYGNQDISGDK | 118-134 for the proteins of SEQ No. 1252 | 2de |
| SEQ ID No. 1658 | QADHAILVFDQAR | 51-63 for the proteins of SEQ No. 1133 | 2d |
| SEQ ID No. 1659 | QAEHALLVFGQER | 51-63 for the proteins of SEQ No. 1127, 1130, 1242 | OXA |

-continued

| Peptide SEQ ID No. | Amino acid sequence | Position of the peptide in the OXA protein(s) | Clinical interest |
|---|---|---|---|
| SEQ ID No. 1660 | QAITK | 251-255 for the proteins of SEQ No. 1136, 1142, 1208, 1243; 247-251 for the protein of sequence SEQ ID No. 1234 | 2df |
| SEQ ID No. 1661 | QAMLTEANSDYIIR | 193-206 for the proteins of SEQ No. 1142 | 2df |
| SEQ ID No. 1662 | QEVQFVSALAR | 171-181 for the proteins of SEQ No. 1227 | 2df |
| SEQ ID No. 1663 | QFASIK | 243-248 for the proteins of SEQ No. 1105 | 2d |
| SEQ ID No. 1664 | QGMPGSIR | 254-261 for the proteins of SEQ No. 1205 | 2df |
| SEQ ID No. 1665 | QGMSGSIR | 254-261 for the proteins of SEQ No. 1224 | 2df |
| SEQ ID No. 1666 | QGQTQQSYGNDLAR | 58-71 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1170, 1174, 1175, 1176, 1177, 1178, 1179, 1180, 1181, 1182, 1183, 1184, 1185, 1186, 1194, 1195, 1196, 1197, 1202, 1203, 1204, 1206, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 52-65 for the protein of sequence SEQ ID No. 1189; 52-65 for the protein of sequence SEQ ID No. 1190 | 2df |
| SEQ ID No. 1667 | QIDYGNADPSTIK | 143-155 for the proteins of SEQ No. 1127, 1130, 1242 | OXA |
| SEQ ID No. 1668 | QIDYGNVDPSTIK | 143-155 for the proteins of SEQ No. 1131 | 2d |
| SEQ ID No. 1669 | QIGEAR | 129-134 for the proteins of SEQ No. 1136, 1208, 1234, 1243 | 2df |
| SEQ ID No. 1670 | QIGQAR | 129-134 for the proteins of SEQ No. 1142 | 2df |
| SEQ ID No. 1671 | QIMLIEQTPAFTLR | 190-203 for the proteins of SEQ No. 1228 | 2df |
| SEQ ID No. 1672 | QLGSAIDQFWLR | 152-163 for the proteins of SEQ No. 1137 | 2df |
| SEQ ID No. 1673 | QLHDNK | 199-204 for the proteins of SEQ No. 1139 | 2df |
| SEQ ID No. 1674 | QLIFVHTVVQK | 229-239 for the proteins of SEQ No. 1105 | 2d |
| SEQ ID No. 1675 | QLIFVHTVVQKPGK | 229-242 for the proteins of SEQ No. 1105 | 2d |
| SEQ ID No. 1676 | QLPVK | 178-182 for the proteins of SEQ No. 1191; 184-188 for the protein of sequence SEQ ID No. 1137 | OXA |
| SEQ ID No. 1677 | QLPVKPR | 184-190 for the proteins of SEQ No. 1137 | 2df |
| SEQ ID No. 1678 | QLSLDVLDK | 265-273 for the proteins of SEQ No. 1168, 1171, 1216 | 2df |
| SEQ ID No. 1679 | QLVYAR | 237-242 for the proteins of SEQ No. 1191 | 2d |
| SEQ ID No. 1680 | QMMLTEASTDYIIR | 217-230 for the proteins of SEQ No. 1139 | 2df |

-continued

| Peptide SEQ ID No. | Amino acid sequence | Position of the peptide in the OXA protein(s) | Clinical interest |
|---|---|---|---|
| SEQ ID No. 1681 | QMSIVEATPDYVLHGK | 214-229 for the proteins of SEQ No. 1140 | 2df |
| SEQ ID No. 1682 | QPTDPAR | 99-105 for the proteins of SEQ No. 1191 | 2d |
| SEQ ID No. 1683 | QPTDPTR | 93-99 for the proteins of SEQ No. 1254, 1255, 1257, 1258 | 2d |
| SEQ ID No. 1684 | QPVSAGIR | 246-253 for the proteins of SEQ No. 1254, 1255, 1257, 1258 | 2d |
| SEQ ID No. 1685 | QQLVK | 275-279 for the proteins of SEQ No. 1139 | 2df |
| SEQ ID No. 1686 | QTLVFAR | 232-238 for the proteins of SEQ No. 1254, 1255, 1257, 1258 | 2d |
| SEQ ID No. 1687 | QVGAEK | 126-131 for the proteins of SEQ No. 1228 | 2df |
| SEQ ID No. 1688 | QVVFAR | 238-243 for the proteins of SEQ No. 1107 | 2d |
| SEQ ID No. 1689 | SADEVLPYGGK | 84-94 for the proteins of SEQ No. 1138 | 2d |
| SEQ ID No. 1690 | SADEVLPYGGKPQR | 84-97 for the proteins of SEQ No. 1138 | 2d |
| SEQ ID No. 1691 | SCATNDLAR | 50-58 for the proteins of SEQ No. 1110, 1193, 1250, 1259; 41-49 for the protein of sequence SEQ ID No. 1106; 41-49 for the protein of sequence SEQ ID No. 1111; 41-49 for the protein of sequence SEQ ID No. 1112 | OXA |
| SEQ ID No. 1692 | SCATNNLAR | 50-58 for the proteins of SEQ No. 1115, 1116, 1117, 1126, 1141, 1200, 1229, 1262 | OXA |
| SEQ ID No. 1693 | SDIPGGSK | 251-258 for the proteins of SEQ No. 1107 | 2d |
| SEQ ID No. 1694 | SDWGK | 29-33 for the proteins of SEQ No. 1133 | 2d |
| SEQ ID No. 1695 | SEDNFHISSQQHEK | 27-40 for the proteins of SEQ No. 1122, 1123, 1129, 1172, 1207, 1264 | 2df |
| SEQ ID No. 1696 | SEMPASIR | 252-259 for the proteins of SEQ No. 1124, 1145, 1198, 1217, 1218, 1219, 1220, 1221, 1222, 1244, 1251; 253-260 for the protein of sequence SEQ ID No. 1132; 253-260 for the protein of sequence SEQ ID No. 1199 | 2df |
| SEQ ID No. 1697 | SEMPASTR | 252-259 for the proteins of SEQ No. 1223 | 2df |
| SEQ ID No. 1698 | SFAAHNQDQDLR | 103-114 for the proteins of SEQ No. 1114, 1249 | 2d |
| SEQ ID No. 1699 | SFAGHNK | 103-109 for the proteins of SEQ No. 1133 | 2d |
| SEQ ID No. 1700 | SFAGHNQDQDLR | 103-114 for the proteins of SEQ No. 1127, 1130, 1131, 1242 | 2d |
| SEQ ID No. 1701 | SFAGHNQDQNLR | 103-114 for the proteins of SEQ No. 1113, 1121 | 2d |
| SEQ ID No. 1702 | SFLESWAK | 100-107 for the proteins of SEQ No. 1144 | 2d |

-continued

| Peptide SEQ ID No. | Amino acid sequence | Position of the peptide in the OXA protein(s) | Clinical interest |
|---|---|---|---|
| SEQ ID No. 1703 | SFTAWEK | 109-115 for the proteins of SEQ No. 1124, 1132, 1145, 1199, 1217, 1218, 1219, 1220, 1221, 1222, 1223, 1244, 1251; 104-110 for the protein of sequence SEQ ID No. 1227 | 2df |
| SEQ ID No. 1704 | SFTTWEK | 109-115 for the proteins of SEQ No. 1198 | 2df |
| SEQ ID No. 1705 | SGSGWLR | 207-213 for the proteins of SEQ No. 1107 | 2d |
| SEQ ID No. 1706 | SGWGMAVDPQVGWYVGFVEK | 221-240 for the proteins of SEQ No. 1168, 1171, 1216 | 2df |
| SEQ ID No. 1707 | SGWGMDVSPQVGWLTGWVEK | 219-238 for the proteins of SEQ No. 1224 | 2df |
| SEQ ID No. 1708 | SGWGMDVTPQVGWLTGWVEK | 219-238 for the proteins of SEQ No. 1205 | 2df |
| SEQ ID No. 1709 | SIHPASTFK | 69-77 for the proteins of SEQ No. 1137 | 2df |
| SEQ ID No. 1710 | SIPTK | 252-256 for the proteins of SEQ No. 1110, 1115, 1116, 1117, 1126, 1141, 1193, 1200, 1229, 1248, 1250, 1259, 1262, 1263; 243-247 for the protein of sequence SEQ ID No. 1106; 243-247 for the protein of sequence SEQ ID No. 1111; 243-247 for the protein of sequence SEQ ID No. 1112 | OXA |
| SEQ ID No. 1711 | SISTK | 252-256 for the proteins of SEQ No. 1247 | 2d |
| SEQ ID No. 1712 | SLGLSNNLSR | 76-85 for the proteins of SEQ No. 1139 | 2df |
| SEQ ID No. 1713 | SLSMSGK | 4-10 for the proteins of SEQ No. 1109 | 2de |
| SEQ ID No. 1714 | SMLFIEEK | 202-209 for the proteins of SEQ No. 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1169, 1174, 1175, 1176, 1177, 1178, 1179, 1180, 1182, 1183, 1184, 1185, 1186, 1192, 1194, 1195, 1196, 1197, 1202, 1203, 1204, 1209, 1210, 1211, 1212, 1213, 1214, 1215, 1225, 1226, 1230, 1231, 1232, 1233, 1236, 1237, 1238, 1240, 1241, 1245, 1253, 1260, 1261, 1265, 1266; 196-203 for the protein of sequence SEQ ID No. 1189; 196-203 for the protein of sequence SEQ ID No. 1190 | 2df |
| SEQ ID No. 1715 | SNGEK | 239-243 for the proteins of SEQ No. 1205, 1224 | 2df |
| SEQ ID No. 1716 | SNGLTHSWLGSSLK | 141-154 for the proteins of SEQ No. 1256 | 2d |
| SEQ ID No. 1717 | SNGYK | 208-212 for the proteins of SEQ No. 1124, 1132, 1145, 1199, 1217, 1218, 1219, 1220, 1221, 1222, 1223, 1244, 1251 | 2df |
| SEQ ID No. 1718 | SPTWELK | 79-85 for the proteins of SEQ No. 1107 | 2d |
| SEQ ID No. 1719 | SPTWELKPEYNPSPR | 79-93 for the proteins of SEQ No. 1107 | 2d |
| SEQ ID No. 1720 | SQDIVR | 208-213 for the proteins of SEQ No. 1140 | 2df |
| SEQ ID No. 1721 | SQQKPTDPTIWLK | 100-112 for the proteins of SEQ No. 1109 | 2de |

-continued

| Peptide SEQ ID No. | Amino acid sequence | Position of the peptide in the OXA protein(s) | Clinical interest |
|---|---|---|---|
| SEQ ID No. 1722 | SQVGWLTGWVEQPDGK | 225-240 for the proteins of SEQ No. 1244 | 2df |
| SEQ ID No. 1723 | SSSNSCTTNNAAR | 46-58 for the proteins of SEQ No. 1247 | 2d |
| SEQ ID No. 1724 | SSSNSCTTNNATR | 46-58 for the proteins of SEQ No. 1263 | 2de |
| SEQ ID No. 1725 | SVYGELR | 139-145 for the proteins of SEQ No. 1228 | 2df |
| SEQ ID No. 1726 | SWILR | 204-208 for the proteins of SEQ No. 1131 | 2d |
| SEQ ID No. 1727 | SYFDEAQTQGVIIIK | 44-58 for the proteins of SEQ No. 1122, 1123, 1129, 1172, 1205, 1207, 1224, 1264 | 2df |
| SEQ ID No. 1728 | SYLEK | 139-143 for the proteins of SEQ No. 1113, 1121 | 2d |
| SEQ ID No. 1729 | SYPMWEK | 111-117 for the proteins of SEQ No. 1205, 1224 | 2df |
| SEQ ID No. 1730 | TAYIPASTFK | 61-70 for the proteins of SEQ No. 1247, 1263; 77-86 for the protein of sequence SEQ ID No. 1168; 77-86 for the protein of sequence SEQ ID No. 1171; 77-86 for the protein of sequence SEQ ID No. 1216 | 2df |
| SEQ ID No. 1731 | TDDLFK | 243-248 for the proteins of SEQ No. 1127, 1130, 1131, 1242 | 2d |
| SEQ ID No. 1732 | TDINEIFK | 95-102 for the proteins of SEQ No. 1132, 1145, 1198, 1199, 1217, 1218, 1219, 1220, 1221, 1222, 1223, 1244, 1251 | 2df |
| SEQ ID No. 1733 | TFIHNDPR | 51-58 for the proteins of SEQ No. 1228 | 2df |
| SEQ ID No. 1734 | TGAGFTANR | 216-224 for the proteins of SEQ No. 1118, 1134; 201-209 for the protein of sequence SEQ ID No. 1119 | 2d |
| SEQ ID No. 1735 | TGFNDGQK | 197-204 for the proteins of SEQ No. 1143 | 2d |
| SEQ ID No. 1736 | TGLADSK | 210-216 for the proteins of SEQ No. 1187, 1188; 209-215 for the protein of sequence SEQ ID No. 1144 | 2d |
| SEQ ID No. 1737 | TGLDLMQK | 140-147 for the proteins of SEQ No. 1205 | 2df |
| SEQ ID No. 1738 | TGLELMQK | 140-147 for the proteins of SEQ No. 1122, 1123, 1129, 1172, 1207, 1264 | 2df |
| SEQ ID No. 1739 | TGMGYPK | 198-204 for the proteins of SEQ No. 1105 | 2d |
| SEQ ID No. 1740 | TGNGR | 197-201 for the proteins of SEQ No. 1252 | 2de |
| SEQ ID No. 1741 | TGTGSFIDAR | 200-209 for the proteins of SEQ No. 1256 | 2d |
| SEQ ID No. 1742 | TGTGSLSDAK | 211-220 for the proteins of SEQ No. 1109 | 2de |
| SEQ ID No. 1743 | TGVATEYQPEIGWWAGWVER | 213-232 for the proteins of SEQ No. 1137 | 2df |
| SEQ ID No. 1744 | TGVSYPLLADGTR | 202-214 for the proteins of SEQ No. 1254, 1255, 1257, 1258 | 2d |

-continued

| Peptide SEQ ID No. | Amino acid sequence | Position of the peptide in the OXA protein(s) | Clinical interest |
|---|---|---|---|
| SEQ ID No. 1745 | TGWAAMDIK | 217-225 for the proteins of SEQ No. 1132, 1199 | 2df |
| SEQ ID No. 1746 | TGWAMDIK | 217-224 for the proteins of SEQ No. 1124, 1145, 1198, 1218, 1219, 1220, 1221, 1222, 1223, 1244, 1251 | 2df |
| SEQ ID No. 1747 | TGWAMDVK | 217-224 for the proteins of SEQ No. 1217 | 2df |
| SEQ ID No. 1748 | TGWATR | 206-211 for the proteins of SEQ No. 1228 | 2df |
| SEQ ID No. 1749 | TGWCFDCTPELGWWVGWVK | 205-223 for the proteins of SEQ No. 1138 | 2d |
| SEQ ID No. 1750 | TGWEGR | 211-216 for the proteins of SEQ No. 1108, 1114, 1125, 1127, 1128, 1130, 1131, 1173, 1201, 1239, 1242, 1246, 1249; 200-205 for the protein of sequence SEQ ID No. 1120 | OXA |
| SEQ ID No. 1751 | TGWFVDK | 230-236 for the proteins of SEQ No. 1140 | 2df |
| SEQ ID No. 1752 | TGYDTK | 209-214 for the proteins of SEQ No. 1234 | 2df |
| SEQ ID No. 1753 | TGYGVR | 233-238 for the proteins of SEQ No. 1139 | 2df |
| SEQ ID No. 1754 | TGYSAR | 209-214 for the proteins of SEQ No. 1208 | 2df |
| SEQ ID No. 1755 | TGYSTR | 209-214 for the proteins of SEQ No. 1136, 1142, 1243 | 2df |
| SEQ ID No. 1756 | THESSNWGK | 25-33 for the proteins of SEQ No. 1113, 1121 | 2d |
| SEQ ID No. 1757 | TICTAIADAGTGK | 25-37 for the proteins of SEQ No. 1254, 1255, 1257, 1258 | 2d |
| SEQ ID No. 1758 | TIGGAPDAYWVDDSLQISAR | 169-188 for the proteins of SEQ No. 1140 | 2df |
| SEQ ID No. 1759 | TLPFSASSYETLR | 177-189 for the proteins of SEQ No. 1228 | 2df |
| SEQ ID No. 1760 | TLPFSLK | 189-195 for the proteins of SEQ No. 1157, 1161, 1169 | 2df |
| SEQ ID No. 1761 | TLPFSPK | 189-195 for the proteins of SEQ No. 1147, 1153, 1170, 1181, 1186, 1197, 1203, 1225, 1240, 1241, 1253 | 2df |
| SEQ ID No. 1762 | TLPFSQEVQDEVQSILFIEEK | 189-209 for the proteins of SEQ No. 1206 | 2df |
| SEQ ID No. 1763 | TLPFSQEVQDEVQSMLFIEEK | 189-209 for the proteins of SEQ No. 1150, 1192 | 2df |
| SEQ ID No. 1764 | TLPFSQK | 189-195 for the proteins of SEQ No. 1146, 1148, 1149, 1151, 1152, 1154, 1155, 1156, 1158, 1159, 1160, 1162, 1163, 1164, 1165, 1166, 1167, 1174, 1175, 1176, 1177, 1178, 1179, 1180, 1182, 1183, 1184, 1185, 1194, 1195, 1196, 1202, 1204, 1209, 1210, 1211, 1212, 1213, 1214, 1215, 1226, 1230, 1231, 1232, 1233, 1236, 1238, 1245, 1260, 1261, 1265, 1266; 183-189 for the protein of sequence SEQ ID No. 1189; 183-189 for the protein of sequence SEQ ID No. 1190 | 2df |
| SEQ ID No. 1765 | TLPSSQK | 189-195 for the proteins of SEQ No. 1237 | 2df |

| Peptide SEQ ID No. | Amino acid sequence | Position of the peptide in the OXA protein(s) | Clinical interest |
|---|---|---|---|
| SEQ ID No. 1766 | TLQNGWFEGFIISK | 225-238 for the proteins of SEQ No. 1118, 1134; 210-223 for the protein of sequence SEQ ID No. 1119 | 2d |
| SEQ ID No. 1767 | TMQEYLNK | 123-130 for the proteins of SEQ No. 1143 | 2d |
| SEQ ID No. 1768 | TNGNSTSVYNESR | 51-63 for the proteins of SEQ No. 1113, 1121 | 2d |
| SEQ ID No. 1769 | TQTYQAYDAAR | 72-82 for the proteins of SEQ No. 1140 | 2df |
| SEQ ID No. 1770 | TTDPTIWEK | 93-101 for the proteins of SEQ No. 1256 | 2d |
| SEQ ID No. 1771 | TTTTEVFK | 96-103 for the proteins of SEQ No. 1153, 1186 | 2df |
| SEQ ID No. 1772 | TWASNDFSR | 41-49 for the proteins of SEQ No. 1143 | 2d |
| SEQ ID No. 1773 | TWDMVQR | 191-197 for the proteins of SEQ No. 1137 | 2df |
| SEQ ID No. 1774 | TWMQFSVVWVSQEITQK | 113-129 for the proteins of SEQ No. 1118, 1134; 98-114 for the protein of sequence SEQ ID No. 1119 | 2d |
| SEQ ID No. 1775 | TYPMWEK | 111-117 for the proteins of SEQ No. 1122, 1123, 1129, 1172, 1207, 1264 | 2df |
| SEQ ID No. 1776 | TYVVDPAR | 58-65 for the proteins of SEQ No. 1137 | 2df |
| SEQ ID No. 1777 | VAFSLNIEMK | 244-253 for the proteins of SEQ No. 1205 | 2df |
| SEQ ID No. 1778 | VANSLIGLSTGAVR | 70-83 for the proteins of SEQ No. 1138 | 2d |
| SEQ ID No. 1779 | VEHQR | 187-191 for the proteins of SEQ No. 1108, 1113, 1114, 1121, 1125, 1127, 1128, 1130, 1131, 1133, 1173, 1201, 1239, 1242, 1246, 1249; 176-180 for the protein of sequence SEQ ID No. 1120 | OXA |
| SEQ ID No. 1780 | VELGK | 248-252 for the proteins of SEQ No. 1138 | 2d |
| SEQ ID No. 1781 | VFDDAGVSGTFVLMDITADR | 38-57 for the proteins of SEQ No. 1137 | 2df |
| SEQ ID No. 1782 | VFLDSWAK | 88-95 for the proteins of SEQ No. 1135 | 2d |
| SEQ ID No. 1783 | VFLESWAK | 101-108 for the proteins of SEQ No. 1187, 1188, 1235 | 2d |
| SEQ ID No. 1784 | VFLSSWAQDMNLSSAIK | 89-105 for the proteins of SEQ No. 1143 | 2d |
| SEQ ID No. 1785 | VGFER | 134-138 for the proteins of SEQ No. 1137 | 2df |
| SEQ ID No. 1786 | VILVFDQVR | 55-63 for the proteins of SEQ No. 1114, 1249 | 2d |
| SEQ ID No. 1787 | VITFTK | 228-233 for the proteins of SEQ No. 1252 | 2de |
| SEQ ID No. 1788 | VMAAMVR | 158-164 for the proteins of SEQ No. 1139 | 2df |

-continued

| Peptide SEQ ID No. | Amino acid sequence | Position of the peptide in the OXA protein(s) | Clinical interest |
|---|---|---|---|
| SEQ ID No. 1789 | VPLAVMGYDAGILVDAHNPR | 58-77 for the proteins of SEQ No. 1256 | 2d |
| SEQ ID No. 1790 | VQANVK | 195-200 for the proteins of SEQ No. 1124, 1132, 1145, 1198, 1199, 1217, 1218, 1219, 1220, 1221, 1222, 1223, 1244, 1251 | 2df |
| SEQ ID No. 1791 | VQDEVK | 196-201 for the proteins of SEQ No. 1202 | 2df |
| SEQ ID No. 1792 | VQDEVQSMLFIEEK | 196-209 for the proteins of SEQ No. 1146, 1147, 1148, 1149, 1150, 1151, 1153, 1154, 1155, 1156, 1157, 1158, 1159, 1160, 1162, 1163, 1164, 1165, 1166, 1167, 1169, 1174, 1175, 1176, 1177, 1178, 1179, 1180, 1182, 1183, 1184, 1185, 1186, 1192, 1194, 1195, 1196, 1197, 1203, 1204, 1209, 1210, 1211, 1212, 1213, 1215, 1225, 1226, 1230, 1231, 1232, 1233, 1236, 1237, 1238, 1240, 1241, 1245, 1253, 1260, 1261, 1265, 1266; 190-203 for the protein of sequence SEQ ID No. 1189; 190-203 for the protein of sequence SEQ ID No. 1190 | 2df |
| SEQ ID No. 1793 | VQDEVQSMLFIEEMNGNK | 196-213 for the proteins of SEQ No. 1170, 1181 | 2df |
| SEQ ID No. 1794 | VQDGVQSMLFIEEK | 196-209 for the proteins of SEQ No. 1214 | 2df |
| SEQ ID No. 1795 | VQHEVQSMLFIEEK | 196-209 for the proteins of SEQ No. 1152 | 2df |
| SEQ ID No. 1796 | VSCLPCYQVVSHK | 138-150 for the proteins of SEQ No. 1140 | 2df |
| SEQ ID No. 1797 | VSCVWCYQALAR | 114-125 for the proteins of SEQ No. 1228 | 2df |
| SEQ ID No. 1798 | VSDVCSEVTAEGWQEVR | 37-53 for the proteins of SEQ No. 1139 | 2df |
| SEQ ID No. 1799 | VSEVEGWQIHGK | 186-197 for the proteins of SEQ No. 1105 | 2d |
| SEQ ID No. 1800 | VSFSLNIEMK | 244-253 for the proteins of SEQ No. 1224 | 2df |
| SEQ ID No. 1801 | VSPCSSFK | 54-61 for the proteins of SEQ No. 1107 | 2d |
| SEQ ID No. 1802 | VSQVPAYK | 105-112 for the proteins of SEQ No. 1135 | 2d |
| SEQ ID No. 1803 | VVFAR | 229-233 for the proteins of SEQ No. 1256; 239-243 for the protein of sequence SEQ ID No. 1107; 240-244 for the protein of sequence SEQ ID No. 1109 | OXA |
| SEQ ID No. 1804 | WDGAK | 97-101 for the proteins of SEQ No. 1113, 1121 | 2d |
| SEQ ID No. 1805 | WDGEK | 104-108 for the proteins of SEQ No. 1151, 1160, 1177, 1180, 1182 | 2df |
| SEQ ID No. 1806 | WDGHIYDFPDWNR | 92-104 for the proteins of SEQ No. 1228 | 2df |
| SEQ ID No. 1807 | WDGIK | 97-101 for the proteins of SEQ No. 1114, 1249 | 2d |
| SEQ ID No. 1808 | WDGKPR | 92-97 for the proteins of SEQ No. 1110, 1115, 1116, 1117, 1126, 1141, 1193, 1200, 1229, 1247, 1250, 1259, 1262, 1263; 83-88 for the protein of sequence SEQ ID No. 1106; 83-88 | OXA |

-continued

| Peptide SEQ ID No. | Amino acid sequence | Position of the peptide in the OXA protein(s) | Clinical interest |
|---|---|---|---|
| | | for the protein of sequence SEQ ID No. 1111; 83-88 for the protein of sequence SEQ ID No. 1112; 116-121 for the protein of sequence SEQ ID No. 1140; 107-112 for the protein of sequence SEQ ID No. 1168; 107-112 for the protein of sequence SEQ ID No. 1171; 107-112 for the protein of sequence SEQ ID No. 1216; 93-98 for the protein of sequence SEQ ID No. 1248 | |
| SEQ ID No. 1809 | WDGQK | 104-108 for the proteins of SEQ No. 1146, 1147, 1150, 1153, 1154, 1155, 1157, 1161, 1163, 1164, 1165, 1169, 1170, 1181, 1186, 1192, 1197, 1203, 1204, 1206, 1225, 1226, 1240, 1241, 1253, 1261, 1266; 98-102 for the protein of sequence SEQ ID No. 1189; 98-102 for the protein of sequence SEQ ID No. 1190 | 2df |
| SEQ ID No. 1810 | WDGQTR | 95-100 for the proteins of SEQ No. 1136, 1142, 1208, 1234, 1243 | 2df |
| SEQ ID No. 1811 | WDGVK | 97-101 for the proteins of SEQ No. 1127, 1130, 1133, 1242 | 2d |
| SEQ ID No. 1812 | WDGVNR | 97-102 for the proteins of SEQ No. 1108, 1125, 1128, 1131, 1173, 1201, 1239, 1246; 86-91 for the protein of sequence SEQ ID No. 1120 | OXA |
| SEQ ID No. 1813 | WDYKPEFNGYK | 78-88 for the proteins of SEQ No. 1256; 89-99 for the protein of sequence SEQ ID No. 1109 | OXA |
| SEQ ID No. 1814 | WETYSVVWFSQQITEWLGMER | 97-117 for the proteins of SEQ No. 1105 | 2d |
| SEQ ID No. 1815 | WNGQK | 104-108 for the proteins of SEQ No. 1152, 1176, 1202, 1265 | 2df |
| SEQ ID No. 1816 | YAQAK | 155-159 for the proteins of SEQ No. 1140 | 2df |
| SEQ ID No. 1817 | YFSDFNAK | 34-41 for the proteins of SEQ No. 1113, 1121 | 2d |
| SEQ ID No. 1818 | YGTHLDR | 68-74 for the proteins of SEQ No. 1168, 1171, 1216 | 2df |
| SEQ ID No. 1819 | YIIHNK | 54-59 for the proteins of SEQ No. 1144, 1187, 1188, 1235 | 2d |
| SEQ ID No. 1820 | YLDELVK | 245-251 for the proteins of SEQ No. 1143 | 2d |
| SEQ ID No. 1821 | YLMITEAGR | 195-203 for the proteins of SEQ No. 1242 | OXA |
| SEQ ID No. 1822 | YLNLFSYGNANIGGGIDK | 135-152 for the proteins of SEQ No. 1247, 1263 | OXA |
| SEQ ID No. 1823 | YNGEK | 96-100 for the proteins of SEQ No. 1187, 1188, 1235 | 2d |
| SEQ ID No. 1824 | YPHNPR | 88-93 for the proteins of SEQ No. 1252 | 2de |
| SEQ ID No. 1825 | YPVWYSQQVAHHLGAQR | 103-120 for the proteins of SEQ No. 1255 | 2d |
| SEQ ID No. 1826 | YSNVLAFK | 106-113 for the proteins of SEQ No. 1143 | 2d |
| SEQ ID No. 1827 | YSPASTFK | 68-75 for the proteins of SEQ No. 1108, 1113, 1114, 1121, 1125, 1127, 1128, 1130, 1131, 1133, 1173, 1201, 1239, 1242, 1246, 1249; 57-64 for the protein of sequence SEQ ID No. 1120 | OXA |

| Peptide SEQ ID No. | Amino acid sequence | Position of the peptide in the OXA protein(s) | Clinical interest |
|---|---|---|---|
| SEQ ID No. 1828 | YSVVPVYQQLAR | 141-152 for the proteins of SEQ No. 1139 | 2df |
| SEQ ID No. 1829 | YSVVWYSQLTAK | 109-120 for the proteins of SEQ No. 1191 | 2d |
| SEQ ID No. 1830 | YSVVWYSQQVAHHLGAQR | 103-120 for the proteins of SEQ No. 1254, 1257, 1258 | 2d |
| SEQ ID No. 1831 | YTPASTFK | 55-62 for the proteins of SEQ No. 1191 | 2d |
| SEQ ID No. 1832 | YTSAFGYGNADVSGEPGK | 130-147 for the proteins of SEQ No. 1191 | 2d |
| SEQ ID No. 1833 | YVFVSALTGNLGSNLTSSIK | 228-247 for the proteins of SEQ No. 1119; 243-262 for the protein of sequence SEQ ID No. 1118 | 2d |
| SEQ ID No. 1834 | YVFVSALTGSLGSNLTSSIK | 243-262 for the proteins of SEQ No. 1134 | 2d |
| SEQ ID No. 1835 | YVGHDR | 50-55 for the proteins of SEQ No. 1138 | 2d |
| SEQ ID No. 2160 | ANQAFLPASTFK | 62-73 for the proteins of SEQ No. 1136, 1142, 1208, 1234, 1243 | 2df |
| SEQ ID No. 2161 | DEHQVFK | 88-94 for the proteins of SEQ No. 1136, 1142, 1208, 1234, 1243 | 2df |
| SEQ ID No. 2162 | DHNLITAMK | 108-116 for the proteins of SEQ No. 1136, 1208, 1234 | 2df |
| SEQ ID No. 2163 | DIATWNR | 101-107 for the proteins of SEQ No. 1136, 1208, 1234 | 2df |
| SEQ ID No. 2164 | IPNSLIALDLGVVK | 74-87 for the proteins of SEQ No. 1136, 1142, 1208, 1234, 1243 | 2df |
| SEQ ID No. 2165 | ISATEQISFLR | 164-174 for the proteins of SEQ No. 1136, 1208, 1234 | 2df |
| SEQ ID No. 2166 | QAMLTEANGDYIIR | 193-206 for the proteins of SEQ No. 1136, 1208, 1234, 1243 | 2df |
| SEQ ID No. 2167 | QQGFTNNLK | 52-60 for the proteins of SEQ No. 1136, 1142, 1208, 1234, 1243 | 2df |
| SEQ ID No. 2168 | SQGVVVLWNENK | 40-51 for the proteins of SEQ No. 1136, 1208, 1234, 1243 | 2df |
| SEQ ID No. 2169 | SWNAHFTEHK | 30-39 for the proteins of SEQ No. 1136, 1208, 1234, 1243 | 2df |
| SEQ ID No. 2170 | VLALSAVFLVASIIGMPAVAK | 3-23 for the proteins of SEQ No. 1136, 1208, 1234, 1243 | 2df |
| SEQ ID No. 2171 | YSVVPVYQEFAR | 117-128 for the proteins of SEQ No. 1136, 1142, 1208, 1234, 1243 | 2df |

In the clinical interest column, the entries 2d, 2de, 2df correspond to the functional subgroups of OXA beta-lactamases which the corresponding peptide makes it possible to detect. Therefore, the detection of a 2df peptide will indicate the presence of a carbapenemase beta-lactamase capable of hydrolysing carbapenems.

The entry 2de will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The entry OXA indicates a common peptide between at least two of the subgroups 2d, 2de and 2df. The corresponding peptide indicates the presence of an OXA beta-lactamase and the presence of a mechanism of resistance at least to penicillins and to first-generation cephalosporins.

The detection of a mechanism of resistance to ESBL (extended-spectrum beta-lactamase) cephalosporins, induced by the OXA protein, is characterised by the detection of at least one resistance-marking 2de peptide chosen from the sequences SEQ ID No. 1277, 1297, 1323, 1344, 1368, 1369, 1373, 1375, 1392, 1421, 1423, 1427, 1429, 1439, 1444, 1446, 1450, 1451, 1457, 1465, 1468, 1490, 1491, 1495, 1498, 1534, 1543, 1545, 1575, 1589, 1597, 1598, 1600, 1602, 1657, 1713, 1721, 1724, 1740, 1742, 1787, 1824, 1268, 1269, 1270, 1271, 1272, 1278, 1279, 1280, 1281, 1283, 1285, 1288, 1290, 1295, 1299, 1300, 1301, 1302, 1303, 1304, 1305, 1306, 1307, 1308, 1309, 1310, 1314, 1315, 1316, 1317, 1318, 1319, 1320, 1332, 1337, 1339, 1340, 1341, 1342, 1350, 1354, 1355, 1356, 1357, 1358, 1359, 1360, 1365, 1366, 1367, 1386, 1389, 1390, 1391, 1393, 1394, 1402, 1404, 1405, 1407, 1408, 1413, 1414, 1419, 1420, 1425, 1432, 1433, 1440, 1447, 1448, 1456, 1471, 1472, 1477, 1478, 1480, 1485, 1487, 1488, 1499, 1504, 1506, 1508, 1509, 1510, 1513, 1514, 1515, 1516, 1521, 1522, 1525, 1526, 1530, 1533, 1539, 1540, 1548, 1550, 1551, 1552, 1553, 1554, 1555, 1556, 1559, 1567, 1569, 1570, 1571, 1572, 1574, 1577, 1582, 1590, 1592, 1595, 1596, 1605, 1609, 1610, 1611, 1612, 1613, 1614, 1615, 1616, 1617, 1618, 1620, 1626, 1627, 1628, 1632, 1633, 1634, 1635, 1637, 1638, 1639, 1640, 1652, 1653, 1656, 1660, 1661, 1662, 1664, 1665, 1666, 1669, 1670, 1671, 1672, 1673, 1677, 1678, 1680, 1681, 1685, 1687, 1695, 1696, 1697, 1703, 1704, 1706, 1707, 1708, 1709, 1712, 1714, 1715, 1717, 1720, 1722, 1725, 1727, 1729, 1730, 1732, 1733, 1737, 1738, 1743, 1746, 1748, 1751, 1752, 1753, 1754, 1755, 1758, 1759, 1760, 1761, 1762, 1763, 1764, 1765, 1769, 1771, 1773, 1775, 1776, 1777, 1781, 1785, 1788, 1790, 1791, 1792, 1793, 1794, 1795, 1796, 1797, 1798, 1800, 1805, 1806, 1809, 1810, 1815, 1816, 1818, 1828, 2160, 2161, 2162, 2163, 2164, 2165, 2166, 2167, 2168, 2169, 2170, 2171.

The detection of a mechanism of resistance to carbapenems or to cephalosporins, induced by the expression of the GES protein, is characterised by the detection of at least one peptide belonging to the GES protein and to its different sequence variants SEQ ID No. 2114 to SEQ ID No. 2130.

SEQ ID No. 2114:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2115:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVKWSPATERFLASGHMTV

LEAAQAAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2116:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQLAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2117:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMNDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2118:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMSDNTPG

-continued

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2119:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVKWSPATERFLASGHMTV

LEAAQAAVQLSDNGATNLLLREIGGPAAMTQYFRKIGDSVSRLDRKEPEMSDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2120:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGSRNDIGFFKAQERDYAVAVYTTAPKLSAVERDELVASVGQVITQLILS

TDK

SEQ ID No. 2121:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGARNDIGFFKAQERDYAVAVYTTAPKLSAVERDELVASVGQVITQLILS

TDK

SEQ ID No. 2122:
MRFIHALLLAGTAHSAYASEKLTFKTDLEKLEREKAAQIGVAIVDPQGEIVAGHRTAQ

RFAMCSTFKFPLAALVFERIDSGTERGDRKLSYGPDMIVEWSPATERFLASGHMTV

LEAAQAAVQLCDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2123:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVKWSPATERFLASGHMTV

LEAAQAAVQLSDNGATNLLLREIGGPAAMTQYFRKIGDSVSRLDRKEPEMNDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2124:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKESEMSDNTPG

DLRDTTTPIAMARTVAKVLYGGALTSTSTHTIERWLIGNQTGDATLRAGFPKDWVVG

-continued

EKTGTCANGGRNDIGFFKAQERDYAVAVYTTAPKLSAVERDELVASVGQVITQLILS

TDK

SEQ ID No. 2125:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMSDNTPG

DLRDTTTPIAMARTVAKVLYGGALTSTSTHTIERWLIGNQTGDATLRAGFPKDWVVG

EKTGTCANGARNDIGFFKAQERDYAVAVYTTAPKLSAVERDELVASVGQVITQLILS

TDK

SEQ ID No. 2126:
MRFIHALLLAGIAHSAYASEKLTFKTDLEKLEREKAAEIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMSDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2127:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVKWSPATERFLASGHMTV

LEAAQAAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGARNDIGFFKAQERDYAVAVYTTAPKLSAVERDELVASVGQVITQLILS

TDK

SEQ ID No. 2128:
MRFIHALLLAGIAHSAYASEKLTFKTDLEKLEREKAAQIGVAIVDPQGEIVAGHRTAQ

RFAMCSTFKFPLAALVFERIDSGTERGDRKLSYGPDMIVKWSPATERFLASGHMTV

LEAAQAAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2129:
MRFIHALLLAGIAHSAYASEKLTFKTDLEKLEREKAAQIGVAIVDPQGEIVAGHRTAQ

RFAMCSTFKFPLAALVFERIDSGTERGDRKLSYGPDMIVKWSPATERFLASGHMTV

LEAAQAAVQLSDNGATNLLLREIGGPAAMTQYFRKIGDSVSRLDRKEPEMSDNTPG

DLRDTTTPIAMARTVAKVLYGGALTSTSTHTIERWLIGNQTGDATLRAGFPKDWVVG

EKTGTCANGGRNDIGFFKAQERDYAVAVYTTAPKLSAVERDELVASVGQVITQLILS

TDK

SEQ ID No. 2130:
MRFIHALLLAGIAHSAYASEKLTFKTDLEKLEREKAAQIGVAIVDPQGEIVAGHRMAQ

RFAMCSTFKFPLAALVFERIDSGTERGDRKLSYGPDMIVEWSPATERFLASGHMTV

LEAAQAAVQLSDNGATNLLLREIGGPAAMTQYFRKIGDSVSRLDRKEPEMGDNTPG

DLRDTTTPIAMARTVAKVLYGGALTSTSTHTIERWLIGNQTGDATLRAGFPKDWVVG

EKTGACANGARNDIGFFKAQERDYAVAVYTTAPKLSAVERDELVASVGQVITQLILS

TDK said peptides being chosen, preferably, from the peptides of sequence SEQ ID No. 2131 to SEQ ID No. 2159 as defined hereafter:

| Peptide SEQ ID No. | Amino acid sequence | Position of the peptide in the GES protein(s) | Clinical interest |
|---|---|---|---|
| SEQ ID No. 2131 | AAEIGVAIVDPQGEIVAGHR | 36-55 for the proteins of SEQ No. 2126 | carba |
| SEQ ID No. 2132 | AAQIGVAIVDPQGEIVAGHR | 36-55 for the proteins of SEQ No. 2114, 2115, 2116, 2117, 2118, 2119, 2120, 2121, 2122, 2123, 2124, 2125, 2127, 2128, 2129, 2130 | ESBL |
| SEQ ID No. 2133 | AGFPK | 218-222 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2134 | DTTTPIAMAR | 174-183 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2135 | DWVVGEK | 223-229 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2136 | DYAVAVYTTAPK | 250-261 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2137 | EIGGPAAMTQYFR | 136-148 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2138 | EPEMGDNTPGDLR | 161-173 for the proteins of SEQ No. 2114, 2115, 2116, 2120, 2121, 2122, 2127, 2128, 2130 | ESBL |
| SEQ ID No. 2139 | EPEMNDNTPGDLR | 161-173 for the proteins of SEQ No. 2117, 2123 | carba |
| SEQ ID No. 2140 | EPEMSDNTPGDLR | 161-173 for the proteins of SEQ No. 2118, 2119, 2125, 2126, 2129 | carba |
| SEQ ID No. 2141 | ESEMSDNTPGDLR | 161-173 for the proteins of SEQ No. 2124 | carba |
| SEQ ID No. 2142 | FAMCSTFK | 60-67 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2143 | FIHALLLAGIAHSAYASEK | 3-21 for the proteins of SEQ No. 2114, 2115, 2116, 2117, 2118, 2119, 2120, 2121, 2123, 2124, 2125, 2126, 2127, 2128, 2129, 2130 | ESBL |
| SEQ ID No. 2144 | FIHALLLAGTAHSAYASEK | 3-21 for the proteins of SEQ No. 2122 | carba |
| SEQ ID No. 2145 | FPLAALVFER | 68-77 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2146 | IDSGTER | 78-84 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2147 | IGDSVSR | 150-156 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2148 | LSAVER | 262-267 for the proteins of SEQ No. 2114, 2115, 2116, 2117, 2118, 2119, 2120, 2121, 2122, 2123, 2124, 2125, 2126, 2127, 2128, 2129, 2130 | ESBL |

| Peptide SEQ ID No. | Amino acid sequence | Position of the peptide in the GES protein(s) | Clinical interest |
|---|---|---|---|
| SEQ ID No. 2149 | LSYGPDMIVEWSPATER | 89-105 for the proteins of SEQ No. 2114, 2116, 2117, 2118, 2120, 2121, 2122, 2124, 2125, 2126, 2130 | ESBL |
| SEQ ID No. 2150 | LSYGPDMIVK | 89-98 for the proteins of SEQ No. 2115, 2119, 2123, 2127, 2128, 2129 | carba |
| SEQ ID No. 2151 | NDIGFFK | 239-245 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2152 | TDLEK | 26-30 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2153 | TGACANGAR | 230-238 for the proteins of SEQ No. 2130 | carba |
| SEQ ID No. 2154 | TGTCANGAR | 230-238 for the proteins of SEQ No. 2121, 2125, 2127 | carba |
| SEQ ID No. 2155 | TGTCANGGR | 230-238 for the proteins of SEQ No. 2114, 2115, 2116, 2117, 2118, 2119, 2122, 2123, 2124, 2126, 2128, 2129 | ESBL |
| SEQ ID No. 2156 | TGTCANGSR | 230-238 for the proteins of SEQ No. 2120 | carba |
| SEQ ID No. 2157 | VLYGGALTSTSTHTIER | 188-204 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2158 | WLIGNQTGDATLR | 205-217 for the proteins of SEQ No. 2114, 2115, 2116, 2117, 2118, 2119, 2120, 2121, 2122, 2123, 2124, 2125, 2126, 2127, 2128, 2129, 2130 | ESBL |
| SEQ ID No. 2159 | WSPATER | 99-105 for the proteins of SEQ No. 2114, 2115, 2116, 2117, 2118, 2119, 2120, 2121, 2122, 2123, 2124, 2125, 2126, 2127, 2128, 2129, 2130 | carba |

In the clinical interest column, the ESBL and carba entries correspond to the GES beta-lactamase activities which the corresponding peptide makes it possible to detect. Therefore, the detection of a carba peptide will indicate the presence of a carbapenemase beta-lactamase capable of hydrolysing carbapenems, penicillins, first-generation cephalosporins such as cephaloridine and cefalotin, and at least one antibiotic from the oxyimino-beta-lactam class such as cefotaxime, ceftazidime or the monobactames such as aztreonam.

If no peptide referred to as carba is detected, the detection of a peptide referred to as ESBL will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The detection of a mechanism of resistance to cephalosporinases with an extended spectrum (ESBL) induced by the GES protein is thus characterised by the detection of at least one resistance-marking ESBL peptide chosen from the sequences SEQ ID No. 2131 to SEQ ID No. 2159.

Certain peptide sequences can be common to several resistance mechanisms. Therefore, the following sequences are identical:

SEQ ID No. 834 and SEQ ID No. 978
SEQ ID No. 833 and SEQ ID No. 977
SEQ ID No. 832 and SEQ ID No. 976
SEQ ID No. 831 and SEQ ID No. 975
SEQ ID No. 826 and SEQ ID No. 974
SEQ ID No. 825 and SEQ ID No. 973
SEQ ID No. 824 and SEQ ID No. 972
SEQ ID No. 823 and SEQ ID No. 971
SEQ ID No. 822 and SEQ ID No. 970
SEQ ID No. 817 and SEQ ID No. 969
SEQ ID No. 813 and SEQ ID No. 967
SEQ ID No. 802 and SEQ ID No. 964
SEQ ID No. 798 and SEQ ID No. 963
SEQ ID No. 666 and SEQ ID No. 895
SEQ ID No. 350 and SEQ ID No. 1035
SEQ ID No. 349 and SEQ ID No. 1031
SEQ ID No. 347 and SEQ ID No. 1030
SEQ ID No. 346 and SEQ ID No. 1029
SEQ ID No. 345 and SEQ ID No. 1028
SEQ ID No. 343 and SEQ ID No. 1037 and SEQ ID No. 725
SEQ ID No. 342 and SEQ ID No. 1026
SEQ ID No. 341 and SEQ ID No. 1025
SEQ ID No. 340 and SEQ ID No. 1024
SEQ ID No. 339 and SEQ ID No. 1023

SEQ ID No. 338 and SEQ ID No. 1020
SEQ ID No. 337 and SEQ ID No. 1036 and SEQ ID No. 719
SEQ ID No. 337 and SEQ ID No. 1036
SEQ ID No. 336 and SEQ ID No. 841 and SEQ ID No. 981
SEQ ID No. 323 and SEQ ID No. 840 and SEQ ID No. 980
SEQ ID No. 315 and SEQ ID No. 839 and SEQ ID No. 948 and SEQ ID No. 979
SEQ ID No. 240 and SEQ ID No. 679
SEQ ID No. 184 and SEQ ID No. 626
SEQ ID No. 182 and SEQ ID No. 625
SEQ ID No. 1034 and SEQ ID No. 1999
SEQ ID No. 1032 and SEQ ID No. 1988
SEQ ID No. 1027 and SEQ ID No. 1970
SEQ ID No. 1022 and SEQ ID No. 1952
SEQ ID No. 1021 and SEQ ID No. 1937
SEQ ID No. 1019 and SEQ ID No. 1933
SEQ ID No. 809 and SEQ ID No. 966
SEQ ID No. 1033 and SEQ ID No. 1989

In all cases, the sequences above indicate the expression of a mechanism of resistance to cephalosporins.

The method of the invention and its advantages will become apparent from the rest of the present description which presents several non-limiting examples of implementation of said method.

EXAMPLE 1

Identification of Microorganisms from a Sample by Biochemical Profile

1. Culturing of the Sample on a Culture Medium

The optimum culture media and the optimum culture conditions are different according to the species of microorganism. By default, the sample is seeded on different media:
 sheep blood Columbia agar (bioMérieux ref. 43041) for 18 to 24 h at 35° C., in an aerobic or anaerobic atmosphere;
 TSA agar (bioMérieux ref. 43011) for 18 to 24 h at 37° C.

2. Identification of the Microorganisms

The identification is performed as follows:
1. Selection of isolated colonies
2. While maintaining the aseptic conditions, transfer of 3.0 mL of aqueous sterile saline solution (0.45-0.50% NaCl, pH 4.5 to 7.0) into a transparent plastic (polystyrene) test tube
3. With the aid of a stirrer or a sterile swab, transfer of a sufficient number of identical colonies into the saline solution tube prepared in step 2, and adjustment of the bacterial suspension between 0.50 and 0.63 McFarland with a calibrated DENSICHEK from VITEK®
4. Positioning of the bacterial suspension tube and of a VITEK® identification card on a VITEK® cartridge
5. Loading of the cartridge into the VITEK® instrument
6. The filling, sealing, incubation and reading operations are automatic
7. Acquisition of a biochemical profile
8. Identification with the VITEK® system performed by comparing to the biochemical profiles of known strains

EXAMPLE 2

Preparation of a Primary Urine Sample by Microorganism Enrichment

The following protocol is performed in 16 steps (steps 5 to 12 are optional and could be omitted if the enriched sample is subsequently treated according to examples 4 and onwards):
1. Centrifuging of 5 mL of contaminated urine, at 2000 g for 30 seconds
2. Recovery of the supernatant
3. Centrifuging at 15000 g for 5 minutes
4. Elimination of the supernatant
5. Washing of the pellet with 3 mL of distilled water by resuspension
6. Centrifuging at 15000 g for 5 minutes
7. Elimination of the supernatant
8. Place the pellet in the presence of solvent (8 acetone volumes for 1 methanol volume) for 1/10 dilution
9. Leave for 1 hour at −20° C.
10. Centrifuging at 15000 g for 5 minutes
11. Elimination of the supernatant
12. Place the pellet in the presence of solvent (8 acetone volumes for 1 methanol volume) for 1/10 dilution
13. Leave for 1 hour at −20° C.
14. Centrifuging at 15000 g for 5 minutes
15. Elimination of the supernatant
16. The pellet constitutes the microorganism-enriched sample

EXAMPLE 3

Identification of Microorganisms from a Sample by MALDI-TOF

The identification is performed as follows:
1. Transfer, with the aid of a 1 µl oese, of a portion of microorganism colony obtained according to example 1, or of an enriched sample according to example 2, and uniform deposition on a plate for MALDI-TOF mass spectrometry
2. Covering the deposit with 1 µl of matrix. The matrix used is a saturated solution of HCCA (alpha-cyano-4-hydroxycinnamic acid) in organic solvent (50% acetonitrile and 2.5% trifluoroacetic acid)
3. Drying at ambient temperature
4. Introducing the plate into the mass spectrometer
5. Acquiring a mass spectrum
6. Comparing the obtained spectrum with the spectra contained in a knowledge base
7. Identification of the microorganism by comparing the obtained peaks with those in the knowledge base

EXAMPLE 4

Identification of Microorganisms from a Sample by ESI-TOF

The identification is performed as follows:
1. Sampling of a microorganism colony, obtained according to example 1, or of an enriched sample according to example 2, and suspension in 100 µl of demineralised water.

2. Centrifuging at 3000 g for 5 minutes.
3. Elimination of the supernatant.
4. Resuspension in 100 µl of demineralised water.
5. Centrifuging at 3000 g for 5 minutes.
6. Elimination of the supernatant.
7. Resuspension in 100 µl of an acetonitrile, demineralised water and formic acid mixture (50/50/0.1%).
8. Filtration with a filter with a porosity of 0.45 µm.
9. Injection into a mass spectrometer in single MS mode.
10. Acquisition of a mass spectrum.
11. Comparing the obtained spectrum with the spectra contained in a knowledge base.
12. Identification of the microorganism by referring to reference spectra.

EXAMPLE 5

Obtaining Digested Proteins from Microorganisms

The following protocol is conventionally performed in 17 steps:
1. Sampling of a microorganism colony, obtained according to example 1, or of an enriched sample according to example 2, and suspension in 10 to 100 µl of a 6M guanidine hydrochloride solution, 50 mM Tris-HCl, pH=8.0.
2. Addition of dithiothreitol (DTT) to achieve an end concentration of 5 mM.
3. Reduction for 20 minutes at 95° C. in a water bath.
4. Cooling the tubes to ambient temperature
5. Addition of iodoacetamide to obtain an end concentration of 12.5 mM.
6. Alkylation for 40 minutes at ambient temperature and in the dark.
7. Dilution by a factor of 6 with a 50 mM $NH_4HCO_3$ solution, pH=8.0 to obtain an end guanidine hydrochloride concentration of 1M.
8. Addition of 1 µg of trypsin.
9. Digestion at 37° C. for between 6 hours and one night.
10. Addition of formic acid down to a pH below 4 to stop the reaction.
11. The sample volume is made up to 1 mL with water/0.5% (v/v) formic acid
12. Balancing of the Waters Oasis HLB columns with 1 ml of methanol and then 1 ml of $H_2O$/0.1% (v/v) formic acid
13. Deposition of the sample which runs off by gravity
14. Washing with 1 ml of $H_2O$/0.1% (v/v) formic acid
15. Elution with 1 ml of a mixture of 80% methanol and 20% water/0.1% (v/v) formic acid
16. The eluate is evaporated with a SpeedVac® SPD2010 evaporator (Thermo Electron Corporation, Waltham, Mass., United States of America) over 2 hours, in order to obtain a volume of around 100 µl.
17. The eluate is then taken up in a water/0.5% (v/v) formic acid solution in a quantity sufficient for (QSF) 250 µl

EXAMPLE 6

Identification of a Resistance to TEM Beta-Lactams

Samples Sam10 to Sam61 are identified according to one of the methods described in examples 1, 3 or 4. The identification of the species is set out in TABLE 1.

TABLE 1

| Names | Species |
|---|---|
| Sam10 | P. mirabilis |
| Sam11 | E. coli |
| Sam12 | E. aerogenes |
| Sam13 | E. coli |
| Sam14 | E. coli |
| Sam15 | E. coli |
| Sam16 | S. marcescens |
| Sam17 | E. coli |
| Sam18 | E. coli |
| Sam19 | P. mirabilis |
| Sam20 | C. freundii |
| Sam21 | E. coli |
| Sam22 | P. mirabilis |
| Sam23 | E. coli |
| Sam24 | K. pneumoniae |
| Sam25 | E. coli |
| Sam26 | K. oxytoca |
| Sam27 | P. mirabilis |
| Sam28 | E. coli |
| Sam29 | P. mirabilis |
| Sam30 | P. rettgeri |
| Sam31 | P. stuartii |
| Sam32 | S. Derby |
| Sam33 | E. coli |
| Sam34 | E. coli |
| Sam35 | E. coli |
| Sam36 | E. coli |
| Sam37 | E. coli |
| Sam38 | E. coli |
| Sam39 | E. coli |
| Sam40 | E. coli |
| Sam41 | E. coli |
| Sam42 | E. coli |
| Sam43 | E. coli |
| Sam44 | E. coli |
| Sam45 | K. pneumoniae |
| Sam46 | E. coli |
| Sam47 | K. pneumoniae |
| Sam48 | P. mirabilis |
| Sam49 | P. mirabilis |
| Sam50 | P. mirabilis |
| Sam51 | P. mirabilis |
| Sam52 | P. mirabilis |
| Sam53 | K. pneumoniae |
| Sam54 | P. mirabilis |
| Sam55 | E. coli |
| Sam56 | E. coli |
| Sam57 | P. mirabilis |
| Sam58 | E. aerogenes |
| Sam59 | E. aerogenes |
| Sam60 | E. coli |
| Sam61 | E. coli |

Samples Sam10 to Sam61 correspond to a species able to comprise a TEM resistance mechanism (Enterobacteriaceae . . . ). The following method is then performed to search for such a mechanism.

Each sample is treated according to example 5, then a volume of 50 µl of digested proteins is injected and analysed according to the following conditions:

Dionex Ultimate 3000 chromatographic channel from the Dionex Corporation (Sunnyvale, United States of America).

Waters BEH130 C18 Column, 2.1 mm inner diameter, 100 mm length, 3.5 µm particle size (Waters, Saint-Quentin En Yvelines, France).

Solvent A: $H_2O$+0.1% formic acid.

Solvent B: ACN+0.1% formic acid.

HPLC gradient defined in Table 2 hereafter:

TABLE 2

| Time (min) | Flow (μl) | Solvent A (%) | Solvent B (%) |
|---|---|---|---|
| 0 | 300 | 98 | 2 |
| 3 | 300 | 98 | 2 |
| 34 | 300 | 54.6 | 45.4 |
| 35 | 300 | 0 | 100 |
| 55 | 300 | 0 | 100 |
| 55.1 | 300 | 98 | 2 |
| 74 | 300 | 98 | 2 |

The eluate coming from the chromatographic column is directly injected into the ionising source of the QTRAP® 5500 mass spectrometer from Applied Biosystems (Foster City, United States of America).

The peptides coming from the digestion of the microorganism proteins are analysed by the mass spectrometer in MRM mode. Only the peptides indicated in TABLE 3 are detected. To this end, the fragment(s) of the peptides indicated in TABLE 3 is/are detected. The charge state of the precursor, and the possible existence of an oxidised methionine, are also indicated in TABLE 3.

TABLE 3

| Transition number | Peptide | Methionine oxidation | Fragment ion | Charge state of the precursor | Clinical interest |
|---|---|---|---|---|---|
| 1 | DAENQLGAR | no | y4 monocharged | 2 | TEM |
| 2 | DAENQLGAR | no | y6 monocharged | 2 | TEM |
| 3 | DAENQLGAR | no | y7 monocharged | 2 | TEM |
| 4 | ELTAFLHNIGDHVTR | no | y4 monocharged | 2 | TEM |
| 5 | ELTAFLHNIGDHVTR | no | y8 monocharged | 2 | TEM |
| 6 | ELTAFLHNIGDHVTR | no | y9 monocharged | 2 | TEM |
| 7 | ELTAFLHNMGDNVTR | no | y7 monocharged | 2 | 2b |
| 8 | ELTAFLHNMGDNVTR | no | y8 monocharged | 2 | 2b |
| 9 | ELTAFLHNMGDNVTR | no | y9 monocharged | 2 | 2b |
| 10 | FPMISTFK | yes | y5 monocharged | 2 | 2br |
| 11 | FPMISTFK | yes | y6 monocharged | 2 | 2br |
| 12 | FPMISTFK | yes | y7 monocharged | 2 | 2br |
| 13 | FPMISTFK | no | y5 monocharged | 2 | 2br |
| 14 | FPMISTFK | no | y6 monocharged | 2 | 2br |
| 15 | FPMISTFK | no | y7 monocharged | 2 | 2br |
| 16 | GEPELNEAIPNDER | no | y12 dicharged | 2 | 2be |
| 17 | GEPELNEAIPNDER | no | y5 monocharged | 2 | 2be |
| 18 | GEPELNEAIPNDER | no | y7 monocharged | 2 | 2be |
| 19 | GSLGIIAALGPDGKPSR | no | y10 monocharged | 2 | 2br |
| 20 | GSLGIIAALGPDGKPSR | no | y8 monocharged | 2 | 2br |
| 21 | GSLGIIAALGPDGKPSR | no | y9 monocharged | 2 | 2br |
| 22 | IHYSQNDLVEYSPVTEK | no | y6 monocharged | 3 | TEM |
| 23 | IHYSQNDLVEYSPVTEK | no | y7 monocharged | 3 | TEM |
| 24 | IHYSQNDLVEYSPVTEK | no | y8 monocharged | 3 | TEM |
| 25 | ILESFRPEER | no | b6 monocharged | 2 | TEM |
| 26 | ILESFRPEER | no | b8 monocharged | 2 | TEM |
| 27 | ILESFRPEER | no | y7 dicharged | 2 | TEM |
| 28 | IVVIYTTGGQATMDER | yes | y7 monocharged | 2 | 2be |
| 29 | IVVIYTTGGQATMDER | yes | y8 monocharged | 2 | 2be |
| 30 | IVVIYTTGGQATMDER | yes | y9 monocharged | 2 | 2be |
| 31 | IVVIYTTGGQATMDER | no | y6 monocharged | 2 | 2be |

TABLE 3-continued

| Transition number | Peptide | Methionine oxidation | Fragment ion | Charge state of the precursor | Clinical interest |
|---|---|---|---|---|---|
| 32 | IVVIYTTGGQATMDER | no | y8 monocharged | 2 | 2be |
| 33 | IVVIYTTGGQATMDER | no | y9 monocharged | 2 | 2be |
| 34 | LDSWEPELNEAIPNDER | no | y5 monocharged | 3 | 2be |
| 35 | LDSWEPELNEAIPNDER | no | y6 monocharged | 3 | 2be |
| 36 | LDSWEPELNEAIPNDER | no | y7 monocharged | 3 | 2be |
| 37 | QIAEICASLIK | no | y6 monocharged | 2 | TEM |
| 38 | QIAEICASLIK | no | y7 monocharged | 2 | TEM |
| 39 | QIAEICASLIK | no | y8 monocharged | 2 | TEM |
| 40 | SGANER | no | y3 monocharged | 2 | TEM |
| 41 | SGANER | no | y4 monocharged | 2 | TEM |
| 42 | SGANER | no | y5 monocharged | 2 | TEM |
| 43 | SGGSER | no | y3 monocharged | 2 | 2be |
| 44 | SGGSER | no | y4 monocharged | 2 | 2be |
| 45 | SGGSER | no | y5 monocharged | 2 | 2be |
| 46 | VDAGQEQLDR | no | y7 monocharged | 2 | TEM |
| 47 | VDAGQEQLDR | no | y8 monocharged | 2 | TEM |
| 48 | VDAGQEQLDR | no | y9 monocharged | 2 | TEM |
| 49 | VKPAEDK | no | y4 monocharged | 2 | 2be |
| 50 | VKPAEDK | no | y5 monocharged | 2 | 2be |
| 51 | VKPAEDK | no | y6 monocharged | 2 | 2be |
| 52 | WEPELNEAIPIDER | no | y12 dicharged | 2 | 2be |
| 53 | WEPELNEAIPIDER | no | y5 monocharged | 2 | 2be |
| 54 | WEPELNEAIPIDER | no | y7 monocharged | 2 | 2be |
| 55 | DTTMPAAMATK | yes | y7 monocharged | 2 | TEM |
| 56 | DTTMPAAMATK | yes | y8 monocharged | 2 | TEM |
| 57 | DTTMPAAMATK | yes | y9 monocharged | 2 | TEM |
| 58 | DTTMPAAMATK | no | y7 monocharged | 2 | TEM |
| 59 | DTTMPAAMATK | no | y8 monocharged | 2 | TEM |
| 60 | DTTMPAAMATK | no | y9 monocharged | 2 | TEM |
| 61 | ELTAFLHNMGDHVTR | no | y13 dicharged | 2 | TEM |
| 62 | ELTAFLHNMGDHVTR | no | y4 monocharged | 2 | TEM |
| 63 | ELTAFLHNMGDHVTR | no | y8 monocharged | 2 | TEM |
| 64 | EPELNEAIPNDER | no | y5 monocharged | 2 | TEM |
| 65 | EPELNEAIPNDER | no | y7 monocharged | 2 | TEM |
| 66 | EPELNEAIPNDER | no | y8 monocharged | 2 | TEM |
| 67 | FPMMSTFK | yes | y6 monocharged | 2 | TEM |
| 68 | FPMMSTFK | yes | y7 monocharged | 2 | TEM |
| 69 | FPMMSTFK | yes | y7 dicharged | 2 | TEM |
| 70 | FPMMSTFK | no | y6 monocharged | 2 | TEM |

TABLE 3-continued

| Transition number | Peptide | Methionine oxidation | Fragment ion | Charge state of the precursor | Clinical interest |
|---|---|---|---|---|---|
| 71 | FPMMSTFK | no | y7 monocharged | 2 | TEM |
| 72 | FPMMSTFK | no | y7 dicharged | 2 | TEM |
| 73 | GIIAALGPDGKPSR | no | y7 monocharged | 2 | TEM |
| 74 | GIIAALGPDGKPSR | no | y8 monocharged | 2 | TEM |
| 75 | GIIAALGPDGKPSR | no | y9 monocharged | 2 | TEM |
| 76 | IDAGQEQLGR | no | y7 monocharged | 2 | TEM |
| 77 | IDAGQEQLGR | no | y8 monocharged | 2 | TEM |
| 78 | IDAGQEQLGR | no | y9 monocharged | 2 | TEM |
| 79 | IHYSQNDLVK | no | y7 monocharged | 2 | 2be |
| 80 | IHYSQNDLVK | no | y8 monocharged | 2 | 2be |
| 81 | IHYSQNDLVK | no | y9 dicharged | 2 | 2be |
| 82 | IHYSQSDVVEYSPVTEK | no | y16 dicharged | 2 | TEM |
| 83 | IHYSQSDVVEYSPVTEK | no | y5 monocharged | 2 | TEM |
| 84 | IHYSQSDVVEYSPVTEK | no | y6 monocharged | 2 | TEM |
| 85 | IVVIYMTGGQATMDER | no | y6 monocharged | 2 | 2be |
| 86 | IVVIYMTGGQATMDER | no | y8 monocharged | 2 | 2be |
| 87 | IVVIYMTGGQATMDER | no | y9 monocharged | 2 | 2be |
| 88 | LDCWEPELNEAIPNDER | no | y5 monocharged | 3 | 2be |
| 89 | LDCWEPELNEAIPNDER | no | y6 monocharged | 3 | 2be |
| 90 | LDCWEPELNEAIPNDER | no | y7 monocharged | 3 | 2be |
| 91 | MSIQHFR | yes | y4 monocharged | 2 | TEM |
| 92 | MSIQHFR | yes | y5 monocharged | 2 | TEM |
| 93 | MSIQHFR | yes | y6 monocharged | 2 | TEM |
| 94 | MSIQHFR | no | y4 monocharged | 2 | TEM |
| 95 | MSIQHFR | no | y5 monocharged | 2 | TEM |
| 96 | MSIQHFR | no | y6 monocharged | 2 | TEM |
| 97 | QQLIDWMEADK | no | y5 monocharged | 2 | TEM |
| 98 | QQLIDWMEADK | no | y6 monocharged | 2 | TEM |
| 99 | QQLIDWMEADK | no | y7 monocharged | 2 | TEM |
| 100 | SGASER | no | y3 monocharged | 2 | 2be |
| 101 | SGASER | no | y4 monocharged | 2 | 2be |
| 102 | SGASER | no | y5 monocharged | 2 | 2be |
| 103 | VALIPFLAAFCLPVFAHPETLVK | no | y11 dicharged | 3 | 2ber |
| 104 | VALIPFLAAFCLPVFAHPETLVK | no | y6 monocharged | 3 | 2ber |
| 105 | VALIPFLAAFCLPVFAHPETLVK | no | y8 monocharged | 3 | 2ber |
| 106 | VGYIELDLNSGK | no | y7 monocharged | 2 | TEM |
| 107 | VGYIELDLNSGK | no | y8 monocharged | 2 | TEM |
| 108 | VGYIELDLNSGK | no | y9 monocharged | 2 | TEM |
| 109 | VLLCGAELSR | no | y6 monocharged | 2 | TEM |

TABLE 3-continued

| Transition number | Peptide | Methionine oxidation | Fragment ion | Charge state of the precursor | Clinical interest |
|---|---|---|---|---|---|
| 110 | VLLCGAELSR | no | y7 monocharged | 2 | TEM |
| 111 | VLLCGAELSR | no | y8 monocharged | 2 | TEM |
| 112 | DAEDQLGAR | no | y5 monocharged | 2 | TEM |
| 113 | DAEDQLGAR | no | y6 monocharged | 2 | TEM |
| 114 | DAEDQLGAR | no | y7 monocharged | 2 | TEM |
| 115 | ETTTPAAMATTLR | yes | y7 monocharged | 2 | 2be |
| 116 | ETTTPAAMATTLR | yes | y9 monocharged | 2 | 2be |
| 117 | ETTTPAAMATTLR | yes | y9 dicharged | 2 | 2be |
| 118 | ETTTPAAMATTLR | no | y7 monocharged | 2 | 2be |
| 119 | ETTTPAAMATTLR | no | y9 monocharged | 2 | 2be |
| 120 | ETTTPAAMATTLR | no | y9 dicharged | 2 | 2be |
| 121 | FPMVSTFK | yes | y6 monocharged | 2 | TEM |
| 122 | FPMVSTFK | yes | y7 monocharged | 2 | TEM |
| 123 | FPMVSTFK | yes | y7 dicharged | 2 | TEM |
| 124 | FPMVSTFK | no | y6 monocharged | 2 | TEM |
| 125 | FPMVSTFK | no | y7 monocharged | 2 | TEM |
| 126 | FPMVSTFK | no | y7 dicharged | 2 | TEM |
| 127 | GSGGIIAALGPDGKPSR | no | y7 monocharged | 2 | 2br |
| 128 | GSGGIIAALGPDGKPSR | no | y8 monocharged | 2 | 2br |
| 129 | GSGGIIAALGPDGKPSR | no | y9 monocharged | 2 | 2br |
| 130 | HLTDGMTVR | yes | y5 monocharged | 2 | TEM |
| 131 | HLTDGMTVR | yes | y7 monocharged | 2 | TEM |
| 132 | HLTDGMTVR | yes | y8 monocharged | 2 | TEM |
| 133 | HLTDGMTVR | no | y4 monocharged | 2 | TEM |
| 134 | HLTDGMTVR | no | y7 monocharged | 2 | TEM |
| 135 | HLTDGMTVR | no | y8 monocharged | 2 | TEM |
| 136 | IVIIYTTGSQATMDER | no | b4 monocharged | 2 | 2br |
| 137 | IVIIYTTGSQATMDER | no | y2 monocharged | 2 | 2br |
| 138 | IVIIYTTGSQATMDER | no | y9 monocharged | 2 | 2br |
| 139 | IVVIYTTGSQATMDEQNR | yes | y5 monocharged | 3 | 2br |
| 140 | IVVIYTTGSQATMDEQNR | yes | y6 monocharged | 3 | 2br |
| 141 | IVVIYTTGSQATMDEQNR | yes | y7 monocharged | 3 | 2br |
| 142 | IVVIYTTGSQATMDEQNR | no | y5 monocharged | 3 | 2br |
| 143 | IVVIYTTGSQATMDEQNR | no | y6 monocharged | 3 | 2br |
| 144 | IVVIYTTGSQATMDEQNR | no | y7 monocharged | 3 | 2br |
| 145 | LDHWEPELNEAVPNDER | no | y5 monocharged | 3 | 2be |
| 146 | LDHWEPELNEAVPNDER | no | y6 monocharged | 3 | 2be |
| 147 | LDHWEPELNEAVPNDER | no | y7 monocharged | 3 | 2be |
| 148 | LLTGELLTLASQQQLIDWMEADK | yes | b8 monocharged | 3 | TEM |

TABLE 3-continued

| Transition number | Peptide | Methionine oxidation | Fragment ion | Charge state of the precursor | Clinical interest |
|---|---|---|---|---|---|
| 149 | LLTGELLTLASQQQLIDWMEADK | yes | y6 monocharged | 3 | TEM |
| 150 | LLTGELLTLASQQQLIDWMEADK | yes | y7 monocharged | 3 | TEM |
| 151 | LLTGELLTLASQQQLIDWMEADK | no | b4 monocharged | 3 | TEM |
| 152 | LLTGELLTLASQQQLIDWMEADK | no | y6 monocharged | 3 | TEM |
| 153 | LLTGELLTLASQQQLIDWMEADK | no | y7 monocharged | 3 | TEM |
| 154 | QIAEIGASLIK | no | y7 monocharged | 2 | TEM |
| 155 | QIAEIGASLIK | no | y8 monocharged | 2 | TEM |
| 156 | QIAEIGASLIK | no | y9 monocharged | 2 | TEM |
| 157 | QTAEIGASLIK | no | y7 monocharged | 2 | 2be |
| 158 | QTAEIGASLIK | no | y8 monocharged | 2 | 2be |
| 159 | QTAEIGASLIK | no | y9 monocharged | 2 | 2be |
| 160 | SGADER | no | y3 monocharged | 2 | TEM |
| 161 | SGADER | no | y4 monocharged | 2 | TEM |
| 162 | SGADER | no | y5 monocharged | 2 | TEM |
| 163 | SGASK | no | y2 monocharged | 2 | 2be |
| 164 | SGASK | no | y3 monocharged | 2 | 2be |
| 165 | SGASK | no | y4 monocharged | 2 | 2be |
| 166 | VAGPLLR | no | y4 monocharged | 2 | TEM |
| 167 | VAGPLLR | no | y5 monocharged | 2 | TEM |
| 168 | VAGPLLR | no | y6 monocharged | 2 | TEM |
| 169 | VGYIEMDLNSGK | yes | y10 dicharged | 2 | 2be |
| 170 | VGYIEMDLNSGK | yes | y7 monocharged | 2 | 2be |
| 171 | VGYIEMDLNSGK | yes | y8 monocharged | 2 | 2be |
| 172 | VGYIEMDLNSGK | no | y7 monocharged | 2 | 2be |
| 173 | VGYIEMDLNSGK | no | y8 monocharged | 2 | 2be |
| 174 | VGYIEMDLNSGK | no | y9 monocharged | 2 | 2be |
| 175 | WEPELNEAIPNDER | no | y12 dicharged | 2 | TEM |
| 176 | WEPELNEAIPNDER | no | y5 monocharged | 2 | TEM |
| 177 | WEPELNEAIPNDER | no | y7 monocharged | 2 | TEM |
| 178 | ELTAFLHNMGEHVTR | no | y7 monocharged | 2 | 2b |
| 179 | ELTAFLHNMGEHVTR | no | y8 monocharged | 2 | 2b |
| 180 | ELTAFLHNMGEHVTR | no | y9 monocharged | 2 | 2b |
| 181 | FPMLSTFK | yes | y6 monocharged | 2 | TEM |
| 182 | FPMLSTFK | yes | y7 monocharged | 2 | TEM |
| 183 | FPMLSTFK | yes | y7 dicharged | 2 | TEM |
| 184 | FPMLSTFK | no | y6 monocharged | 2 | TEM |
| 185 | FPMLSTFK | no | y7 monocharged | 2 | TEM |
| 186 | FPMLSTFK | no | y7 dicharged | 2 | TEM |
| 187 | GSCGIIAALGPDGKPSR | no | y7 monocharged | 2 | 2br |

TABLE 3-continued

| Transition number | Peptide | Methionine oxidation | Fragment ion | Charge state of the precursor | Clinical interest |
|---|---|---|---|---|---|
| 188 | GSCGIIAALGPDGKPSR | no | y8 monocharged | 2 | 2br |
| 189 | GSCGIIAALGPDGKPSR | no | y9 monocharged | 2 | 2br |
| 190 | GSSGIIAALGPDGKPSR | no | y7 monocharged | 2 | TEM |
| 191 | GSSGIIAALGPDGKPSR | no | y8 monocharged | 2 | TEM |
| 192 | GSSGIIAALGPDGKPSR | no | y9 monocharged | 2 | TEM |
| 193 | ILESFRPEK | no | y5 monocharged | 2 | TEM |
| 194 | ILESFRPEK | no | y6 monocharged | 2 | TEM |
| 195 | ILESFRPEK | no | y7 monocharged | 2 | TEM |
| 196 | IVVIYTTGSQATMDELNR | yes | y5 monocharged | 3 | 2br |
| 197 | IVVIYTTGSQATMDELNR | yes | y6 monocharged | 3 | 2br |
| 198 | IVVIYTTGSQATMDELNR | yes | y7 monocharged | 3 | 2br |
| 199 | IVVIYTTGSQATMDELNR | no | y5 monocharged | 3 | 2br |
| 200 | IVVIYTTGSQATMDELNR | no | y6 monocharged | 3 | 2br |
| 201 | IVVIYTTGSQATMDELNR | no | y7 monocharged | 3 | 2br |
| 202 | IVVIYTTGSQATMDER | no | y6 monocharged | 2 | TEM |
| 203 | IVVIYTTGSQATMDER | no | y8 monocharged | 2 | TEM |
| 204 | IVVIYTTGSQATMDER | no | y9 monocharged | 2 | TEM |
| 205 | LHCWEPELNEAIPNDER | no | y5 monocharged | 3 | 2be |
| 206 | LHCWEPELNEAIPNDER | no | y6 monocharged | 3 | 2be |
| 207 | LHCWEPELNEAIPNDER | no | y7 monocharged | 3 | 2be |
| 208 | LLTGELLTLASR | no | y6 monocharged | 2 | TEM |
| 209 | LLTGELLTLASR | no | y7 monocharged | 2 | TEM |
| 210 | LLTGELLTLASR | no | y9 monocharged | 2 | TEM |
| 211 | QQLIDWMADK | yes | y6 monocharged | 2 | 2ber |
| 212 | QQLIDWMADK | yes | y7 monocharged | 2 | 2ber |
| 213 | QQLIDWMADK | yes | y8 monocharged | 2 | 2ber |
| 214 | QQLIDWMADK | no | y6 monocharged | 2 | 2ber |
| 215 | QQLIDWMADK | no | y7 monocharged | 2 | 2ber |
| 216 | QQLIDWMADK | no | y8 monocharged | 2 | 2ber |
| 217 | SALPAGWFIADK | no | y7 monocharged | 2 | TEM |
| 218 | SALPAGWFIADK | no | y9 monocharged | 2 | TEM |
| 219 | SALPAGWFIADK | no | y9 dicharged | 2 | TEM |
| 220 | SGAGVR | no | y3 monocharged | 2 | 2be |
| 221 | SGAGVR | no | y4 monocharged | 2 | 2be |
| 222 | SGAGVR | no | y5 monocharged | 2 | 2be |
| 223 | SGTGER | no | y3 monocharged | 2 | 2be |
| 224 | SGTGER | no | y4 monocharged | 2 | 2be |
| 225 | SGTGER | no | y5 monocharged | 2 | 2be |
| 226 | VALIPFFAAFCIPVFAHPETLVK | no | y11 dicharged | 3 | 2br |

TABLE 3-continued

| Transition number | Peptide | Methionine oxidation | Fragment ion | Charge state of the precursor | Clinical interest |
|---|---|---|---|---|---|
| 227 | VALIPFFAAFCIPVFAHPETLVK | no | y6 monocharged | 3 | 2br |
| 228 | VALIPFFAAFCIPVFAHPETLVK | no | y7 monocharged | 3 | 2br |
| 229 | VLLCGAVLSR | no | y6 monocharged | 2 | TEM |
| 230 | VLLCGAVLSR | no | y7 monocharged | 2 | TEM |
| 231 | VLLCGAVLSR | no | y8 monocharged | 2 | TEM |
| 232 | YSPVTEK | no | y4 monocharged | 2 | 2be |
| 233 | YSPVTEK | no | y5 monocharged | 2 | 2be |
| 234 | YSPVTEK | no | y6 monocharged | 2 | 2be |
| 235 | CEPELNEAIPNDER | no | y12 dicharged | 2 | 2br |
| 236 | CEPELNEAIPNDER | no | y5 monocharged | 2 | 2br |
| 237 | CEPELNEAIPNDER | no | y8 monocharged | 2 | 2br |
| 238 | DAEDQVGAR | no | y5 monocharged | 2 | 2be |
| 239 | DAEDQVGAR | no | y6 monocharged | 2 | 2be |
| 240 | DAEDQVGAR | no | y7 monocharged | 2 | 2be |
| 241 | DTTMPVAMATTLR | no | y7 monocharged | 2 | TEM |
| 242 | DTTMPVAMATTLR | no | y9 monocharged | 2 | TEM |
| 243 | DTTMPVAMATTLR | no | y9 dicharged | 2 | TEM |
| 244 | ELTAFLR | no | y4 monocharged | 2 | 2be |
| 245 | ELTAFLR | no | y5 monocharged | 2 | 2be |
| 246 | ELTAFLR | no | y6 monocharged | 2 | 2be |
| 247 | GSTGIIAALGPDGKPSR | no | y10 monocharged | 2 | TEM |
| 248 | GSTGIIAALGPDGKPSR | no | y7 monocharged | 2 | TEM |
| 249 | GSTGIIAALGPDGKPSR | no | y9 monocharged | 2 | TEM |
| 250 | HLTGGMTVR | yes | y5 monocharged | 2 | 2b |
| 251 | HLTGGMTVR | yes | y6 monocharged | 2 | 2b |
| 252 | HLTGGMTVR | yes | y7 monocharged | 2 | 2b |
| 253 | HLTGGMTVR | no | y5 monocharged | 2 | 2b |
| 254 | HLTGGMTVR | no | y6 monocharged | 2 | 2b |
| 255 | HLTGGMTVR | no | y7 monocharged | 2 | 2b |
| 256 | IVVIYMTGSQATMDELNR | yes | y6 monocharged | 3 | 2ber |
| 257 | IVVIYMTGSQATMDELNR | yes | y7 monocharged | 3 | 2ber |
| 258 | IVVIYMTGSQATMDELNR | yes | y8 monocharged | 3 | 2ber |
| 259 | IVVIYMTGSQATMDELNR | no | y5 monocharged | 3 | 2ber |
| 260 | IVVIYMTGSQATMDELNR | no | y6 monocharged | 3 | 2ber |
| 261 | IVVIYMTGSQATMDELNR | no | y7 monocharged | 3 | 2ber |
| 262 | LDHWEPELNEAIPNDER | no | y5 monocharged | 3 | 2be |
| 263 | LDHWEPELNEAIPNDER | no | y6 monocharged | 3 | 2be |
| 264 | LDHWEPELNEAIPNDER | no | y7 monocharged | 3 | 2be |
| 265 | LLTSELLTLASR | no | y10 monocharged | 2 | TEM |

TABLE 3-continued

| Transition number | Peptide | Methionine oxidation | Fragment ion | Charge state of the precursor | Clinical interest |
|---|---|---|---|---|---|
| 266 | LLTSELLTLASR | no | y7 monocharged | 2 | TEM |
| 267 | LLTSELLTLASR | no | y9 monocharged | 2 | TEM |
| 268 | QIAEIGGSLIK | no | y7 monocharged | 2 | 2ber |
| 269 | QIAEIGGSLIK | no | y8 monocharged | 2 | 2ber |
| 270 | QIAEIGGSLIK | no | y9 monocharged | 2 | 2ber |
| 271 | QQLIDWMEVDK | yes | y6 monocharged | 2 | TEM |
| 272 | QQLIDWMEVDK | yes | y7 monocharged | 2 | TEM |
| 273 | QQLIDWMEVDK | yes | y8 monocharged | 2 | TEM |
| 274 | QQLIDWMEVDK | no | y5 monocharged | 2 | TEM |
| 275 | QQLIDWMEVDK | no | y6 monocharged | 2 | TEM |
| 276 | QQLIDWMEVDK | no | y7 monocharged | 2 | TEM |
| 277 | SVLPAGWFIADK | no | y10 dicharged | 2 | 2be |
| 278 | SVLPAGWFIADK | no | y9 monocharged | 2 | 2be |
| 279 | SVLPAGWFIADK | no | y9 dicharged | 2 | 2be |
| 280 | VAGPLMR | yes | y4 monocharged | 2 | 2br |
| 281 | VAGPLMR | yes | y5 monocharged | 2 | 2br |
| 282 | VAGPLMR | yes | y6 monocharged | 2 | 2br |
| 283 | VAGPLMR | no | y4 monocharged | 2 | 2br |
| 284 | VAGPLMR | no | y5 monocharged | 2 | 2br |
| 285 | VAGPLMR | no | y6 monocharged | 2 | 2br |
| 286 | VALIPFFAAFCLPVFAHPDTLVK | no | y11 dicharged | 3 | TEM |
| 287 | VALIPFFAAFCLPVFAHPDTLVK | no | y17 dicharged | 3 | TEM |
| 288 | VALIPFFAAFCLPVFAHPDTLVK | no | y6 monocharged | 3 | TEM |
| 289 | VALIPFFAAFCLPVFAHPK | no | y15 dicharged | 3 | TEM |
| 290 | VALIPFFAAFCLPVFAHPK | no | y7 monocharged | 3 | TEM |
| 291 | VALIPFFAAFCLPVFAHPK | no | y9 dicharged | 3 | TEM |
| 292 | VEDAEDQLGAR | no | y7 monocharged | 2 | 2b |
| 293 | VEDAEDQLGAR | no | y8 monocharged | 2 | 2b |
| 294 | VEDAEDQLGAR | no | y9 monocharged | 2 | 2b |
| 295 | DAEDQLGSTSGYIELDLNSGK | no | y7 monocharged | 3 | 2ber |
| 296 | DAEDQLGSTSGYIELDLNSGK | no | y8 monocharged | 3 | 2ber |
| 297 | DAEDQLGSTSGYIELDLNSGK | no | y9 monocharged | 3 | 2ber |
| 298 | DTTMPAAMATTLR | no | y7 monocharged | 2 | TEM |
| 299 | DTTMPAAMATTLR | no | y8 monocharged | 2 | TEM |
| 300 | DTTMPAAMATTLR | no | y9 monocharged | 2 | TEM |
| 301 | DTTTPAAMATTLR | yes | y7 monocharged | 2 | TEM |
| 302 | DTTTPAAMATTLR | yes | y8 monocharged | 2 | TEM |
| 303 | DTTTPAAMATTLR | yes | y9 dicharged | 2 | TEM |
| 304 | DTTTPAAMATTLR | no | y7 monocharged | 2 | TEM |

TABLE 3-continued

| Transition number | Peptide | Methionine oxidation | Fragment ion | Charge state of the precursor | Clinical interest |
|---|---|---|---|---|---|
| 305 | DTTTPAAMATTLR | no | y9 monocharged | 2 | TEM |
| 306 | DTTTPAAMATTLR | no | y9 dicharged | 2 | TEM |
| 307 | GSHGIIAALGPDGKPSR | no | b6 monocharged | 2 | 2br |
| 308 | GSHGIIAALGPDGKPSR | no | y15 dicharged | 2 | 2br |
| 309 | GSHGIIAALGPDGKPSR | no | y8 monocharged | 2 | 2br |
| 310 | HLPDGMTVR | no | y5 monocharged | 2 | TEM |
| 311 | HLPDGMTVR | no | y7 monocharged | 2 | TEM |
| 312 | HLPDGMTVR | no | y8 monocharged | 2 | TEM |
| 313 | IHYSQSDLVEYSPVTEK | no | y16 dicharged | 2 | 2be |
| 314 | IHYSQSDLVEYSPVTEK | no | y7 monocharged | 2 | 2be |
| 315 | IHYSQSDLVEYSPVTEK | no | y8 monocharged | 2 | 2be |
| 316 | IVVIYMTGSQATMDER | no | y6 monocharged | 2 | TEM |
| 317 | IVVIYMTGSQATMDER | no | y8 monocharged | 2 | TEM |
| 318 | IVVIYMTGSQATMDER | no | y9 monocharged | 2 | TEM |
| 319 | LLTDELLTLASR | no | y5 monocharged | 2 | 2be |
| 320 | LLTDELLTLASR | no | y6 monocharged | 2 | 2be |
| 321 | LLTDELLTLASR | no | y7 monocharged | 2 | 2be |
| 322 | NMGDHVTR | yes | y4 monocharged | 2 | 2be |
| 323 | NMGDHVTR | yes | y5 monocharged | 2 | 2be |
| 324 | NMGDHVTR | yes | y6 monocharged | 2 | 2be |
| 325 | NMGDHVTR | no | y4 monocharged | 2 | 2be |
| 326 | NMGDHVTR | no | y5 monocharged | 2 | 2be |
| 327 | NMGDHVTR | no | y6 monocharged | 2 | 2be |
| 328 | QIVEIGASLIK | no | y7 monocharged | 2 | 2be |
| 329 | QIVEIGASLIK | no | y8 monocharged | 2 | 2be |
| 330 | QIVEIGASLIK | no | y9 monocharged | 2 | 2be |
| 331 | SGAGER | no | y3 monocharged | 2 | TEM |
| 332 | SGAGER | no | y4 monocharged | 2 | TEM |
| 333 | SGAGER | no | y5 monocharged | 2 | TEM |
| 334 | VAEPLLR | no | y4 monocharged | 2 | 2b |
| 335 | VAEPLLR | no | y5 monocharged | 2 | 2b |
| 336 | VAEPLLR | no | y6 monocharged | 2 | 2b |
| 337 | VALIPFFAAFCFPVFAHPETLVK | no | b11 monocharged | 3 | TEM |
| 338 | VALIPFFAAFCFPVFAHPETLVK | no | y11 dicharged | 3 | TEM |
| 339 | VALIPFFAAFCFPVFAHPETLVK | no | y6 monocharged | 3 | TEM |
| 340 | VALIPFFAAFCLPVFAHPETLVK | no | b7 monocharged | 3 | TEM |
| 341 | VALIPFFAAFCLPVFAHPETLVK | no | y11 dicharged | 3 | TEM |
| 342 | VALIPFFAAFCLPVFAHPETLVK | no | y6 monocharged | 3 | TEM |

TABLE 3-continued

| Transition number | Peptide | Methionine oxidation | Fragment ion | Charge state of the precursor | Clinical interest |
|---|---|---|---|---|---|
| 343 | VDAGQEQLGR | no | y5 monocharged | 2 | TEM |
| 344 | VDAGQEQLGR | no | y7 monocharged | 2 | TEM |
| 345 | VDAGQEQLGR | no | y8 monocharged | 2 | TEM |
| 346 | VGYIELDPNSGK | no | y5 monocharged | 2 | 2be |
| 347 | VGYIELDPNSGK | no | y7 monocharged | 2 | 2be |
| 348 | VGYIELDPNSGK | no | y8 monocharged | 2 | 2be |

The transitions mentioned in TABLE 3 are detected by using the parameters set out in TABLE 4. The precursor peptide retention time and the transitions, i.e. the (m/z)1 ratio in Q1 and (m/z)2 ratio in Q3, as well as the collision energy used to fragment the precursor ion, are indicated in TABLE 4. The threshold above which the transition is considered to be detected is also indicated in TABLE 4.

TABLE 4

| Transition number | Retention time (minutes) | (m/z) filtered in Q1 | (m/z) filtered in Q3 | Collision energy (eV) | Positivity threshold |
|---|---|---|---|---|---|
| 1 | 9.9 | 487.24 | 416.26 | 26 | 2500 |
| 2 | 9.9 | 487.24 | 658.36 | 26 | 2500 |
| 3 | 9.9 | 487.24 | 787.41 | 26 | 2500 |
| 4 | 19.3 | 861.95 | 512.29 | 43 | 2500 |
| 5 | 19.3 | 861.95 | 911.47 | 43 | 2500 |
| 6 | 19.3 | 861.95 | 1048.53 | 43 | 2500 |
| 7 | 19.3 | 859.42 | 792.37 | 43 | 2500 |
| 8 | 19.3 | 859.42 | 906.41 | 43 | 2500 |
| 9 | 19.3 | 859.42 | 1043.47 | 43 | 2500 |
| 10 | 18.1 | 493.751 | 595.34 | 27 | 2500 |
| 11 | 18.1 | 493.751 | 742.38 | 27 | 2500 |
| 12 | 18.1 | 493.751 | 839.43 | 27 | 2500 |
| 13 | 19.8 | 485.757 | 595.34 | 26 | 2500 |
| 14 | 19.8 | 485.757 | 726.39 | 26 | 2500 |
| 15 | 19.8 | 485.757 | 823.44 | 26 | 2500 |
| 16 | 15 | 791.87 | 698.84 | 40 | 2500 |
| 17 | 15 | 791.87 | 630.28 | 40 | 2500 |
| 18 | 15 | 791.87 | 814.41 | 40 | 2500 |
| 19 | 19.1 | 804.96 | 997.54 | 40 | 5000 |
| 20 | 19.1 | 804.96 | 813.42 | 40 | 5000 |
| 21 | 19.1 | 804.96 | 926.51 | 40 | 5000 |
| 22 | 16.6 | 674.67 | 660.36 | 38 | 2500 |
| 23 | 16.6 | 674.67 | 823.42 | 38 | 2500 |
| 24 | 16.6 | 674.67 | 952.46 | 38 | 2500 |
| 25 | 14.6 | 638.34 | 746.42 | 33 | 2500 |
| 26 | 14.6 | 638.34 | 972.51 | 33 | 2500 |
| 27 | 14.6 | 638.34 | 460.73 | 33 | 2500 |
| 28 | 15.9 | 885.44 | 866.37 | 44 | 2500 |
| 29 | 15.9 | 885.44 | 923.39 | 44 | 2500 |
| 30 | 15.9 | 885.44 | 980.41 | 44 | 2500 |
| 31 | 17 | 877.44 | 722.31 | 44 | 2500 |
| 32 | 17 | 877.44 | 907.39 | 44 | 2500 |
| 33 | 17 | 877.44 | 964.42 | 44 | 2500 |
| 34 | 19.5 | 676.32 | 630.28 | 38 | 2500 |
| 35 | 19.5 | 676.32 | 743.37 | 38 | 2500 |
| 36 | 19.5 | 676.32 | 814.41 | 38 | 2500 |
| 37 | 18.6 | 623.35 | 691.38 | 32 | 2500 |
| 38 | 18.6 | 623.35 | 804.46 | 32 | 2500 |
| 39 | 18.6 | 623.35 | 933.51 | 32 | 2500 |
| 40 | 1.3 | 317.15 | 418.2 | 19 | 6000 |
| 41 | 1.3 | 317.15 | 489.24 | 19 | 6000 |
| 42 | 1.3 | 317.15 | 546.26 | 19 | 6000 |
| 43 | 1 | 296.64 | 391.19 | 18 | 2500 |
| 44 | 1 | 296.64 | 448.22 | 18 | 2500 |
| 45 | 1 | 296.64 | 505.24 | 18 | 2500 |
| 46 | 10.5 | 565.78 | 845.41 | 30 | 2500 |
| 47 | 10.6 | 565.78 | 916.45 | 30 | 2500 |
| 48 | 10.6 | 565.78 | 1031.48 | 30 | 2500 |
| 49 | 4.1 | 393.72 | 462.22 | 22 | 2500 |
| 50 | 4.1 | 393.72 | 559.27 | 22 | 2500 |
| 51 | 4.1 | 393.72 | 687.37 | 22 | 2500 |
| 52 | 20.1 | 855.92 | 698.36 | 43 | 2500 |
| 53 | 20.1 | 855.92 | 629.33 | 43 | 2500 |
| 54 | 20.1 | 855.92 | 813.44 | 43 | 2500 |
| 55 | 17 | 585.26 | 705.36 | 31 | 4000 |
| 56 | 17 | 585.26 | 852.4 | 31 | 4000 |
| 57 | 16.9 | 585.26 | 953.44 | 31 | 4000 |
| 58 | 13.2 | 569.27 | 689.37 | 30 | 2500 |
| 59 | 13.2 | 569.27 | 820.41 | 30 | 2500 |
| 60 | 13.2 | 569.27 | 921.45 | 30 | 2500 |
| 61 | 18.3 | 870.93 | 749.86 | 43 | 2500 |
| 62 | 18.3 | 870.93 | 512.29 | 43 | 2500 |
| 63 | 18.3 | 870.93 | 929.43 | 43 | 2500 |
| 64 | 14.9 | 763.36 | 630.28 | 39 | 2500 |
| 65 | 14.9 | 763.36 | 814.41 | 39 | 2500 |
| 66 | 14.9 | 763.36 | 943.45 | 39 | 2500 |
| 67 | 14.9 | 510.73 | 776.33 | 27 | 2500 |
| 68 | 14.9 | 510.73 | 873.38 | 27 | 2500 |
| 69 | 14.9 | 510.73 | 437.2 | 27 | 2500 |
| 70 | 18.9 | 494.74 | 744.34 | 27 | 2500 |
| 71 | 18.9 | 494.74 | 841.39 | 27 | 2500 |
| 72 | 18.9 | 494.74 | 421.2 | 27 | 2500 |
| 73 | 15.5 | 676.39 | 756.4 | 35 | 2500 |
| 74 | 15.5 | 676.39 | 813.42 | 35 | 2500 |
| 75 | 15.5 | 676.39 | 926.51 | 35 | 2500 |
| 76 | 11.5 | 543.78 | 787.41 | 29 | 2500 |
| 77 | 11.5 | 543.78 | 858.44 | 29 | 2500 |
| 78 | 11.5 | 543.78 | 973.47 | 29 | 2500 |
| 79 | 12.5 | 608.82 | 803.43 | 32 | 2500 |
| 80 | 12.5 | 608.82 | 966.49 | 32 | 2500 |
| 81 | 12.5 | 608.82 | 552.28 | 32 | 2500 |
| 82 | 15.5 | 990.98 | 934.44 | 49 | 2500 |
| 83 | 15.5 | 990.98 | 573.32 | 49 | 2500 |
| 84 | 15.5 | 990.98 | 660.36 | 49 | 2500 |
| 85 | 19 | 892.44 | 722.31 | 44 | 2500 |
| 86 | 19 | 892.44 | 907.39 | 44 | 2500 |
| 87 | 19 | 892.44 | 964.42 | 44 | 2500 |
| 88 | 19.4 | 700.65 | 630.28 | 39 | 2500 |
| 89 | 19.4 | 700.65 | 743.37 | 39 | 2500 |
| 90 | 19.4 | 700.65 | 814.41 | 39 | 2500 |
| 91 | 10.4 | 467.73 | 587.3 | 26 | 2500 |
| 92 | 10.4 | 467.73 | 700.39 | 26 | 2500 |
| 93 | 10.4 | 467.73 | 787.42 | 26 | 2500 |
| 94 | 12.8 | 459.73 | 587.3 | 25 | 2500 |
| 95 | 12.8 | 459.73 | 700.39 | 25 | 2500 |
| 96 | 12.8 | 459.73 | 787.42 | 25 | 2500 |
| 97 | 20.1 | 688.83 | 593.26 | 35 | 2500 |
| 98 | 20.1 | 688.83 | 779.34 | 35 | 2500 |
| 99 | 20.1 | 688.83 | 894.37 | 35 | 2500 |
| 100 | 1.4 | 303.646 | 391.19 | 18 | 13000 |
| 101 | 1.4 | 303.646 | 462.23 | 18 | 13000 |
| 102 | 1.4 | 303.646 | 519.25 | 18 | 13000 |
| 103 | 31.6 | 851.81 | 619.35 | 47 | 2500 |

TABLE 4-continued

| Transition number | Retention time (minutes) | (m/z) filtered in Q1 | (m/z) filtered in Q3 | Collision energy (eV) | Positivity threshold |
|---|---|---|---|---|---|
| 104 | 31.6 | 851.81 | 686.41 | 47 | 2500 |
| 105 | 31.6 | 851.81 | 894.5 | 47 | 2500 |
| 106 | 18.8 | 654.35 | 746.4 | 34 | 2500 |
| 107 | 18.8 | 654.35 | 875.45 | 34 | 2500 |
| 108 | 18.8 | 654.35 | 988.53 | 34 | 2500 |
| 109 | 16.3 | 559.31 | 632.34 | 30 | 2500 |
| 110 | 16.3 | 559.31 | 792.37 | 30 | 2500 |
| 111 | 16.3 | 559.31 | 905.45 | 30 | 2500 |
| 112 | 10.5 | 487.73 | 544.32 | 26 | 2500 |
| 113 | 10.5 | 487.73 | 659.35 | 26 | 2500 |
| 114 | 10.5 | 487.73 | 788.39 | 26 | 2500 |
| 115 | 12.6 | 690.35 | 779.41 | 35 | 2500 |
| 116 | 12.6 | 690.35 | 947.5 | 35 | 2500 |
| 117 | 12.6 | 690.35 | 474.26 | 35 | 2500 |
| 118 | 15.9 | 682.35 | 763.41 | 35 | 2500 |
| 119 | 15.9 | 682.35 | 931.5 | 35 | 2500 |
| 120 | 15.9 | 682.35 | 466.26 | 35 | 2500 |
| 121 | 19.8 | 486.75 | 728.36 | 26 | 2500 |
| 122 | 19.8 | 486.75 | 825.42 | 26 | 2500 |
| 123 | 19.8 | 486.75 | 413.21 | 26 | 2500 |
| 124 | 18.4 | 478.75 | 712.37 | 26 | 2500 |
| 125 | 18.4 | 478.75 | 809.42 | 26 | 2500 |
| 126 | 18.4 | 478.75 | 405.21 | 26 | 2500 |
| 127 | 16.3 | 776.93 | 756.4 | 39 | 2500 |
| 128 | 16.3 | 776.93 | 813.42 | 39 | 2500 |
| 129 | 16.3 | 776.93 | 926.51 | 39 | 2500 |
| 130 | 12.2 | 523.26 | 579.3 | 28 | 2500 |
| 131 | 12.2 | 523.26 | 795.37 | 28 | 2500 |
| 132 | 12.2 | 523.26 | 908.45 | 28 | 2500 |
| 133 | 12 | 515.26 | 506.28 | 28 | 2500 |
| 134 | 12 | 515.26 | 779.37 | 28 | 2500 |
| 135 | 12 | 515.26 | 892.46 | 28 | 2500 |
| 136 | 18 | 899.46 | 439.33 | 36 | 2500 |
| 137 | 18 | 899.46 | 304.16 | 57 | 2500 |
| 138 | 18 | 899.46 | 994.43 | 36 | 2500 |
| 139 | 15.6 | 681.33 | 661.29 | 38 | 2500 |
| 140 | 15.6 | 681.33 | 808.33 | 38 | 2500 |
| 141 | 15.6 | 681.33 | 909.37 | 38 | 2500 |
| 142 | 16.6 | 676 | 661.29 | 38 | 3100 |
| 143 | 16.6 | 676 | 792.33 | 38 | 3100 |
| 144 | 16.6 | 676 | 893.38 | 38 | 3100 |
| 145 | 17.2 | 688.32 | 630.28 | 38 | 2500 |
| 146 | 17.2 | 688.32 | 729.35 | 38 | 2500 |
| 147 | 17.2 | 688.32 | 800.39 | 38 | 2500 |
| 148 | 27 | 878.12 | 841.5 | 48 | 2500 |
| 149 | 27 | 878.12 | 795.34 | 48 | 2500 |
| 150 | 27 | 878.12 | 910.37 | 48 | 2500 |
| 151 | 27.9 | 872.79 | 462.22 | 48 | 2500 |
| 152 | 27.9 | 872.79 | 779.34 | 48 | 2500 |
| 153 | 27.9 | 872.79 | 894.37 | 48 | 2500 |
| 154 | 18.8 | 571.84 | 701.46 | 30 | 2500 |
| 155 | 18.8 | 571.84 | 830.5 | 30 | 2500 |
| 156 | 18.8 | 571.84 | 901.54 | 30 | 2500 |
| 157 | 16.6 | 565.82 | 701.46 | 30 | 2500 |
| 158 | 16.6 | 565.82 | 830.5 | 30 | 2500 |
| 159 | 16.6 | 565.82 | 901.54 | 30 | 2500 |
| 160 | 1.5 | 317.64 | 419.19 | 19 | 9000 |
| 161 | 1.5 | 317.64 | 490.23 | 19 | 9000 |
| 162 | 1.5 | 317.64 | 547.25 | 19 | 9000 |
| 163 | 0.9 | 225.12 | 234.14 | 18 | 2500 |
| 164 | 0.9 | 225.12 | 305.18 | 13 | 2500 |
| 165 | 0.9 | 225.12 | 362.2 | 13 | 2500 |
| 166 | 14.1 | 363.24 | 498.34 | 21 | 2500 |
| 167 | 14.1 | 363.24 | 555.36 | 21 | 2500 |
| 168 | 14.1 | 363.24 | 626.4 | 21 | 2500 |
| 169 | 14.7 | 671.32 | 593.28 | 35 | 4500 |
| 170 | 14.7 | 671.32 | 780.36 | 35 | 4500 |
| 171 | 14.7 | 671.32 | 909.4 | 35 | 4500 |
| 172 | 17.5 | 663.32 | 764.36 | 34 | 2500 |
| 173 | 17.5 | 663.32 | 893.4 | 34 | 2500 |
| 174 | 17.5 | 663.32 | 1006.49 | 34 | 2500 |
| 175 | 18 | 856.4 | 698.84 | 43 | 2500 |
| 176 | 18 | 856.4 | 630.28 | 43 | 2500 |
| 177 | 18 | 856.4 | 814.41 | 43 | 2500 |
| 178 | 18.6 | 877.94 | 829.4 | 44 | 2500 |
| 179 | 18.6 | 877.94 | 943.44 | 44 | 2500 |
| 180 | 18.6 | 877.94 | 1080.5 | 44 | 2500 |
| 181 | 18.1 | 493.75 | 742.38 | 27 | 2500 |
| 182 | 18.1 | 493.75 | 839.43 | 27 | 2500 |
| 183 | 18.1 | 493.75 | 420.22 | 27 | 2500 |
| 184 | 19.8 | 485.76 | 726.39 | 26 | 2500 |
| 185 | 19.8 | 485.76 | 823.44 | 26 | 2500 |
| 186 | 19.8 | 485.76 | 412.22 | 26 | 2500 |
| 187 | 16.5 | 828.43 | 756.4 | 41 | 2500 |
| 188 | 16.5 | 828.43 | 813.42 | 41 | 2500 |
| 189 | 16.5 | 828.43 | 926.51 | 41 | 2500 |
| 190 | 16.1 | 791.93 | 756.4 | 40 | 2500 |
| 191 | 16.1 | 791.93 | 813.42 | 40 | 2500 |
| 192 | 16.1 | 791.93 | 926.51 | 40 | 2500 |
| 193 | 15.7 | 559.81 | 676.38 | 30 | 2500 |
| 194 | 14.1 | 559.81 | 763.41 | 30 | 2500 |
| 195 | 14.1 | 559.81 | 892.45 | 30 | 2500 |
| 196 | 16.6 | 676.34 | 646.31 | 38 | 2500 |
| 197 | 16.6 | 676.34 | 793.96 | 38 | 2500 |
| 198 | 16.6 | 676.34 | 894.4 | 38 | 2500 |
| 199 | 18.9 | 671.01 | 646.31 | 38 | 4000 |
| 200 | 18.9 | 671.01 | 777.96 | 38 | 4000 |
| 201 | 18.9 | 671.01 | 878.4 | 38 | 4000 |
| 202 | 16.9 | 892.45 | 722.31 | 44 | 2500 |
| 203 | 16.9 | 892.45 | 937.4 | 44 | 2500 |
| 204 | 16.9 | 892.45 | 994.43 | 44 | 2500 |
| 205 | 17.9 | 707.99 | 630.28 | 39 | 6000 |
| 206 | 17.9 | 707.99 | 743.37 | 39 | 6000 |
| 207 | 17.9 | 707.99 | 814.41 | 39 | 6000 |
| 208 | 22.5 | 643.89 | 660.4 | 33 | 2500 |
| 209 | 22.5 | 643.89 | 773.49 | 33 | 2500 |
| 210 | 22.5 | 643.89 | 959.55 | 33 | 2500 |
| 211 | 17.5 | 632.31 | 781.32 | 33 | 3000 |
| 212 | 17.5 | 632.31 | 894.4 | 33 | 3000 |
| 213 | 17.5 | 632.31 | 1007.49 | 33 | 3000 |
| 214 | 19.8 | 624.31 | 765.32 | 32 | 2500 |
| 215 | 19.8 | 624.31 | 878.41 | 32 | 2500 |
| 216 | 19.8 | 624.31 | 991.49 | 32 | 2500 |
| 217 | 21.4 | 638.34 | 836.43 | 33 | 2500 |
| 218 | 21.4 | 638.34 | 1004.52 | 33 | 2500 |
| 219 | 21.5 | 638.34 | 502.76 | 33 | 2500 |
| 220 | 3.2 | 273.65 | 331.21 | 17 | 2500 |
| 221 | 3.2 | 273.65 | 402.25 | 17 | 2500 |
| 222 | 3.2 | 273.65 | 459.27 | 17 | 2500 |
| 223 | 1.3 | 303.65 | 361.18 | 18 | 21000 |
| 224 | 1.3 | 303.65 | 462.23 | 18 | 21000 |
| 225 | 1.3 | 303.65 | 519.25 | 18 | 21000 |
| 226 | 31.3 | 863.138 | 619.35 | 47 | 2500 |
| 227 | 31.3 | 863.138 | 686.41 | 47 | 2500 |
| 228 | 31.3 | 863.138 | 823.47 | 47 | 2500 |
| 229 | 17.7 | 544.32 | 602.36 | 29 | 2500 |
| 230 | 17.7 | 544.32 | 762.39 | 29 | 2500 |
| 231 | 17.7 | 544.32 | 875.48 | 29 | 2500 |
| 232 | 9.8 | 412.21 | 476.27 | 23 | 2500 |
| 233 | 9.8 | 412.21 | 573.32 | 23 | 2500 |
| 234 | 9.8 | 412.21 | 660.36 | 23 | 2500 |
| 235 | 15.2 | 843.38 | 698.84 | 42 | 2500 |
| 236 | 15.2 | 843.38 | 630.28 | 42 | 2500 |
| 237 | 15.2 | 843.38 | 943.45 | 42 | 2500 |
| 238 | 8.7 | 480.72 | 530.3 | 26 | 2500 |
| 239 | 8.7 | 480.72 | 645.33 | 26 | 2500 |
| 240 | 8.7 | 480.72 | 774.37 | 26 | 2500 |
| 241 | 18.8 | 704.35 | 763.41 | 36 | 2500 |
| 242 | 18.8 | 704.35 | 959.53 | 36 | 2500 |
| 243 | 18.8 | 704.35 | 480.27 | 36 | 2500 |
| 244 | 18.3 | 425.25 | 506.31 | 24 | 2500 |
| 245 | 18.3 | 425.25 | 607.36 | 24 | 2500 |
| 246 | 18.3 | 425.25 | 720.44 | 24 | 2500 |
| 247 | 16.4 | 798.94 | 997.54 | 40 | 2500 |
| 248 | 16.3 | 798.94 | 756.4 | 40 | 2500 |
| 249 | 16.3 | 798.94 | 926.51 | 40 | 2500 |
| 250 | 8.3 | 494.26 | 850.45 | 27 | 2500 |
| 251 | 8.3 | 494.26 | 636.31 | 27 | 2500 |
| 252 | 8.3 | 494.26 | 737.36 | 27 | 2500 |
| 253 | 10.9 | 486.26 | 834.45 | 26 | 2500 |
| 254 | 10.9 | 486.26 | 620.32 | 26 | 2500 |
| 255 | 10.9 | 486.26 | 721.37 | 26 | 2500 |

TABLE 4-continued

| Transition number | Retention time (minutes) | (m/z) filtered in Q1 | (m/z) filtered in Q3 | Collision energy (eV) | Positivity threshold |
|---|---|---|---|---|---|
| 256 | 19.3 | 691.67 | 793.36 | 39 | 2500 |
| 257 | 19.3 | 691.67 | 894.4 | 39 | 2500 |
| 258 | 19.3 | 691.67 | 965.44 | 39 | 2500 |
| 259 | 20.6 | 681.01 | 646.31 | 38 | 2500 |
| 260 | 20.6 | 681.01 | 777.36 | 38 | 2500 |
| 261 | 20.6 | 681.01 | 878.4 | 38 | 2500 |
| 262 | 18 | 692.99 | 630.28 | 39 | 2500 |
| 263 | 18 | 692.99 | 743.37 | 39 | 2500 |
| 264 | 18 | 692.99 | 814.41 | 39 | 2500 |
| 265 | 23 | 658.89 | 1090.61 | 34 | 2500 |
| 266 | 23 | 658.89 | 773.49 | 34 | 2500 |
| 267 | 23 | 658.89 | 989.56 | 34 | 2500 |
| 268 | 17.9 | 564.83 | 687.44 | 30 | 2500 |
| 269 | 17.9 | 564.83 | 816.48 | 30 | 2500 |
| 270 | 17.9 | 564.83 | 887.52 | 30 | 2500 |
| 271 | 18.9 | 710.84 | 823.37 | 36 | 2500 |
| 272 | 18.9 | 710.84 | 938.39 | 36 | 2500 |
| 273 | 18.9 | 710.84 | 1051.48 | 36 | 2500 |
| 274 | 20.9 | 702.84 | 621.29 | 36 | 2500 |
| 275 | 20.9 | 702.84 | 807.37 | 36 | 2500 |
| 276 | 20.9 | 702.84 | 922.4 | 36 | 2500 |
| 277 | 22.6 | 652.36 | 559.31 | 34 | 2500 |
| 278 | 22.6 | 652.36 | 1004.52 | 34 | 2500 |
| 279 | 22.6 | 652.36 | 502.76 | 34 | 2500 |
| 280 | 11.1 | 380.21 | 532.29 | 22 | 2500 |
| 281 | 11.1 | 380.21 | 589.31 | 22 | 2500 |
| 282 | 11.1 | 380.21 | 660.35 | 22 | 2500 |
| 283 | 13.1 | 372.22 | 516.3 | 21 | 2500 |
| 284 | 13.1 | 372.22 | 573.32 | 21 | 2500 |
| 285 | 13.1 | 372.22 | 644.35 | 21 | 2500 |
| 286 | 31.3 | 858.47 | 612.34 | 47 | 2500 |
| 287 | 31.3 | 858.47 | 967.1 | 47 | 2500 |
| 288 | 31.3 | 858.47 | 672.39 | 47 | 2500 |
| 289 | 30.5 | 715.73 | 874.95 | 40 | 2500 |
| 290 | 30.5 | 715.73 | 795.45 | 40 | 2500 |
| 291 | 30.6 | 715.73 | 534.79 | 40 | 2500 |
| 292 | 11.7 | 601.79 | 788.39 | 31 | 2500 |
| 293 | 11.7 | 601.79 | 859.43 | 31 | 2500 |
| 294 | 11.7 | 601.79 | 974.45 | 31 | 2500 |
| 295 | 20 | 738.01 | 746.4 | 41 | 2500 |
| 296 | 20 | 738.01 | 875.45 | 41 | 2500 |
| 297 | 20 | 738.01 | 988.53 | 41 | 2500 |
| 298 | 17.6 | 690.34 | 763.61 | 35 | 2500 |
| 299 | 17.6 | 690.34 | 834.45 | 35 | 2500 |
| 300 | 17.6 | 690.34 | 931.5 | 35 | 2500 |
| 301 | 19.5 | 683.34 | 779.41 | 35 | 6000 |
| 302 | 19.5 | 683.34 | 850.45 | 35 | 6000 |
| 303 | 19.5 | 683.34 | 474.25 | 35 | 6000 |
| 304 | 16.1 | 675.34 | 763.41 | 35 | 2500 |
| 305 | 16.1 | 675.34 | 931.5 | 35 | 2500 |
| 306 | 16.1 | 675.34 | 466.25 | 35 | 2500 |
| 307 | 14.4 | 816.94 | 565.31 | 41 | 2500 |
| 308 | 14.4 | 816.94 | 744.92 | 41 | 2500 |
| 309 | 14.4 | 816.94 | 813.42 | 41 | 2500 |
| 310 | 13 | 513.26 | 563.3 | 28 | 2500 |
| 311 | 13 | 513.26 | 775.38 | 28 | 2500 |
| 312 | 13 | 513.26 | 888.46 | 28 | 2500 |
| 313 | 16.6 | 997.99 | 941.45 | 49 | 2500 |
| 314 | 16.6 | 997.99 | 573.32 | 49 | 2500 |
| 315 | 16.6 | 997.99 | 952.46 | 49 | 2500 |
| 316 | 18.9 | 907.44 | 722.32 | 45 | 2500 |
| 317 | 18.9 | 907.44 | 937.4 | 45 | 2500 |
| 318 | 18.9 | 907.44 | 994.43 | 45 | 2500 |
| 319 | 23.7 | 672.89 | 547.32 | 35 | 2500 |
| 320 | 23.7 | 672.89 | 660.4 | 35 | 2500 |
| 321 | 23.7 | 672.89 | 773.49 | 35 | 2500 |
| 322 | 17.1 | 473.21 | 528.29 | 26 | 2500 |
| 323 | 17.9 | 473.21 | 627.32 | 26 | 2500 |
| 324 | 17.8 | 473.21 | 684.34 | 26 | 2500 |
| 325 | 8.4 | 465.22 | 512.29 | 25 | 9000 |
| 326 | 8.4 | 465.22 | 627.32 | 25 | 9000 |
| 327 | 8.4 | 465.22 | 684.34 | 25 | 9000 |
| 328 | 19.8 | 585.86 | 701.46 | 31 | 2500 |
| 329 | 19.8 | 585.86 | 830.5 | 31 | 2500 |
| 330 | 19.8 | 585.86 | 929.57 | 31 | 2500 |
| 331 | 1.3 | 288.64 | 361.18 | 18 | 8000 |
| 332 | 1.3 | 288.64 | 432.22 | 18 | 8000 |
| 333 | 1.3 | 288.64 | 489.24 | 18 | 8000 |
| 334 | 14.5 | 399.25 | 498.34 | 23 | 6000 |
| 335 | 14.5 | 399.25 | 627.38 | 23 | 6000 |
| 336 | 14.5 | 399.25 | 698.42 | 23 | 6000 |
| 337 | 31.3 | 874.47 | 823.47 | 48 | 2500 |
| 338 | 31.3 | 874.47 | 619.41 | 48 | 2500 |
| 339 | 31.3 | 874.47 | 686.41 | 48 | 2500 |
| 340 | 31.3 | 863.14 | 823.47 | 47 | 2500 |
| 341 | 31.3 | 863.14 | 619.34 | 47 | 2500 |
| 342 | 31.3 | 863.14 | 686.41 | 47 | 2500 |
| 343 | 10.6 | 536.77 | 602.38 | 29 | 2500 |
| 344 | 10.6 | 536.77 | 787.41 | 29 | 2500 |
| 345 | 10.6 | 536.77 | 858.44 | 29 | 2500 |
| 346 | 16.5 | 646.33 | 502.26 | 33 | 7000 |
| 347 | 16.5 | 646.33 | 730.37 | 33 | 7000 |
| 348 | 16.5 | 646.33 | 859.42 | 33 | 7000 |

The other machine parameters used are as follows:

| | |
|---|---|
| Scan type: | MRM |
| MRM planned: | yes |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 50.00 psi |
| Heating gas: | 40.00 psi |
| Collision gas which induces dissociation: | 9.00 psi |
| Dynamic filling: | activated |
| Declustering potential (DP): | 80.00 V |
| Entry potential before Q0 (EP): | 10.00 V |
| Collision cell exit potential (CXP): | 35 V |
| Total cycle time: | 1.2 sec |
| Detection window: | 90 sec |

The areas obtained for each of the transitions and for each of the microorganisms studied were measured. When the areas of the 3 transitions of the same peptide are greater than or equal to the positivity threshold described in TABLE 4, the detection of the peptide is considered to be positive and is labelled "1" in TABLE 5. When at least one transition comprises an area less than the positivity threshold described in TABLE 4, the corresponding peptide is considered non-detected and is labelled 0 in TABLE 5.

TABLE 5

| Transition number | Sam10 | Sam11 | Sam12 | Sam13 | Sam14 | Sam15 | Sam16 | Sam17 | Sam18 | Sam19 | Sam20 | Sam21 | Sam22 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |
| 22-24 | 0 | 1 | 0 | 0 | 1 | 0 | 0 | 0 | 0 | 0 | 0 | 1 | 0 |
| 25-27 | 0 | 1 | 0 | 1 | 1 | 0 | 0 | 1 | 1 | 1 | 0 | 1 | 0 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 0 | 0 | 0 | 0 | 1 | 0 | 1 | 1 | 1 | 1 | 0 | 1 | 0 |
| 37-39 | 0 | 0 | 0 | 0 | 0 | 0 | 0 | 0 | 0 | 0 | 0 | 0 | 0 |
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 0 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 0 | 1 | 1 | 1 | 1 | 1 | 1 | 1 | 1 | 1 | 1 | 1 | 0 |
| 76-78 | 0 | 0 | 0 | 0 | 0 | 0 | 0 | 0 | 0 | 0 | 0 | 0 | 0 |
| 79-81 | 0 | 0 | 0 | 1 | 0 | 0 | 0 | 0 | 1 | 0 | 0 | 0 | 0 |
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 0 | 1 | 1 | 1 | 1 | 1 | 1 | 1 | 1 | 1 | 0 | 1 | 0 |
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 0 | 1 | 1 | 1 | 1 | 1 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 0 | 0 | 0 | 1 | 1 | 0 | 0 | 0 | 1 | 1 | 0 | 0 | 0 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 0 | 1 | 0 | 1 | 1 | 0 | 1 | 1 | 1 | 0 | 0 | 1 | 0 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 0 | 1 | 1 | 1 | 1 | 1 | 1 | 1 | 1 | 1 | 0 | 1 | 0 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 0 | 1 | 1 | 1 | 1 | 1 | 1 | 1 | 1 | 1 | 1 | 1 | 1 |
| 169-171 | 0 | 0 | 0 | 0 | 0 | 0 | 0 | 0 | 0 | 0 | 0 | 0 | 0 |
| 172-174 | 0 | 0 | 0 | 0 | 0 | 0 | 0 | 0 | 0 | 0 | 0 | 0 | 0 |
| 175-177 | 0 | 1 | 0 | 0 | 0 | 0 | 0 | 0 | 0 | 0 | 0 | 0 | 0 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 0 | 0 | 0 | 0 | 0 | 0 | 0 | 0 | 0 | 0 | 0 | 0 | 0 |
| 190-192 | 0 | 0 | 0 | 0 | 0 | 0 | 0 | 0 | 0 | 0 | 0 | 0 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 0 | 0 | 1 | 1 | 1 | 1 | 0 | 1 | 1 | 0 | 1 | 1 | 0 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |
| 232-234 | 0 | 0 | 1 | 1 | 0 | 1 | 0 | 1 | 1 | 0 | 1 | 0 | 0 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |

TABLE 5-continued

| Transition number | | | | | | | | | | | | | |
|---|---|---|---|---|---|---|---|---|---|---|---|---|---|
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |
| 262-264 | 0 | 0 | 0 | 0 | 0 | 1 | 0 | 0 | 0 | 0 | 0 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 0 | 1 | 0 | 1 | 1 | 0 | 1 | 1 | 1 | 0 | 0 | 1 | 0 |
| 301-303 | 0 | 0 | 0 | 0 | 0 | 0 | 0 | 0 | 0 | 0 | 0 | 0 | 0 |
| 304-306 | 0 | 0 | 0 | 0 | 0 | 0 | 0 | 0 | 0 | 0 | 0 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |
| 340-342 | 0 | 0 | 0 | 0 | 0 | 0 | 0 | 0 | 0 | 0 | 0 | 0 | 0 |
| 343-345 | 0 | 1 | 1 | 1 | 1 | 1 | 1 | 1 | 1 | 1 | 0 | 1 | 0 |
| 346-348 | 0 | 0 | 0 | 0 | 0 | 0 | 0 | 0 | 0 | 0 | 0 | 0 | 0 |
| TEM peptides | 0 | 11 | 8 | 13 | 13 | 9 | 9 | 12 | 14 | 9 | 5 | 12 | 2 |
| 2b peptides | 0 | 0 | 0 | 0 | 0 | 0 | 0 | 0 | 0 | 0 | 0 | 0 | 0 |
| 2br peptides | 0 | 0 | 0 | 0 | 0 | 0 | 0 | 0 | 0 | 0 | 0 | 0 | 0 |
| 2be peptides | 0 | 0 | 1 | 2 | 1 | 2 | 1 | 2 | 3 | 1 | 1 | 1 | 0 |
| 2ber peptides | 0 | 0 | 0 | 0 | 0 | 0 | 0 | 0 | 0 | 0 | 0 | 0 | 0 |

| Transition number | Sam23 | Sam24 | Sam25 | Sam26 | Sam27 | Sam28 | Sam29 | Sam30 | Sam31 | Sam32 | Sam33 | Sam34 | Sam35 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |
| 22-24 | 0 | 0 | 0 | 0 | 0 | 0 | 0 | 0 | 0 | 0 | 0 | 1 | 1 |
| 25-27 | 1 | 1 | 0 | 1 | 1 | 0 | 0 | 0 | 0 | 0 | 0 | 1 | 1 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 1 | 0 | 0 | 0 | 0 | 0 | 0 | 0 | 0 | 0 | 1 | 0 | 0 |
| 37-39 | 0 | 0 | 0 | 0 | 0 | 0 | 0 | 0 | 0 | 0 | 0 | 0 | 0 |
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 0 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 1 | 1 | 1 | 1 | 1 | 0 | 1 | 1 | 1 | 1 | 1 | 0 | 0 |
| 76-78 | 0 | 0 | 0 | 0 | 0 | 0 | 0 | 0 | 0 | 0 | 0 | 0 | 0 |
| 79-81 | 0 | 1 | 0 | 1 | 1 | 0 | 0 | 0 | 0 | 1 | 0 | 0 | 0 |
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 1 | 1 | 0 | 1 | 1 | 0 | 0 | 1 | 0 | 0 | 0 | 1 | 1 |

TABLE 5-continued

| | | | | | | | | | | | | | |
|---|---|---|---|---|---|---|---|---|---|---|---|---|---|
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 1 | 1 | 1 | 1 | 1 | 0 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 1 | 1 | 0 | 1 | 0 | 0 | 0 | 0 | 0 | 0 | 0 | 1 | 1 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 1 | 1 | 0 | 1 | 1 | 0 | 0 | 0 | 0 | 1 | 1 | 1 | 1 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 1 | 1 | 0 | 1 | 1 | 0 | 1 | 0 | 0 | 0 | 0 | 1 | 1 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 1 | 1 | 1 | 1 | 1 | 1 | 1 | 1 | 1 | 1 | 1 | 1 | 1 |
| 169-171 | 0 | 0 | 0 | 0 | 0 | 0 | 0 | 0 | 0 | 0 | 0 | 0 | 0 |
| 172-174 | 0 | 0 | 0 | 0 | 0 | 0 | 0 | 0 | 0 | 0 | 0 | 0 | 0 |
| 175-177 | 0 | 1 | 0 | 1 | 1 | 0 | 0 | 0 | 0 | 0 | 0 | 1 | 1 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 0 | 0 | 0 | 0 | 0 | 0 | 0 | 0 | 0 | 0 | 0 | 0 | 1 |
| 190-192 | 0 | 0 | 0 | 0 | 0 | 0 | 0 | 0 | 0 | 0 | 0 | 1 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 1 | 1 | 1 | 1 | 0 | 1 | 0 | 0 | 0 | 1 | 1 | 1 | 1 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |
| 232-234 | 0 | 1 | 1 | 1 | 1 | 0 | 1 | 0 | 0 | 1 | 0 | 0 | 0 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |
| 262-264 | 0 | 0 | 0 | 0 | 0 | 0 | 0 | 0 | 0 | 0 | 1 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 1 | 1 | 0 | 0 | 0 | 0 | 0 | 1 | 0 | 0 | 0 | 0 | 0 |
| 301-303 | 0 | 0 | 0 | 0 | 0 | 0 | 0 | 0 | 0 | 0 | 0 | 0 | 0 |
| 304-306 | 0 | 0 | 0 | 0 | 0 | 0 | 0 | 0 | 0 | 0 | 0 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 340-342 | 0 | 0 | 0 | 0 | 0 | 0 | 0 | 0 | 0 | 0 | 0 | 0 | 0 |
| 343-345 | 1 | 1 | 1 | 1 | 1 | 0 | 1 | 1 | 0 | 1 | 1 | 1 | 1 |
| 346-348 | 0 | 0 | 0 | 0 | 0 | 0 | 0 | 0 | 0 | 0 | 0 | 0 | 0 |
| TEM peptides | 12 | 14 | 6 | 13 | 11 | 2 | 6 | 6 | 3 | 9 | 7 | 12 | 12 |
| 2b peptides | 0 | 0 | 0 | 0 | 0 | 0 | 0 | 0 | 0 | 0 | 0 | 0 | 0 |
| 2br peptides | 0 | 0 | 0 | 0 | 0 | 0 | 0 | 0 | 0 | 0 | 0 | 0 | 1 |
| 2be peptides | 1 | 2 | 1 | 2 | 2 | 0 | 1 | 0 | 0 | 3 | 1 | 0 | 0 |
| 2ber peptides | 0 | 0 | 0 | 0 | 0 | 0 | 0 | 0 | 0 | 0 | 0 | 0 | 0 |

| Transition number | Sam36 | Sam37 | Sam38 | Sam39 | Sam40 | Sam41 | Sam42 | Sam43 | Sam44 | Sam45 | Sam46 | Sam47 | Sam48 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |
| 22-24 | 0 | 0 | 1 | 1 | 0 | 1 | 0 | 0 | 0 | 0 | 0 | 0 | 0 |
| 25-27 | 1 | 0 | 1 | 1 | 1 | 1 | 1 | 0 | 0 | 0 | 1 | 0 | 0 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 0 | 0 | 0 | 0 | 0 | 0 | 0 | 0 | 0 | 0 | 0 | 0 | 0 |
| 37-39 | 0 | 0 | 0 | 0 | 0 | 0 | 0 | 0 | 0 | 0 | 0 | 0 | 0 |
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 1 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 1 | 1 | 1 | 1 | 1 | 1 | 1 | 1 | 1 | 1 | 1 | 1 | 1 |
| 76-78 | 0 | 0 | 0 | 0 | 0 | 0 | 0 | 0 | 0 | 0 | 0 | 0 | 0 |
| 79-81 | 0 | 0 | 0 | 0 | 0 | 0 | 0 | 0 | 0 | 0 | 1 | 0 | 0 |
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 1 | 0 | 1 | 1 | 1 | 1 | 1 | 0 | 0 | 0 | 1 | 0 | 0 |
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 1 | 1 | 1 | 1 | 1 | 1 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 1 | 0 | 1 | 1 | 1 | 1 | 1 | 0 | 0 | 0 | 1 | 0 | 0 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 1 | 1 | 1 | 1 | 1 | 1 | 1 | 1 | 1 | 0 | 1 | 0 | 0 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 1 | 0 | 1 | 1 | 1 | 1 | 1 | 0 | 0 | 0 | 1 | 0 | 0 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 1 | 1 | 1 | 1 | 1 | 1 | 1 | 1 | 1 | 1 | 1 | 1 | 0 |
| 169-171 | 0 | 0 | 0 | 0 | 0 | 0 | 0 | 0 | 0 | 0 | 0 | 0 | 0 |
| 172-174 | 0 | 0 | 0 | 0 | 0 | 0 | 0 | 0 | 0 | 0 | 0 | 0 | 0 |
| 175-177 | 1 | 0 | 1 | 1 | 1 | 1 | 0 | 0 | 0 | 1 | 1 | 0 | 0 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 190-192 | 0 | 0 | 0 | 0 | 0 | 0 | 0 | 0 | 0 | 0 | 0 | 0 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 1 | 1 | 1 | 1 | 1 | 1 | 1 | 1 | 1 | 1 | 1 | 1 | 0 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |
| 232-234 | 0 | 0 | 0 | 0 | 0 | 0 | 0 | 0 | 1 | 0 | 1 | 0 | 0 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |
| 262-264 | 0 | 0 | 0 | 0 | 0 | 0 | 0 | 0 | 0 | 0 | 0 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 1 | 0 | 1 | 1 | 0 | 1 | 1 | 0 | 0 | 0 | 0 | 0 | 0 |
| 301-303 | 0 | 0 | 0 | 0 | 0 | 0 | 0 | 0 | 0 | 0 | 0 | 0 | 0 |
| 304-306 | 0 | 0 | 0 | 0 | 0 | 0 | 0 | 0 | 0 | 0 | 1 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |
| 340-342 | 0 | 0 | 0 | 0 | 0 | 0 | 0 | 0 | 0 | 0 | 0 | 0 | 0 |
| 343-345 | 1 | 1 | 1 | 1 | 1 | 1 | 1 | 1 | 1 | 1 | 1 | 1 | 0 |
| 346-348 | 0 | 0 | 0 | 0 | 0 | 0 | 0 | 0 | 0 | 0 | 0 | 0 | 0 |
| TEM peptides | 12 | 6 | 13 | 13 | 11 | 13 | 12 | 6 | 7 | 6 | 14 | 5 | 2 |
| 2b peptides | 0 | 0 | 0 | 0 | 0 | 0 | 0 | 0 | 0 | 0 | 0 | 0 | 0 |
| 2br peptides | 0 | 0 | 0 | 0 | 0 | 0 | 0 | 0 | 0 | 0 | 0 | 0 | 0 |
| 2be peptides | 0 | 0 | 0 | 0 | 0 | 0 | 0 | 0 | 1 | 0 | 2 | 0 | 0 |
| 2ber peptides | 0 | 0 | 0 | 0 | 0 | 0 | 0 | 0 | 0 | 0 | 0 | 0 | 0 |

| Transition number | Sam49 | Sam50 | Sam51 | Sam52 | Sam53 | Sam54 | Sam55 | Sam56 | Sam57 | Sam58 | Sam59 | Sam60 | Sam61 |
|---|---|---|---|---|---|---|---|---|---|---|---|---|---|
| 1-3 | 0 | 0 | 0 | 0 | 0 | 0 | 0 | 0 | 0 | 0 | 0 | 0 | 0 |
| 4-6 | 0 | 0 | 0 | 0 | 0 | 0 | 0 | 0 | 0 | 0 | 0 | 0 | 0 |
| 7-9 | 0 | 0 | 0 | 0 | 0 | 0 | 0 | 0 | 0 | 0 | 0 | 0 | 0 |
| 10-12 | 0 | 0 | 0 | 0 | 0 | 0 | 0 | 0 | 0 | 0 | 0 | 0 | 0 |
| 13-15 | 0 | 0 | 0 | 0 | 0 | 0 | 0 | 0 | 0 | 0 | 0 | 0 | 0 |
| 16-18 | 0 | 0 | 0 | 0 | 0 | 0 | 0 | 0 | 0 | 0 | 0 | 0 | 0 |
| 19-21 | 0 | 0 | 0 | 0 | 0 | 0 | 0 | 0 | 0 | 0 | 0 | 0 | 0 |
| 22-24 | 0 | 0 | 0 | 0 | 1 | 0 | 0 | 1 | 0 | 0 | 0 | 0 | 0 |
| 25-27 | 0 | 1 | 1 | 1 | 1 | 0 | 1 | 1 | 1 | 1 | 1 | 1 | 1 |
| 28-30 | 0 | 0 | 0 | 0 | 0 | 0 | 0 | 0 | 0 | 0 | 0 | 0 | 0 |
| 31-33 | 0 | 0 | 0 | 0 | 0 | 0 | 0 | 0 | 0 | 0 | 0 | 0 | 0 |
| 34-36 | 0 | 0 | 0 | 0 | 0 | 0 | 0 | 0 | 0 | 1 | 1 | 0 | 1 |
| 37-39 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 40-42 | 0 | 0 | 0 | 0 | 0 | 0 | 0 | 0 | 0 | 0 | 0 | 0 | 0 |
| 43-45 | 0 | 0 | 0 | 0 | 0 | 0 | 0 | 0 | 0 | 0 | 0 | 0 | 0 |
| 46-48 | 0 | 0 | 0 | 0 | 0 | 0 | 0 | 0 | 0 | 0 | 0 | 0 | 0 |
| 49-51 | 0 | 0 | 0 | 0 | 0 | 0 | 0 | 0 | 0 | 0 | 0 | 0 | 0 |
| 52-54 | 0 | 0 | 0 | 0 | 0 | 0 | 0 | 0 | 0 | 0 | 0 | 0 | 0 |
| 55-57 | 0 | 0 | 0 | 0 | 0 | 0 | 0 | 0 | 0 | 0 | 0 | 0 | 0 |
| 58-60 | 0 | 0 | 0 | 0 | 0 | 0 | 0 | 0 | 0 | 0 | 0 | 0 | 0 |
| 61-63 | 0 | 0 | 0 | 0 | 0 | 0 | 0 | 0 | 0 | 0 | 0 | 0 | 0 |
| 64-66 | 0 | 0 | 0 | 0 | 0 | 0 | 0 | 0 | 0 | 0 | 0 | 0 | 0 |
| 67-69 | 0 | 0 | 0 | 0 | 0 | 0 | 0 | 0 | 0 | 0 | 0 | 0 | 0 |
| 70-72 | 0 | 0 | 0 | 0 | 0 | 0 | 0 | 0 | 0 | 0 | 0 | 0 | 0 |
| 73-75 | 0 | 0 | 0 | 1 | 1 | 0 | 1 | 1 | 1 | 1 | 0 | 1 | 1 |
| 76-78 | 0 | 0 | 0 | 0 | 0 | 0 | 0 | 0 | 0 | 0 | 0 | 0 | 0 |
| 79-81 | 0 | 0 | 0 | 1 | 0 | 0 | 1 | 0 | 1 | 0 | 1 | 0 | 1 |
| 82-84 | 0 | 0 | 0 | 0 | 0 | 0 | 0 | 0 | 0 | 0 | 0 | 0 | 0 |
| 85-87 | 0 | 0 | 0 | 0 | 0 | 0 | 0 | 0 | 0 | 0 | 0 | 0 | 0 |
| 88-90 | 0 | 0 | 0 | 0 | 0 | 0 | 0 | 0 | 0 | 0 | 0 | 0 | 0 |
| 91-93 | 0 | 0 | 0 | 0 | 0 | 0 | 0 | 0 | 0 | 0 | 0 | 0 | 0 |
| 94-96 | 0 | 0 | 0 | 0 | 0 | 0 | 0 | 0 | 0 | 0 | 0 | 0 | 0 |
| 97-99 | 0 | 1 | 0 | 0 | 1 | 0 | 0 | 1 | 1 | 1 | 1 | 0 | 0 |
| 100-102 | 0 | 0 | 0 | 0 | 0 | 0 | 0 | 0 | 0 | 0 | 0 | 0 | 0 |
| 103-105 | 0 | 0 | 0 | 0 | 0 | 0 | 0 | 0 | 0 | 0 | 0 | 0 | 0 |
| 106-108 | 1 | 1 | 1 | 1 | 1 | 0 | 1 | 1 | 1 | 1 | 1 | 1 | 1 |
| 109-111 | 0 | 0 | 0 | 0 | 0 | 0 | 0 | 0 | 0 | 0 | 0 | 0 | 0 |
| 112-114 | 0 | 1 | 1 | 1 | 1 | 0 | 1 | 1 | 0 | 0 | 0 | 0 | 0 |
| 115-117 | 0 | 0 | 0 | 0 | 0 | 0 | 0 | 0 | 0 | 0 | 0 | 0 | 0 |
| 118-120 | 0 | 0 | 0 | 0 | 0 | 0 | 0 | 0 | 0 | 0 | 0 | 0 | 0 |
| 121-123 | 0 | 0 | 0 | 0 | 0 | 0 | 0 | 0 | 0 | 0 | 0 | 0 | 0 |
| 124-126 | 0 | 0 | 0 | 0 | 0 | 0 | 0 | 0 | 0 | 0 | 0 | 0 | 0 |
| 127-129 | 0 | 0 | 0 | 0 | 0 | 0 | 0 | 0 | 0 | 0 | 0 | 0 | 0 |
| 130-132 | 0 | 0 | 0 | 0 | 0 | 0 | 0 | 0 | 0 | 0 | 0 | 0 | 0 |
| 133-135 | 0 | 1 | 0 | 1 | 1 | 0 | 1 | 1 | 1 | 1 | 1 | 1 | 0 |
| 136-138 | 0 | 0 | 0 | 0 | 0 | 0 | 0 | 0 | 0 | 0 | 0 | 0 | 0 |
| 139-141 | 0 | 0 | 0 | 0 | 0 | 0 | 0 | 0 | 0 | 0 | 0 | 0 | 0 |
| 142-144 | 0 | 0 | 0 | 0 | 0 | 0 | 0 | 0 | 0 | 0 | 0 | 0 | 0 |
| 145-147 | 0 | 0 | 0 | 0 | 0 | 0 | 0 | 0 | 0 | 0 | 0 | 0 | 0 |
| 148-150 | 0 | 0 | 0 | 0 | 0 | 0 | 0 | 0 | 0 | 0 | 0 | 0 | 0 |
| 151-153 | 0 | 0 | 0 | 0 | 0 | 0 | 0 | 0 | 0 | 0 | 0 | 0 | 0 |
| 154-156 | 0 | 1 | 0 | 1 | 1 | 0 | 0 | 1 | 1 | 1 | 1 | 1 | 0 |
| 157-159 | 0 | 0 | 0 | 0 | 0 | 0 | 0 | 0 | 0 | 0 | 0 | 0 | 0 |
| 160-162 | 0 | 0 | 0 | 0 | 0 | 0 | 0 | 0 | 0 | 0 | 0 | 0 | 0 |
| 163-165 | 0 | 0 | 0 | 0 | 0 | 0 | 0 | 0 | 0 | 0 | 0 | 0 | 0 |
| 166-168 | 1 | 1 | 1 | 1 | 1 | 0 | 1 | 1 | 1 | 1 | 1 | 1 | 1 |
| 169-171 | 0 | 0 | 0 | 0 | 0 | 0 | 0 | 0 | 0 | 0 | 0 | 0 | 0 |
| 172-174 | 0 | 0 | 0 | 0 | 0 | 0 | 0 | 0 | 0 | 0 | 0 | 0 | 0 |
| 175-177 | 1 | 1 | 1 | 1 | 1 | 0 | 1 | 1 | 1 | 0 | 0 | 1 | 0 |
| 178-180 | 0 | 0 | 0 | 0 | 0 | 0 | 0 | 0 | 0 | 0 | 0 | 0 | 0 |
| 181-183 | 0 | 0 | 0 | 0 | 0 | 0 | 0 | 0 | 0 | 0 | 0 | 0 | 0 |
| 184-186 | 0 | 0 | 0 | 0 | 0 | 0 | 0 | 0 | 0 | 0 | 0 | 0 | 0 |
| 187-189 | 1 | 1 | 0 | 0 | 0 | 0 | 0 | 0 | 0 | 0 | 0 | 0 | 0 |
| 190-192 | 0 | 0 | 1 | 0 | 0 | 0 | 0 | 0 | 0 | 0 | 1 | 0 | 0 |
| 193-195 | 0 | 0 | 0 | 0 | 0 | 0 | 0 | 0 | 0 | 0 | 0 | 0 | 0 |
| 196-198 | 0 | 0 | 0 | 0 | 0 | 0 | 0 | 0 | 0 | 0 | 0 | 0 | 0 |
| 199-201 | 0 | 0 | 0 | 0 | 0 | 0 | 0 | 0 | 0 | 0 | 0 | 0 | 0 |
| 202-204 | 0 | 0 | 0 | 0 | 0 | 0 | 0 | 0 | 0 | 0 | 0 | 0 | 0 |
| 205-207 | 0 | 0 | 0 | 0 | 0 | 0 | 0 | 0 | 0 | 0 | 0 | 0 | 0 |
| 208-210 | 0 | 0 | 0 | 0 | 1 | 0 | 1 | 1 | 0 | 1 | 1 | 1 | 1 |
| 211-213 | 0 | 0 | 0 | 0 | 0 | 0 | 0 | 0 | 0 | 0 | 0 | 0 | 0 |
| 214-216 | 0 | 0 | 0 | 0 | 0 | 0 | 0 | 0 | 0 | 0 | 0 | 0 | 0 |
| 217-219 | 0 | 0 | 0 | 0 | 0 | 0 | 0 | 0 | 0 | 0 | 0 | 0 | 0 |
| 220-222 | 0 | 0 | 0 | 0 | 0 | 0 | 0 | 0 | 0 | 0 | 0 | 0 | 0 |
| 223-225 | 0 | 0 | 0 | 0 | 0 | 0 | 0 | 0 | 0 | 0 | 0 | 0 | 0 |
| 226-228 | 0 | 0 | 0 | 0 | 0 | 0 | 0 | 0 | 0 | 0 | 0 | 0 | 0 |
| 229-231 | 0 | 0 | 0 | 0 | 0 | 0 | 0 | 0 | 0 | 0 | 0 | 0 | 0 |
| 232-234 | 0 | 0 | 0 | 1 | 0 | 0 | 1 | 0 | 1 | 0 | 1 | 0 | 1 |
| 235-237 | 0 | 0 | 0 | 0 | 0 | 0 | 0 | 0 | 0 | 0 | 0 | 0 | 0 |
| 238-240 | 0 | 0 | 0 | 0 | 0 | 0 | 0 | 0 | 0 | 0 | 0 | 0 | 0 |
| 241-243 | 0 | 0 | 0 | 0 | 0 | 0 | 0 | 0 | 0 | 0 | 0 | 0 | 0 |
| 244-246 | 0 | 0 | 0 | 0 | 0 | 0 | 0 | 0 | 0 | 0 | 0 | 0 | 0 |
| 247-249 | 0 | 0 | 0 | 0 | 0 | 0 | 0 | 0 | 0 | 0 | 0 | 0 | 0 |
| 250-252 | 0 | 0 | 0 | 0 | 0 | 0 | 0 | 0 | 0 | 0 | 0 | 0 | 0 |
| 253-255 | 0 | 0 | 0 | 0 | 0 | 0 | 0 | 0 | 0 | 0 | 0 | 0 | 0 |
| 256-258 | 0 | 0 | 0 | 0 | 0 | 0 | 0 | 0 | 0 | 0 | 0 | 0 | 0 |
| 259-261 | 0 | 0 | 0 | 0 | 0 | 0 | 0 | 0 | 0 | 0 | 0 | 0 | 0 |
| 262-264 | 0 | 0 | 0 | 0 | 0 | 0 | 0 | 0 | 0 | 0 | 0 | 0 | 0 |
| 265-267 | 0 | 0 | 0 | 0 | 0 | 0 | 0 | 0 | 0 | 0 | 0 | 0 | 0 |
| 268-270 | 0 | 0 | 0 | 0 | 0 | 0 | 0 | 0 | 0 | 0 | 0 | 0 | 0 |
| 271-273 | 0 | 0 | 0 | 0 | 0 | 0 | 0 | 0 | 0 | 0 | 0 | 0 | 0 |
| 274-276 | 0 | 0 | 0 | 0 | 0 | 0 | 0 | 0 | 0 | 0 | 0 | 0 | 0 |
| 277-279 | 0 | 0 | 0 | 0 | 0 | 0 | 0 | 0 | 0 | 0 | 0 | 0 | 0 |

TABLE 5-continued

| | | | | | | | | | | | | | |
|---|---|---|---|---|---|---|---|---|---|---|---|---|---|
| 280-282 | 0 | 0 | 0 | 0 | 0 | 0 | 0 | 0 | 0 | 0 | 0 | 0 | 0 |
| 283-285 | 0 | 0 | 0 | 0 | 0 | 0 | 0 | 0 | 0 | 0 | 0 | 0 | 0 |
| 286-288 | 0 | 0 | 0 | 0 | 0 | 0 | 0 | 0 | 0 | 0 | 0 | 0 | 0 |
| 289-291 | 0 | 0 | 0 | 0 | 0 | 0 | 0 | 0 | 0 | 0 | 0 | 0 | 0 |
| 292-294 | 0 | 0 | 0 | 0 | 0 | 0 | 0 | 0 | 0 | 0 | 0 | 0 | 0 |
| 295-297 | 0 | 0 | 0 | 0 | 0 | 0 | 0 | 0 | 0 | 0 | 0 | 0 | 0 |
| 298-300 | 0 | 0 | 0 | 0 | 0 | 0 | 1 | 1 | 0 | 0 | 1 | 0 | 0 |
| 301-303 | 0 | 0 | 0 | 0 | 0 | 0 | 0 | 0 | 0 | 0 | 0 | 0 | 0 |
| 304-306 | 0 | 0 | 0 | 1 | 1 | 0 | 0 | 0 | 1 | 0 | 0 | 0 | 0 |
| 307-309 | 0 | 0 | 0 | 0 | 0 | 0 | 0 | 0 | 0 | 0 | 0 | 0 | 0 |
| 310-312 | 0 | 0 | 0 | 0 | 0 | 0 | 0 | 0 | 0 | 0 | 0 | 0 | 0 |
| 313-315 | 0 | 0 | 0 | 0 | 0 | 0 | 0 | 0 | 0 | 0 | 0 | 0 | 0 |
| 316-318 | 0 | 0 | 0 | 0 | 0 | 0 | 0 | 0 | 0 | 0 | 0 | 0 | 0 |
| 319-321 | 0 | 0 | 0 | 0 | 0 | 0 | 0 | 0 | 0 | 0 | 0 | 0 | 0 |
| 322-324 | 0 | 0 | 0 | 0 | 0 | 0 | 0 | 0 | 0 | 0 | 0 | 0 | 0 |
| 325-327 | 0 | 0 | 0 | 0 | 0 | 0 | 0 | 0 | 0 | 0 | 0 | 0 | 0 |
| 328-330 | 0 | 0 | 0 | 0 | 0 | 0 | 0 | 0 | 0 | 0 | 0 | 0 | 0 |
| 331-333 | 0 | 0 | 0 | 0 | 0 | 0 | 0 | 0 | 0 | 0 | 0 | 0 | 0 |
| 334-336 | 0 | 0 | 0 | 0 | 0 | 0 | 0 | 0 | 0 | 0 | 0 | 0 | 0 |
| 337-339 | 0 | 0 | 0 | 0 | 0 | 0 | 0 | 0 | 0 | 0 | 0 | 0 | 0 |
| 340-342 | 0 | 0 | 0 | 0 | 0 | 0 | 0 | 0 | 0 | 0 | 0 | 0 | 0 |
| 343-345 | 1 | 1 | 1 | 1 | 1 | 1 | 1 | 1 | 1 | 1 | 1 | 1 | 1 |
| 346-348 | 0 | 0 | 0 | 0 | 0 | 0 | 0 | 0 | 0 | 0 | 0 | 0 | 0 |
| TEM peptides | 5 | 10 | 7 | 12 | 13 | 1 | 12 | 13 | 12 | 10 | 13 | 9 | 9 |
| 2b peptides | 0 | 0 | 0 | 0 | 0 | 0 | 0 | 0 | 0 | 0 | 0 | 0 | 0 |
| 2br peptides | 1 | 1 | 0 | 0 | 0 | 0 | 0 | 0 | 0 | 0 | 0 | 0 | 0 |
| 2be peptides | 0 | 0 | 0 | 2 | 0 | 0 | 2 | 0 | 2 | 1 | 3 | 2 | 3 |
| 2ber peptides | 0 | 0 | 0 | 0 | 0 | 0 | 0 | 0 | 0 | 0 | 0 | 0 | 0 |

Sample Sam10 does not present any peptide which is characteristic of TEMs. The bacteria present in sample Sam10 may be sensitive to cephalosporins and to penicillins.

Samples Sam11 to Sam61 comprise at least one peptide which is characteristic of TEMs. The bacteria present in samples Sam11 to Sam61 therefore express a beta-lactamase which confers on them a resistance to penicillins.

No peptide specific to phenotype 2b is observed, and no sample tested is identified as being resistant solely to penicillins.

Samples Sam35, Sam49 and Sam50 comprise at least one peptide specific to phenotype 2br. Samples Sam35, Sam49 and Sam50 are therefore resistant to penicillins associated with an inhibitor of the clavulanic acid and tazobactam type.

No peptide specific to phenotype 2ber is observed, and no sample tested is identified as belonging only to this phenotype.

Samples Sam12 to Sam21, Sam23 to Sam27, Sam29, Sam32, Sam33, Sam44, Sam46, Sam52, Sam55 and Sam57 to Sam61 comprise at least one peptide specific to the phenotype 2be or to the phenotype 2ber. Samples Sam12 to Sam21, Sam23 to Sam27, Sam29, Sam32, Sam33, Sam44, Sam46, Sam52, Sam55, and Sam57 to Sam61 are therefore resistant to penicillins, to cephalosporins and to monobactams.

EXAMPLE 7

Identification of a Resistance to CMY Beta-Lactams

The samples corresponding to a species able to comprise a CMY resistance mechanism can be detected by employing the following method.

Each sample is treated according to example 5, then analysed according to example 6 by detecting the peptides from TABLE 6 instead of the peptides from TABLE 3.

TABLE 6

| Transition number | Peptide | Fragment ion | Charge state of the precursor | Retention time | (m/z) filtered in Q1 | (m/z) filtered in Q3 | Collision energy |
|---|---|---|---|---|---|---|---|
| 1 | LSDPVTK | y6 | 2 | 10 | 380.22 | 646.34 | 22 |
| 2 | LSDPVTK | y5 | 2 | 10 | 380.22 | 559.31 | 22 |
| 3 | LSDPVTK | y4 | 2 | 10 | 380.22 | 444.28 | 22 |
| 4 | ADSIINGSDSK | y9 | 2 | 10.2 | 553.77 | 920.47 | 29 |
| 5 | ADSIINGSDSK | y8 | 2 | 10.2 | 553.77 | 833.44 | 29 |
| 6 | ADSIINGSDSK | y7 | 2 | 10.2 | 553.77 | 720.35 | 29 |
| 7 | ASWVHK | y5 | 2 | 11.6 | 364.2 | 656.35 | 21 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 8 | ASWVHK | y4 | 2 | 11.6 | 364.2 | 569.32 | 21 |
| 9 | ASWVHK | y3 | 2 | 11.6 | 364.2 | 383.24 | 21 |
| 10 | SYPNPVR | y6 | 2 | 11.6 | 416.72 | 745.4 | 23 |
| 11 | SYPNPVR | y5 | 2 | 11.6 | 416.72 | 582.34 | 23 |
| 12 | SYPNPVR | y4 | 2 | 11.6 | 416.72 | 485.28 | 23 |
| 13 | VEAAWR | y5 | 2 | 12.3 | 366.2 | 632.32 | 21 |
| 14 | VEAAWR | y4 | 2 | 12.3 | 366.2 | 503.27 | 21 |
| 15 | VEAAWR | y3 | 2 | 12.3 | 366.2 | 432.24 | 21 |
| 16 | QWQGIR | y5 | 2 | 13.8 | 394.21 | 659.36 | 22 |
| 17 | QWQGIR | y4 | 2 | 13.8 | 394.21 | 473.28 | 22 |
| 18 | QWQGIR | y3 | 2 | 13.8 | 394.21 | 345.22 | 22 |
| 19 | VLQPLK | y5 | 2 | 14 | 349.23 | 598.39 | 20 |
| 20 | VLQPLK | y4 | 2 | 14 | 349.23 | 485.31 | 20 |
| 21 | VLQPLK | y3 | 2 | 14 | 349.23 | 357.25 | 20 |
| 22 | SSVIDMAR | y7 | 2 | 14.2 | 439.72 | 791.41 | 24 |
| 23 | SSVIDMAR | y6 | 2 | 14.2 | 439.72 | 704.38 | 24 |
| 24 | SSVIDMAR | y5 | 2 | 14.2 | 439.72 | 605.31 | 24 |
| 25 | WVQANMDASHVQEK | y9 | 2 | 14.4 | 821.89 | 1044.48 | 41 |
| 26 | WVQANMDASHVQEK | y8 | 2 | 14.4 | 821.89 | 913.44 | 41 |
| 27 | WVQANMDASHVQEK | y7 | 2 | 14.4 | 821.89 | 798.41 | 41 |
| 28 | TLQQGIALAQSR | y9 | 2 | 15.2 | 643.36 | 943.53 | 33 |
| 29 | TLQQGIALAQSR | y8 | 2 | 15.2 | 643.36 | 815.47 | 33 |
| 30 | TLQQGIALAQSR | y7 | 2 | 15.2 | 643.36 | 758.45 | 33 |
| 31 | TEQQIADIVNR | y9 | 2 | 15.6 | 643.84 | 1056.58 | 33 |
| 32 | TEQQIADIVNR | y8 | 2 | 15.6 | 643.84 | 928.52 | 33 |
| 33 | TEQQIADIVNR | y7 | 2 | 15.6 | 643.84 | 800.46 | 33 |
| 34 | LAHTWITVPQNEQK | y9 | 2 | 16 | 832.94 | 1056.57 | 42 |
| 35 | LAHTWITVPQNEQK | y8 | 2 | 16 | 832.94 | 943.48 | 42 |
| 36 | LAHTWITVPQNEQK | y7 | 2 | 16 | 832.94 | 842.44 | 42 |
| 37 | DYAWGYR | y6 | 2 | 16.4 | 465.71 | 815.38 | 25 |
| 38 | DYAWGYR | y5 | 2 | 16.4 | 465.71 | 652.32 | 25 |
| 39 | DYAWGYR | y4 | 2 | 16.4 | 465.71 | 581.28 | 25 |
| 40 | YWPELTGK | y7 | 2 | 17.4 | 497.26 | 830.44 | 27 |
| 41 | YWPELTGK | y6 | 2 | 17.4 | 497.26 | 644.36 | 27 |
| 42 | YWPELTGK | y5 | 2 | 17.4 | 497.26 | 547.31 | 27 |
| 43 | TFNGVLGGDAIAR | y9 | 2 | 17.6 | 645.84 | 871.5 | 33 |
| 44 | TFNGVLGGDAIAR | y8 | 2 | 17.6 | 645.84 | 772.43 | 33 |
| 45 | TFNGVLGGDAIAR | y7 | 2 | 17.6 | 645.84 | 659.35 | 33 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 46 | NLGIVMLANK | y9 | 2 | 19.1 | 536.81 | 958.58 | 29 |
| 47 | NLGIVMLANK | y8 | 2 | 19.1 | 536.81 | 845.49 | 29 |
| 48 | NLGIVMLANK | y7 | 2 | 19.1 | 536.81 | 788.47 | 29 |
| 49 | TGSTGGFGSYVAFVPEK | y9 | 2 | 19.5 | 852.42 | 1039.55 | 43 |
| 50 | TGSTGGFGSYVAFVPEK | y8 | 2 | 19.5 | 852.42 | 952.51 | 43 |
| 51 | TGSTGGFGSYVAFVPEK | y7 | 2 | 19.5 | 852.42 | 789.45 | 43 |
| 52 | ADIANNHPVTQQTLFELGSVSK | y9 | 3 | 20 | 790.41 | 979.55 | 44 |
| 53 | ADIANNHPVTQQTLFELGSVSK | y8 | 3 | 20 | 790.41 | 866.46 | 44 |
| 54 | ADIANNHPVTQQTLFELGSVSK | y7 | 3 | 20 | 790.41 | 719.39 | 44 |
| 55 | VALAALPAVEVNPPAPAVK | y9 | 2 | 20.4 | 914.04 | 892.53 | 45 |
| 56 | VALAALPAVEVNPPAPAVK | y8 | 2 | 20.4 | 914.04 | 793.46 | 45 |
| 57 | VALAALPAVEVNPPAPAVK | y7 | 2 | 20.4 | 914.04 | 679.41 | 45 |
| 58 | LLHLATYTAGGLPLQIPDDVR | y9 | 3 | 22.4 | 755.09 | 1052.57 | 42 |
| 59 | LLHLATYTAGGLPLQIPDDVR | y8 | 3 | 22.4 | 755.09 | 955.52 | 42 |
| 60 | LLHLATYTAGGLPLQIPDDVR | y7 | 3 | 22.4 | 755.09 | 842.44 | 42 |
| 61 | TITPLMQEQAIPGMAVAVIYQGK | y9 | 3 | 22.5 | 820.44 | 948.55 | 45 |
| 62 | TITPLMQEQAIPGMAVAVIYQGK | y8 | 3 | 22.5 | 820.44 | 877.51 | 45 |
| 63 | TITPLMQEQAIPGMAVAVIYQGK | y7 | 3 | 22.5 | 820.44 | 778.45 | 45 |
| 64 | AALLHFYQNWQPQWTPGAK | y9 | 3 | 23.2 | 752.72 | 1012.52 | 42 |
| 65 | AALLHFYQNWQPQWTPGAK | y8 | 3 | 23.2 | 752.72 | 884.46 | 42 |
| 66 | AALLHFYQNWQPQWTPGAK | y7 | 3 | 23.2 | 752.72 | 787.41 | 42 |
| 67 | LYANSSIGLFGALAVK | y9 | 2 | 25.1 | 812.46 | 875.53 | 41 |
| 68 | LYANSSIGLFGALAVK | y8 | 2 | 25.1 | 812.46 | 818.51 | 41 |
| 69 | LYANSSIGLFGALAVK | y7 | 2 | 25.1 | 812.46 | 705.43 | 41 |
| 70 | SLCCALLLTASFSTFAAAK | y9 | 3 | 25.4 | 678.01 | 929.47 | 38 |
| 71 | SLCCALLLTASFSTFAAAK | y8 | 3 | 25.4 | 678.01 | 842.44 | 38 |
| 72 | SLCCALLLTASFSTFAAAK | y7 | 3 | 25.4 | 678.01 | 695.37 | 38 |
| 73 | IGDMYQGLGWEMLNWPLK | y9 | 3 | 28.5 | 717.68 | 1216.62 | 40 |
| 74 | IGDMYQGLGWEMLNWPLK | y8 | 3 | 28.5 | 717.68 | 1030.54 | 40 |
| 75 | IGDMYQGLGWEMLNWPLK | y7 | 3 | 28.5 | 717.68 | 901.5 | 40 |
| 76 | AHYFNYGVANR | y7 | 2 | 15.5 | 656.32 | 793.4 | 34 |
| 77 | AHYFNYGVANR | y8 | 2 | 15.5 | 656.32 | 940.46 | 34 |
| 78 | AHYFNYGVANR | y9 | 2 | 15.5 | 656.32 | 1103.53 | 34 |
| 79 | ANIGGVDDK | y5 | 2 | 9.6 | 444.72 | 533.26 | 25 |
| 80 | ANIGGVDDK | y6 | 2 | 9.6 | 444.72 | 590.28 | 25 |
| 81 | ANIGGVDDK | y7 | 2 | 9.6 | 444.72 | 703.36 | 25 |
| 82 | ESGSQVLFNK | y6 | 2 | 15.1 | 554.79 | 748.44 | 29 |
| 83 | ESGSQVLFNK | y7 | 2 | 15.1 | 554.79 | 835.47 | 29 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 84 | ESGSQVLFNK | y8 | 2 | 15.1 | 554.79 | 892.49 | 29 |
| 85 | GAMQLDDK | y5 | 2 | 11.5 | 439.21 | 618.31 | 24 |
| 86 | GAMQLDDK | y6 | 2 | 11.5 | 439.21 | 749.35 | 24 |
| 87 | GAMQLDDK | y7 | 2 | 11.5 | 439.21 | 820.39 | 24 |
| 88 | GIGIVMLANR | y6 | 2 | 18.7 | 522.31 | 703.39 | 28 |
| 89 | GIGIVMLANR | y7 | 2 | 18.7 | 522.31 | 816.48 | 28 |
| 90 | GIGIVMLANR | y8 | 2 | 18.7 | 522.31 | 873.5 | 28 |
| 91 | HAPWLK | y4 | 2 | 15 | 376.22 | 543.33 | 22 |
| 92 | HAPWLK | y5 | 2 | 15 | 376.22 | 614.37 | 22 |
| 93 | HAPWLK | b5 | 2 | 15 | 376.22 | 605.32 | 22 |
| 94 | IPGMAVAVLK | y6 | 2 | 18.1 | 499.81 | 600.41 | 27 |
| 95 | IPGMAVAVLK | y7 | 2 | 18.1 | 499.81 | 731.45 | 27 |
| 96 | IPGMAVAVLK | y8 | 2 | 18.1 | 499.81 | 788.47 | 27 |
| 97 | PVVDASIQPLLK | y7 | 2 | 19.3 | 640.38 | 798.51 | 33 |
| 98 | PVVDASIQPLLK | y8 | 2 | 19.3 | 640.38 | 869.55 | 33 |
| 99 | PVVDASIQPLLK | y9 | 2 | 19.3 | 640.38 | 984.57 | 33 |
| 100 | QAMASYAYGYSK | y7 | 2 | 15.5 | 670.3 | 851.39 | 34 |
| 101 | QAMASYAYGYSK | y8 | 2 | 15.5 | 670.3 | 938.43 | 34 |
| 102 | QAMASYAYGYSK | y9 | 2 | 15.5 | 670.3 | 1009.46 | 34 |
| 103 | QWAPVYSPGSHR | y8 | 2 | 14.8 | 692.84 | 902.45 | 35 |
| 104 | QWAPVYSPGSHR | y9 | 2 | 14.8 | 692.84 | 999.5 | 35 |
| 105 | QWAPVYSPGSHR | y10 | 2 | 14.8 | 692.84 | 1070.54 | 35 |
| 106 | QYSNPSIGLFGHLAASSLK | y11 | 2 | 22 | 995.52 | 1143.65 | 49 |
| 107 | QYSNPSIGLFGHLAASSLK | y12 | 2 | 22 | 995.52 | 1200.67 | 49 |
| 108 | QYSNPSIGLFGHLAASSLK | y11 | 2 | 22 | 664.02 | 1143.65 | 37 |
| 109 | TGSTNGFGAYVAFVPAR | y9 | 2 | 19.4 | 857.93 | 993.55 | 43 |
| 110 | TGSTNGFGAYVAFVPAR | y10 | 2 | 19.4 | 857.93 | 1050.57 | 43 |
| 111 | TGSTNGFGAYVAFVPAR | y11 | 2 | 19.4 | 857.93 | 1197.64 | 43 |
| 112 | TLTATLGAYAVVK | y8 | 2 | 18.3 | 654.38 | 820.49 | 34 |
| 113 | TLTATLGAYAVVK | y9 | 2 | 18.3 | 654.38 | 921.54 | 34 |
| 114 | TLTATLGAYAVVK | y10 | 2 | 18.3 | 654.38 | 992.58 | 34 |
| 115 | VNPGMLADEAYGIK | y8 | 2 | 18.8 | 739.37 | 866.43 | 38 |
| 116 | VNPGMLADEAYGIK | y9 | 2 | 18.8 | 739.37 | 979.51 | 38 |
| 117 | VNPGMLADEAYGIK | y10 | 2 | 18.8 | 739.37 | 1110.55 | 38 |
| 118 | PSGMSYEEAMTR | y10 | 2 | 15.5 | 679.79 | 1174.49 | 35 |
| 119 | PSGMSYEEAMTR | y9 | 2 | 15.5 | 679.79 | 1117.47 | 35 |
| 120 | PSGMSYEEAMTR | y8 | 2 | 15.5 | 679.79 | 986.42 | 35 |
| 121 | PYYFTWGK | y7 | 2 | 20.3 | 531.26 | 964.46 | 29 |

TABLE 6-continued

| Transition number | Peptide | Fragment ion | Charge state of the precursor | Retention time | (m/z) filtered in Q1 | (m/z) filtered in Q3 | Collision energy |
|---|---|---|---|---|---|---|---|
| 122 | PYYFTWGK | y6 | 2 | 20.3 | 531.26 | 801.39 | 29 |
| 123 | PYYFTWGK | y5 | 2 | 20.3 | 531.26 | 638.33 | 29 |

The areas obtained for each of the transitions and for each of the microorganisms studied were measured. When the areas of the 3 transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 8

Identification of a Resistance to CTX-M Beta-Lactams

The samples corresponding to a species able to comprise a CTX-M resistance mechanism can be detected by employing the following method.

Each sample is treated according to example 5, then analysed according to example 6 by detecting the peptides from TABLE 7 instead of the peptides from TABLE 3.

TABLE 7

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 1 | AGLPK | 2 | y4 | 9.5 | 243.16 | 414.27 | 16 |
| 2 | AGLPK | 2 | y3 | 9.5 | 243.16 | 357.25 | 16 |
| 3 | AGLPK | 2 | y2 | 9.5 | 243.16 | 244.17 | 16 |
| 4 | AGLPTSWTVGDK | 2 | y9 | 16.6 | 616.32 | 990.49 | 32 |
| 5 | AGLPTSWTVGDK | 2 | y8 | 16.6 | 616.32 | 893.44 | 32 |
| 6 | AGLPTSWTVGDK | 2 | y7 | 16.6 | 616.32 | 792.39 | 32 |
| 7 | AIGDETFR | 2 | y7 | 14 | 454.73 | 837.41 | 25 |
| 8 | AIGDETFR | 2 | y6 | 14 | 454.73 | 724.33 | 25 |
| 9 | AIGDETFR | 2 | y5 | 14 | 454.73 | 667.3 | 25 |
| 10 | ALAETQR | 2 | y6 | 7.4 | 394.72 | 717.39 | 22 |
| 11 | ALAETQR | 2 | y5 | 7.4 | 394.72 | 604.3 | 22 |
| 12 | ALAETQR | 2 | y4 | 7.4 | 394.72 | 533.27 | 22 |
| 13 | ALGDSQR | 2 | y6 | 7 | 373.69 | 675.34 | 21 |
| 14 | ALGDSQR | 2 | y5 | 7 | 373.69 | 562.26 | 21 |
| 15 | ALGDSQR | 2 | y4 | 7 | 373.69 | 505.24 | 21 |
| 16 | AMAQTLR | 2 | y6 | 12.1 | 395.72 | 719.39 | 22 |
| 17 | AMAQTLR | 2 | y5 | 12.1 | 395.72 | 588.35 | 22 |
| 18 | AMAQTLR | 2 | y4 | 12.1 | 395.72 | 517.31 | 22 |
| 19 | APLILVTYFTQPQPK | 2 | y9 | 22.4 | 858.49 | 1109.6 | 43 |
| 20 | APLILVTYFTQPQPK | 2 | y8 | 22.4 | 858.49 | 1008.5 | 43 |
| 21 | APLILVTYFTQPQPK | 2 | y7 | 22.4 | 858.49 | 845.45 | 43 |
| 22 | APLVLVTYFTQPQQNAESR | 3 | y9 | 21.4 | 721.38 | 1057.5 | 40 |
| 23 | APLVLVTYFTQPQQNAESR | 3 | y8 | 21.4 | 721.38 | 929.44 | 40 |
| 24 | APLVLVTYFTQPQQNAESR | 3 | y7 | 21.4 | 721.38 | 832.39 | 40 |
| 25 | AQLVTWLK | 2 | y7 | 21 | 479.79 | 887.53 | 26 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 26 | AQLVTWLK | 2 | y6 | 21 | 479.79 | 759.48 | 26 |
| 27 | AQLVTWLK | 2 | y5 | 21 | 479.79 | 646.39 | 26 |
| 28 | AQLVTWMK | 2 | y7 | 19 | 488.77 | 905.49 | 27 |
| 29 | AQLVTWMK | 2 | y6 | 19 | 488.77 | 777.43 | 27 |
| 30 | AQLVTWMK | 2 | y5 | 19 | 488.77 | 664.35 | 27 |
| 31 | DILAAAAK | 2 | y7 | 12.1 | 386.73 | 657.43 | 22 |
| 32 | DILAAAAK | 2 | y6 | 12.1 | 386.73 | 544.35 | 22 |
| 33 | DILAAAAK | 2 | y5 | 12.1 | 386.73 | 431.26 | 22 |
| 34 | DTTSPR | 2 | y5 | 4.6 | 338.67 | 561.3 | 20 |
| 35 | DTTSPR | 2 | y4 | 4.6 | 338.67 | 460.25 | 20 |
| 36 | DTTSPR | 2 | y3 | 4.6 | 338.67 | 359.2 | 20 |
| 37 | DTTTPLAMAQTLK | 2 | y9 | 17 | 695.87 | 972.55 | 36 |
| 38 | DTTTPLAMAQTLK | 2 | y8 | 17 | 695.87 | 875.5 | 36 |
| 39 | DTTTPLAMAQTLK | 2 | y7 | 17 | 695.87 | 762.42 | 36 |
| 40 | DTTTPR | 2 | y5 | 4.8 | 345.67 | 575.31 | 20 |
| 41 | DTTTPR | 2 | y4 | 4.8 | 345.67 | 474.27 | 20 |
| 42 | DTTTPR | 2 | y3 | 4.8 | 345.67 | 373.22 | 20 |
| 43 | DVLAAAAK | 2 | y7 | 10.5 | 379.72 | 643.41 | 22 |
| 44 | DVLAAAAK | 2 | y6 | 10.5 | 379.72 | 544.35 | 22 |
| 45 | DVLAAAAK | 2 | y5 | 10.5 | 379.72 | 431.26 | 22 |
| 46 | DVLASAAK | 2 | y7 | 10.8 | 387.72 | 659.41 | 22 |
| 47 | DVLASAAK | 2 | y6 | 10.8 | 387.72 | 560.34 | 22 |
| 48 | DVLASAAK | 2 | y5 | 10.8 | 387.72 | 447.26 | 22 |
| 49 | DVLASAAR | 2 | y7 | 11.4 | 401.72 | 687.41 | 23 |
| 50 | DVLASAAR | 2 | y6 | 11.4 | 401.72 | 588.35 | 23 |
| 51 | DVLASAAR | 2 | y5 | 11.4 | 401.72 | 475.26 | 23 |
| 52 | FAMCSTSK | 2 | y7 | 11.1 | 466.2 | 784.33 | 26 |
| 53 | FAMCSTSK | 2 | y6 | 11.1 | 466.2 | 713.3 | 26 |
| 54 | FAMCSTSK | 2 | y5 | 11.1 | 466.2 | 582.26 | 26 |
| 55 | FPMCSTSK | 2 | y7 | 12.1 | 479.21 | 810.35 | 26 |
| 56 | FPMCSTSK | 2 | y6 | 12.1 | 479.21 | 713.3 | 26 |
| 57 | FPMCSTSK | 2 | y5 | 12.1 | 479.21 | 582.26 | 26 |
| 58 | GNTTGAASIQAGLPASWVVGDK | 3 | y9 | 19.5 | 700.7 | 958.5 | 39 |
| 59 | GNTTGAASIQAGLPASWVVGDK | 3 | y8 | 19.5 | 700.7 | 861.45 | 39 |
| 60 | GNTTGAASIQAGLPASWVVGDK | 3 | y7 | 19.5 | 700.7 | 790.41 | 39 |
| 61 | GNTTGAASIQAGLPTSWVVGDK | 3 | y9 | 19.3 | 710.7 | 988.51 | 40 |
| 62 | GNTTGAASIQAGLPTSWVVGDK | 3 | y8 | 19.3 | 710.7 | 891.46 | 40 |
| 63 | GNTTGAASIQAGLPTSWVVGDK | 3 | y7 | 19.3 | 710.7 | 790.41 | 40 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 64 | GNTTGAASIR | 2 | y9 | 9 | 474.25 | 890.47 | 26 |
| 65 | GNTTGAASIR | 2 | y8 | 9 | 474.25 | 776.43 | 26 |
| 66 | GNTTGAASIR | 2 | y7 | 9 | 474.25 | 675.38 | 26 |
| 67 | GNTTGSASIR | 2 | y9 | 8.5 | 482.25 | 906.46 | 26 |
| 68 | GNTTGSASIR | 2 | y8 | 8.5 | 482.25 | 792.42 | 26 |
| 69 | GNTTGSASIR | 2 | y7 | 8.5 | 482.25 | 691.37 | 26 |
| 70 | HLLNQR | 2 | y5 | 10.2 | 390.73 | 643.39 | 22 |
| 71 | HLLNQR | 2 | y4 | 10.2 | 390.73 | 530.3 | 22 |
| 72 | HLLNQR | 2 | y3 | 10.2 | 390.73 | 417.22 | 22 |
| 73 | LAALEK | 2 | y5 | 11 | 322.7 | 531.31 | 19 |
| 74 | LAALEK | 2 | y4 | 11 | 322.7 | 460.28 | 19 |
| 75 | LAALEK | 2 | y3 | 11 | 322.7 | 389.24 | 19 |
| 76 | LAELER | 2 | y5 | 12.1 | 365.71 | 617.33 | 21 |
| 77 | LAELER | 2 | y4 | 12.1 | 365.71 | 546.29 | 21 |
| 78 | LAELER | 2 | y3 | 12.1 | 365.71 | 417.25 | 21 |
| 79 | LGVALIDTADNTQVLYR | 2 | y9 | 21.4 | 931.5 | 1079.6 | 46 |
| 80 | LGVALIDTADNTQVLYR | 2 | y8 | 21.4 | 931.5 | 1008.5 | 46 |
| 81 | LGVALIDTADNTQVLYR | 2 | y7 | 21.4 | 931.5 | 893.48 | 46 |
| 82 | LGVALINTADNSQILYR | 2 | y9 | 21.1 | 931.01 | 1079.6 | 46 |
| 83 | LGVALINTADNSQILYR | 2 | y8 | 21.1 | 931.01 | 1008.5 | 46 |
| 84 | LGVALINTADNSQILYR | 2 | y7 | 21.1 | 931.01 | 893.48 | 46 |
| 85 | LIAHLGGPDK | 2 | y9 | 12.7 | 510.8 | 907.5 | 27 |
| 86 | LIAHLGGPDK | 2 | y8 | 12.7 | 510.8 | 794.42 | 27 |
| 87 | LIAHLGGPDK | 2 | y7 | 12.7 | 510.8 | 723.38 | 27 |
| 88 | LIAHVGGPASVTAFAR | 2 | y9 | 17.5 | 783.94 | 919.5 | 39 |
| 89 | LIAHVGGPASVTAFAR | 2 | y8 | 17.5 | 783.94 | 822.45 | 39 |
| 90 | LIAHVGGPASVTAFAR | 2 | y7 | 17.5 | 783.94 | 751.41 | 39 |
| 91 | LIAQLGGPGGVTAFAR | 2 | y9 | 19.3 | 764.44 | 875.47 | 39 |
| 92 | LIAQLGGPGGVTAFAR | 2 | y8 | 19.3 | 764.44 | 778.42 | 39 |
| 93 | LIAQLGGPGGVTAFAR | 2 | y7 | 19.3 | 764.44 | 721.4 | 39 |
| 94 | NLTLGK | 2 | y5 | 12.2 | 323.2 | 531.35 | 19 |
| 95 | NLTLGK | 2 | y4 | 12.2 | 323.2 | 418.27 | 19 |
| 96 | NLTLGK | 2 | y3 | 12.2 | 323.2 | 317.22 | 19 |
| 97 | QLGDETFR | 2 | y7 | 14.4 | 483.24 | 837.41 | 26 |
| 98 | QLGDETFR | 2 | y6 | 14.4 | 483.24 | 724.33 | 26 |
| 99 | QLGDETFR | 2 | y5 | 14.4 | 483.24 | 667.3 | 26 |
| 100 | QLLNQPVEIK | 2 | y9 | 16.2 | 591.35 | 1053.6 | 31 |
| 101 | QLLNQPVEIK | 2 | y8 | 16.2 | 591.35 | 940.55 | 31 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 102 | QLLNQPVEIK | 2 | y7 | 16.2 | 591.35 | 827.46 | 31 |
| 103 | QLTLGHALGETQR | 2 | y9 | 14.9 | 712.39 | 968.49 | 36 |
| 104 | QLTLGHALGETQR | 2 | y8 | 14.9 | 712.39 | 911.47 | 36 |
| 105 | QLTLGHALGETQR | 2 | y7 | 14.9 | 712.39 | 774.41 | 36 |
| 106 | QSESDK | 2 | y5 | 1.7 | 347.16 | 565.25 | 20 |
| 107 | QSESDK | 2 | y4 | 1.7 | 347.16 | 478.21 | 20 |
| 108 | QSESDK | 2 | y3 | 1.7 | 347.16 | 349.17 | 20 |
| 109 | QSETQK | 2 | y5 | 3.7 | 360.68 | 592.29 | 21 |
| 110 | QSETQK | 2 | y4 | 3.7 | 360.68 | 505.26 | 21 |
| 111 | QSETQK | 2 | y3 | 3.7 | 360.68 | 376.22 | 21 |
| 112 | QSGGR | 2 | y4 | 5.5 | 252.63 | 376.19 | 16 |
| 113 | QSGGR | 2 | y3 | 5.5 | 252.63 | 289.16 | 16 |
| 114 | QSGGR | 2 | b4 | 5.5 | 252.63 | 330.14 | 16 |
| 115 | SDLVNYNPIAEK | 2 | y9 | 17.1 | 681.85 | 1047.6 | 35 |
| 116 | SDLVNYNPIAEK | 2 | y8 | 17.1 | 681.85 | 948.48 | 35 |
| 117 | SDLVNYNPIAEK | 2 | y7 | 17.1 | 681.85 | 834.44 | 35 |
| 118 | SESEPNLLNQR | 2 | y9 | 13.3 | 643.82 | 1070.6 | 33 |
| 119 | SESEPNLLNQR | 2 | y8 | 13.3 | 643.82 | 983.53 | 33 |
| 120 | SESEPNLLNQR | 2 | y7 | 13.3 | 643.82 | 854.48 | 33 |
| 121 | SLGDETFR | 2 | y7 | 14.6 | 462.72 | 837.41 | 25 |
| 122 | SLGDETFR | 2 | y6 | 14.6 | 462.72 | 724.33 | 25 |
| 123 | SLGDETFR | 2 | y5 | 14.6 | 462.72 | 667.3 | 25 |
| 124 | SSGGR | 2 | y4 | 5.9 | 232.12 | 376.19 | 15 |
| 125 | SSGGR | 2 | y3 | 5.9 | 232.12 | 289.16 | 15 |
| 126 | SWVVGDK | 2 | y6 | 14.2 | 395.71 | 703.38 | 22 |
| 127 | SWVVGDK | 2 | y5 | 14.2 | 395.71 | 517.3 | 22 |
| 128 | SWVVGDK | 2 | y4 | 14.2 | 395.71 | 418.23 | 22 |
| 129 | TEPTLNTAIPGDPR | 2 | y9 | 15.6 | 741.38 | 940.48 | 38 |
| 130 | TEPTLNTAIPGDPR | 2 | y8 | 15.6 | 741.38 | 826.44 | 38 |
| 131 | TEPTLNTAIPGDPR | 2 | y7 | 15.6 | 741.38 | 725.39 | 38 |
| 132 | TGSGDYGTTNDIAVIWPK | 2 | y8 | 19.9 | 947.96 | 941.55 | 47 |
| 133 | TGSGDYGTTNDIAVIWPK | 2 | y7 | 19.9 | 947.96 | 826.52 | 47 |
| 134 | TGSGDYGTTNDIAVIWPK | 2 | y6 | 19.9 | 947.96 | 713.43 | 47 |
| 135 | TGSGDYGTTNDIAVIWPQGR | 3 | y9 | 19.7 | 703.34 | 1039.6 | 39 |
| 136 | TGSGDYGTTNDIAVIWPQGR | 3 | y8 | 19.7 | 703.34 | 926.52 | 39 |
| 137 | TGSGDYGTTNDIAVIWPQGR | 3 | y7 | 19.7 | 703.34 | 855.48 | 39 |
| 138 | TGSGGYGTTNDIAVIWPK | 2 | y9 | 19.5 | 918.96 | 1055.6 | 45 |
| 139 | TGSGGYGTTNDIAVIWPK | 2 | y8 | 19.5 | 918.96 | 941.55 | 45 |

TABLE 7-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 140 | TGSGGYGTTNDIAVIWPK | 2 | y7 | 19.5 | 918.96 | 826.52 | 45 |
| 141 | VMAAAAVLK | 2 | y8 | 15.3 | 437.26 | 774.45 | 24 |
| 142 | VMAAAAVLK | 2 | y7 | 15.3 | 437.26 | 643.41 | 24 |
| 143 | VMAAAAVLK | 2 | y6 | 15.3 | 437.26 | 572.38 | 24 |
| 144 | VMAVAAVLK | 2 | y8 | 16.3 | 451.28 | 802.49 | 25 |
| 145 | VMAVAAVLK | 2 | y7 | 16.3 | 451.28 | 671.45 | 25 |
| 146 | VMAVAAVLK | 2 | y6 | 16.3 | 451.28 | 600.41 | 25 |
| 147 | VTAFAR | 2 | y5 | 11.6 | 332.69 | 565.31 | 20 |
| 148 | VTAFAR | 2 | y4 | 11.6 | 332.69 | 464.26 | 20 |
| 149 | VTAFAR | 2 | y3 | 11.6 | 332.69 | 393.22 | 20 |

The areas obtained for each of the transitions and for each of the microorganisms studied were measured. When the areas of the 3 transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 9

Identification of a Resistance to SHV Beta-Lactams

The samples corresponding to a species able to comprise an SHV resistance mechanism can be detected by employing the following method.

Each sample is treated according to example 5, then analysed according to example 6 by detecting the peptides from TABLE 8 instead of the peptides from TABLE 3.

TABLE 8

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 1 | AGAGER | 2 | y5 | 5 | 280.64 | 489.24 | 17 |
| 2 | AGAGER | 2 | y4 | 5 | 280.64 | 432.22 | 17 |
| 3 | AGAGER | 2 | y3 | 5 | 280.64 | 361.18 | 17 |
| 4 | ATTTPASMAATLR | 2 | y9 | 15.1 | 646.34 | 917.49 | 33 |
| 5 | ATTTPASMAATLR | 2 | y8 | 15.1 | 646.34 | 820.43 | 33 |
| 6 | ATTTPASMAATLR | 2 | y7 | 15.1 | 646.34 | 749.4 | 33 |
| 7 | CIISLLATLPLAVHASPQPLEQIK | 3 | y9 | 27.3 | 871.5 | 1039.6 | 48 |
| 8 | CIISLLATLPLAVHASPQPLEQIK | 3 | y8 | 27.3 | 871.5 | 952.55 | 48 |
| 9 | CIISLLATLPLAVHASPQPLEQIK | 3 | y7 | 27.3 | 871.5 | 855.49 | 48 |
| 10 | DMPASMAER | 2 | y8 | 12 | 504.22 | 892.4 | 27 |
| 11 | DMPASMAER | 2 | y7 | 12 | 504.22 | 761.36 | 27 |
| 12 | DMPASMAER | 2 | y6 | 12 | 504.22 | 664.31 | 27 |
| 13 | DSPASMAER | 2 | y8 | 8.8 | 482.21 | 848.39 | 26 |
| 14 | DSPASMAER | 2 | y7 | 8.8 | 482.21 | 761.36 | 26 |
| 15 | DSPASMAER | 2 | y6 | 8.8 | 482.21 | 664.31 | 26 |
| 16 | DTLASMAER | 2 | y8 | 13.3 | 497.24 | 878.44 | 27 |
| 17 | DTLASMAER | 2 | y7 | 13.3 | 497.24 | 777.39 | 27 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 18 | DTLASMAER | 2 | y6 | 13.3 | 497.24 | 664.31 | 27 |
| 19 | DTPASMAER | 2 | y8 | 9.2 | 489.22 | 862.41 | 27 |
| 20 | DTPASMAER | 2 | y7 | 9.2 | 489.22 | 761.36 | 27 |
| 21 | DTPASMAER | 2 | y6 | 9.2 | 489.22 | 664.31 | 27 |
| 22 | DTPASMAK | 2 | y7 | 8.5 | 410.7 | 705.36 | 23 |
| 23 | DTPASMAK | 2 | y6 | 8.5 | 410.7 | 604.31 | 23 |
| 24 | DTPASMAK | 2 | y5 | 8.5 | 410.7 | 507.26 | 23 |
| 25 | DTTTPASMAATLR | 2 | y9 | 15.2 | 668.33 | 917.49 | 34 |
| 26 | DTTTPASMAATLR | 2 | y8 | 15.2 | 668.33 | 820.43 | 34 |
| 27 | DTTTPASMAATLR | 2 | y7 | 15.2 | 668.33 | 749.4 | 34 |
| 28 | DTTTPASMAGTLR | 2 | y9 | 15.1 | 661.32 | 903.47 | 34 |
| 29 | DTTTPASMAGTLR | 2 | y8 | 15.1 | 661.32 | 806.42 | 34 |
| 30 | DTTTPASMAGTLR | 2 | y7 | 15.1 | 661.32 | 735.38 | 34 |
| 31 | DTTTPASMTATLR | 2 | y9 | 14.9 | 683.34 | 947.5 | 35 |
| 32 | DTTTPASMTATLR | 2 | y8 | 14.9 | 683.34 | 850.45 | 35 |
| 33 | DTTTPASMTATLR | 2 | y7 | 14.9 | 683.34 | 779.41 | 35 |
| 34 | FPMISTFK | 2 | y7 | 19.7 | 485.76 | 823.44 | 26 |
| 35 | FPMISTFK | 2 | y6 | 19.7 | 485.76 | 726.39 | 26 |
| 36 | FPMISTFK | 2 | y5 | 19.7 | 485.76 | 595.34 | 26 |
| 37 | FPMMSTFK | 2 | y7 | 19.3 | 494.74 | 841.39 | 27 |
| 38 | FPMMSTFK | 2 | y6 | 19.3 | 494.74 | 744.34 | 27 |
| 39 | FPMMSTFK | 2 | y5 | 19.3 | 494.74 | 613.3 | 27 |
| 40 | GIVALLGGNIK | 2 | y9 | 18.4 | 527.83 | 884.56 | 28 |
| 41 | GIVALLGGNIK | 2 | y8 | 18.4 | 527.83 | 785.49 | 28 |
| 42 | GIVALLGGNIK | 2 | y7 | 18.4 | 527.83 | 714.45 | 28 |
| 43 | GIVALLGPDNK | 2 | y8 | 16.9 | 548.82 | 827.46 | 29 |
| 44 | GIVALLGPDNK | 2 | y7 | 16.9 | 548.82 | 756.43 | 29 |
| 45 | GIVALLGPDNK | 2 | y6 | 16.9 | 548.82 | 643.34 | 29 |
| 46 | GIVALLGPNHK | 2 | y9 | 16.3 | 559.84 | 948.56 | 30 |
| 47 | GIVALLGPNHK | 2 | y8 | 16.3 | 559.84 | 849.49 | 30 |
| 48 | GIVALLGPNHK | 2 | y7 | 16.3 | 559.84 | 778.46 | 30 |
| 49 | GIVALLGPNNK | 2 | y9 | 16.5 | 548.33 | 925.55 | 29 |
| 50 | GIVALLGPNNK | 2 | y8 | 16.5 | 548.33 | 826.48 | 29 |
| 51 | GIVALLGPNNK | 2 | y7 | 16.5 | 548.33 | 755.44 | 29 |
| 52 | GIVALLGPNNNAER | 2 | y9 | 16.4 | 719.39 | 984.49 | 37 |
| 53 | GIVALLGPNNNAER | 2 | y8 | 16.4 | 719.39 | 871.4 | 37 |
| 54 | GIVALLGPNNNAER | 2 | y7 | 16.4 | 719.39 | 814.38 | 37 |
| 55 | GIVALR | 2 | y5 | 14.2 | 314.71 | 571.39 | 19 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 56 | GIVALR | 2 | y4 | 14.2 | 314.71 | 458.31 | 19 |
| 57 | GIVALR | 2 | y3 | 14.2 | 314.71 | 359.24 | 19 |
| 58 | GPNNK | 2 | y4 | 5.3 | 265.14 | 472.25 | 17 |
| 59 | GPNNK | 2 | y3 | 5.3 | 265.14 | 375.2 | 17 |
| 60 | GPNNK | 2 | b4 | 5.3 | 265.14 | 383.17 | 17 |
| 61 | GTTTPASMAATLR | 2 | y9 | 15.3 | 639.33 | 917.49 | 33 |
| 62 | GTTTPASMAATLR | 2 | y8 | 15.3 | 639.33 | 820.43 | 33 |
| 63 | GTTTPASMAATLR | 2 | y7 | 15.3 | 639.33 | 749.4 | 33 |
| 64 | HLADGMTVGELCAAAITMSDNSAAK | 3 | y9 | 20 | 845.39 | 924.41 | 46 |
| 65 | HLADGMTVGELCAAAITMSDNSAAK | 3 | y8 | 20 | 845.39 | 823.36 | 46 |
| 66 | HLADGMTVGELCAAAITMSDNSAAK | 3 | y7 | 20 | 845.39 | 692.32 | 46 |
| 67 | HLLQWMVDDR | 2 | y9 | 21.2 | 656.83 | 1175.6 | 34 |
| 68 | HLLQWMVDDR | 2 | y8 | 21.2 | 656.83 | 1062.5 | 34 |
| 69 | HLLQWMVDDR | 2 | y7 | 21.2 | 656.83 | 949.42 | 34 |
| 70 | IHYLQQDLVDYSPVSEK | 3 | y9 | 19.9 | 678.68 | 1023.5 | 38 |
| 71 | IHYLQQDLVDYSPVSEK | 3 | y8 | 19.9 | 678.68 | 924.43 | 38 |
| 72 | IHYLQQDLVDYSPVSEK | 3 | y7 | 19.9 | 678.68 | 809.4 | 38 |
| 73 | IVVIYLR | 2 | y6 | 19.1 | 438.29 | 762.49 | 24 |
| 74 | IVVIYLR | 2 | y5 | 19.1 | 438.29 | 663.42 | 24 |
| 75 | IVVIYLR | 2 | y4 | 19.1 | 438.29 | 564.35 | 24 |
| 76 | LCIISLLAALPLAVHASPQPLEQIK | 3 | y9 | 29.8 | 899.19 | 1039.6 | 49 |
| 77 | LCIISLLAALPLAVHASPQPLEQIK | 3 | y8 | 29.8 | 899.19 | 952.55 | 49 |
| 78 | LCIISLLAALPLAVHASPQPLEQIK | 3 | y7 | 29.8 | 899.19 | 855.49 | 49 |
| 79 | LCIISLLATLPLAVHASPQPLDQIK | 3 | y9 | 29.5 | 904.52 | 1025.6 | 49 |
| 80 | LCIISLLATLPLAVHASPQPLDQIK | 3 | y8 | 29.5 | 904.52 | 938.53 | 49 |
| 81 | LCIISLLATLPLAVHASPQPLDQIK | 3 | y7 | 29.5 | 904.52 | 841.48 | 49 |
| 82 | LCIISLLATLPLAVHASPQPLEQIK | 3 | y9 | 29.6 | 909.19 | 1039.6 | 49 |
| 83 | LCIISLLATLPLAVHASPQPLEQIK | 3 | y8 | 29.6 | 909.19 | 952.55 | 49 |
| 84 | LCIISLLATLPLAVHASPQPLEQIK | 3 | y7 | 29.6 | 909.19 | 855.49 | 49 |
| 85 | LCIISLLATLPLAVHSSPQPLEQIK | 3 | y9 | 29.3 | 914.53 | 1039.6 | 50 |
| 86 | LCIISLLATLPLAVHSSPQPLEQIK | 3 | y8 | 29.3 | 914.53 | 952.55 | 50 |
| 87 | LCIISLLATLPLAVHSSPQPLEQIK | 3 | y7 | 29.3 | 914.53 | 855.49 | 50 |
| 88 | LCIISLLATLPLAVHTSPQPLEQIK | 3 | y9 | 29.5 | 919.2 | 1039.6 | 50 |
| 89 | LCIISLLATLPLAVHTSPQPLEQIK | 3 | y8 | 29.5 | 919.2 | 952.55 | 50 |
| 90 | LCIISLLATLPLAVHTSPQPLEQIK | 3 | y7 | 29.5 | 919.2 | 855.49 | 50 |
| 91 | LCIISLLATLPLTVHASPQPLEQIK | 3 | y9 | 29.3 | 919.2 | 1039.6 | 50 |
| 92 | LCIISLLATLPLTVHASPQPLEQIK | 3 | y8 | 29.3 | 919.2 | 952.55 | 50 |
| 93 | LCIISLLATLPLTVHASPQPLEQIK | 3 | y7 | 29.3 | 919.2 | 855.49 | 50 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 94 | LCIISLLATLPLVVHASPQPLEQIK | 3 | y9 | 30.3 | 918.54 | 1039.6 | 50 |
| 95 | LCIISLLATLPLVVHASPQPLEQIK | 3 | y8 | 30.3 | 918.54 | 952.55 | 50 |
| 96 | LCIISLLATLPLVVHASPQPLEQIK | 3 | y7 | 30.3 | 918.54 | 855.49 | 50 |
| 97 | LCIISLLATLSLAVHASPQPLEQIK | 3 | y9 | 29.5 | 905.85 | 1039.6 | 49 |
| 98 | LCIISLLATLSLAVHASPQPLEQIK | 3 | y8 | 29.5 | 905.85 | 952.55 | 49 |
| 99 | LCIISLLATLSLAVHASPQPLEQIK | 3 | y7 | 29.5 | 905.85 | 855.49 | 49 |
| 100 | LCIISLLATMPLAVHASPQPLEQIK | 3 | y9 | 27.4 | 915.18 | 1039.6 | 50 |
| 101 | LCIISLLATMPLAVHASPQPLEQIK | 3 | y8 | 27.4 | 915.18 | 952.55 | 50 |
| 102 | LCIISLLATMPLAVHASPQPLEQIK | 3 | y7 | 27.4 | 915.18 | 855.49 | 50 |
| 103 | LCIISLLAVLPLAVHASPQPLEQIK | 3 | y9 | 30.5 | 908.53 | 1039.6 | 49 |
| 104 | LCIISLLAVLPLAVHASPQPLEQIK | 3 | y8 | 30.5 | 908.53 | 952.55 | 49 |
| 105 | LCIISLLAVLPLAVHASPQPLEQIK | 3 | y7 | 30.5 | 908.53 | 855.49 | 49 |
| 106 | LLISQR | 2 | y5 | 12.9 | 365.23 | 616.38 | 21 |
| 107 | LLISQR | 2 | y4 | 12.9 | 365.23 | 503.29 | 21 |
| 108 | LLISQR | 2 | y3 | 12.9 | 365.23 | 390.21 | 21 |
| 109 | LLLATVGGPAGLTAFLR | 2 | y9 | 24 | 835.5 | 945.55 | 42 |
| 110 | LLLATVGGPAGLTAFLR | 2 | y8 | 24 | 835.5 | 848.5 | 42 |
| 111 | LLLATVGGPAGLTAFLR | 2 | y7 | 24 | 835.5 | 777.46 | 42 |
| 112 | LLNSQR | 2 | y5 | 9.4 | 365.71 | 617.34 | 21 |
| 113 | LLNSQR | 2 | y4 | 9.4 | 365.71 | 504.25 | 21 |
| 114 | LLNSQR | 2 | y3 | 9.4 | 365.71 | 390.21 | 21 |
| 115 | LLTNQR | 2 | y5 | 9.8 | 372.72 | 631.35 | 21 |
| 116 | LLTNQR | 2 | y4 | 9.8 | 372.72 | 518.27 | 21 |
| 117 | LLTNQR | 2 | y3 | 9.8 | 372.72 | 417.22 | 21 |
| 118 | LLTSQR | 2 | y5 | 9.8 | 359.22 | 604.34 | 21 |
| 119 | LLTSQR | 2 | y4 | 9.8 | 359.22 | 491.26 | 21 |
| 120 | LLTSQR | 2 | y3 | 9.8 | 359.22 | 390.21 | 21 |
| 121 | LNIISLLATLPLAVHASPQPLEQIK | 3 | y9 | 29.6 | 893.87 | 1039.6 | 49 |
| 122 | LNIISLLATLPLAVHASPQPLEQIK | 3 | y8 | 29.6 | 893.87 | 952.55 | 49 |
| 123 | LNIISLLATLPLAVHASPQPLEQIK | 3 | y7 | 29.6 | 893.87 | 855.49 | 49 |
| 124 | LSASSQR | 2 | y6 | 6.2 | 374.7 | 635.31 | 21 |
| 125 | LSASSQR | 2 | y5 | 6.2 | 374.7 | 548.28 | 21 |
| 126 | LSASSQR | 2 | y4 | 6.2 | 374.7 | 477.24 | 21 |
| 127 | LSESQLSGR | 2 | y8 | 10.5 | 488.76 | 863.42 | 27 |
| 128 | LSESQLSGR | 2 | y7 | 10.5 | 488.76 | 776.39 | 27 |
| 129 | LSESQLSGR | 2 | y6 | 10.5 | 488.76 | 647.35 | 27 |
| 130 | LSESQLSGSVGMIEMDLASGR | 3 | y9 | 21.1 | 723.02 | 991.49 | 40 |
| 131 | LSESQLSGSVGMIEMDLASGR | 3 | y8 | 21.1 | 723.02 | 878.4 | 40 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 132 | LSESQLSGSVGMIEMDLASGR | 3 | y7 | 21.1 | 723.02 | 749.36 | 40 |
| 133 | MVVIYLR | 2 | y6 | 18.9 | 447.27 | 762.49 | 25 |
| 134 | MVVIYLR | 2 | y5 | 18.9 | 447.27 | 663.42 | 25 |
| 135 | MVVIYLR | 2 | y4 | 18.9 | 447.27 | 564.35 | 25 |
| 136 | NEALPGDAR | 2 | y8 | 10.6 | 471.74 | 828.42 | 26 |
| 137 | NEALPGDAR | 2 | y7 | 10.6 | 471.74 | 699.38 | 26 |
| 138 | NEALPGDAR | 2 | y6 | 10.6 | 471.74 | 628.34 | 26 |
| 139 | NQHIAGIGAALIEHWQR | 2 | y9 | 21.2 | 957.51 | 1123.6 | 47 |
| 140 | NQHIAGIGAALIEHWQR | 2 | y8 | 21.2 | 957.51 | 1052.6 | 47 |
| 141 | NQHIAGIGAALIEHWQR | 2 | y7 | 21.2 | 957.51 | 981.53 | 47 |
| 142 | NQQIAGIGAALIEHWQR | 2 | y9 | 22.1 | 953.01 | 1123.6 | 47 |
| 143 | NQQIAGIGAALIEHWQR | 2 | y8 | 22.1 | 953.01 | 1052.6 | 47 |
| 144 | NQQIAGIGAALIEHWQR | 2 | y7 | 22.1 | 953.01 | 981.53 | 47 |
| 145 | NQQIAGLGAALIEHWQR | 2 | y9 | 22.3 | 953.01 | 1123.6 | 47 |
| 146 | NQQIAGLGAALIEHWQR | 2 | y8 | 22.3 | 953.01 | 1052.6 | 47 |
| 147 | NQQIAGLGAALIEHWQR | 2 | y7 | 22.3 | 953.01 | 981.53 | 47 |
| 148 | NTTTPASMAATLR | 2 | y9 | 15.3 | 667.84 | 917.49 | 34 |
| 149 | NTTTPASMAATLR | 2 | y8 | 15.3 | 667.84 | 820.43 | 34 |
| 150 | NTTTPASMAATLR | 2 | y7 | 15.3 | 667.84 | 749.4 | 34 |
| 151 | NVLTSQR | 2 | y6 | 9.6 | 409.23 | 703.41 | 23 |
| 152 | NVLTSQR | 2 | y5 | 9.6 | 409.23 | 604.34 | 23 |
| 153 | NVLTSQR | 2 | y4 | 9.6 | 409.23 | 491.26 | 23 |
| 154 | QIDDNVTR | 2 | y7 | 9.4 | 480.74 | 832.42 | 26 |
| 155 | QIDDNVTR | 2 | y6 | 9.4 | 480.74 | 719.33 | 26 |
| 156 | QIDDNVTR | 2 | y5 | 9.4 | 480.74 | 604.3 | 26 |
| 157 | QIGDK | 2 | y4 | 5.8 | 280.66 | 432.25 | 17 |
| 158 | QIGDK | 2 | y3 | 5.8 | 280.66 | 319.16 | 17 |
| 159 | QIGDK | 2 | b4 | 5.8 | 280.66 | 414.2 | 17 |
| 160 | QIGDNVTR | 2 | y7 | 9.5 | 451.74 | 774.41 | 25 |
| 161 | QIGDNVTR | 2 | y6 | 9.5 | 451.74 | 661.33 | 25 |
| 162 | QIGDNVTR | 2 | y5 | 9.5 | 451.74 | 604.3 | 25 |
| 163 | QIGENVTR | 2 | y7 | 9.5 | 458.75 | 788.43 | 25 |
| 164 | QIGENVTR | 2 | y6 | 9.5 | 458.75 | 675.34 | 25 |
| 165 | QIGENVTR | 2 | y5 | 9.5 | 458.75 | 618.32 | 25 |
| 166 | QLLQWMVDAR | 2 | y9 | 21.5 | 630.33 | 1131.6 | 33 |
| 167 | QLLQWMVDAR | 2 | y8 | 21.5 | 630.33 | 1018.5 | 33 |
| 168 | QLLQWMVDAR | 2 | y7 | 21.5 | 630.33 | 905.43 | 33 |
| 169 | QLLQWMVDDGVAGPLIR | 2 | y9 | 25 | 956.01 | 897.52 | 47 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 170 | QLLQWMVDDGVAGPLIR | 2 | y8 | 25 | 956.01 | 782.49 | 47 |
| 171 | QLLQWMVDDGVAGPLIR | 2 | y7 | 25 | 956.01 | 725.47 | 47 |
| 172 | QLLQWMVDDR | 2 | y9 | 21.7 | 652.33 | 1175.6 | 34 |
| 173 | QLLQWMVDDR | 2 | y8 | 21.7 | 652.33 | 1062.5 | 34 |
| 174 | QLLQWMVDDR | 2 | y7 | 21.7 | 652.33 | 949.42 | 34 |
| 175 | QLLQWMVDGR | 2 | y8 | 21.3 | 623.32 | 1004.5 | 32 |
| 176 | QLLQWMVDGR | 2 | y7 | 21.3 | 623.32 | 891.41 | 32 |
| 177 | QLLQWMVDGR | 2 | y6 | 21.3 | 623.32 | 763.36 | 32 |
| 178 | QLLQWMVEDR | 2 | y9 | 21.9 | 659.33 | 1189.6 | 34 |
| 179 | QLLQWMVEDR | 2 | y8 | 21.9 | 659.33 | 1076.5 | 34 |
| 180 | QLLQWMVEDR | 2 | y7 | 21.9 | 659.33 | 963.44 | 34 |
| 181 | QQDLVDYSPVSEK | 2 | y9 | 15.6 | 754.37 | 1023.5 | 38 |
| 182 | QQDLVDYSPVSEK | 2 | y8 | 15.6 | 754.37 | 924.43 | 38 |
| 183 | QQDLVDYSPVSEK | 2 | y7 | 15.6 | 754.37 | 809.4 | 38 |
| 184 | QQHLVDYSPVSEK | 2 | y9 | 13.9 | 765.38 | 1023.5 | 39 |
| 185 | QQHLVDYSPVSEK | 2 | y8 | 13.9 | 765.38 | 924.43 | 39 |
| 186 | QQHLVDYSPVSEK | 2 | y7 | 13.9 | 765.38 | 809.4 | 39 |
| 187 | QSESQLSGR | 2 | y8 | 7.6 | 496.24 | 863.42 | 27 |
| 188 | QSESQLSGR | 2 | y7 | 7.6 | 496.24 | 776.39 | 27 |
| 189 | QSESQLSGR | 2 | y6 | 7.6 | 496.24 | 647.35 | 27 |
| 190 | QSESQLSGSVGMIEMDLASGR | 3 | y9 | 19.7 | 728.01 | 991.49 | 40 |
| 191 | QSESQLSGSVGMIEMDLASGR | 3 | y8 | 19.7 | 728.01 | 878.4 | 40 |
| 192 | QSESQLSGSVGMIEMDLASGR | 3 | y7 | 19.7 | 728.01 | 749.36 | 40 |
| 193 | SQLQLLQWMVDDR | 2 | y9 | 26.3 | 816.41 | 1175.6 | 41 |
| 194 | SQLQLLQWMVDDR | 2 | y8 | 26.3 | 816.41 | 1062.5 | 41 |
| 195 | SQLQLLQWMVDDR | 2 | y7 | 26.3 | 816.41 | 949.42 | 41 |
| 196 | SVLPAGWFIADK | 2 | y9 | 22.9 | 652.36 | 1004.5 | 34 |
| 197 | SVLPAGWFIADK | 2 | y8 | 22.9 | 652.36 | 907.47 | 34 |
| 198 | SVLPAGWFIADK | 2 | y7 | 22.9 | 652.36 | 836.43 | 34 |
| 199 | SVLPAGWFIADR | 2 | y9 | 23 | 666.36 | 1032.5 | 34 |
| 200 | SVLPAGWFIADR | 2 | y8 | 23 | 666.36 | 935.47 | 34 |
| 201 | SVLPAGWFIADR | 2 | y7 | 23 | 666.36 | 864.44 | 34 |
| 202 | SVLSAGWFIADK | 2 | y9 | 22.7 | 647.35 | 994.5 | 33 |
| 203 | SVLSAGWFIADK | 2 | y8 | 22.7 | 647.35 | 907.47 | 33 |
| 204 | SVLSAGWFIADK | 2 | y7 | 22.7 | 647.35 | 836.43 | 33 |
| 205 | TGAAER | 2 | y5 | 4.8 | 302.66 | 503.26 | 18 |
| 206 | TGAAER | 2 | y4 | 4.8 | 302.66 | 446.24 | 18 |
| 207 | TGAAER | 2 | y3 | 4.8 | 302.66 | 375.2 | 18 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 208 | TGAAK | 2 | y4 | 6 | 224.13 | 346.21 | 15 |
| 209 | TGAAK | 2 | y3 | 6 | 224.13 | 289.19 | 15 |
| 210 | TGAAK | 2 | b4 | 6 | 224.13 | 301.15 | 15 |
| 211 | TGAGER | 2 | y5 | 4.9 | 295.65 | 489.24 | 18 |
| 212 | TGAGER | 2 | y4 | 4.9 | 295.65 | 432.22 | 18 |
| 213 | TGAGER | 2 | y3 | 4.9 | 295.65 | 361.18 | 18 |
| 214 | TGAGK | 2 | y4 | 6.1 | 217.12 | 332.19 | 15 |
| 215 | TGAGK | 2 | y3 | 6.1 | 217.12 | 275.17 | 15 |
| 216 | TGAGK | 2 | b4 | 6.1 | 217.12 | 287.13 | 15 |
| 217 | TGASER | 2 | y5 | 4.5 | 310.65 | 519.25 | 19 |
| 218 | TGASER | 2 | y4 | 4.5 | 310.65 | 462.23 | 19 |
| 219 | TGASER | 2 | y3 | 4.5 | 310.65 | 391.19 | 19 |
| 220 | TGASK | 2 | y4 | 5.8 | 232.13 | 362.2 | 15 |
| 221 | TGASK | 2 | y3 | 5.8 | 232.13 | 305.18 | 15 |
| 222 | TGASK | 2 | b4 | 5.8 | 232.13 | 317.15 | 15 |
| 223 | TGASR | 2 | y4 | 5.8 | 246.13 | 390.21 | 16 |
| 224 | TGASR | 2 | y3 | 5.8 | 246.13 | 333.19 | 16 |
| 225 | TGASR | 2 | y2 | 5.8 | 246.13 | 262.15 | 16 |
| 226 | TLTAWCADER | 2 | y9 | 15.9 | 611.78 | 1121.5 | 32 |
| 227 | TLTAWCADER | 2 | y8 | 15.9 | 611.78 | 1008.4 | 32 |
| 228 | TLTAWCADER | 2 | y7 | 15.9 | 611.78 | 907.37 | 32 |
| 229 | TLTAWHADER | 2 | y9 | 14.4 | 600.29 | 1098.5 | 31 |
| 230 | TLTAWHADER | 2 | y8 | 14.4 | 600.29 | 985.45 | 31 |
| 231 | TLTAWHADER | 2 | y7 | 14.4 | 600.29 | 884.4 | 31 |
| 232 | TLTAWR | 2 | y5 | 15 | 374.21 | 646.37 | 21 |
| 233 | TLTAWR | 2 | y4 | 15 | 374.21 | 533.28 | 21 |
| 234 | TLTAWR | 2 | y3 | 15 | 374.21 | 432.24 | 21 |
| 235 | TVGGPAGLTAFLR | 2 | y9 | 19.7 | 630.36 | 945.55 | 33 |
| 236 | TVGGPAGLTAFLR | 2 | y8 | 19.7 | 630.36 | 848.5 | 33 |
| 237 | TVGGPAGLTAFLR | 2 | y7 | 19.7 | 630.36 | 777.46 | 33 |
| 238 | TVVIYLR | 2 | y6 | 17.4 | 432.27 | 762.49 | 24 |
| 239 | TVVIYLR | 2 | y5 | 17.4 | 432.27 | 663.42 | 24 |
| 240 | TVVIYLR | 2 | y4 | 17.4 | 432.27 | 564.35 | 24 |
| 241 | VAGPLIR | 2 | y6 | 14.1 | 363.24 | 626.4 | 21 |
| 242 | VAGPLIR | 2 | y5 | 14.1 | 363.24 | 555.36 | 21 |
| 243 | VAGPLIR | 2 | y4 | 14.1 | 363.24 | 498.34 | 21 |
| 244 | VALCGAVLAR | 2 | y9 | 17.2 | 515.3 | 930.52 | 28 |
| 245 | VALCGAVLAR | 2 | y8 | 17.2 | 515.3 | 859.48 | 28 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 246 | VALCGAVLAR | 2 | y7 | 17.2 | 515.3 | 746.4 | 28 |
| 247 | VDAGDEQLER | 2 | y9 | 10.9 | 566.27 | 1032.5 | 30 |
| 248 | VDAGDEQLER | 2 | y8 | 10.9 | 566.27 | 917.43 | 30 |
| 249 | VDAGDEQLER | 2 | y7 | 10.9 | 566.27 | 846.4 | 30 |
| 250 | VDAGDK | 2 | y5 | 4.1 | 302.65 | 505.23 | 18 |
| 251 | VDAGDK | 2 | y4 | 4.1 | 302.65 | 390.2 | 18 |
| 252 | VDAGDK | 2 | y3 | 4.1 | 302.65 | 319.16 | 18 |
| 253 | VGMIEMDLASGR | 2 | y9 | 18.7 | 639.81 | 991.49 | 33 |
| 254 | VGMIEMDLASGR | 2 | y8 | 18.7 | 639.81 | 878.4 | 33 |
| 255 | VGMIEMDLASGR | 2 | y7 | 18.7 | 639.81 | 749.36 | 33 |
| 256 | VGMIEMDLASR | 2 | y9 | 18.7 | 611.3 | 1065.5 | 32 |
| 257 | VGMIEMDLASR | 2 | y8 | 18.7 | 611.3 | 934.47 | 32 |
| 258 | VGMIEMDLASR | 2 | y7 | 18.7 | 611.3 | 821.38 | 32 |
| 259 | VGMIEMDLASSR | 2 | y9 | 18.4 | 654.82 | 1021.5 | 34 |
| 260 | VGMIEMDLASSR | 2 | y8 | 18.4 | 654.82 | 908.41 | 34 |
| 261 | VGMIEMDLASSR | 2 | y7 | 18.4 | 654.82 | 779.37 | 34 |
| 262 | VLLCGAVLAR | 2 | y9 | 19.3 | 536.32 | 972.57 | 29 |
| 263 | VLLCGAVLAR | 2 | y8 | 19.3 | 536.32 | 859.48 | 29 |
| 264 | VLLCGAVLAR | 2 | y7 | 19.3 | 536.32 | 746.4 | 29 |
| 265 | VVLCGAMLAR | 2 | y8 | 18.1 | 545.3 | 891.45 | 29 |
| 266 | VVLCGAMLAR | 2 | y7 | 18.1 | 545.3 | 778.37 | 29 |
| 267 | VVLCGAMLAR | 2 | y6 | 18.1 | 545.3 | 618.34 | 29 |
| 268 | VVLCGAVLAR | 2 | y9 | 18 | 529.31 | 958.55 | 28 |
| 269 | VVLCGAVLAR | 2 | y8 | 18 | 529.31 | 859.48 | 28 |
| 270 | VVLCGAVLAR | 2 | y7 | 18 | 529.31 | 746.4 | 28 |
| 271 | VVLCGTVLAR | 2 | y9 | 16.6 | 544.32 | 988.56 | 29 |
| 272 | VVLCGTVLAR | 2 | y8 | 16.6 | 544.32 | 889.49 | 29 |
| 273 | VVLCGTVLAR | 2 | y7 | 16.6 | 544.32 | 776.41 | 29 |
| 274 | WETDR | 2 | y4 | 9.8 | 353.66 | 520.24 | 21 |
| 275 | WETDR | 2 | y3 | 9.8 | 353.66 | 391.19 | 21 |
| 276 | WETDR | 2 | b4 | 9.8 | 353.66 | 532.2 | 21 |
| 277 | WETELNEAFPGDAR | 2 | y9 | 19 | 817.88 | 976.45 | 41 |
| 278 | WETELNEAFPGDAR | 2 | y8 | 19 | 817.88 | 862.41 | 41 |
| 279 | WETELNEAFPGDAR | 2 | y7 | 19 | 817.88 | 733.36 | 41 |
| 280 | WETELNEALPADAR | 2 | y9 | 18.9 | 807.89 | 956.48 | 41 |
| 281 | WETELNEALPADAR | 2 | y8 | 18.9 | 807.89 | 842.44 | 41 |
| 282 | WETELNEALPADAR | 2 | y7 | 18.9 | 807.89 | 713.39 | 41 |
| 283 | WETELNEALPGDAR | 2 | y9 | 18.5 | 800.88 | 942.46 | 40 |

TABLE 8-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 284 | WETELNEALPGDAR | 2 | y8 | 18.5 | 800.88 | 828.42 | 40 |
| 285 | WETELNEALPGDAR | 2 | y7 | 18.5 | 800.88 | 699.38 | 40 |
| 286 | WETELNEALSGDAR | 2 | y9 | 18 | 795.87 | 932.44 | 40 |
| 287 | WETELNEALSGDAR | 2 | y8 | 18 | 795.87 | 818.4 | 40 |
| 288 | WETELNEALSGDAR | 2 | y7 | 18 | 795.87 | 689.36 | 40 |
| 289 | WETELNEVLPGDAR | 2 | y9 | 19.4 | 814.9 | 970.5 | 41 |
| 290 | WETELNEVLPGDAR | 2 | y8 | 19.4 | 814.9 | 856.45 | 41 |
| 291 | WETELNEVLPGDAR | 2 | y7 | 19.4 | 814.9 | 727.41 | 41 |
| 292 | WETER | 2 | y4 | 10.4 | 360.67 | 534.25 | 21 |
| 293 | WETER | 2 | y3 | 10.4 | 360.67 | 405.21 | 21 |
| 294 | WETER | 2 | b4 | 10.4 | 360.67 | 546.22 | 21 |

The areas obtained for each of the transitions and for each of the microorganisms studied were measured. When the areas of the 3 transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 10

Identification of a Resistance to FOX Beta-Lactams

The samples corresponding to a species able to comprise a FOX resistance mechanism can be detected by employing the following method.

Each sample is treated according to example 5, then analysed according to example 6 by detecting the peptides from TABLE 9 instead of the peptides from TABLE 3.

TABLE 9

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 1 | AHYFNYGVANR | 2 | y9 | 15.5 | 656.32 | 1103.53 | 34 |
| 2 | AHYFNYGVANR | 2 | y8 | 15.5 | 656.32 | 940.46 | 34 |
| 3 | AHYFNYGVANR | 2 | y7 | 15.5 | 656.32 | 793.4 | 34 |
| 4 | AMGEQR | 2 | y5 | 5.3 | 346.16 | 620.28 | 20 |
| 5 | AMGEQR | 2 | y4 | 5.3 | 346.16 | 489.24 | 20 |
| 6 | AMGEQR | 2 | y3 | 5.3 | 346.16 | 432.22 | 20 |
| 7 | ESGQR | 2 | y4 | 4.3 | 288.64 | 447.23 | 18 |
| 8 | ESGQR | 2 | y3 | 4.3 | 288.64 | 360.2 | 18 |
| 9 | ESGQR | 2 | b4 | 4.3 | 288.64 | 402.16 | 18 |
| 10 | FAVPK | 2 | y4 | 11.3 | 281.17 | 414.27 | 17 |
| 11 | FAVPK | 2 | y3 | 11.3 | 281.17 | 343.23 | 17 |
| 12 | FAVPK | 2 | b4 | 11.3 | 281.17 | 415.23 | 17 |
| 13 | GGFELDDK | 2 | y7 | 14.5 | 440.71 | 823.38 | 24 |
| 14 | GGFELDDK | 2 | y6 | 14.5 | 440.71 | 766.36 | 24 |
| 15 | GGFELDDK | 2 | y5 | 14.5 | 440.71 | 619.29 | 24 |
| 16 | GIAIVMLANR | 2 | y9 | 19.3 | 529.31 | 1000.6 | 28 |

TABLE 9-continued

| Transition number | Peptide | Charge state of the precursor | first-generation fragment ion | Retention time (minutes) | (m/z) filtered in Q1 | (m/z) filtered in Q3 | Collision energy (eV) |
|---|---|---|---|---|---|---|---|
| 17 | GIAIVMLANR | 2 | y8 | 19.3 | 529.31 | 887.51 | 28 |
| 18 | GIAIVMLANR | 2 | y7 | 19.3 | 529.31 | 816.48 | 28 |
| 19 | IPGMAVAVLK | 2 | y9 | 18.1 | 499.81 | 885.52 | 27 |
| 20 | IPGMAVAVLK | 2 | y8 | 18.1 | 499.81 | 788.47 | 27 |
| 21 | IPGMAVAVLK | 2 | y7 | 18.1 | 499.81 | 731.45 | 27 |
| 22 | NYPIEAR | 2 | y6 | 12.2 | 431.72 | 748.4 | 24 |
| 23 | NYPIEAR | 2 | y5 | 12.2 | 431.72 | 585.34 | 24 |
| 24 | NYPIEAR | 2 | y4 | 12.2 | 431.72 | 488.28 | 24 |
| 25 | SWSPVYPAGTHR | 2 | y9 | 15.5 | 679.34 | 997.52 | 35 |
| 26 | SWSPVYPAGTHR | 2 | y8 | 15.5 | 679.34 | 900.47 | 35 |
| 27 | SWSPVYPAGTHR | 2 | y7 | 15.5 | 679.34 | 801.4 | 35 |
| 28 | TGSADLLK | 2 | y7 | 14 | 402.73 | 703.4 | 23 |
| 29 | TGSADLLK | 2 | y6 | 14 | 402.73 | 646.38 | 23 |
| 30 | TGSADLLK | 2 | y5 | 14 | 402.73 | 559.34 | 23 |
| 31 | TGSTGGFGAYVAFVPAR | 2 | y9 | 19.5 | 829.42 | 993.55 | 41 |
| 32 | TGSTGGFGAYVAFVPAR | 2 | y8 | 19.5 | 829.42 | 922.51 | 41 |
| 33 | TGSTGGFGAYVAFVPAR | 2 | y7 | 19.5 | 829.42 | 759.45 | 41 |
| 34 | TLTATLGAYAAVK | 2 | y9 | 17.2 | 640.37 | 893.51 | 33 |
| 35 | TLTATLGAYAAVK | 2 | y8 | 17.2 | 640.37 | 792.46 | 33 |
| 36 | TLTATLGAYAAVK | 2 | y7 | 17.2 | 640.37 | 679.38 | 33 |
| 37 | VSEQTLFEIGSVSK | 2 | y9 | 19.6 | 762.4 | 979.55 | 39 |
| 38 | VSEQTLFEIGSVSK | 2 | y8 | 19.6 | 762.4 | 866.46 | 39 |
| 39 | VSEQTLFEIGSVSK | 2 | y7 | 19.6 | 762.4 | 719.39 | 39 |
| 40 | VSQHAPWLK | 2 | y8 | 15.3 | 533.3 | 966.52 | 28 |
| 41 | VSQHAPWLK | 2 | y7 | 15.3 | 533.3 | 879.48 | 28 |
| 42 | VSQHAPWLK | 2 | y6 | 15.3 | 533.3 | 751.42 | 28 |
| 43 | VTPGVLAAEAYGIK | 2 | y9 | 18.4 | 694.89 | 935.52 | 36 |
| 44 | VTPGVLAAEAYGIK | 2 | y8 | 18.4 | 694.89 | 822.44 | 36 |
| 45 | VTPGVLAAEAYGIK | 2 | y7 | 18.4 | 694.89 | 751.4 | 36 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 11

Identification of a Resistance to TEM or CTX-M Beta-Lactams

The samples corresponding to a species able to comprise a TEM or CTX-M resistance mechanism can be detected by employing the following method.

Each sample is treated according to example 5, then analysed according to example 6 by detecting the peptides from TABLE 10 instead of the peptides from TABLE 3.

TABLE 10

| Transition number | Protein | Peptide | First-generation fragment ion | Charge state of the precursor | Clinical interest |
|---|---|---|---|---|---|
| 1 | CTX-M | AMAQTLR | y4 monocharged | 2 | 2be |
| 2 | CTX-M | AMAQTLR | y5 monocharged | 2 | 2be |
| 3 | CTX-M | AMAQTLR | y6 monocharged | 2 | 2be |
| 4 | CTX-M | AQLVTWLK | y5 monocharged | 2 | 2be |
| 5 | CTX-M | AQLVTWLK | y6 monocharged | 2 | 2be |
| 6 | CTX-M | AQLVTWLK | y7 monocharged | 2 | 2be |
| 7 | CTX-M | FAMCSTSK | y5 monocharged | 2 | 2be |
| 8 | CTX-M | FAMCSTSK | y6 monocharged | 2 | 2be |
| 9 | CTX-M | FAMCSTSK | y7 monocharged | 2 | 2be |
| 10 | CTX-M | LAALEK | y3 monocharged | 2 | 2be |
| 11 | CTX-M | LAALEK | y4 monocharged | 2 | 2be |
| 12 | CTX-M | LAALEK | y5 monocharged | 2 | 2be |
| 13 | CTX-M | LGVALINTADNSQILYR | y7 monocharged | 2 | 2be |
| 14 | CTX-M | LGVALINTADNSQILYR | y8 monocharged | 2 | 2be |
| 15 | CTX-M | LGVALINTADNSQILYR | y9 monocharged | 2 | 2be |
| 16 | CTX-M | NLTLGK | y3 monocharged | 2 | 2be |
| 17 | CTX-M | NLTLGK | y4 monocharged | 2 | 2be |
| 18 | CTX-M | NLTLGK | y5 monocharged | 2 | 2be |
| 19 | CTX-M | QSETQK | y3 monocharged | 2 | 2be |
| 20 | CTX-M | QSETQK | y4 monocharged | 2 | 2be |
| 21 | CTX-M | QSETQK | y5 monocharged | 2 | 2be |
| 22 | CTX-M | SDLVNYNPIAEK | y7 monocharged | 2 | 2be |
| 23 | CTX-M | SDLVNYNPIAEK | y8 monocharged | 2 | 2be |
| 24 | CTX-M | SDLVNYNPIAEK | y9 monocharged | 2 | 2be |
| 25 | CTX-M | TEPTLNTAIPGDPR | y7 monocharged | 2 | 2be |
| 26 | CTX-M | TEPTLNTAIPGDPR | y8 monocharged | 2 | 2be |
| 27 | CTX-M | TEPTLNTAIPGDPR | y9 monocharged | 2 | 2be |
| 28 | CTX-M | VMAAAAVLK | y6 monocharged | 2 | 2be |
| 29 | CTX-M | VMAAAAVLK | y7 monocharged | 2 | 2be |
| 30 | CTX-M | VMAAAAVLK | y8 monocharged | 2 | 2be |
| 31 | TEM | DAEDQLGAR | y5 monocharged | 2 | TEM |
| 32 | TEM | DAEDQLGAR | y6 monocharged | 2 | TEM |
| 33 | TEM | DAEDQLGAR | y7 monocharged | 2 | TEM |
| 34 | TEM | DTTMPAAMATTLR | y7 monocharged | 2 | TEM |
| 35 | TEM | DTTMPAAMATTLR | y8 monocharged | 2 | TEM |
| 36 | TEM | DTTMPAAMATTLR | y9 monocharged | 2 | TEM |

TABLE 10-continued

| Transition number | Protein | Peptide | First-generation fragment ion | Charge state of the precursor | Clinical interest |
|---|---|---|---|---|---|
| 37 | TEM | DTTTPAAMATTLR | y7 monocharged | 2 | TEM |
| 38 | TEM | DTTTPAAMATTLR | y9 dicharged | 2 | TEM |
| 39 | TEM | DTTTPAAMATTLR | y9 monocharged | 2 | TEM |
| 40 | TEM | EPELNEAIPNDER | y5 monocharged | 2 | TEM |
| 41 | TEM | EPELNEAIPNDER | y7 monocharged | 2 | TEM |
| 42 | TEM | EPELNEAIPNDER | y8 monocharged | 2 | TEM |
| 43 | TEM | GIIAALGPDGKPSR | y7 monocharged | 2 | TEM |
| 44 | TEM | GIIAALGPDGKPSR | y8 monocharged | 2 | TEM |
| 45 | TEM | GIIAALGPDGKPSR | y9 monocharged | 2 | TEM |
| 46 | TEM | GSCGIIAALGPDGKPSR | y7 monocharged | 2 | 2br |
| 47 | TEM | GSCGIIAALGPDGKPSR | y8 monocharged | 2 | 2br |
| 48 | TEM | GSCGIIAALGPDGKPSR | y9 monocharged | 2 | 2br |
| 49 | TEM | GSSGIIAALGPDGKPSR | y7 monocharged | 2 | TEM |
| 50 | TEM | GSSGIIAALGPDGKPSR | y8 monocharged | 2 | TEM |
| 51 | TEM | GSSGIIAALGPDGKPSR | y9 monocharged | 2 | TEM |
| 52 | TEM | HLTDGMTVR | y4 monocharged | 2 | TEM |
| 53 | TEM | HLTDGMTVR | y7 monocharged | 2 | TEM |
| 54 | TEM | HLTDGMTVR | y8 monocharged | 2 | TEM |
| 55 | TEM | IHYSQNDLVEYSPVTEK | y6 monocharged | 3 | TEM |
| 56 | TEM | IHYSQNDLVEYSPVTEK | y7 monocharged | 3 | TEM |
| 57 | TEM | IHYSQNDLVEYSPVTEK | y8 monocharged | 3 | TEM |
| 58 | TEM | IHYSQNDLVK | y7 monocharged | 2 | 2be |
| 59 | TEM | IHYSQNDLVK | y8 monocharged | 2 | 2be |
| 60 | TEM | IHYSQNDLVK | y9 dicharged | 2 | 2be |
| 61 | TEM | ILESFRPEER | b6 monocharged | 2 | TEM |
| 62 | TEM | ILESFRPEER | b8 monocharged | 2 | TEM |
| 63 | TEM | ILESFRPEER | y7 dicharged | 2 | TEM |
| 64 | TEM | LDHWEPELNEAIPNDER | y5 monocharged | 3 | 2be |
| 65 | TEM | LDHWEPELNEAIPNDER | y6 monocharged | 3 | 2be |
| 66 | TEM | LDHWEPELNEAIPNDER | y7 monocharged | 3 | 2be |
| 67 | TEM | LDSWEPELNEAIPNDER | y5 monocharged | 3 | 2be |
| 68 | TEM | LDSWEPELNEAIPNDER | y6 monocharged | 3 | 2be |
| 69 | TEM | LDSWEPELNEAIPNDER | y7 monocharged | 3 | 2be |
| 70 | TEM | LLTGELLTLASR | y6 monocharged | 2 | TEM |
| 71 | TEM | LLTGELLTLASR | y7 monocharged | 2 | TEM |
| 72 | TEM | LLTGELLTLASR | y9 monocharged | 2 | TEM |
| 73 | TEM | QIAEIGASLIK | y7 monocharged | 2 | TEM |
| 74 | TEM | QIAEIGASLIK | y8 monocharged | 2 | TEM |

TABLE 10-continued

| Transition number | Protein | Peptide | First-generation fragment ion | Charge state of the precursor | Clinical interest |
|---|---|---|---|---|---|
| 75 | TEM | QIAEIGASLIK | y9 monocharged | 2 | TEM |
| 76 | TEM | QQLIDWMEADK | y5 monocharged | 2 | TEM |
| 77 | TEM | QQLIDWMEADK | y6 monocharged | 2 | TEM |
| 78 | TEM | QQLIDWMEADK | y7 monocharged | 2 | TEM |
| 79 | TEM | VAGPLLR | y4 monocharged | 2 | TEM |
| 80 | TEM | VAGPLLR | y5 monocharged | 2 | TEM |
| 81 | TEM | VAGPLLR | y6 monocharged | 2 | TEM |
| 82 | TEM | VDAGQEQLGR | y5 monocharged | 2 | TEM |
| 83 | TEM | VDAGQEQLGR | y7 monocharged | 2 | TEM |
| 84 | TEM | VDAGQEQLGR | y8 monocharged | 2 | TEM |
| 85 | TEM | VGYIELDLNSGK | y7 monocharged | 2 | TEM |
| 86 | TEM | VGYIELDLNSGK | y8 monocharged | 2 | TEM |
| 87 | TEM | VGYIELDLNSGK | y9 monocharged | 2 | TEM |
| 88 | TEM | WEPELNEAIPNDER | y12 dicharged | 2 | TEM |
| 89 | TEM | WEPELNEAIPNDER | y5 monocharged | 2 | TEM |
| 90 | TEM | WEPELNEAIPNDER | y7 monocharged | 2 | TEM |
| 91 | TEM | YSPVTEK | y4 monocharged | 2 | 2be |
| 92 | TEM | YSPVTEK | y5 monocharged | 2 | 2be |
| 93 | TEM | YSPVTEK | y6 monocharged | 2 | 2be |

In the clinical interest column, the entries TEM, 2b, 2br, 2be and 2ber correspond to the same meanings as in TABLE 4.

The transitions mentioned in TABLE 10 are detected by using the parameters set out in TABLE 11.

TABLE 11

| Transition number | Retention time (minutes) | (m/z) filtered in Q1 | (m/z) filtered in Q3 | Collision energy (eV) | Positivity threshold |
|---|---|---|---|---|---|
| 1 | 12.1 | 395.72 | 517.31 | 22 | 2500 |
| 2 | 12.1 | 395.72 | 588.35 | 22 | 2500 |
| 3 | 12.1 | 395.72 | 719.39 | 22 | 2500 |
| 4 | 21 | 479.79 | 646.39 | 26 | 2500 |
| 5 | 21 | 479.79 | 759.48 | 26 | 2500 |
| 6 | 21 | 479.79 | 887.53 | 26 | 2500 |
| 7 | 11.1 | 466.2 | 582.26 | 26 | 2500 |
| 8 | 11.1 | 466.2 | 713.3 | 26 | 2500 |
| 9 | 11.1 | 466.2 | 784.33 | 26 | 2500 |
| 10 | 11 | 322.7 | 389.24 | 19 | 2500 |
| 11 | 11 | 322.7 | 460.28 | 19 | 2500 |
| 12 | 11 | 322.7 | 531.31 | 19 | 2500 |
| 13 | 21.1 | 931.01 | 893.48 | 46 | 2500 |
| 14 | 21.1 | 931.01 | 1008.51 | 46 | 2500 |
| 15 | 21.1 | 931.01 | 1079.55 | 46 | 2500 |
| 16 | 12.2 | 323.2 | 317.22 | 19 | 2500 |
| 17 | 12.2 | 323.2 | 418.27 | 19 | 2500 |
| 18 | 12.2 | 323.2 | 531.35 | 19 | 2500 |
| 19 | 3.7 | 360.68 | 376.22 | 21 | 2500 |
| 20 | 3.7 | 360.68 | 505.26 | 21 | 2500 |
| 21 | 3.7 | 360.68 | 592.29 | 21 | 2500 |
| 22 | 17.1 | 681.85 | 834.44 | 35 | 2500 |
| 23 | 17.1 | 681.85 | 948.48 | 35 | 2500 |
| 24 | 17.1 | 681.85 | 1047.55 | 35 | 2500 |
| 25 | 15.6 | 741.38 | 725.39 | 38 | 2500 |
| 26 | 15.6 | 741.38 | 826.44 | 38 | 2500 |
| 27 | 15.6 | 741.38 | 940.48 | 38 | 2500 |
| 28 | 15.3 | 437.26 | 572.38 | 24 | 2500 |
| 29 | 15.3 | 437.26 | 643.41 | 24 | 2500 |
| 30 | 15.3 | 437.26 | 774.45 | 24 | 2500 |
| 31 | 10.5 | 487.73 | 544.32 | 26 | 2500 |
| 32 | 10.5 | 487.73 | 659.35 | 26 | 2500 |
| 33 | 10.5 | 487.73 | 788.39 | 26 | 2500 |
| 34 | 17.6 | 690.34 | 763.61 | 35 | 2500 |
| 35 | 17.6 | 690.34 | 834.45 | 35 | 2500 |
| 36 | 17.6 | 690.34 | 931.5 | 35 | 2500 |
| 37 | 16.1 | 675.34 | 763.41 | 35 | 2500 |
| 38 | 16.1 | 675.34 | 466.25 | 35 | 2500 |
| 39 | 16.1 | 675.34 | 931.5 | 35 | 2500 |
| 40 | 14.9 | 763.36 | 630.28 | 39 | 2500 |
| 41 | 14.9 | 763.36 | 814.41 | 39 | 2500 |
| 42 | 14.9 | 763.36 | 943.45 | 39 | 2500 |
| 43 | 15.5 | 676.39 | 756.4 | 35 | 2500 |
| 44 | 15.5 | 676.39 | 813.42 | 35 | 2500 |
| 45 | 15.5 | 676.39 | 926.51 | 35 | 2500 |
| 46 | 16.5 | 828.43 | 756.4 | 41 | 2500 |
| 47 | 16.5 | 828.43 | 813.42 | 41 | 2500 |
| 48 | 16.5 | 828.43 | 926.51 | 41 | 2500 |
| 49 | 16.1 | 791.93 | 756.4 | 40 | 2500 |
| 50 | 16.1 | 791.93 | 813.42 | 40 | 2500 |
| 51 | 16.1 | 791.93 | 926.51 | 40 | 2500 |

TABLE 11-continued

| Transition number | Retention time (minutes) | (m/z) filtered in Q1 | (m/z) filtered in Q3 | Collision energy (eV) | Positivity threshold |
|---|---|---|---|---|---|
| 52 | 12 | 515.26 | 506.28 | 28 | 2500 |
| 53 | 12 | 515.26 | 779.37 | 28 | 2500 |
| 54 | 12 | 515.26 | 892.46 | 28 | 2500 |
| 55 | 16.6 | 674.67 | 660.36 | 38 | 2500 |
| 56 | 16.6 | 674.67 | 823.42 | 38 | 2500 |
| 57 | 16.6 | 674.67 | 952.46 | 38 | 2500 |
| 58 | 12.5 | 608.82 | 803.43 | 32 | 2500 |
| 59 | 12.5 | 608.82 | 966.49 | 32 | 2500 |
| 60 | 12.5 | 608.82 | 552.28 | 32 | 2500 |
| 61 | 14.6 | 638.34 | 746.42 | 33 | 2500 |
| 62 | 14.6 | 638.34 | 972.51 | 33 | 2500 |
| 63 | 14.6 | 638.34 | 460.73 | 33 | 2500 |
| 64 | 18 | 692.99 | 630.28 | 39 | 2500 |
| 65 | 18 | 692.99 | 743.37 | 39 | 2500 |
| 66 | 18 | 692.99 | 814.41 | 39 | 2500 |
| 67 | 19.5 | 676.32 | 630.28 | 38 | 2500 |
| 68 | 19.5 | 676.32 | 743.37 | 38 | 2500 |
| 69 | 19.5 | 676.32 | 814.41 | 38 | 2500 |
| 70 | 22.5 | 643.89 | 660.4 | 33 | 2500 |
| 71 | 22.5 | 643.89 | 773.49 | 33 | 2500 |
| 72 | 22.5 | 643.89 | 959.55 | 33 | 2500 |
| 73 | 18.8 | 571.84 | 701.46 | 30 | 2500 |
| 74 | 18.8 | 571.84 | 830.5 | 30 | 2500 |
| 75 | 18.8 | 571.84 | 901.54 | 30 | 2500 |
| 76 | 20.1 | 688.83 | 593.26 | 35 | 2500 |
| 77 | 20.1 | 688.83 | 779.34 | 35 | 2500 |
| 78 | 20.1 | 688.83 | 894.37 | 35 | 2500 |
| 79 | 14.1 | 363.24 | 498.34 | 21 | 2500 |
| 80 | 14.1 | 363.24 | 555.36 | 21 | 2500 |
| 81 | 14.1 | 363.24 | 626.4 | 21 | 2500 |
| 82 | 10.6 | 536.77 | 602.38 | 29 | 2500 |
| 83 | 10.6 | 536.77 | 787.41 | 29 | 2500 |
| 84 | 10.6 | 536.77 | 858.44 | 29 | 2500 |
| 85 | 18.8 | 654.35 | 746.4 | 34 | 2500 |
| 86 | 18.8 | 654.35 | 875.45 | 34 | 2500 |
| 87 | 18.8 | 654.35 | 988.53 | 34 | 2500 |
| 88 | 18 | 856.4 | 698.84 | 43 | 2500 |
| 89 | 18 | 856.4 | 630.28 | 43 | 2500 |
| 90 | 18 | 856.4 | 814.41 | 43 | 2500 |
| 91 | 9.8 | 412.21 | 476.27 | 23 | 2500 |
| 92 | 9.8 | 412.21 | 573.32 | 23 | 2500 |
| 93 | 9.8 | 412.21 | 660.36 | 23 | 2500 |

When the areas of at least two transitions of the same peptide are greater than or equal to the positivity threshold described in TABLE 11, the detection of the peptide is considered to be positive. When more than two transitions of the same peptide comprise an area less than the positivity threshold described in TABLE 11, the corresponding peptide is considered non-detected.

A sample contains bacteria which express the TEM protein, when at least one peptide corresponding to the TEM resistance mechanism is detected. These bacteria are resistant to penicillins.

A sample contains bacteria which express the TEM protein, phenotype 2b, when at least one peptide corresponding to the TEM resistance mechanism clinical interest 2b is detected. These bacteria are only resistant to penicillins.

A sample contains bacteria which express the TEM protein, phenotype 2br, when at least one peptide corresponding to the TEM resistance mechanism clinical interest 2br is detected. These bacteria are resistant to penicillins associated with an inhibitor of the clavulanic acid and tazobactam type.

A sample contains bacteria which express the CTX-M protein or the TEM protein, phenotype 2be, when at least one peptide corresponding to the CTX-M or TEM resistance mechanism clinical interest 2be is detected. These bacteria are resistant to penicillins, to cephalosporins and to monobactams.

A sample contains bacteria which express the TEM protein, phenotype 2ber, when at least one peptide corresponding to the TEM resistance mechanism clinical interest 2ber, is detected. These bacteria are resistant to penicillins, to cephalosporins and to monobactams, and are insensitive to inhibition by clavulanic acid, sulfobactam or tazobactam.

EXAMPLE 12

Identification of a Resistance to PER Beta-Lactams

Samples Sam74 to Sam78 are identified according to one of the methods described in examples 1, 3 or 4. The identification of the species is set out in TABLE 12.

TABLE 12

| Names | Species |
|---|---|
| Ech74 | A. baumannii |
| Ech75 | A. baumannii |
| Ech76 | P. aeruginosa |
| Ech77 | P. aeruginosa |
| Ech78 | P. aeruginosa |

Samples Sam74 to Sam78 correspond to a species able to comprise a PER resistance mechanism. Each sample is treated according to example 5, then analysed according to example 6 by detecting the peptides from TABLE 13 instead of the peptides from TABLE 3.

TABLE 13

| Transition number | Peptide | Retention time (minutes) | (m/z) filtered in Q1 | (m/z) filtered in Q3 | Collision energy (eV) | positivity threshold |
|---|---|---|---|---|---|---|
| 1 | AAAQLLR | 12.91 | 371.73 | 401.29 | 16.9 | 2000 |
| 2 | AAAQLLR | 12.89 | 371.73 | 529.35 | 16.9 | 2000 |
| 3 | AAAQLLR | 12.91 | 371.73 | 600.38 | 16.9 | 2000 |
| 4 | AAAQVLQK | 10.24 | 414.75 | 487.32 | 19.4 | 2000 |
| 5 | AAAQVLQK | 10.24 | 414.75 | 615.38 | 19.4 | 2000 |
| 6 | AAAQVLQK | 10.18 | 414.75 | 686.42 | 19.4 | 2000 |
| 7 | AAVLQNTWSPMMK | 19.35 | 738.87 | 506.25 | 37.9 | 2000 |
| 8 | AAVLQNTWSPMMK | 19.35 | 738.87 | 593.28 | 37.9 | 2000 |

TABLE 13-continued

| Transition number | Peptide | Retention time (minutes) | (m/z) filtered in Q1 | (m/z) filtered in Q3 | Collision energy (eV) | positivity threshold |
|---|---|---|---|---|---|---|
| 9 | AAVLQNTWSPMMK | 19.35 | 738.87 | 994.45 | 37.9 | 2000 |
| 10 | EQIESIVIGK | 17.24 | 558.32 | 317.22 | 27.6 | 2000 |
| 11 | EQIESIVIGK | 17.26 | 558.32 | 616.40 | 27.6 | 2000 |
| 12 | EQIESIVIGK | 17.24 | 558.32 | 745.45 | 27.6 | 2000 |
| 13 | EQIETIVTGK | 15.48 | 559.31 | 305.18 | 27.6 | 2000 |
| 14 | EQIETIVTGK | 15.48 | 559.31 | 618.38 | 27.6 | 2000 |
| 15 | EQIETIVTGK | 15.48 | 559.31 | 747.43 | 27.6 | 2000 |
| 16 | ETEVVANEAQMHADDQVQYK | 14.17 | 769.02 | 838.87 | 30.9 | 5000 |
| 17 | ETEVVANEAQMHADDQVQYK | 14.17 | 769.02 | 874.39 | 30.9 | 5000 |
| 18 | ETEVVANEAQMHADDQVQYK | 14.17 | 769.02 | 923.92 | 30.9 | 5000 |
| 19 | FPMQSVFK | 19.09 | 492.26 | 418.72 | 23.8 | 2000 |
| 20 | FPMQSVFK | 19.09 | 492.26 | 739.38 | 23.8 | 2000 |
| 21 | FPMQSVFK | 19.07 | 492.26 | 836.43 | 23.8 | 2000 |
| 22 | GAAEILK | 12.66 | 351.21 | 322.70 | 15.8 | 2000 |
| 23 | GAAEILK | 12.65 | 351.21 | 502.32 | 15.8 | 2000 |
| 24 | GAAEILK | 12.65 | 351.21 | 573.36 | 15.8 | 2000 |
| 25 | GLLPAGTIVAHK | 16.8 | 588.86 | 447.26 | 29.3 | 2000 |
| 26 | GLLPAGTIVAHK | 16.8 | 588.86 | 503.81 | 29.3 | 2000 |
| 27 | GLLPAGTIVAHK | 16.82 | 588.86 | 893.52 | 29.3 | 2000 |
| 28 | GLLPAGTVVAHK | 15.73 | 581.85 | 440.26 | 28.9 | 2000 |
| 29 | GLLPAGTVVAHK | 15.73 | 581.85 | 496.80 | 28.9 | 2000 |
| 30 | GLLPAGTVVAHK | 15.75 | 581.85 | 879.51 | 28.9 | 2000 |
| 31 | GQIESIVIGK | 16.8 | 522.31 | 616.40 | 25.5 | 5000 |
| 32 | GQIESIVIGK | 16.8 | 522.31 | 745.45 | 25.5 | 5000 |
| 33 | GQIESIVIGK | 16.8 | 522.31 | 858.53 | 25.5 | 5000 |
| 34 | LDLNK | 10.5 | 301.68 | 342.20 | 12.9 | 2000 |
| 35 | LDLNK | 10.5 | 301.68 | 374.24 | 12.9 | 2000 |
| 36 | LDLNK | 10.52 | 301.68 | 489.27 | 12.9 | 2000 |
| 37 | LDLNQSVTVNR | 15.11 | 629.84 | 338.19 | 31.6 | 2000 |
| 38 | LDLNQSVTVNR | 15.11 | 629.84 | 489.28 | 31.6 | 2000 |
| 39 | LDLNQSVTVNR | 15.11 | 629.84 | 675.38 | 31.6 | 2000 |
| 40 | LDLNQTVIVNR | 17.29 | 642.87 | 501.31 | 32.4 | 2000 |
| 41 | LDLNQTVIVNR | 17.29 | 642.87 | 600.38 | 32.4 | 2000 |
| 42 | LDLNQTVIVNR | 17.28 | 642.87 | 701.43 | 32.4 | 2000 |
| 43 | LHLAMLVLHQVDQGK | 19.84 | 567.99 | 568.83 | 24.7 | 2000 |
| 44 | LHLAMLVLHQVDQGK | 19.84 | 567.99 | 669.86 | 24.7 | 2000 |
| 45 | LHLAMLVLHQVDQGK | 19.84 | 567.99 | 726.41 | 24.7 | 2000 |
| 46 | MHLAMLVLHQVDQGK | 19.35 | 573.97 | 332.19 | 24.9 | 2000 |

TABLE 13-continued

| Transition number | Peptide | Retention time (minutes) | (m/z) filtered in Q1 | (m/z) filtered in Q3 | Collision energy (eV) | positivity threshold |
|---|---|---|---|---|---|---|
| 47 | MHLAMLVLHQVDQGK | 19.35 | 573.97 | 669.86 | 24.9 | 2000 |
| 48 | MHLAMLVLHQVDQGK | 19.35 | 573.97 | 726.41 | 24.9 | 2000 |
| 49 | NWTSMK | 12.59 | 383.68 | 365.19 | 17.6 | 2000 |
| 50 | NWTSMK | 12.59 | 383.68 | 466.23 | 17.6 | 2000 |
| 51 | NWTSMK | 12.61 | 383.68 | 652.31 | 17.6 | 2000 |
| 52 | QLSETSQALLWK | 18.84 | 702.38 | 1162.61 | 35.8 | 2000 |
| 53 | QLSETSQALLWK | 18.84 | 702.38 | 446.28 | 35.8 | 2000 |
| 54 | QLSETSQALLWK | 18.84 | 702.38 | 845.49 | 35.8 | 2000 |
| 55 | TGTSGIK | 3.31 | 332.19 | 404.25 | 14.7 | 2000 |
| 56 | TGTSGIK | 3.29 | 332.19 | 505.30 | 14.7 | 2000 |
| 57 | TGTSGIK | 3.23 | 332.19 | 562.32 | 14.7 | 2000 |
| 58 | TGTSGVR | 1.56 | 339.18 | 418.24 | 15.1 | 2000 |
| 59 | TGTSGVR | 1.56 | 339.18 | 519.29 | 15.1 | 2000 |
| 60 | TGTSGVR | 1.56 | 339.18 | 576.31 | 15.1 | 2000 |
| 61 | TNEAIIAQVAQAAYQFELK | 26.27 | 703.37 | 1168.60 | 28.9 | 2000 |
| 62 | TNEAIIAQVAQAAYQFELK | 26.21 | 703.37 | 827.43 | 28.9 | 2000 |
| 63 | TNEAIIAQVAQAAYQFELK | 26.25 | 703.37 | 898.47 | 28.9 | 2000 |
| 64 | TNEAIIAQVAQTAYQFELK | 25.39 | 713.38 | 1198.61 | 29.2 | 2000 |
| 65 | TNEAIIAQVAQTAYQFELK | 25.37 | 713.38 | 827.43 | 29.2 | 2000 |
| 66 | TNEAIIAQVAQTAYQFELK | 25.37 | 713.38 | 898.47 | 29.2 | 2000 |
| 67 | TQLSETSQALLWK | 19.41 | 502.27 | 559.36 | 38.7 | 2000 |
| 68 | TQLSETSQALLWK | 19.41 | 502.27 | 630.40 | 22.7 | 2000 |
| 69 | TQLSETSQALLWK | 19.43 | 752.90 | 1162.61 | 22.7 | 2000 |
| 70 | TVAVNR | 7.08 | 330.20 | 388.23 | 14.6 | 2000 |
| 71 | TVAVNR | 7.08 | 330.20 | 459.27 | 14.6 | 2000 |
| 72 | TVAVNR | 7.05 | 330.20 | 558.34 | 14.6 | 2000 |
| 73 | VLQNTWAPIMK | 19.32 | 650.86 | 488.29 | 32.8 | 2000 |
| 74 | VLQNTWAPIMK | 19.3 | 650.86 | 559.33 | 32.8 | 2000 |
| 75 | VLQNTWAPIMK | 19.3 | 650.86 | 745.41 | 32.8 | 2000 |
| 76 | WMVETTTGPER | 15.5 | 653.81 | 761.38 | 33 | 2000 |
| 77 | WMVETTTGPER | 15.48 | 653.81 | 890.42 | 33 | 2000 |
| 78 | WMVETTTGPER | 15.48 | 653.81 | 989.49 | 33 | 2000 |
| 79 | WMVETTTGPQR | 15.19 | 653.32 | 457.25 | 33 | 2000 |
| 80 | WMVETTTGPQR | 15.19 | 653.32 | 889.44 | 33 | 2000 |
| 81 | WMVETTTGPQR | 15.23 | 653.32 | 988.51 | 33 | 2000 |

The other machine parameters used are as follows:

| | |
|---|---|
| Scan type: | MRM |
| MRM planned: | yes |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 40.00 psi |
| Heating gas: | 40.00 psi |
| Collision gas which induces dissociation: | 9.00 psi |
| Dynamic filling: | activated |
| Declustering potential (DP): | 100.00 V |
| Entry potential before Q0 (EP): | 10.00 V |
| Collision cell exit potential (CXP): | 15 V |
| Total cycle time: | 1 sec |
| Detection window: | 240 sec |

The areas obtained for each of the transitions and for each of the microorganisms studied were measured. When the areas of the transitions are greater than or equal to the positivity threshold described in TABLE 13, the detection of the transition is considered to be positive and is labelled "1" in TABLE 14. When a transition has an area less than the positivity threshold described in TABLE 13, the transition is considered non-detected and is labelled "0" in TABLE 14.

For a given peptide, when at least 3 transitions are labelled "1", the peptide is considered as being detected.

TABLE 14

| Transition number | Sam74 | Sam75 | Sam76 | Sam77 | Sam78 |
|---|---|---|---|---|---|
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |
| 5 | 0 | 0 | 0 | 0 | 0 |
| 6 | 0 | 0 | 0 | 0 | 0 |
| 7 | 0 | 1 | 0 | 1 | 0 |
| 8 | 0 | 0 | 0 | 0 | 1 |
| 9 | 1 | 1 | 1 | 1 | 1 |
| 10 | 1 | 1 | 1 | 1 | 1 |
| 11 | 1 | 1 | 1 | 1 | 1 |
| 12 | 1 | 1 | 1 | 1 | 1 |
| 13 | 0 | 0 | 0 | 0 | 0 |
| 14 | 0 | 0 | 0 | 0 | 0 |
| 15 | 0 | 0 | 0 | 0 | 0 |
| 16 | 0 | 0 | 0 | 0 | 0 |
| 17 | 1 | 1 | 0 | 0 | 0 |
| 18 | 0 | 0 | 0 | 0 | 0 |
| 19 | 1 | 1 | 0 | 0 | 0 |
| 20 | 1 | 1 | 0 | 0 | 0 |
| 21 | 1 | 1 | 0 | 0 | 0 |
| 22 | 1 | 1 | 1 | 1 | 1 |
| 23 | 1 | 1 | 1 | 1 | 1 |
| 24 | 1 | 1 | 1 | 1 | 1 |
| 25 | 0 | 0 | 0 | 0 | 0 |
| 26 | 0 | 0 | 0 | 0 | 0 |
| 27 | 0 | 0 | 0 | 0 | 0 |
| 28 | 1 | 1 | 1 | 1 | 1 |
| 29 | 1 | 1 | 1 | 1 | 1 |
| 30 | 1 | 1 | 1 | 1 | 1 |
| 31 | 0 | 0 | 0 | 0 | 0 |
| 32 | 0 | 0 | 0 | 0 | 0 |
| 33 | 1 | 1 | 0 | 0 | 0 |
| 34 | 0 | 0 | 0 | 0 | 0 |
| 35 | 0 | 0 | 0 | 0 | 0 |
| 36 | 0 | 0 | 0 | 0 | 0 |
| 37 | 0 | 0 | 1 | 1 | 1 |
| 38 | 0 | 0 | 0 | 0 | 0 |

TABLE 14-continued

| Transition number | Sam74 | Sam75 | Sam76 | Sam77 | Sam78 |
|---|---|---|---|---|---|
| 39 | 0 | 0 | 0 | 0 | 0 |
| 40 | 1 | 1 | 1 | 1 | 1 |
| 41 | 1 | 1 | 1 | 1 | 1 |
| 42 | 1 | 1 | 1 | 1 | 1 |
| 43 | 0 | 0 | 0 | 0 | 0 |
| 44 | 0 | 0 | 0 | 0 | 0 |
| 45 | 0 | 0 | 0 | 0 | 0 |
| 46 | 0 | 0 | 0 | 0 | 0 |
| 47 | 0 | 0 | 0 | 0 | 0 |
| 48 | 0 | 0 | 0 | 0 | 0 |
| 49 | 0 | 0 | 0 | 0 | 0 |
| 50 | 0 | 0 | 0 | 0 | 0 |
| 51 | 0 | 0 | 0 | 0 | 0 |
| 52 | 0 | 0 | 0 | 0 | 0 |
| 53 | 0 | 0 | 0 | 0 | 0 |
| 54 | 0 | 0 | 0 | 0 | 0 |
| 55 | 1 | 1 | 0 | 1 | 1 |
| 56 | 1 | 1 | 0 | 0 | 0 |
| 57 | 1 | 1 | 0 | 0 | 0 |
| 58 | 0 | 0 | 0 | 0 | 0 |
| 59 | 0 | 0 | 0 | 0 | 0 |
| 60 | 0 | 0 | 0 | 0 | 0 |
| 61 | 0 | 0 | 0 | 0 | 0 |
| 62 | 0 | 0 | 0 | 0 | 0 |
| 63 | 0 | 0 | 0 | 0 | 0 |
| 64 | 0 | 0 | 0 | 0 | 0 |
| 65 | 0 | 0 | 0 | 0 | 0 |
| 66 | 0 | 0 | 0 | 0 | 0 |
| 67 | 1 | 1 | 1 | 1 | 1 |
| 68 | 1 | 1 | 1 | 1 | 1 |
| 69 | 1 | 1 | 1 | 1 | 0 |
| 70 | 0 | 0 | 0 | 0 | 0 |
| 71 | 0 | 0 | 0 | 0 | 0 |
| 72 | 0 | 0 | 0 | 0 | 0 |
| 73 | 1 | 1 | 1 | 1 | 1 |
| 74 | 1 | 1 | 1 | 1 | 1 |
| 75 | 1 | 1 | 1 | 1 | 1 |
| 76 | 1 | 1 | 1 | 1 | 1 |
| 77 | 1 | 1 | 1 | 1 | 1 |
| 78 | 1 | 1 | 1 | 1 | 1 |
| 79 | 0 | 0 | 0 | 0 | 0 |
| 80 | 0 | 0 | 0 | 0 | 0 |
| 81 | 0 | 0 | 0 | 0 | 0 |

Samples Sam74 to Sam78 comprise at least one peptide which is characteristic of PERs. The bacteria present in samples Sam74 to Sam78 therefore express a beta-lactamase which confers on them a resistance to penicillins, cephalosporins and monobactams.

EXAMPLE 13

Identification of a Resistance to VEB Beta-Lactams

Samples Sam79 to Sam82 are identified according to one of the methods described in examples 1, 3 or 4. The identification of the species is set out in TABLE 15.

TABLE 15

| Names | Species |
|---|---|
| Sam79 | *A. baumannii* |
| Sam80 | *A. baumannii* |
| Sam81 | *A. baumannii* |
| Sam82 | *E. coli* |

Samples Sam79 to Sam82 correspond to a species able to comprise a VEB resistance mechanism. Each sample is treated according to example 5, then analysed according to example 6 by detecting the peptides from TABLE 16 instead of the peptides from TABLE 3.

TABLE 16

| Transition number | Peptide | Retention time (minutes) | (m/z) filtered in Q1 | (m/z) filtered in Q3 | Collision energy (eV) | Positivity threshold |
|---|---|---|---|---|---|---|
| 1 | ANEEQMHK | 1.44 | 493.72 | 458.20 | 23.9 | 2000 |
| 2 | ANEEQMHK | 1.44 | 493.72 | 672.31 | 23.9 | 2000 |
| 3 | ANEEQMHK | 1.44 | 493.72 | 801.36 | 23.9 | 2000 |
| 4 | DWNTQYQNWATPTAMNK | 19.05 | 1034.96 | 661.33 | 54.7 | 2000 |
| 5 | DWNTQYQNWATPTAMNK | 19 | 690.31 | 661.33 | 28.5 | 2000 |
| 6 | DWNTQYQNWATPTAMNK | 19.02 | 690.31 | 762.38 | 28.5 | 2000 |
| 7 | ETSEINEK | 6.84 | 475.23 | 390.20 | 22.8 | 2000 |
| 8 | ETSEINEK | 6.84 | 475.23 | 503.28 | 22.8 | 2000 |
| 9 | ETSEINEK | 6.83 | 475.23 | 719.36 | 22.8 | 2000 |
| 10 | ETTTGSNR | 1.38 | 433.20 | 433.22 | 20.4 | 1500 |
| 11 | ETTTGSNR | 1.38 | 433.20 | 534.26 | 20.4 | 1500 |
| 12 | ETTTGSNR | 1.38 | 433.20 | 635.31 | 20.4 | 1500 |
| 13 | FLNANHFTDISIK | 18.72 | 507.27 | 573.30 | 22.8 | 2000 |
| 14 | FLNANHFTDISIK | 18.72 | 507.27 | 630.32 | 22.8 | 2000 |
| 15 | FLNANHFTDISIK | 18.74 | 507.27 | 686.87 | 22.8 | 2000 |
| 16 | FPIALAVLSEIDK | 27.01 | 708.41 | 634.88 | 36.1 | 2000 |
| 17 | FPIALAVLSEIDK | 27.04 | 708.41 | 704.38 | 36.1 | 2000 |
| 18 | FPIALAVLSEIDK | 27.01 | 708.41 | 874.49 | 36.1 | 2000 |
| 19 | GNLSFEQK | 12.65 | 461.74 | 551.28 | 22.1 | 2000 |
| 20 | GNLSFEQK | 12.65 | 461.74 | 638.31 | 22.1 | 2000 |
| 21 | GNLSFEQK | 12.65 | 461.74 | 751.40 | 22.1 | 2000 |
| 22 | GQLPK | 7.19 | 271.67 | 243.16 | 11.2 | 2000 |
| 23 | GQLPK | 7.19 | 271.67 | 357.25 | 11.2 | 2000 |
| 24 | GQLPK | 7.19 | 271.67 | 485.31 | 11.2 | 2000 |
| 25 | IEITPQDLLPK | 21.67 | 633.87 | 405.74 | 31.9 | 2000 |
| 26 | IEITPQDLLPK | 21.67 | 633.87 | 810.47 | 31.9 | 2000 |
| 27 | IEITPQDLLPK | 21.63 | 633.87 | 911.52 | 31.9 | 2000 |
| 28 | IENVLK | 12.89 | 358.22 | 359.27 | 16.2 | 2000 |
| 29 | IENVLK | 12.91 | 358.22 | 473.31 | 16.2 | 2000 |
| 30 | IENVLK | 12.89 | 358.22 | 602.35 | 16.2 | 2000 |
| 31 | IGVAIFNSNEK | 18.09 | 596.32 | 738.34 | 29.7 | 2000 |
| 32 | IGVAIFNSNEK | 18.09 | 596.32 | 851.43 | 29.7 | 2000 |
| 33 | IGVAIFNSNEK | 18.09 | 596.32 | 922.46 | 29.7 | 2000 |
| 34 | IISDIAK | 12.6 | 380.23 | 331.23 | 17.4 | 2000 |
| 35 | IISDIAK | 12.58 | 380.23 | 533.29 | 17.4 | 2000 |
| 36 | IISDIAK | 12.56 | 380.23 | 646.38 | 17.4 | 2000 |
| 37 | INNDFHFPMQSVMK | 20.04 | 569.94 | 740.84 | 24.8 | 2000 |
| 38 | INNDFHFPMQSVMK | 20.04 | 569.94 | 797.86 | 24.8 | 2000 |

TABLE 16-continued

| Transition number | Peptide | Retention time (minutes) | (m/z) filtered Q1 | (m/z) in filtered in Q3 | Collision energy (eV) | Positivity threshold |
|---|---|---|---|---|---|---|
| 39 | INNDFHFPMQSVMK | 20.05 | 569.94 | 820.41 | 24.8 | 2000 |
| 40 | LIGGTDSVQK | 11.48 | 509.28 | 734.37 | 24.8 | 2000 |
| 41 | LIGGTDSVQK | 11.46 | 509.28 | 791.39 | 24.8 | 2000 |
| 42 | LIGGTDSVQK | 11.46 | 509.28 | 904.47 | 24.8 | 2000 |
| 43 | LLIDTYNNK | 15.7 | 547.30 | 639.31 | 26.9 | 2000 |
| 44 | LLIDTYNNK | 15.7 | 547.30 | 754.34 | 26.9 | 2000 |
| 45 | LLIDTYNNK | 15.7 | 547.30 | 867.42 | 26.9 | 2000 |
| 46 | MWSPIK | 16.91 | 381.20 | 357.25 | 17.5 | 2000 |
| 47 | MWSPIK | 16.91 | 381.20 | 444.28 | 17.5 | 2000 |
| 48 | MWSPIK | 16.87 | 381.20 | 630.36 | 17.5 | 2000 |
| 49 | NQLLSK | 10.59 | 351.71 | 347.23 | 15.8 | 2000 |
| 50 | NQLLSK | 10.59 | 351.71 | 460.31 | 15.8 | 2000 |
| 51 | NQLLSK | 10.59 | 351.71 | 588.37 | 15.8 | 2000 |
| 52 | NTIVAHK | 23.75 | 391.73 | 454.28 | 18.1 | 2000 |
| 53 | NTIVAHK | 23.73 | 391.73 | 567.36 | 18.1 | 2000 |
| 54 | NTIVAHK | 23.75 | 391.73 | 668.41 | 18.1 | 2000 |
| 55 | SYDFIWK | 19.92 | 479.74 | 446.28 | 23.1 | 2000 |
| 56 | SYDFIWK | 19.9 | 479.74 | 593.35 | 23.1 | 2000 |
| 57 | SYDFIWK | 19.9 | 479.74 | 708.37 | 23.1 | 2000 |
| 58 | TWSPIK | 14.95 | 366.21 | 357.25 | 16.6 | 2000 |
| 59 | TWSPIK | 14.93 | 366.21 | 444.28 | 16.6 | 2000 |
| 60 | TWSPIK | 14.95 | 366.21 | 630.36 | 16.6 | 2000 |

The other machine parameters used are as follows:

| | |
|---|---|
| Scan type: | MRM |
| MRM planned: | yes |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 40.00 psi |
| Heating gas: | 40.00 psi |
| Collision gas which induces dissociation: | 9.00 psi |
| Dynamic filling: | activated |
| Declustering potential (DP): | 100.00 V |
| Entry potential before Q0 (EP): | 10.00 V |
| Collision cell exit potential (CXP): | 15 V |
| Total cycle time: | 1.2 sec |
| Detection window: | 240 sec |

The areas obtained for each of the transitions and for each of the microorganisms studied were measured. When the areas of the transitions are greater than or equal to the positivity threshold described in TABLE 16, the detection of the transition is considered to be positive and is labelled "1" in TABLE 17. When a transition has an area less than the positivity threshold described in TABLE 16, the transition is considered non-detected and is labelled "0" in TABLE 17.

For a given peptide, when at least 3 transitions are labelled "1", the peptide is considered as being detected.

TABLE 17

| Transition number | Sam79 | Sam80 | Sam81 | Sam82 |
|---|---|---|---|---|
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 1 | 1 | 1 | 1 |
| 11 | 1 | 1 | 1 | 1 |
| 12 | 1 | 1 | 1 | 0 |
| 13 | 0 | 1 | 1 | 0 |
| 14 | 0 | 1 | 1 | 0 |
| 15 | 0 | 1 | 1 | 0 |
| 16 | 0 | 0 | 0 | 0 |
| 17 | 0 | 0 | 0 | 0 |

TABLE 17-continued

| Transition number | Sam79 | Sam80 | Sam81 | Sam82 |
|---|---|---|---|---|
| 18 | 0 | 0 | 0 | 0 |
| 19 | 0 | 0 | 0 | 0 |
| 20 | 0 | 0 | 0 | 0 |
| 21 | 0 | 0 | 0 | 0 |
| 22 | 0 | 0 | 0 | 0 |
| 23 | 0 | 0 | 0 | 0 |
| 24 | 0 | 0 | 0 | 0 |
| 25 | 1 | 1 | 1 | 1 |
| 26 | 1 | 1 | 1 | 1 |
| 27 | 1 | 1 | 1 | 1 |
| 28 | 0 | 0 | 0 | 0 |
| 29 | 0 | 0 | 0 | 0 |
| 30 | 0 | 0 | 0 | 0 |
| 31 | 0 | 0 | 0 | 0 |
| 32 | 0 | 0 | 0 | 0 |
| 33 | 0 | 0 | 0 | 0 |
| 34 | 0 | 0 | 0 | 0 |
| 35 | 0 | 0 | 0 | 0 |
| 36 | 0 | 0 | 0 | 0 |
| 37 | 0 | 0 | 0 | 0 |
| 38 | 0 | 0 | 0 | 0 |
| 39 | 0 | 0 | 0 | 0 |
| 40 | 1 | 1 | 1 | 0 |
| 41 | 0 | 1 | 0 | 0 |
| 42 | 1 | 0 | 1 | 0 |
| 43 | 0 | 0 | 0 | 0 |
| 44 | 0 | 0 | 0 | 0 |
| 45 | 0 | 0 | 0 | 0 |
| 46 | 0 | 0 | 0 | 0 |
| 47 | 0 | 0 | 0 | 0 |
| 48 | 0 | 0 | 0 | 0 |
| 49 | 0 | 0 | 0 | 0 |
| 50 | 0 | 0 | 0 | 0 |
| 51 | 0 | 0 | 0 | 0 |
| 52 | 0 | 0 | 0 | 0 |
| 53 | 0 | 0 | 0 | 0 |
| 54 | 0 | 0 | 0 | 0 |
| 55 | 1 | 1 | 1 | 0 |
| 56 | 1 | 1 | 1 | 0 |
| 57 | 1 | 1 | 1 | 0 |
| 58 | 0 | 0 | 0 | 0 |
| 59 | 0 | 0 | 0 | 0 |
| 60 | 0 | 0 | 0 | 0 |

Samples Sam79 to Sam82 comprise at least one peptide which is characteristic of VEBs. The bacteria present in samples Sam79 to Sam82 therefore express a beta-lactamase which confers on them a resistance to penicillins, cephalosporins and monobactams.

EXAMPLE 14

Identification of a Resistance to MOX Beta-Lactams

Sample Sam83 is identified according to one of the methods described in examples 1, 3 or 4. The identification of the species is set out in TABLE 18.

TABLE 18

| Names | Species |
|---|---|
| Sam83 | E. coli |

Sample Sam83 corresponds to a species able to comprise a MOX resistance mechanism. Each sample is treated according to example 5, then analysed according to example 6 by detecting the peptides from TABLE 19 instead of the peptides from TABLE 3.

TABLE 19

| Transition number | Peptide | Retention time (minutes) | (m/z) filtered in Q1 | (m/z) filtered in Q3 | Collision energy (eV) | Positivity threshold |
|---|---|---|---|---|---|---|
| 1 | AHYFNYGVADR | 14.36 | 656.807 | 621.289 | 33.2 | 2000 |
| 2 | AHYFNYGVADR | 14.36 | 656.807 | 941.448 | 33.2 | 2000 |
| 3 | AHYFNYGVADR | 14.34 | 656.807 | 1104.511 | 33.2 | 2000 |
| 4 | ANISGVDDK | 9.88 | 459.73 | 533.257 | 21.9 | 2000 |
| 5 | ANISGVDDK | 9.86 | 459.73 | 620.289 | 21.9 | 2000 |
| 6 | ANISGVDDK | 9.86 | 459.73 | 733.373 | 21.9 | 2000 |
| 7 | ANISGVHDK | 7.75 | 470.746 | 555.289 | 22.6 | 2000 |
| 8 | ANISGVHDK | 7.67 | 470.746 | 642.321 | 22.6 | 2000 |
| 9 | ANISGVHDK | 7.69 | 470.746 | 755.405 | 22.6 | 2000 |
| 10 | ASLFAPWLK | 23.52 | 516.797 | 543.329 | 25.2 | 2000 |
| 11 | ASLFAPWLK | 23.56 | 516.797 | 614.366 | 25.2 | 2000 |
| 12 | ASLFAPWLK | 23.56 | 516.797 | 761.434 | 25.2 | 2000 |
| 13 | EDKPFR | 8.09 | 396.206 | 419.24 | 18.3 | 2000 |
| 14 | EDKPFR | 8.07 | 396.206 | 547.335 | 18.3 | 2000 |
| 15 | EDKPFR | 8.09 | 396.206 | 662.362 | 18.3 | 2000 |
| 16 | ESGNLMLFNK | 18.39 | 576.79 | 408.224 | 28.6 | 2000 |

TABLE 19-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 17 | ESGNLMLFNK | 18.39 | 576.79 | 521.308 | 28.6 | 2000 |
| 18 | ESGNLMLFNK | 18.39 | 576.79 | 652.349 | 28.6 | 2000 |
| 19 | ESGSQMLFNK | 15.08 | 570.771 | 408.224 | 28.3 | 2000 |
| 20 | ESGSQMLFNK | 15.14 | 570.771 | 521.308 | 28.3 | 2000 |
| 21 | ESGSQMLFNK | 15.12 | 570.771 | 652.349 | 28.3 | 2000 |
| 22 | GHPVLFNK | 12.74 | 456.259 | 408.224 | 21.7 | 2000 |
| 23 | GHPVLFNK | 12.78 | 456.259 | 521.308 | 21.7 | 2000 |
| 24 | GHPVLFNK | 12.78 | 456.259 | 717.429 | 21.7 | 2000 |
| 25 | GIGVVMLANR | 18.19 | 515.297 | 604.324 | 25.1 | 2000 |
| 26 | GIGVVMLANR | 18.17 | 515.297 | 703.392 | 25.1 | 2000 |
| 27 | GIGVVMLANR | 18.17 | 515.297 | 859.482 | 25.1 | 2000 |
| 28 | MQAYYR | 11.12 | 416.195 | 501.246 | 19.5 | 2000 |
| 29 | MQAYYR | 11.14 | 416.195 | 572.283 | 19.5 | 2000 |
| 30 | MQAYYR | 11.12 | 416.195 | 700.341 | 19.5 | 2000 |
| 31 | NSPIEAR | 9.4 | 393.709 | 375.199 | 18.2 | 2000 |
| 32 | NSPIEAR | 9.4 | 393.709 | 488.283 | 18.2 | 2000 |
| 33 | NSPIEAR | 9.4 | 393.709 | 585.335 | 18.2 | 2000 |
| 34 | NSPIEGTLK | 13.36 | 479.764 | 379.226 | 23.1 | 2000 |
| 35 | NSPIEGTLK | 13.36 | 479.764 | 547.309 | 23.1 | 2000 |
| 36 | NSPIEGTLK | 13.34 | 479.764 | 757.445 | 23.1 | 2000 |
| 37 | NYPNEGTLK | 11.6 | 518.259 | 379.706 | 25.3 | 2000 |
| 38 | NYPNEGTLK | 11.62 | 518.259 | 661.352 | 25.3 | 2000 |
| 39 | NYPNEGTLK | 11.58 | 518.259 | 758.404 | 25.3 | 2000 |
| 40 | QPFDR | 9.48 | 331.666 | 437.214 | 14.6 | 2000 |
| 41 | QPFDR | 9.5 | 331.666 | 488.214 | 14.6 | 2000 |
| 42 | QPFDR | 9.48 | 331.666 | 534.267 | 14.6 | 2000 |
| 43 | QWTPAYSPGSHR | 13.34 | 693.831 | 486.238 | 35.3 | 2000 |
| 44 | QWTPAYSPGSHR | 13.34 | 693.831 | 640.316 | 35.3 | 2000 |
| 45 | QWTPAYSPGSHR | 13.34 | 693.831 | 971.469 | 35.3 | 2000 |
| 46 | QWTPAYSR | 13.46 | 504.749 | 496.251 | 24.5 | 2000 |
| 47 | QWTPAYSR | 13.48 | 504.749 | 593.304 | 24.5 | 2000 |
| 48 | QWTPAYSR | 13.46 | 504.749 | 694.352 | 24.5 | 2000 |
| 49 | QYANPSIGLFGYLAASSMK | 25.46 | 673.34 | 594.292 | 28 | 2000 |
| 50 | QYANPSIGLFGYLAASSMK | 25.5 | 673.34 | 594.31 | 28 | 2000 |
| 51 | QYANPSIGLFGYLAASSMK | 25.5 | 673.34 | 927.46 | 28 | 2000 |
| 52 | QYSNPSIGLFGHLAASSMK | 21.21 | 670.003 | 609.819 | 27.9 | 2000 |
| 53 | QYSNPSIGLFGHLAASSMK | 21.17 | 670.003 | 758.403 | 27.9 | 2000 |
| 54 | QYSNPSIGLFGHLAASSMK | 21.21 | 670.003 | 858.941 | 27.9 | 2000 |

TABLE 19-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 55 | TGSSNGFGAYVAFVPAR | 20.79 | 850.923 | 343.209 | 100 | 2000 |
| 56 | TGSSNGFGAYVAFVPAR | 20.78 | 850.923 | 380.229 | 100 | 2000 |
| 57 | TGSSNGFGAYVAFVPAR | 20.78 | 850.923 | 442.277 | 100 | 2000 |
| 58 | TGSTNGFGAYVAFVPAK | 20.45 | 843.928 | 315.203 | 100 | 2000 |
| 59 | TGSTNGFGAYVAFVPAK | 20.46 | 843.928 | 366.226 | 100 | 2000 |
| 60 | TGSTNGFGAYVAFVPAK | 20.46 | 843.928 | 414.271 | 100 | 2000 |
| 61 | TGSTSGFGAYVAFVPAK | 20.64 | 553.951 | 632.377 | 24.3 | 2000 |
| 62 | TGSTSGFGAYVAFVPAK | 20.66 | 830.422 | 315.203 | 43.1 | 2000 |
| 63 | TGSTSGFGAYVAFVPAK | 20.66 | 830.422 | 414.271 | 43.1 | 2000 |
| 64 | TLTATLGAYAVVQGSFELDDK | 18.71 | 733.711 | 569.275 | 29.8 | 2000 |
| 65 | TLTATLGAYAVVQGSFELDDK | 18.71 | 733.711 | 654.328 | 29.8 | 2000 |
| 66 | TLTATLGAYAVVQGSFELDDK | 18.71 | 733.711 | 1137.542 | 29.8 | 2000 |
| 67 | VSPGMLADEAYGIK | 18.63 | 725.866 | 632.816 | 37.1 | 2000 |
| 68 | VSPGMLADEAYGIK | 18.63 | 725.866 | 866.425 | 37.1 | 2000 |
| 69 | VSPGMLADEAYGIK | 18.65 | 725.866 | 1167.571 | 37.1 | 2000 |
| 70 | VTPAMLAEEPYGIK | 19.05 | 506.934 | 577.334 | 22.8 | 2000 |
| 71 | VTPAMLAEEPYGIK | 19.05 | 759.897 | 659.839 | 39 | 2000 |
| 72 | VTPAMLAEEPYGIK | 19.07 | 759.897 | 906.457 | 39 | 2000 |
| 73 | YAYPVSEQTLLAGNSAK | 18.09 | 604.644 | 547.283 | 25.8 | 2000 |
| 74 | YAYPVSEQTLLAGNSAK | 18.07 | 604.644 | 660.368 | 25.8 | 2000 |
| 75 | YAYPVSEQTLLAGNSAK | 18.09 | 906.462 | 707.88 | 47.4 | 2000 |

The other machine parameters used are as follows:

| | |
|---|---|
| Scan type: | MRM |
| MRM planned: | yes |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 40.00 psi |
| Cone voltage: | 5500.00 V |
| Source temperature: | 500.00° C. |
| Nebulising gas: | 40.00 psi |
| Heating gas: | 40.00 psi |
| Collision gas which induces dissociation: | 9.00 psi |
| Dynamic filling: | activated |
| Declustering potential (DP): | 100.00 V |
| Entry potential before Q0 (EP): | 10.00 V |
| Collision cell exit potential (CXP): | 15 V |
| Total cycle time: | 1 sec |
| Detection window: | 240 sec |

The areas obtained for each of the transitions and for each of the microorganisms studied were measured. When the areas of the transitions are greater than or equal to the positivity threshold described in TABLE 19, the detection of the transition is considered to be positive and is labelled "1" in TABLE 20. When a transition has an area less than the positivity threshold described in TABLE 19, the transition is considered non-detected and is labelled "0" in TABLE 20.

For a given peptide, when at least 3 transitions are labelled "1", the peptide is considered as being detected.

TABLE 20

| Transition number | Sam83 |
|---|---|
| 1 | 0 |
| 2 | 0 |
| 3 | 0 |
| 4 | 0 |
| 5 | 0 |
| 6 | 0 |
| 7 | 1 |
| 8 | 1 |
| 9 | 1 |
| 10 | 0 |
| 11 | 0 |
| 12 | 0 |
| 13 | 0 |
| 14 | 0 |
| 15 | 0 |
| 16 | 0 |
| 17 | 0 |

TABLE 20-continued

| Transition number | Sam83 |
|---|---|
| 18 | 0 |
| 19 | 0 |
| 20 | 0 |
| 21 | 0 |
| 22 | 0 |
| 23 | 0 |
| 24 | 0 |
| 25 | 0 |
| 26 | 0 |
| 27 | 0 |
| 28 | 0 |
| 29 | 0 |
| 30 | 0 |
| 31 | 0 |
| 32 | 0 |
| 33 | 0 |
| 34 | 0 |
| 35 | 0 |
| 36 | 0 |
| 37 | 0 |
| 38 | 0 |
| 39 | 0 |
| 40 | 0 |
| 41 | 0 |
| 42 | 0 |
| 43 | 1 |
| 44 | 1 |
| 45 | 1 |
| 46 | 0 |
| 47 | 0 |
| 48 | 0 |
| 49 | 0 |
| 50 | 0 |
| 51 | 0 |
| 52 | 0 |
| 53 | 0 |
| 54 | 0 |
| 55 | 0 |
| 56 | 0 |
| 57 | 0 |
| 58 | 0 |
| 59 | 0 |
| 60 | 0 |
| 61 | 0 |
| 62 | 0 |
| 63 | 0 |
| 64 | 0 |
| 65 | 0 |
| 66 | 0 |
| 67 | 1 |
| 68 | 1 |
| 69 | 1 |
| 70 | 0 |
| 71 | 0 |
| 72 | 0 |
| 73 | 0 |
| 74 | 0 |
| 75 | 0 |

Sample Sam83 comprises at least one peptide which is characteristic of MOXs. The bacteria present in sample Sam83 therefore express a beta-lactamase which confers on them a resistance to penicillins and to cephalosporins, with the exception of fourth-generation cephalosporins.

EXAMPLE 15

Identification of a Resistance to ACC Beta-Lactams

The samples corresponding to a species able to comprise an ACC resistance mechanism can be detected by employing the following method.

Each sample is treated according to example 5, then analysed according to example 6 by detecting the peptides from TABLE 21 instead of the peptides from TABLE 3.

TABLE 21

| Transition number | Peptide | Retention time (minutes) | (m/z) filtered in Q1 | (m/z) filtered in Q3 | Collision energy (eV) |
|---|---|---|---|---|---|
| 1 | ALTDTHIGYFK | 15.83 | 422.56 | 457.24 | 25 |
| 2 | ALTDTHIGYFK | 15.83 | 422.56 | 514.27 | 25 |
| 3 | ALTDTHIGYFK | 15.83 | 422.56 | 627.35 | 25 |
| 4 | AWKPADPAGTHR | 10.49 | 436.23 | 470.25 | 26 |
| 5 | AWKPADPAGTHR | 10.49 | 436.23 | 638.34 | 26 |
| 6 | AWKPADPAGTHR | 10.49 | 436.23 | 669.34 | 26 |
| 7 | DEPVHGNMEILGNEAYGIK | 18.07 | 696 | 851.43 | 39 |
| 8 | DEPVHGNMEILGNEAYGIK | 18.07 | 696 | 1009.4 | 39 |
| 9 | DEPVHGNMEILGNEAYGIK | 18.07 | 696 | 1122.49 | 39 |
| 10 | DTVDGLIQPLMQK | 20.72 | 729.39 | 857.49 | 37 |
| 11 | DTVDGLIQPLMQK | 20.72 | 729.39 | 970.58 | 37 |
| 12 | DTVDGLIQPLMQK | 20.72 | 729.39 | 1027.6 | 37 |
| 13 | DTVDSLIQPLMQK | 21.62 | 744.39 | 857.49 | 38 |
| 14 | DTVDSLIQPLMQK | 21.62 | 744.39 | 1057.61 | 38 |
| 15 | DTVDSLIQPLMQK | 21.62 | 744.39 | 1172.63 | 38 |

TABLE 21-continued

| Transition number | Peptide | Retention time (minutes) | (m/z) filtered in Q1 | (m/z) filtered in Q3 | Collision energy (eV) |
|---|---|---|---|---|---|
| 16 | IQHALTATHTGYFK | 12.76 | 397.71 | 514.27 | 23 |
| 17 | IQHALTATHTGYFK | 12.76 | 397.71 | 615.31 | 23 |
| 18 | IQHALTATHTGYFK | 12.76 | 397.71 | 752.37 | 23 |
| 19 | LDGNSTLQK | 9.44 | 488.26 | 576.34 | 26 |
| 20 | LDGNSTLQK | 9.44 | 488.26 | 747.4 | 26 |
| 21 | LDGNSTLQK | 9.44 | 488.26 | 862.43 | 26 |
| 22 | LSLDK | 10.73 | 288.17 | 375.22 | 18 |
| 23 | LSLDK | 10.73 | 288.17 | 429.23 | 18 |
| 24 | LSLDK | 10.73 | 288.17 | 462.26 | 18 |
| 25 | LSLEQSVSHYVPELR | 20.3 | 586.31 | 776.43 | 33 |
| 26 | LSLEQSVSHYVPELR | 20.3 | 586.31 | 913.49 | 33 |
| 27 | LSLEQSVSHYVPELR | 20.3 | 586.31 | 1000.52 | 33 |
| 28 | NEPIHVNMEVLGNEAYGIR | 19.55 | 719.02 | 879.43 | 40 |
| 29 | NEPIHVNMEVLGNEAYGIR | 19.55 | 719.02 | 992.52 | 40 |
| 30 | NEPIHVNMEVLGNEAYGIR | 19.55 | 719.02 | 1163.55 | 40 |
| 31 | NNIPGMSVAVTIR | 18.3 | 457.92 | 559.36 | 27 |
| 32 | NNIPGMSVAVTIR | 18.3 | 686.37 | 933.52 | 35 |
| 33 | NNIPGMSVAVTIR | 18.3 | 686.37 | 1030.57 | 35 |
| 34 | NTDQLMAYLK | 18.78 | 598.8 | 625.34 | 31 |
| 35 | NTDQLMAYLK | 18.78 | 598.8 | 738.42 | 31 |
| 36 | NTDQLMAYLK | 18.78 | 598.8 | 981.51 | 31 |
| 37 | NTTQLMTYLK | 17.75 | 606.82 | 768.43 | 32 |
| 38 | NTTQLMTYLK | 17.75 | 606.82 | 896.49 | 32 |
| 39 | NTTQLMTYLK | 17.75 | 606.82 | 997.54 | 32 |
| 40 | NYIYNYGLASK | 15.9 | 653.33 | 752.39 | 34 |
| 41 | NYIYNYGLASK | 15.9 | 653.33 | 915.46 | 34 |
| 42 | NYIYNYGLASK | 15.9 | 653.33 | 1028.54 | 34 |
| 43 | SISHYVPELR | 15 | 400.88 | 514.3 | 24 |
| 44 | SISHYVPELR | 15 | 400.88 | 613.37 | 24 |
| 45 | SISHYVPELR | 15 | 400.88 | 776.43 | 24 |
| 46 | TFAAILASYAQASGK | 21.64 | 749.9 | 811.39 | 38 |
| 47 | TFAAILASYAQASGK | 21.64 | 749.9 | 882.43 | 38 |
| 48 | TFAAILASYAQASGK | 21.64 | 749.9 | 995.52 | 38 |
| 49 | TLLPK | 12.05 | 286.19 | 357.25 | 18 |
| 50 | TLLPK | 12.05 | 286.19 | 425.28 | 18 |
| 51 | TLLPK | 12.05 | 286.19 | 470.33 | 18 |
| 52 | TNASDLIR | 12.95 | 445.24 | 516.31 | 25 |
| 53 | TNASDLIR | 12.95 | 445.24 | 603.35 | 25 |

TABLE 21-continued

| Transition number | Peptide | Retention time (minutes) | (m/z) filtered in Q1 | (m/z) filtered in Q3 | Collision energy (eV) |
|---|---|---|---|---|---|
| 54 | TNASDLIR | 12.95 | 445.24 | 674.38 | 25 |
| 55 | VTVAYK | 10.34 | 340.7 | 381.21 | 20 |
| 56 | VTVAYK | 10.34 | 340.7 | 480.28 | 20 |
| 57 | VTVAYK | 10.34 | 340.7 | 581.33 | 20 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 16

Identification of a Resistance to ACT Beta-Lactams

The samples corresponding to a species able to comprise an ACT resistance mechanism can be detected by employing the following method.

Each sample is treated according to example 5, then analysed according to example 6 by detecting the peptides from TABLE 22 instead of the peptides from TABLE 3.

TABLE 22

| Transition number | Peptide | Retention time (minutes) | (m/z) filtered in Q1 | (m/z) filtered in Q3 | Collision energy (eV) |
|---|---|---|---|---|---|
| 1 | AEEAHYAWGYR | 14.21 | 676.81 | 815.38 | 34.8 |
| 2 | AEEAHYAWGYR | 14.21 | 676.81 | 952.44 | 34.8 |
| 3 | AEEAHYAWGYR | 14.21 | 676.81 | 1152.52 | 34.8 |
| 4 | AIHVSPGMLDAEAYGVK | 18.71 | 586.64 | 666.35 | 33.3 |
| 5 | AIHVSPGMLDAEAYGVK | 18.71 | 586.64 | 737.38 | 33.3 |
| 6 | AIHVSPGMLDAEAYGVK | 18.74 | 586.64 | 852.41 | 33.3 |
| 7 | AVHVSPGMLDAEAYGVK | 17.93 | 581.96 | 666.35 | 33.1 |
| 8 | AVHVSPGMLDAEAYGVK | 17.93 | 581.96 | 737.38 | 33.1 |
| 9 | AVHVSPGMLDAEAYGVK | 17.93 | 581.96 | 852.41 | 33.1 |
| 10 | DMANWVMVNMKPDSLQDSSLK | 22.23 | 803.71 | 896.45 | 44.2 |
| 11 | DMANWVMVNMKPDSLQDSSLK | 22.21 | 803.71 | 989.49 | 44.2 |
| 12 | DMANWVMVNMKPDSLQDSSLK | 22.23 | 803.71 | 1082.03 | 44.2 |
| 13 | DNASLLR | 12.76 | 394.72 | 401.29 | 22.4 |
| 14 | DNASLLR | 12.76 | 394.72 | 488.32 | 22.4 |
| 15 | DNASLLR | 12.76 | 394.72 | 559.36 | 22.4 |
| 16 | EGITLAQSR | 13.23 | 487.77 | 574.33 | 26.5 |
| 17 | EGITLAQSR | 13.25 | 487.77 | 675.38 | 26.5 |
| 18 | EGITLAQSR | 13.23 | 487.77 | 788.46 | 26.5 |
| 19 | EVNPPAPPVNASWVHK | 16.59 | 581.31 | 700.38 | 33.1 |
| 20 | EVNPPAPPVNASWVHK | 16.61 | 581.31 | 757.4 | 33.1 |
| 21 | EVNPPAPPVNASWVHK | 16.61 | 581.31 | 1134.61 | 33.1 |
| 22 | FYQNWQPQWKPGTTR | 17.43 | 968.98 | 531.29 | 47.6 |
| 23 | FYQNWQPQWKPGTTR | 17.43 | 968.98 | 1070.57 | 47.6 |

TABLE 22-continued

| Transition number | Peptide | Retention time (minutes) | (m/z) filtered in Q1 | (m/z) filtered in Q3 | Collision energy (eV) |
|---|---|---|---|---|---|
| 24 | FYQNWQPQWKPGTTR | 17.43 | 968.98 | 1198.63 | 47.6 |
| 25 | GEISLDDPVTR | 16.1 | 601.31 | 702.34 | 31.5 |
| 26 | GEISLDDPVTR | 16.1 | 601.31 | 815.43 | 31.5 |
| 27 | GEISLDDPVTR | 16.12 | 601.31 | 902.46 | 31.5 |
| 28 | GEISLGDPVTK | 15.7 | 558.3 | 559.31 | 29.6 |
| 29 | GEISLGDPVTK | 15.68 | 558.3 | 616.33 | 29.6 |
| 30 | GEISLGDPVTK | 15.68 | 558.3 | 816.45 | 29.6 |
| 31 | GLTLAQSR | 12.67 | 423.25 | 461.25 | 23.6 |
| 32 | GLTLAQSR | 12.68 | 423.25 | 574.33 | 23.6 |
| 33 | GLTLAQSR | 12.65 | 423.25 | 675.38 | 23.6 |
| 34 | LDHTWINVPK | 16.79 | 611.83 | 497.78 | 31.9 |
| 35 | LDHTWINVPK | 16.79 | 611.83 | 756.44 | 31.9 |
| 36 | LDHTWINVPK | 16.79 | 611.83 | 857.49 | 31.9 |
| 37 | MLDLATYTAGGLPLQVPDEVK | 23.87 | 744.39 | 512.79 | 41.2 |
| 38 | MLDLATYTAGGLPLQVPDEVK | 23.89 | 744.39 | 587.3 | 41.2 |
| 39 | MLDLATYTAGGLPLQVPDEVK | 23.89 | 1116.09 | 587.3 | 54.1 |
| 40 | QGIALAQSR | 12.72 | 472.27 | 574.33 | 25.8 |
| 41 | QGIALAQSR | 12.7 | 472.27 | 645.37 | 25.8 |
| 42 | QGIALAQSR | 12.72 | 472.27 | 758.45 | 25.8 |
| 43 | QGISLAQSR | 12.83 | 480.27 | 661.36 | 26.1 |
| 44 | QGISLAQSR | 12.83 | 480.27 | 774.45 | 26.1 |
| 45 | QGISLAQSR | 12.83 | 480.27 | 831.47 | 26.1 |
| 46 | QIGIVMLANK | 18.95 | 543.82 | 576.32 | 28.9 |
| 47 | QIGIVMLANK | 18.95 | 543.82 | 675.39 | 28.9 |
| 48 | QIGIVMLANK | 18.95 | 543.82 | 845.49 | 28.9 |
| 49 | QIGIVMLANTSYPNPAR | 21.86 | 615.66 | 554.31 | 34.8 |
| 50 | QIGIVMLANTSYPNPAR | 21.86 | 615.66 | 717.37 | 34.8 |
| 51 | QIGIVMLANTSYPNPAR | 21.86 | 922.99 | 554.31 | 45.6 |
| 52 | QLAEVVANTVTPLMK | 21.94 | 807.45 | 488.29 | 40.5 |
| 53 | QLAEVVANTVTPLMK | 21.94 | 807.45 | 974.53 | 40.5 |
| 54 | QLAEVVANTVTPLMK | 21.94 | 807.45 | 1073.6 | 40.5 |
| 55 | QLAEVVER | 13.05 | 472.26 | 502.3 | 25.8 |
| 56 | QLAEVVER | 13.03 | 472.26 | 631.34 | 25.8 |
| 57 | QLAEVVER | 13.03 | 472.26 | 702.38 | 25.8 |
| 58 | QLGIVMLANK | 19.27 | 543.82 | 576.32 | 28.9 |
| 59 | QLGIVMLANK | 19.27 | 543.82 | 675.39 | 28.9 |
| 60 | QLGIVMLANK | 19.27 | 543.82 | 845.49 | 28.9 |
| 61 | SYPNPAR | 9.83 | 402.7 | 343.21 | 22.7 |

TABLE 22-continued

| Transition number | Peptide | Retention time (minutes) | (m/z) filtered in Q1 | (m/z) filtered in Q3 | Collision energy (eV) |
|---|---|---|---|---|---|
| 62 | SYPNPAR | 9.83 | 402.7 | 457.25 | 22.7 |
| 63 | SYPNPAR | 9.83 | 402.7 | 554.31 | 22.7 |
| 64 | TFTGVLGGDAIAR | 18.42 | 639.35 | 659.35 | 33.1 |
| 65 | TFTGVLGGDAIAR | 18.39 | 639.35 | 772.43 | 33.1 |
| 66 | TFTGVLGGDAIAR | 18.42 | 639.35 | 1029.57 | 33.1 |
| 67 | TGSTGGFGSYVAFIPEK | 21.14 | 573.29 | 373.21 | 32.7 |
| 68 | TGSTGGFGSYVAFIPEK | 21.14 | 573.29 | 633.36 | 32.7 |
| 69 | TGSTGGFGSYVAFIPEK | 21.14 | 573.29 | 704.4 | 32.7 |
| 70 | TVTPLMK | 13.65 | 395.23 | 488.29 | 22.4 |
| 71 | TVTPLMK | 13.65 | 395.23 | 589.34 | 22.4 |
| 72 | TVTPLMK | 13.62 | 395.23 | 688.41 | 22.4 |
| 73 | TVVEGSDNK | 4.64 | 474.74 | 520.24 | 25.9 |
| 74 | TVVEGSDNK | 4.64 | 474.74 | 649.28 | 25.9 |
| 75 | TVVEGSDNK | 4.64 | 474.74 | 748.35 | 25.9 |
| 76 | VALAPLPAR | 15.96 | 454.29 | 553.35 | 25 |
| 77 | VALAPLPAR | 15.99 | 454.29 | 624.38 | 25 |
| 78 | VALAPLPAR | 15.96 | 454.29 | 737.47 | 25 |
| 79 | VALAPLPVAEVNPPAPPVK | 21.12 | 627.04 | 705.43 | 35.4 |
| 80 | VALAPLPVAEVNPPAPPVK | 21.14 | 627.04 | 762.94 | 35.4 |
| 81 | VALAPLPVAEVNPPAPPVK | 21.14 | 627.04 | 819.47 | 35.4 |
| 82 | VEAAYR | 8.39 | 354.69 | 409.22 | 20.6 |
| 83 | VEAAYR | 8.39 | 354.69 | 480.26 | 20.6 |
| 84 | VEAAYR | 8.39 | 354.69 | 609.3 | 20.6 |
| 85 | VFKPLK | 11.66 | 366.24 | 357.25 | 21.1 |
| 86 | VFKPLK | 11.66 | 366.24 | 485.35 | 21.1 |
| 87 | VFKPLK | 11.66 | 366.24 | 632.41 | 21.1 |
| 88 | VGAMYQGLGWEMLNWPVDAK | 26.23 | 755.7 | 529.3 | 41.8 |
| 89 | VGAMYQGLGWEMLNWPVDAK | 26.23 | 755.7 | 829.42 | 41.8 |
| 90 | VGAMYQGLGWEMLNWPVDAK | 26.26 | 755.7 | 1073.55 | 41.8 |
| 91 | VLKPLK | 10.38 | 349.25 | 357.25 | 20.4 |
| 92 | VLKPLK | 10.36 | 349.25 | 485.35 | 20.4 |
| 93 | VLKPLK | 10.36 | 349.25 | 598.43 | 20.4 |
| 94 | VSPGMLDAQAYGMK | 17.62 | 734.35 | 641.3 | 37.3 |
| 95 | VSPGMLDAQAYGMK | 17.62 | 734.35 | 883.4 | 37.3 |
| 96 | VSPGMLDAQAYGMK | 17.62 | 734.35 | 996.48 | 37.3 |
| 97 | VSPGMLDAQAYGVK | 17.36 | 718.37 | 625.32 | 36.6 |
| 98 | VSPGMLDAQAYGVK | 17.36 | 718.37 | 851.43 | 36.6 |
| 99 | VSPGMLDAQAYGVK | 17.36 | 718.37 | 964.51 | 36.6 |

TABLE 22-continued

| Transition number | Peptide | Retention time (minutes) | (m/z) filtered in Q1 | (m/z) filtered in Q3 | Collision energy (eV) |
|---|---|---|---|---|---|
| 100 | YWPQLTGK | 17.33 | 496.76 | 322.19 | 26.9 |
| 101 | YWPQLTGK | 17.33 | 496.76 | 643.38 | 26.9 |
| 102 | YWPQLTGK | 17.31 | 496.76 | 829.46 | 26.9 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 17

Identification of a Resistance to CMY Beta-Lactams

The samples corresponding to a species able to comprise a CMY resistance mechanism can be detected by employing the following method.

Each sample is treated according to example 5, then analysed according to example 6 by detecting the peptides from TABLE 23 instead of the peptides from TABLE 3.

TABLE 23

| Transition number | Peptide | Retention time (minutes) | (m/z) filtered in Q1 | (m/z) filtered in Q3 | Collision energy (eV) |
|---|---|---|---|---|---|
| 1 | AALLR | 10.85 | 272.18 | 288.2 | 17 |
| 2 | AALLR | 10.85 | 272.18 | 401.29 | 17 |
| 3 | AALLR | 10.85 | 272.18 | 472.32 | 17 |
| 4 | ADSIINGSDNK | 10.62 | 567.28 | 747.36 | 30 |
| 5 | ADSIINGSDNK | 10.62 | 567.28 | 860.45 | 30 |
| 6 | ADSIINGSDNK | 10.62 | 567.28 | 947.48 | 30 |
| 7 | AELLR | 11.13 | 301.19 | 401.29 | 18 |
| 8 | AELLR | 11.13 | 301.19 | 427.26 | 18 |
| 9 | AELLR | 11.13 | 301.19 | 530.33 | 18 |
| 10 | ALQQAISLTHK | 13.79 | 605.35 | 698.42 | 32 |
| 11 | ALQQAISLTHK | 13.79 | 605.35 | 769.46 | 32 |
| 12 | ALQQAISLTHK | 13.79 | 605.35 | 897.52 | 32 |
| 13 | AVHVSPGQLDAEAYGVK | 15.59 | 580.97 | 737.38 | 33 |
| 14 | AVHVSPGQLDAEAYGVK | 15.59 | 580.97 | 776.4 | 33 |
| 15 | AVHVSPGQLDAEAYGVK | 15.59 | 580.97 | 852.41 | 33 |
| 16 | DYAC[CAM]GYR | 9.86 | 452.68 | 555.23 | 25 |
| 17 | DYAC[CAM]GYR | 9.86 | 452.68 | 626.27 | 25 |
| 18 | DYAC[CAM]GYR | 9.86 | 452.68 | 789.33 | 25 |
| 19 | DYALGYR | 13.44 | 429.21 | 508.29 | 24 |
| 20 | DYALGYR | 13.44 | 429.21 | 579.32 | 24 |
| 21 | DYALGYR | 13.44 | 429.21 | 742.39 | 24 |
| 22 | EGKPVHASPGQLDAEAYGVK | 13.47 | 685.02 | 737.38 | 38 |
| 23 | EGKPVHASPGQLDAEAYGVK | 13.47 | 685.02 | 852.41 | 38 |
| 24 | EGKPVHASPGQLDAEAYGVK | 13.47 | 685.02 | 965.49 | 38 |

TABLE 23-continued

| Transition number | Peptide | Retention time (minutes) | (m/z) filtered in Q1 | (m/z) filtered in Q3 | Collision energy (eV) |
|---|---|---|---|---|---|
| 25 | EGKPVHGSPGQLDAEAYGVK | 13.08 | 510.51 | 537.3 | 29 |
| 26 | EGKPVHGSPGQLDAEAYGVK | 13.08 | 510.51 | 666.35 | 29 |
| 27 | EGKPVHGSPGQLDAEAYGVK | 13.08 | 510.51 | 737.38 | 29 |
| 28 | EGKPVHVSPEQLDAEAYGVK | 15.07 | 539.03 | 737.38 | 30 |
| 29 | EGKPVHVSPEQLDAEAYGVK | 15.07 | 539.03 | 852.41 | 30 |
| 30 | EGKPVHVSPEQLDAEAYGVK | 15.07 | 718.37 | 852.41 | 40 |
| 31 | EGKPVHVSPGQFDAEAYGVK | 15.01 | 529.52 | 537.3 | 29 |
| 32 | EGKPVHVSPGQFDAEAYGVK | 15.01 | 529.52 | 632.33 | 29 |
| 33 | EGKPVHVSPGQFDAEAYGVK | 15.01 | 705.69 | 999.48 | 39 |
| 34 | EGKPVHVSPGQLDAEAYC[CAM]VK | 14.63 | 546.77 | 569.28 | 30 |
| 35 | EGKPVHVSPGQLDAEAYC[CAM]VK | 14.63 | 546.77 | 640.31 | 30 |
| 36 | EGKPVHVSPGQLDAEAYC[CAM]VK | 14.63 | 546.77 | 769.35 | 30 |
| 37 | EGKPVHVSPGQLDAEAYGVK | 14.65 | 521.02 | 537.3 | 29 |
| 38 | EGKPVHVSPGQLDAEAYGVK | 14.65 | 521.02 | 737.38 | 29 |
| 39 | EGKPVHVSPGQLDAEAYGVK | 14.65 | 521.02 | 852.41 | 29 |
| 40 | EGKPVHVSPGQLDAGAYGVK | 14.19 | 503.02 | 594.32 | 28 |
| 41 | EGKPVHVSPGQLDAGAYGVK | 14.19 | 503.02 | 665.36 | 28 |
| 42 | EGKPVHVSPGQLDAGAYGVK | 14.19 | 503.02 | 780.39 | 28 |
| 43 | EGKPVHVSPGQLNAEAYGVK | 14.25 | 520.78 | 537.3 | 29 |
| 44 | EGKPVHVSPGQLNAEAYGVK | 14.25 | 520.78 | 737.38 | 29 |
| 45 | EGKPVHVSPGQLNAEAYGVK | 14.25 | 520.78 | 834.45 | 29 |
| 46 | EGKPVHVTPGQLDAEAYGVK | 14.72 | 524.53 | 848.46 | 29 |
| 47 | EGKPVHVTPGQLDAEAYGVK | 14.72 | 699.03 | 852.41 | 39 |
| 48 | EGKPVHVTPGQLDAEAYGVK | 14.72 | 699.03 | 1247.63 | 39 |
| 49 | EGKPVYVSPGQLDAEAYGVK | 16.73 | 703.03 | 852.41 | 39 |
| 50 | EGKPVYVSPGQLDAEAYGVK | 16.73 | 703.03 | 860.45 | 39 |
| 51 | EGKPVYVSPGQLDAEAYGVK | 16.73 | 703.03 | 1247.63 | 39 |
| 52 | ESGASVSEQTLFDIGSVSK | 20.37 | 970.98 | 976.42 | 48 |
| 53 | ESGASVSEQTLFDIGSVSK | 20.37 | 970.98 | 1066.58 | 48 |
| 54 | ESGASVSEQTLFDIGSVSK | 20.37 | 970.98 | 1194.64 | 48 |
| 55 | FSDPVTK | 11.61 | 397.21 | 559.31 | 22 |
| 56 | FSDPVTK | 11.61 | 397.21 | 646.34 | 22 |
| 57 | FSDPVTK | 11.61 | 397.21 | 647.3 | 22 |
| 58 | FYQNWQPQWAPGAK | 18.61 | 860.92 | 867.38 | 43 |
| 59 | FYQNWQPQWAPGAK | 18.61 | 860.92 | 982.51 | 43 |
| 60 | FYQNWQPQWAPGAK | 18.61 | 860.92 | 1168.59 | 43 |
| 61 | FYQNWQPQWTPGAK | 18.53 | 875.92 | 884.46 | 44 |
| 62 | FYQNWQPQWTPGAK | 18.53 | 875.92 | 1012.52 | 44 |

TABLE 23-continued

| Transition number | Peptide | Retention time (minutes) | (m/z) filtered in Q1 | (m/z) filtered in Q3 | Collision energy (eV) |
|---|---|---|---|---|---|
| 63 | FYQNWQPQWTPGAK | 18.53 | 875.92 | 1198.6 | 44 |
| 64 | HAPWLK | 11.85 | 376.22 | 543.33 | 22 |
| 65 | HAPWLK | 11.85 | 376.22 | 605.32 | 22 |
| 66 | HAPWLK | 11.85 | 376.22 | 614.37 | 22 |
| 67 | IPDDVR | 9.9 | 357.69 | 504.24 | 21 |
| 68 | IPDDVR | 9.9 | 357.69 | 540.27 | 21 |
| 69 | IPDDVR | 9.9 | 357.69 | 601.29 | 21 |
| 70 | LAHTWIK | 12.56 | 434.76 | 547.32 | 24 |
| 71 | LAHTWIK | 12.56 | 434.76 | 684.38 | 24 |
| 72 | LAHTWIK | 12.56 | 434.76 | 755.42 | 24 |
| 73 | LAHTWITVPENEQK | 15.87 | 555.96 | 609.31 | 32 |
| 74 | LAHTWITVPENEQK | 15.87 | 555.96 | 744.35 | 32 |
| 75 | LAHTWITVPENEQK | 15.87 | 555.96 | 823.45 | 32 |
| 76 | LAHTWITVPQSEQK | 15.75 | 546.63 | 1029.56 | 31 |
| 77 | LAHTWITVPQSEQK | 15.75 | 819.44 | 1029.56 | 41 |
| 78 | LAHTWITVPQSEQK | 15.75 | 819.44 | 1215.64 | 41 |
| 79 | LDAEAYGVK | 12.86 | 483.25 | 537.3 | 26 |
| 80 | LDAEAYGVK | 12.86 | 483.25 | 737.38 | 26 |
| 81 | LDAEAYGVK | 12.86 | 483.25 | 852.41 | 26 |
| 82 | LLHLATYTAGGLPLK | 19.26 | 523.31 | 584.38 | 30 |
| 83 | LLHLATYTAGGLPLK | 19.26 | 523.31 | 655.41 | 30 |
| 84 | LLHLATYTAGGLPLK | 19.26 | 523.31 | 756.46 | 30 |
| 85 | LLHLATYTAGGLPLQFPDDVR | 22.76 | 575.06 | 601.29 | 32 |
| 86 | LLHLATYTAGGLPLQFPDDVR | 22.76 | 766.41 | 1086.56 | 42 |
| 87 | LLHLATYTAGGLPLQFPDDVR | 22.76 | 766.41 | 1098.59 | 42 |
| 88 | NYAWGYR | 14.18 | 465.22 | 581.28 | 25 |
| 89 | NYAWGYR | 14.18 | 465.22 | 652.32 | 25 |
| 90 | NYAWGYR | 14.18 | 465.22 | 815.38 | 25 |
| 91 | NYPIPAR | 12.32 | 415.73 | 456.29 | 23 |
| 92 | NYPIPAR | 12.32 | 415.73 | 553.35 | 23 |
| 93 | NYPIPAR | 12.32 | 415.73 | 716.41 | 23 |
| 94 | NYPNEAR | 6.92 | 432.2 | 489.21 | 24 |
| 95 | NYPNEAR | 6.92 | 432.2 | 586.29 | 24 |
| 96 | NYPNEAR | 6.92 | 432.2 | 749.36 | 24 |
| 97 | SLC[CAM]C[CAM]ALLLTAPLSTFAAAK | 26.05 | 670.02 | 905.51 | 38 |
| 98 | SLC[CAM]C[CAM]ALLLTAPLSTFAAAK | 26.05 | 1004.53 | 1077.59 | 49 |
| 99 | SLC[CAM]C[CAM]ALLLTAPLSTFAAAK | 26.05 | 1004.53 | 1190.68 | 49 |
| 100 | SNVTDMAR | 10.56 | 447.21 | 492.22 | 25 |

TABLE 23-continued

| Transition number | Peptide | Retention time (minutes) | (m/z) filtered in Q1 | (m/z) filtered in Q3 | Collision energy (eV) |
|---|---|---|---|---|---|
| 101 | SNVTDMAR | 10.56 | 447.21 | 593.27 | 25 |
| 102 | SNVTDMAR | 10.56 | 447.21 | 692.34 | 25 |
| 103 | TALLHFYQNWQPQWAPGAK | 21.7 | 752.72 | 854.45 | 42 |
| 104 | TALLHFYQNWQPQWAPGAK | 21.7 | 752.72 | 974.51 | 42 |
| 105 | TALLHFYQNWQPQWAPGAK | 21.7 | 752.72 | 1088.55 | 42 |
| 106 | TDSIINGSDSK | 10.86 | 568.78 | 720.35 | 30 |
| 107 | TDSIINGSDSK | 10.86 | 568.78 | 833.44 | 30 |
| 108 | TDSIINGSDSK | 10.86 | 568.78 | 920.47 | 30 |
| 109 | TFIGVLGGDAIAR | 20.29 | 645.36 | 659.35 | 33 |
| 110 | TFIGVLGGDAIAR | 20.29 | 645.36 | 772.43 | 33 |
| 111 | TFIGVLGGDAIAR | 20.29 | 645.36 | 928.52 | 33 |
| 112 | TFNGVLGGDC[CAM]IAR | 16.85 | 690.34 | 748.34 | 35 |
| 113 | TFNGVLGGDC[CAM]IAR | 16.85 | 690.34 | 861.42 | 35 |
| 114 | TFNGVLGGDC[CAM]IAR | 16.85 | 690.34 | 1131.56 | 35 |
| 115 | TFNGVLGGEAIAR | 17.2 | 435.57 | 673.36 | 26 |
| 116 | TFNGVLGGEAIAR | 17.2 | 652.85 | 673.36 | 34 |
| 117 | TFNGVLGGEAIAR | 17.2 | 652.85 | 786.45 | 34 |
| 118 | TGSTVGFGSYVAFVPEK | 20.65 | 873.44 | 1039.55 | 43 |
| 119 | TGSTVGFGSYVAFVPEK | 20.65 | 873.44 | 1096.57 | 43 |
| 120 | TGSTVGFGSYVAFVPEK | 20.65 | 873.44 | 1243.64 | 43 |
| 121 | TGYTGGFGSYVAFVPEK | 20.58 | 890.43 | 1039.55 | 44 |
| 122 | TGYTGGFGSYVAFVPEK | 20.58 | 890.43 | 1096.57 | 44 |
| 123 | TGYTGGFGSYVAFVPEK | 20.58 | 890.43 | 1243.64 | 44 |
| 124 | TLQQGIELAQSR | 15.04 | 448.58 | 461.25 | 26 |
| 125 | TLQQGIELAQSR | 15.04 | 672.37 | 703.37 | 35 |
| 126 | TLQQGIELAQSR | 15.04 | 672.37 | 873.48 | 35 |
| 127 | TSSADLLAFVK | 20.76 | 576.32 | 805.48 | 30 |
| 128 | TSSADLLAFVK | 20.76 | 576.32 | 876.52 | 30 |
| 129 | TSSADLLAFVK | 20.76 | 576.32 | 963.55 | 30 |
| 130 | TSSADLLR | 12.72 | 431.73 | 587.35 | 24 |
| 131 | TSSADLLR | 12.72 | 431.73 | 674.38 | 24 |
| 132 | TSSADLLR | 12.72 | 431.73 | 761.42 | 24 |
| 133 | TYYFTWGK | 18.46 | 533.26 | 801.39 | 28 |
| 134 | TYYFTWGK | 18.46 | 533.26 | 919.4 | 28 |
| 135 | TYYFTWGK | 18.46 | 533.26 | 964.46 | 28 |
| 136 | VAALPAVEVNPPAPAVK | 18.04 | 821.98 | 964.55 | 41 |
| 137 | VAALPAVEVNPPAPAVK | 18.04 | 821.98 | 1021.57 | 41 |
| 138 | VAALPAVEVNPPAPAVK | 18.04 | 821.98 | 1120.64 | 41 |

TABLE 23-continued

| Transition number | Peptide | Retention time (minutes) | (m/z) filtered in Q1 | (m/z) filtered in Q3 | Collision energy (eV) |
|---|---|---|---|---|---|
| 139 | VAFAALPAVEVNPPAPAVK | 21.03 | 621.02 | 679.41 | 35 |
| 140 | VAFAALPAVEVNPPAPAVK | 21.03 | 621.02 | 793.46 | 35 |
| 141 | VAFAALPAVEVNPPAPAVK | 21.03 | 931.03 | 1021.57 | 46 |
| 142 | VALAAIPAVEVNPPAPAVK | 20.17 | 457.52 | 679.41 | 26 |
| 143 | VALAAIPAVEVNPPAPAVK | 20.17 | 609.7 | 679.41 | 34 |
| 144 | VALAAIPAVEVNPPAPAVK | 20.17 | 609.7 | 793.46 | 34 |
| 145 | VALAALHTVEVNPPAPAVK | 18 | 475.03 | 582.36 | 27 |
| 146 | VALAALHTVEVNPPAPAVK | 18 | 475.03 | 679.41 | 27 |
| 147 | VALAALHTVEVNPPAPAVK | 18 | 633.03 | 679.41 | 36 |
| 148 | VALAALPAVEINPPAPAVK | 21.5 | 614.37 | 679.41 | 35 |
| 149 | VALAALPAVEINPPAPAVK | 21.5 | 614.37 | 793.46 | 35 |
| 150 | VALAALPAVEINPPAPAVK | 21.5 | 614.37 | 935.56 | 35 |
| 151 | VALAALPTVEVNPPAPAVK | 20.41 | 619.7 | 679.41 | 35 |
| 152 | VALAALPTVEVNPPAPAVK | 20.41 | 619.7 | 793.46 | 35 |
| 153 | VALAALPTVEVNPPAPAVK | 20.41 | 619.7 | 1021.57 | 35 |
| 154 | VAPAVEVNPPAPAVK | 15.16 | 729.92 | 793.46 | 37 |
| 155 | VAPAVEVNPPAPAVK | 15.16 | 729.92 | 892.53 | 37 |
| 156 | VAPAVEVNPPAPAVK | 15.16 | 729.92 | 1021.57 | 37 |
| 157 | VEAYWR | 13.37 | 412.21 | 524.26 | 23 |
| 158 | VEAYWR | 13.37 | 412.21 | 595.3 | 23 |
| 159 | VEAYWR | 13.37 | 412.21 | 724.34 | 23 |
| 160 | VILEANPTAAPR | 14.25 | 417.91 | 612.35 | 25 |
| 161 | VILEANPTAAPR | 14.25 | 626.36 | 797.43 | 33 |
| 162 | VILEANPTAAPR | 14.25 | 626.36 | 1039.55 | 33 |
| 163 | VSLEANPTAAPR | 13.15 | 613.33 | 726.39 | 32 |
| 164 | VSLEANPTAAPR | 13.15 | 613.33 | 797.43 | 32 |
| 165 | VSLEANPTAAPR | 13.15 | 613.33 | 926.47 | 32 |
| 166 | WIQVNMDASR | 16.68 | 610.3 | 693.3 | 32 |
| 167 | WIQVNMDASR | 16.68 | 610.3 | 792.37 | 32 |
| 168 | WIQVNMDASR | 16.68 | 610.3 | 920.43 | 32 |
| 169 | WVQANMDASR | 12.82 | 589.27 | 764.34 | 31 |
| 170 | WVQANMDASR | 12.82 | 589.27 | 892.39 | 31 |
| 171 | WVQANMDASR | 12.82 | 589.27 | 991.46 | 31 |
| 172 | WVQVNMDASR | 15.27 | 603.29 | 792.37 | 32 |
| 173 | WVQVNMDASR | 15.27 | 603.29 | 920.43 | 32 |
| 174 | WVQVNMDASR | 15.27 | 603.29 | 1019.49 | 32 |
| 175 | YWSELTGK | 14.9 | 492.25 | 547.31 | 27 |

TABLE 23-continued

| Transition number | Peptide | Retention time (minutes) | (m/z) filtered in Q1 | (m/z) filtered in Q3 | Collision energy (eV) |
|---|---|---|---|---|---|
| 176 | YWSELTGK | 14.9 | 492.25 | 634.34 | 27 |
| 177 | YWSELTGK | 14.9 | 492.25 | 820.42 | 27 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 18

Identification of a Resistance to CTX-M Beta-Lactams

The samples corresponding to a species able to comprise a CTX-M resistance mechanism can be detected by employing the following method.

Each sample is treated according to example 5, then analysed according to example 6 by detecting the peptides from TABLE 24 instead of the peptides from TABLE 3.

TABLE 24

| Transition number | Peptide | Retention time (minutes) | (m/z) filtered in Q1 | (m/z) filtered in Q3 | Collision energy (eV) |
|---|---|---|---|---|---|
| 1 | AGADVASLR | 11.83 | 430.24 | 446.27 | 24 |
| 2 | AGADVASLR | 11.83 | 430.24 | 485.24 | 24 |
| 3 | AGADVASLR | 11.83 | 430.24 | 660.37 | 24 |
| 4 | AGLPASWVVGDK | 18.32 | 600.32 | 790.41 | 31 |
| 5 | AGLPASWVVGDK | 18.32 | 600.32 | 861.45 | 31 |
| 6 | AGLPASWVVGDK | 18.32 | 600.32 | 958.5 | 31 |
| 7 | AGLPTSWTAGDK | 15.73 | 602.3 | 764.36 | 32 |
| 8 | AGLPTSWTAGDK | 15.73 | 602.3 | 865.41 | 32 |
| 9 | AGLPTSWTAGDK | 15.73 | 602.3 | 962.46 | 32 |
| 10 | AGLPTSWTVGDR | 17.31 | 630.32 | 820.39 | 33 |
| 11 | AGLPTSWTVGDR | 17.31 | 630.32 | 921.44 | 33 |
| 12 | AGLPTSWTVGDR | 17.31 | 630.32 | 1018.5 | 33 |
| 13 | AGLPTSWVVGDK | 18.62 | 615.33 | 790.41 | 32 |
| 14 | AGLPTSWVVGDK | 18.62 | 615.33 | 891.46 | 32 |
| 15 | AGLPTSWVVGDK | 18.62 | 615.33 | 988.51 | 32 |
| 16 | AIGDDTFR | 12.79 | 447.72 | 653.29 | 25 |
| 17 | AIGDDTFR | 12.79 | 447.72 | 710.31 | 25 |
| 18 | AIGDDTFR | 12.79 | 447.72 | 823.39 | 25 |
| 19 | AMAVAAVLK | 16.36 | 437.26 | 501.34 | 24 |
| 20 | AMAVAAVLK | 16.36 | 437.26 | 600.41 | 24 |
| 21 | AMAVAAVLK | 16.36 | 437.26 | 671.45 | 24 |
| 22 | APLILVTYFTQPEQK | 23.95 | 583.33 | 730.37 | 33 |
| 23 | APLILVTYFTQPEQK | 23.95 | 874.49 | 1040.5 | 43 |
| 24 | APLILVTYFTQPEQK | 23.95 | 874.49 | 1141.55 | 43 |
| 25 | APLVLVTYFTQPEPK | 23.37 | 568.32 | 699.37 | 32 |

TABLE 24-continued

| Transition number | Peptide | Retention time (minutes) | (m/z) filtered in Q1 | (m/z) filtered in Q3 | Collision energy (eV) |
|---|---|---|---|---|---|
| 26 | APLVLVTYFTQPEPK | 23.37 | 568.32 | 846.44 | 32 |
| 27 | APLVLVTYFTQPEPK | 23.37 | 851.97 | 1110.55 | 42 |
| 28 | APLVLVTYFTQPQQNAENR | 22.93 | 730.38 | 956.45 | 41 |
| 29 | APLVLVTYFTQPQQNAENR | 22.93 | 1095.07 | 1185.56 | 53 |
| 30 | APLVLVTYFTQPQQNAENR | 22.93 | 1095.07 | 1233.69 | 53 |
| 31 | APLVLVTYFTQPQQNAER | 23.02 | 692.37 | 745.36 | 39 |
| 32 | APLVLVTYFTQPQQNAER | 23.02 | 692.37 | 842.41 | 39 |
| 33 | APLVLVTYFTQPQQNAER | 23.02 | 692.37 | 857.51 | 39 |
| 34 | APLVLVTYFTQSEPK | 23.53 | 564.98 | 689.35 | 32 |
| 35 | APLVLVTYFTQSEPK | 23.53 | 846.96 | 1100.53 | 42 |
| 36 | APLVLVTYFTQSEPK | 23.53 | 846.96 | 1199.59 | 42 |
| 37 | AQLVAWLK | 19.52 | 464.78 | 517.31 | 25 |
| 38 | AQLVAWLK | 19.52 | 464.78 | 616.38 | 25 |
| 39 | AQLVAWLK | 19.52 | 464.78 | 729.47 | 25 |
| 40 | AQLVMWLK | 20.53 | 494.79 | 577.32 | 27 |
| 41 | AQLVMWLK | 20.53 | 494.79 | 676.39 | 27 |
| 42 | AQLVMWLK | 20.53 | 494.79 | 789.47 | 27 |
| 43 | ASDLVNYNPIAEK | 16.72 | 717.37 | 834.44 | 37 |
| 44 | ASDLVNYNPIAEK | 16.72 | 717.37 | 948.48 | 37 |
| 45 | ASDLVNYNPIAEK | 16.72 | 717.37 | 1047.55 | 37 |
| 46 | DFLAAAAK | 14.5 | 403.72 | 431.26 | 23 |
| 47 | DFLAAAAK | 14.5 | 403.72 | 518.26 | 23 |
| 48 | DFLAAAAK | 14.5 | 403.72 | 544.35 | 23 |
| 49 | DILASAAK | 12.62 | 394.73 | 447.26 | 22 |
| 50 | DILASAAK | 12.62 | 394.73 | 560.34 | 22 |
| 51 | DILASAAK | 12.62 | 394.73 | 571.31 | 22 |
| 52 | DNTQVLYR | 12.19 | 504.76 | 550.33 | 27 |
| 53 | DNTQVLYR | 12.19 | 504.76 | 678.39 | 27 |
| 54 | DNTQVLYR | 12.19 | 504.76 | 779.44 | 27 |
| 55 | DTTTPLAMAQALR | 19.92 | 694.86 | 760.41 | 36 |
| 56 | DTTTPLAMAQALR | 19.92 | 694.86 | 873.5 | 36 |
| 57 | DTTTPLAMAQALR | 19.92 | 694.86 | 970.55 | 36 |
| 58 | DTTTPLAMAQSLR | 19.22 | 702.86 | 776.41 | 36 |
| 59 | DTTTPLAMAQSLR | 19.22 | 702.86 | 889.49 | 36 |
| 60 | DTTTPLAMAQSLR | 19.22 | 702.86 | 986.55 | 36 |
| 61 | DTTTPLAMAQTLR | 18.99 | 709.87 | 719.39 | 36 |
| 62 | DTTTPLAMAQTLR | 18.99 | 709.87 | 790.42 | 36 |
| 63 | DTTTPLAMAQTLR | 18.99 | 709.87 | 1000.56 | 36 |

TABLE 24-continued

| Transition number | Peptide | Retention time (minutes) | (m/z) filtered in Q1 | (m/z) filtered in Q3 | Collision energy (eV) |
|---|---|---|---|---|---|
| 64 | DVLAAAAR | 12.11 | 393.73 | 459.27 | 22 |
| 65 | DVLAAAAR | 12.11 | 393.73 | 572.35 | 22 |
| 66 | DVLAAAAR | 12.11 | 393.73 | 671.42 | 22 |
| 67 | EIGDETFR | 12.99 | 483.73 | 552.28 | 26 |
| 68 | EIGDETFR | 12.99 | 483.73 | 667.3 | 26 |
| 69 | EIGDETFR | 12.99 | 483.73 | 724.33 | 26 |
| 70 | EQLVTWLK | 19.13 | 508.79 | 547.32 | 27 |
| 71 | EQLVTWLK | 19.13 | 508.79 | 646.39 | 27 |
| 72 | EQLVTWLK | 19.13 | 508.79 | 759.48 | 27 |
| 73 | GNTTGSASIQAGLPK | 13.81 | 701.37 | 813.48 | 36 |
| 74 | GNTTGSASIQAGLPK | 13.81 | 701.37 | 1028.57 | 36 |
| 75 | GNTTGSASIQAGLPK | 13.81 | 701.37 | 1129.62 | 36 |
| 76 | HDVLASAAK | 9.32 | 456.25 | 659.41 | 25 |
| 77 | HDVLASAAK | 9.32 | 456.25 | 765.39 | 25 |
| 78 | HDVLASAAK | 9.32 | 456.25 | 774.44 | 25 |
| 79 | HDVLASAAR | 9.88 | 470.25 | 588.35 | 26 |
| 80 | HDVLASAAR | 9.88 | 470.25 | 687.41 | 26 |
| 81 | HDVLASAAR | 9.88 | 470.25 | 802.44 | 26 |
| 82 | HLTLGSALGETQR | 15.07 | 691.87 | 918.46 | 35 |
| 83 | HLTLGSALGETQR | 15.07 | 691.87 | 1031.55 | 35 |
| 84 | HLTLGSALGETQR | 15.07 | 691.87 | 1132.6 | 35 |
| 85 | LAELEQQSGGR | 11.17 | 594.3 | 761.35 | 31 |
| 86 | LAELEQQSGGR | 11.17 | 594.3 | 874.44 | 31 |
| 87 | LAELEQQSGGR | 11.17 | 594.3 | 1003.48 | 31 |
| 88 | LAGLER | 11.22 | 329.7 | 474.27 | 20 |
| 89 | LAGLER | 11.22 | 329.7 | 484.28 | 20 |
| 90 | LAGLER | 11.22 | 329.7 | 545.3 | 20 |
| 91 | LDGTEPTLNTAIPGDPR | 16.6 | 589.64 | 1053.57 | 33 |
| 92 | LDGTEPTLNTAIPGDPR | 16.6 | 883.95 | 1053.57 | 44 |
| 93 | LDGTEPTLNTAIPGDPR | 16.6 | 883.95 | 1154.62 | 44 |
| 94 | LGVALIDTADNAQTLYR | 20.27 | 917.49 | 980.48 | 45 |
| 95 | LGVALIDTADNAQTLYR | 20.27 | 917.49 | 1051.52 | 45 |
| 96 | LGVALIDTADNAQTLYR | 20.27 | 917.49 | 1152.56 | 45 |
| 97 | LGVALIDTADNTHVLYR | 19.46 | 624.34 | 801.42 | 35 |
| 98 | LGVALIDTADNTHVLYR | 19.46 | 624.34 | 902.48 | 35 |
| 99 | LGVALIDTADNTHVLYR | 19.46 | 624.34 | 1189.6 | 35 |
| 100 | LGVALIDTK | 16.93 | 465.29 | 589.36 | 25 |
| 101 | LGVALIDTK | 16.93 | 465.29 | 660.39 | 25 |

TABLE 24-continued

| Transition number | Peptide | Retention time (minutes) | (m/z) filtered in Q1 | (m/z) filtered in Q3 | Collision energy (eV) |
|---|---|---|---|---|---|
| 102 | LGVALIDTK | 16.93 | 465.29 | 816.48 | 25 |
| 103 | LGVALINTADNSR | 16.92 | 672.37 | 777.35 | 35 |
| 104 | LGVALINTADNSR | 16.92 | 672.37 | 890.43 | 35 |
| 105 | LGVALINTADNSR | 16.92 | 672.37 | 1003.52 | 35 |
| 106 | LGVALINTADNTQTLYR | 19.63 | 621.67 | 1081.53 | 35 |
| 107 | LGVALINTADNTQTLYR | 19.63 | 932 | 1081.53 | 46 |
| 108 | LGVALINTADNTQTLYR | 19.63 | 932 | 1182.57 | 46 |
| 109 | LGVPLIDTADNTQVLYR | 21.54 | 944.51 | 1008.51 | 47 |
| 110 | LGVPLIDTADNTQVLYR | 21.54 | 944.51 | 1079.55 | 47 |
| 111 | LGVPLIDTADNTQVLYR | 21.54 | 944.51 | 1180.6 | 47 |
| 112 | LIAHLGGPGK | 12.27 | 321.53 | 358.21 | 20 |
| 113 | LIAHLGGPGK | 12.27 | 321.53 | 415.23 | 20 |
| 114 | LIAHLGGPGK | 12.27 | 321.53 | 528.31 | 20 |
| 115 | LIAQLGGQGGVTAFAR | 18.73 | 779.94 | 963.5 | 39 |
| 116 | LIAQLGGQGGVTAFAR | 18.73 | 779.94 | 1020.52 | 39 |
| 117 | LIAQLGGQGGVTAFAR | 18.73 | 779.94 | 1133.61 | 39 |
| 118 | LISHVGGPASVTAFAR | 16.27 | 528.29 | 565.31 | 30 |
| 119 | LISHVGGPASVTAFAR | 16.27 | 528.29 | 664.38 | 30 |
| 120 | LISHVGGPASVTAFAR | 16.27 | 791.94 | 1033.54 | 40 |
| 121 | LLLNQR | 12.81 | 378.74 | 417.22 | 22 |
| 122 | LLLNQR | 12.81 | 378.74 | 530.3 | 22 |
| 123 | LLLNQR | 12.81 | 378.74 | 643.39 | 22 |
| 124 | NLTLGNALGDTQR | 16.67 | 686.86 | 931.46 | 35 |
| 125 | NLTLGNALGDTQR | 16.67 | 686.86 | 1044.54 | 35 |
| 126 | NLTLGNALGDTQR | 16.67 | 686.86 | 1145.59 | 35 |
| 127 | NLTLGSALGETQR | 17.15 | 453.91 | 590.29 | 27 |
| 128 | NLTLGSALGETQR | 17.15 | 680.36 | 918.46 | 35 |
| 129 | NLTLGSALGETQR | 17.15 | 680.36 | 1031.55 | 35 |
| 130 | QLGDDTFR | 13.1 | 476.23 | 653.29 | 26 |
| 131 | QLGDDTFR | 13.1 | 476.23 | 710.31 | 26 |
| 132 | QLGDDTFR | 13.1 | 476.23 | 823.39 | 26 |
| 133 | SDLVNYSPIAEK | 16.24 | 668.34 | 807.42 | 34 |
| 134 | SDLVNYSPIAEK | 16.24 | 668.34 | 921.47 | 34 |
| 135 | SDLVNYSPIAEK | 16.24 | 668.34 | 1020.54 | 34 |
| 136 | SESEPSLLNQR | 13.8 | 630.31 | 730.42 | 33 |
| 137 | SESEPSLLNQR | 13.8 | 630.31 | 827.47 | 33 |
| 138 | SESEPSLLNQR | 13.8 | 630.31 | 1043.55 | 33 |
| 139 | SLGDESFR | 12.8 | 455.72 | 653.29 | 25 |

TABLE 24-continued

| Transition number | Peptide | Retention time (minutes) | (m/z) filtered in Q1 | (m/z) filtered in Q3 | Collision energy (eV) |
|---|---|---|---|---|---|
| 140 | SLGDESFR | 12.8 | 455.72 | 710.31 | 25 |
| 141 | SLGDESFR | 12.8 | 455.72 | 823.39 | 25 |
| 142 | SSDLINYNPIAEK | 17.68 | 732.37 | 834.44 | 37 |
| 143 | SSDLINYNPIAEK | 17.68 | 732.37 | 948.48 | 37 |
| 144 | SSDLINYNPIAEK | 17.68 | 732.37 | 1061.56 | 37 |
| 145 | SSDLINYNPITEK | 17.72 | 747.38 | 864.45 | 38 |
| 146 | SSDLINYNPITEK | 17.72 | 747.38 | 978.49 | 38 |
| 147 | SSDLINYNPITEK | 17.72 | 747.38 | 1091.57 | 38 |
| 148 | SWGVGDK | 11.6 | 374.68 | 475.25 | 21 |
| 149 | SWGVGDK | 11.6 | 374.68 | 602.26 | 21 |
| 150 | SWGVGDK | 11.6 | 374.68 | 661.33 | 21 |
| 151 | TELTLNTAIPGDPR | 17.63 | 749.4 | 826.44 | 38 |
| 152 | TELTLNTAIPGDPR | 17.63 | 749.4 | 940.48 | 38 |
| 153 | TELTLNTAIPGDPR | 17.63 | 749.4 | 957.53 | 38 |
| 154 | TEPTLNSAIPGDPR | 15.33 | 734.38 | 812.43 | 37 |
| 155 | TEPTLNSAIPGDPR | 15.33 | 734.38 | 926.47 | 37 |
| 156 | TEPTLNSAIPGDPR | 15.33 | 734.38 | 1237.65 | 37 |
| 157 | TEQTLNTAIPGDPR | 14.47 | 756.89 | 940.48 | 38 |
| 158 | TEQTLNTAIPGDPR | 14.47 | 756.89 | 972.5 | 38 |
| 159 | TEQTLNTAIPGDPR | 14.47 | 756.89 | 1154.62 | 38 |
| 160 | TESTLNTAIPGDPR | 14.52 | 736.37 | 940.48 | 37 |
| 161 | TESTLNTAIPGDPR | 14.52 | 736.37 | 1053.57 | 37 |
| 162 | TESTLNTAIPGDPR | 14.52 | 736.37 | 1154.62 | 37 |
| 163 | TETTLNTAIPGDPR | 14.88 | 743.38 | 826.44 | 38 |
| 164 | TETTLNTAIPGDPR | 14.88 | 743.38 | 940.48 | 38 |
| 165 | TETTLNTAIPGDPR | 14.88 | 743.38 | 945.49 | 38 |
| 166 | TGSC[CAM]DYGTTNDIAVIWPK | 20.38 | 999.47 | 1055.59 | 49 |
| 167 | TGSC[CAM]DYGTTNDIAVIWPK | 20.38 | 999.47 | 1156.64 | 49 |
| 168 | TGSC[CAM]DYGTTNDIAVIWPK | 20.38 | 999.47 | 1172.42 | 49 |
| 169 | TGSC[CAM]GYGTTNDIAVIWPK | 20.21 | 970.46 | 1055.59 | 48 |
| 170 | TGSC[CAM]GYGTTNDIAVIWPK | 20.21 | 970.46 | 1114.41 | 48 |
| 171 | TGSC[CAM]GYGTTNDIAVIWPK | 20.21 | 970.46 | 1156.64 | 48 |
| 172 | TGSGDYGTTNDIAVIWPEGR | 20.27 | 1055 | 1069.41 | 51 |
| 173 | TGSGDYGTTNDIAVIWPEGR | 20.27 | 1055 | 1155.62 | 51 |
| 174 | TGSGDYGTTNDIAVIWPEGR | 20.27 | 1055 | 1182.49 | 51 |
| 175 | TGSGGYGTTNDIAVIWPEGR | 20.16 | 684.33 | 757.4 | 38 |
| 176 | TGSGGYGTTNDIAVIWPEGR | 20.16 | 684.33 | 927.5 | 38 |
| 177 | TGSGGYGTTNDIAVIWPEGR | 20.16 | 684.33 | 1011.4 | 38 |

TABLE 24-continued

| Transition number | Peptide | Retention time (minutes) | (m/z) filtered in Q1 | (m/z) filtered in Q3 | Collision energy (eV) |
|---|---|---|---|---|---|
| 178 | TGSGGYGTTNDIAVIWPQGR | 19.81 | 684 | 756.42 | 38 |
| 179 | TGSGGYGTTNDIAVIWPQGR | 19.81 | 684 | 926.52 | 38 |
| 180 | TGSGGYGTTNDIAVIWPQGR | 19.81 | 684 | 1011.4 | 38 |
| 181 | TIGDDTFR | 12.86 | 462.72 | 538.26 | 25 |
| 182 | TIGDDTFR | 12.86 | 462.72 | 653.29 | 25 |
| 183 | TIGDDTFR | 12.86 | 462.72 | 710.31 | 25 |
| 184 | TQLVTWLK | 19.07 | 494.79 | 646.39 | 27 |
| 185 | TQLVTWLK | 19.07 | 494.79 | 759.48 | 27 |
| 186 | TQLVTWLK | 19.07 | 494.79 | 887.53 | 27 |
| 187 | VEIKPSDLINYNPIAEK | 20.21 | 648.35 | 769.41 | 36 |
| 188 | VEIKPSDLINYNPIAEK | 20.21 | 648.35 | 882.49 | 36 |
| 189 | VEIKPSDLINYNPIAEK | 20.21 | 648.35 | 948.48 | 36 |
| 190 | VEIKPSDLVNYNPIAEK | 19.33 | 643.68 | 769.41 | 36 |
| 191 | VEIKPSDLVNYNPIAEK | 19.33 | 643.68 | 882.49 | 36 |
| 192 | VEIKPSDLVNYNPIAEK | 19.33 | 643.68 | 948.48 | 36 |
| 193 | VIGDDTFR | 13.3 | 461.73 | 538.26 | 25 |
| 194 | VIGDDTFR | 13.3 | 461.73 | 710.31 | 25 |
| 195 | VIGDDTFR | 13.3 | 461.73 | 823.39 | 25 |
| 196 | VMAAAALLK | 17.06 | 444.27 | 586.39 | 25 |
| 197 | VMAAAALLK | 17.06 | 444.27 | 657.43 | 25 |
| 198 | VMAAAALLK | 17.06 | 444.27 | 788.47 | 25 |
| 199 | VMAAAAVLEQSETQK | 16.62 | 788.41 | 962.48 | 40 |
| 200 | VMAAAAVLEQSETQK | 16.62 | 788.41 | 1061.55 | 40 |
| 201 | VMAAAAVLEQSETQK | 16.62 | 788.41 | 1132.58 | 40 |
| 202 | WAKPSGAVGDVAQR | 12.73 | 481.26 | 628.34 | 28 |
| 203 | WAKPSGAVGDVAQR | 12.73 | 481.26 | 645.33 | 28 |
| 204 | WAKPSGAVGDVAQR | 12.73 | 481.26 | 698.36 | 28 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 19

Identification of a Resistance to DHA Beta-Lactams

The samples corresponding to a species able to comprise a DHA resistance mechanism can be detected by employing the following method.

Each sample is treated according to example 5, then analysed according to example 6 by detecting the peptides from TABLE 25 instead of the peptides from TABLE 3.

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 20

Identification of a Resistance to FOX Beta-Lactams

The samples corresponding to a species able to comprise a FOX resistance mechanism can be detected by employing the following method.

Each sample is treated according to example 5, then analysed according to example 6 by detecting the peptides from TABLE 26 instead of the peptides from TABLE 3.

TABLE 25

| Transition number | Peptide | Retention time (minutes) | (m/z) filtered in Q1 | (m/z) filtered in Q3 | Collision energy (eV) |
|---|---|---|---|---|---|
| 1 | ADLLHFYQQWQPSR | 20.9 | 596.97 | 673.34 | 34 |
| 2 | ADLLHFYQQWQPSR | 20.9 | 596.97 | 988.49 | 34 |
| 3 | ADLLHFYQQWQPSR | 20.9 | 596.97 | 1116.55 | 34 |
| 4 | AELLHFYQQWQPSR | 19.23 | 601.64 | 673.34 | 34 |
| 5 | AELLHFYQQWQPSR | 19.23 | 601.64 | 801.4 | 34 |
| 6 | AELLHFYQQWQPSR | 19.23 | 601.64 | 1130.56 | 34 |
| 7 | EMMLNDPAEK | 13.78 | 589.26 | 786.4 | 31 |
| 8 | EMMLNDPAEK | 13.78 | 589.26 | 917.44 | 31 |
| 9 | EMMLNDPAEK | 13.78 | 589.26 | 1048.48 | 31 |
| 10 | GKPYYFNYGFADVQAK | 18.12 | 623.31 | 631.34 | 35 |
| 11 | GKPYYFNYGFADVQAK | 18.12 | 623.31 | 778.41 | 35 |
| 12 | GKPYYFNYGFADVQAK | 18.12 | 623.31 | 835.43 | 35 |
| 13 | TAAINQGLGWEMYDWPQQK | 21.57 | 746.02 | 964.45 | 41 |
| 14 | TAAINQGLGWEMYDWPQQK | 21.57 | 746.02 | 1095.49 | 41 |
| 15 | TAAINQGLGWEMYDWPQQK | 21.57 | 1118.53 | 1224.54 | 54 |
| 16 | WAEMNIEPSR | 15.85 | 616.79 | 715.37 | 32 |
| 17 | WAEMNIEPSR | 15.85 | 616.79 | 975.46 | 32 |
| 18 | WAEMNIEPSR | 15.85 | 616.79 | 1046.49 | 32 |

TABLE 26

| Transition number | Peptide | Retention time (minutes) | (m/z) filtered in Q1 | (m/z) filtered in Q3 | Collision energy (eV) |
|---|---|---|---|---|---|
| 1 | ATPGVLAAEAYGIK | 17.72 | 680.88 | 751.4 | 35 |
| 2 | ATPGVLAAEAYGIK | 17.72 | 680.88 | 822.44 | 35 |
| 3 | ATPGVLAAEAYGIK | 17.72 | 680.88 | 935.52 | 35 |
| 4 | FAEANMGYQGDAAVK | 14.08 | 786.36 | 908.45 | 40 |
| 5 | FAEANMGYQGDAAVK | 14.08 | 786.36 | 1039.49 | 40 |
| 6 | FAEANMGYQGDAAVK | 14.08 | 786.36 | 1224.57 | 40 |
| 7 | FAEANMGYQGDALVK | 16.35 | 538.59 | 602.35 | 31 |
| 8 | FAEANMGYQGDALVK | 16.35 | 538.59 | 730.41 | 31 |
| 9 | FAEANMGYQGDALVK | 16.35 | 807.38 | 950.49 | 41 |
| 10 | GEAPLTAAVDGIIQPMLK | 25.85 | 912.5 | 1014.57 | 45 |
| 11 | GEAPLTAAVDGIIQPMLK | 25.85 | 912.5 | 1113.63 | 45 |
| 12 | GEAPLTAAVDGIIQPMLK | 25.85 | 912.5 | 1184.67 | 45 |
| 13 | HWSPVYPAGTHR | 12.55 | 469.9 | 541.28 | 27 |
| 14 | HWSPVYPAGTHR | 12.55 | 469.9 | 607.3 | 27 |
| 15 | HWSPVYPAGTHR | 12.55 | 469.9 | 638.34 | 27 |
| 16 | IPGIAVAVLK | 19.45 | 490.83 | 600.41 | 27 |
| 17 | IPGIAVAVLK | 19.45 | 490.83 | 770.51 | 27 |
| 18 | IPGIAVAVLK | 19.45 | 490.83 | 867.57 | 27 |
| 19 | LMSQTLLPK | 16.18 | 515.8 | 699.44 | 28 |
| 20 | LMSQTLLPK | 16.18 | 515.8 | 786.47 | 28 |
| 21 | LMSQTLLPK | 16.18 | 515.8 | 917.51 | 28 |
| 22 | MQTYYR | 10.72 | 431.2 | 602.29 | 24 |
| 23 | MQTYYR | 10.72 | 431.2 | 687.28 | 24 |
| 24 | MQTYYR | 10.72 | 431.2 | 730.35 | 24 |
| 25 | VSHHAPWLK | 11.49 | 537.8 | 614.37 | 29 |
| 26 | VSHHAPWLK | 11.49 | 537.8 | 751.42 | 29 |
| 27 | VSHHAPWLK | 11.49 | 537.8 | 888.48 | 29 |
| 28 | VTPGMLAAEAYGIK | 19 | 710.88 | 822.44 | 36 |
| 29 | VTPGMLAAEAYGIK | 19 | 710.88 | 1123.58 | 36 |
| 30 | VTPGMLAAEAYGIK | 19 | 710.88 | 1220.63 | 36 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 21

Identification of a Resistance to MIR Beta-Lactams

The samples corresponding to a species able to comprise an MIR resistance mechanism can be detected by employing the following method.

Each sample is treated according to example 5, then analysed according to example 6 by detecting the peptides from TABLE 27 instead of the peptides from TABLE 3.

TABLE 27

| Transition number | Peptide | Retention time (minutes) | (m/z) filtered in Q1 | (m/z) filtered in Q3 | Collision energy (eV) |
|---|---|---|---|---|---|
| 1 | AEEAHFAWGYR | 16.38 | 446.21 | 568.77 | 20.9 |
| 2 | AEEAHFAWGYR | 16.36 | 446.21 | 633.29 | 20.9 |
| 3 | AEEAHFAWGYR | 16.36 | 446.21 | 652.32 | 20.9 |
| 4 | DMASWLIANMKPDSLHAPSLK | 24.18 | 775.73 | 811.44 | 31.1 |
| 5 | DMASWLIANMKPDSLHAPSLK | 24.18 | 775.73 | 867.98 | 31.1 |
| 6 | DMASWLIANMKPDSLHAPSLK | 24.18 | 775.73 | 1004.54 | 31.1 |
| 7 | DMASWLIANMKPDSLQAPSLK | 25.04 | 772.73 | 528.29 | 31 |
| 8 | DMASWLIANMKPDSLQAPSLK | 25.04 | 772.73 | 806.94 | 31 |
| 9 | DMASWLIANMKPDSLQAPSLK | 25.04 | 772.73 | 863.48 | 31 |
| 10 | DMASWVIANMKPDSLQAPSLK | 24 | 768.06 | 806.94 | 30.9 |
| 11 | DMASWVIANMKPDSLQAPSLK | 24 | 768.06 | 856.47 | 30.9 |
| 12 | DMASWVIANMKPDSLQAPSLK | 24 | 768.06 | 949.51 | 30.9 |
| 13 | GEIALGDPVAK | 15.79 | 535.3 | 586.32 | 26.2 |
| 14 | GEIALGDPVAK | 15.77 | 535.3 | 699.4 | 26.2 |
| 15 | GEIALGDPVAK | 15.77 | 535.3 | 770.44 | 26.2 |
| 16 | TVVGGSDNK | 3.35 | 438.73 | 520.24 | 20.7 |
| 17 | TVVGGSDNK | 3.35 | 438.73 | 577.26 | 20.7 |
| 18 | TVVGGSDNK | 3.35 | 438.73 | 676.33 | 20.7 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 22

Identification of a Resistance to SHV Beta-Lactams

The samples corresponding to a species able to comprise an SHV resistance mechanism can be detected by employing the following method.

Each sample is treated according to example 5, then analysed according to example 6 by detecting the peptides from TABLE 28 instead of the peptides from TABLE 3.

TABLE 28

| Transition number | Peptide | Retention time (minutes) | (m/z) filtered in Q1 | (m/z) filtered in Q3 | Collision energy (eV) |
|---|---|---|---|---|---|
| 1 | EIGDNVTR | 10.07 | 452.23 | 489.28 | 25 |
| 2 | EIGDNVTR | 10.07 | 452.23 | 529.23 | 25 |
| 3 | EIGDNVTR | 10.07 | 452.23 | 661.33 | 25 |
| 4 | GIVALLGPHNK | 16.52 | 373.56 | 398.21 | 23 |
| 5 | GIVALLGPHNK | 16.52 | 373.56 | 552.29 | 23 |
| 6 | GIVALLGPHNK | 16.52 | 373.56 | 665.37 | 23 |
| 7 | HLADGMTVGELR | 14.93 | 433.56 | 474.27 | 26 |
| 8 | HLADGMTVGELR | 14.93 | 433.56 | 494.24 | 26 |
| 9 | HLADGMTVGELR | 14.93 | 433.56 | 573.34 | 26 |

TABLE 28-continued

| Transition number | Peptide | Retention time (minutes) | (m/z) filtered in Q1 | (m/z) filtered in Q3 | Collision energy (eV) |
|---|---|---|---|---|---|
| 10 | IHYSQQDLVDYSPVSEK | 16.22 | 669.99 | 872.39 | 37 |
| 11 | IHYSQQDLVDYSPVSEK | 16.22 | 669.99 | 924.43 | 37 |
| 12 | IHYSQQDLVDYSPVSEK | 16.22 | 669.99 | 985.47 | 37 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 23

Identification of a Resistance to CARB Beta-Lactams

The samples corresponding to a species able to comprise a CARB resistance mechanism can be detected by employing the following method.

Each sample is treated according to example 5, then analysed according to example 6 by detecting the peptides from TABLE 29 instead of the peptides from TABLE 3.

TABLE 29

| Transition number | Peptide | Retention time (minutes) | (m/z) filtered in Q1 | (m/z) filtered in Q3 | Collision energy (eV) |
|---|---|---|---|---|---|
| 1 | ADLVTYSPVIEK | 17.48 | 667.86 | 672.39 | 34.4 |
| 2 | ADLVTYSPVIEK | 17.48 | 667.86 | 835.46 | 34.4 |
| 3 | ADLVTYSPVIEK | 17.48 | 667.86 | 936.5 | 34.4 |
| 4 | ADLVTYSPVLEK | 18.01 | 667.86 | 672.39 | 34.4 |
| 5 | ADLVTYSPVLEK | 18.01 | 667.86 | 835.46 | 34.4 |
| 6 | ADLVTYSPVLEK | 18.01 | 667.86 | 936.5 | 34.4 |
| 7 | AIASTLNK | 10.86 | 409.24 | 475.29 | 23 |
| 8 | AIASTLNK | 10.86 | 409.24 | 562.32 | 23 |
| 9 | AIASTLNK | 10.86 | 409.24 | 633.36 | 23 |
| 10 | AIASTLNQLLFGSTLSEASQK | 25.39 | 727.06 | 362.2 | 40.4 |
| 11 | AIASTLNQLLFGSTLSEASQK | 25.39 | 727.06 | 649.32 | 40.4 |
| 12 | AIASTLNQLLFGSTLSEASQK | 25.39 | 727.06 | 998.02 | 40.4 |
| 13 | AIEVSLSAR | 15.46 | 473.27 | 533.3 | 25.8 |
| 14 | AIEVSLSAR | 15.46 | 473.27 | 632.37 | 25.8 |
| 15 | AIEVSLSAR | 15.46 | 473.27 | 761.42 | 25.8 |
| 16 | DTTTPIAMVTTLEK | 21.41 | 507.6 | 591.34 | 29.4 |
| 17 | DTTTPIAMVTTLEK | 21.41 | 507.6 | 690.4 | 29.4 |
| 18 | DTTTPIAMVTTLEK | 21.41 | 507.6 | 892.48 | 29.4 |
| 19 | DTTTPK | 1.54 | 331.67 | 345.21 | 19.6 |
| 20 | DTTTPK | 1.54 | 331.67 | 446.26 | 19.6 |
| 21 | DTTTPK | 1.54 | 331.67 | 547.31 | 19.6 |
| 22 | FLFGSALSEMNK | 21.32 | 672.34 | 879.42 | 34.6 |
| 23 | FLFGSALSEMNK | 21.32 | 672.34 | 936.45 | 34.6 |
| 24 | FLFGSALSEMNK | 21.32 | 672.34 | 1083.51 | 34.6 |

TABLE 29-continued

| Transition number | Peptide | Retention time (minutes) | (m/z) filtered in Q1 | (m/z) filtered in Q3 | Collision energy (eV) |
|---|---|---|---|---|---|
| 25 | FPLSSTFK | 17.51 | 463.75 | 390.22 | 25.4 |
| 26 | FPLSSTFK | 17.51 | 463.75 | 682.38 | 25.4 |
| 27 | FPLSSTFK | 17.51 | 463.75 | 779.43 | 25.4 |
| 28 | FPLTSTFK | 17.85 | 470.76 | 397.23 | 25.7 |
| 29 | FPLTSTFK | 17.85 | 470.76 | 696.39 | 25.7 |
| 30 | FPLTSTFK | 17.85 | 470.76 | 793.45 | 25.7 |
| 31 | FQQVEQDAK | 10.02 | 546.77 | 590.28 | 29.1 |
| 32 | FQQVEQDAK | 10.02 | 546.77 | 689.35 | 29.1 |
| 33 | FQQVEQDAK | 10.02 | 546.77 | 817.41 | 29.1 |
| 34 | FQQVEQDVK | 11.76 | 560.79 | 618.31 | 29.7 |
| 35 | FQQVEQDVK | 11.76 | 560.79 | 717.38 | 29.7 |
| 36 | FQQVEQDVK | 11.76 | 560.79 | 845.44 | 29.7 |
| 37 | FQSVEQEIK | 14.17 | 554.29 | 745.41 | 29.4 |
| 38 | FQSVEQEIK | 14.17 | 554.29 | 832.44 | 29.4 |
| 39 | FQSVEQEIK | 14.17 | 554.29 | 960.5 | 29.4 |
| 40 | FSESNLVTYSPVTEK | 17.84 | 567.62 | 462.74 | 32.4 |
| 41 | FSESNLVTYSPVTEK | 17.84 | 567.62 | 777.39 | 32.4 |
| 42 | FSESNLVTYSPVTEK | 17.85 | 567.62 | 924.47 | 32.4 |
| 43 | GIESSLSAR | 12.88 | 460.25 | 533.3 | 25.3 |
| 44 | GIESSLSAR | 12.88 | 460.25 | 620.34 | 25.3 |
| 45 | GIESSLSAR | 12.88 | 460.25 | 749.38 | 25.3 |
| 46 | GNEVGDALFR | 17.15 | 539.27 | 678.36 | 28.7 |
| 47 | GNEVGDALFR | 17.15 | 539.27 | 777.43 | 28.7 |
| 48 | GNEVGDALFR | 17.15 | 539.27 | 906.47 | 28.7 |
| 49 | GVPSDWIVADR | 18.32 | 607.81 | 529.77 | 31.7 |
| 50 | GVPSDWIVADR | 18.32 | 607.81 | 759.42 | 31.7 |
| 51 | GVPSDWIVADR | 18.32 | 607.81 | 1058.53 | 31.7 |
| 52 | GVTDFLR | 17.69 | 404.22 | 326.18 | 22.8 |
| 53 | GVTDFLR | 17.69 | 404.22 | 550.3 | 22.8 |
| 54 | GVTDFLR | 17.69 | 404.22 | 651.35 | 22.8 |
| 55 | IEPDLNEGK | 12.13 | 507.76 | 386.7 | 27.3 |
| 56 | IEPDLNEGK | 12.13 | 507.76 | 772.38 | 27.3 |
| 57 | IEPDLNEGK | 12.13 | 507.76 | 901.43 | 27.3 |
| 58 | IEPELNEGK | 12.2 | 514.77 | 393.7 | 27.6 |
| 59 | IEPELNEGK | 12.2 | 514.77 | 786.4 | 27.6 |
| 60 | IEPELNEGK | 12.2 | 514.77 | 915.44 | 27.6 |
| 61 | IGEQIAK | 10.58 | 379.72 | 459.29 | 21.7 |
| 62 | IGEQIAK | 10.58 | 379.72 | 588.34 | 21.7 |

TABLE 29-continued

| Transition number | Peptide | Retention time (minutes) | (m/z) filtered in Q1 | (m/z) filtered in Q3 | Collision energy (eV) |
|---|---|---|---|---|---|
| 63 | IGEQIAK | 10.58 | 379.72 | 645.36 | 21.7 |
| 64 | IGLAVHDLETGK | 16.05 | 626.85 | 799.39 | 32.6 |
| 65 | IGLAVHDLETGK | 16.05 | 626.85 | 898.46 | 32.6 |
| 66 | IGLAVHDLETGK | 16.05 | 626.85 | 969.5 | 32.6 |
| 67 | KPIVAALYITETDASFEER | 21.09 | 718.38 | 667.31 | 39.9 |
| 68 | KPIVAALYITETDASFEER | 21.09 | 718.38 | 787.37 | 39.9 |
| 69 | KPIVAALYITETDASFEER | 21.09 | 718.38 | 853.37 | 39.9 |
| 70 | LESWMVNNQVTGNLLR | 22.01 | 625.32 | 564.81 | 32.5 |
| 71 | LESWMVNNQVTGNLLR | 22.01 | 625.32 | 673.4 | 32.5 |
| 72 | LESWMVNNQVTGNLLR | 22.01 | 625.32 | 772.47 | 32.5 |
| 73 | LEYWMVNNQVTGNLLR | 22.96 | 650.67 | 564.81 | 33.6 |
| 74 | LEYWMVNNQVTGNLLR | 22.96 | 650.67 | 673.4 | 33.6 |
| 75 | LEYWMVNNQVTGNLLR | 22.96 | 650.67 | 772.47 | 33.6 |
| 76 | LLFGSALSEMNQK | 21.03 | 719.37 | 389.21 | 36.7 |
| 77 | LLFGSALSEMNQK | 21.03 | 719.37 | 736.33 | 36.7 |
| 78 | LLFGSALSEMNQK | 21.03 | 719.37 | 1211.57 | 36.7 |
| 79 | LLIDETLSIK | 20.7 | 572.85 | 805.43 | 30.2 |
| 80 | LLIDETLSIK | 20.7 | 572.85 | 918.51 | 30.2 |
| 81 | LLIDETLSIK | 20.7 | 572.85 | 1031.6 | 30.2 |
| 82 | LLYDAEHGK | 11.75 | 523.27 | 656.3 | 28 |
| 83 | LLYDAEHGK | 11.75 | 523.27 | 819.36 | 28 |
| 84 | LLYDAEHGK | 11.75 | 523.27 | 932.45 | 28 |
| 85 | LLYDAEQGEINPK | 15.72 | 745.38 | 358.21 | 37.8 |
| 86 | LLYDAEQGEINPK | 15.72 | 745.38 | 632.3 | 37.8 |
| 87 | LLYDAEQGEINPK | 15.72 | 745.38 | 785.42 | 37.8 |
| 88 | LLYDAEQGK | 13.05 | 518.77 | 647.3 | 27.8 |
| 89 | LLYDAEQGK | 13.05 | 518.77 | 810.36 | 27.8 |
| 90 | LLYDAEQGK | 13.05 | 518.77 | 923.45 | 27.8 |
| 91 | MCDNQNYGVTYMK | 14.67 | 541.89 | 641.33 | 31.1 |
| 92 | MCDNQNYGVTYMK | 14.67 | 541.89 | 698.35 | 31.1 |
| 93 | MCDNQNYGVTYMK | 14.67 | 541.89 | 861.42 | 31.1 |
| 94 | NAVIAK | 7.68 | 308.2 | 331.23 | 18.6 |
| 95 | NAVIAK | 7.68 | 308.2 | 430.3 | 18.6 |
| 96 | NAVIAK | 7.68 | 308.2 | 501.34 | 18.6 |
| 97 | NDAIVK | 8.38 | 330.19 | 359.27 | 19.5 |
| 98 | NDAIVK | 8.38 | 330.19 | 430.3 | 19.5 |
| 99 | NDAIVK | 8.38 | 330.19 | 545.33 | 19.5 |
| 100 | QQLESWLK | 17.65 | 516.28 | 533.31 | 27.7 |

TABLE 29-continued

| Transition number | Peptide | Retention time (minutes) | (m/z) filtered in Q1 | (m/z) filtered in Q3 | Collision energy (eV) |
|---|---|---|---|---|---|
| 101 | QQLESWLK | 17.65 | 516.28 | 662.35 | 27.7 |
| 102 | QQLESWLK | 17.65 | 516.28 | 775.44 | 27.7 |
| 103 | QVEQDVK | 6.63 | 423.22 | 361.21 | 23.6 |
| 104 | QVEQDVK | 6.63 | 423.22 | 489.27 | 23.6 |
| 105 | QVEQDVK | 6.63 | 423.22 | 618.31 | 23.6 |
| 106 | SGAGGFGAR | 9.32 | 390.19 | 507.27 | 22.2 |
| 107 | SGAGGFGAR | 9.32 | 390.19 | 564.29 | 22.2 |
| 108 | SGAGGFGAR | 9.32 | 390.19 | 635.33 | 22.2 |
| 109 | SIGDDTTR | 7.76 | 432.71 | 492.24 | 24 |
| 110 | SIGDDTTR | 7.76 | 432.71 | 607.27 | 24 |
| 111 | SIGDDTTR | 7.76 | 432.71 | 664.29 | 24 |
| 112 | SITAIVWSEEK | 18.92 | 631.84 | 405.2 | 32.8 |
| 113 | SITAIVWSEEK | 18.92 | 631.84 | 777.38 | 32.8 |
| 114 | SITAIVWSEEK | 18.92 | 631.84 | 1062.55 | 32.8 |
| 115 | SITDFLR | 19.34 | 426.24 | 435.27 | 23.8 |
| 116 | SITDFLR | 19.34 | 426.24 | 550.3 | 23.8 |
| 117 | SITDFLR | 19.34 | 426.24 | 651.35 | 23.8 |
| 118 | STIEIK | 11.83 | 345.71 | 389.24 | 20.2 |
| 119 | STIEIK | 11.83 | 345.71 | 502.32 | 20.2 |
| 120 | STIEIK | 11.83 | 345.71 | 603.37 | 20.2 |
| 121 | SVLPAGWNIADR | 19.61 | 649.85 | 500.25 | 33.6 |
| 122 | SVLPAGWNIADR | 19.61 | 649.85 | 556.8 | 33.6 |
| 123 | SVLPAGWNIADR | 19.61 | 649.85 | 999.5 | 33.6 |
| 124 | SVLPEGWNIADR | 19.62 | 678.85 | 529.26 | 34.9 |
| 125 | SVLPEGWNIADR | 19.62 | 678.85 | 585.8 | 34.9 |
| 126 | SVLPEGWNIADR | 19.62 | 678.85 | 1057.51 | 34.9 |
| 127 | SVLPVK | 13.24 | 321.71 | 343.23 | 19.2 |
| 128 | SVLPVK | 13.24 | 321.71 | 456.32 | 19.2 |
| 129 | SVLPVK | 13.24 | 321.71 | 555.39 | 19.2 |
| 130 | SVLPVTWSIADR | 21.34 | 672.37 | 522.78 | 34.6 |
| 131 | SVLPVTWSIADR | 21.34 | 672.37 | 1044.55 | 34.6 |
| 132 | SVLPVTWSIADR | 21.34 | 672.37 | 1157.63 | 34.6 |
| 133 | TGAGGYGSR | 3.77 | 413.2 | 596.28 | 23.2 |
| 134 | TGAGGYGSR | 3.77 | 413.2 | 667.32 | 23.2 |
| 135 | TGAGGYGSR | 3.77 | 413.2 | 724.34 | 23.2 |
| 136 | TIACAK | 3.86 | 332.18 | 378.18 | 19.6 |
| 137 | TIACAK | 3.86 | 332.18 | 449.22 | 19.6 |
| 138 | TIACAK | 3.86 | 332.18 | 562.3 | 19.6 |

TABLE 29-continued

| Transition number | Peptide | Retention time (minutes) | (m/z) filtered in Q1 | (m/z) filtered in Q3 | Collision energy (eV) |
|---|---|---|---|---|---|
| 139 | TILMENSR | 13.19 | 482.25 | 505.24 | 26.2 |
| 140 | TILMENSR | 13.19 | 482.25 | 636.28 | 26.2 |
| 141 | TILMENSR | 13.19 | 482.25 | 749.36 | 26.2 |
| 142 | TLACANVLQR | 14.83 | 573.31 | 466.24 | 30.2 |
| 143 | TLACANVLQR | 14.83 | 573.31 | 860.44 | 30.2 |
| 144 | TLACANVLQR | 14.83 | 573.31 | 931.48 | 30.2 |
| 145 | TVLMENSR | 11.76 | 475.24 | 505.24 | 25.9 |
| 146 | TVLMENSR | 11.76 | 475.24 | 636.28 | 25.9 |
| 147 | TVLMENSR | 11.76 | 475.24 | 749.36 | 25.9 |
| 148 | VEPELNEGK | 11.18 | 507.76 | 393.7 | 27.3 |
| 149 | VEPELNEGK | 11.18 | 507.76 | 447.22 | 27.3 |
| 150 | VEPELNEGK | 11.18 | 507.76 | 560.3 | 27.3 |
| 151 | VNLNSTVEIK | 15.48 | 558.82 | 790.43 | 29.6 |
| 152 | VNLNSTVEIK | 15.48 | 558.82 | 903.52 | 29.6 |
| 153 | VNLNSTVEIK | 15.48 | 558.82 | 1017.56 | 29.6 |
| 154 | VNLNSTVEVK | 14.23 | 551.81 | 776.42 | 29.3 |
| 155 | VNLNSTVEVK | 14.23 | 551.81 | 889.5 | 29.3 |
| 156 | VNLNSTVEVK | 14.23 | 551.81 | 1003.54 | 29.3 |
| 157 | VNPNSTVEIK | 12.41 | 550.8 | 444.25 | 29.2 |
| 158 | VNPNSTVEIK | 12.41 | 550.8 | 887.48 | 29.2 |
| 159 | VNPNSTVEIK | 12.41 | 550.8 | 1001.53 | 29.2 |
| 160 | VNSNSTVEIK | 11.24 | 545.79 | 790.43 | 29 |
| 161 | VNSNSTVEIK | 11.24 | 545.79 | 877.46 | 29 |
| 162 | VNSNSTVEIK | 11.24 | 545.79 | 991.51 | 29 |
| 163 | WETELNEAVPGDK | 16.5 | 744.35 | 358.19 | 37.8 |
| 164 | WETELNEAVPGDK | 16.5 | 744.35 | 415.21 | 37.8 |
| 165 | WETELNEAVPGDK | 16.5 | 744.35 | 471.75 | 37.8 |
| 166 | WSIADR | 14.14 | 374.19 | 361.18 | 21.5 |
| 167 | WSIADR | 14.14 | 374.19 | 474.27 | 21.5 |
| 168 | WSIADR | 14.14 | 374.19 | 561.3 | 21.5 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 24

Identification of a Resistance to OXA Beta-Lactams

The samples corresponding to a species able to comprise an OXA resistance mechanism can be detected by employing the following method.

Each sample is treated according to example 5, then analysed according to example 6 by detecting the peptides from TABLE 30 instead of the peptides from TABLE 3.

TABLE 30

| Transition number | Peptide | Retention time (minutes) | (m/z) filtered in Q1 | (m/z) filtered in Q3 | Collision energy (eV) |
|---|---|---|---|---|---|
| 1 | AAAYELAENLFEAGQADGWR | 24.48 | 728.01 | 1249.6 | 40 |
| 2 | AAAYELAENLFEAGQADGWR | 24.48 | 1091.51 | 1193.58 | 53 |
| 3 | AAAYELAENLFEAGQADGWR | 24.48 | 1091.51 | 1249.6 | 53 |
| 4 | AAEGFIPASTFK | 17.74 | 619.82 | 763.43 | 32 |
| 5 | AAEGFIPASTFK | 17.74 | 619.82 | 910.5 | 32 |
| 6 | AAEGFIPASTFK | 17.74 | 619.82 | 967.52 | 32 |
| 7 | ADGQVVAFALNMQMK | 21.27 | 811.91 | 982.48 | 41 |
| 8 | ADGQVVAFALNMQMK | 21.29 | 811.91 | 1053.52 | 41 |
| 9 | ADGQVVAFALNMQMK | 21.27 | 811.91 | 1152.59 | 41 |
| 10 | ADINEIFK | 17.3 | 475.25 | 650.35 | 26 |
| 11 | ADINEIFK | 17.3 | 475.25 | 763.43 | 26 |
| 12 | ADINEIFK | 17.3 | 475.25 | 878.46 | 26 |
| 13 | ADWGK | 6.9 | 288.64 | 390.21 | 18 |
| 14 | ADWGK | 6.91 | 288.64 | 430.17 | 18 |
| 15 | ADWGK | 6.89 | 288.64 | 505.24 | 18 |
| 16 | AEGAIVISDER | 13.52 | 387.2 | 419.19 | 23 |
| 17 | AEGAIVISDER | 13.53 | 387.2 | 506.22 | 23 |
| 18 | AEGAIVISDER | 13.52 | 387.2 | 619.3 | 23 |
| 19 | AFALNLDIDK | 20.16 | 560.31 | 717.38 | 30 |
| 20 | AFALNLDIDK | 20.16 | 560.31 | 830.46 | 30 |
| 21 | AFALNLDIDK | 20.16 | 560.31 | 901.5 | 30 |
| 22 | AFAPMSTFK | 16.96 | 500.25 | 710.35 | 27 |
| 23 | AFAPMSTFK | 16.96 | 500.25 | 781.39 | 27 |
| 24 | AFAPMSTFK | 16.96 | 500.25 | 928.46 | 27 |
| 25 | AFGYGNADVSGDPGQNNGLDR | 15.12 | 708.65 | 873.42 | 39 |
| 26 | AFGYGNADVSGDPGQNNGLDR | 15.12 | 708.65 | 970.47 | 39 |
| 27 | AFGYGNADVSGDPGQNNGLDR | 15.12 | 708.65 | 1154.47 | 39 |
| 28 | AFTMTK | 11.32 | 349.68 | 480.25 | 20 |
| 29 | AFTMTK | 11.33 | 349.68 | 552.25 | 20 |
| 30 | AFTMTK | 11.33 | 349.68 | 627.32 | 20 |
| 31 | AGDDIALR | 12.23 | 415.72 | 587.35 | 23 |
| 32 | AGDDIALR | 12.23 | 415.72 | 702.38 | 23 |
| 33 | AGDDIALR | 12.23 | 415.72 | 759.4 | 23 |
| 34 | AGHVYAFALNIDMPR | 20.63 | 558.95 | 631.32 | 32 |
| 35 | AGHVYAFALNIDMPR | 20.63 | 558.95 | 745.37 | 32 |
| 36 | AGHVYAFALNIDMPR | 20.63 | 558.95 | 817.4 | 32 |
| 37 | AGLWR | 13.44 | 301.67 | 361.2 | 18 |
| 38 | AGLWR | 13.44 | 301.67 | 474.28 | 18 |

TABLE 30-continued

| Transition number | Peptide | Retention time (minutes) | (m/z) filtered in Q1 | (m/z) filtered in Q3 | Collision energy (eV) |
|---|---|---|---|---|---|
| 39 | AGLWR | 13.44 | 301.67 | 531.3 | 18 |
| 40 | AHTEYVPASTFK | 13.18 | 450.89 | 553.3 | 27 |
| 41 | AHTEYVPASTFK | 13.18 | 450.89 | 602.26 | 27 |
| 42 | AHTEYVPASTFK | 13.18 | 450.89 | 650.35 | 27 |
| 43 | AIIPWDGKPR | 15.84 | 384.89 | 428.23 | 23 |
| 44 | AIIPWDGKPR | 15.84 | 384.89 | 457.29 | 23 |
| 45 | AIIPWDGKPR | 15.84 | 384.89 | 572.32 | 23 |
| 46 | AISDITITR | 14.8 | 495.28 | 603.38 | 27 |
| 47 | AISDITITR | 14.8 | 495.28 | 718.41 | 27 |
| 48 | AISDITITR | 14.8 | 495.28 | 805.44 | 27 |
| 49 | ALGQDR | 11.25 | 330.18 | 475.23 | 20 |
| 50 | ALGQDR | 11.25 | 330.18 | 485.24 | 20 |
| 51 | ALGQDR | 11.25 | 330.18 | 588.31 | 20 |
| 52 | ALQAK | 1.86 | 265.67 | 346.21 | 17 |
| 53 | ALQAK | 1.87 | 265.67 | 384.22 | 17 |
| 54 | ALQAK | 1.87 | 265.67 | 459.29 | 17 |
| 55 | AMETFSPASTFK | 17.06 | 658.81 | 737.38 | 34 |
| 56 | AMETFSPASTFK | 17.05 | 658.81 | 985.5 | 34 |
| 57 | AMETFSPASTFK | 17.06 | 658.81 | 1114.54 | 34 |
| 58 | AMLFLQER | 18.48 | 504.27 | 545.3 | 27 |
| 59 | AMLFLQER | 18.48 | 504.27 | 692.37 | 27 |
| 60 | AMLFLQER | 18.48 | 504.27 | 805.46 | 27 |
| 61 | AMLVFDPVR | 19.87 | 524.29 | 732.4 | 28 |
| 62 | AMLVFDPVR | 19.87 | 524.29 | 845.49 | 28 |
| 63 | AMLVFDPVR | 19.87 | 524.29 | 976.53 | 28 |
| 64 | AMTLLESGPGWELHGK | 19.32 | 575.96 | 923.47 | 33 |
| 65 | AMTLLESGPGWELHGK | 19.32 | 575.96 | 980.49 | 33 |
| 66 | AMTLLESGPGWELHGK | 19.32 | 575.96 | 1067.53 | 33 |
| 67 | ANLHITLHGK | 12.18 | 368.55 | 403.24 | 22 |
| 68 | ANLHITLHGK | 12.18 | 368.55 | 555.32 | 22 |
| 69 | ANLHITLHGK | 12.18 | 368.55 | 668.41 | 22 |
| 70 | ANQLIVK | 11.87 | 393.25 | 600.41 | 22 |
| 71 | ANQLIVK | 11.86 | 393.25 | 639.38 | 22 |
| 72 | ANQLIVK | 11.86 | 393.25 | 714.45 | 22 |
| 73 | ANTEYVPASTFK | 14.54 | 664.33 | 912.48 | 34 |
| 74 | ANTEYVPASTFK | 14.54 | 664.33 | 1041.53 | 34 |
| 75 | ANTEYVPASTFK | 14.54 | 664.33 | 1142.57 | 34 |
| 76 | ANVSR | 9.57 | 273.65 | 361.22 | 17 |

TABLE 30-continued

| Transition number | Peptide | Retention time (minutes) | (m/z) filtered in Q1 | (m/z) filtered in Q3 | Collision energy (eV) |
|---|---|---|---|---|---|
| 77 | ANVSR | 9.57 | 273.65 | 372.19 | 17 |
| 78 | ANVSR | 9.57 | 273.65 | 475.26 | 17 |
| 79 | APIGWFIGWATR | 25.58 | 687.87 | 850.46 | 35 |
| 80 | APIGWFIGWATR | 25.58 | 687.87 | 1093.56 | 35 |
| 81 | APIGWFIGWATR | 25.58 | 687.87 | 1206.64 | 35 |
| 82 | APLGWFIGWATHEER | 24.69 | 590.63 | 742.35 | 34 |
| 83 | APLGWFIGWATHEER | 24.69 | 590.63 | 985.45 | 34 |
| 84 | APLGWFIGWATHEER | 24.69 | 590.63 | 1098.53 | 34 |
| 85 | AQDEVQSMLFIEEK | 20.15 | 833.9 | 996.51 | 42 |
| 86 | AQDEVQSMLFIEEK | 20.14 | 833.9 | 1124.57 | 42 |
| 87 | AQDEVQSMLFIEEK | 20.15 | 833.9 | 1223.63 | 42 |
| 88 | AQGVIVLWNENK | 18.95 | 685.87 | 902.47 | 35 |
| 89 | AQGVIVLWNENK | 18.95 | 685.87 | 1015.56 | 35 |
| 90 | AQGVIVLWNENK | 18.95 | 685.87 | 1171.65 | 35 |
| 91 | ASAIAVYQDLAR | 18.05 | 639.35 | 765.39 | 33 |
| 92 | ASAIAVYQDLAR | 18.05 | 639.35 | 864.46 | 33 |
| 93 | ASAIAVYQDLAR | 18.05 | 639.35 | 935.49 | 33 |
| 94 | ASAILVYQDLAR | 19.08 | 660.37 | 765.39 | 34 |
| 95 | ASAILVYQDLAR | 19.08 | 660.37 | 864.46 | 34 |
| 96 | ASAILVYQDLAR | 19.08 | 660.37 | 977.54 | 34 |
| 97 | ASAIPVYQDLAR | 17.45 | 652.35 | 765.39 | 34 |
| 98 | ASAIPVYQDLAR | 17.45 | 652.35 | 864.46 | 34 |
| 99 | ASAIPVYQDLAR | 17.45 | 652.35 | 961.51 | 34 |
| 100 | ASAIPVYQDLPR | 17.59 | 665.36 | 791.4 | 34 |
| 101 | ASAIPVYQDLPR | 17.59 | 665.36 | 890.47 | 34 |
| 102 | ASAIPVYQDLPR | 17.6 | 665.36 | 987.53 | 34 |
| 103 | ASAIQVYQDLAR | 18.37 | 667.86 | 765.39 | 34 |
| 104 | ASAIQVYQDLAR | 18.37 | 667.86 | 864.46 | 34 |
| 105 | ASAIQVYQDLAR | 18.37 | 667.86 | 992.52 | 34 |
| 106 | ASAISVYQDLAR | 17.93 | 647.34 | 765.39 | 33 |
| 107 | ASAISVYQDLAR | 17.93 | 647.34 | 864.46 | 33 |
| 108 | ASAISVYQDLAR | 17.93 | 647.34 | 951.49 | 33 |
| 109 | ASALPVYQDLAR | 17.77 | 652.35 | 864.46 | 34 |
| 110 | ASALPVYQDLAR | 17.77 | 652.35 | 961.51 | 34 |
| 111 | ASALPVYQDLAR | 17.77 | 652.35 | 1074.59 | 34 |
| 112 | ASAMPVYQDLAR | 16.64 | 661.33 | 765.39 | 34 |
| 113 | ASAMPVYQDLAR | 16.64 | 661.33 | 864.46 | 34 |
| 114 | ASAMPVYQDLAR | 16.64 | 661.33 | 961.51 | 34 |

TABLE 30-continued

| Transition number | Peptide | Retention time (minutes) | (m/z) filtered in Q1 | (m/z) filtered in Q3 | Collision energy (eV) |
|---|---|---|---|---|---|
| 115 | ASAVPVYQDLAR | 16.29 | 645.35 | 765.39 | 33 |
| 116 | ASAVPVYQDLAR | 16.29 | 645.35 | 864.46 | 33 |
| 117 | ASAVPVYQDLAR | 16.29 | 645.35 | 961.51 | 33 |
| 118 | ASIEYVPASTFK | 16.7 | 656.84 | 749.42 | 34 |
| 119 | ASIEYVPASTFK | 16.7 | 656.84 | 912.48 | 34 |
| 120 | ASIEYVPASTFK | 16.7 | 656.84 | 1041.53 | 34 |
| 121 | ASNVPVYQELAR | 18.48 | 673.86 | 779.4 | 35 |
| 122 | ASNVPVYQELAR | 18.48 | 673.86 | 878.47 | 35 |
| 123 | ASNVPVYQELAR | 18.48 | 673.86 | 975.53 | 35 |
| 124 | ASPASTFK | 10.29 | 404.71 | 553.3 | 23 |
| 125 | ASPASTFK | 10.29 | 404.71 | 650.35 | 23 |
| 126 | ASPASTFK | 10.28 | 404.71 | 737.38 | 23 |
| 127 | ASTAYIPASTFK | 15.69 | 628.83 | 763.43 | 33 |
| 128 | ASTAYIPASTFK | 15.69 | 628.83 | 926.5 | 33 |
| 129 | ASTAYIPASTFK | 15.69 | 628.83 | 997.54 | 33 |
| 130 | ASTEYVPASTFK | 14.59 | 650.82 | 749.42 | 34 |
| 131 | ASTEYVPASTFK | 14.59 | 650.82 | 912.48 | 34 |
| 132 | ASTEYVPASTFK | 14.6 | 650.82 | 1041.53 | 34 |
| 133 | ASTTEVFK | 11.78 | 441.73 | 623.34 | 24 |
| 134 | ASTTEVFK | 11.78 | 441.73 | 724.39 | 24 |
| 135 | ASTTEVFK | 11.78 | 441.73 | 811.42 | 24 |
| 136 | ATSTEIFK | 13.15 | 448.74 | 637.36 | 25 |
| 137 | ATSTEIFK | 13.15 | 448.74 | 724.39 | 25 |
| 138 | ATSTEIFK | 13.15 | 448.74 | 825.44 | 25 |
| 139 | ATTNEIFK | 13.21 | 462.25 | 650.35 | 25 |
| 140 | ATTNEIFK | 13.21 | 462.25 | 751.4 | 25 |
| 141 | ATTNEIFK | 13.21 | 462.25 | 852.45 | 25 |
| 142 | ATTTAVFK | 11.9 | 419.74 | 464.29 | 23 |
| 143 | ATTTAVFK | 11.9 | 419.74 | 565.33 | 23 |
| 144 | ATTTAVFK | 11.9 | 419.74 | 666.38 | 23 |
| 145 | ATTTEIFK | 13.64 | 455.75 | 637.36 | 25 |
| 146 | ATTTEIFK | 13.65 | 455.75 | 738.4 | 25 |
| 147 | ATTTEIFK | 13.65 | 455.75 | 839.45 | 25 |
| 148 | ATTTEVFK | 11.98 | 448.74 | 623.34 | 25 |
| 149 | ATTTEVFK | 11.98 | 448.74 | 724.39 | 25 |
| 150 | ATTTEVFK | 11.98 | 448.74 | 825.44 | 25 |
| 151 | AVSDITILEQTDNYTLHGK | 19.19 | 706.7 | 974.49 | 39 |
| 152 | AVSDITILEQTDNYTLHGK | 19.19 | 706.7 | 1048.51 | 39 |

TABLE 30-continued

| Transition number | Peptide | Retention time (minutes) | (m/z) filtered in Q1 | (m/z) filtered in Q3 | Collision energy (eV) |
|---|---|---|---|---|---|
| 153 | AVSDITILEQTDNYTLHGK | 19.18 | 706.7 | 1176.56 | 39 |
| 154 | AVSDITILEQTYNYTLHGK | 22.29 | 722.71 | 995.49 | 40 |
| 155 | AVSDITILEQTYNYTLHGK | 22.29 | 722.71 | 998.5 | 40 |
| 156 | AVSDITILEQTYNYTLHGK | 22.28 | 722.71 | 1224.6 | 40 |
| 157 | AVVPHFEAGDWDVQGK | 17.81 | 585.62 | 743.34 | 33 |
| 158 | AVVPHFEAGDWDVQGK | 17.81 | 585.62 | 792.88 | 33 |
| 159 | AVVPHFEAGDWDVQGK | 17.81 | 585.62 | 904.42 | 33 |
| 160 | AWEHDMSLR | 13.99 | 572.76 | 758.36 | 30 |
| 161 | AWEHDMSLR | 13.99 | 572.76 | 887.4 | 30 |
| 162 | AWEHDMSLR | 13.99 | 572.76 | 1073.48 | 30 |
| 163 | AWIGSSLQISPLEQLEFLGK | 26.98 | 739.4 | 963.51 | 41 |
| 164 | AWIGSSLQISPLEQLEFLGK | 26.99 | 739.4 | 1173.65 | 41 |
| 165 | AWIGSSLQISPLEQLEFLGK | 26.98 | 1108.6 | 1173.65 | 54 |
| 166 | DAFLK | 12.42 | 297.17 | 407.27 | 18 |
| 167 | DAFLK | 12.43 | 297.17 | 447.22 | 18 |
| 168 | DAFLK | 12.42 | 297.17 | 478.3 | 18 |
| 169 | DDFILHGK | 13.99 | 472.75 | 714.43 | 26 |
| 170 | DDFILHGK | 13.99 | 472.75 | 798.38 | 26 |
| 171 | DDFILHGK | 13.99 | 472.75 | 829.46 | 26 |
| 172 | DDVLK | 8.62 | 295.16 | 359.27 | 18 |
| 173 | DDVLK | 8.63 | 295.16 | 443.21 | 18 |
| 174 | DDVLK | 8.62 | 295.16 | 474.29 | 18 |
| 175 | DEFHVFR | 15.39 | 475.23 | 705.38 | 26 |
| 176 | DEFHVFR | 15.39 | 475.23 | 775.34 | 26 |
| 177 | DEFHVFR | 15.39 | 475.23 | 834.43 | 26 |
| 178 | DEFQIFR | 19.02 | 477.74 | 520.2 | 26 |
| 179 | DEFQIFR | 19.02 | 477.74 | 563.33 | 26 |
| 180 | DEFQIFR | 19.02 | 477.74 | 710.4 | 26 |
| 181 | DEFQVFR | 17.29 | 470.73 | 549.31 | 26 |
| 182 | DEFQVFR | 17.28 | 470.73 | 619.27 | 26 |
| 183 | DEFQVFR | 17.29 | 470.73 | 696.38 | 26 |
| 184 | DELVR | 9.33 | 316.17 | 387.27 | 19 |
| 185 | DELVR | 9.35 | 316.17 | 457.23 | 19 |
| 186 | DELVR | 9.33 | 316.17 | 516.31 | 19 |
| 187 | DFDYGNQDFSGDK | 14.72 | 754.3 | 967.41 | 38 |
| 188 | DFDYGNQDFSGDK | 14.72 | 754.3 | 1130.47 | 38 |
| 189 | DFDYGNQDFSGDK | 14.72 | 754.3 | 1245.5 | 38 |
| 190 | DFTLGEAMQASTVPVYQELAR | 24.19 | 776.05 | 975.53 | 43 |

TABLE 30-continued

| Transition number | Peptide | Retention time (minutes) | (m/z) filtered in Q1 | (m/z) filtered in Q3 | Collision energy (eV) |
|---|---|---|---|---|---|
| 191 | DFTLGEAMQASTVPVYQELAR | 24.19 | 776.05 | 1074.59 | 43 |
| 192 | DFTLGEAMQASTVPVYQELAR | 24.19 | 1163.57 | 1175.64 | 56 |
| 193 | DHDLITAMK | 14.23 | 522.26 | 563.32 | 28 |
| 194 | DHDLITAMK | 14.23 | 522.26 | 695.34 | 28 |
| 195 | DHDLITAMK | 14.23 | 522.26 | 791.43 | 28 |
| 196 | DIAAWNR | 13.63 | 423.22 | 546.28 | 24 |
| 197 | DIAAWNR | 13.63 | 423.22 | 617.32 | 24 |
| 198 | DIAAWNR | 13.62 | 423.22 | 730.4 | 24 |
| 199 | DILYIQELAGGWK | 24.49 | 753.4 | 888.46 | 38 |
| 200 | DILYIQELAGGWK | 24.48 | 753.4 | 1001.54 | 38 |
| 201 | DILYIQELAGGWK | 24.49 | 753.4 | 1164.6 | 38 |
| 202 | DITILEK | 15.9 | 416.24 | 603.37 | 23 |
| 203 | DITILEK | 15.91 | 416.24 | 685.38 | 23 |
| 204 | DITILEK | 15.91 | 416.24 | 716.46 | 23 |
| 205 | DLLSAK | 12.45 | 323.69 | 429.23 | 19 |
| 206 | DLLSAK | 12.44 | 323.69 | 500.27 | 19 |
| 207 | DLLSAK | 12.45 | 323.69 | 531.35 | 19 |
| 208 | DLMITEAGR | 15.07 | 503.26 | 533.27 | 27 |
| 209 | DLMITEAGR | 15.07 | 503.26 | 646.35 | 27 |
| 210 | DLMITEAGR | 15.07 | 503.26 | 777.39 | 27 |
| 211 | DLMIVEAGR | 16.68 | 502.27 | 531.29 | 27 |
| 212 | DLMIVEAGR | 16.68 | 502.27 | 644.37 | 27 |
| 213 | DLMIVEAGR | 16.68 | 502.27 | 775.41 | 27 |
| 214 | DLMIVEAK | 16.23 | 459.75 | 473.24 | 25 |
| 215 | DLMIVEAK | 16.23 | 459.75 | 559.34 | 25 |
| 216 | DLMIVEAK | 16.23 | 459.75 | 690.39 | 25 |
| 217 | DLSGNPGK | 6.69 | 394.2 | 472.25 | 22 |
| 218 | DLSGNPGK | 6.69 | 394.2 | 559.28 | 22 |
| 219 | DLSGNPGK | 6.7 | 394.2 | 672.37 | 22 |
| 220 | DLSLR | 12.37 | 302.18 | 375.24 | 18 |
| 221 | DLSLR | 12.35 | 302.18 | 429.23 | 18 |
| 222 | DLSLR | 12.36 | 302.18 | 488.32 | 18 |
| 223 | DLTLR | 12.48 | 309.18 | 389.25 | 19 |
| 224 | DLTLR | 12.47 | 309.18 | 443.25 | 19 |
| 225 | DLTLR | 12.47 | 309.18 | 502.33 | 19 |
| 226 | DMTLGDAIK | 15.97 | 482.24 | 503.28 | 26 |
| 227 | DMTLGDAIK | 15.97 | 482.24 | 616.37 | 26 |
| 228 | DMTLGDAIK | 15.97 | 482.24 | 717.41 | 26 |

TABLE 30-continued

| Transition number | Peptide | Retention time (minutes) | (m/z) filtered in Q1 | (m/z) filtered in Q3 | Collision energy (eV) |
|---|---|---|---|---|---|
| 229 | DMTLGDAMALSAVPVYQELAR | 25.76 | 751.04 | 975.53 | 42 |
| 230 | DMTLGDAMALSAVPVYQELAR | 25.76 | 1126.06 | 1145.63 | 55 |
| 231 | DMTLGDAMALSAVPVYQELAR | 25.75 | 1126.06 | 1232.66 | 55 |
| 232 | DMTLGDAMK | 14.46 | 491.22 | 634.32 | 27 |
| 233 | DMTLGDAMK | 14.46 | 491.22 | 735.37 | 27 |
| 234 | DMTLGDAMK | 14.46 | 491.22 | 866.41 | 27 |
| 235 | DMTLGEAMALSAVPVYQDLAR | 25.92 | 751.04 | 961.51 | 42 |
| 236 | DMTLGEAMALSAVPVYQDLAR | 25.92 | 1126.06 | 1131.62 | 55 |
| 237 | DMTLGEAMALSAVPVYQDLAR | 25.92 | 1126.06 | 1218.65 | 55 |
| 238 | DMTLGEAMALSAVPVYQELAR | 26.48 | 755.71 | 779.4 | 42 |
| 239 | DMTLGEAMALSAVPVYQELAR | 26.48 | 755.71 | 975.53 | 42 |
| 240 | DMTLGEAMALSAVPVYQELAR | 26.47 | 1133.07 | 1232.66 | 55 |
| 241 | DMTLGEAMK | 15.09 | 498.23 | 535.25 | 27 |
| 242 | DMTLGEAMK | 15.09 | 498.23 | 648.34 | 27 |
| 243 | DMTLGEAMK | 15.09 | 498.23 | 749.39 | 27 |
| 244 | DMTLGQAMQASAVPVYQELAR | 23.29 | 760.38 | 779.4 | 42 |
| 245 | DMTLGQAMQASAVPVYQELAR | 23.29 | 760.38 | 975.53 | 42 |
| 246 | DMTLGQAMQASAVPVYQELAR | 23.29 | 760.38 | 976.42 | 42 |
| 247 | DQDLR | 2.54 | 323.66 | 403.23 | 19 |
| 248 | DQDLR | 2.55 | 323.66 | 472.2 | 19 |
| 249 | DQDLR | 2.55 | 323.66 | 531.29 | 19 |
| 250 | DQQIGWFVGWASKPGK | 21.64 | 601.98 | 830.45 | 34 |
| 251 | DQQIGWFVGWASKPGK | 21.64 | 902.46 | 929.52 | 45 |
| 252 | DQQIGWFVGWASKPGK | 21.64 | 902.46 | 1076.59 | 45 |
| 253 | DQQVQVYGNDLNR | 13.59 | 774.87 | 851.4 | 39 |
| 254 | DQQVQVYGNDLNR | 13.58 | 774.87 | 950.47 | 39 |
| 255 | DQQVQVYGNDLNR | 13.59 | 774.87 | 1078.53 | 39 |
| 256 | DQTLESAFK | 15.21 | 519.76 | 581.29 | 28 |
| 257 | DQTLESAFK | 15.21 | 519.76 | 694.38 | 28 |
| 258 | DQTLESAFK | 15.21 | 519.76 | 795.42 | 28 |
| 259 | DSIVWYSQELTR | 19.61 | 748.87 | 896.45 | 38 |
| 260 | DSIVWYSQELTR | 19.61 | 748.87 | 1082.53 | 38 |
| 261 | DSIVWYSQELTR | 19.61 | 748.87 | 1181.59 | 38 |
| 262 | DSIVWYSQQLTR | 19.1 | 748.38 | 895.46 | 38 |
| 263 | DSIVWYSQQLTR | 19.11 | 748.38 | 1081.54 | 38 |
| 264 | DSIVWYSQQLTR | 19.1 | 748.38 | 1180.61 | 38 |
| 265 | DSNLR | 1.77 | 302.66 | 402.25 | 18 |
| 266 | DSNLR | 1.77 | 302.66 | 430.19 | 18 |

TABLE 30-continued

| Transition number | Peptide | Retention time (minutes) | (m/z) filtered in Q1 | (m/z) filtered in Q3 | Collision energy (eV) |
|---|---|---|---|---|---|
| 267 | DSNLR | 1.77 | 302.66 | 489.28 | 18 |
| 268 | DSYIAWGGEAWK | 19.67 | 691.82 | 833.39 | 35 |
| 269 | DSYIAWGGEAWK | 19.67 | 691.82 | 904.43 | 35 |
| 270 | DSYIAWGGEAWK | 19.66 | 691.82 | 1017.52 | 35 |
| 271 | DTLNPEWPYK | 17.3 | 631.81 | 819.4 | 33 |
| 272 | DTLNPEWPYK | 17.3 | 631.81 | 933.45 | 33 |
| 273 | DTLNPEWPYK | 17.3 | 631.81 | 1046.53 | 33 |
| 274 | DVDEVFYK | 15.62 | 507.74 | 685.36 | 27 |
| 275 | DVDEVFYK | 15.62 | 507.74 | 800.38 | 27 |
| 276 | DVDEVFYK | 15.62 | 507.74 | 899.45 | 27 |
| 277 | DWILR | 17.44 | 351.7 | 415.2 | 20 |
| 278 | DWILR | 17.44 | 351.7 | 528.28 | 20 |
| 279 | DWILR | 17.44 | 351.7 | 587.37 | 20 |
| 280 | EAFLR | 12.51 | 318.18 | 435.27 | 19 |
| 281 | EAFLR | 12.51 | 318.18 | 461.24 | 19 |
| 282 | EAFLR | 12.51 | 318.18 | 506.31 | 19 |
| 283 | EAIVR | 7.84 | 294.18 | 387.27 | 18 |
| 284 | EAIVR | 7.84 | 294.18 | 413.24 | 18 |
| 285 | EAIVR | 7.84 | 294.18 | 458.31 | 18 |
| 286 | EAIVTEATPEYIVHSK | 16.43 | 596.31 | 746.42 | 34 |
| 287 | EAIVTEATPEYIVHSK | 16.43 | 596.31 | 972.51 | 34 |
| 288 | EAIVTEATPEYIVHSK | 16.42 | 596.31 | 1073.56 | 34 |
| 289 | EALVTEAAPEYLVHSK | 17.3 | 586.31 | 875.46 | 33 |
| 290 | EALVTEAAPEYLVHSK | 17.3 | 586.31 | 972.51 | 33 |
| 291 | EALVTEAAPEYLVHSK | 17.3 | 586.31 | 1114.59 | 33 |
| 292 | EALVTEAPEYLVHSK | 17.58 | 562.63 | 637.32 | 32 |
| 293 | EALVTEAPEYLVHSK | 17.58 | 562.63 | 972.51 | 32 |
| 294 | EALVTEAPEYLVHSK | 17.58 | 562.63 | 1043.55 | 32 |
| 295 | EEIVR | 8.41 | 323.18 | 387.27 | 19 |
| 296 | EEIVR | 8.4 | 323.18 | 471.24 | 19 |
| 297 | EEIVR | 8.4 | 323.18 | 516.31 | 19 |
| 298 | EEVLAALPAQLK | 19.48 | 641.37 | 740.47 | 33 |
| 299 | EEVLAALPAQLK | 19.47 | 641.37 | 811.5 | 33 |
| 300 | EEVLAALPAQLK | 19.47 | 641.37 | 924.59 | 33 |
| 301 | EFSAEAVNGVFVLC[CAM]K | 21.1 | 835.42 | 936.5 | 42 |
| 302 | EFSAEAVNGVFVLC[CAM]K | 21.1 | 835.42 | 1106.6 | 42 |
| 303 | EFSAEAVNGVFVLC[CAM]K | 21.1 | 835.42 | 1235.65 | 42 |
| 304 | EFSSESVHGVFVLC[CAM]K | 18.26 | 575.62 | 666.36 | 33 |

TABLE 30-continued

| Transition number | Peptide | Retention time (minutes) | (m/z) filtered in Q1 | (m/z) filtered in Q3 | Collision energy (eV) |
|---|---|---|---|---|---|
| 305 | EFSSESVHGVFVLC[CAM]K | 18.26 | 575.62 | 822.45 | 33 |
| 306 | EFSSESVHGVFVLC[CAM]K | 18.26 | 575.62 | 959.51 | 33 |
| 307 | EGMSGSIR | 9.88 | 418.7 | 432.26 | 23 |
| 308 | EGMSGSIR | 9.88 | 418.7 | 519.29 | 23 |
| 309 | EGMSGSIR | 9.88 | 418.7 | 707.35 | 23 |
| 310 | EGMTGSIR | 10.63 | 425.71 | 432.26 | 24 |
| 311 | EGMTGSIR | 10.63 | 425.71 | 533.3 | 24 |
| 312 | EGMTGSIR | 10.63 | 425.71 | 664.34 | 24 |
| 313 | EIAVWNR | 14.78 | 444.24 | 475.24 | 25 |
| 314 | EIAVWNR | 14.77 | 444.24 | 574.31 | 25 |
| 315 | EIAVWNR | 14.77 | 444.24 | 645.35 | 25 |
| 316 | EIAYK | 8.46 | 312.17 | 381.21 | 19 |
| 317 | EIAYK | 8.46 | 312.17 | 477.23 | 19 |
| 318 | EIAYK | 8.46 | 312.17 | 494.3 | 19 |
| 319 | EIFER | 11.7 | 347.18 | 451.23 | 20 |
| 320 | EIFER | 11.7 | 347.18 | 519.24 | 20 |
| 321 | EIFER | 11.7 | 347.18 | 564.31 | 20 |
| 322 | EIFYHYR | 13.31 | 514.25 | 785.37 | 28 |
| 323 | EIFYHYR | 13.31 | 514.25 | 853.39 | 28 |
| 324 | EIFYHYR | 13.32 | 514.25 | 898.46 | 28 |
| 325 | EIGDDK | 1.99 | 338.66 | 434.19 | 20 |
| 326 | EIGDDK | 1.99 | 338.66 | 530.21 | 20 |
| 327 | EIGDDK | 1.99 | 338.66 | 547.27 | 20 |
| 328 | EIGDGK | 1.76 | 309.66 | 376.18 | 19 |
| 329 | EIGDGK | 1.75 | 309.66 | 472.2 | 19 |
| 330 | EIGDGK | 1.75 | 309.66 | 489.27 | 19 |
| 331 | EIGEDK | 2.32 | 345.67 | 448.2 | 20 |
| 332 | EIGEDK | 2.33 | 345.67 | 544.22 | 20 |
| 333 | EIGEDK | 2.33 | 345.67 | 561.29 | 20 |
| 334 | EIGEDNAR | 10.05 | 452.21 | 604.27 | 25 |
| 335 | EIGEDNAR | 10.05 | 452.21 | 661.29 | 25 |
| 336 | EIGEDNAR | 10.06 | 452.21 | 774.37 | 25 |
| 337 | EIGENK | 1.86 | 345.18 | 447.22 | 20 |
| 338 | EIGENK | 1.86 | 345.18 | 543.24 | 20 |
| 339 | EIGENK | 1.86 | 345.18 | 560.3 | 20 |
| 340 | EIGSEIDK | 11.04 | 445.73 | 591.3 | 25 |
| 341 | EIGSEIDK | 11.04 | 445.73 | 648.32 | 25 |
| 342 | EIGSEIDK | 11.04 | 445.73 | 761.4 | 25 |

TABLE 30-continued

| Transition number | Peptide | Retention time (minutes) | (m/z) filtered in Q1 | (m/z) filtered in Q3 | Collision energy (eV) |
|---|---|---|---|---|---|
| 343 | EMIYLK | 15.11 | 398.72 | 536.34 | 23 |
| 344 | EMIYLK | 15.11 | 398.72 | 650.32 | 23 |
| 345 | EMIYLK | 15.11 | 398.72 | 667.38 | 23 |
| 346 | EMLYVER | 14.12 | 470.23 | 566.29 | 26 |
| 347 | EMLYVER | 14.12 | 470.23 | 679.38 | 26 |
| 348 | EMLYVER | 14.12 | 470.23 | 810.42 | 26 |
| 349 | ENIEK | 11.07 | 316.67 | 389.24 | 19 |
| 350 | ENIEK | 11.07 | 316.67 | 486.22 | 19 |
| 351 | ENIEK | 11.07 | 316.67 | 503.28 | 19 |
| 352 | ENQLIVK | 12.15 | 422.25 | 472.35 | 24 |
| 353 | ENQLIVK | 12.15 | 422.25 | 600.41 | 24 |
| 354 | ENQLIVK | 12.15 | 422.25 | 714.45 | 24 |
| 355 | EQAILLFR | 19.88 | 495.29 | 548.36 | 27 |
| 356 | EQAILLFR | 19.88 | 495.29 | 661.44 | 27 |
| 357 | EQAILLFR | 19.88 | 495.29 | 732.48 | 27 |
| 358 | EQIQFLLR | 19.45 | 523.8 | 548.36 | 28 |
| 359 | EQIQFLLR | 19.45 | 523.8 | 676.41 | 28 |
| 360 | EQIQFLLR | 19.45 | 523.8 | 789.5 | 28 |
| 361 | EQLAFDPQVQQQVK | 16.43 | 829.43 | 954.54 | 41 |
| 362 | EQLAFDPQVQQQVK | 16.42 | 829.43 | 1069.56 | 41 |
| 363 | EQLAFDPQVQQQVK | 16.42 | 829.43 | 1216.63 | 41 |
| 364 | EQVDFVQR | 13.09 | 510.76 | 549.31 | 27 |
| 365 | EQVDFVQR | 13.09 | 510.76 | 664.34 | 27 |
| 366 | EQVDFVQR | 13.09 | 510.76 | 763.41 | 27 |
| 367 | EVGEIR | 9.35 | 351.69 | 474.27 | 20 |
| 368 | EVGEIR | 9.35 | 351.69 | 528.27 | 20 |
| 369 | EVGEIR | 9.35 | 351.69 | 573.34 | 20 |
| 370 | EVGEVR | 6.91 | 344.68 | 460.25 | 20 |
| 371 | EVGEVR | 6.91 | 344.68 | 514.25 | 20 |
| 372 | EVGEVR | 6.91 | 344.68 | 559.32 | 20 |
| 373 | EYLPASTFK | 15.41 | 528.27 | 553.3 | 28 |
| 374 | EYLPASTFK | 15.41 | 528.27 | 650.35 | 28 |
| 375 | EYLPASTFK | 15.41 | 528.27 | 763.43 | 28 |
| 376 | EYLPVSTFK | 17.16 | 542.29 | 581.33 | 29 |
| 377 | EYLPVSTFK | 17.16 | 542.29 | 678.38 | 29 |
| 378 | EYLPVSTFK | 17.16 | 542.29 | 791.47 | 29 |
| 379 | EYNTSGTFVFYDGK | 18.2 | 814.37 | 1033.5 | 41 |
| 380 | EYNTSGTFVFYDGK | 18.2 | 814.37 | 1120.53 | 41 |

TABLE 30-continued

| Transition number | Peptide | Retention time (minutes) | (m/z) filtered in Q1 | (m/z) filtered in Q3 | Collision energy (eV) |
|---|---|---|---|---|---|
| 381 | EYNTSGTFVFYDGK | 18.2 | 814.37 | 1221.58 | 41 |
| 382 | EYVPASTFK | 13.89 | 521.27 | 553.3 | 28 |
| 383 | EYVPASTFK | 13.89 | 521.27 | 650.35 | 28 |
| 384 | EYVPASTFK | 13.89 | 521.27 | 749.42 | 28 |
| 385 | FAPESTFK | 13.67 | 463.73 | 482.26 | 25 |
| 386 | FAPESTFK | 13.67 | 463.73 | 611.3 | 25 |
| 387 | FAPESTFK | 13.67 | 463.73 | 708.36 | 25 |
| 388 | FAQYAK | 9.39 | 364.19 | 509.27 | 21 |
| 389 | FAQYAK | 9.39 | 364.19 | 580.31 | 21 |
| 390 | FAQYAK | 9.39 | 364.19 | 581.27 | 21 |
| 391 | FDYGNR | 10.1 | 386.17 | 509.25 | 22 |
| 392 | FDYGNR | 10.1 | 386.17 | 597.23 | 22 |
| 393 | FDYGNR | 10.09 | 386.17 | 624.27 | 22 |
| 394 | FEDLYK | 13.52 | 407.7 | 423.26 | 23 |
| 395 | FEDLYK | 13.52 | 407.7 | 538.29 | 23 |
| 396 | FEDLYK | 13.52 | 407.7 | 667.33 | 23 |
| 397 | FEDTFHISNQK | 14.33 | 455.89 | 476.25 | 27 |
| 398 | FEDTFHISNQK | 14.33 | 455.89 | 589.33 | 27 |
| 399 | FEDTFHISNQK | 14.33 | 455.89 | 726.39 | 27 |
| 400 | FEDTFHTSNQQHEK | 10.66 | 583.26 | 870.41 | 33 |
| 401 | FEDTFHTSNQQHEK | 10.66 | 583.26 | 971.45 | 33 |
| 402 | FEDTFHTSNQQHEK | 10.66 | 583.26 | 1108.51 | 33 |
| 403 | FEYGNQDVSGDSGK | 11.95 | 751.82 | 764.34 | 38 |
| 404 | FEYGNQDVSGDSGK | 11.95 | 751.82 | 1063.47 | 38 |
| 405 | FEYGNQDVSGDSGK | 11.95 | 751.82 | 1226.53 | 38 |
| 406 | FFSDFQAK | 16 | 495.24 | 608.3 | 27 |
| 407 | FFSDFQAK | 16 | 495.24 | 695.34 | 27 |
| 408 | FFSDFQAK | 16 | 495.24 | 842.4 | 27 |
| 409 | FFSDLQAEGAIVIADER | 20.44 | 627.65 | 1143.6 | 35 |
| 410 | FFSDLQAEGAIVIADER | 20.43 | 940.97 | 1143.6 | 46 |
| 411 | FFSDLQAEGAIVIADER | 20.44 | 940.97 | 1179.57 | 46 |
| 412 | FFSDLR | 15.38 | 392.7 | 490.26 | 22 |
| 413 | FFSDLR | 15.38 | 392.7 | 610.29 | 22 |
| 414 | FFSDLR | 15.38 | 392.7 | 637.33 | 22 |
| 415 | FFSEFQAK | 16.13 | 502.25 | 622.32 | 27 |
| 416 | FFSEFQAK | 16.13 | 502.25 | 709.35 | 27 |
| 417 | FFSEFQAK | 16.13 | 502.25 | 856.42 | 27 |
| 418 | FGLEGQLR | 15.8 | 460.25 | 473.28 | 25 |

TABLE 30-continued

| Transition number | Peptide | Retention time (minutes) | (m/z) filtered in Q1 | (m/z) filtered in Q3 | Collision energy (eV) |
|---|---|---|---|---|---|
| 419 | FGLEGQLR | 15.8 | 460.25 | 602.33 | 25 |
| 420 | FGLEGQLR | 15.8 | 460.25 | 772.43 | 25 |
| 421 | FLESLYLNNLPASK | 20.75 | 804.94 | 856.49 | 40 |
| 422 | FLESLYLNNLPASK | 20.75 | 804.94 | 1019.55 | 40 |
| 423 | FLESLYLNNLPASK | 20.75 | 804.94 | 1219.67 | 40 |
| 424 | FLLEGQLR | 18.06 | 488.28 | 602.33 | 26 |
| 425 | FLLEGQLR | 18.06 | 488.28 | 715.41 | 26 |
| 426 | FLLEGQLR | 18.06 | 488.28 | 828.49 | 26 |
| 427 | FQQYVDR | 11.19 | 478.24 | 552.28 | 26 |
| 428 | FQQYVDR | 11.19 | 478.24 | 680.34 | 26 |
| 429 | FQQYVDR | 11.19 | 478.24 | 808.39 | 26 |
| 430 | FSDYVQR | 11.83 | 457.72 | 565.31 | 25 |
| 431 | FSDYVQR | 11.83 | 457.72 | 680.34 | 25 |
| 432 | FSDYVQR | 11.83 | 457.72 | 767.37 | 25 |
| 433 | FSTASTFK | 12.71 | 444.73 | 553.3 | 25 |
| 434 | FSTASTFK | 12.7 | 444.73 | 654.35 | 25 |
| 435 | FSTASTFK | 12.7 | 444.73 | 741.38 | 25 |
| 436 | FSWDGK | 14.32 | 370.17 | 505.24 | 21 |
| 437 | FSWDGK | 14.32 | 370.17 | 592.27 | 21 |
| 438 | FSWDGK | 14.32 | 370.17 | 593.24 | 21 |
| 439 | FSYGNQNISGGIDK | 14.61 | 750.36 | 803.43 | 38 |
| 440 | FSYGNQNISGGIDK | 14.61 | 750.36 | 1045.53 | 38 |
| 441 | FSYGNQNISGGIDK | 14.61 | 750.36 | 1102.55 | 38 |
| 442 | FSYGNQNISGGTDK | 12.74 | 744.34 | 791.39 | 38 |
| 443 | FSYGNQNISGGTDK | 12.74 | 744.34 | 1033.49 | 38 |
| 444 | FSYGNQNISGGTDK | 12.74 | 744.34 | 1090.51 | 38 |
| 445 | FSYGSQNISGGIDK | 14.74 | 736.85 | 803.43 | 37 |
| 446 | FSYGSQNISGGIDK | 14.74 | 736.85 | 1075.54 | 37 |
| 447 | FSYGSQNISGGIDK | 14.75 | 736.85 | 1238.6 | 37 |
| 448 | FTEYVK | 11.81 | 393.71 | 538.29 | 22 |
| 449 | FTEYVK | 11.81 | 393.71 | 639.33 | 22 |
| 450 | FTEYVK | 11.81 | 393.71 | 640.3 | 22 |
| 451 | FVPASTYK | 11.76 | 456.74 | 498.26 | 25 |
| 452 | FVPASTYK | 11.76 | 456.74 | 569.29 | 25 |
| 453 | FVPASTYK | 11.77 | 456.74 | 666.35 | 25 |
| 454 | FVYDLAQGQLPFKPEVQQQVK | 20.48 | 821.44 | 955.52 | 45 |
| 455 | FVYDLAQGQLPFKPEVQQQVK | 20.48 | 821.44 | 1108.59 | 45 |
| 456 | FVYDLAQGQLPFKPEVQQQVK | 20.49 | 821.44 | 1109.07 | 45 |

TABLE 30-continued

| Transition number | Peptide | Retention time (minutes) | (m/z) filtered in Q1 | (m/z) filtered in Q3 | Collision energy (eV) |
|---|---|---|---|---|---|
| 457 | FWLEDQLR | 20.39 | 553.79 | 660.33 | 29 |
| 458 | FWLEDQLR | 20.39 | 553.79 | 773.42 | 29 |
| 459 | FWLEDQLR | 20.38 | 553.79 | 959.49 | 29 |
| 460 | FWLEGPLK | 20.63 | 495.28 | 543.31 | 27 |
| 461 | FWLEGPLK | 20.63 | 495.28 | 656.4 | 27 |
| 462 | FWLEGPLK | 20.63 | 495.28 | 842.48 | 27 |
| 463 | FWLEGQLR | 19.49 | 524.78 | 602.33 | 28 |
| 464 | FWLEGQLR | 19.49 | 524.78 | 715.41 | 28 |
| 465 | FWLEGQLR | 19.48 | 524.78 | 901.49 | 28 |
| 466 | FYPASSFK | 14.74 | 473.74 | 636.34 | 26 |
| 467 | FYPASSFK | 14.74 | 473.74 | 799.4 | 26 |
| 468 | FYPASSFK | 14.74 | 473.74 | 800.36 | 26 |
| 469 | FYPASTFK | 14.98 | 480.74 | 553.3 | 26 |
| 470 | FYPASTFK | 14.99 | 480.74 | 650.35 | 26 |
| 471 | FYPASTFK | 14.98 | 480.74 | 813.41 | 26 |
| 472 | GAIQVSAVPVFQQIAR | 21.6 | 842.48 | 958.55 | 42 |
| 473 | GAIQVSAVPVFQQIAR | 21.6 | 842.48 | 1057.62 | 42 |
| 474 | GAIQVSAVPVFQQIAR | 21.59 | 842.48 | 1128.65 | 42 |
| 475 | GAIQVSAVPVFQQITR | 21.52 | 857.49 | 988.56 | 43 |
| 476 | GAIQVSAVPVFQQITR | 21.51 | 857.49 | 1087.63 | 43 |
| 477 | GAIQVSAVPVFQQITR | 21.52 | 857.49 | 1158.66 | 43 |
| 478 | GELPVSEDALEMTK | 18.1 | 759.87 | 936.43 | 38 |
| 479 | GELPVSEDALEMTK | 18.11 | 759.87 | 1023.47 | 38 |
| 480 | GELPVSEDALEMTK | 18.11 | 759.87 | 1122.53 | 38 |
| 481 | GISSSVR | 8.65 | 353.2 | 448.25 | 21 |
| 482 | GISSSVR | 8.65 | 353.2 | 535.28 | 21 |
| 483 | GISSSVR | 8.67 | 353.2 | 648.37 | 21 |
| 484 | GNQTLVFAR | 14.83 | 503.28 | 605.38 | 27 |
| 485 | GNQTLVFAR | 14.83 | 503.28 | 706.42 | 27 |
| 486 | GNQTLVFAR | 14.83 | 503.28 | 834.48 | 27 |
| 487 | GPLEISAFEEAR | 18.95 | 659.84 | 809.38 | 34 |
| 488 | GPLEISAFEEAR | 18.94 | 659.84 | 922.46 | 34 |
| 489 | GPLEISAFEEAR | 18.94 | 659.84 | 1051.51 | 34 |
| 490 | GPLTITPIQEVK | 18.14 | 648.38 | 814.47 | 34 |
| 491 | GPLTITPIQEVK | 18.15 | 648.38 | 927.55 | 34 |
| 492 | GPLTITPIQEVK | 18.14 | 648.38 | 1028.6 | 34 |
| 493 | GSLLLWDQK | 19.61 | 530.3 | 576.28 | 28 |
| 494 | GSLLLWDQK | 19.61 | 530.3 | 689.36 | 28 |

TABLE 30-continued

| Transition number | Peptide | Retention time (minutes) | (m/z) filtered in Q1 | (m/z) filtered in Q3 | Collision energy (eV) |
|---|---|---|---|---|---|
| 495 | GSLLLWDQK | 19.61 | 530.3 | 802.45 | 28 |
| 496 | GTFVLYDVQR | 17.93 | 599.32 | 680.34 | 31 |
| 497 | GTFVLYDVQR | 17.93 | 599.32 | 793.42 | 31 |
| 498 | GTFVLYDVQR | 17.93 | 599.32 | 892.49 | 31 |
| 499 | GTIVVADER | 11.82 | 480.26 | 490.23 | 26 |
| 500 | GTIVVADER | 11.82 | 480.26 | 589.29 | 26 |
| 501 | GTIVVADER | 11.82 | 480.26 | 688.36 | 26 |
| 502 | GTIVVLDAR | 15.77 | 472.28 | 573.34 | 26 |
| 503 | GTIVVLDAR | 15.77 | 472.28 | 672.4 | 26 |
| 504 | GTIVVLDAR | 15.77 | 472.28 | 785.49 | 26 |
| 505 | GTIVVVDER | 13.6 | 494.28 | 518.26 | 27 |
| 506 | GTIVVVDER | 13.6 | 494.28 | 617.33 | 27 |
| 507 | GTIVVVDER | 13.6 | 494.28 | 716.39 | 27 |
| 508 | GTLPFSAR | 14.96 | 424.73 | 577.31 | 24 |
| 509 | GTLPFSAR | 14.96 | 424.73 | 690.39 | 24 |
| 510 | GTLPFSAR | 14.97 | 424.73 | 791.44 | 24 |
| 511 | HIADSK | 11.91 | 335.68 | 420.21 | 20 |
| 512 | HIADSK | 11.9 | 335.68 | 524.25 | 20 |
| 513 | HIADSK | 11.91 | 335.68 | 533.29 | 20 |
| 514 | HNGTDGAWIISSLR | 19.36 | 509.6 | 575.35 | 29 |
| 515 | HNGTDGAWIISSLR | 19.35 | 509.6 | 653.26 | 29 |
| 516 | HNGTDGAWIISSLR | 19.36 | 509.6 | 688.44 | 29 |
| 517 | HTLSVFDQER | 14.25 | 411.21 | 432.22 | 25 |
| 518 | HTLSVFDQER | 14.25 | 411.21 | 547.25 | 25 |
| 519 | HTLSVFDQER | 14.25 | 411.21 | 694.32 | 25 |
| 520 | HVTFASFR | 14.36 | 322.17 | 338.18 | 20 |
| 521 | HVTFASFR | 14.36 | 322.17 | 409.22 | 20 |
| 522 | HVTFASFR | 14.36 | 322.17 | 485.25 | 20 |
| 523 | IAISLMGYDAGFLR | 23.93 | 763.91 | 898.44 | 39 |
| 524 | IAISLMGYDAGFLR | 23.93 | 763.91 | 1029.48 | 39 |
| 525 | IAISLMGYDAGFLR | 23.94 | 763.91 | 1229.6 | 39 |
| 526 | IALSLMGFDSGILK | 24.91 | 732.91 | 836.45 | 37 |
| 527 | IALSLMGFDSGILK | 24.91 | 732.91 | 967.49 | 37 |
| 528 | IALSLMGFDSGILK | 24.91 | 732.91 | 1167.61 | 37 |
| 529 | IANALIGLENHK | 15.95 | 431.58 | 697.36 | 26 |
| 530 | IANALIGLENHK | 15.95 | 646.87 | 697.36 | 33 |
| 531 | IANALIGLENHK | 15.95 | 646.87 | 810.45 | 33 |
| 532 | IDTFWLDNSLK | 21.79 | 676.35 | 689.38 | 35 |

TABLE 30-continued

| Transition number | Peptide | Retention time (minutes) | (m/z) filtered in Q1 | (m/z) filtered in Q3 | Collision energy (eV) |
|---|---|---|---|---|---|
| 533 | IDTFWLDNSLK | 21.79 | 676.35 | 875.46 | 35 |
| 534 | IDTFWLDNSLK | 21.79 | 676.35 | 1123.58 | 35 |
| 535 | IDYYNLDR | 14.85 | 536.26 | 680.34 | 29 |
| 536 | IDYYNLDR | 14.85 | 536.26 | 843.4 | 29 |
| 537 | IDYYNLDR | 14.85 | 536.26 | 958.43 | 29 |
| 538 | IFNALIALDSGVIK | 24.74 | 737.44 | 802.47 | 37 |
| 539 | IFNALIALDSGVIK | 24.74 | 737.44 | 915.55 | 37 |
| 540 | IFNALIALDSGVIK | 24.74 | 737.44 | 1028.64 | 37 |
| 541 | IFNSLLALDSGALDNER | 22.76 | 924.48 | 976.43 | 46 |
| 542 | IFNSLLALDSGALDNER | 22.77 | 924.48 | 1089.52 | 46 |
| 543 | IFNSLLALDSGALDNER | 22.76 | 924.48 | 1160.55 | 46 |
| 544 | IFNTLIGLENGIVK | 23.29 | 765.95 | 829.48 | 39 |
| 545 | IFNTLIGLENGIVK | 23.3 | 765.95 | 942.56 | 39 |
| 546 | IFNTLIGLENGIVK | 23.3 | 765.95 | 1055.65 | 39 |
| 547 | IGLDLMQK | 17.7 | 459.26 | 634.32 | 25 |
| 548 | IGLDLMQK | 17.7 | 459.26 | 747.41 | 25 |
| 549 | IGLDLMQK | 17.7 | 459.26 | 804.43 | 25 |
| 550 | IGLEK | 8.54 | 280.18 | 389.24 | 17 |
| 551 | IGLEK | 8.55 | 280.18 | 413.24 | 17 |
| 552 | IGLEK | 8.54 | 280.18 | 446.26 | 17 |
| 553 | IGLELMQQEVQR | 18.73 | 722.38 | 787.41 | 37 |
| 554 | IGLELMQQEVQR | 18.73 | 722.38 | 918.45 | 37 |
| 555 | IGLELMQQEVQR | 18.73 | 722.38 | 1031.53 | 37 |
| 556 | IGLELMSK | 17.52 | 445.75 | 478.27 | 25 |
| 557 | IGLELMSK | 17.52 | 445.75 | 720.4 | 25 |
| 558 | IGLELMSK | 17.52 | 445.75 | 777.42 | 25 |
| 559 | IGLELMSNEVK | 18.73 | 616.83 | 707.34 | 32 |
| 560 | IGLELMSNEVK | 18.73 | 616.83 | 820.42 | 32 |
| 561 | IGLELMSNEVK | 18.73 | 616.83 | 949.47 | 32 |
| 562 | IGLER | 10.96 | 294.18 | 304.16 | 18 |
| 563 | IGLER | 10.96 | 294.18 | 417.25 | 18 |
| 564 | IGLER | 10.96 | 294.18 | 474.27 | 18 |
| 565 | IGLNK | 9.59 | 272.68 | 374.24 | 17 |
| 566 | IGLNK | 9.59 | 272.68 | 398.24 | 17 |
| 567 | IGLNK | 9.59 | 272.68 | 431.26 | 17 |
| 568 | IGLNLMQK | 17.1 | 458.77 | 633.34 | 25 |
| 569 | IGLNLMQK | 17.09 | 458.77 | 746.42 | 25 |
| 570 | IGLNLMQK | 17.11 | 458.77 | 803.44 | 25 |

TABLE 30-continued

| Transition number | Peptide | Retention time (minutes) | (m/z) filtered in Q1 | (m/z) filtered in Q3 | Collision energy (eV) |
|---|---|---|---|---|---|
| 571 | IGPSLMQSELQR | 17.02 | 679.86 | 760.39 | 35 |
| 572 | IGPSLMQSELQR | 17.02 | 679.86 | 891.44 | 35 |
| 573 | IGPSLMQSELQR | 17.02 | 679.86 | 1188.6 | 35 |
| 574 | IGYGNMQIGTEVDQFWLK | 24.31 | 700.35 | 935.5 | 39 |
| 575 | IGYGNMQIGTEVDQFWLK | 24.32 | 1050.02 | 1164.54 | 51 |
| 576 | IGYGNMQIGTEVDQFWLK | 24.3 | 1050.02 | 1222.61 | 51 |
| 577 | IINHNLPVK | 11.88 | 349.88 | 456.32 | 21 |
| 578 | IINHNLPVK | 11.88 | 349.88 | 570.36 | 21 |
| 579 | IINHNLPVK | 11.88 | 349.88 | 592.32 | 21 |
| 580 | IINHNLPVR | 12.04 | 359.22 | 598.37 | 22 |
| 581 | IINHNLPVR | 12.04 | 538.32 | 598.37 | 29 |
| 582 | IINHNLPVR | 12.04 | 538.32 | 849.47 | 29 |
| 583 | ILFQQGTQQAC[CAM]AER | 14.51 | 550.61 | 606.27 | 32 |
| 584 | ILFQQGTQQAC[CAM]AER | 14.51 | 825.41 | 1020.45 | 41 |
| 585 | ILFQQGTQQAC[CAM]AER | 14.51 | 825.41 | 1148.51 | 41 |
| 586 | ILNNWFK | 18.98 | 467.76 | 594.3 | 26 |
| 587 | ILNNWFK | 18.98 | 467.76 | 708.35 | 26 |
| 588 | ILNNWFK | 18.97 | 467.76 | 821.43 | 26 |
| 589 | ILNTLISLEEK | 19.98 | 636.87 | 718.4 | 33 |
| 590 | ILNTLISLEEK | 19.98 | 636.87 | 1046.57 | 33 |
| 591 | ILNTLISLEEK | 19.98 | 636.87 | 1159.66 | 33 |
| 592 | INIVK | 11.43 | 293.7 | 359.27 | 18 |
| 593 | INIVK | 11.43 | 293.7 | 440.29 | 18 |
| 594 | INIVK | 11.43 | 293.7 | 473.31 | 18 |
| 595 | INLYGNALSR | 16.05 | 560.81 | 617.34 | 30 |
| 596 | INLYGNALSR | 16.05 | 560.81 | 780.4 | 30 |
| 597 | INLYGNALSR | 16.05 | 560.81 | 893.48 | 30 |
| 598 | IPFSLNLEMK | 21.68 | 596.33 | 834.44 | 31 |
| 599 | IPFSLNLEMK | 21.67 | 596.33 | 981.51 | 31 |
| 600 | IPFSLNLEMK | 21.67 | 596.33 | 1078.56 | 31 |
| 601 | IPHTLFALDADAVR | 20 | 513.62 | 531.29 | 30 |
| 602 | IPHTLFALDADAVR | 20 | 513.62 | 646.32 | 30 |
| 603 | IPHTLFALDADAVR | 20 | 769.92 | 1191.64 | 39 |
| 604 | IPHTLFALDAGAAR | 18.58 | 726.9 | 744.4 | 37 |
| 605 | IPHTLFALDAGAAR | 18.58 | 726.9 | 891.47 | 37 |
| 606 | IPHTLFALDAGAAR | 18.58 | 726.9 | 1004.55 | 37 |
| 607 | IPHTLFALDAGAVR | 19.72 | 494.28 | 588.31 | 29 |
| 608 | IPHTLFALDAGAVR | 19.71 | 494.28 | 780.44 | 29 |

TABLE 30-continued

| Transition number | Peptide | Retention time (minutes) | (m/z) filtered in Q1 | (m/z) filtered in Q3 | Collision energy (eV) |
|---|---|---|---|---|---|
| 609 | IPHTLFALDAGAVR | 19.72 | 740.92 | 1133.63 | 38 |
| 610 | IPNAIIGLETGVIK | 21.75 | 719.44 | 816.48 | 37 |
| 611 | IPNAIIGLETGVIK | 21.75 | 719.44 | 929.57 | 37 |
| 612 | IPNAIIGLETGVIK | 21.75 | 719.44 | 1227.73 | 37 |
| 613 | IPNALIGLETGAIK | 20.96 | 705.42 | 788.45 | 36 |
| 614 | IPNALIGLETGAIK | 20.96 | 705.42 | 901.54 | 36 |
| 615 | IPNALIGLETGAIK | 20.96 | 705.42 | 1014.62 | 36 |
| 616 | IPNSLIAFDTGAVR | 20.24 | 737.41 | 765.39 | 37 |
| 617 | IPNSLIAFDTGAVR | 20.24 | 737.41 | 836.43 | 37 |
| 618 | IPNSLIAFDTGAVR | 20.24 | 737.41 | 949.51 | 37 |
| 619 | IPSAIIGLETGVIK | 21.66 | 705.93 | 816.48 | 36 |
| 620 | IPSAIIGLETGVIK | 21.67 | 705.93 | 929.57 | 36 |
| 621 | IPSAIIGLETGVIK | 21.66 | 705.93 | 1200.72 | 36 |
| 622 | ISAFNQVK | 13.02 | 453.76 | 488.28 | 25 |
| 623 | ISAFNQVK | 13.02 | 453.76 | 706.39 | 25 |
| 624 | ISAFNQVK | 13.02 | 453.76 | 793.42 | 25 |
| 625 | ISAHEQILFLR | 18.28 | 442.92 | 548.36 | 26 |
| 626 | ISAHEQILFLR | 18.28 | 442.92 | 789.5 | 26 |
| 627 | ISAHEQILFLR | 18.28 | 663.88 | 918.54 | 34 |
| 628 | ISAMEQTR | 9.84 | 468.23 | 664.31 | 26 |
| 629 | ISAMEQTR | 9.84 | 468.23 | 735.35 | 26 |
| 630 | ISAMEQTR | 9.84 | 468.23 | 822.38 | 26 |
| 631 | ISAMEQVK | 11.65 | 453.24 | 634.32 | 25 |
| 632 | ISAMEQVK | 11.65 | 453.24 | 705.36 | 25 |
| 633 | ISAMEQVK | 11.65 | 453.24 | 792.39 | 25 |
| 634 | ISATEQVAFLR | 17.7 | 412.23 | 435.27 | 25 |
| 635 | ISATEQVAFLR | 17.71 | 412.23 | 506.31 | 25 |
| 636 | ISATEQVAFLR | 17.7 | 412.23 | 605.38 | 25 |
| 637 | ISATQQIAFLR | 18.58 | 624.36 | 747.45 | 32 |
| 638 | ISATQQIAFLR | 18.58 | 624.36 | 1047.59 | 32 |
| 639 | ISATQQIAFLR | 18.58 | 624.36 | 1134.63 | 32 |
| 640 | ISAVNQVEFLESLFLNK | 28.77 | 976.03 | 988.51 | 48 |
| 641 | ISAVNQVEFLESLFLNK | 28.77 | 976.03 | 1110.62 | 48 |
| 642 | ISAVNQVEFLESLFLNK | 28.77 | 976.03 | 1239.66 | 48 |
| 643 | ISAVNQVK | 10.32 | 429.76 | 488.28 | 24 |
| 644 | ISAVNQVK | 10.32 | 429.76 | 658.39 | 24 |
| 645 | ISAVNQVK | 10.32 | 429.76 | 745.42 | 24 |
| 646 | ISPEEQIQFLR | 18.87 | 680.37 | 933.52 | 35 |

TABLE 30-continued

| Transition number | Peptide | Retention time (minutes) | (m/z) filtered in Q1 | (m/z) filtered in Q3 | Collision energy (eV) |
|---|---|---|---|---|---|
| 647 | ISPEEQIQFLR | 18.87 | 680.37 | 1062.56 | 35 |
| 648 | ISPEEQIQFLR | 18.87 | 680.37 | 1159.61 | 35 |
| 649 | ISPEEQVR | 10.49 | 479.25 | 531.29 | 26 |
| 650 | ISPEEQVR | 10.49 | 479.25 | 660.33 | 26 |
| 651 | ISPEEQVR | 10.49 | 479.25 | 757.38 | 26 |
| 652 | ISPEGQVR | 9.86 | 443.24 | 459.27 | 25 |
| 653 | ISPEGQVR | 9.86 | 443.24 | 588.31 | 25 |
| 654 | ISPEGQVR | 9.86 | 443.24 | 685.36 | 25 |
| 655 | ISPLEQLAFLR | 24.02 | 643.88 | 876.49 | 33 |
| 656 | ISPLEQLAFLR | 24.01 | 643.88 | 989.58 | 33 |
| 657 | ISPLEQLAFLR | 24.02 | 643.88 | 1086.63 | 33 |
| 658 | ITAFQQVDFLR | 21.11 | 669.36 | 777.43 | 34 |
| 659 | ITAFQQVDFLR | 21.12 | 669.36 | 905.48 | 34 |
| 660 | ITAFQQVDFLR | 21.12 | 669.36 | 1123.59 | 34 |
| 661 | ITPIQEVNFADDFANNR | 21.25 | 655.32 | 736.34 | 37 |
| 662 | ITPIQEVNFADDFANNR | 21.25 | 655.32 | 851.36 | 37 |
| 663 | ITPIQEVNFADDFANNR | 21.25 | 655.32 | 922.4 | 37 |
| 664 | ITPIQEVNFADDLANNR | 20.95 | 643.99 | 817.38 | 36 |
| 665 | ITPIQEVNFADDLANNR | 20.95 | 965.49 | 1149.53 | 47 |
| 666 | ITPIQEVNFADDLANNR | 20.96 | 965.49 | 1248.6 | 47 |
| 667 | ITPQQEAQFAYK | 14.52 | 712.36 | 856.42 | 36 |
| 668 | ITPQQEAQFAYK | 14.52 | 712.36 | 984.48 | 36 |
| 669 | ITPQQEAQFAYK | 14.52 | 712.36 | 1209.59 | 36 |
| 670 | ITPQQEAQFTYK | 14.33 | 485.25 | 558.29 | 28 |
| 671 | ITPQQEAQFTYK | 14.33 | 727.37 | 1014.49 | 37 |
| 672 | ITPQQEAQFTYK | 14.33 | 727.37 | 1239.6 | 37 |
| 673 | ITPVQEVNFADDLAHNR | 18.98 | 646.99 | 840.4 | 36 |
| 674 | ITPVQEVNFADDLAHNR | 18.98 | 646.99 | 862.92 | 36 |
| 675 | ITPVQEVNFADDLAHNR | 18.98 | 646.99 | 911.43 | 36 |
| 676 | IVAFALK | 17.21 | 381.25 | 478.3 | 22 |
| 677 | IVAFALK | 17.22 | 381.25 | 549.34 | 22 |
| 678 | IVAFALK | 17.21 | 381.25 | 648.41 | 22 |
| 679 | IVAFALNMEMR | 17.95 | 647.84 | 864.41 | 34 |
| 680 | IVAFALNMEMR | 17.95 | 647.84 | 1011.48 | 34 |
| 681 | IVAFALNMEMR | 17.97 | 647.84 | 1082.51 | 34 |
| 682 | IVESTTLADGTVVHGK | 13.69 | 542.96 | 697.4 | 31 |
| 683 | IVESTTLADGTVVHGK | 13.69 | 542.96 | 812.43 | 31 |
| 684 | IVESTTLADGTVVHGK | 13.68 | 542.96 | 883.46 | 31 |

TABLE 30-continued

| Transition number | Peptide | Retention time (minutes) | (m/z) filtered in Q1 | (m/z) filtered in Q3 | Collision energy (eV) |
|---|---|---|---|---|---|
| 685 | IYNSLIGLNEK | 17.37 | 632.35 | 673.39 | 33 |
| 686 | IYNSLIGLNEK | 17.37 | 632.35 | 786.47 | 33 |
| 687 | IYNSLIGLNEK | 17.37 | 632.35 | 987.55 | 33 |
| 688 | KPDIGWWVGWIER | 24.47 | 547.96 | 660.35 | 31 |
| 689 | KPDIGWWVGWIER | 24.47 | 547.96 | 883.45 | 31 |
| 690 | KPDIGWWVGWIER | 24.46 | 821.43 | 1188.59 | 41 |
| 691 | LAC[CAM]ATNNLAR | 11.22 | 552.28 | 688.37 | 29 |
| 692 | LAC[CAM]ATNNLAR | 11.22 | 552.28 | 759.41 | 29 |
| 693 | LAC[CAM]ATNNLAR | 11.22 | 552.28 | 919.44 | 29 |
| 694 | LAQGELPFPAPVQSTVR | 19.84 | 905.5 | 954.54 | 45 |
| 695 | LAQGELPFPAPVQSTVR | 19.84 | 905.5 | 1101.61 | 45 |
| 696 | LAQGELPFPAPVQSTVR | 19.84 | 905.5 | 1198.66 | 45 |
| 697 | LAQNELPYPIEIQK | 19.09 | 828.45 | 929.47 | 41 |
| 698 | LAQNELPYPIEIQK | 19.09 | 828.45 | 987.55 | 41 |
| 699 | LAQNELPYPIEIQK | 19.08 | 828.45 | 1100.64 | 41 |
| 700 | LAQNELQYPIEIQK | 17.98 | 843.96 | 890.5 | 42 |
| 701 | LAQNELQYPIEIQK | 17.98 | 843.96 | 1018.56 | 42 |
| 702 | LAQNELQYPIEIQK | 17.98 | 843.96 | 1131.64 | 42 |
| 703 | LDFGNK | 11.75 | 347.18 | 465.25 | 20 |
| 704 | LDFGNK | 11.74 | 347.18 | 547.25 | 20 |
| 705 | LDFGNK | 11.75 | 347.18 | 580.27 | 20 |
| 706 | LDGSLNR | 9.48 | 387.71 | 402.25 | 22 |
| 707 | LDGSLNR | 9.48 | 387.71 | 546.3 | 22 |
| 708 | LDGSLNR | 9.48 | 387.71 | 661.33 | 22 |
| 709 | LEILQQALAELGLYPK | 29.81 | 900.02 | 1003.58 | 45 |
| 710 | LEILQQALAELGLYPK | 29.81 | 900.02 | 1074.62 | 45 |
| 711 | LEILQQALAELGLYPK | 29.81 | 900.02 | 1202.68 | 45 |
| 712 | LENQEQVK | 7.6 | 494.26 | 631.34 | 27 |
| 713 | LENQEQVK | 7.59 | 494.26 | 745.38 | 27 |
| 714 | LENQEQVK | 7.59 | 494.26 | 874.43 | 27 |
| 715 | LETQEEVEK | 9.88 | 552.77 | 633.31 | 29 |
| 716 | LETQEEVEK | 9.88 | 552.77 | 862.42 | 29 |
| 717 | LETQEEVEK | 9.88 | 552.77 | 991.46 | 29 |
| 718 | LETQEEVK | 9.5 | 488.25 | 504.27 | 26 |
| 719 | LETQEEVK | 9.49 | 488.25 | 733.37 | 26 |
| 720 | LETQEEVK | 9.49 | 488.25 | 862.42 | 26 |
| 721 | LFAAEGVK | 13.53 | 417.74 | 503.28 | 23 |
| 722 | LFAAEGVK | 13.53 | 417.74 | 574.32 | 23 |

TABLE 30-continued

| Transition number | Peptide | Retention time (minutes) | (m/z) filtered in Q1 | (m/z) filtered in Q3 | Collision energy (eV) |
|---|---|---|---|---|---|
| 723 | LFAAEGVK | 13.53 | 417.74 | 721.39 | 23 |
| 724 | LFESAGVK | 12.99 | 425.74 | 461.27 | 24 |
| 725 | LFESAGVK | 12.99 | 425.74 | 590.31 | 24 |
| 726 | LFESAGVK | 12.99 | 425.74 | 737.38 | 24 |
| 727 | LFGAAGVK | 13.94 | 381.73 | 445.28 | 22 |
| 728 | LFGAAGVK | 13.94 | 381.73 | 502.3 | 22 |
| 729 | LFGAAGVK | 13.94 | 381.73 | 649.37 | 22 |
| 730 | LGVDR | 8.51 | 280.16 | 290.15 | 17 |
| 731 | LGVDR | 8.51 | 280.16 | 389.21 | 17 |
| 732 | LGVDR | 8.5 | 280.16 | 446.24 | 17 |
| 733 | LLNLLSQSK | 17.97 | 508.31 | 562.32 | 27 |
| 734 | LLNLLSQSK | 17.97 | 508.31 | 789.45 | 27 |
| 735 | LLNLLSQSK | 17.97 | 508.31 | 902.53 | 27 |
| 736 | LLQDER | 9.34 | 387.21 | 547.25 | 22 |
| 737 | LLQDER | 9.31 | 387.21 | 599.3 | 22 |
| 738 | LLQDER | 9.34 | 387.21 | 660.33 | 22 |
| 739 | LLVQDGDC[CAM]GR | 11.92 | 566.77 | 679.25 | 30 |
| 740 | LLVQDGDC[CAM]GR | 11.92 | 566.77 | 807.3 | 30 |
| 741 | LLVQDGDC[CAM]GR | 11.92 | 566.77 | 906.37 | 30 |
| 742 | LNEVGYGNR | 10.74 | 511.26 | 566.27 | 27 |
| 743 | LNEVGYGNR | 10.74 | 511.26 | 665.34 | 27 |
| 744 | LNEVGYGNR | 10.73 | 511.26 | 794.38 | 27 |
| 745 | LNYGNADPSTK | 10.76 | 590.29 | 732.35 | 31 |
| 746 | LNYGNADPSTK | 10.76 | 590.29 | 789.37 | 31 |
| 747 | LNYGNADPSTK | 10.76 | 590.29 | 952.44 | 31 |
| 748 | LNYGNK | 7.21 | 354.69 | 481.24 | 21 |
| 749 | LNYGNK | 7.24 | 354.69 | 562.26 | 21 |
| 750 | LNYGNK | 7.22 | 354.69 | 595.28 | 21 |
| 751 | LPASK | 1.93 | 258.16 | 305.18 | 16 |
| 752 | LPASK | 1.93 | 258.16 | 369.21 | 16 |
| 753 | LPASK | 1.93 | 258.16 | 402.23 | 16 |
| 754 | LPHTLFALDADAVR | 19.98 | 769.92 | 977.51 | 39 |
| 755 | LPHTLFALDADAVR | 19.98 | 769.92 | 1090.59 | 39 |
| 756 | LPHTLFALDADAVR | 19.98 | 769.92 | 1191.64 | 39 |
| 757 | LPHTLFALDAGAVR | 19.7 | 740.92 | 919.5 | 38 |
| 758 | LPHTLFALDAGAVR | 19.67 | 740.92 | 1032.58 | 38 |
| 759 | LPHTLFALDAGAVR | 19.7 | 740.92 | 1133.63 | 38 |
| 760 | LPLAIMGFDSGILQSPK | 25.08 | 893.99 | 944.5 | 44 |

TABLE 30-continued

| Transition number | Peptide | Retention time (minutes) | (m/z) filtered in Q1 | (m/z) filtered in Q3 | Collision energy (eV) |
|---|---|---|---|---|---|
| 761 | LPLAIMGFDSGILQSPK | 25.08 | 893.99 | 1091.57 | 44 |
| 762 | LPLAIMGFDSGILQSPK | 25.08 | 893.99 | 1148.59 | 44 |
| 763 | LPLAIMGYDADILLDATTPR | 27.86 | 720.39 | 773.42 | 40 |
| 764 | LPLAIMGYDADILLDATTPR | 27.87 | 720.39 | 886.5 | 40 |
| 765 | LPLAIMGYDADILLDATTPR | 27.87 | 720.39 | 1160.57 | 40 |
| 766 | LPSSLIALETGAVR | 20.6 | 713.92 | 816.46 | 36 |
| 767 | LPSSLIALETGAVR | 20.6 | 713.92 | 929.54 | 36 |
| 768 | LPSSLIALETGAVR | 20.6 | 713.92 | 1216.69 | 36 |
| 769 | LPVSAQTLQYTANILK | 21.84 | 880.5 | 950.53 | 44 |
| 770 | LPVSAQTLQYTANILK | 21.84 | 880.5 | 1063.61 | 44 |
| 771 | LPVSAQTLQYTANILK | 21.85 | 880.5 | 1164.66 | 44 |
| 772 | LPVSER | 9.57 | 350.7 | 490.26 | 20 |
| 773 | LPVSER | 9.57 | 350.7 | 526.29 | 20 |
| 774 | LPVSER | 9.57 | 350.7 | 587.31 | 20 |
| 775 | LPVSPTAVDMTER | 16.21 | 708.36 | 1019.48 | 36 |
| 776 | LPVSPTAVDMTER | 16.21 | 708.36 | 1106.51 | 36 |
| 777 | LPVSPTAVDMTER | 16.21 | 708.36 | 1205.58 | 36 |
| 778 | LSASK | 10.72 | 253.15 | 305.18 | 16 |
| 779 | LSASK | 10.71 | 253.15 | 359.19 | 16 |
| 780 | LSASK | 10.71 | 253.15 | 392.21 | 16 |
| 781 | LSAVPIYQEVAR | 17.96 | 673.38 | 765.39 | 35 |
| 782 | LSAVPIYQEVAR | 17.96 | 673.38 | 975.53 | 35 |
| 783 | LSAVPIYQEVAR | 17.95 | 673.38 | 1074.59 | 35 |
| 784 | LSAVPVYQELAR | 18.45 | 449.25 | 616.34 | 26 |
| 785 | LSAVPVYQELAR | 18.44 | 673.38 | 779.4 | 35 |
| 786 | LSAVPVYQELAR | 18.44 | 673.38 | 975.53 | 35 |
| 787 | LSC[CAM]TLVIDEASGDLLHR | 20.38 | 633.66 | 797.43 | 36 |
| 788 | LSC[CAM]TLVIDEASGDLLHR | 20.38 | 633.66 | 868.46 | 36 |
| 789 | LSC[CAM]TLVIDEASGDLLHR | 20.38 | 633.66 | 1112.53 | 36 |
| 790 | LSLQHGWFIGWIEK | 23.95 | 571.98 | 632.34 | 33 |
| 791 | LSLQHGWFIGWIEK | 23.95 | 571.98 | 892.49 | 33 |
| 792 | LSLQHGWFIGWIEK | 23.95 | 571.98 | 969.49 | 33 |
| 793 | LSQNSLPFSQEAMNSVK | 18.64 | 627.31 | 1140.54 | 35 |
| 794 | LSQNSLPFSQEAMNSVK | 18.63 | 940.46 | 1140.54 | 46 |
| 795 | LSQNSLPFSQEAMNSVK | 18.64 | 940.46 | 1237.59 | 46 |
| 796 | LSVNPK | 9.8 | 329.2 | 457.28 | 19 |
| 797 | LSVNPK | 9.79 | 329.2 | 511.29 | 19 |
| 798 | LSVNPK | 9.8 | 329.2 | 544.31 | 19 |

TABLE 30-continued

| Transition number | Peptide | Retention time (minutes) | (m/z) filtered in Q1 | (m/z) filtered in Q3 | Collision energy (eV) |
|---|---|---|---|---|---|
| 799 | LTVGAR | 9.51 | 308.69 | 402.25 | 19 |
| 800 | LTVGAR | 9.51 | 308.69 | 442.27 | 19 |
| 801 | LTVGAR | 9.51 | 308.69 | 503.29 | 19 |
| 802 | LYGFALNIDMPGGEADIGK | 23.35 | 661 | 843.42 | 37 |
| 803 | LYGFALNIDMPGGEADIGK | 23.35 | 990.99 | 1089.49 | 49 |
| 804 | LYGFALNIDMPGGEADIGK | 23.35 | 990.99 | 1202.57 | 49 |
| 805 | LYHNELPFR | 15.29 | 396.88 | 414.21 | 24 |
| 806 | LYHNELPFR | 15.29 | 396.88 | 419.24 | 24 |
| 807 | LYHNELPFR | 15.29 | 396.88 | 657.3 | 24 |
| 808 | LYHNK | 8.54 | 337.68 | 414.21 | 20 |
| 809 | LYHNK | 8.53 | 337.68 | 528.26 | 20 |
| 810 | LYHNK | 8.53 | 337.68 | 561.28 | 20 |
| 811 | LYQNDLPFR | 17.2 | 583.3 | 761.39 | 31 |
| 812 | LYQNDLPFR | 17.2 | 583.3 | 889.45 | 31 |
| 813 | LYQNDLPFR | 17.2 | 583.3 | 1052.52 | 31 |
| 814 | MDDLFK | 15.5 | 384.68 | 522.29 | 22 |
| 815 | MDDLFK | 15.5 | 384.68 | 622.25 | 22 |
| 816 | MDDLFK | 15.5 | 384.68 | 637.32 | 22 |
| 817 | MEDLHK | 6.66 | 386.69 | 512.28 | 22 |
| 818 | MEDLHK | 6.65 | 386.69 | 626.26 | 22 |
| 819 | MEDLHK | 6.66 | 386.69 | 641.33 | 22 |
| 820 | MLIALIGLENHK | 21.33 | 451.26 | 527.26 | 27 |
| 821 | MLIALIGLENHK | 21.33 | 451.26 | 697.36 | 27 |
| 822 | MLIALIGLENHK | 21.33 | 451.26 | 810.45 | 27 |
| 823 | MLLIK | 15.81 | 309.21 | 373.28 | 19 |
| 824 | MLLIK | 15.81 | 309.21 | 471.3 | 19 |
| 825 | MLLIK | 15.81 | 309.21 | 486.36 | 19 |
| 826 | MLNALIGLEHHK | 16.89 | 459.26 | 550.27 | 27 |
| 827 | MLNALIGLEHHK | 16.89 | 459.26 | 720.38 | 27 |
| 828 | MLNALIGLEHHK | 16.89 | 459.26 | 833.46 | 27 |
| 829 | MLNALIGLENHK | 18.39 | 451.58 | 697.36 | 27 |
| 830 | MLNALIGLENHK | 18.38 | 676.87 | 697.36 | 35 |
| 831 | MLNALIGLENHK | 18.39 | 676.87 | 810.45 | 35 |
| 832 | MLNALIGLENQK | 19.71 | 672.37 | 688.36 | 35 |
| 833 | MLNALIGLENQK | 19.71 | 672.37 | 801.45 | 35 |
| 834 | MLNALIGLENQK | 19.71 | 672.37 | 914.53 | 35 |
| 835 | MLNALIGLEYHK | 19.6 | 701.38 | 746.38 | 36 |
| 836 | MLNALIGLEYHK | 19.6 | 701.38 | 859.47 | 36 |

TABLE 30-continued

| Transition number | Peptide | Retention time (minutes) | (m/z) filtered in Q1 | (m/z) filtered in Q3 | Collision energy (eV) |
|---|---|---|---|---|---|
| 837 | MLNALIGLEYHK | 19.6 | 701.38 | 1157.63 | 36 |
| 838 | MLNALIGLQHGK | 17.5 | 432.25 | 582.34 | 26 |
| 839 | MLNALIGLQHGK | 17.5 | 432.25 | 639.36 | 26 |
| 840 | MLNALIGLQHGK | 17.5 | 432.25 | 752.44 | 26 |
| 841 | MLNALISLEHHK | 17.2 | 352.2 | 359.17 | 21 |
| 842 | MLNALISLEHHK | 17.21 | 469.26 | 750.39 | 27 |
| 843 | MLNALISLEHHK | 17.2 | 469.26 | 863.47 | 27 |
| 844 | MQAYVDAFDYGNR | 17.56 | 775.34 | 957.41 | 39 |
| 845 | MQAYVDAFDYGNR | 17.56 | 775.34 | 1056.47 | 39 |
| 846 | MQAYVDAFDYGNR | 17.56 | 775.34 | 1219.54 | 39 |
| 847 | MQEGLNK | 8.68 | 410.21 | 560.3 | 23 |
| 848 | MQEGLNK | 8.66 | 410.21 | 673.3 | 23 |
| 849 | MQEGLNK | 8.68 | 410.21 | 688.36 | 23 |
| 850 | MSPASTYK | 9.49 | 442.71 | 569.29 | 24 |
| 851 | MSPASTYK | 9.49 | 442.71 | 666.35 | 24 |
| 852 | MSPASTYK | 9.49 | 442.71 | 753.38 | 24 |
| 853 | NEHDPVLPYR | 13.09 | 413.88 | 435.24 | 25 |
| 854 | NEHDPVLPYR | 13.09 | 620.31 | 744.44 | 32 |
| 855 | NEHDPVLPYR | 13.09 | 620.31 | 859.47 | 32 |
| 856 | NEHQIFK | 9.91 | 458.24 | 509.21 | 25 |
| 857 | NEHQIFK | 9.91 | 458.24 | 622.29 | 25 |
| 858 | NEHQIFK | 9.91 | 458.24 | 672.38 | 25 |
| 859 | NEHQVFK | 7.74 | 451.23 | 658.37 | 25 |
| 860 | NEHQVFK | 7.74 | 451.23 | 755.35 | 25 |
| 861 | NEHQVFK | 7.74 | 451.23 | 787.41 | 25 |
| 862 | NEITYK | 9.35 | 384.2 | 524.31 | 22 |
| 863 | NEITYK | 9.35 | 384.2 | 621.29 | 22 |
| 864 | NEITYK | 9.35 | 384.2 | 653.35 | 22 |
| 865 | NELLMK | 13.08 | 374.21 | 504.32 | 21 |
| 866 | NELLMK | 13.09 | 374.21 | 601.3 | 21 |
| 867 | NELLMK | 13.09 | 374.21 | 633.36 | 21 |
| 868 | NELPFR | 14.39 | 388.21 | 419.24 | 22 |
| 869 | NELPFR | 14.39 | 388.21 | 532.32 | 22 |
| 870 | NELPFR | 14.4 | 388.21 | 661.37 | 22 |
| 871 | NISSYGNNLVR | 14.36 | 618.82 | 835.44 | 32 |
| 872 | NISSYGNNLVR | 14.36 | 618.82 | 922.47 | 32 |
| 873 | NISSYGNNLVR | 14.36 | 618.82 | 1009.51 | 32 |
| 874 | NISTYGNNLTR | 13.1 | 626.82 | 674.36 | 33 |

TABLE 30-continued

| Transition number | Peptide | Retention time (minutes) | (m/z) filtered in Q1 | (m/z) filtered in Q3 | Collision energy (eV) |
|---|---|---|---|---|---|
| 875 | NISTYGNNLTR | 13.09 | 626.82 | 837.42 | 33 |
| 876 | NISTYGNNLTR | 13.1 | 626.82 | 1025.5 | 33 |
| 877 | NLFNEVHTTGVLVIR | 20.69 | 571.32 | 757.49 | 33 |
| 878 | NLFNEVHTTGVLVIR | 20.7 | 571.32 | 858.54 | 33 |
| 879 | NLFNEVHTTGVLVIR | 20.7 | 571.32 | 995.6 | 33 |
| 880 | NLSTYGNALAR | 14.34 | 590.31 | 764.4 | 31 |
| 881 | NLSTYGNALAR | 14.35 | 590.31 | 865.45 | 31 |
| 882 | NLSTYGNALAR | 14.35 | 590.31 | 952.48 | 31 |
| 883 | NMENLELFGK | 19.08 | 597.79 | 820.46 | 31 |
| 884 | NMENLELFGK | 19.08 | 597.79 | 949.5 | 31 |
| 885 | NMENLELFGK | 19.08 | 597.79 | 1080.54 | 31 |
| 886 | NMLLLEENNGYK | 16.71 | 719.36 | 853.37 | 37 |
| 887 | NMLLLEENNGYK | 16.69 | 719.36 | 966.45 | 37 |
| 888 | NMLLLEENNGYK | 16.68 | 719.36 | 1079.54 | 37 |
| 889 | NMLLLEESNGYK | 18.12 | 705.85 | 939.44 | 36 |
| 890 | NMLLLEESNGYK | 18.13 | 705.85 | 1052.53 | 36 |
| 891 | NMLLLEESNGYK | 18.11 | 705.85 | 1165.61 | 36 |
| 892 | NMLLLEK | 16.99 | 430.75 | 502.32 | 24 |
| 893 | NMLLLEK | 16.98 | 430.75 | 615.41 | 24 |
| 894 | NMLLLEK | 16.98 | 430.75 | 746.45 | 24 |
| 895 | NMTLGDAMK | 14.42 | 490.73 | 521.24 | 27 |
| 896 | NMTLGDAMK | 14.42 | 490.73 | 634.32 | 27 |
| 897 | NMTLGDAMK | 14.42 | 490.73 | 735.37 | 27 |
| 898 | NNGLTEAWLESSLK | 20.61 | 781.4 | 862.47 | 39 |
| 899 | NNGLTEAWLESSLK | 20.6 | 781.4 | 933.5 | 39 |
| 900 | NNGLTEAWLESSLK | 20.62 | 781.4 | 1163.59 | 39 |
| 901 | NQLPFK | 13.49 | 373.71 | 391.23 | 21 |
| 902 | NQLPFK | 13.49 | 373.71 | 504.32 | 21 |
| 903 | NQLPFK | 13.49 | 373.71 | 632.38 | 21 |
| 904 | NQLPFQVEHQR | 14.33 | 698.36 | 796.41 | 36 |
| 905 | NQLPFQVEHQR | 14.33 | 698.36 | 1040.53 | 36 |
| 906 | NQLPFQVEHQR | 14.33 | 698.36 | 1153.61 | 36 |
| 907 | NSAIENTIDNMYLQDLENSTK | 22.77 | 805.04 | 934.45 | 44 |
| 908 | NSAIENTIDNMYLQDLENSTK | 22.77 | 805.04 | 1047.53 | 44 |
| 909 | NSAIENTIDNMYLQDLENSTK | 22.77 | 805.04 | 1210.6 | 44 |
| 910 | NSAIENTIENMYLQDLDNSTK | 23.13 | 805.04 | 920.43 | 44 |
| 911 | NSAIENTIENMYLQDLDNSTK | 23.13 | 805.04 | 1033.52 | 44 |
| 912 | NSAIENTIENMYLQDLDNSTK | 23.14 | 805.04 | 1196.58 | 44 |

TABLE 30-continued

| Transition number | Peptide | Retention time (minutes) | (m/z) filtered in Q1 | (m/z) filtered in Q3 | Collision energy (eV) |
|---|---|---|---|---|---|
| 913 | NSAIENTIENMYLQDLENSTK | 23.7 | 809.72 | 934.45 | 44 |
| 914 | NSAIENTIENMYLQDLENSTK | 23.7 | 809.72 | 1047.53 | 44 |
| 915 | NSAIENTIENMYLQDLENSTK | 23.7 | 809.72 | 1217.55 | 44 |
| 916 | NSAVWVYELFAK | 24.66 | 713.87 | 869.48 | 36 |
| 917 | NSAVWVYELFAK | 24.66 | 713.87 | 1055.56 | 36 |
| 918 | NSAVWVYELFAK | 24.65 | 713.87 | 1154.62 | 36 |
| 919 | NSQVPAYK | 9.78 | 453.74 | 478.27 | 25 |
| 920 | NSQVPAYK | 9.78 | 453.74 | 577.33 | 25 |
| 921 | NSQVPAYK | 9.78 | 453.74 | 705.39 | 25 |
| 922 | NSTVWIYELFAK | 25.64 | 735.88 | 883.49 | 37 |
| 923 | NSTVWIYELFAK | 25.64 | 735.88 | 1069.57 | 37 |
| 924 | NSTVWIYELFAK | 25.64 | 735.88 | 1168.64 | 37 |
| 925 | NSTVWVYELFAK | 24.42 | 728.88 | 770.41 | 37 |
| 926 | NSTVWVYELFAK | 24.43 | 728.88 | 869.48 | 37 |
| 927 | NSTVWVYELFAK | 24.42 | 728.88 | 1055.56 | 37 |
| 928 | NSTVWVYQLFAK | 23.9 | 728.39 | 769.42 | 37 |
| 929 | NSTVWVYQLFAK | 23.91 | 728.39 | 1054.57 | 37 |
| 930 | NSTVWVYQLFAK | 23.91 | 728.39 | 1153.64 | 37 |
| 931 | NTSGALVIQTDK | 13.34 | 623.84 | 816.48 | 32 |
| 932 | NTSGALVIQTDK | 13.34 | 623.84 | 944.54 | 32 |
| 933 | NTSGALVIQTDK | 13.34 | 623.84 | 1031.57 | 32 |
| 934 | NTSGVLVIQTDK | 14.9 | 637.85 | 816.48 | 33 |
| 935 | NTSGVLVIQTDK | 14.9 | 637.85 | 972.57 | 33 |
| 936 | NTSGVLVIQTDK | 14.91 | 637.85 | 1059.6 | 33 |
| 937 | NVDEMFYYYDGSK | 18.86 | 815.84 | 895.38 | 41 |
| 938 | NVDEMFYYYDGSK | 18.86 | 815.84 | 1042.45 | 41 |
| 939 | NVDEMFYYYDGSK | 18.85 | 815.84 | 1173.49 | 41 |
| 940 | NWILR | 16.3 | 351.21 | 414.21 | 20 |
| 941 | NWILR | 16.29 | 351.21 | 527.3 | 20 |
| 942 | NWILR | 16.3 | 351.21 | 587.37 | 20 |
| 943 | NWNAAMDLR | 16.54 | 545.76 | 605.31 | 29 |
| 944 | NWNAAMDLR | 16.55 | 545.76 | 676.34 | 29 |
| 945 | NWNAAMDLR | 16.54 | 545.76 | 790.39 | 29 |
| 946 | NYVDAFHYGNQDISGDK | 15.76 | 648.29 | 933.43 | 36 |
| 947 | NYVDAFHYGNQDISGDK | 15.77 | 648.29 | 1096.49 | 36 |
| 948 | NYVDAFHYGNQDISGDK | 15.76 | 971.93 | 1233.55 | 48 |
| 949 | QADHAILVFDQAR | 16.58 | 495.26 | 523.23 | 29 |
| 950 | QADHAILVFDQAR | 16.61 | 495.26 | 636.31 | 29 |

TABLE 30-continued

| Transition number | Peptide | Retention time (minutes) | (m/z) filtered in Q1 | (m/z) filtered in Q3 | Collision energy (eV) |
|---|---|---|---|---|---|
| 951 | QADHAILVFDQAR | 16.58 | 495.26 | 735.38 | 29 |
| 952 | QAEHALLVFGQER | 16.86 | 499.93 | 636.31 | 29 |
| 953 | QAEHALLVFGQER | 16.85 | 499.93 | 735.38 | 29 |
| 954 | QAEHALLVFGQER | 16.87 | 499.93 | 763.41 | 29 |
| 955 | QAITK | 11 | 280.67 | 361.24 | 17 |
| 956 | QAITK | 11 | 280.67 | 414.23 | 17 |
| 957 | QAITK | 11.01 | 280.67 | 432.28 | 17 |
| 958 | QAMLTEANSDYIIR | 18.26 | 812.9 | 951.49 | 41 |
| 959 | QAMLTEANSDYIIR | 18.25 | 812.9 | 1080.53 | 41 |
| 960 | QAMLTEANSDYIIR | 18.26 | 812.9 | 1181.58 | 41 |
| 961 | QEVQFVSALAR | 17.69 | 624.34 | 763.45 | 32 |
| 962 | QEVQFVSALAR | 17.68 | 624.34 | 891.5 | 32 |
| 963 | QEVQFVSALAR | 17.68 | 624.34 | 990.57 | 32 |
| 964 | QFASIK | 11.66 | 347.2 | 434.2 | 20 |
| 965 | QFASIK | 11.66 | 347.2 | 547.29 | 20 |
| 966 | QFASIK | 11.68 | 347.2 | 565.33 | 20 |
| 967 | QGMPGSIR | 11.4 | 423.22 | 529.31 | 24 |
| 968 | QGMPGSIR | 11.43 | 423.22 | 660.35 | 24 |
| 969 | QGMPGSIR | 11.4 | 423.22 | 717.37 | 24 |
| 970 | QGMSGSIR | 9.44 | 418.21 | 519.29 | 23 |
| 971 | QGMSGSIR | 9.45 | 418.21 | 650.33 | 23 |
| 972 | QGMSGSIR | 9.44 | 418.21 | 707.35 | 23 |
| 973 | QGQTQQSYGNDLAR | 11.16 | 783.37 | 895.43 | 39 |
| 974 | QGQTQQSYGNDLAR | 11.17 | 783.37 | 1023.49 | 39 |
| 975 | QGQTQQSYGNDLAR | 11.16 | 783.37 | 1151.54 | 39 |
| 976 | QIDYGNADPSTIK | 13.41 | 711.35 | 845.44 | 36 |
| 977 | QIDYGNADPSTIK | 13.42 | 711.35 | 902.46 | 36 |
| 978 | QIDYGNADPSTIK | 13.42 | 711.35 | 1065.52 | 36 |
| 979 | QIDYGNVDPSTIK | 15.08 | 725.36 | 873.47 | 37 |
| 980 | QIDYGNVDPSTIK | 15.07 | 725.36 | 930.49 | 37 |
| 981 | QIDYGNVDPSTIK | 15.07 | 725.36 | 1093.55 | 37 |
| 982 | QIGQAR | 2.3 | 336.69 | 431.24 | 20 |
| 983 | QIGQAR | 2.33 | 336.69 | 498.27 | 20 |
| 984 | QIGQAR | 2.32 | 336.69 | 544.32 | 20 |
| 985 | QIMLIEQTPAFTLR | 24.42 | 830.96 | 933.52 | 42 |
| 986 | QIMLIEQTPAFTLR | 24.42 | 830.96 | 1062.56 | 42 |
| 987 | QIMLIEQTPAFTLR | 24.42 | 830.96 | 1175.64 | 42 |
| 988 | QLGSAIDQFWLR | 22.67 | 717.38 | 864.44 | 37 |

TABLE 30-continued

| Transition number | Peptide | Retention time (minutes) | (m/z) filtered in Q1 | (m/z) filtered in Q3 | Collision energy (eV) |
| --- | --- | --- | --- | --- | --- |
| 989 | QLGSAIDQFWLR | 22.68 | 717.38 | 977.52 | 37 |
| 990 | QLGSAIDQFWLR | 22.67 | 717.38 | 1192.61 | 37 |
| 991 | QLPVK | 9.57 | 292.69 | 343.23 | 18 |
| 992 | QLPVK | 9.58 | 292.69 | 438.27 | 18 |
| 993 | QLPVK | 9.57 | 292.69 | 456.32 | 18 |
| 994 | QLSLDVLDK | 18.63 | 515.79 | 589.32 | 28 |
| 995 | QLSLDVLDK | 18.62 | 515.79 | 789.44 | 28 |
| 996 | QLSLDVLDK | 18.63 | 515.79 | 902.52 | 28 |
| 997 | QLVYAR | 11.04 | 375.22 | 508.29 | 22 |
| 998 | QLVYAR | 11.04 | 375.22 | 575.32 | 22 |
| 999 | QLVYAR | 11.04 | 375.22 | 621.37 | 22 |
| 1000 | QMMLTEASTDYIIR | 19.82 | 836.41 | 867.46 | 42 |
| 1001 | QMMLTEASTDYIIR | 19.82 | 836.41 | 1067.54 | 42 |
| 1002 | QMMLTEASTDYIIR | 19.82 | 836.41 | 1168.58 | 42 |
| 1003 | QMSIVEATPDYVLHGK | 18.77 | 894.45 | 1029.54 | 44 |
| 1004 | QMSIVEATPDYVLHGK | 18.77 | 894.45 | 1100.57 | 44 |
| 1005 | QMSIVEATPDYVLHGK | 18.77 | 894.45 | 1229.62 | 44 |
| 1006 | QTLVFAR | 14.65 | 417.75 | 492.29 | 23 |
| 1007 | QTLVFAR | 14.65 | 417.75 | 605.38 | 23 |
| 1008 | QTLVFAR | 14.65 | 417.75 | 706.42 | 23 |
| 1009 | QVVFAR | 12.06 | 360.21 | 492.29 | 21 |
| 1010 | QVVFAR | 12.04 | 360.21 | 545.31 | 21 |
| 1011 | QVVFAR | 12.06 | 360.21 | 591.36 | 21 |
| 1012 | SADEVLPYGGKPQR | 12.96 | 506.26 | 642.37 | 29 |
| 1013 | SADEVLPYGGKPQR | 12.96 | 506.26 | 805.43 | 29 |
| 1014 | SADEVLPYGGKPQR | 12.96 | 506.26 | 902.48 | 29 |
| 1015 | SC[CAM]ATNDLAR | 9.37 | 504.23 | 689.36 | 27 |
| 1016 | SC[CAM]ATNDLAR | 9.37 | 504.23 | 760.39 | 27 |
| 1017 | SC[CAM]ATNDLAR | 9.37 | 504.23 | 920.43 | 27 |
| 1018 | SC[CAM]ATNNLAR | 8.66 | 503.74 | 688.37 | 27 |
| 1019 | SC[CAM]ATNNLAR | 8.66 | 503.74 | 759.41 | 27 |
| 1020 | SC[CAM]ATNNLAR | 8.67 | 503.74 | 919.44 | 27 |
| 1021 | SDIPGGSK | 7.63 | 380.7 | 558.32 | 22 |
| 1022 | SDIPGGSK | 7.63 | 380.7 | 614.28 | 22 |
| 1023 | SDIPGGSK | 7.63 | 380.7 | 673.35 | 22 |
| 1024 | SDWGK | 5.75 | 296.64 | 390.21 | 18 |
| 1025 | SDWGK | 5.75 | 296.64 | 446.17 | 18 |
| 1026 | SDWGK | 5.75 | 296.64 | 505.24 | 18 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1027 | SEDNFHISSQQHEK | 10.36 | 422.19 | 541.27 | 24 |
| 1028 | SEDNFHISSQQHEK | 10.36 | 422.19 | 730.28 | 24 |
| 1029 | SEDNFHISSQQHEK | 10.36 | 422.19 | 756.36 | 24 |
| 1030 | SEMPASIR | 12.02 | 445.72 | 674.37 | 25 |
| 1031 | SEMPASIR | 12.02 | 445.72 | 716.33 | 25 |
| 1032 | SEMPASIR | 12.02 | 445.72 | 803.41 | 25 |
| 1033 | SEMPASTR | 8.2 | 439.71 | 662.33 | 24 |
| 1034 | SEMPASTR | 8.19 | 439.71 | 704.29 | 24 |
| 1035 | SEMPASTR | 8.19 | 439.71 | 791.37 | 24 |
| 1036 | SFAAHNQDQDLR | 10.35 | 467.89 | 531.29 | 27 |
| 1037 | SFAAHNQDQDLR | 10.35 | 467.89 | 871.37 | 27 |
| 1038 | SFAAHNQDQDLR | 10.35 | 467.89 | 888.42 | 27 |
| 1039 | SFAGHNK | 9.4 | 380.69 | 455.24 | 22 |
| 1040 | SFAGHNK | 9.4 | 380.69 | 526.27 | 22 |
| 1041 | SFAGHNK | 9.38 | 380.69 | 673.34 | 22 |
| 1042 | SFAGHNQDQDLR | 10.18 | 694.32 | 888.42 | 36 |
| 1043 | SFAGHNQDQDLR | 10.18 | 694.32 | 1025.48 | 36 |
| 1044 | SFAGHNQDQDLR | 10.18 | 694.32 | 1082.5 | 36 |
| 1045 | SFAGHNQDQNLR | 9.8 | 462.89 | 530.3 | 27 |
| 1046 | SFAGHNQDQNLR | 9.8 | 462.89 | 773.39 | 27 |
| 1047 | SFAGHNQDQNLR | 9.8 | 462.89 | 887.43 | 27 |
| 1048 | SFLESWAK | 18.27 | 484.25 | 491.26 | 26 |
| 1049 | SFLESWAK | 18.27 | 484.25 | 620.3 | 26 |
| 1050 | SFLESWAK | 18.27 | 484.25 | 733.39 | 26 |
| 1051 | SFTAWEK | 14.44 | 434.71 | 462.23 | 24 |
| 1052 | SFTAWEK | 14.44 | 434.71 | 533.27 | 24 |
| 1053 | SFTAWEK | 14.44 | 434.71 | 634.32 | 24 |
| 1054 | SFTTWEK | 14.1 | 449.72 | 462.23 | 25 |
| 1055 | SFTTWEK | 14.1 | 449.72 | 563.28 | 25 |
| 1056 | SFTTWEK | 14.1 | 449.72 | 664.33 | 25 |
| 1057 | SGSGWLR | 13.25 | 381.7 | 531.3 | 22 |
| 1058 | SGSGWLR | 13.25 | 381.7 | 618.34 | 22 |
| 1059 | SGSGWLR | 13.25 | 381.7 | 675.36 | 22 |
| 1060 | SGWGMAVDPQVGWYVGFVEK | 24.65 | 738.02 | 841.45 | 41 |
| 1061 | SGWGMAVDPQVGWYVGFVEK | 24.65 | 738.02 | 1029.45 | 41 |
| 1062 | SGWGMAVDPQVGWYVGFVEK | 24.68 | 1106.53 | 1128.51 | 54 |
| 1063 | SGWGMDVSPQVGWLTGWVEK | 26.32 | 1110.03 | 1144.51 | 54 |
| 1064 | SGWGMDVSPQVGWLTGWVEK | 26.32 | 1110.03 | 1174.63 | 54 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1065 | SGWGMDVSPQVGWLTGWVEK | 26.32 | 1110.03 | 1201.53 | 54 |
| 1066 | SGWGMDVTPQVGWLTGWVEK | 26.61 | 745.03 | 832.46 | 41 |
| 1067 | SGWGMDVTPQVGWLTGWVEK | 26.61 | 745.03 | 1018.54 | 41 |
| 1068 | SGWGMDVTPQVGWLTGWVEK | 26.61 | 745.03 | 1075.56 | 41 |
| 1069 | SIHPASTFK | 10.74 | 494.27 | 650.35 | 27 |
| 1070 | SIHPASTFK | 10.73 | 494.27 | 787.41 | 27 |
| 1071 | SIHPASTFK | 10.73 | 494.27 | 900.49 | 27 |
| 1072 | SISTK | 10.41 | 268.16 | 335.19 | 17 |
| 1073 | SISTK | 10.42 | 268.16 | 389.2 | 17 |
| 1074 | SISTK | 10.42 | 268.16 | 448.28 | 17 |
| 1075 | SLGLSNNLSR | 14.23 | 530.79 | 690.35 | 28 |
| 1076 | SLGLSNNLSR | 14.23 | 530.79 | 803.44 | 28 |
| 1077 | SLGLSNNLSR | 14.23 | 530.79 | 860.46 | 28 |
| 1078 | SLSMSGK | 9.31 | 355.18 | 509.24 | 21 |
| 1079 | SLSMSGK | 9.32 | 355.18 | 563.25 | 21 |
| 1080 | SLSMSGK | 9.32 | 355.18 | 622.32 | 21 |
| 1081 | SMLFIEEK | 17.82 | 498.76 | 518.28 | 27 |
| 1082 | SMLFIEEK | 17.82 | 498.76 | 665.35 | 27 |
| 1083 | SMLFIEEK | 17.82 | 498.76 | 778.43 | 27 |
| 1084 | SNGLTHSWLGSSLK | 16.78 | 743.89 | 877.48 | 38 |
| 1085 | SNGLTHSWLGSSLK | 16.78 | 743.89 | 1014.54 | 38 |
| 1086 | SNGLTHSWLGSSLK | 16.78 | 743.89 | 1115.58 | 38 |
| 1087 | SPTWELKPEYNPSPR | 16.02 | 600.97 | 733.36 | 34 |
| 1088 | SPTWELKPEYNPSPR | 16.02 | 600.97 | 808.91 | 34 |
| 1089 | SPTWELKPEYNPSPR | 16.02 | 600.97 | 959.46 | 34 |
| 1090 | SQDIVR | 8.4 | 359.2 | 502.3 | 21 |
| 1091 | SQDIVR | 8.38 | 359.2 | 543.28 | 21 |
| 1092 | SQDIVR | 8.4 | 359.2 | 630.36 | 21 |
| 1093 | SQQKPTDPTIWLK | 16.6 | 514.62 | 660.41 | 30 |
| 1094 | SQQKPTDPTIWLK | 16.6 | 514.62 | 757.46 | 30 |
| 1095 | SQQKPTDPTIWLK | 16.6 | 514.62 | 785.38 | 30 |
| 1096 | SQVGWLTGWVEQPDGK | 22.27 | 893.94 | 1015.5 | 44 |
| 1097 | SQVGWLTGWVEQPDGK | 22.28 | 893.94 | 1116.53 | 44 |
| 1098 | SQVGWLTGWVEQPDGK | 22.28 | 893.94 | 1229.62 | 44 |
| 1099 | SSSNSC[CAM]TTNNAAR | 16.84 | 685.29 | 907.41 | 35 |
| 1100 | SSSNSC[CAM]TTNNAAR | 16.85 | 685.29 | 994.44 | 35 |
| 1101 | SSSNSC[CAM]TTNNAAR | 16.84 | 685.29 | 1108.48 | 35 |
| 1102 | SVYGELR | 12.65 | 412.22 | 417.25 | 23 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1103 | SVYGELR | 12.65 | 412.22 | 474.27 | 23 |
| 1104 | SVYGELR | 12.65 | 412.22 | 637.33 | 23 |
| 1105 | SWILR | 16.33 | 337.7 | 401.29 | 20 |
| 1106 | SWILR | 16.32 | 337.7 | 500.29 | 20 |
| 1107 | SWILR | 16.33 | 337.7 | 587.37 | 20 |
| 1108 | SYLEK | 9.09 | 320.17 | 389.24 | 19 |
| 1109 | SYLEK | 9.09 | 320.17 | 493.23 | 19 |
| 1110 | SYLEK | 9.1 | 320.17 | 552.3 | 19 |
| 1111 | TAYIPASTFK | 15.43 | 549.8 | 650.35 | 29 |
| 1112 | TAYIPASTFK | 15.43 | 549.8 | 763.43 | 29 |
| 1113 | TAYIPASTFK | 15.43 | 549.8 | 926.5 | 29 |
| 1114 | TDDLFK | 13.48 | 369.69 | 407.27 | 21 |
| 1115 | TDDLFK | 13.48 | 369.69 | 522.29 | 21 |
| 1116 | TDDLFK | 13.48 | 369.69 | 637.32 | 21 |
| 1117 | TDINEIFK | 17.44 | 490.26 | 650.35 | 27 |
| 1118 | TDINEIFK | 17.44 | 490.26 | 763.43 | 27 |
| 1119 | TDINEIFK | 17.44 | 490.26 | 878.46 | 27 |
| 1120 | TFIHNDPR | 18.92 | 500.25 | 751.38 | 27 |
| 1121 | TFIHNDPR | 18.92 | 500.25 | 825.39 | 27 |
| 1122 | TFIHNDPR | 18.92 | 500.25 | 898.45 | 27 |
| 1123 | TGAGFTANR | 9.64 | 447.72 | 461.25 | 25 |
| 1124 | TGAGFTANR | 9.64 | 447.72 | 665.34 | 25 |
| 1125 | TGAGFTANR | 9.64 | 447.72 | 793.4 | 25 |
| 1126 | TGFNDGQK | 7.5 | 433.7 | 561.26 | 24 |
| 1127 | TGFNDGQK | 7.5 | 433.7 | 708.33 | 24 |
| 1128 | TGFNDGQK | 7.5 | 433.7 | 765.35 | 24 |
| 1129 | TGLADSK | 9.7 | 346.18 | 533.29 | 20 |
| 1130 | TGLADSK | 9.67 | 346.18 | 545.26 | 20 |
| 1131 | TGLADSK | 9.7 | 346.18 | 590.31 | 20 |
| 1132 | TGLDLMQK | 15.32 | 453.24 | 634.32 | 25 |
| 1133 | TGLDLMQK | 15.32 | 453.24 | 747.41 | 25 |
| 1134 | TGLDLMQK | 15.32 | 453.24 | 804.43 | 25 |
| 1135 | TGLELMQK | 15.03 | 460.25 | 648.34 | 25 |
| 1136 | TGLELMQK | 15.03 | 460.25 | 761.42 | 25 |
| 1137 | TGLELMQK | 15.03 | 460.25 | 818.44 | 25 |
| 1138 | TGMGYPK | 10.28 | 377.18 | 464.25 | 22 |
| 1139 | TGMGYPK | 10.28 | 377.18 | 595.29 | 22 |
| 1140 | TGMGYPK | 10.28 | 377.18 | 652.31 | 22 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1141 | TGNGR | 0.8 | 252.63 | 330.14 | 16 |
| 1142 | TGNGR | 0.8 | 252.63 | 346.18 | 16 |
| 1143 | TGNGR | 0.81 | 252.63 | 403.2 | 16 |
| 1144 | TGTGSFIDAR | 13.35 | 512.76 | 708.37 | 28 |
| 1145 | TGTGSFIDAR | 13.35 | 512.76 | 765.39 | 28 |
| 1146 | TGTGSFIDAR | 13.35 | 512.76 | 866.44 | 28 |
| 1147 | TGTGSLSDAK | 8.32 | 468.74 | 620.32 | 26 |
| 1148 | TGTGSLSDAK | 8.32 | 468.74 | 677.35 | 26 |
| 1149 | TGTGSLSDAK | 8.32 | 468.74 | 778.39 | 26 |
| 1150 | TGVATEYQPEIGWWAGWVER | 25.49 | 779.04 | 903.45 | 43 |
| 1151 | TGVATEYQPEIGWWAGWVER | 25.5 | 779.04 | 1146.55 | 43 |
| 1152 | TGVATEYQPEIGWWAGWVER | 25.52 | 1168.06 | 1189.57 | 56 |
| 1153 | TGVSYPLLADGTR | 17.4 | 675.36 | 842.47 | 35 |
| 1154 | TGVSYPLLADGTR | 17.41 | 675.36 | 1005.54 | 35 |
| 1155 | TGVSYPLLADGTR | 17.4 | 675.36 | 1092.57 | 35 |
| 1156 | TGWAMDIK | 16.71 | 461.23 | 577.3 | 25 |
| 1157 | TGWAMDIK | 16.71 | 461.23 | 763.38 | 25 |
| 1158 | TGWAMDIK | 16.72 | 461.23 | 820.4 | 25 |
| 1159 | TGWATR | 9.71 | 346.18 | 517.24 | 20 |
| 1160 | TGWATR | 9.69 | 346.18 | 533.28 | 20 |
| 1161 | TGWATR | 9.69 | 346.18 | 590.3 | 20 |
| 1162 | TGWC[CAM]FDC[CAM]TPELGWWVGWVK | 28.39 | 795.36 | 960.51 | 44 |
| 1163 | TGWC[CAM]FDC[CAM]TPELGWWVGWVK | 28.39 | 795.36 | 1017.53 | 44 |
| 1164 | TGWC[CAM]FDC[CAM]TPELGWWVGWVK | 28.38 | 795.36 | 1028.36 | 44 |
| 1165 | TGWEGR | 9.1 | 353.17 | 531.22 | 21 |
| 1166 | TGWEGR | 9.09 | 353.17 | 547.26 | 21 |
| 1167 | TGWEGR | 9.09 | 353.17 | 604.28 | 21 |
| 1168 | TGWFVDK | 16.08 | 426.72 | 694.36 | 24 |
| 1169 | TGWFVDK | 16.1 | 426.72 | 706.32 | 24 |
| 1170 | TGWFVDK | 16.08 | 426.72 | 751.38 | 24 |
| 1171 | TGYDTK | 2.09 | 342.66 | 526.25 | 20 |
| 1172 | TGYDTK | 2.09 | 342.66 | 538.21 | 20 |
| 1173 | TGYDTK | 2.08 | 342.66 | 583.27 | 20 |
| 1174 | TGYGVR | 8.09 | 326.67 | 478.23 | 19 |
| 1175 | TGYGVR | 8.1 | 326.67 | 494.27 | 19 |
| 1176 | TGYGVR | 8.1 | 326.67 | 551.29 | 19 |
| 1177 | TGYSAR | 2.24 | 327.66 | 480.21 | 19 |
| 1178 | TGYSAR | 2.24 | 327.66 | 496.25 | 19 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1179 | TGYSAR | 2.24 | 327.66 | 553.27 | 19 |
| 1180 | TGYSTR | 2.08 | 342.67 | 510.22 | 20 |
| 1181 | TGYSTR | 2.08 | 342.67 | 526.26 | 20 |
| 1182 | TGYSTR | 2.08 | 342.67 | 583.28 | 20 |
| 1183 | THESSNWGK | 5.36 | 523.24 | 678.32 | 28 |
| 1184 | THESSNWGK | 5.37 | 523.24 | 807.36 | 28 |
| 1185 | THESSNWGK | 5.37 | 523.24 | 944.42 | 28 |
| 1186 | TIC[CAM]TAIADAGTGK | 14.35 | 639.82 | 732.39 | 33 |
| 1187 | TIC[CAM]TAIADAGTGK | 14.35 | 639.82 | 904.47 | 33 |
| 1188 | TIC[CAM]TAIADAGTGK | 14.35 | 639.82 | 1064.5 | 33 |
| 1189 | TIGGAPDAYWVDDSLQISAR | 21.22 | 712.35 | 1004.5 | 40 |
| 1190 | TIGGAPDAYWVDDSLQISAR | 21.22 | 712.35 | 1103.57 | 40 |
| 1191 | TIGGAPDAYWVDDSLQISAR | 21.21 | 1068.02 | 1103.57 | 52 |
| 1192 | TLPFSASSYETLR | 18.73 | 736.37 | 855.42 | 37 |
| 1193 | TLPFSASSYETLR | 18.73 | 736.37 | 1013.49 | 37 |
| 1194 | TLPFSASSYETLR | 18.73 | 736.37 | 1160.56 | 37 |
| 1195 | TLPFSPK | 15 | 395.23 | 478.27 | 22 |
| 1196 | TLPFSPK | 15 | 395.23 | 575.32 | 22 |
| 1197 | TLPFSPK | 15 | 395.23 | 688.4 | 22 |
| 1198 | TLPFSQEVQDEVQSILFIEEK | 28.55 | 827.09 | 891.52 | 45 |
| 1199 | TLPFSQEVQDEVQSILFIEEK | 28.56 | 827.09 | 978.55 | 45 |
| 1200 | TLPFSQEVQDEVQSILFIEEK | 28.56 | 827.09 | 1106.61 | 45 |
| 1201 | TLPFSQEVQDEVQSMLFIEEK | 27.7 | 833.08 | 996.51 | 46 |
| 1202 | TLPFSQEVQDEVQSMLFIEEK | 27.69 | 833.08 | 1124.57 | 46 |
| 1203 | TLPFSQEVQDEVQSMLFIEEK | 27.7 | 833.08 | 1223.63 | 46 |
| 1204 | TLQNGWFEGFIISK | 24.12 | 820.43 | 940.51 | 41 |
| 1205 | TLQNGWFEGFIISK | 24.11 | 820.43 | 1126.59 | 41 |
| 1206 | TLQNGWFEGFIISK | 24.11 | 820.43 | 1183.61 | 41 |
| 1207 | TMQEYLNK | 12.6 | 513.75 | 666.35 | 28 |
| 1208 | TMQEYLNK | 12.6 | 513.75 | 794.4 | 28 |
| 1209 | TMQEYLNK | 12.6 | 513.75 | 925.44 | 28 |
| 1210 | TQTYQAYDAAR | 11.2 | 644.3 | 666.32 | 33 |
| 1211 | TQTYQAYDAAR | 11.2 | 644.3 | 957.44 | 33 |
| 1212 | TQTYQAYDAAR | 11.2 | 644.3 | 1058.49 | 33 |
| 1213 | TTDPTIWEK | 14.39 | 545.77 | 676.37 | 29 |
| 1214 | TTDPTIWEK | 14.39 | 545.77 | 773.42 | 29 |
| 1215 | TTDPTIWEK | 14.39 | 545.77 | 888.45 | 29 |
| 1216 | TTTTEVFK | 12.06 | 463.75 | 522.29 | 25 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1217 | TTTTEVFK | 12.06 | 463.75 | 623.34 | 25 |
| 1218 | TTTTEVFK | 12.06 | 463.75 | 724.39 | 25 |
| 1219 | TWASNDFSR | 13.73 | 542.25 | 638.29 | 29 |
| 1220 | TWASNDFSR | 13.73 | 542.25 | 725.32 | 29 |
| 1221 | TWASNDFSR | 13.73 | 542.25 | 796.36 | 29 |
| 1222 | TWDMVQR | 14.28 | 468.22 | 648.31 | 26 |
| 1223 | TWDMVQR | 14.28 | 468.22 | 761.33 | 26 |
| 1224 | TWDMVQR | 14.28 | 468.22 | 834.39 | 26 |
| 1225 | TYVVDPAR | 12.15 | 460.75 | 557.3 | 25 |
| 1226 | TYVVDPAR | 12.14 | 460.75 | 656.37 | 25 |
| 1227 | TYVVDPAR | 12.15 | 460.75 | 819.44 | 25 |
| 1228 | VAFSLNIEMK | 20.65 | 576.31 | 747.41 | 30 |
| 1229 | VAFSLNIEMK | 20.65 | 576.31 | 834.44 | 30 |
| 1230 | VAFSLNIEMK | 20.65 | 576.31 | 981.51 | 30 |
| 1231 | VANSLIGLSTGAVR | 17.97 | 679.39 | 760.43 | 35 |
| 1232 | VANSLIGLSTGAVR | 17.97 | 679.39 | 873.52 | 35 |
| 1233 | VANSLIGLSTGAVR | 17.97 | 679.39 | 986.6 | 35 |
| 1234 | VELGK | 7.74 | 273.17 | 342.2 | 17 |
| 1235 | VELGK | 7.75 | 273.17 | 399.22 | 17 |
| 1236 | VELGK | 7.74 | 273.17 | 446.26 | 17 |
| 1237 | VFLDSWAK | 18.2 | 483.26 | 606.29 | 26 |
| 1238 | VFLDSWAK | 18.2 | 483.26 | 719.37 | 26 |
| 1239 | VFLDSWAK | 18.2 | 483.26 | 866.44 | 26 |
| 1240 | VFLESWAK | 18.11 | 490.27 | 620.3 | 27 |
| 1241 | VFLESWAK | 18.11 | 490.27 | 733.39 | 27 |
| 1242 | VFLESWAK | 18.11 | 490.27 | 880.46 | 27 |
| 1243 | VFLSSWAQDMNLSSAIK | 23.66 | 948.98 | 978.49 | 47 |
| 1244 | VFLSSWAQDMNLSSAIK | 23.66 | 948.98 | 1106.55 | 47 |
| 1245 | VFLSSWAQDMNLSSAIK | 23.66 | 948.98 | 1177.59 | 47 |
| 1246 | VGFER | 10.32 | 304.16 | 433.21 | 18 |
| 1247 | VGFER | 10.32 | 304.16 | 451.23 | 18 |
| 1248 | VGFER | 10.32 | 304.16 | 508.25 | 18 |
| 1249 | VILVFDQVR | 19.69 | 544.83 | 664.34 | 29 |
| 1250 | VILVFDQVR | 19.69 | 544.83 | 763.41 | 29 |
| 1251 | VILVFDQVR | 19.69 | 544.83 | 876.49 | 29 |
| 1252 | VMAAMVR | 12.3 | 389.21 | 476.26 | 22 |
| 1253 | VMAAMVR | 12.3 | 389.21 | 547.3 | 22 |
| 1254 | VMAAMVR | 12.3 | 389.21 | 678.34 | 22 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1255 | VPLAVMGYDAGILVDAHNPR | 21.61 | 703.37 | 709.34 | 39 |
| 1256 | VPLAVMGYDAGILVDAHNPR | 21.61 | 703.37 | 808.41 | 39 |
| 1257 | VPLAVMGYDAGILVDAHNPR | 21.61 | 703.37 | 921.49 | 39 |
| 1258 | VQDEVQSMLFIEEK | 20.48 | 847.92 | 996.51 | 42 |
| 1259 | VQDEVQSMLFIEEK | 20.48 | 847.92 | 1124.57 | 42 |
| 1260 | VQDEVQSMLFIEEK | 20.47 | 847.92 | 1223.63 | 42 |
| 1261 | VQDGVQSMLFIEEK | 20.26 | 811.91 | 996.51 | 41 |
| 1262 | VQDGVQSMLFIEEK | 20.27 | 811.91 | 1124.57 | 41 |
| 1263 | VQDGVQSMLFIEEK | 20.25 | 811.91 | 1223.63 | 41 |
| 1264 | VSC[CAM]LPC[CAM]YQVVSHK | 14.32 | 526.26 | 569.34 | 30 |
| 1265 | VSC[CAM]LPC[CAM]YQVVSHK | 14.32 | 526.26 | 860.46 | 30 |
| 1266 | VSC[CAM]LPC[CAM]YQVVSHK | 14.31 | 526.26 | 1020.49 | 30 |
| 1267 | VSC[CAM]VWC[CAM]YQALAR | 18.41 | 756.86 | 881.43 | 38 |
| 1268 | VSC[CAM]VWC[CAM]YQALAR | 18.41 | 756.86 | 1067.51 | 38 |
| 1269 | VSC[CAM]VWC[CAM]YQALAR | 18.41 | 756.86 | 1166.58 | 38 |
| 1270 | VSDVC[CAM]SEVTAEGWQEVR | 17.33 | 650.97 | 774.39 | 37 |
| 1271 | VSDVC[CAM]SEVTAEGWQEVR | 17.34 | 975.95 | 1075.52 | 48 |
| 1272 | VSDVC[CAM]SEVTAEGWQEVR | 17.34 | 975.95 | 1174.59 | 48 |
| 1273 | VSEVEGWQIHGK | 13.92 | 456.9 | 582.34 | 27 |
| 1274 | VSEVEGWQIHGK | 13.92 | 456.9 | 768.42 | 27 |
| 1275 | VSEVEGWQIHGK | 13.92 | 456.9 | 825.44 | 27 |
| 1276 | VSFSLNIEMK | 20.65 | 584.31 | 834.44 | 31 |
| 1277 | VSFSLNIEMK | 20.64 | 584.31 | 981.51 | 31 |
| 1278 | VSFSLNIEMK | 20.65 | 584.31 | 1068.54 | 31 |
| 1279 | VSPC[CAM]SSFK | 11.04 | 456.22 | 468.25 | 25 |
| 1280 | VSPC[CAM]SSFK | 11.04 | 456.22 | 628.28 | 25 |
| 1281 | VSPC[CAM]SSFK | 11.04 | 456.22 | 725.33 | 25 |
| 1282 | VSQVPAYK | 10.68 | 446.25 | 478.27 | 25 |
| 1283 | VSQVPAYK | 10.68 | 446.25 | 577.33 | 25 |
| 1284 | VSQVPAYK | 10.68 | 446.25 | 705.39 | 25 |
| 1285 | VVFAR | 11.17 | 296.18 | 393.22 | 18 |
| 1286 | VVFAR | 11.17 | 296.18 | 417.25 | 18 |
| 1287 | VVFAR | 11.17 | 296.18 | 492.29 | 18 |
| 1288 | WDGAK | 4.9 | 288.64 | 302.11 | 18 |
| 1289 | WDGAK | 4.9 | 288.64 | 390.2 | 18 |
| 1290 | WDGAK | 4.9 | 288.64 | 430.17 | 18 |
| 1291 | WDGHIYDFPDWNR | 20.52 | 574.25 | 590.27 | 33 |
| 1292 | WDGHIYDFPDWNR | 20.52 | 574.25 | 687.32 | 33 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1293 | WDGHIYDFPDWNR | 20.52 | 574.25 | 887.37 | 33 |
| 1294 | WDGIK | 12.03 | 309.67 | 359.13 | 19 |
| 1295 | WDGIK | 12.03 | 309.67 | 432.25 | 19 |
| 1296 | WDGIK | 12.03 | 309.67 | 472.22 | 19 |
| 1297 | WDGKPR | 6.36 | 379.7 | 457.29 | 22 |
| 1298 | WDGKPR | 6.35 | 379.7 | 572.32 | 22 |
| 1299 | WDGKPR | 6.36 | 379.7 | 584.28 | 22 |
| 1300 | WDGQTR | 7.41 | 381.68 | 461.25 | 22 |
| 1301 | WDGQTR | 7.41 | 381.68 | 576.27 | 22 |
| 1302 | WDGQTR | 7.41 | 381.68 | 588.24 | 22 |
| 1303 | WDGVK | 10.1 | 302.66 | 359.13 | 18 |
| 1304 | WDGVK | 10.1 | 302.66 | 418.23 | 18 |
| 1305 | WDGVK | 10.1 | 302.66 | 458.2 | 18 |
| 1306 | WDGVNR | 10.39 | 373.68 | 445.25 | 21 |
| 1307 | WDGVNR | 10.39 | 373.68 | 560.28 | 21 |
| 1308 | WDGVNR | 10.42 | 373.68 | 572.25 | 21 |
| 1309 | YAQAK | 12.58 | 290.66 | 363.17 | 18 |
| 1310 | YAQAK | 12.58 | 290.66 | 417.25 | 18 |
| 1311 | YAQAK | 12.58 | 290.66 | 434.2 | 18 |
| 1312 | YFSDFNAK | 14.21 | 496.23 | 681.32 | 27 |
| 1313 | YFSDFNAK | 14.21 | 496.23 | 828.39 | 27 |
| 1314 | YFSDFNAK | 14.21 | 496.23 | 828.39 | 27 |
| 1315 | YGTHLDR | 8.51 | 431.21 | 641.34 | 24 |
| 1316 | YGTHLDR | 8.52 | 431.21 | 687.31 | 24 |
| 1317 | YGTHLDR | 8.51 | 431.21 | 698.36 | 24 |
| 1318 | YLDELVK | 15.52 | 440.24 | 488.31 | 24 |
| 1319 | YLDELVK | 15.53 | 440.24 | 603.33 | 24 |
| 1320 | YLDELVK | 15.52 | 440.24 | 716.42 | 24 |
| 1321 | YLMITEAGR | 15.86 | 527.27 | 533.27 | 28 |
| 1322 | YLMITEAGR | 15.86 | 527.27 | 646.35 | 28 |
| 1323 | YLMITEAGR | 15.86 | 527.27 | 777.39 | 28 |
| 1324 | YLNLFSYGNANIGGGIDK | 22.16 | 639.32 | 773.42 | 36 |
| 1325 | YLNLFSYGNANIGGGIDK | 22.16 | 958.48 | 1015.52 | 47 |
| 1326 | YLNLFSYGNANIGGGIDK | 22.16 | 958.48 | 1178.58 | 47 |
| 1327 | YPVVWYSQQVAHHLGAQR | 18.11 | 535.53 | 544.32 | 30 |
| 1328 | YPVVWYSQQVAHHLGAQR | 18.11 | 535.53 | 681.38 | 30 |
| 1329 | YPVVWYSQQVAHHLGAQR | 18.11 | 535.53 | 889.48 | 30 |
| 1330 | YSNVLAFK | 16.44 | 471.26 | 478.3 | 26 |

TABLE 30-continued

| Transition number | Peptide | Retention time (minutes) | (m/z) filtered in Q1 | (m/z) filtered in Q3 | Collision energy (eV) |
|---|---|---|---|---|---|
| 1331 | YSNVLAFK | 16.44 | 471.26 | 691.41 | 26 |
| 1332 | YSNVLAFK | 16.44 | 471.26 | 778.45 | 26 |
| 1333 | YSPASTFK | 12.22 | 450.73 | 553.3 | 25 |
| 1334 | YSPASTFK | 12.22 | 450.73 | 650.35 | 25 |
| 1335 | YSPASTFK | 12.22 | 450.73 | 737.38 | 25 |
| 1336 | YSVVPVYQQLAR | 18.42 | 711.89 | 778.42 | 36 |
| 1337 | YSVVPVYQQLAR | 18.42 | 711.89 | 974.54 | 36 |
| 1338 | YSVVPVYQQLAR | 18.43 | 711.89 | 1073.61 | 36 |
| 1339 | YSVVWYSQLTAK | 19.75 | 722.88 | 810.44 | 37 |
| 1340 | YSVVWYSQLTAK | 19.76 | 722.88 | 996.51 | 37 |
| 1341 | YSVVWYSQLTAK | 19.76 | 722.88 | 1095.58 | 37 |
| 1342 | YSVVWYSQQVAHHLGAQR | 18.61 | 533.02 | 544.32 | 30 |
| 1343 | YSVVWYSQQVAHHLGAQR | 18.61 | 533.02 | 681.38 | 30 |
| 1344 | YSVVWYSQQVAHHLGAQR | 18.61 | 533.02 | 889.48 | 30 |
| 1345 | YTPASTFK | 11.95 | 305.49 | 553.3 | 19 |
| 1346 | YTPASTFK | 11.98 | 457.73 | 553.3 | 25 |
| 1347 | YTPASTFK | 11.98 | 457.73 | 650.35 | 25 |
| 1348 | YTSAFGYGNADVSGEPGK | 15.03 | 607.28 | 673.35 | 34 |
| 1349 | YTSAFGYGNADVSGEPGK | 15.02 | 607.28 | 788.38 | 34 |
| 1350 | YTSAFGYGNADVSGEPGK | 15.02 | 910.41 | 1030.48 | 45 |
| 1351 | YVFVSALTGNLGSNLTSSIK | 23.66 | 691.04 | 906.49 | 39 |
| 1352 | YVFVSALTGNLGSNLTSSIK | 23.66 | 1036.06 | 1165.63 | 51 |
| 1353 | YVFVSALTGNLGSNLTSSIK | 23.67 | 1036.06 | 1190.64 | 51 |
| 1354 | YVFVSALTGSLGSNLTSSIK | 24.04 | 682.04 | 906.49 | 38 |
| 1355 | YVFVSALTGSLGSNLTSSIK | 24.04 | 1022.55 | 1106.61 | 50 |
| 1356 | YVFVSALTGSLGSNLTSSIK | 24.04 | 1022.55 | 1163.63 | 50 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 25

Identification of a Resistance to ACC Beta-Lactams

Samples Sam96 to Sam101 are identified according to one of the methods described in examples 1, 3 or 4. The identification of the species is set out in TABLE 31.

TABLE 31

| Names | Species |
|---|---|
| Sam96 | K. oxytoca |
| Sam97 | S. livingstone |
| Sam98 | Salmonella spp |
| Sam99 | S. enterica ssp enterica |
| Sam100 | K. pneumoniae |
| Sam101 | H. alvei |

Samples Sam96 to Sam101 correspond to a species able to comprise an ACC resistance mechanism. Each sample is treated according to example 5, then analysed according to example 6 by detecting the peptides from TABLE 32 instead of the peptides from TABLE 3.

TABLE 32

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | ANIDESK | 2 | y4 monocharged | 2.45 | 388.69 | 478.21 | 17.9 | 2500 |
| 2 | ANIDESK | 2 | y5 monocharged | 2.37 | 388.69 | 591.3 | 17.9 | 2500 |
| 3 | ANIDESK | 2 | y6 monocharged | 2.41 | 388.69 | 705.34 | 17.9 | 2500 |
| 4 | AWKPADAAGTHR | 3 | y9 dicharged | 10.61 | 427.56 | 448.22 | 20.3 | 2500 |
| 5 | AWKPADAAGTHR | 3 | y4 monocharged | 10.61 | 427.56 | 470.25 | 20.3 | 2500 |
| 6 | AWKPADAAGTHR | 3 | y10 dicharged | 10.61 | 427.56 | 512.27 | 20.3 | 2500 |
| 7 | DEPVHVNMEILGNEAYGIK | 3 | y9 dicharged | 20.81 | 710.02 | 482.76 | 29.1 | 2500 |
| 8 | DEPVHVNMEILGNEAYGIK | 3 | y8 monocharged | 20.81 | 710.02 | 851.43 | 29.1 | 2500 |
| 9 | DEPVHVNMEILGNEAYGIK | 3 | y9 monocharged | 20.81 | 710.02 | 964.51 | 29.1 | 2500 |
| 10 | DTVDDLIQPLMQK | 3 | y5 monocharged | 22.36 | 505.93 | 616.35 | 22.8 | 2500 |
| 11 | DTVDDLIQPLMQK | 2 | y5 monocharged | 22.36 | 758.39 | 616.35 | 39 | 2500 |
| 12 | DTVDDLIQPLMQK | 2 | y10 monocharged | 22.36 | 758.39 | 1200.63 | 39 | 2500 |
| 13 | ILSSLEGNK | 2 | y6 monocharged | 13.47 | 480.77 | 647.34 | 23.1 | 2500 |
| 14 | ILSSLEGNK | 2 | y7 monocharged | 13.47 | 480.77 | 734.37 | 23.1 | 2500 |
| 15 | ILSSLEGNK | 2 | y8 monocharged | 13.47 | 480.77 | 847.45 | 23.1 | 2500 |
| 16 | LSLDQSVSHYVPELR | 3 | y12 dicharged | 20.27 | 581.64 | 715.36 | 25.1 | 2500 |
| 17 | LSLDQSVSHYVPELR | 3 | y13 dicharged | 20.27 | 581.64 | 771.9 | 25.1 | 2500 |
| 18 | LSLDQSVSHYVPELR | 3 | y14 dicharged | 20.27 | 581.64 | 815.42 | 25.1 | 2500 |
| 19 | MGIVMLANK | 2 | y5 monocharged | 18.15 | 488.77 | 576.32 | 23.6 | 2500 |
| 20 | MGIVMLANK | 2 | y6 monocharged | 18.15 | 488.77 | 675.39 | 23.6 | 2500 |
| 21 | MGIVMLANK | 2 | y8 monocharged | 18.13 | 488.77 | 845.49 | 23.6 | 2500 |
| 22 | MQQALTATHTGYFK | 3 | y9 dicharged | 15.01 | 532.93 | 513.26 | 23.6 | 2500 |
| 23 | MQQALTATHTGYFK | 3 | y11 dicharged | 15.01 | 532.93 | 605.32 | 23.6 | 2500 |
| 24 | MQQALTATHTGYFK | 3 | y12 dicharged | 15.01 | 532.93 | 669.35 | 23.6 | 2500 |
| 25 | NNIPGMSVAVTVNGK | 2 | y5 monocharged | 17.45 | 750.9 | 518.29 | 38.5 | 2500 |
| 26 | NNIPGMSVAVTVNGK | 2 | y12 dicharged | 17.43 | 750.9 | 580.31 | 38.5 | 2500 |
| 27 | NNIPGMSVAVTVNGK | 2 | y12 monocharged | 17.43 | 750.9 | 1159.61 | 38.5 | 2500 |
| 28 | NTTQLMAYLK | 2 | y5 monocharged | 19.34 | 591.81 | 625.34 | 29.5 | 2500 |
| 29 | NTTQLMAYLK | 2 | y6 monocharged | 19.34 | 591.81 | 738.42 | 29.5 | 2500 |
| 30 | NTTQLMAYLK | 2 | y8 monocharged | 19.36 | 591.81 | 967.53 | 29.5 | 2500 |
| 31 | NYIYNYGLAAK | 2 | y7 monocharged | 16.98 | 645.33 | 736.4 | 32.5 | 2500 |
| 32 | NYIYNYGLAAK | 2 | y8 monocharged | 16.98 | 645.33 | 899.46 | 32.5 | 2500 |
| 33 | NYIYNYGLAAK | 2 | y9 monocharged | 16.98 | 645.33 | 1012.55 | 32.5 | 2500 |
| 34 | NYSIDQR | 2 | y3 monocharged | 10.93 | 448.22 | 418.2 | 21.3 | 2500 |
| 35 | NYSIDQR | 2 | y4 monocharged | 10.91 | 448.22 | 531.29 | 21.3 | 2500 |
| 36 | NYSIDQR | 2 | y5 monocharged | 10.91 | 448.22 | 618.32 | 21.3 | 2500 |
| 37 | QPQQPVTENTLFEVGSLSK | 3 | y5 monocharged | 20.77 | 701.36 | 491.28 | 28.8 | 2500 |
| 38 | QPQQPVTENTLFEVGSLSK | 3 | y7 monocharged | 20.77 | 701.36 | 719.39 | 28.8 | 2500 |

TABLE 32-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 39 | QPQQPVTENTLFEVGSLSK | 3 | y8 monocharged | 20.79 | 701.36 | 866.46 | 28.8 | 2500 |
| 40 | SLGVSYEDAIEK | 2 | y6 monocharged | 16.42 | 655.83 | 704.35 | 33.1 | 2500 |
| 41 | SLGVSYEDAIEK | 2 | y8 monocharged | 16.42 | 655.83 | 954.44 | 33.1 | 2500 |
| 42 | SLGVSYEDAIEK | 2 | y10 monocharged | 16.42 | 655.83 | 1110.53 | 33.1 | 2500 |
| 43 | SVATPIVPPLPPQENVWINK | 3 | y10 dicharged | 22.31 | 733.74 | 612.82 | 29.8 | 2500 |
| 44 | SVATPIVPPLPPQENVWINK | 3 | y13 dicharged | 22.29 | 733.74 | 766.42 | 29.8 | 2500 |
| 45 | SVATPIVPPLPPQENVWINK | 3 | y10 monocharged | 22.35 | 733.74 | 1224.64 | 29.8 | 2500 |
| 46 | TFAATLASYAQVSGK | 3 | y6 monocharged | 19.93 | 505.6 | 589.33 | 22.8 | 2500 |
| 47 | TFAATLASYAQVSGK | 2 | y8 monocharged | 19.93 | 757.9 | 839.43 | 38.9 | 2500 |
| 48 | TFAATLASYAQVSGK | 2 | y9 monocharged | 19.93 | 757.9 | 910.46 | 38.9 | 2500 |
| 49 | TGSTNGFGAYIAFVPAK | 3 | y3 monocharged | 21.68 | 567.63 | 315.2 | 24.7 | 2500 |
| 50 | TGSTNGFGAYIAFVPAK | 3 | y6 monocharged | 21.68 | 567.63 | 632.38 | 24.7 | 2500 |
| 51 | TGSTNGFGAYIAFVPAK | 2 | y3 monocharged | 21.68 | 850.94 | 315.2 | 44.2 | 2500 |
| 52 | TLLPQLGMHHSYLK | 3 | y11 dicharged | 17.99 | 546.63 | 655.84 | 24 | 2500 |
| 53 | TLLPQLGMHHSYLK | 3 | y12 dicharged | 17.95 | 546.63 | 712.38 | 24 | 2500 |
| 54 | TLLPQLGMHHSYLK | 2 | y11 dicharged | 17.97 | 819.45 | 655.84 | 42.4 | 2500 |
| 55 | TTSSDLLR | 2 | y4 monocharged | 13 | 446.74 | 516.31 | 21.2 | 2500 |
| 56 | TTSSDLLR | 2 | y5 monocharged | 13 | 446.74 | 603.35 | 21.2 | 2500 |
| 57 | TTSSDLLR | 2 | y6 monocharged | 13 | 446.74 | 690.38 | 21.2 | 2500 |
| 58 | VPADQMENYAWGYNK | 3 | y4 monocharged | 17.53 | 595.94 | 481.24 | 25.6 | 2500 |
| 59 | VPADQMENYAWGYNK | 3 | y5 monocharged | 17.53 | 595.94 | 667.32 | 25.6 | 2500 |
| 60 | VPADQMENYAWGYNK | 3 | y6 monocharged | 17.53 | 595.94 | 738.36 | 25.6 | 2500 |
| 61 | VYSNIGTGLLGMIAAK | 3 | y6 monocharged | 24.59 | 536.63 | 590.33 | 23.7 | 2500 |
| 62 | VYSNIGTGLLGMIAAK | 3 | y7 monocharged | 24.59 | 536.63 | 703.42 | 23.7 | 2500 |
| 63 | VYSNIGTGLLGMIAAK | 2 | y11 monocharged | 24.59 | 804.45 | 1031.59 | 41.6 | 2500 |
| 64 | YVQANMGQLK | 2 | y4 monocharged | 13.88 | 576.3 | 445.28 | 28.6 | 2500 |
| 65 | YVQANMGQLK | 2 | y7 monocharged | 13.88 | 576.3 | 761.4 | 28.6 | 2500 |
| 66 | YVQANMGQLK | 2 | y8 monocharged | 13.88 | 576.3 | 889.46 | 28.6 | 2500 |

The other machine parameters used are as follows:

| | |
|---|---|
| Scan type: | MRM |
| MRM planned: | no |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 50.00 psi |
| Heating gas: | 50.00 psi |

-continued

| | |
|---|---|
| Collision gas which induces dissociation: | 9.00 psi |
| Dynamic filling: | activated |
| Declustering potential (DP): | 100.00 V |
| Entry potential before Q0 (EP): | 6.00 V |
| Collision cell exit potential (CXP): | 15 V |
| Total cycle time: | 1.32 sec |

The areas obtained for each of the transitions and for each of the microorganisms studied were measured. When the areas of the transitions are greater than or equal to the positivity threshold described in TABLE 32, the detection of the transition is considered to be positive and is labelled "1" in TABLE 33. When a transition has an area less than the positivity threshold described in TABLE 32, the transition is considered non-detected and is labelled "0" in TABLE 33.

For a given peptide, when at least 3 transitions are labelled "1", the peptide is considered as being detected.

TABLE 33

| Transition number | Sam96 | Sam97 | Sam98 | Sam99 | Sam100 | Sam101 |
|---|---|---|---|---|---|---|
| 1 | 0 | 1 | 1 | 1 | 1 | 0 |
| 2 | 0 | 1 | 1 | 1 | 1 | 0 |
| 3 | 0 | 1 | 1 | 1 | 1 | 0 |
| 4 | 1 | 1 | 1 | 1 | 1 | 1 |
| 5 | 1 | 1 | 1 | 1 | 1 | 1 |
| 6 | 1 | 1 | 1 | 1 | 1 | 1 |
| 7 | 1 | 1 | 1 | 1 | 1 | 0 |
| 8 | 1 | 1 | 1 | 1 | 1 | 0 |
| 9 | 1 | 1 | 1 | 1 | 1 | 0 |
| 10 | 1 | 1 | 1 | 1 | 1 | 0 |
| 11 | 1 | 1 | 1 | 1 | 1 | 0 |
| 12 | 1 | 1 | 1 | 1 | 1 | 0 |
| 13 | 1 | 1 | 1 | 1 | 1 | 0 |
| 14 | 1 | 1 | 1 | 1 | 1 | 0 |
| 15 | 1 | 1 | 1 | 1 | 1 | 0 |
| 16 | 1 | 1 | 1 | 1 | 1 | 1 |
| 17 | 1 | 1 | 1 | 1 | 1 | 1 |
| 18 | 1 | 1 | 1 | 1 | 1 | 1 |
| 19 | 1 | 1 | 1 | 1 | 1 | 0 |
| 20 | 1 | 1 | 1 | 1 | 1 | 0 |
| 21 | 1 | 1 | 1 | 1 | 1 | 0 |
| 22 | 1 | 1 | 1 | 1 | 1 | 1 |
| 23 | 1 | 1 | 1 | 1 | 1 | 1 |
| 24 | 1 | 1 | 1 | 1 | 1 | 1 |
| 25 | 1 | 1 | 1 | 1 | 1 | 1 |
| 26 | 1 | 1 | 1 | 1 | 1 | 1 |
| 27 | 1 | 1 | 1 | 1 | 1 | 1 |
| 28 | 1 | 1 | 1 | 1 | 1 | 0 |
| 29 | 1 | 1 | 1 | 1 | 1 | 0 |
| 30 | 1 | 1 | 1 | 1 | 1 | 0 |
| 31 | 1 | 1 | 1 | 1 | 1 | 0 |
| 32 | 1 | 1 | 1 | 1 | 1 | 0 |
| 33 | 1 | 1 | 1 | 1 | 1 | 0 |
| 34 | 1 | 1 | 1 | 1 | 1 | 0 |
| 35 | 1 | 1 | 1 | 1 | 1 | 0 |
| 36 | 1 | 1 | 1 | 1 | 1 | 0 |
| 37 | 1 | 1 | 1 | 1 | 1 | 0 |
| 38 | 1 | 1 | 1 | 1 | 1 | 0 |
| 39 | 1 | 1 | 1 | 1 | 1 | 0 |
| 40 | 1 | 1 | 1 | 1 | 1 | 1 |
| 41 | 1 | 1 | 1 | 1 | 1 | 1 |
| 42 | 1 | 1 | 1 | 1 | 1 | 1 |
| 43 | 1 | 1 | 1 | 1 | 1 | 1 |
| 44 | 1 | 1 | 1 | 1 | 1 | 1 |
| 45 | 1 | 1 | 1 | 1 | 1 | 1 |
| 46 | 1 | 1 | 1 | 1 | 1 | 0 |
| 47 | 1 | 1 | 1 | 1 | 1 | 0 |
| 48 | 1 | 1 | 1 | 1 | 1 | 0 |
| 49 | 1 | 1 | 1 | 1 | 1 | 1 |
| 50 | 1 | 1 | 1 | 1 | 1 | 1 |
| 51 | 1 | 1 | 1 | 1 | 1 | 1 |
| 52 | 1 | 1 | 1 | 1 | 1 | 0 |
| 53 | 1 | 1 | 1 | 1 | 1 | 0 |
| 54 | 1 | 1 | 1 | 1 | 1 | 0 |
| 55 | 1 | 1 | 1 | 1 | 1 | 1 |
| 56 | 1 | 1 | 1 | 1 | 1 | 1 |
| 57 | 1 | 1 | 1 | 1 | 1 | 1 |
| 58 | 1 | 0 | 0 | 0 | 1 | 0 |
| 59 | 1 | 0 | 0 | 0 | 1 | 0 |
| 60 | 1 | 0 | 0 | 0 | 1 | 0 |
| 61 | 1 | 1 | 1 | 1 | 1 | 1 |
| 62 | 1 | 1 | 1 | 1 | 1 | 1 |
| 63 | 1 | 1 | 1 | 1 | 1 | 1 |
| 64 | 1 | 1 | 1 | 1 | 1 | 1 |
| 65 | 1 | 1 | 1 | 1 | 1 | 1 |
| 66 | 1 | 1 | 1 | 1 | 1 | 1 |

Samples Sam96 to Sam101 comprise at least one peptide which is characteristic of the ACC proteins. The bacteria present in samples Sam96 to Sam101 therefore express a beta-lactamase which confers on them a resistance to penicillins and to cephalosporins, with the exception of fourth-generation cephalosporins.

EXAMPLE 26

Identification of a Resistance to CMY Beta-Lactams

Samples Sam102 to Sam108 are identified according to one of the methods described in examples 1, 3 or 4. The identification of the species is set out in TABLE 34.

TABLE 34

| Names | Species |
|---|---|
| Sam102 | P. mirabilis |
| Sam103 | S. senftenberg |
| Sam104 | P. mirabilis |
| Sam105 | K. oxytoca |
| Sam106 | E. coli |
| Sam107 | S. enterica ssp enterica |
| Sam108 | P. mirabilis |

Samples Sam102 to Sam108 correspond to a species able to comprise a CMY resistance mechanism. Each sample is treated according to example 5, then analysed according to example 6 by detecting the peptides from TABLE 35 instead of the peptides from TABLE 3.

TABLE 35

| Transition number | Peptide | Retention time (minutes) | (m/z) filtered in Q1 | (m/z) filtered in Q3 | Collision energy (eV) | Positivity threshold |
|---|---|---|---|---|---|---|
| 1 | AALLHFYQNWQPQWTPGAK | 22.2 | 752.72 | 372.22 | 30.4 | 2500 |
| 2 | AALLHFYQNWQPQWTPGAK | 22.1 | 752.72 | 442.74 | 30.4 | 2500 |
| 3 | AALLHFYQNWQPQWTPGAK | 22.2 | 752.72 | 884.46 | 30.4 | 2500 |
| 4 | ADIANNHPVTQQTLFELGSVSK | 19.9 | 790.41 | 427.27 | 31.6 | 2500 |
| 5 | ADIANNHPVTQQTLFELGSVSK | 19.9 | 790.41 | 719.39 | 31.6 | 2500 |
| 6 | ADIANNHPVTQQTLFELGSVSK | 19.9 | 790.41 | 866.46 | 31.6 | 2500 |

TABLE 35-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 7 | ADSIINGSDSK | 11.3 | 553.77 | 493.23 | 27.3 | 2500 |
| 8 | ADSIINGSDSK | 11.3 | 553.77 | 607.27 | 27.3 | 2500 |
| 9 | ADSIINGSDSK | 11.3 | 553.77 | 720.35 | 27.3 | 2500 |
| 10 | ANIGGVDDK | 10 | 444.73 | 533.26 | 21.1 | 2500 |
| 11 | ANIGGVDDK | 10 | 444.73 | 590.28 | 21.1 | 2500 |
| 12 | ANIGGVDDK | 10.1 | 444.73 | 703.36 | 21.1 | 2500 |
| 13 | ASWVHK | 9.3 | 364.2 | 383.24 | 16.5 | 2500 |
| 14 | ASWVHK | 9.3 | 364.2 | 569.32 | 16.5 | 2500 |
| 15 | ASWVHK | 9.3 | 364.2 | 656.35 | 16.5 | 2500 |
| 16 | DYAWGYR | 15.6 | 465.71 | 395.2 | 22.3 | 2500 |
| 17 | DYAWGYR | 15.6 | 465.71 | 581.28 | 22.3 | 2500 |
| 18 | DYAWGYR | 15.6 | 465.71 | 652.32 | 22.3 | 2500 |
| 19 | ESGSQVLFNK | 14.5 | 554.79 | 408.22 | 27.4 | 2500 |
| 20 | ESGSQVLFNK | 14.5 | 554.79 | 521.31 | 27.4 | 2500 |
| 21 | ESGSQVLFNK | 14.5 | 554.79 | 620.38 | 27.4 | 2500 |
| 22 | GAMQLDDK | 11.4 | 439.21 | 490.25 | 20.8 | 2500 |
| 23 | GAMQLDDK | 11.4 | 439.21 | 618.31 | 20.8 | 2500 |
| 24 | GAMQLDDK | 11.4 | 439.21 | 749.35 | 20.8 | 2500 |
| 25 | GIGIVMLANR | 19.9 | 522.31 | 604.32 | 25.5 | 2500 |
| 26 | GIGIVMLANR | 19.9 | 522.31 | 703.39 | 25.5 | 2500 |
| 27 | GIGIVMLANR | 19.9 | 522.31 | 873.5 | 25.5 | 2500 |
| 28 | IGDMYQGLGWEMLNWPLK | 27.9 | 717.69 | 357.25 | 29.3 | 2500 |
| 29 | IGDMYQGLGWEMLNWPLK | 27.9 | 717.69 | 657.37 | 29.3 | 2500 |
| 30 | IGDMYQGLGWEMLNWPLK | 27.9 | 717.69 | 901.5 | 29.3 | 2500 |
| 31 | IPGMAVAVLK | 19.3 | 499.81 | 600.41 | 24.2 | 2500 |
| 32 | IPGMAVAVLK | 19.3 | 499.81 | 788.47 | 24.2 | 2500 |
| 33 | IPGMAVAVLK | 19.3 | 499.81 | 885.52 | 24.2 | 2500 |
| 34 | LAHTWITVPQNEQK | 16.5 | 832.94 | 743.37 | 43.2 | 2500 |
| 35 | LAHTWITVPQNEQK | 16.5 | 832.94 | 943.48 | 43.2 | 2500 |
| 36 | LAHTWITVPQNEQK | 16.5 | 832.94 | 1242.65 | 43.2 | 2500 |
| 37 | LLHLATYTAGGLPLQIPDDVR | 22.8 | 755.09 | 526.79 | 30.5 | 2500 |
| 38 | LLHLATYTAGGLPLQIPDDVR | 23 | 755.09 | 601.29 | 30.5 | 2500 |
| 39 | LLHLATYTAGGLPLQIPDDVR | 23 | 755.09 | 1052.57 | 30.5 | 2500 |
| 40 | LSDPVTK | 11.1 | 380.22 | 444.28 | 17.4 | 2500 |
| 41 | LSDPVTK | 11.1 | 380.22 | 559.31 | 17.4 | 2500 |
| 42 | LSDPVTK | 11.1 | 380.22 | 646.34 | 17.4 | 2500 |
| 43 | NLGIVMLANK | 19.6 | 536.81 | 576.32 | 26.3 | 2500 |
| 44 | NLGIVMLANK | 19.6 | 536.81 | 675.39 | 26.3 | 2500 |

TABLE 35-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 45 | NLGIVMLANK | 19.6 | 536.81 | 845.49 | 26.3 | 2500 |
| 46 | QAMASYAYGYSK | 14.1 | 670.3 | 454.23 | 33.9 | 2500 |
| 47 | QAMASYAYGYSK | 14.2 | 670.3 | 617.29 | 33.9 | 2500 |
| 48 | QAMASYAYGYSK | 14.1 | 670.3 | 688.33 | 33.9 | 2500 |
| 49 | QWAPVYSPGSHR | 14.7 | 692.84 | 553.28 | 35.2 | 2500 |
| 50 | QWAPVYSPGSHR | 14.8 | 692.84 | 640.32 | 35.2 | 2500 |
| 51 | QWAPVYSPGSHR | 14.8 | 692.84 | 999.5 | 35.2 | 2500 |
| 52 | QWQGIR | 13.1 | 394.21 | 345.22 | 18.2 | 2500 |
| 53 | QWQGIR | 13.1 | 394.21 | 473.28 | 18.2 | 2500 |
| 54 | QWQGIR | 13.1 | 394.21 | 659.36 | 18.2 | 2500 |
| 55 | SSVIDMAR | 14.3 | 439.72 | 492.22 | 20.8 | 2500 |
| 56 | SSVIDMAR | 14.3 | 439.72 | 605.31 | 20.8 | 2500 |
| 57 | SSVIDMAR | 14.3 | 439.72 | 704.38 | 20.8 | 2500 |
| 58 | SYPNPVR | 11.6 | 416.72 | 371.24 | 19.5 | 2500 |
| 59 | SYPNPVR | 11.6 | 416.72 | 485.28 | 19.5 | 2500 |
| 60 | SYPNPVR | 11.6 | 416.72 | 582.34 | 19.5 | 2500 |
| 61 | TEQQIADIVNR | 15.8 | 643.84 | 616.34 | 32.4 | 2500 |
| 62 | TEQQIADIVNR | 15.8 | 643.84 | 687.38 | 32.4 | 2500 |
| 63 | TEQQIADIVNR | 15.8 | 643.84 | 800.46 | 32.4 | 2500 |
| 64 | TFNGVLGGDAIAR | 17.9 | 645.84 | 602.33 | 32.5 | 2500 |
| 65 | TFNGVLGGDAIAR | 17.9 | 645.84 | 659.35 | 32.5 | 2500 |
| 66 | TFNGVLGGDAIAR | 17.9 | 645.84 | 772.43 | 32.5 | 2500 |
| 67 | TITPLMQEQAIPGMAVAVIYQGK | 24.9 | 820.44 | 617.34 | 32.5 | 2500 |
| 68 | TITPLMQEQAIPGMAVAVIYQGK | 25 | 820.44 | 778.45 | 32.5 | 2500 |
| 69 | TITPLMQEQAIPGMAVAVIYQGK | 24.9 | 820.44 | 1233.67 | 32.5 | 2500 |
| 70 | TLQQGIALAQSR | 15.5 | 643.37 | 574.33 | 32.4 | 2500 |
| 71 | TLQQGIALAQSR | 15.5 | 643.37 | 645.37 | 32.4 | 2500 |
| 72 | TLQQGIALAQSR | 15.5 | 643.37 | 815.47 | 32.4 | 2500 |
| 73 | TLTATLGAYAVVK | 19.7 | 654.38 | 707.41 | 33 | 2500 |
| 74 | TLTATLGAYAVVK | 19.7 | 654.38 | 820.49 | 33 | 2500 |
| 75 | TLTATLGAYAVVK | 19.7 | 654.38 | 921.54 | 33 | 2500 |
| 76 | VALAALPAVEVNPPAPAVK | 21.1 | 609.7 | 644.87 | 26 | 2500 |
| 77 | VALAALPAVEVNPPAPAVK | 21 | 609.7 | 679.41 | 26 | 2500 |
| 78 | VALAALPAVEVNPPAPAVK | 21 | 609.7 | 793.46 | 26 | 2500 |
| 79 | VEAAWR | 12 | 366.2 | 432.24 | 16.6 | 2500 |
| 80 | VEAAWR | 12 | 366.2 | 503.27 | 16.6 | 2500 |
| 81 | VEAAWR | 12 | 366.2 | 632.32 | 16.6 | 2500 |
| 82 | VLQPLK | 13.1 | 349.23 | 357.25 | 15.6 | 2500 |

TABLE 35-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 83 | VLQPLK | 13.1 | 349.23 | 485.31 | 15.6 | 2500 |
| 84 | VLQPLK | 13 | 349.23 | 598.39 | 15.6 | 2500 |
| 85 | VNPGMLADEAYGIK | 18.8 | 739.37 | 632.82 | 37.9 | 2500 |
| 86 | VNPGMLADEAYGIK | 18.9 | 739.37 | 795.39 | 37.9 | 2500 |
| 87 | VNPGMLADEAYGIK | 18.9 | 739.37 | 866.43 | 37.9 | 2500 |
| 88 | WVQANMDASHVQEK | 13.4 | 548.26 | 615.28 | 24.1 | 2500 |
| 89 | WVQANMDASHVQEK | 13.4 | 548.26 | 679.31 | 24.1 | 2500 |
| 90 | WVQANMDASHVQEK | 13.4 | 548.26 | 728.85 | 24.1 | 2500 |
| 91 | YWPELTGK | 17.8 | 497.26 | 305.18 | 24.1 | 2500 |
| 92 | YWPELTGK | 17.8 | 497.26 | 418.27 | 24.1 | 2500 |
| 93 | YWPELTGK | 17.8 | 497.26 | 644.36 | 24.1 | 2500 |

The other machine parameters used are as follows:

| | |
|---|---|
| Scan type: | MRM |
| MRM planned: | yes |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 50.00 psi |
| Heating gas: | 50.00 psi |
| Collision gas which induces dissociation: | 9.00 psi |
| Dynamic filling: | activated |
| Declustering potential (DP): | 100.00 V |
| Entry potential before Q0 (EP): | 6.00 V |
| Collision cell exit potential (CXP): | 15 V |
| Total cycle time: | 0.04 sec |
| Detection window: | 120 sec |

The areas obtained for each of the transitions and for each of the microorganisms studied were measured. When the areas of the transitions are greater than or equal to the positivity threshold described in TABLE 35, the detection of the transition is considered to be positive and is labelled "1" in TABLE 36. When a transition has an area less than the positivity threshold described in TABLE 35, the transition is considered non-detected and is labelled "0" in TABLE 36.

For a given peptide, when at least 3 transitions are labelled "1", the peptide is considered as being detected.

TABLE 36

| Transition number | Sam102 | Sam103 | Sam104 | Sam105 | Sam106 | Sam107 | Sam108 |
|---|---|---|---|---|---|---|---|
| 1 | 0 | 0 | 0 | 1 | 0 | 0 | 1 |
| 2 | 0 | 0 | 0 | 1 | 0 | 0 | 1 |
| 3 | 0 | 0 | 0 | 1 | 0 | 0 | 1 |
| 4 | 0 | 0 | 0 | 0 | 1 | 0 | 0 |
| 5 | 0 | 0 | 0 | 0 | 1 | 0 | 0 |
| 6 | 0 | 0 | 0 | 0 | 1 | 0 | 0 |
| 7 | 1 | 1 | 1 | 1 | 1 | 1 | 1 |
| 8 | 1 | 1 | 1 | 1 | 1 | 1 | 1 |
| 9 | 1 | 1 | 1 | 1 | 1 | 1 | 1 |
| 10 | 0 | 0 | 0 | 0 | 0 | 0 | 0 |
| 11 | 0 | 0 | 0 | 0 | 0 | 0 | 0 |
| 12 | 0 | 0 | 0 | 0 | 0 | 0 | 0 |
| 13 | 1 | 1 | 1 | 1 | 1 | 1 | 1 |
| 14 | 1 | 1 | 1 | 1 | 1 | 1 | 1 |
| 15 | 1 | 1 | 1 | 1 | 1 | 1 | 1 |
| 16 | 0 | 1 | 0 | 1 | 1 | 1 | 0 |
| 17 | 0 | 1 | 0 | 1 | 1 | 1 | 0 |
| 18 | 0 | 1 | 0 | 1 | 1 | 1 | 0 |
| 19 | 0 | 0 | 0 | 1 | 0 | 0 | 0 |
| 20 | 0 | 0 | 0 | 1 | 0 | 0 | 0 |
| 21 | 0 | 0 | 0 | 1 | 0 | 0 | 0 |
| 22 | 0 | 0 | 0 | 0 | 0 | 0 | 1 |
| 23 | 0 | 0 | 0 | 0 | 0 | 0 | 1 |
| 24 | 0 | 0 | 0 | 0 | 0 | 0 | 1 |
| 25 | 0 | 0 | 0 | 0 | 0 | 0 | 0 |
| 26 | 0 | 0 | 0 | 0 | 0 | 0 | 0 |
| 27 | 0 | 0 | 0 | 0 | 0 | 0 | 0 |
| 28 | 0 | 0 | 0 | 1 | 0 | 0 | 0 |
| 29 | 0 | 0 | 0 | 1 | 0 | 0 | 0 |
| 30 | 0 | 0 | 0 | 1 | 0 | 0 | 0 |
| 31 | 0 | 0 | 0 | 0 | 0 | 0 | 0 |
| 32 | 0 | 0 | 0 | 0 | 0 | 0 | 0 |
| 33 | 0 | 0 | 0 | 0 | 0 | 0 | 0 |
| 34 | 1 | 1 | 1 | 1 | 1 | 1 | 1 |
| 35 | 1 | 1 | 1 | 1 | 1 | 1 | 1 |
| 36 | 1 | 1 | 1 | 1 | 1 | 1 | 1 |
| 37 | 0 | 0 | 0 | 0 | 0 | 0 | 0 |
| 38 | 0 | 0 | 0 | 0 | 0 | 0 | 0 |
| 39 | 0 | 0 | 0 | 0 | 0 | 0 | 0 |
| 40 | 1 | 1 | 1 | 1 | 0 | 1 | 1 |
| 41 | 1 | 1 | 1 | 1 | 0 | 1 | 1 |
| 42 | 1 | 1 | 1 | 1 | 0 | 1 | 1 |
| 43 | 1 | 1 | 1 | 1 | 1 | 1 | 1 |
| 44 | 1 | 1 | 1 | 1 | 1 | 1 | 1 |
| 45 | 1 | 1 | 1 | 1 | 1 | 1 | 1 |
| 46 | 0 | 0 | 0 | 0 | 0 | 0 | 0 |

TABLE 36-continued

| Transition number | Sam102 | Sam103 | Sam104 | Sam105 | Sam106 | Sam107 | Sam108 |
|---|---|---|---|---|---|---|---|
| 47 | 0 | 0 | 0 | 0 | 0 | 0 | 0 |
| 48 | 0 | 0 | 0 | 0 | 0 | 0 | 0 |
| 49 | 0 | 0 | 0 | 0 | 0 | 0 | 0 |
| 50 | 0 | 0 | 0 | 0 | 0 | 0 | 0 |
| 51 | 0 | 0 | 0 | 0 | 0 | 0 | 0 |
| 52 | 1 | 1 | 1 | 1 | 1 | 1 | 1 |
| 53 | 1 | 1 | 1 | 1 | 1 | 1 | 1 |
| 54 | 1 | 1 | 1 | 1 | 1 | 1 | 1 |
| 55 | 1 | 1 | 1 | 1 | 1 | 1 | 1 |
| 56 | 1 | 1 | 1 | 1 | 1 | 1 | 1 |
| 57 | 1 | 1 | 1 | 1 | 1 | 1 | 1 |
| 58 | 0 | 1 | 1 | 1 | 1 | 0 | 1 |
| 59 | 0 | 1 | 1 | 1 | 1 | 0 | 1 |
| 60 | 0 | 1 | 1 | 1 | 1 | 0 | 1 |
| 61 | 1 | 1 | 1 | 1 | 1 | 1 | 1 |
| 62 | 1 | 1 | 1 | 1 | 1 | 1 | 1 |
| 63 | 1 | 1 | 1 | 1 | 1 | 1 | 1 |
| 64 | 1 | 1 | 1 | 1 | 1 | 1 | 1 |
| 65 | 1 | 1 | 1 | 1 | 1 | 1 | 1 |
| 66 | 1 | 1 | 1 | 1 | 1 | 1 | 1 |
| 67 | 1 | 0 | 0 | 0 | 0 | 1 | 0 |
| 68 | 1 | 0 | 0 | 0 | 0 | 1 | 0 |
| 69 | 1 | 0 | 0 | 0 | 0 | 1 | 0 |
| 70 | 1 | 1 | 1 | 1 | 1 | 1 | 1 |
| 71 | 1 | 1 | 1 | 1 | 1 | 1 | 1 |
| 72 | 1 | 1 | 1 | 1 | 1 | 1 | 1 |
| 73 | 0 | 0 | 0 | 0 | 0 | 0 | 0 |
| 74 | 0 | 0 | 0 | 0 | 0 | 0 | 0 |
| 75 | 0 | 0 | 0 | 0 | 0 | 0 | 0 |
| 76 | 1 | 1 | 1 | 1 | 1 | 1 | 1 |
| 77 | 1 | 1 | 1 | 1 | 1 | 1 | 1 |
| 78 | 1 | 1 | 1 | 1 | 1 | 1 | 1 |
| 79 | 1 | 1 | 1 | 1 | 1 | 1 | 1 |
| 80 | 1 | 1 | 1 | 1 | 1 | 1 | 1 |
| 81 | 1 | 1 | 1 | 1 | 1 | 1 | 1 |
| 82 | 1 | 1 | 1 | 1 | 1 | 1 | 1 |
| 83 | 1 | 1 | 1 | 1 | 1 | 1 | 1 |
| 84 | 1 | 1 | 1 | 1 | 1 | 1 | 1 |
| 85 | 0 | 0 | 1 | 0 | 1 | 1 | 1 |
| 86 | 0 | 0 | 1 | 0 | 1 | 1 | 1 |
| 87 | 0 | 0 | 1 | 0 | 1 | 1 | 1 |
| 88 | 1 | 1 | 1 | 1 | 1 | 1 | 1 |
| 89 | 1 | 1 | 1 | 1 | 1 | 1 | 1 |
| 90 | 1 | 1 | 1 | 1 | 1 | 1 | 1 |
| 91 | 1 | 1 | 1 | 1 | 0 | 1 | 1 |
| 92 | 1 | 1 | 1 | 1 | 0 | 1 | 1 |
| 93 | 1 | 1 | 1 | 1 | 0 | 1 | 1 |

Samples Sam102 to Sam108 comprise at least one peptide which is characteristic of the CMY proteins. The bacteria present in samples Sam102 to Sam108 therefore express a beta-lactamase which confers on them a resistance to penicillins and to cephalosporins, with the exception of fourth-generation cephalosporins.

EXAMPLE 27

Identification of a Resistance to CTX-M Beta-Lactams

Samples Sam109 to Sam118 are identified according to one of the methods described in examples 1, 3 or 4. The identification of the species is set out in TABLE 37.

TABLE 37

| Names | Species |
|---|---|
| Sam109 | *E. aerogenes* |
| Sam110 | *E. coli* |
| Sam111 | *E. coli* |
| Sam112 | *E. coli* |
| Sam113 | *E. coli* |
| Sam114 | *K. pneumoniae* |
| Sam115 | *K. pneumoniae* |
| Sam116 | *P. mirabilis* |
| Sam117 | *Salmonella* spp |
| Sam118 | *Salmonella* spp |

Samples Sam109 to Sam118 correspond to a species able to comprise a CTX-M resistance mechanism. Each sample is treated according to example 5, then analysed according to example 6 by detecting the peptides from TABLE 38 instead of the peptides from TABLE 3.

TABLE 38

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 1 | AGLPK | 2 | 1 | y4 | 8.4 | 243.16 | 414.27 | 9.6 | 3000 |
| 2 | AGLPK | 2 | 1 | y3 | 8.4 | 243.16 | 357.25 | 9.6 | 3000 |
| 3 | AGLPK | 2 | 2 | y3 | 8.4 | 243.16 | 179.13 | 9.6 | 3000 |
| 4 | AGLPTSWTVGDK | 2 | 1 | y9 | 18 | 616.32 | 990.49 | 30.9 | 2000 |
| 5 | AGLPTSWTVGDK | 2 | 1 | y7 | 18 | 616.32 | 792.39 | 30.9 | 2000 |
| 6 | AGLPTSWTVGDK | 2 | 2 | y9 | 17.9 | 616.32 | 495.75 | 30.9 | 2000 |
| 7 | AIGDETFR | 2 | 1 | y6 | 13.5 | 454.73 | 724.33 | 21.7 | 2000 |
| 8 | AIGDETFR | 2 | 1 | y5 | 13.5 | 454.73 | 667.31 | 21.7 | 2000 |
| 9 | AIGDETFR | 2 | 1 | y4 | 13.5 | 454.73 | 552.28 | 21.7 | 2000 |
| 10 | ALAETQR | 2 | 1 | y5 | 7.5 | 394.72 | 604.31 | 18.2 | 2000 |
| 11 | ALAETQR | 2 | 1 | y4 | 7.5 | 394.72 | 533.27 | 18.2 | 2000 |

TABLE 38-continued

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 12 | ALAETQR | 2 | 2 | y6 | 7.5 | 394.72 | 359.2 | 18.2 | 2000 |
| 13 | ALGDSQR | 2 | 1 | y5 | 3.5 | 373.69 | 562.26 | 17 | 2000 |
| 14 | ALGDSQR | 2 | 1 | y3 | 3.6 | 373.69 | 390.21 | 17 | 2000 |
| 15 | ALGDSQR | 2 | 2 | y6 | 3.5 | 373.69 | 338.18 | 17 | 2000 |
| 16 | AMAQTLR | 2 | 1 | y5 | 10.7 | 395.72 | 588.35 | 18.3 | 2000 |
| 17 | AMAQTLR | 2 | 1 | y4 | 10.7 | 395.72 | 517.31 | 18.3 | 2000 |
| 18 | AMAQTLR | 2 | 1 | y3 | 10.7 | 395.72 | 389.25 | 18.3 | 2000 |
| 19 | APLILVTYFTQPQPK | 2 | 1 | y10 | 24.6 | 858.49 | 1208.63 | 44.7 | 2000 |
| 20 | APLILVTYFTQPQPK | 3 | 1 | y6 | 24.6 | 572.66 | 698.38 | 24.8 | 2000 |
| 21 | APLILVTYFTQPQPK | 3 | 1 | y4 | 24.6 | 572.66 | 469.28 | 24.8 | 2000 |
| 22 | APLVLVTYFTQPQQNAESR | 3 | 1 | y8 | 23.6 | 721.38 | 929.44 | 29.4 | 2000 |
| 23 | APLVLVTYFTQPQQNAESR | 3 | 1 | y6 | 23.6 | 721.38 | 704.33 | 29.4 | 2000 |
| 24 | APLVLVTYFTQPQQNAESR | 3 | 2 | y8 | 23.6 | 721.38 | 465.23 | 29.4 | 2000 |
| 25 | AQLVTWLK | 2 | 1 | y6 | 20 | 479.79 | 759.48 | 23.1 | 2000 |
| 26 | AQLVTWLK | 2 | 1 | y5 | 20 | 479.79 | 646.39 | 23.1 | 2000 |
| 27 | AQLVTWLK | 2 | 1 | y4 | 20 | 479.79 | 547.32 | 23.1 | 2000 |
| 28 | AQLVTWMK | 2 | 1 | y6 | 18.5 | 488.77 | 777.43 | 23.6 | 2000 |
| 29 | AQLVTWMK | 2 | 1 | y5 | 18.6 | 488.77 | 664.35 | 23.6 | 2000 |
| 30 | AQLVTWMK | 2 | 1 | y4 | 18.5 | 488.77 | 565.28 | 23.6 | 2000 |
| 31 | DILAAAAK | 2 | 1 | y6 | 14.1 | 386.73 | 544.35 | 17.8 | 2000 |
| 32 | DILAAAAK | 2 | 1 | y5 | 14.1 | 386.73 | 431.26 | 17.8 | 2000 |
| 33 | DILAAAAK | 2 | 1 | y4 | 14.1 | 386.73 | 360.22 | 17.8 | 2000 |
| 34 | DTTSPR | 2 | 1 | y5 | 1 | 338.67 | 561.3 | 15 | 2000 |
| 35 | DTTSPR | 2 | 1 | y4 | 1 | 338.67 | 460.25 | 15 | 2000 |
| 36 | DTTSPR | 2 | 1 | y3 | 1 | 338.67 | 359.2 | 15 | 2000 |
| 37 | DTTTPLAMAQTLK | 2 | 1 | y9 | 19.4 | 695.87 | 972.56 | 35.4 | 2000 |
| 38 | DTTTPLAMAQTLK | 2 | 1 | y7 | 19.4 | 695.87 | 762.42 | 35.4 | 2000 |
| 39 | DTTTPLAMAQTLK | 2 | 2 | y9 | 19.4 | 695.87 | 486.78 | 35.4 | 2000 |
| 40 | DTTTPR | 2 | 1 | y5 | 1 | 345.67 | 575.32 | 15.4 | 2000 |
| 41 | DTTTPR | 2 | 1 | y4 | 1 | 345.67 | 474.27 | 15.4 | 2000 |
| 42 | DTTTPR | 2 | 1 | y3 | 1 | 345.67 | 373.22 | 15.4 | 2000 |
| 43 | DVLAAAAK | 2 | 1 | y6 | 12.2 | 379.72 | 544.35 | 17.4 | 2000 |
| 44 | DVLAAAAK | 2 | 1 | y5 | 12.2 | 379.72 | 431.26 | 17.4 | 2000 |
| 45 | DVLAAAAK | 2 | 1 | y4 | 12.2 | 379.72 | 360.22 | 17.4 | 2000 |
| 46 | DVLASAAK | 2 | 1 | y6 | 11.4 | 387.72 | 560.34 | 17.8 | 2000 |
| 47 | DVLASAAK | 2 | 1 | y5 | 11.4 | 387.72 | 447.26 | 17.8 | 2000 |
| 48 | DVLASAAK | 2 | 1 | y4 | 11.4 | 387.72 | 376.22 | 17.8 | 2000 |
| 49 | DVLASAAR | 2 | 1 | y6 | 11.9 | 401.73 | 588.35 | 18.6 | 2000 |

TABLE 38-continued

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 50 | DVLASAAR | 2 | 1 | y5 | 11.9 | 401.73 | 475.26 | 18.6 | 2000 |
| 51 | DVLASAAR | 2 | 1 | y4 | 11.9 | 401.73 | 404.23 | 18.6 | 2000 |
| 52 | FAMCSTSK | 2 | 1 | y7 | 11.6 | 466.2 | 784.33 | 22.3 | 2000 |
| 53 | FAMCSTSK | 2 | 1 | y6 | 11.6 | 466.2 | 713.3 | 22.3 | 2000 |
| 54 | FAMCSTSK | 2 | 1 | y5 | 11.6 | 466.2 | 582.26 | 22.3 | 2000 |
| 55 | FPMCSTSK | 2 | 1 | y7 | 12.3 | 479.21 | 810.35 | 23.1 | 2000 |
| 56 | FPMCSTSK | 2 | 1 | y6 | 12.3 | 479.21 | 713.3 | 23.1 | 2000 |
| 57 | FPMCSTSK | 2 | 2 | y7 | 12.3 | 479.21 | 405.68 | 23.1 | 2000 |
| 58 | GNTTGAASIQAGLPASWVVGDK | 3 | 1 | y9 | 21.1 | 700.7 | 958.5 | 29.1 | 2000 |
| 59 | GNTTGAASIQAGLPASWVVGDK | 3 | 1 | y7 | 21.1 | 700.7 | 790.41 | 29.1 | 2000 |
| 60 | GNTTGAASIQAGLPASWVVGDK | 3 | 2 | y9 | 21.2 | 700.7 | 479.75 | 29.1 | 2000 |
| 61 | GNTTGAASIQAGLPTSWVVGDK | 3 | 1 | y9 | 21.3 | 710.7 | 988.51 | 29.1 | 8500 |
| 62 | GNTTGAASIQAGLPTSWVVGDK | 3 | 2 | y9 | 21.3 | 710.7 | 494.76 | 29.1 | 8500 |
| 63 | GNTTGAASIQAGLPTSWVVGDK | 3 | 1 | y3 | 21.3 | 710.7 | 319.16 | 29.1 | 8500 |
| 64 | GNTTGAASIR | 2 | 1 | y7 | 9.3 | 474.25 | 675.38 | 22.8 | 2000 |
| 65 | GNTTGAASIR | 2 | 1 | y6 | 9.3 | 474.25 | 574.33 | 22.8 | 2000 |
| 66 | GNTTGAASIR | 2 | 1 | y4 | 9.3 | 474.25 | 446.27 | 22.8 | 2000 |
| 67 | GNTTGSASIR | 2 | 1 | y8 | 8 | 482.25 | 792.42 | 23.2 | 2000 |
| 68 | GNTTGSASIR | 2 | 1 | y7 | 8 | 482.25 | 691.37 | 23.2 | 2000 |
| 69 | GNTTGSASIR | 2 | 1 | y6 | 8 | 482.25 | 590.33 | 23.2 | 2000 |
| 70 | HLLNQR | 2 | 1 | y5 | 8.1 | 390.73 | 643.39 | 18 | 2000 |
| 71 | HLLNQR | 2 | 1 | y4 | 8.1 | 390.73 | 530.31 | 18 | 2000 |
| 72 | HLLNQR | 2 | 1 | y3 | 8.1 | 390.73 | 417.22 | 18 | 2000 |
| 73 | LAALEK | 2 | 1 | y5 | 11.3 | 322.7 | 531.31 | 14.1 | 2000 |
| 74 | LAALEK | 2 | 1 | y4 | 11.3 | 322.7 | 460.28 | 14.1 | 2000 |
| 75 | LAALEK | 2 | 1 | y3 | 11.3 | 322.7 | 389.24 | 14.1 | 2000 |
| 76 | LAELER | 2 | 1 | y5 | 11.7 | 365.71 | 617.33 | 16.6 | 2000 |
| 77 | LAELER | 2 | 1 | y4 | 11.7 | 365.71 | 546.29 | 16.6 | 2000 |
| 78 | LAELER | 2 | 1 | y3 | 11.7 | 365.71 | 417.25 | 16.6 | 2000 |
| 79 | LGVALIDTADNTQVLYR | 3 | 1 | y6 | 21.5 | 621.34 | 779.44 | 26.3 | 2000 |
| 80 | LGVALIDTADNTQVLYR | 3 | 1 | y5 | 21.5 | 621.34 | 678.39 | 26.3 | 2000 |
| 81 | LGVALIDTADNTQVLYR | 3 | 1 | y4 | 21.5 | 621.34 | 550.34 | 26.3 | 2000 |
| 82 | LGVALIDTADNTQVLYR | 3 | 1 | y3 | 21.4 | 621.34 | 451.27 | 26.3 | 2000 |
| 83 | LGVALINTADNSQILYR | 3 | 1 | y6 | 21.4 | 621.01 | 779.44 | 26.3 | 2000 |
| 84 | LGVALINTADNSQILYR | 3 | 1 | y5 | 21.4 | 621.01 | 692.41 | 26.3 | 2000 |
| 85 | LGVALINTADNSQILYR | 3 | 1 | y4 | 21.4 | 621.01 | 564.35 | 26.3 | 2000 |
| 86 | LGVALINTADNSQILYR | 3 | 1 | y3 | 21.4 | 621.01 | 451.27 | 26.3 | 2000 |
| 87 | LIAHLGGPDK | 3 | 1 | y6 | 13.2 | 340.87 | 586.32 | 17.6 | 2000 |

TABLE 38-continued

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 88 | LIAHLGGPDK | 3 | 2 | y9 | 13.2 | 340.87 | 454.25 | 17.6 | 2000 |
| 89 | LIAHLGGPDK | 3 | 2 | y8 | 13.2 | 340.87 | 397.71 | 17.6 | 2000 |
| 90 | LIAHVGGPASVTAFAR | 3 | 1 | y5 | 17.7 | 522.96 | 565.31 | 23.3 | 2000 |
| 91 | LIAHVGGPASVTAFAR | 3 | 1 | y4 | 17.7 | 522.96 | 464.26 | 23.3 | 2000 |
| 92 | LIAHVGGPASVTAFAR | 3 | 1 | y3 | 17.7 | 522.96 | 393.22 | 23.3 | 2000 |
| 93 | LIAQLGGPGGVTAFAR | 2 | 1 | y11 | 20.3 | 764.44 | 989.52 | 39.3 | 2000 |
| 94 | LIAQLGGPGGVTAFAR | 2 | 1 | y9 | 20.3 | 764.44 | 875.47 | 39.3 | 2000 |
| 95 | LIAQLGGPGGVTAFAR | 3 | 1 | y5 | 20.3 | 509.96 | 565.31 | 22.9 | 2000 |
| 96 | NLTLGK | 2 | 1 | y5 | 12.3 | 323.2 | 531.35 | 14.2 | 2000 |
| 97 | NLTLGK | 2 | 1 | y4 | 12.3 | 323.2 | 418.27 | 14.2 | 2000 |
| 98 | NLTLGK | 2 | 1 | y3 | 12.3 | 323.2 | 317.22 | 14.2 | 2000 |
| 99 | QLGDETFR | 2 | 1 | y6 | 13.6 | 483.24 | 724.33 | 23.3 | 2000 |
| 100 | QLGDETFR | 2 | 1 | y4 | 13.6 | 483.24 | 552.28 | 23.3 | 2000 |
| 101 | QLGDETFR | 2 | 1 | y3 | 13.6 | 483.24 | 423.24 | 23.3 | 2000 |
| 102 | QLTLGHALGETQR | 3 | 2 | y11 | 15.6 | 475.26 | 591.82 | 21.8 | 2000 |
| 103 | QLTLGHALGETQR | 3 | 1 | y5 | 15.6 | 475.26 | 590.29 | 21.8 | 2000 |
| 104 | QLTLGHALGETQR | 3 | 2 | y10 | 15.6 | 475.26 | 541.29 | 21.8 | 2000 |
| 105 | QSESDK | 2 | 1 | y5 | 0.8 | 347.16 | 565.25 | 15.5 | 2000 |
| 106 | QSESDK | 2 | 1 | y4 | 0.8 | 347.16 | 478.21 | 15.5 | 2000 |
| 107 | QSESDK | 2 | 1 | y3 | 0.8 | 347.16 | 349.17 | 15.5 | 2000 |
| 108 | QSETQK | 2 | 1 | y5 | 0.8 | 360.68 | 592.29 | 16.3 | 2000 |
| 109 | QSETQK | 2 | 1 | y4 | 0.8 | 360.68 | 505.26 | 16.3 | 2000 |
| 110 | QSETQK | 2 | 1 | y3 | 0.8 | 360.68 | 376.22 | 16.3 | 2000 |
| 111 | QSGGR | 2 | 1 | y4 | 0.7 | 252.63 | 376.19 | 10.1 | 2000 |
| 112 | QSGGR | 2 | 1 | y3 | 0.7 | 252.63 | 289.16 | 10.1 | 2000 |
| 113 | QSGGR | 2 | 2 | y4 | 0.7 | 252.63 | 188.6 | 10.1 | 2000 |
| 114 | SDLVNYNPIAEK | 2 | 1 | y8 | 17.3 | 681.85 | 948.48 | 34.6 | 2000 |
| 115 | SDLVNYNPIAEK | 2 | 1 | y6 | 17.4 | 681.85 | 671.37 | 34.6 | 2000 |
| 116 | SDLVNYNPIAEK | 2 | 1 | y5 | 17.4 | 681.85 | 557.33 | 34.6 | 2000 |
| 117 | SESEPNLLNQR | 2 | 1 | y7 | 14.6 | 643.82 | 854.48 | 32.4 | 2000 |
| 118 | SESEPNLLNQR | 2 | 2 | y7 | 14.6 | 643.82 | 427.75 | 32.4 | 2000 |
| 119 | SESEPNLLNQR | 3 | 1 | y3 | 14.6 | 429.55 | 417.22 | 20.4 | 2000 |
| 120 | SLGDETFR | 2 | 1 | y6 | 13.9 | 462.73 | 724.33 | 22.1 | 2000 |
| 121 | SLGDETFR | 2 | 1 | y5 | 13.8 | 462.73 | 667.31 | 22.1 | 2000 |
| 122 | SLGDETFR | 2 | 1 | y4 | 13.9 | 462.73 | 552.28 | 22.1 | 2000 |
| 123 | SSGGR | 2 | 1 | y4 | 0.7 | 232.12 | 376.19 | 9 | 2000 |
| 124 | SSGGR | 2 | 1 | y3 | 0.7 | 232.12 | 289.16 | 9 | 2000 |
| 125 | SSGGR | 2 | 2 | y4 | 0.7 | 232.12 | 188.6 | 9 | 2000 |

TABLE 38-continued

| Transition number | Peptide | Charge state of the precursor | Charge state of the fragment | Fragment ion | Retention time (minutes) | (m/z) filtered in Q1 | (m/z) filtered in Q3 | Collision energy (eV) | Positivity threshold |
|---|---|---|---|---|---|---|---|---|---|
| 126 | SWVVGDK | 2 | 1 | y5 | 13.9 | 395.71 | 517.3 | 18.3 | 2000 |
| 127 | SWVVGDK | 2 | 1 | y4 | 13.9 | 395.71 | 418.23 | 18.3 | 2000 |
| 128 | SWVVGDK | 2 | 1 | y3 | 13.9 | 395.71 | 319.16 | 18.3 | 2000 |
| 129 | TEPTLNTAIPGDPR | 2 | 2 | y12 | 16.3 | 741.38 | 626.34 | 38 | 2000 |
| 130 | TEPTLNTAIPGDPR | 2 | 1 | y5 | 16.3 | 741.38 | 541.27 | 38 | 2000 |
| 131 | TEPTLNTAIPGDPR | 3 | 1 | y5 | 16.3 | 494.59 | 541.27 | 22.4 | 2000 |
| 132 | TGSGDYGTTNDIAVIWPK | 2 | 1 | y8 | 20.9 | 947.96 | 941.55 | 49.8 | 2000 |
| 133 | TGSGDYGTTNDIAVIWPK | 3 | 2 | y6 | 21 | 632.31 | 357.22 | 26.7 | 2000 |
| 134 | TGSGDYGTTNDIAVIWPK | 3 | 2 | y5 | 20.9 | 632.31 | 321.7 | 26.7 | 2000 |
| 135 | TGSGDYGTTNDIAVIWPQGR | 3 | 1 | y6 | 20.5 | 703.34 | 756.42 | 28.9 | 2000 |
| 136 | TGSGDYGTTNDIAVIWPQGR | 3 | 1 | y5 | 20.5 | 703.34 | 643.33 | 28.9 | 2000 |
| 137 | TGSGDYGTTNDIAVIWPQGR | 3 | 1 | y4 | 20.5 | 703.34 | 457.25 | 28.9 | 2000 |
| 138 | TGSGGYGTTNDIAVIWPK | 2 | 1 | y3 | 20.9 | 918.96 | 430.25 | 48.1 | 2000 |
| 139 | TGSGGYGTTNDIAVIWPK | 3 | 1 | y6 | 20.9 | 612.98 | 713.43 | 26.1 | 2000 |
| 140 | TGSGGYGTTNDIAVIWPK | 3 | 1 | y5 | 20.9 | 612.98 | 642.4 | 26.1 | 2000 |
| 141 | VMAAAAVLK | 2 | 1 | y8 | 15.7 | 437.27 | 774.45 | 20.7 | 2000 |
| 142 | VMAAAAVLK | 2 | 1 | y7 | 15.7 | 437.27 | 643.41 | 20.7 | 2000 |
| 143 | VMAAAAVLK | 2 | 1 | y6 | 15.7 | 437.27 | 572.38 | 20.7 | 2000 |
| 144 | VMAVAAVLK | 2 | 1 | y7 | 18.2 | 451.28 | 671.45 | 21.5 | 2000 |
| 145 | VMAVAAVLK | 2 | 1 | y6 | 18.2 | 451.28 | 600.41 | 21.5 | 2000 |
| 146 | VMAVAAVLK | 2 | 1 | y5 | 18.2 | 451.28 | 501.34 | 21.5 | 2000 |
| 147 | VTAFAR | 2 | 1 | y5 | 11 | 332.69 | 565.31 | 14.7 | 2000 |
| 148 | VTAFAR | 2 | 1 | y4 | 11 | 332.69 | 464.26 | 14.7 | 2000 |
| 149 | VTAFAR | 2 | 1 | y3 | 11 | 332.69 | 393.22 | 14.7 | 2000 |

The other machine parameters used are as follows:

| | |
|---|---|
| Scan type: | MRM |
| MRM planned: | yes |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 50.00 psi |
| Heating gas: | 50.00 psi |
| Collision gas which induces dissociation: | 9.00 psi |
| Dynamic filling: | activated |
| Declustering potential (DP): | 100.00 V |
| Entry potential before Q0 (EP): | 6.00 V |

-continued

| | |
|---|---|
| Collision cell exit potential (CXP): | 15 V |
| Total cycle time: | 0.04 sec |
| Detection window: | 120 sec |

The areas obtained for each of the transitions and for each of the microorganisms studied were measured. When the areas of the transitions are greater than or equal to the positivity threshold described in TABLE 38, the detection of the transition is considered to be positive and is labelled "1" in TABLE 39. When a transition has an area less than the positivity threshold described in TABLE 38, the transition is considered non-detected and is labelled "0" in TABLE 39.

For a given peptide, when at least 3 transitions are labelled "1", the peptide is considered as being detected.

TABLE 39

| Transition number | Sam109 | Sam110 | Sam111 | Sam112 | Sam113 | Sam114 | Sam115 | Sam116 | Sam117 | Sam118 |
|---|---|---|---|---|---|---|---|---|---|---|
| 1 | 0 | 0 | 0 | 0 | 0 | 0 | 0 | 0 | 1 | 0 |
| 2 | 1 | 1 | 0 | 0 | 1 | 0 | 0 | 0 | 1 | 1 |
| 3 | 1 | 1 | 0 | 0 | 1 | 0 | 0 | 0 | 1 | 1 |
| 4 | 0 | 0 | 0 | 0 | 0 | 0 | 0 | 1 | 0 | 0 |
| 5 | 0 | 0 | 0 | 0 | 0 | 0 | 0 | 0 | 0 | 0 |
| 6 | 0 | 0 | 0 | 0 | 0 | 0 | 0 | 1 | 0 | 0 |
| 7 | 0 | 1 | 0 | 0 | 1 | 0 | 0 | 0 | 0 | 0 |
| 8 | 0 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 0 | 0 | 0 | 0 | 0 | 0 | 0 | 0 | 0 | 0 |
| 11 | 0 | 0 | 0 | 0 | 0 | 0 | 0 | 0 | 0 | 0 |
| 12 | 0 | 0 | 0 | 0 | 0 | 0 | 0 | 0 | 0 | 0 |
| 13 | 0 | 0 | 0 | 0 | 0 | 0 | 0 | 0 | 0 | 0 |
| 14 | 0 | 0 | 0 | 0 | 0 | 0 | 0 | 0 | 0 | 0 |
| 15 | 0 | 0 | 0 | 0 | 0 | 0 | 0 | 0 | 0 | 0 |
| 16 | 1 | 1 | 1 | 1 | 1 | 0 | 1 | 1 | 0 | 1 |
| 17 | 1 | 1 | 1 | 1 | 1 | 0 | 1 | 1 | 0 | 1 |
| 18 | 1 | 1 | 1 | 1 | 1 | 0 | 1 | 1 | 0 | 1 |
| 19 | 0 | 0 | 0 | 0 | 0 | 0 | 0 | 0 | 0 | 0 |
| 20 | 0 | 0 | 0 | 0 | 0 | 0 | 0 | 0 | 0 | 0 |
| 21 | 0 | 0 | 0 | 0 | 0 | 0 | 0 | 0 | 0 | 0 |
| 22 | 0 | 0 | 0 | 0 | 0 | 0 | 0 | 0 | 0 | 0 |
| 23 | 0 | 0 | 0 | 0 | 0 | 0 | 0 | 0 | 0 | 0 |
| 24 | 0 | 0 | 0 | 0 | 0 | 0 | 0 | 0 | 0 | 0 |
| 25 | 1 | 1 | 0 | 0 | 1 | 0 | 1 | 0 | 1 | 0 |
| 26 | 1 | 1 | 1 | 0 | 1 | 1 | 1 | 1 | 1 | 0 |
| 27 | 1 | 1 | 0 | 0 | 1 | 0 | 1 | 0 | 1 | 0 |
| 28 | 0 | 0 | 0 | 0 | 0 | 0 | 0 | 0 | 0 | 0 |
| 29 | 0 | 0 | 0 | 0 | 0 | 0 | 0 | 0 | 0 | 0 |
| 30 | 1 | 1 | 0 | 0 | 1 | 0 | 1 | 0 | 0 | 0 |
| 31 | 0 | 1 | 1 | 0 | 1 | 0 | 0 | 0 | 1 | 1 |
| 32 | 0 | 0 | 0 | 0 | 0 | 0 | 0 | 0 | 0 | 0 |
| 33 | 0 | 0 | 0 | 0 | 0 | 0 | 0 | 0 | 0 | 0 |
| 34 | 0 | 0 | 0 | 0 | 0 | 0 | 0 | 0 | 0 | 0 |
| 35 | 0 | 0 | 0 | 0 | 0 | 0 | 0 | 0 | 0 | 0 |
| 36 | 0 | 0 | 0 | 0 | 0 | 0 | 0 | 0 | 0 | 0 |
| 37 | 0 | 0 | 0 | 0 | 0 | 0 | 0 | 1 | 1 | 0 |
| 38 | 0 | 0 | 0 | 0 | 0 | 0 | 0 | 1 | 1 | 0 |
| 39 | 0 | 0 | 0 | 0 | 0 | 0 | 0 | 0 | 1 | 0 |
| 40 | 0 | 0 | 0 | 0 | 1 | 0 | 0 | 0 | 0 | 0 |
| 41 | 0 | 0 | 0 | 0 | 1 | 0 | 1 | 0 | 0 | 1 |
| 42 | 0 | 0 | 0 | 0 | 0 | 0 | 0 | 0 | 0 | 1 |
| 43 | 1 | 0 | 0 | 0 | 0 | 0 | 0 | 0 | 1 | 0 |
| 44 | 1 | 0 | 0 | 0 | 0 | 0 | 0 | 0 | 1 | 0 |
| 45 | 1 | 0 | 0 | 0 | 0 | 0 | 0 | 0 | 1 | 0 |
| 46 | 1 | 0 | 0 | 0 | 0 | 0 | 0 | 0 | 0 | 1 |
| 47 | 1 | 0 | 0 | 0 | 0 | 0 | 0 | 0 | 0 | 1 |
| 48 | 0 | 0 | 0 | 0 | 1 | 0 | 0 | 0 | 0 | 1 |
| 49 | 0 | 1 | 0 | 0 | 1 | 0 | 1 | 0 | 0 | 0 |
| 50 | 0 | 1 | 0 | 0 | 1 | 0 | 1 | 0 | 0 | 0 |
| 51 | 0 | 1 | 0 | 0 | 1 | 0 | 1 | 0 | 0 | 0 |
| 52 | 1 | 0 | 1 | 1 | 0 | 1 | 0 | 1 | 1 | 1 |
| 53 | 1 | 0 | 1 | 1 | 0 | 1 | 0 | 1 | 1 | 1 |
| 54 | 1 | 0 | 1 | 1 | 1 | 1 | 1 | 1 | 1 | 1 |
| 55 | 0 | 0 | 0 | 0 | 1 | 0 | 0 | 0 | 0 | 0 |
| 56 | 0 | 0 | 0 | 0 | 1 | 0 | 0 | 0 | 0 | 0 |
| 57 | 0 | 0 | 0 | 0 | 1 | 0 | 0 | 0 | 0 | 0 |
| 58 | 0 | 0 | 0 | 0 | 0 | 0 | 0 | 0 | 0 | 1 |
| 59 | 0 | 0 | 0 | 0 | 0 | 0 | 0 | 0 | 0 | 0 |
| 60 | 0 | 0 | 0 | 0 | 0 | 0 | 0 | 0 | 0 | 1 |
| 61 | 1 | 0 | 0 | 0 | 0 | 0 | 0 | 0 | 0 | 0 |
| 62 | 1 | 0 | 0 | 0 | 0 | 0 | 0 | 0 | 0 | 0 |
| 63 | 1 | 0 | 0 | 0 | 0 | 0 | 0 | 0 | 0 | 0 |
| 64 | 0 | 1 | 0 | 0 | 1 | 1 | 1 | 0 | 0 | 0 |
| 65 | 0 | 1 | 0 | 0 | 1 | 1 | 1 | 0 | 0 | 0 |
| 66 | 0 | 1 | 0 | 0 | 1 | 1 | 1 | 0 | 0 | 0 |
| 67 | 0 | 0 | 0 | 0 | 0 | 0 | 0 | 0 | 1 | 0 |
| 68 | 0 | 0 | 0 | 0 | 0 | 0 | 0 | 0 | 1 | 0 |
| 69 | 0 | 0 | 0 | 0 | 0 | 0 | 0 | 0 | 1 | 0 |
| 70 | 0 | 0 | 0 | 0 | 0 | 0 | 0 | 0 | 0 | 0 |
| 71 | 0 | 0 | 0 | 0 | 0 | 1 | 0 | 0 | 1 | 0 |
| 72 | 0 | 0 | 0 | 0 | 0 | 0 | 0 | 0 | 1 | 0 |
| 73 | 1 | 1 | 0 | 0 | 1 | 1 | 0 | 0 | 0 | 1 |
| 74 | 1 | 1 | 0 | 1 | 1 | 1 | 1 | 0 | 0 | 0 |
| 75 | 1 | 1 | 0 | 0 | 1 | 1 | 1 | 0 | 0 | 1 |
| 76 | 0 | 0 | 1 | 1 | 0 | 0 | 0 | 1 | 0 | 1 |
| 77 | 0 | 0 | 1 | 1 | 0 | 0 | 0 | 1 | 0 | 1 |

TABLE 39-continued

| Transition number | Sam109 | Sam110 | Sam111 | Sam112 | Sam113 | Sam114 | Sam115 | Sam116 | Sam117 | Sam118 |
|---|---|---|---|---|---|---|---|---|---|---|
| 78 | 0 | 0 | 1 | 1 | 0 | 0 | 0 | 1 | 0 | 1 |
| 79 | 0 | 0 | 0 | 0 | 0 | 0 | 0 | 0 | 0 | 0 |
| 80 | 0 | 0 | 0 | 0 | 0 | 0 | 0 | 0 | 0 | 0 |
| 81 | 0 | 0 | 0 | 0 | 0 | 0 | 0 | 0 | 0 | 0 |
| 82 | 0 | 0 | 0 | 0 | 0 | 0 | 0 | 0 | 0 | 0 |
| 83 | 0 | 0 | 0 | 0 | 0 | 0 | 0 | 0 | 0 | 0 |
| 84 | 0 | 0 | 0 | 0 | 0 | 0 | 0 | 0 | 0 | 0 |
| 85 | 0 | 0 | 0 | 0 | 0 | 0 | 0 | 0 | 0 | 0 |
| 86 | 0 | 0 | 0 | 0 | 0 | 0 | 0 | 0 | 0 | 0 |
| 87 | 1 | 0 | 0 | 0 | 0 | 1 | 0 | 0 | 1 | 0 |
| 88 | 1 | 0 | 0 | 0 | 0 | 1 | 0 | 0 | 1 | 0 |
| 89 | 1 | 0 | 0 | 0 | 0 | 1 | 1 | 0 | 1 | 0 |
| 90 | 0 | 0 | 0 | 0 | 0 | 1 | 0 | 0 | 0 | 0 |
| 91 | 0 | 0 | 0 | 0 | 0 | 1 | 1 | 0 | 0 | 0 |
| 92 | 0 | 0 | 0 | 0 | 0 | 1 | 1 | 0 | 0 | 0 |
| 93 | 0 | 0 | 0 | 0 | 0 | 0 | 0 | 0 | 0 | 0 |
| 94 | 0 | 0 | 0 | 0 | 0 | 0 | 0 | 1 | 0 | 0 |
| 95 | 0 | 0 | 0 | 0 | 0 | 0 | 0 | 0 | 0 | 0 |
| 96 | 0 | 0 | 0 | 0 | 0 | 0 | 0 | 0 | 0 | 0 |
| 97 | 0 | 0 | 0 | 0 | 0 | 0 | 0 | 0 | 0 | 0 |
| 98 | 0 | 0 | 0 | 0 | 0 | 0 | 0 | 0 | 0 | 0 |
| 99 | 0 | 0 | 0 | 0 | 0 | 0 | 0 | 0 | 0 | 0 |
| 100 | 0 | 0 | 0 | 0 | 0 | 0 | 0 | 0 | 1 | 0 |
| 101 | 0 | 0 | 0 | 0 | 0 | 0 | 0 | 0 | 0 | 0 |
| 102 | 0 | 1 | 0 | 0 | 1 | 0 | 1 | 0 | 0 | 0 |
| 103 | 0 | 1 | 0 | 0 | 1 | 1 | 1 | 1 | 0 | 1 |
| 104 | 0 | 1 | 0 | 0 | 1 | 1 | 1 | 0 | 0 | 0 |
| 105 | 0 | 0 | 0 | 0 | 0 | 0 | 0 | 0 | 0 | 0 |
| 106 | 0 | 0 | 0 | 0 | 0 | 0 | 0 | 0 | 0 | 0 |
| 107 | 0 | 0 | 0 | 0 | 0 | 0 | 0 | 0 | 0 | 0 |
| 108 | 0 | 0 | 0 | 0 | 0 | 0 | 0 | 0 | 0 | 0 |
| 109 | 0 | 0 | 0 | 0 | 0 | 0 | 0 | 0 | 0 | 0 |
| 110 | 0 | 0 | 0 | 0 | 0 | 0 | 0 | 0 | 0 | 0 |
| 111 | 0 | 0 | 0 | 0 | 0 | 0 | 0 | 0 | 0 | 0 |
| 112 | 0 | 0 | 0 | 0 | 0 | 0 | 0 | 0 | 0 | 0 |
| 113 | 0 | 0 | 0 | 0 | 0 | 0 | 0 | 0 | 0 | 0 |
| 114 | 0 | 0 | 1 | 1 | 0 | 0 | 0 | 1 | 1 | 1 |
| 115 | 0 | 1 | 1 | 1 | 0 | 0 | 0 | 1 | 1 | 1 |
| 116 | 0 | 0 | 1 | 1 | 0 | 0 | 0 | 1 | 1 | 1 |
| 117 | 0 | 0 | 0 | 0 | 0 | 0 | 0 | 0 | 0 | 1 |
| 118 | 0 | 0 | 0 | 0 | 0 | 0 | 0 | 0 | 0 | 1 |
| 119 | 0 | 0 | 0 | 1 | 0 | 0 | 0 | 0 | 0 | 1 |
| 120 | 0 | 0 | 0 | 0 | 0 | 0 | 0 | 0 | 0 | 0 |
| 121 | 0 | 0 | 0 | 0 | 0 | 0 | 0 | 0 | 0 | 0 |
| 122 | 0 | 0 | 0 | 0 | 0 | 0 | 0 | 0 | 0 | 0 |
| 123 | 0 | 0 | 0 | 0 | 0 | 0 | 0 | 0 | 0 | 0 |
| 124 | 0 | 0 | 0 | 0 | 0 | 0 | 0 | 0 | 0 | 0 |
| 125 | 0 | 0 | 0 | 0 | 0 | 0 | 0 | 0 | 0 | 0 |
| 126 | 0 | 0 | 0 | 0 | 0 | 0 | 0 | 0 | 0 | 0 |
| 127 | 0 | 0 | 0 | 0 | 0 | 0 | 0 | 0 | 0 | 0 |
| 128 | 0 | 0 | 0 | 0 | 0 | 0 | 0 | 0 | 0 | 0 |
| 129 | 1 | 1 | 0 | 1 | 1 | 1 | 1 | 1 | 1 | 1 |
| 130 | 1 | 1 | 0 | 1 | 1 | 1 | 1 | 1 | 1 | 1 |
| 131 | 1 | 1 | 0 | 1 | 1 | 1 | 1 | 1 | 1 | 1 |
| 132 | 0 | 0 | 0 | 0 | 0 | 0 | 0 | 0 | 0 | 0 |
| 133 | 0 | 0 | 0 | 0 | 0 | 0 | 0 | 0 | 0 | 0 |
| 134 | 0 | 0 | 0 | 0 | 0 | 0 | 0 | 0 | 0 | 0 |
| 135 | 1 | 1 | 0 | 0 | 1 | 0 | 1 | 0 | 0 | 0 |
| 136 | 1 | 1 | 1 | 0 | 1 | 0 | 1 | 0 | 0 | 0 |
| 137 | 0 | 1 | 0 | 0 | 1 | 0 | 1 | 0 | 0 | 0 |
| 138 | 0 | 0 | 0 | 1 | 0 | 0 | 0 | 0 | 0 | 1 |
| 139 | 1 | 0 | 0 | 1 | 0 | 0 | 0 | 0 | 0 | 1 |
| 140 | 1 | 0 | 0 | 0 | 0 | 0 | 0 | 0 | 0 | 1 |
| 141 | 1 | 1 | 0 | 1 | 1 | 1 | 1 | 1 | 1 | 1 |
| 142 | 1 | 1 | 0 | 1 | 1 | 1 | 1 | 1 | 1 | 1 |
| 143 | 1 | 1 | 0 | 1 | 1 | 1 | 1 | 1 | 1 | 1 |
| 144 | 0 | 0 | 1 | 0 | 0 | 0 | 0 | 0 | 0 | 0 |
| 145 | 0 | 0 | 1 | 0 | 0 | 0 | 0 | 0 | 0 | 0 |
| 146 | 0 | 0 | 1 | 0 | 0 | 0 | 0 | 0 | 0 | 0 |
| 147 | 0 | 0 | 0 | 0 | 0 | 0 | 0 | 0 | 0 | 0 |
| 148 | 0 | 0 | 0 | 0 | 0 | 0 | 0 | 0 | 0 | 0 |
| 149 | 0 | 0 | 0 | 0 | 0 | 0 | 0 | 0 | 0 | 0 |

Samples Sam109 to Sam118 comprise at least one peptide which is characteristic of the CTX-M proteins. The bacteria present in samples Sam109 to Sam118 therefore express a beta-lactamase which confers on them a resistance to penicillins, to cephalosporins and to monobactams.

EXAMPLE 28

Identification of a Resistance to DHA Beta-Lactams

Samples Sam119 to Sam124 are identified according to one of the methods described in examples 1, 3 or 4. The identification of the species is set out in TABLE 40.

TABLE 40

| Names | Species |
|---|---|
| Sam119 | E. coli |
| Sam120 | K. oxytoca |
| Sam121 | K. pneumoniae |
| Sam122 | K. pneumoniae |
| Sam123 | K. pneumoniae |
| Sam124 | K. pneumoniae |

Samples Sam119 to Sam124 correspond to a species able to comprise a DHA resistance mechanism. Each sample is treated according to example 5, then analysed according to example 6 by detecting the peptides from TABLE 41 instead of the peptides from TABLE 3.

TABLE 41

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | AAQAILSALEMK | 2 | y8 monocharged | 21.45 | 623.35 | 904.52 | 31.3 | 2500 |
| 2 | AAQAILSALEMK | 2 | y7 monocharged | 21.45 | 623.35 | 791.43 | 31.3 | 2500 |
| 3 | AAQAILSALEMK | 2 | y6 monocharged | 21.45 | 623.35 | 678.35 | 31.3 | 2500 |
| 4 | ADLLNFYQQWQPSR | 2 | y3 monocharged | 22.92 | 883.44 | 359.2 | 46.1 | 2500 |
| 5 | ADLLNFYQQWQPSR | 3 | y5 monocharged | 22.92 | 589.29 | 673.34 | 25.4 | 2500 |
| 6 | ADLLNFYQQWQPSR | 3 | y3 monocharged | 22.92 | 589.29 | 359.2 | 25.4 | 2500 |
| 7 | AGNADLEMAMYLAQTR | 3 | y6 monocharged | 21.53 | 585.61 | 751.41 | 25.2 | 2500 |
| 8 | AGNADLEMAMYLAQTR | 3 | y5 monocharged | 21.53 | 585.61 | 588.35 | 25.2 | 2500 |
| 9 | AGNADLEMAMYLAQTR | 3 | y4 monocharged | 21.53 | 585.61 | 475.26 | 25.2 | 2500 |
| 10 | EMALNDPAAK | 2 | y8 monocharged | 13.12 | 530.26 | 799.43 | 26 | 2500 |
| 11 | EMALNDPAAK | 2 | y6 monocharged | 13.12 | 530.26 | 615.31 | 26 | 2500 |
| 12 | EMALNDPAAK | 2 | y4 monocharged | 13.12 | 530.26 | 386.24 | 26 | 2500 |
| 13 | GKPYYFNYGFADIQAK | 3 | y8 monocharged | 19.85 | 627.98 | 849.45 | 26.5 | 2500 |
| 14 | GKPYYFNYGFADIQAK | 3 | y6 monocharged | 19.85 | 627.98 | 645.36 | 26.5 | 2500 |
| 15 | GKPYYFNYGFADIQAK | 3 | y5 monocharged | 19.85 | 627.98 | 574.32 | 26.5 | 2500 |
| 16 | NYPNTER | 2 | y5 monocharged | 7.63 | 447.21 | 616.31 | 21.2 | 2500 |
| 17 | NYPNTER | 2 | y3 monocharged | 7.63 | 447.21 | 405.21 | 21.2 | 2500 |
| 18 | NYPNTER | 2 | y5 dicharged | 7.63 | 447.21 | 308.66 | 21.2 | 2500 |
| 19 | QPVTENTLFELGSVSK | 2 | y8 monocharged | 20.9 | 874.96 | 866.46 | 45.6 | 2500 |
| 20 | QPVTENTLFELGSVSK | 3 | y8 monocharged | 20.9 | 583.64 | 866.46 | 25.2 | 2500 |
| 21 | QPVTENTLFELGSVSK | 3 | y5 monocharged | 20.9 | 583.64 | 477.27 | 25.2 | 2500 |
| 22 | QVAIVILANK | 2 | y8 monocharged | 18.75 | 534.84 | 841.55 | 26.2 | 2500 |
| 23 | QVAIVILANK | 2 | y6 monocharged | 18.75 | 534.84 | 657.43 | 26.2 | 2500 |
| 24 | QVAIVILANK | 2 | y5 monocharged | 18.75 | 534.84 | 558.36 | 26.2 | 2500 |
| 25 | TFTGVLGAVSVAK | 2 | y11 monocharged | 20.03 | 625.36 | 1001.6 | 31.4 | 2500 |
| 26 | TFTGVLGAVSVAK | 2 | y8 monocharged | 20.03 | 625.36 | 744.46 | 31.4 | 2500 |
| 27 | TFTGVLGAVSVAK | 2 | y7 monocharged | 20.03 | 625.36 | 631.38 | 31.4 | 2500 |
| 28 | TGATTGFGAYVAFIPEK | 2 | y3 monocharged | 22.12 | 865.44 | 373.21 | 45.1 | 2500 |

TABLE 41-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 29 | TGATTGFGAYVAFIPEK | 3 | y6 monocharged | 22.12 | 577.3 | 704.4 | 25 | 2500 |
| 30 | TGATTGFGAYVAFIPEK | 3 | y3 monocharged | 22.12 | 577.3 | 373.21 | 25 | 2500 |
| 31 | VSPGQLDAESYGVK | 2 | y8 monocharged | 15.43 | 725.37 | 868.41 | 37.1 | 2500 |
| 32 | VSPGQLDAESYGVK | 2 | y13 dicharged | 15.43 | 725.37 | 675.83 | 37.1 | 2500 |
| 33 | VSPGQLDAESYGVK | 2 | y12 dicharged | 15.43 | 725.37 | 632.31 | 37.1 | 2500 |
| 34 | WAEMNMEPSR | 2 | y8 monocharged | 15.78 | 625.77 | 993.41 | 31.4 | 2500 |
| 35 | WAEMNMEPSR | 2 | y6 monocharged | 15.78 | 625.77 | 733.33 | 31.4 | 2500 |
| 36 | WAEMNMEPSR | 2 | y3 monocharged | 15.78 | 625.77 | 359.2 | 31.4 | 2500 |
| 37 | YQPELALPQWK | 2 | y4 monocharged | 20.97 | 686.87 | 558.3 | 34.9 | 2500 |
| 38 | YQPELALPQWK | 2 | y9 dicharged | 20.97 | 686.87 | 541.31 | 34.9 | 2500 |
| 39 | YQPELALPQWK | 3 | y4 monocharged | 20.97 | 458.25 | 558.3 | 21.3 | 2500 |

The other machine parameters used are as follows:

| Scan type: | MRM |
|---|---|
| MRM planned: | no |
| Polarity: | Positive |
| Ionising source: | Turbo V™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 50.00 psi |
| Heating gas: | 50.00 psi |
| Collision gas which induces dissociation: | 9.00 psi |
| Dynamic filling: | activated |
| Declustering potential (DP): | 100.00 V |
| Entry potential before Q0 (EP): | 6.00 V |
| Collision cell exit potential (CXP): | 15 V |
| Total cycle time: | 1.17 sec |

The areas obtained for each of the transitions and for each of the microorganisms studied were measured. When the areas of the transitions are greater than or equal to the positivity threshold described in TABLE 41, the detection of the transition is considered to be positive and is labelled "1" in TABLE 42. When a transition has an area less than the positivity threshold described in TABLE 41, the transition is considered non-detected and is labelled "0" in TABLE 42.

For a given peptide, when at least 3 transitions are labelled "1", the peptide is considered as being detected.

TABLE 42

| Transition number | Sam119 | Sam120 | Sam121 | Sam122 | Sam123 | Sam124 |
|---|---|---|---|---|---|---|
| 1 | 1 | 0 | 1 | 1 | 0 | 0 |
| 2 | 0 | 0 | 0 | 0 | 0 | 0 |
| 3 | 0 | 0 | 0 | 0 | 0 | 0 |
| 4 | 0 | 0 | 1 | 0 | 1 | 0 |
| 5 | 0 | 1 | 1 | 0 | 0 | 0 |
| 6 | 0 | 1 | 1 | 0 | 0 | 0 |
| 7 | 0 | 0 | 0 | 1 | 0 | 0 |
| 8 | 0 | 0 | 0 | 1 | 0 | 0 |
| 9 | 0 | 0 | 0 | 1 | 0 | 0 |
| 10 | 1 | 1 | 1 | 1 | 1 | 1 |
| 11 | 1 | 1 | 1 | 1 | 1 | 1 |
| 12 | 1 | 1 | 1 | 0 | 1 | 1 |
| 13 | 1 | 1 | 1 | 0 | 1 | 0 |
| 14 | 1 | 1 | 1 | 0 | 1 | 0 |
| 15 | 1 | 0 | 1 | 0 | 0 | 0 |
| 16 | 0 | 0 | 1 | 1 | 0 | 1 |
| 17 | 0 | 0 | 1 | 1 | 0 | 1 |
| 18 | 0 | 0 | 1 | 1 | 1 | 1 |
| 19 | 1 | 1 | 1 | 1 | 1 | 1 |
| 20 | 1 | 0 | 1 | 1 | 1 | 1 |
| 21 | 1 | 1 | 1 | 1 | 1 | 1 |
| 22 | 0 | 1 | 1 | 1 | 1 | 1 |
| 23 | 0 | 0 | 1 | 1 | 1 | 1 |
| 24 | 1 | 1 | 1 | 1 | 1 | 1 |
| 25 | 1 | 1 | 1 | 1 | 1 | 1 |
| 26 | 1 | 1 | 1 | 1 | 1 | 1 |
| 27 | 1 | 1 | 1 | 1 | 1 | 1 |
| 28 | 0 | 0 | 1 | 1 | 0 | 0 |
| 29 | 0 | 0 | 1 | 1 | 1 | 0 |
| 30 | 0 | 0 | 1 | 1 | 0 | 0 |
| 31 | 1 | 1 | 1 | 1 | 1 | 1 |
| 32 | 0 | 1 | 1 | 1 | 1 | 1 |
| 33 | 0 | 1 | 1 | 1 | 1 | 1 |
| 34 | 1 | 1 | 1 | 1 | 1 | 1 |
| 35 | 0 | 1 | 1 | 1 | 1 | 1 |
| 36 | 1 | 0 | 1 | 1 | 1 | 1 |
| 37 | 1 | 0 | 1 | 1 | 0 | 1 |
| 38 | 1 | 1 | 1 | 1 | 1 | 1 |
| 39 | 1 | 1 | 1 | 1 | 1 | 1 |

Samples 119 to Sam124 comprise at least one peptide which is characteristic of the DHA proteins. The bacteria present in samples Sam119 to Sam124 therefore express a beta-lactamase which confers on them a resistance to penicillins and to cephalosporins, with the exception of fourth-generation cephalosporins.

EXAMPLE 29

Identification of a Resistance to FOX Beta-Lactams

Samples Sam125 to Sam130 are identified according to one of the methods described in examples 1, 3 or 4. The identification of the species is set out in TABLE 43.

TABLE 43

| Names | Species |
|---|---|
| Sam125 | E. coli |
| Sam126 | E. coli |

TABLE 43-continued

| Names | Species |
|---|---|
| Sam127 | K. oxytoca |
| Sam128 | K. oxytoca |
| Sam129 | K. pneumoniae |
| Sam13 | K. pneumoniae |

Samples Sam125 to Sam130 correspond to a species able to comprise a FOX resistance mechanism. Each sample is treated according to example 5, then analysed according to example 6 by detecting the peptides from TABLE 44 instead of the peptides from TABLE 3.

TABLE 44

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | AHYFNYGVANR | 3 | y3 monocharged | 14.08 | 437.88 | 360.2 | 20.7 | 2500 |
| 2 | AHYFNYGVANR | 3 | y4 monocharged | 14.08 | 437.88 | 459.27 | 20.7 | 2500 |
| 3 | AHYFNYGVANR | 3 | y5 monocharged | 14.08 | 437.88 | 516.29 | 20.7 | 2500 |
| 4 | AMGEQR | 2 | y5 dicharged | 1.08 | 346.16 | 310.65 | 15.5 | 2500 |
| 5 | AMGEQR | 2 | y4 monocharged | 1.08 | 346.16 | 489.24 | 15.5 | 2500 |
| 6 | AMGEQR | 2 | y5 monocharged | 1.08 | 346.16 | 620.28 | 15.5 | 2500 |
| 7 | ESGQR | 2 | y3 dicharged | 0.8 | 288.64 | 180.6 | 12.2 | 2500 |
| 8 | ESGQR | 2 | y3 monocharged | 0.76 | 288.64 | 360.2 | 12.2 | 2500 |
| 9 | ESGQR | 2 | y4 monocharged | 0.82 | 288.64 | 447.23 | 12.2 | 2500 |
| 10 | FAVPK | 3 | y4 monocharged | 12.95 | 187.79 | 414.27 | 12.9 | 2500 |
| 11 | FAVPK | 2 | y3 monocharged | 12.95 | 281.17 | 343.23 | 11.8 | 2500 |
| 12 | FAVPK | 2 | y4 monocharged | 12.93 | 281.17 | 414.27 | 11.8 | 2500 |
| 13 | GGFELDDK | 2 | y6 dicharged | 14.31 | 440.71 | 383.69 | 20.9 | 2500 |
| 14 | GGFELDDK | 2 | y4 monocharged | 14.34 | 440.71 | 490.25 | 20.9 | 2500 |
| 15 | GGFELDDK | 2 | y5 monocharged | 14.31 | 440.71 | 619.29 | 20.9 | 2500 |
| 16 | GIAIVMLANR | 2 | y4 monocharged | 20.15 | 529.31 | 473.28 | 25.9 | 2500 |
| 17 | GIAIVMLANR | 2 | y5 monocharged | 20.13 | 529.31 | 604.32 | 25.9 | 2500 |
| 18 | GIAIVMLANR | 2 | y6 monocharged | 20.13 | 529.31 | 703.39 | 25.9 | 2500 |
| 19 | IPGMAVAVLK | 2 | y9 dicharged | 19.17 | 499.81 | 443.27 | 24.2 | 2500 |
| 20 | IPGMAVAVLK | 2 | y8 monocharged | 19.17 | 499.81 | 788.47 | 24.2 | 2500 |
| 21 | IPGMAVAVLK | 2 | y9 monocharged | 19.15 | 499.81 | 885.52 | 24.2 | 2500 |
| 22 | NYPIEAR | 2 | y3 monocharged | 12.04 | 431.73 | 375.2 | 20.3 | 2500 |
| 23 | NYPIEAR | 2 | y4 monocharged | 12.04 | 431.73 | 488.28 | 20.3 | 2500 |
| 24 | NYPIEAR | 2 | y5 monocharged | 12.06 | 431.73 | 585.34 | 20.3 | 2500 |
| 25 | SWSPVYPAGTHR | 3 | y9 dicharged | 14.97 | 453.23 | 499.26 | 21.1 | 2500 |
| 26 | SWSPVYPAGTHR | 3 | y10 dicharged | 14.97 | 453.23 | 542.78 | 21.1 | 2500 |
| 27 | SWSPVYPAGTHR | 3 | y6 monocharged | 14.97 | 453.23 | 638.34 | 21.1 | 2500 |
| 28 | TGSADLLK | 2 | y5 monocharged | 12.97 | 402.73 | 559.35 | 18.7 | 2500 |
| 29 | TGSADLLK | 2 | y6 monocharged | 12.95 | 402.73 | 646.38 | 18.7 | 2500 |

TABLE 44-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 30 | TGSADLLK | 2 | y7 monocharged | 12.97 | 402.73 | 703.4 | 18.7 | 2500 |
| 31 | TGSTGGFGAYVAFVPAR | 3 | y5 monocharged | 21.03 | 553.28 | 589.35 | 24.2 | 2500 |
| 32 | TGSTGGFGAYVAFVPAR | 3 | y6 monocharged | 21.03 | 553.28 | 660.38 | 24.2 | 2500 |
| 33 | TGSTGGFGAYVAFVPAR | 2 | y3 monocharged | 21.03 | 829.42 | 343.21 | 43 | 2500 |
| 34 | TGSTGGFGAYVAFVPAR | 2 | y6 monocharged | 21.03 | 829.42 | 660.38 | 43 | 2500 |
| 35 | TLTATLGAYAAVK | 2 | y7 monocharged | 18.68 | 640.37 | 679.38 | 32.2 | 2500 |
| 36 | TLTATLGAYAAVK | 2 | y8 monocharged | 18.68 | 640.37 | 792.46 | 32.2 | 2500 |
| 37 | TLTATLGAYAAVK | 2 | y9 monocharged | 18.66 | 640.37 | 893.51 | 32.2 | 2500 |
| 38 | VSEQTLFEIGSVSK | 2 | y5 monocharged | 20.34 | 762.4 | 477.27 | 39.2 | 2500 |
| 39 | VSEQTLFEIGSVSK | 2 | y7 monocharged | 20.34 | 762.4 | 719.39 | 39.2 | 2500 |
| 40 | VSEQTLFEIGSVSK | 2 | y8 monocharged | 20.34 | 762.4 | 866.46 | 39.2 | 2500 |
| 41 | VSQHAPWLK | 3 | y6 dicharged | 14.1 | 355.87 | 376.22 | 18.1 | 2500 |
| 42 | VSQHAPWLK | 3 | y8 dicharged | 14.1 | 355.87 | 483.76 | 18.1 | 2500 |
| 43 | VSQHAPWLK | 3 | y4 monocharged | 14.1 | 355.87 | 543.33 | 18.1 | 2500 |
| 44 | VTPGVLAAEAYGIK | 2 | y12 dicharged | 19.37 | 694.89 | 594.84 | 35.3 | 2500 |
| 45 | VTPGVLAAEAYGIK | 2 | y7 monocharged | 19.37 | 694.89 | 751.4 | 35.3 | 2500 |
| 46 | VTPGVLAAEAYGIK | 2 | y8 monocharged | 19.37 | 694.89 | 822.44 | 35.3 | 2500 |

The other machine parameters used are as follows:

| Scan type: | MRM |
|---|---|
| MRM planned: | no |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 50.00 psi |
| Heating gas: | 50.00 psi |
| Collision gas which induces dissociation: | 9.00 psi |
| Dynamic filling: | activated |
| Declustering potential (DP): | 100.00 V |
| Entry potential before Q0 (EP): | 6.00 V |
| Collision cell exit potential (CXP): | 15 V |
| Total cycle time: | 1.38 sec |

The areas obtained for each of the transitions and for each of the microorganisms studied were measured. When the areas of the transitions are greater than or equal to the positivity threshold described in TABLE 44, the detection of the transition is considered to be positive and is labelled "1" in TABLE 45. When a transition has an area less than the positivity threshold described in TABLE 44, the transition is considered non-detected and is labelled "0" in TABLE 45.

For a given peptide, when at least 2 transitions are labelled "1", the peptide is considered as being detected.

TABLE 45

| transition number | Sam125 | Sam126 | Sam127 | Sam128 | Sam129 | Sam130 |
|---|---|---|---|---|---|---|
| 1 | 0 | 0 | 1 | 1 | 0 | 0 |
| 2 | 1 | 0 | 1 | 1 | 0 | 0 |
| 3 | 1 | 1 | 1 | 1 | 0 | 1 |
| 4 | 1 | 1 | 0 | 1 | 1 | 1 |
| 5 | 1 | 1 | 0 | 1 | 1 | 1 |
| 6 | 1 | 1 | 1 | 1 | 1 | 1 |
| 7 | 0 | 0 | 0 | 0 | 0 | 0 |
| 8 | 0 | 0 | 1 | 0 | 0 | 0 |
| 9 | 0 | 0 | 0 | 0 | 0 | 0 |
| 10 | 0 | 0 | 0 | 0 | 0 | 0 |
| 11 | 0 | 0 | 0 | 0 | 0 | 0 |
| 12 | 0 | 0 | 0 | 0 | 0 | 0 |
| 13 | 1 | 1 | 1 | 1 | 1 | 1 |
| 14 | 1 | 0 | 0 | 1 | 0 | 1 |
| 15 | 1 | 0 | 0 | 1 | 0 | 1 |
| 16 | 1 | 0 | 1 | 1 | 1 | 1 |
| 17 | 1 | 1 | 1 | 1 | 1 | 1 |
| 18 | 1 | 1 | 1 | 1 | 1 | 1 |
| 19 | 1 | 1 | 1 | 1 | 1 | 1 |
| 20 | 1 | 1 | 1 | 1 | 1 | 1 |
| 21 | 1 | 1 | 1 | 1 | 1 | 1 |
| 22 | 1 | 1 | 1 | 1 | 1 | 1 |
| 23 | 1 | 1 | 1 | 1 | 1 | 1 |
| 24 | 1 | 1 | 1 | 1 | 1 | 1 |
| 25 | 1 | 1 | 1 | 1 | 1 | 1 |
| 26 | 1 | 1 | 1 | 1 | 1 | 1 |
| 27 | 1 | 1 | 1 | 1 | 1 | 1 |
| 28 | 1 | 1 | 1 | 1 | 1 | 1 |
| 29 | 1 | 1 | 1 | 1 | 1 | 1 |
| 30 | 1 | 1 | 1 | 1 | 1 | 1 |
| 31 | 1 | 0 | 1 | 1 | 1 | 1 |
| 32 | 0 | 1 | 1 | 1 | 1 | 1 |
| 33 | 0 | 1 | 1 | 0 | 1 | 1 |

TABLE 45-continued

| transition number | Sam125 | Sam126 | Sam127 | Sam128 | Sam129 | Sam130 |
|---|---|---|---|---|---|---|
| 34 | 0 | 1 | 1 | 1 | 1 | 1 |
| 35 | 0 | 0 | 0 | 0 | 0 | 1 |
| 36 | 1 | 1 | 1 | 0 | 1 | 1 |
| 37 | 1 | 0 | 1 | 0 | 1 | 1 |
| 38 | 1 | 1 | 1 | 1 | 1 | 1 |
| 39 | 1 | 1 | 1 | 1 | 1 | 1 |
| 40 | 1 | 1 | 1 | 1 | 1 | 1 |
| 41 | 1 | 1 | 1 | 1 | 1 | 1 |
| 42 | 1 | 1 | 0 | 0 | 1 | 1 |
| 43 | 1 | 1 | 1 | 1 | 1 | 1 |
| 44 | 0 | 0 | 0 | 0 | 0 | 0 |
| 45 | 0 | 0 | 0 | 0 | 0 | 0 |
| 46 | 0 | 0 | 0 | 0 | 0 | 0 |

Samples Sam125 to Sam130 comprise at least one peptide which is characteristic of the FOX proteins. The bacteria present in samples Sam125 to Sam130 therefore express a beta-lactamase which confers on them a resistance to penicillins and to cephalosporins, with the exception of fourth-generation cephalosporins.

EXAMPLE 30

Identification of a Resistance to SHV Beta-Lactams

Samples Sam131 to Sam144 are identified according to one of the methods described in examples 1, 3 or 4. The identification of the species is set out in TABLE 46.

TABLE 46

| Names | Species |
|---|---|
| Sam131 | E. aerogenes |
| Sam132 | E. coli |
| Sam133 | E. coli |
| Sam134 | E. coli |
| Sam135 | E. coli |
| Sam136 | K. pneumoniae |
| Sam137 | K. pneumoniae |
| Sam138 | K. pneumoniae |
| Sam139 | K. pneumoniae |
| Sam140 | K. pneumoniae |
| Sam141 | K. pneumoniae |
| Sam142 | K. pneumoniae |
| Sam143 | K. pneumoniae |
| Sam144 | K. pneumoniae |

Samples Sam131 to Sam144 correspond to a species able to comprise an SHV resistance mechanism. Each sample is treated according to example 5, then analysed according to example 6 by detecting the peptides from TABLE 47 instead of the peptides from TABLE 3.

TABLE 47

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | AGAGER | 2 | y3 monocharged | 0.9 | 280.64 | 361.18 | 11.7 | 2000 |
| 2 | AGAGER | 2 | y4 monocharged | 0.9 | 280.64 | 432.22 | 11.7 | 2000 |
| 3 | AGAGER | 2 | y5 monocharged | 0.9 | 280.64 | 489.24 | 11.7 | 2000 |
| 4 | ATTTPASMAATLR | 3 | y5 monocharged | 16.2 | 431.23 | 531.33 | 20.5 | 2000 |
| 5 | ATTTPASMAATLR | 2 | y9 dicharged | 16.2 | 646.34 | 459.25 | 32.6 | 2000 |
| 6 | ATTTPASMAATLR | 2 | y9 monocharged | 16.2 | 646.34 | 917.49 | 32.6 | 2000 |
| 7 | CIISLLATLPLAVHASPQPLEQIK | 3 | y18 dicharged | 27.4 | 871.5 | 957.05 | 34.1 | 2000 |
| 8 | CIISLLATLPLAVHASPQPLEQIK | 3 | y21 dicharged | 27.4 | 871.5 | 1113.65 | 34.1 | 2000 |
| 9 | CIISLLATLPLAVHASPQPLEQIK | 3 | y22 dicharged | 27.3 | 871.5 | 1170.19 | 34.1 | 2000 |
| 10 | DMPASMAER | 2 | y7 dicharged | 12.4 | 504.22 | 381.18 | 24.5 | 2000 |
| 11 | DMPASMAER | 2 | y5 monocharged | 12.4 | 504.22 | 593.27 | 24.5 | 2000 |
| 12 | DMPASMAER | 2 | y7 monocharged | 12.4 | 504.22 | 761.36 | 24.5 | 2000 |
| 13 | DSPASMAER | 2 | y7 dicharged | 10.5 | 482.21 | 381.18 | 23.2 | 2000 |
| 14 | DSPASMAER | 2 | y5 monocharged | 10.5 | 482.21 | 593.27 | 23.2 | 2000 |
| 15 | DSPASMAER | 2 | y6 monocharged | 10.5 | 482.21 | 664.31 | 23.2 | 2000 |
| 16 | DTLASMAER | 2 | y5 monocharged | 14 | 497.24 | 593.27 | 24.1 | 2000 |
| 17 | DTLASMAER | 2 | y6 monocharged | 14 | 497.24 | 664.31 | 24.1 | 2000 |
| 18 | DTLASMAER | 2 | y7 monocharged | 14 | 497.24 | 777.39 | 24.1 | 2000 |
| 19 | DTPASMAER | 2 | y7 dicharged | 10.5 | 489.22 | 381.18 | 23.6 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 20 | DTPASMAER | 2 | y5 monocharged | 10.5 | 489.22 | 593.27 | 23.6 | 2000 |
| 21 | DTPASMAER | 2 | y7 monocharged | 10.5 | 489.22 | 761.36 | 23.6 | 2000 |
| 22 | DTPASMAK | 2 | y6 dicharged | 9.1 | 410.7 | 302.66 | 19.1 | 2000 |
| 23 | DTPASMAK | 2 | y5 monocharged | 9.1 | 410.7 | 507.26 | 19.1 | 2000 |
| 24 | DTPASMAK | 2 | y6 monocharged | 9.1 | 410.7 | 604.31 | 19.1 | 2000 |
| 25 | DTTTPASMAATLR | 3 | y5 monocharged | 16.5 | 445.89 | 531.33 | 20.9 | 2000 |
| 26 | DTTTPASMAATLR | 2 | y9 dicharged | 16.5 | 668.33 | 459.25 | 33.8 | 2000 |
| 27 | DTTTPASMAATLR | 2 | y9 monocharged | 16.5 | 668.33 | 917.49 | 33.8 | 2000 |
| 28 | DTTTPASMAGTLR | 3 | y4 monocharged | 15.3 | 441.22 | 446.27 | 20.8 | 2000 |
| 29 | DTTTPASMAGTLR | 2 | y9 dicharged | 15.3 | 661.32 | 452.24 | 33.4 | 2000 |
| 30 | DTTTPASMAGTLR | 2 | y9 monocharged | 15.3 | 661.32 | 903.47 | 33.4 | 2000 |
| 31 | DTTTPASMTATLR | 2 | y9 dicharged | 15.9 | 683.34 | 474.25 | 34.7 | 2000 |
| 32 | DTTTPASMTATLR | 2 | y7 monocharged | 15.9 | 683.34 | 779.41 | 34.7 | 2000 |
| 33 | DTTTPASMTATLR | 2 | y9 monocharged | 15.9 | 683.34 | 947.5 | 34.7 | 2000 |
| 34 | FPMISTFK | 2 | y7 dicharged | 20.2 | 485.76 | 412.22 | 23.4 | 2000 |
| 35 | FPMISTFK | 2 | y5 monocharged | 20.2 | 485.76 | 595.35 | 23.4 | 2000 |
| 36 | FPMISTFK | 2 | y6 monocharged | 20.2 | 485.76 | 726.39 | 23.4 | 2000 |
| 37 | FPMMSTFK | 2 | y7 dicharged | 19.3 | 494.74 | 421.2 | 23.9 | 2000 |
| 38 | FPMMSTFK | 2 | y5 monocharged | 19.3 | 494.74 | 613.3 | 23.9 | 2000 |
| 39 | FPMMSTFK | 2 | y6 monocharged | 19.3 | 494.74 | 744.34 | 23.9 | 2000 |
| 40 | GIVALLGGNIK | 2 | y5 monocharged | 21.1 | 527.84 | 488.28 | 25.8 | 2000 |
| 41 | GIVALLGGNIK | 2 | y6 monocharged | 21.1 | 527.84 | 601.37 | 25.8 | 2000 |
| 42 | GIVALLGGNIK | 2 | y8 monocharged | 21.1 | 527.84 | 785.49 | 25.8 | 2000 |
| 43 | GIVALLGPDNK | 2 | y5 monocharged | 18.9 | 548.82 | 530.26 | 27 | 2000 |
| 44 | GIVALLGPDNK | 2 | y6 monocharged | 19 | 548.82 | 643.34 | 27 | 2000 |
| 45 | GIVALLGPDNK | 2 | y8 monocharged | 18.9 | 548.82 | 827.46 | 27 | 2000 |
| 46 | GIVALLGPNHK | 3 | y9 dicharged | 17.6 | 373.56 | 474.79 | 18.7 | 2000 |
| 47 | GIVALLGPNHK | 3 | y5 monocharged | 17.6 | 373.56 | 552.29 | 18.7 | 2000 |
| 48 | GIVALLGPNHK | 3 | y6 monocharged | 17.6 | 373.56 | 665.37 | 18.7 | 2000 |
| 49 | GIVALLGPNNK | 2 | y5 monocharged | 18.6 | 548.33 | 529.27 | 27 | 2000 |
| 50 | GIVALLGPNNK | 2 | y6 monocharged | 18.6 | 548.33 | 642.36 | 27 | 2000 |
| 51 | GIVALLGPNNK | 2 | y7 monocharged | 18.6 | 548.33 | 755.44 | 27 | 2000 |
| 52 | GIVALLGPNNNAER | 3 | y8 dicharged | 18.8 | 479.93 | 436.2 | 22 | 2000 |
| 53 | GIVALLGPNNNAER | 2 | y7 monocharged | 18.8 | 719.39 | 814.38 | 36.7 | 2000 |
| 54 | GIVALLGPNNNAER | 2 | y8 monocharged | 18.7 | 719.39 | 871.4 | 36.7 | 2000 |
| 55 | GIVALR | 2 | y4 dicharged | 14.1 | 314.71 | 229.66 | 13.7 | 2000 |
| 56 | GIVALR | 2 | y3 monocharged | 14.1 | 314.71 | 359.24 | 13.7 | 2000 |
| 57 | GIVALR | 2 | y4 monocharged | 14.1 | 314.71 | 458.31 | 13.7 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 58 | GPNNK | 2 | y4 dicharged | 0.8 | 265.14 | 236.63 | 10.8 | 2000 |
| 59 | GPNNK | 2 | y3 monocharged | 0.8 | 265.14 | 375.2 | 10.8 | 2000 |
| 60 | GPNNK | 2 | y4 monocharged | 0.8 | 265.14 | 472.25 | 10.8 | 2000 |
| 61 | GTTTPASMAATLR | 2 | y9 dicharged | 16 | 639.33 | 459.25 | 32.2 | 2000 |
| 62 | GTTTPASMAATLR | 2 | y7 monocharged | 16 | 639.33 | 749.4 | 32.2 | 2000 |
| 63 | GTTTPASMAATLR | 2 | y9 monocharged | 16 | 639.33 | 917.49 | 32.2 | 2000 |
| 64 | HLADGMTVGELCAAAITMSDNSAAK | 3 | y6 monocharged | 21.3 | 845.39 | 605.29 | 33.3 | 2000 |
| 65 | HLADGMTVGELCAAAITMSDNSAAK | 3 | y7 monocharged | 21.3 | 845.39 | 692.32 | 33.3 | 2000 |
| 66 | HLADGMTVGELCAAAITMSDNSAAK | 3 | y9 monocharged | 21.3 | 845.39 | 924.41 | 33.3 | 2000 |
| 67 | HLLQWMVDDR | 3 | y3 monocharged | 19.6 | 438.22 | 405.17 | 20.7 | 2000 |
| 68 | HLLQWMVDDR | 3 | y4 monocharged | 19.6 | 438.22 | 504.24 | 20.7 | 2000 |
| 69 | HLLQWMVDDR | 3 | y5 monocharged | 19.6 | 438.22 | 635.28 | 20.7 | 2000 |
| 70 | IHYLQQDLVDYSPVSEK | 3 | y6 monocharged | 19 | 678.68 | 646.34 | 28.1 | 2000 |
| 71 | IHYLQQDLVDYSPVSEK | 3 | y7 monocharged | 19 | 678.68 | 809.4 | 28.1 | 2000 |
| 72 | IHYLQQDLVDYSPVSEK | 3 | y8 monocharged | 18.9 | 678.68 | 924.43 | 28.1 | 2000 |
| 73 | IVVIYLR | 2 | y3 monocharged | 19.3 | 438.29 | 451.27 | 20.7 | 2000 |
| 74 | IVVIYLR | 2 | y4 monocharged | 19.3 | 438.29 | 564.35 | 20.7 | 2000 |
| 75 | IVVIYLR | 2 | y5 monocharged | 19.3 | 438.29 | 663.42 | 20.7 | 2000 |
| 76 | LCIISLLAALPLAVHASPQPLEQIK | 3 | y17 dicharged | 30.7 | 899.19 | 906.52 | 35 | 2000 |
| 77 | LCIISLLAALPLAVHASPQPLEQIK | 3 | y18 dicharged | 30.7 | 899.19 | 942.04 | 35 | 2000 |
| 78 | LCIISLLAALPLAVHASPQPLEQIK | 3 | y22 dicharged | 30.7 | 899.19 | 1155.18 | 35 | 2000 |
| 79 | LCIISLLATLPLAVHASPQPLDQIK | 3 | y19 dicharged | 30.2 | 904.52 | 1006.58 | 35.1 | 2000 |
| 80 | LCIISLLATLPLAVHASPQPLDQIK | 3 | y22 dicharged | 30.2 | 904.52 | 1163.18 | 35.1 | 2000 |
| 81 | LCIISLLATLPLAVHASPQPLDQIK | 3 | y23 dicharged | 30.3 | 904.52 | 1219.72 | 35.1 | 2000 |
| 82 | LCIISLLATLPLAVHASPQPLEQIK | 3 | y15 dicharged | 30.2 | 909.19 | 814.46 | 35.3 | 2000 |
| 83 | LCIISLLATLPLAVHASPQPLEQIK | 3 | y17 dicharged | 30.2 | 909.19 | 921.53 | 35.3 | 2000 |
| 84 | LCIISLLATLPLAVHASPQPLEQIK | 3 | y19 dicharged | 30.2 | 909.19 | 1013.59 | 35.3 | 2000 |
| 85 | LCIISLLATLPLAVHSSPQPLEQIK | 3 | y15 dicharged | 29.3 | 914.53 | 822.46 | 35.4 | 2000 |
| 86 | LCIISLLATLPLAVHSSPQPLEQIK | 3 | y18 dicharged | 29.3 | 914.53 | 965.04 | 35.4 | 2000 |
| 87 | LCIISLLATLPLAVHSSPQPLEQIK | 3 | y21 dicharged | 29.3 | 914.53 | 1121.64 | 35.4 | 2000 |
| 88 | LCIISLLATLPLAVHTSPQPLEQIK | 3 | y15 dicharged | 29.4 | 919.2 | 829.47 | 35.6 | 2000 |
| 89 | LCIISLLATLPLAVHTSPQPLEQIK | 3 | y21 dicharged | 29.5 | 919.2 | 1128.65 | 35.6 | 2000 |
| 90 | LCIISLLATLPLAVHTSPQPLEQIK | 3 | y23 dicharged | 29.4 | 919.2 | 1241.74 | 35.6 | 2000 |
| 91 | LCIISLLATLPLTVHASPQPLEQIK | 3 | y15 dicharged | 29.8 | 919.2 | 829.47 | 35.6 | 2000 |
| 92 | LCIISLLATLPLTVHASPQPLEQIK | 3 | y17 dicharged | 29.8 | 919.2 | 936.53 | 35.6 | 2000 |
| 93 | LCIISLLATLPLTVHASPQPLEQIK | 3 | y22 dicharged | 29.8 | 919.2 | 1185.19 | 35.6 | 2000 |
| 94 | LCIISLLATLPLVVHASPQPLEQIK | 3 | y19 dicharged | 31.3 | 918.54 | 1027.6 | 35.6 | 2000 |
| 95 | LCIISLLATLPLVVHASPQPLEQIK | 3 | y21 dicharged | 31.3 | 918.54 | 1127.66 | 35.6 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 96 | LCIISLLATLPLVVHASPQPLEQIK | 3 | y23 dicharged | 31.3 | 918.54 | 1240.75 | 35.6 | 2000 |
| 97 | LCIISLLATLSLAVHASPQPLEQIK | 3 | y18 dicharged | 31.2 | 905.85 | 952.04 | 35.2 | 2000 |
| 98 | LCIISLLATLSLAVHASPQPLEQIK | 3 | y22 dicharged | 31.3 | 905.85 | 1165.18 | 35.2 | 2000 |
| 99 | LCIISLLATLSLAVHASPQPLEQIK | 3 | y23 dicharged | 31.2 | 905.85 | 1221.72 | 35.2 | 2000 |
| 100 | LCIISLLATMPLAVHASPQPLEQIK | 3 | y18 dicharged | 28.9 | 915.18 | 966.03 | 35.5 | 2000 |
| 101 | LCIISLLATMPLAVHASPQPLEQIK | 3 | y19 dicharged | 28.9 | 915.18 | 1022.57 | 35.5 | 2000 |
| 102 | LCIISLLATMPLAVHASPQPLEQIK | 3 | y23 dicharged | 28.9 | 915.18 | 1235.71 | 35.5 | 2000 |
| 103 | LCIISLLAVLPLAVHASPQPLEQIK | 3 | y17 dicharged | 31 | 908.54 | 920.54 | 35.2 | 2000 |
| 104 | LCIISLLAVLPLAVHASPQPLEQIK | 3 | y22 dicharged | 31.1 | 908.54 | 1169.2 | 35.2 | 2000 |
| 105 | LCIISLLAVLPLAVHASPQPLEQIK | 3 | y23 dicharged | 31.1 | 908.54 | 1225.74 | 35.2 | 2000 |
| 106 | LLISQR | 2 | y3 monocharged | 13.4 | 365.24 | 390.21 | 16.6 | 2000 |
| 107 | LLISQR | 2 | y4 monocharged | 13.4 | 365.24 | 503.29 | 16.6 | 2000 |
| 108 | LLISQR | 2 | y5 monocharged | 13.4 | 365.24 | 616.38 | 16.6 | 2000 |
| 109 | LLLATVGGPAGLTAFLR | 3 | y4 monocharged | 26.9 | 557.34 | 506.31 | 24.4 | 2000 |
| 110 | LLLATVGGPAGLTAFLR | 3 | y5 monocharged | 26.9 | 557.34 | 607.36 | 24.4 | 2000 |
| 111 | LLLATVGGPAGLTAFLR | 2 | y11 monocharged | 26.9 | 835.5 | 1059.6 | 43.4 | 2000 |
| 112 | LLNSQR | 2 | y3 monocharged | 8.4 | 365.71 | 390.21 | 16.6 | 2000 |
| 113 | LLNSQR | 2 | y4 monocharged | 8.4 | 365.71 | 504.25 | 16.6 | 2000 |
| 114 | LLNSQR | 2 | y5 monocharged | 8.4 | 365.71 | 617.34 | 16.6 | 2000 |
| 115 | LLTNQR | 2 | y3 monocharged | 9.3 | 372.72 | 417.22 | 17 | 2000 |
| 116 | LLTNQR | 2 | y4 monocharged | 9.3 | 372.72 | 518.27 | 17 | 2000 |
| 117 | LLTNQR | 2 | y5 monocharged | 9.3 | 372.72 | 631.35 | 17 | 2000 |
| 118 | LLTSQR | 2 | y3 monocharged | 9.5 | 359.22 | 390.21 | 16.2 | 2000 |
| 119 | LLTSQR | 2 | y4 monocharged | 9.5 | 359.22 | 491.26 | 16.2 | 2000 |
| 120 | LLTSQR | 2 | y5 monocharged | 9.5 | 359.22 | 604.34 | 16.2 | 2000 |
| 121 | LNIISLLATLPLAVHASPQPLEQIK | 3 | y17 dicharged | 30.8 | 893.87 | 921.53 | 34.8 | 2000 |
| 122 | LNIISLLATLPLAVHASPQPLEQIK | 3 | y18 dicharged | 30.7 | 893.87 | 957.05 | 34.8 | 2000 |
| 123 | LNIISLLATLPLAVHASPQPLEQIK | 3 | y21 dicharged | 30.8 | 893.87 | 1113.65 | 34.8 | 2000 |
| 124 | LSASSQR | 2 | y4 monocharged | 1.2 | 374.7 | 477.24 | 17.1 | 2000 |
| 125 | LSASSQR | 2 | y5 monocharged | 1.2 | 374.7 | 548.28 | 17.1 | 2000 |
| 126 | LSASSQR | 2 | y6 monocharged | 1.2 | 374.7 | 635.31 | 17.1 | 2000 |
| 127 | LSESQLSGR | 2 | y8 dicharged | 11.6 | 488.76 | 432.22 | 23.6 | 2000 |
| 128 | LSESQLSGR | 2 | y6 monocharged | 11.6 | 488.76 | 647.35 | 23.6 | 2000 |
| 129 | LSESQLSGR | 2 | y7 monocharged | 11.6 | 488.76 | 776.39 | 23.6 | 2000 |
| 130 | LSESQLSGSVGMIEMDLASGR | 3 | y3 monocharged | 23.7 | 723.02 | 319.17 | 29.5 | 2000 |
| 131 | LSESQLSGSVGMIEMDLASGR | 3 | y4 monocharged | 23.7 | 723.02 | 390.21 | 29.5 | 2000 |
| 132 | LSESQLSGSVGMIEMDLASGR | 3 | y6 monocharged | 23.7 | 723.02 | 618.32 | 29.5 | 3000 |
| 133 | MVVIYLR | 2 | y3 monocharged | 19.5 | 447.27 | 451.27 | 21.2 | 3000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 134 | MVVIYLR | 2 | y4 monocharged | 19.5 | 447.27 | 564.35 | 21.2 | 3000 |
| 135 | MVVIYLR | 2 | y5 monocharged | 19.5 | 447.27 | 663.42 | 21.2 | 2000 |
| 136 | NEALPGDAR | 2 | y5 monocharged | 10.9 | 471.74 | 515.26 | 22.6 | 2000 |
| 137 | NEALPGDAR | 2 | y6 monocharged | 10.9 | 471.74 | 628.34 | 22.6 | 2000 |
| 138 | NEALPGDAR | 2 | y7 monocharged | 10.9 | 471.74 | 699.38 | 22.6 | 2000 |
| 139 | NQHIAGIGAALIEHWQR | 3 | y13 dicharged | 20.1 | 638.68 | 711.39 | 26.9 | 2000 |
| 140 | NQHIAGIGAALIEHWQR | 3 | y14 dicharged | 20.1 | 638.68 | 767.93 | 26.9 | 2000 |
| 141 | NQHIAGIGAALIEHWQR | 3 | y15 dicharged | 20.1 | 638.68 | 836.46 | 26.9 | 2000 |
| 142 | NQQIAGIGAALIEHWQR | 3 | y13 dicharged | 22.3 | 635.67 | 711.39 | 26.8 | 2000 |
| 143 | NQQIAGIGAALIEHWQR | 3 | y14 dicharged | 22.3 | 635.67 | 767.93 | 26.8 | 2000 |
| 144 | NQQIAGIGAALIEHWQR | 3 | y15 dicharged | 22.3 | 635.67 | 831.96 | 26.8 | 2000 |
| 145 | NQQIAGLGAALIEHWQR | 3 | y13 dicharged | 22.7 | 635.67 | 711.39 | 26.8 | 2000 |
| 146 | NQQIAGLGAALIEHWQR | 3 | y14 dicharged | 22.7 | 635.67 | 767.93 | 26.8 | 2000 |
| 147 | NQQIAGLGAALIEHWQR | 3 | y15 dicharged | 22.6 | 635.67 | 831.96 | 26.8 | 2000 |
| 148 | NTTTPASMAATLR | 3 | y4 monocharged | 16 | 445.56 | 460.29 | 20.9 | 2000 |
| 149 | NTTTPASMAATLR | 3 | y5 monocharged | 16 | 445.56 | 531.33 | 20.9 | 2000 |
| 150 | NTTTPASMAATLR | 2 | y9 monocharged | 16 | 667.84 | 917.49 | 33.8 | 2000 |
| 151 | NVLTSQR | 2 | y3 monocharged | 10.2 | 409.23 | 390.21 | 19.1 | 2000 |
| 152 | NVLTSQR | 2 | y4 monocharged | 10.2 | 409.23 | 491.26 | 19.1 | 2000 |
| 153 | NVLTSQR | 2 | y5 monocharged | 10.2 | 409.23 | 604.34 | 19.1 | 2000 |
| 154 | QIDDNVTR | 2 | y4 monocharged | 10 | 480.74 | 489.28 | 23.1 | 2000 |
| 155 | QIDDNVTR | 2 | y5 monocharged | 10 | 480.74 | 604.31 | 23.1 | 2000 |
| 156 | QIDDNVTR | 2 | y6 monocharged | 10 | 480.74 | 719.33 | 23.1 | 2000 |
| 157 | QIGDK | 3 | y4 monocharged | 1.1 | 187.44 | 432.25 | 12.9 | 2000 |
| 158 | QIGDK | 2 | y3 monocharged | 1.1 | 280.66 | 319.16 | 11.7 | 2000 |
| 159 | QIGDK | 2 | y4 monocharged | 1.1 | 280.66 | 432.25 | 11.7 | 2000 |
| 160 | QIGDNVTR | 2 | y3 monocharged | 10.2 | 451.74 | 375.24 | 21.5 | 2000 |
| 161 | QIGDNVTR | 2 | y4 monocharged | 10.2 | 451.74 | 489.28 | 21.5 | 2000 |
| 162 | QIGDNVTR | 2 | y6 monocharged | 10.2 | 451.74 | 661.33 | 21.5 | 2000 |
| 163 | QIGENVTR | 2 | y3 monocharged | 10.3 | 458.75 | 375.24 | 21.9 | 2000 |
| 164 | QIGENVTR | 2 | y4 monocharged | 10.3 | 458.75 | 489.28 | 21.9 | 2000 |
| 165 | QIGENVTR | 2 | y6 monocharged | 10.3 | 458.75 | 675.34 | 21.9 | 2000 |
| 166 | QLLQWMVDAR | 2 | y5 monocharged | 22.1 | 630.33 | 591.29 | 31.7 | 2000 |
| 167 | QLLQWMVDAR | 2 | y6 monocharged | 22.1 | 630.33 | 777.37 | 31.7 | 2000 |
| 168 | QLLQWMVDAR | 2 | y7 monocharged | 22.1 | 630.33 | 905.43 | 31.7 | 2000 |
| 169 | QLLQWMVDDGVAGPLIR | 3 | y4 monocharged | 25.7 | 637.68 | 498.34 | 26.8 | 2000 |
| 170 | QLLQWMVDDGVAGPLIR | 3 | y5 monocharged | 25.8 | 637.68 | 555.36 | 26.8 | 2000 |
| 171 | QLLQWMVDDGVAGPLIR | 3 | y6 monocharged | 25.7 | 637.68 | 626.4 | 26.8 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 172 | QLLQWMVDDR | 2 | y4 monocharged | 21.7 | 652.33 | 504.24 | 32.9 | 2000 |
| 173 | QLLQWMVDDR | 2 | y5 monocharged | 21.7 | 652.33 | 635.28 | 32.9 | 2000 |
| 174 | QLLQWMVDDR | 2 | y6 monocharged | 21.7 | 652.33 | 821.36 | 32.9 | 2000 |
| 175 | QLLQWMVDGR | 2 | y4 monocharged | 21.4 | 623.32 | 446.24 | 31.3 | 2000 |
| 176 | QLLQWMVDGR | 2 | y5 monocharged | 21.4 | 623.32 | 577.28 | 31.3 | 2000 |
| 177 | QLLQWMVDGR | 2 | y6 monocharged | 21.4 | 623.32 | 763.36 | 31.3 | 2000 |
| 178 | QLLQWMVEDR | 3 | y4 monocharged | 21.7 | 439.89 | 518.26 | 20.7 | 2000 |
| 179 | QLLQWMVEDR | 2 | y5 monocharged | 21.7 | 659.34 | 649.3 | 33.3 | 2000 |
| 180 | QLLQWMVEDR | 2 | y6 monocharged | 21.7 | 659.34 | 835.38 | 33.3 | 2000 |
| 181 | QQDLVDYSPVSEK | 3 | y5 monocharged | 16 | 503.25 | 559.31 | 22.7 | 2000 |
| 182 | QQDLVDYSPVSEK | 2 | y5 monocharged | 16 | 754.37 | 559.31 | 38.7 | 2000 |
| 183 | QQDLVDYSPVSEK | 2 | y8 monocharged | 16 | 754.37 | 924.43 | 38.7 | 2000 |
| 184 | QQHLVDYSPVSEK | 3 | y6 dicharged | 14.2 | 510.59 | 323.67 | 22.9 | 2000 |
| 185 | QQHLVDYSPVSEK | 3 | y5 monocharged | 14.2 | 510.59 | 559.31 | 22.9 | 2000 |
| 186 | QQHLVDYSPVSEK | 3 | y6 monocharged | 14.3 | 510.59 | 646.34 | 22.9 | 2000 |
| 187 | QSESQLSGR | 2 | y3 monocharged | 7.2 | 496.24 | 319.17 | 24 | 2000 |
| 188 | QSESQLSGR | 2 | y8 dicharged | 7.2 | 496.24 | 432.22 | 24 | 2000 |
| 189 | QSESQLSGR | 2 | y4 monocharged | 7.2 | 496.24 | 432.26 | 24 | 2000 |
| 190 | QSESQLSGSVGMIEMDLASGR | 3 | y3 monocharged | 22.3 | 728.01 | 319.17 | 29.7 | 2000 |
| 191 | QSESQLSGSVGMIEMDLASGR | 3 | y6 monocharged | 22.3 | 728.01 | 618.32 | 29.7 | 2000 |
| 192 | QSESQLSGSVGMIEMDLASGR | 3 | y8 monocharged | 22.3 | 728.01 | 878.4 | 29.7 | 2000 |
| 193 | SQLQLLQWMVDDR | 3 | y4 monocharged | 24.9 | 544.61 | 504.24 | 24 | 2000 |
| 194 | SQLQLLQWMVDDR | 3 | y5 monocharged | 24.9 | 544.61 | 635.28 | 24 | 2000 |
| 195 | SQLQLLQWMVDDR | 3 | y6 monocharged | 24.9 | 544.61 | 821.36 | 24 | 2000 |
| 196 | SVLPAGWFIADK | 2 | y9 dicharged | 23.1 | 652.36 | 502.76 | 32.9 | 2000 |
| 197 | SVLPAGWFIADK | 2 | y10 dicharged | 23.1 | 652.36 | 559.31 | 32.9 | 2000 |
| 198 | SVLPAGWFIADK | 2 | y9 monocharged | 23.1 | 652.36 | 1004.52 | 32.9 | 2000 |
| 199 | SVLPAGWFIADR | 2 | y9 dicharged | 23.4 | 666.36 | 516.77 | 33.7 | 2000 |
| 200 | SVLPAGWFIADR | 2 | y10 dicharged | 23.4 | 666.36 | 573.31 | 33.7 | 2000 |
| 201 | SVLPAGWFIADR | 2 | y9 monocharged | 23.4 | 666.36 | 1032.53 | 33.7 | 2000 |
| 202 | SVLSAGWFIADK | 2 | y7 monocharged | 22.3 | 647.35 | 836.43 | 32.6 | 2000 |
| 203 | SVLSAGWFIADK | 2 | y8 monocharged | 22.3 | 647.35 | 907.47 | 32.6 | 2000 |
| 204 | SVLSAGWFIADK | 2 | y9 monocharged | 22.3 | 647.35 | 994.5 | 32.6 | 2000 |
| 205 | TGAAER | 2 | y3 monocharged | 1 | 302.66 | 375.2 | 13 | 2000 |
| 206 | TGAAER | 2 | y4 monocharged | 1 | 302.66 | 446.24 | 13 | 2000 |
| 207 | TGAAER | 2 | y5 monocharged | 1 | 302.66 | 503.26 | 13 | 2000 |
| 208 | TGAAK | 2 | y4 dicharged | 0.8 | 224.13 | 173.61 | 8.5 | 2000 |
| 209 | TGAAK | 2 | y3 monocharged | 0.8 | 224.13 | 289.19 | 8.5 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 210 | TGAAK | 2 | y4 monocharged | 0.8 | 224.13 | 346.21 | 8.5 | 2000 |
| 211 | TGAGER | 2 | y3 monocharged | 1 | 295.65 | 361.18 | 12.6 | 2000 |
| 212 | TGAGER | 2 | y4 monocharged | 1 | 295.65 | 432.22 | 12.6 | 2000 |
| 213 | TGAGER | 2 | y5 monocharged | 1 | 295.65 | 489.24 | 12.6 | 2000 |
| 214 | TGAGK | 3 | y4 monocharged | 0.7 | 145.09 | 332.19 | 11.6 | 2000 |
| 215 | TGAGK | 2 | y3 monocharged | 0.7 | 217.12 | 275.17 | 8.1 | 2000 |
| 216 | TGAGK | 2 | y4 monocharged | 0.7 | 217.12 | 332.19 | 8.1 | 2000 |
| 217 | TGASER | 2 | y3 monocharged | 1 | 310.65 | 391.19 | 13.4 | 2000 |
| 218 | TGASER | 2 | y4 monocharged | 1 | 310.65 | 462.23 | 13.4 | 2000 |
| 219 | TGASER | 2 | y5 monocharged | 1 | 310.65 | 519.25 | 13.4 | 2000 |
| 220 | TGASK | 2 | y4 dicharged | 0.8 | 232.13 | 181.61 | 9 | 2000 |
| 221 | TGASK | 2 | y3 monocharged | 0.8 | 232.13 | 305.18 | 9 | 2000 |
| 222 | TGASK | 2 | y4 monocharged | 0.8 | 232.13 | 362.2 | 9 | 2000 |
| 223 | TGASR | 3 | y4 monocharged | 0.8 | 164.42 | 390.21 | 12.2 | 2000 |
| 224 | TGASR | 2 | y3 monocharged | 0.8 | 246.13 | 333.19 | 9.8 | 2000 |
| 225 | TGASR | 2 | y4 monocharged | 0.8 | 246.13 | 390.21 | 9.8 | 2000 |
| 226 | TLTAWCADER | 2 | y5 monocharged | 15.5 | 611.78 | 650.26 | 30.6 | 5200 |
| 227 | TLTAWCADER | 2 | y6 monocharged | 15.5 | 611.78 | 836.34 | 30.6 | 5200 |
| 228 | TLTAWCADER | 2 | y8 monocharged | 15.5 | 611.78 | 1008.42 | 30.6 | 5200 |
| 229 | TLTAWHADER | 3 | y6 dicharged | 13.1 | 400.53 | 407.19 | 19.5 | 2000 |
| 230 | TLTAWHADER | 3 | y8 dicharged | 13.1 | 400.53 | 493.23 | 19.5 | 2000 |
| 231 | TLTAWHADER | 3 | y5 monocharged | 13.1 | 400.53 | 627.28 | 19.5 | 2000 |
| 232 | TLTAWR | 2 | y3 monocharged | 14.6 | 374.21 | 432.24 | 17.1 | 2000 |
| 233 | TLTAWR | 2 | y4 monocharged | 14.6 | 374.21 | 533.28 | 17.1 | 2000 |
| 234 | TLTAWR | 2 | y5 monocharged | 14.6 | 374.21 | 646.37 | 17.1 | 2000 |
| 235 | TVGGPAGLTAFLR | 2 | y5 monocharged | 22 | 630.36 | 607.36 | 31.7 | 2000 |
| 236 | TVGGPAGLTAFLR | 2 | y7 monocharged | 22 | 630.36 | 777.46 | 31.7 | 2000 |
| 237 | TVGGPAGLTAFLR | 2 | y11 monocharged | 22 | 630.36 | 1059.6 | 31.7 | 2000 |
| 238 | TVVIYLR | 2 | y3 monocharged | 17.5 | 432.27 | 451.27 | 20.4 | 2000 |
| 239 | TVVIYLR | 2 | y4 monocharged | 17.5 | 432.27 | 564.35 | 20.4 | 2000 |
| 240 | TVVIYLR | 2 | y5 monocharged | 17.4 | 432.27 | 663.42 | 20.4 | 2000 |
| 241 | VAGPLIR | 2 | y4 monocharged | 13.8 | 363.24 | 498.34 | 16.4 | 2000 |
| 242 | VAGPLIR | 2 | y5 monocharged | 13.8 | 363.24 | 555.36 | 16.4 | 2000 |
| 243 | VAGPLIR | 2 | y6 monocharged | 13.8 | 363.24 | 626.4 | 16.4 | 2000 |
| 244 | VALCGAVLAR | 2 | y8 dicharged | 16.4 | 515.3 | 430.25 | 25.1 | 2000 |
| 245 | VALCGAVLAR | 2 | y6 monocharged | 16.4 | 515.3 | 586.37 | 25.1 | 2000 |
| 246 | VALCGAVLAR | 2 | y7 monocharged | 16.4 | 515.3 | 746.4 | 25.1 | 2000 |
| 247 | VDAGDEQLER | 2 | y5 monocharged | 11 | 566.27 | 674.35 | 28 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 248 | VDAGDEQLER | 2 | y7 monocharged | 11 | 566.27 | 846.4 | 28 | 2000 |
| 249 | VDAGDEQLER | 2 | y8 monocharged | 11 | 566.27 | 917.43 | 28 | 2000 |
| 250 | VDAGDK | 2 | y3 monocharged | 1 | 302.65 | 319.16 | 13 | 2000 |
| 251 | VDAGDK | 2 | y4 monocharged | 1 | 302.65 | 390.2 | 13 | 2000 |
| 252 | VDAGDK | 2 | y5 monocharged | 1 | 302.65 | 505.23 | 13 | 2000 |
| 253 | VGMIEMDLASGR | 2 | y6 monocharged | 19.3 | 639.81 | 618.32 | 32.2 | 2000 |
| 254 | VGMIEMDLASGR | 2 | y7 monocharged | 19.3 | 639.81 | 749.36 | 32.2 | 2000 |
| 255 | VGMIEMDLASGR | 2 | y8 monocharged | 19.3 | 639.81 | 878.4 | 32.2 | 2000 |
| 256 | VGMIEMDLASR | 2 | y6 monocharged | 19.2 | 611.3 | 692.34 | 30.6 | 2000 |
| 257 | VGMIEMDLASR | 2 | y7 monocharged | 19.2 | 611.3 | 821.38 | 30.6 | 2000 |
| 258 | VGMIEMDLASR | 2 | y8 monocharged | 19.2 | 611.3 | 934.47 | 30.6 | 2000 |
| 259 | VGMIEMDLASSR | 2 | y6 monocharged | 18.8 | 654.82 | 648.33 | 33.1 | 2000 |
| 260 | VGMIEMDLASSR | 2 | y7 monocharged | 18.8 | 654.82 | 779.37 | 33.1 | 2000 |
| 261 | VGMIEMDLASSR | 2 | y8 monocharged | 18.8 | 654.82 | 908.41 | 33.1 | 2000 |
| 262 | VLLCGAVLAR | 2 | y6 monocharged | 18.2 | 536.32 | 586.37 | 26.3 | 5400 |
| 263 | VLLCGAVLAR | 2 | y7 monocharged | 18.3 | 536.32 | 746.4 | 26.3 | 5400 |
| 264 | VLLCGAVLAR | 2 | y8 monocharged | 18.3 | 536.32 | 859.48 | 26.3 | 5400 |
| 265 | VVLCGAMLAR | 2 | y6 monocharged | 17.7 | 545.3 | 618.34 | 26.8 | 2000 |
| 266 | VVLCGAMLAR | 2 | y7 monocharged | 17.7 | 545.3 | 778.37 | 26.8 | 2000 |
| 267 | VVLCGAMLAR | 2 | y8 monocharged | 17.7 | 545.3 | 891.45 | 26.8 | 2000 |
| 268 | VVLCGAVLAR | 2 | y6 monocharged | 17.2 | 529.31 | 586.37 | 25.9 | 2000 |
| 269 | VVLCGAVLAR | 2 | y7 monocharged | 17.2 | 529.31 | 746.4 | 25.9 | 2000 |
| 270 | VVLCGAVLAR | 2 | y8 monocharged | 17.2 | 529.31 | 859.48 | 25.9 | 2000 |
| 271 | VVLCGTVLAR | 2 | y6 monocharged | 16.9 | 544.32 | 616.38 | 26.8 | 2000 |
| 272 | VVLCGTVLAR | 2 | y7 monocharged | 16.9 | 544.32 | 776.41 | 26.8 | 2000 |
| 273 | VVLCGTVLAR | 2 | y8 monocharged | 16.9 | 544.32 | 889.49 | 26.8 | 2000 |
| 274 | WETDR | 3 | y4 monocharged | 8.2 | 236.11 | 520.24 | 14.4 | 2000 |
| 275 | WETDR | 2 | y3 monocharged | 8.2 | 353.66 | 391.19 | 15.9 | 2000 |
| 276 | WETDR | 2 | y4 monocharged | 8.2 | 353.66 | 520.24 | 15.9 | 2000 |
| 277 | WETELNEAFPGDAR | 3 | y5 monocharged | 19.1 | 545.59 | 515.26 | 24 | 2000 |
| 278 | WETELNEAFPGDAR | 3 | y6 monocharged | 19.1 | 545.59 | 662.33 | 24 | 2000 |
| 279 | WETELNEAFPGDAR | 2 | y5 monocharged | 19.1 | 817.88 | 515.26 | 42.4 | 2000 |
| 280 | WETELNEALPADAR | 3 | y5 monocharged | 18.5 | 538.93 | 529.27 | 23.8 | 2000 |
| 281 | WETELNEALPADAR | 2 | y5 monocharged | 18.5 | 807.89 | 529.27 | 41.8 | 2000 |
| 282 | WETELNEALPADAR | 2 | y7 monocharged | 18.5 | 807.89 | 713.39 | 41.8 | 2000 |
| 283 | WETELNEALPGDAR | 3 | y5 monocharged | 18.2 | 534.26 | 515.26 | 23.6 | 2000 |
| 284 | WETELNEALPGDAR | 2 | y5 monocharged | 18.2 | 800.88 | 515.26 | 41.4 | 2000 |
| 285 | WETELNEALPGDAR | 2 | y7 monocharged | 18.2 | 800.88 | 699.38 | 41.4 | 2000 |

TABLE 47-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 286 | WETELNEALSGDAR | 3 | y5 monocharged | 18.9 | 530.92 | 505.24 | 23.5 | 2000 |
| 287 | WETELNEALSGDAR | 3 | y6 monocharged | 18.9 | 530.92 | 618.32 | 23.5 | 2000 |
| 288 | WETELNEALSGDAR | 2 | y5 monocharged | 18.9 | 795.87 | 505.24 | 41.1 | 2000 |
| 289 | WETELNEVLPGDAR | 3 | y5 monocharged | 20.1 | 543.6 | 515.26 | 23.9 | 2000 |
| 290 | WETELNEVLPGDAR | 2 | y5 monocharged | 20.1 | 814.9 | 515.26 | 42.2 | 2000 |
| 291 | WETELNEVLPGDAR | 2 | y6 monocharged | 20.1 | 814.9 | 628.34 | 42.2 | 2000 |
| 292 | WETER | 3 | y4 monocharged | 9 | 240.78 | 534.25 | 14.5 | 2000 |
| 293 | WETER | 2 | y3 monocharged | 8.9 | 360.67 | 405.21 | 16.3 | 2000 |
| 294 | WETER | 2 | y4 monocharged | 8.9 | 360.67 | 534.25 | 16.3 | 2000 |

The other machine parameters used are as follows:

| | |
|---|---|
| Scan type: | MRM |
| MRM planned: | yes |
| Polarity: | Positive |
| Ionising source: | Turbo V ™ (Applied BioSystems) |
| Q1 setting: | Filtering with unit resolution |
| Q3 setting: | Filtering with unit resolution |
| Inter-scan pause: | 5.00 msec |
| Scanning speed: | 10 Da/s |
| Curtain gas: | 50.00 psi |
| Cone voltage: | 5500.00 V |
| Source temperature: | 500.00° C. |
| Nebulising gas: | 50.00 psi |
| Heating gas: | 50.00 psi |
| Collision gas which induces dissociation: | 9.00 psi |
| Dynamic filling: | activated |
| Declustering potential (DP): | 100.00 V |
| Entry potential before Q0 (EP): | 6.00 V |
| Collision cell exit potential (CXP): | 15 V |
| Total cycle time: | 1 sec |
| Detection window: | 120 sec |

The areas obtained for each of the transitions and for each of the microorganisms studied were measured. When the areas of the transitions are greater than or equal to the positivity threshold described in TABLE 47, the detection of the transition is considered to be positive and is labelled "1" in TABLE 48. When a transition has an area less than the positivity threshold described in TABLE 47, the transition is considered non-detected and is labelled "0" in TABLE 48.

For a given peptide, when at least 3 transitions are labelled "1", the peptide is considered as being detected.

TABLE 48

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 1 | 0 | 0 | 0 | 1 | 0 |
| 3 | 0 | 0 | 0 | 0 | 0 | 0 | 0 | 0 | 0 | 0 | 0 | 0 | 1 | 0 |
| 4 | 0 | 0 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 | 0 |
| 11 | 0 | 0 | 0 | 0 | 1 | 0 | 0 | 0 | 0 | 0 | 0 | 0 | 0 | 0 |
| 12 | 0 | 0 | 0 | 0 | 1 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 | 0 | 0 |
| 14 | 0 | 0 | 0 | 0 | 0 | 0 | 0 | 1 | 0 | 0 | 0 | 0 | 1 | 0 |
| 15 | 0 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 | 0 | 0 |
| 17 | 1 | 0 | 0 | 0 | 0 | 1 | 1 | 1 | 1 | 1 | 1 | 1 | 1 | 1 |
| 18 | 0 | 0 | 0 | 0 | 0 | 0 | 0 | 0 | 0 | 0 | 0 | 0 | 0 | 0 |
| 19 | 1 | 0 | 0 | 0 | 1 | 1 | 1 | 1 | 1 | 0 | 0 | 1 | 1 | 1 |
| 20 | 1 | 0 | 0 | 0 | 1 | 1 | 1 | 0 | 1 | 0 | 0 | 1 | 1 | 1 |
| 21 | 1 | 0 | 1 | 0 | 1 | 1 | 1 | 0 | 1 | 0 | 0 | 1 | 1 | 0 |
| 22 | 0 | 0 | 0 | 0 | 0 | 0 | 0 | 0 | 0 | 0 | 0 | 0 | 0 | 0 |
| 23 | 0 | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 | 0 |
| 25 | 1 | 1 | 1 | 0 | 1 | 1 | 1 | 0 | 1 | 0 | 1 | 1 | 1 | 0 |
| 26 | 1 | 1 | 1 | 0 | 1 | 1 | 1 | 0 | 1 | 1 | 1 | 1 | 1 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 27 | 0 | 1 | 1 | 0 | 1 | 1 | 1 | 0 | 1 | 0 | 1 | 1 | 1 | 0 |
| 28 | 0 | 0 | 0 | 0 | 0 | 0 | 0 | 0 | 0 | 0 | 0 | 0 | 0 | 0 |
| 29 | 0 | 0 | 0 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 | 0 | 0 | 0 |
| 31 | 0 | 0 | 0 | 0 | 0 | 1 | 0 | 0 | 0 | 0 | 0 | 0 | 0 | 0 |
| 32 | 0 | 0 | 0 | 0 | 0 | 0 | 0 | 0 | 0 | 0 | 0 | 0 | 0 | 0 |
| 33 | 0 | 0 | 0 | 0 | 0 | 0 | 0 | 0 | 0 | 0 | 0 | 0 | 0 | 0 |
| 34 | 0 | 0 | 0 | 0 | 0 | 0 | 0 | 0 | 0 | 0 | 0 | 0 | 0 | 0 |
| 35 | 0 | 0 | 0 | 0 | 0 | 0 | 0 | 0 | 0 | 0 | 0 | 0 | 0 | 0 |
| 36 | 0 | 0 | 0 | 0 | 0 | 0 | 0 | 0 | 0 | 0 | 0 | 0 | 0 | 0 |
| 37 | 0 | 0 | 0 | 0 | 0 | 0 | 0 | 0 | 0 | 0 | 0 | 0 | 0 | 0 |
| 38 | 0 | 0 | 0 | 0 | 1 | 0 | 0 | 1 | 0 | 0 | 0 | 0 | 1 | 0 |
| 39 | 0 | 0 | 0 | 0 | 0 | 0 | 0 | 0 | 0 | 0 | 0 | 0 | 0 | 0 |
| 40 | 0 | 0 | 0 | 0 | 0 | 0 | 0 | 0 | 0 | 0 | 0 | 0 | 0 | 0 |
| 41 | 0 | 0 | 0 | 0 | 0 | 0 | 0 | 0 | 0 | 0 | 0 | 0 | 0 | 0 |
| 42 | 0 | 0 | 0 | 0 | 0 | 0 | 0 | 0 | 0 | 0 | 0 | 0 | 0 | 0 |
| 43 | 0 | 0 | 0 | 0 | 1 | 1 | 1 | 0 | 1 | 0 | 0 | 1 | 1 | 0 |
| 44 | 0 | 0 | 0 | 0 | 1 | 1 | 1 | 0 | 1 | 0 | 0 | 1 | 1 | 0 |
| 45 | 0 | 0 | 1 | 1 | 1 | 1 | 1 | 0 | 0 | 0 | 0 | 1 | 1 | 0 |
| 46 | 0 | 0 | 0 | 0 | 0 | 0 | 0 | 0 | 0 | 0 | 0 | 0 | 0 | 0 |
| 47 | 0 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 | 0 |
| 49 | 1 | 1 | 1 | 1 | 1 | 1 | 1 | 1 | 1 | 1 | 1 | 1 | 1 | 1 |
| 50 | 1 | 1 | 1 | 1 | 1 | 1 | 1 | 1 | 1 | 1 | 1 | 1 | 1 | 1 |
| 51 | 1 | 1 | 1 | 1 | 1 | 1 | 1 | 1 | 1 | 1 | 1 | 1 | 1 | 1 |
| 52 | 1 | 0 | 0 | 0 | 0 | 0 | 0 | 0 | 0 | 0 | 0 | 0 | 0 | 0 |
| 53 | 0 | 0 | 0 | 0 | 0 | 0 | 0 | 0 | 0 | 0 | 0 | 0 | 0 | 0 |
| 54 | 1 | 0 | 0 | 0 | 0 | 0 | 0 | 0 | 0 | 0 | 0 | 0 | 0 | 0 |
| 55 | 1 | 1 | 1 | 1 | 1 | 1 | 1 | 1 | 1 | 1 | 1 | 1 | 1 | 1 |
| 56 | 1 | 1 | 1 | 1 | 1 | 1 | 1 | 1 | 1 | 1 | 1 | 1 | 1 | 1 |
| 57 | 1 | 1 | 1 | 1 | 1 | 1 | 1 | 1 | 1 | 1 | 1 | 1 | 1 | 1 |
| 58 | 0 | 0 | 0 | 0 | 0 | 0 | 0 | 0 | 0 | 0 | 0 | 0 | 0 | 0 |
| 59 | 0 | 0 | 0 | 0 | 0 | 0 | 0 | 0 | 0 | 0 | 0 | 0 | 0 | 0 |
| 60 | 0 | 0 | 0 | 0 | 0 | 0 | 0 | 0 | 0 | 0 | 0 | 0 | 0 | 0 |
| 61 | 0 | 0 | 0 | 0 | 0 | 0 | 0 | 0 | 0 | 0 | 0 | 0 | 0 | 0 |
| 62 | 0 | 0 | 0 | 0 | 0 | 0 | 0 | 0 | 0 | 0 | 0 | 0 | 0 | 0 |
| 63 | 0 | 0 | 0 | 0 | 0 | 0 | 0 | 0 | 0 | 0 | 0 | 0 | 0 | 0 |
| 64 | 0 | 0 | 0 | 0 | 0 | 0 | 0 | 0 | 0 | 0 | 0 | 0 | 0 | 0 |
| 65 | 0 | 0 | 0 | 0 | 0 | 0 | 0 | 0 | 0 | 0 | 0 | 0 | 0 | 0 |
| 66 | 0 | 0 | 0 | 0 | 0 | 0 | 0 | 0 | 0 | 0 | 0 | 0 | 0 | 0 |
| 67 | 0 | 0 | 0 | 0 | 0 | 0 | 0 | 0 | 0 | 0 | 0 | 0 | 0 | 0 |
| 68 | 0 | 0 | 0 | 0 | 1 | 0 | 0 | 0 | 0 | 0 | 0 | 0 | 0 | 0 |
| 69 | 0 | 0 | 0 | 0 | 0 | 0 | 0 | 0 | 0 | 0 | 0 | 0 | 0 | 0 |
| 70 | 0 | 0 | 0 | 0 | 0 | 0 | 0 | 0 | 0 | 0 | 0 | 0 | 0 | 0 |
| 71 | 0 | 0 | 0 | 0 | 0 | 0 | 0 | 1 | 0 | 0 | 0 | 0 | 0 | 0 |
| 72 | 0 | 0 | 0 | 0 | 0 | 0 | 0 | 0 | 0 | 0 | 0 | 0 | 0 | 0 |
| 73 | 0 | 0 | 0 | 0 | 0 | 0 | 0 | 1 | 0 | 0 | 0 | 0 | 0 | 0 |
| 74 | 0 | 0 | 0 | 0 | 0 | 0 | 0 | 0 | 0 | 0 | 0 | 0 | 0 | 0 |
| 75 | 0 | 0 | 0 | 0 | 0 | 0 | 0 | 0 | 0 | 0 | 0 | 0 | 0 | 0 |
| 76 | 0 | 0 | 0 | 0 | 0 | 0 | 0 | 0 | 0 | 0 | 0 | 0 | 0 | 0 |
| 77 | 0 | 0 | 0 | 0 | 0 | 0 | 0 | 0 | 0 | 0 | 0 | 0 | 0 | 0 |
| 78 | 0 | 0 | 0 | 0 | 0 | 0 | 0 | 0 | 0 | 0 | 0 | 0 | 0 | 0 |
| 79 | 0 | 0 | 0 | 0 | 0 | 0 | 0 | 0 | 0 | 0 | 0 | 0 | 0 | 0 |
| 80 | 0 | 0 | 0 | 0 | 0 | 0 | 0 | 0 | 0 | 0 | 0 | 0 | 0 | 0 |
| 81 | 0 | 0 | 0 | 0 | 0 | 0 | 0 | 0 | 0 | 0 | 0 | 0 | 0 | 0 |
| 82 | 0 | 0 | 0 | 0 | 0 | 0 | 0 | 0 | 0 | 0 | 0 | 0 | 0 | 0 |
| 83 | 0 | 0 | 0 | 0 | 0 | 0 | 0 | 0 | 0 | 0 | 0 | 0 | 0 | 0 |
| 84 | 0 | 0 | 0 | 0 | 0 | 0 | 0 | 0 | 0 | 0 | 0 | 0 | 0 | 0 |
| 85 | 0 | 0 | 0 | 0 | 0 | 0 | 0 | 0 | 0 | 0 | 0 | 0 | 0 | 0 |
| 86 | 0 | 0 | 0 | 0 | 0 | 0 | 0 | 0 | 0 | 0 | 0 | 0 | 0 | 0 |
| 87 | 0 | 0 | 0 | 0 | 0 | 0 | 0 | 0 | 0 | 0 | 0 | 0 | 0 | 0 |
| 88 | 0 | 0 | 0 | 0 | 0 | 0 | 0 | 0 | 0 | 0 | 0 | 0 | 0 | 0 |
| 89 | 0 | 0 | 0 | 0 | 0 | 0 | 0 | 0 | 0 | 0 | 0 | 0 | 0 | 0 |
| 90 | 0 | 0 | 0 | 0 | 0 | 0 | 0 | 0 | 0 | 0 | 0 | 0 | 0 | 0 |
| 91 | 0 | 0 | 0 | 0 | 0 | 0 | 0 | 0 | 0 | 0 | 0 | 0 | 0 | 0 |
| 92 | 0 | 0 | 0 | 0 | 0 | 0 | 0 | 0 | 0 | 0 | 0 | 0 | 0 | 0 |
| 93 | 0 | 0 | 0 | 0 | 0 | 0 | 0 | 0 | 0 | 0 | 0 | 0 | 0 | 0 |
| 94 | 0 | 0 | 0 | 0 | 0 | 0 | 0 | 0 | 0 | 0 | 0 | 0 | 0 | 0 |
| 95 | 0 | 0 | 0 | 0 | 0 | 0 | 0 | 0 | 0 | 0 | 0 | 0 | 0 | 0 |
| 96 | 0 | 0 | 0 | 0 | 0 | 0 | 0 | 0 | 0 | 0 | 0 | 0 | 0 | 0 |
| 97 | 0 | 0 | 0 | 0 | 0 | 0 | 0 | 0 | 0 | 0 | 0 | 0 | 0 | 0 |
| 98 | 0 | 0 | 0 | 0 | 0 | 0 | 0 | 0 | 0 | 0 | 0 | 0 | 0 | 0 |
| 99 | 0 | 0 | 0 | 0 | 0 | 0 | 0 | 0 | 0 | 0 | 0 | 0 | 0 | 0 |
| 100 | 0 | 0 | 0 | 0 | 0 | 0 | 0 | 0 | 0 | 0 | 0 | 0 | 0 | 0 |
| 101 | 0 | 0 | 0 | 0 | 0 | 0 | 0 | 0 | 0 | 0 | 0 | 0 | 0 | 0 |
| 102 | 0 | 0 | 0 | 0 | 0 | 0 | 0 | 0 | 0 | 0 | 0 | 0 | 0 | 0 |
| 103 | 0 | 0 | 0 | 0 | 0 | 0 | 0 | 0 | 0 | 0 | 0 | 0 | 0 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 104 | 0 | 0 | 0 | 0 | 0 | 0 | 0 | 0 | 0 | 0 | 0 | 0 | 0 | 0 |
| 105 | 0 | 0 | 0 | 0 | 0 | 0 | 0 | 0 | 0 | 0 | 0 | 0 | 0 | 0 |
| 106 | 0 | 0 | 0 | 0 | 0 | 0 | 0 | 0 | 0 | 0 | 1 | 0 | 0 | 0 |
| 107 | 0 | 0 | 0 | 0 | 0 | 0 | 0 | 0 | 0 | 0 | 0 | 0 | 0 | 0 |
| 108 | 0 | 0 | 0 | 0 | 0 | 0 | 0 | 0 | 0 | 0 | 0 | 0 | 0 | 0 |
| 109 | 0 | 0 | 0 | 0 | 0 | 0 | 0 | 0 | 0 | 0 | 0 | 0 | 0 | 0 |
| 110 | 0 | 0 | 0 | 0 | 0 | 0 | 0 | 0 | 0 | 0 | 0 | 0 | 0 | 0 |
| 111 | 0 | 0 | 0 | 0 | 0 | 0 | 0 | 0 | 0 | 0 | 0 | 0 | 0 | 0 |
| 112 | 0 | 0 | 0 | 0 | 0 | 0 | 0 | 0 | 0 | 0 | 0 | 1 | 1 | 1 | 0 |
| 113 | 0 | 0 | 0 | 0 | 0 | 0 | 0 | 0 | 0 | 0 | 0 | 1 | 0 | 0 |
| 114 | 0 | 0 | 0 | 0 | 0 | 0 | 0 | 0 | 0 | 0 | 0 | 0 | 0 | 0 |
| 115 | 0 | 0 | 0 | 0 | 0 | 0 | 0 | 0 | 0 | 0 | 0 | 0 | 0 | 0 |
| 116 | 0 | 0 | 0 | 0 | 0 | 0 | 0 | 0 | 0 | 0 | 0 | 0 | 0 | 0 |
| 117 | 1 | 0 | 0 | 0 | 0 | 0 | 0 | 0 | 0 | 0 | 0 | 0 | 0 | 0 |
| 118 | 0 | 1 | 1 | 1 | 0 | 0 | 0 | 0 | 0 | 0 | 0 | 1 | 0 | 0 |
| 119 | 0 | 0 | 0 | 0 | 0 | 0 | 0 | 0 | 0 | 0 | 0 | 1 | 0 | 0 |
| 120 | 0 | 0 | 0 | 0 | 0 | 0 | 0 | 0 | 0 | 0 | 0 | 1 | 0 | 0 |
| 121 | 0 | 0 | 0 | 0 | 0 | 0 | 0 | 0 | 0 | 0 | 0 | 0 | 0 | 0 |
| 122 | 0 | 0 | 0 | 0 | 0 | 0 | 0 | 0 | 0 | 0 | 0 | 0 | 0 | 0 |
| 123 | 0 | 0 | 0 | 0 | 0 | 0 | 0 | 0 | 0 | 0 | 0 | 0 | 0 | 0 |
| 124 | 0 | 0 | 0 | 0 | 0 | 0 | 0 | 1 | 0 | 0 | 0 | 0 | 0 | 0 |
| 125 | 0 | 0 | 0 | 0 | 0 | 0 | 0 | 1 | 0 | 0 | 0 | 0 | 1 | 0 |
| 126 | 0 | 0 | 0 | 0 | 0 | 0 | 0 | 1 | 0 | 0 | 0 | 0 | 0 | 0 |
| 127 | 1 | 0 | 0 | 0 | 1 | 0 | 0 | 0 | 0 | 0 | 0 | 1 | 1 | 0 |
| 128 | 1 | 0 | 0 | 0 | 1 | 0 | 0 | 0 | 0 | 0 | 0 | 1 | 1 | 0 |
| 129 | 1 | 0 | 0 | 0 | 1 | 0 | 0 | 0 | 0 | 0 | 0 | 1 | 1 | 0 |
| 130 | 0 | 0 | 0 | 0 | 0 | 0 | 0 | 0 | 0 | 0 | 0 | 0 | 0 | 0 |
| 131 | 0 | 0 | 0 | 0 | 0 | 0 | 0 | 0 | 0 | 0 | 0 | 0 | 0 | 0 |
| 132 | 0 | 0 | 1 | 0 | 0 | 0 | 0 | 0 | 0 | 0 | 0 | 0 | 0 | 0 |
| 133 | 0 | 0 | 0 | 1 | 0 | 0 | 1 | 0 | 0 | 0 | 0 | 0 | 0 | 0 |
| 134 | 0 | 1 | 0 | 0 | 0 | 0 | 0 | 0 | 0 | 0 | 1 | 1 | 0 | 1 |
| 135 | 0 | 0 | 0 | 1 | 0 | 0 | 1 | 0 | 1 | 1 | 1 | 1 | 1 | 1 |
| 136 | 0 | 0 | 0 | 0 | 0 | 0 | 0 | 0 | 0 | 0 | 0 | 0 | 0 | 0 |
| 137 | 0 | 0 | 0 | 0 | 0 | 0 | 0 | 0 | 0 | 0 | 0 | 0 | 0 | 0 |
| 138 | 1 | 0 | 0 | 0 | 1 | 1 | 1 | 0 | 1 | 1 | 1 | 1 | 1 | 1 |
| 139 | 0 | 0 | 0 | 0 | 0 | 1 | 0 | 0 | 0 | 0 | 0 | 0 | 0 | 0 |
| 140 | 0 | 0 | 0 | 0 | 0 | 1 | 1 | 1 | 1 | 1 | 1 | 1 | 0 | 1 |
| 141 | 0 | 0 | 0 | 0 | 0 | 0 | 0 | 0 | 0 | 0 | 0 | 0 | 0 | 0 |
| 142 | 0 | 1 | 1 | 1 | 1 | 1 | 1 | 0 | 1 | 1 | 1 | 1 | 1 | 0 |
| 143 | 0 | 1 | 1 | 1 | 1 | 1 | 1 | 0 | 1 | 1 | 1 | 1 | 1 | 0 |
| 144 | 0 | 1 | 1 | 1 | 1 | 1 | 1 | 0 | 1 | 1 | 1 | 1 | 1 | 0 |
| 145 | 0 | 1 | 1 | 1 | 1 | 1 | 1 | 1 | 1 | 1 | 1 | 1 | 1 | 1 |
| 146 | 0 | 1 | 1 | 1 | 1 | 1 | 1 | 1 | 1 | 1 | 1 | 1 | 1 | 1 |
| 147 | 0 | 1 | 1 | 1 | 1 | 1 | 1 | 1 | 1 | 1 | 1 | 1 | 1 | 1 |
| 148 | 0 | 0 | 0 | 0 | 0 | 0 | 0 | 0 | 0 | 0 | 0 | 1 | 0 | 0 |
| 149 | 1 | 1 | 1 | 1 | 1 | 1 | 1 | 1 | 1 | 1 | 1 | 1 | 0 | 1 |
| 150 | 0 | 0 | 0 | 0 | 0 | 0 | 0 | 0 | 0 | 0 | 0 | 1 | 0 | 0 |
| 151 | 0 | 0 | 0 | 0 | 0 | 0 | 0 | 0 | 0 | 0 | 0 | 0 | 0 | 1 |
| 152 | 0 | 0 | 0 | 0 | 0 | 1 | 0 | 0 | 0 | 0 | 0 | 0 | 0 | 1 |
| 153 | 0 | 0 | 0 | 0 | 0 | 0 | 0 | 0 | 0 | 0 | 0 | 0 | 0 | 1 |
| 154 | 0 | 0 | 0 | 0 | 0 | 0 | 0 | 0 | 0 | 0 | 0 | 0 | 0 | 0 |
| 155 | 0 | 0 | 0 | 0 | 0 | 0 | 0 | 0 | 0 | 0 | 0 | 0 | 0 | 0 |
| 156 | 0 | 0 | 0 | 0 | 0 | 0 | 0 | 0 | 0 | 0 | 0 | 0 | 0 | 0 |
| 157 | 0 | 0 | 0 | 0 | 0 | 0 | 0 | 0 | 0 | 0 | 0 | 0 | 0 | 0 |
| 158 | 0 | 0 | 0 | 0 | 0 | 0 | 0 | 0 | 1 | 0 | 0 | 0 | 1 | 0 |
| 159 | 0 | 0 | 0 | 0 | 0 | 0 | 0 | 0 | 1 | 0 | 0 | 0 | 1 | 0 |
| 160 | 1 | 0 | 0 | 0 | 1 | 1 | 1 | 0 | 1 | 0 | 0 | 1 | 1 | 0 |
| 161 | 1 | 1 | 1 | 0 | 1 | 1 | 1 | 1 | 1 | 0 | 0 | 1 | 1 | 0 |
| 162 | 0 | 0 | 0 | 0 | 1 | 1 | 1 | 0 | 0 | 0 | 0 | 1 | 1 | 0 |
| 163 | 0 | 0 | 0 | 0 | 1 | 0 | 0 | 0 | 0 | 0 | 0 | 0 | 0 | 0 |
| 164 | 0 | 0 | 0 | 0 | 0 | 0 | 0 | 0 | 0 | 0 | 0 | 0 | 0 | 0 |
| 165 | 1 | 0 | 0 | 0 | 0 | 0 | 0 | 0 | 0 | 0 | 0 | 0 | 0 | 0 |
| 166 | 0 | 0 | 0 | 0 | 0 | 0 | 0 | 0 | 0 | 0 | 0 | 0 | 0 | 0 |
| 167 | 0 | 0 | 0 | 0 | 0 | 0 | 0 | 0 | 0 | 0 | 0 | 0 | 0 | 0 |
| 168 | 0 | 0 | 0 | 0 | 0 | 0 | 0 | 0 | 0 | 0 | 0 | 0 | 0 | 0 |
| 169 | 0 | 0 | 0 | 0 | 0 | 0 | 0 | 0 | 0 | 0 | 0 | 0 | 0 | 0 |
| 170 | 0 | 0 | 0 | 0 | 0 | 0 | 0 | 0 | 0 | 0 | 0 | 0 | 0 | 0 |
| 171 | 0 | 0 | 0 | 0 | 0 | 0 | 0 | 0 | 0 | 0 | 0 | 0 | 0 | 0 |
| 172 | 0 | 0 | 0 | 0 | 0 | 0 | 0 | 1 | 0 | 0 | 0 | 0 | 0 | 0 |
| 173 | 0 | 0 | 0 | 0 | 0 | 0 | 0 | 0 | 1 | 0 | 0 | 0 | 0 | 0 |
| 174 | 0 | 0 | 0 | 0 | 0 | 1 | 0 | 0 | 1 | 0 | 1 | 0 | 0 | 1 |
| 175 | 0 | 0 | 0 | 0 | 0 | 0 | 0 | 0 | 0 | 0 | 0 | 0 | 0 | 0 |
| 176 | 0 | 0 | 1 | 0 | 0 | 0 | 0 | 0 | 0 | 0 | 0 | 0 | 0 | 0 |
| 177 | 0 | 0 | 0 | 0 | 0 | 0 | 0 | 0 | 0 | 0 | 0 | 0 | 0 | 0 |
| 178 | 0 | 0 | 0 | 0 | 0 | 0 | 0 | 0 | 0 | 0 | 0 | 0 | 0 | 0 |
| 179 | 0 | 0 | 0 | 0 | 0 | 0 | 0 | 0 | 0 | 0 | 0 | 0 | 0 | 0 |
| 180 | 0 | 0 | 0 | 0 | 0 | 0 | 0 | 0 | 0 | 0 | 0 | 0 | 0 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 181 | 0 | 0 | 0 | 0 | 0 | 0 | 1 | 0 | 0 | 0 | 0 | 1 | 1 | 0 |
| 182 | 1 | 0 | 0 | 0 | 1 | 1 | 1 | 0 | 1 | 0 | 0 | 1 | 1 | 0 |
| 183 | 0 | 0 | 0 | 0 | 1 | 1 | 1 | 0 | 0 | 0 | 0 | 1 | 1 | 0 |
| 184 | 0 | 0 | 0 | 0 | 0 | 0 | 0 | 0 | 0 | 0 | 0 | 0 | 0 | 0 |
| 185 | 0 | 0 | 0 | 0 | 0 | 0 | 0 | 0 | 0 | 0 | 0 | 0 | 0 | 0 |
| 186 | 0 | 0 | 0 | 0 | 0 | 0 | 0 | 0 | 0 | 0 | 0 | 0 | 0 | 0 |
| 187 | 0 | 0 | 0 | 0 | 0 | 0 | 0 | 0 | 0 | 0 | 0 | 0 | 0 | 0 |
| 188 | 0 | 0 | 0 | 0 | 0 | 0 | 0 | 0 | 0 | 0 | 0 | 0 | 0 | 0 |
| 189 | 0 | 0 | 0 | 0 | 0 | 0 | 0 | 0 | 0 | 0 | 0 | 0 | 0 | 0 |
| 190 | 0 | 0 | 0 | 0 | 0 | 0 | 0 | 0 | 0 | 0 | 0 | 0 | 0 | 0 |
| 191 | 0 | 0 | 0 | 0 | 0 | 0 | 0 | 0 | 0 | 0 | 0 | 0 | 0 | 0 |
| 192 | 0 | 0 | 0 | 0 | 0 | 0 | 0 | 0 | 0 | 0 | 0 | 0 | 0 | 0 |
| 193 | 0 | 0 | 0 | 0 | 0 | 0 | 0 | 0 | 0 | 0 | 0 | 0 | 0 | 0 |
| 194 | 0 | 0 | 0 | 0 | 0 | 0 | 0 | 0 | 0 | 0 | 0 | 0 | 0 | 0 |
| 195 | 0 | 0 | 0 | 0 | 0 | 0 | 0 | 0 | 0 | 0 | 0 | 0 | 0 | 0 |
| 196 | 0 | 0 | 0 | 0 | 0 | 0 | 0 | 0 | 0 | 0 | 0 | 0 | 0 | 0 |
| 197 | 0 | 0 | 0 | 0 | 0 | 0 | 0 | 0 | 0 | 0 | 0 | 0 | 0 | 0 |
| 198 | 0 | 0 | 0 | 0 | 0 | 0 | 0 | 0 | 0 | 0 | 0 | 0 | 0 | 0 |
| 199 | 0 | 0 | 0 | 0 | 0 | 0 | 0 | 0 | 0 | 0 | 0 | 0 | 0 | 0 |
| 200 | 0 | 0 | 0 | 0 | 0 | 0 | 0 | 0 | 0 | 0 | 0 | 0 | 0 | 0 |
| 201 | 0 | 0 | 0 | 0 | 0 | 0 | 0 | 1 | 0 | 0 | 0 | 0 | 0 | 0 |
| 202 | 0 | 0 | 0 | 0 | 0 | 0 | 0 | 0 | 0 | 0 | 0 | 0 | 0 | 0 |
| 203 | 0 | 0 | 0 | 0 | 0 | 0 | 0 | 0 | 0 | 0 | 0 | 0 | 0 | 0 |
| 204 | 0 | 0 | 0 | 0 | 0 | 0 | 0 | 0 | 0 | 0 | 0 | 0 | 0 | 0 |
| 205 | 1 | 1 | 1 | 1 | 1 | 0 | 1 | 1 | 0 | 0 | 0 | 0 | 0 | 0 |
| 206 | 1 | 1 | 1 | 1 | 1 | 0 | 1 | 1 | 0 | 1 | 1 | 1 | 0 | 0 |
| 207 | 1 | 1 | 1 | 1 | 1 | 1 | 0 | 1 | 0 | 1 | 1 | 1 | 0 | 1 |
| 208 | 0 | 0 | 0 | 0 | 0 | 0 | 0 | 0 | 0 | 0 | 0 | 0 | 0 | 0 |
| 209 | 0 | 0 | 0 | 0 | 0 | 0 | 0 | 0 | 0 | 0 | 0 | 0 | 0 | 0 |
| 210 | 0 | 0 | 0 | 0 | 0 | 0 | 0 | 0 | 0 | 0 | 0 | 0 | 0 | 0 |
| 211 | 0 | 0 | 0 | 0 | 0 | 0 | 0 | 0 | 0 | 0 | 0 | 0 | 0 | 0 |
| 212 | 0 | 0 | 0 | 0 | 0 | 0 | 0 | 0 | 0 | 0 | 0 | 0 | 1 | 0 |
| 213 | 0 | 0 | 0 | 0 | 0 | 0 | 0 | 0 | 1 | 0 | 0 | 0 | 1 | 0 |
| 214 | 0 | 0 | 0 | 0 | 0 | 0 | 0 | 0 | 0 | 0 | 0 | 0 | 0 | 0 |
| 215 | 0 | 0 | 0 | 0 | 0 | 0 | 0 | 0 | 0 | 0 | 0 | 0 | 0 | 0 |
| 216 | 0 | 0 | 0 | 0 | 0 | 0 | 0 | 0 | 0 | 0 | 0 | 0 | 0 | 0 |
| 217 | 0 | 0 | 0 | 0 | 0 | 0 | 0 | 0 | 0 | 0 | 0 | 0 | 1 | 0 |
| 218 | 0 | 1 | 0 | 0 | 0 | 1 | 0 | 0 | 0 | 0 | 1 | 1 | 0 | 0 |
| 219 | 0 | 0 | 1 | 1 | 0 | 0 | 0 | 0 | 0 | 0 | 0 | 0 | 0 | 0 |
| 220 | 0 | 0 | 0 | 0 | 0 | 0 | 0 | 0 | 0 | 0 | 0 | 0 | 0 | 0 |
| 221 | 0 | 0 | 0 | 0 | 0 | 0 | 0 | 0 | 0 | 0 | 0 | 0 | 0 | 0 |
| 222 | 0 | 0 | 0 | 0 | 0 | 0 | 0 | 0 | 0 | 0 | 0 | 0 | 0 | 0 |
| 223 | 0 | 0 | 0 | 0 | 0 | 0 | 0 | 0 | 0 | 0 | 0 | 0 | 0 | 0 |
| 224 | 0 | 0 | 0 | 0 | 0 | 0 | 0 | 0 | 0 | 0 | 0 | 0 | 0 | 0 |
| 225 | 0 | 0 | 0 | 0 | 0 | 0 | 0 | 0 | 0 | 0 | 0 | 0 | 0 | 0 |
| 226 | 1 | 0 | 0 | 0 | 0 | 0 | 1 | 1 | 0 | 0 | 0 | 0 | 0 | 0 |
| 227 | 0 | 0 | 0 | 0 | 0 | 0 | 0 | 0 | 0 | 0 | 0 | 0 | 0 | 0 |
| 228 | 1 | 0 | 0 | 0 | 0 | 0 | 1 | 0 | 0 | 1 | 0 | 0 | 0 | 0 |
| 229 | 0 | 0 | 0 | 0 | 0 | 0 | 0 | 0 | 0 | 0 | 0 | 0 | 0 | 0 |
| 230 | 0 | 0 | 0 | 0 | 0 | 0 | 0 | 0 | 0 | 0 | 0 | 0 | 0 | 0 |
| 231 | 0 | 0 | 0 | 0 | 0 | 0 | 0 | 0 | 0 | 0 | 0 | 0 | 0 | 0 |
| 232 | 0 | 0 | 1 | 0 | 1 | 1 | 1 | 0 | 0 | 0 | 0 | 1 | 1 | 0 |
| 233 | 0 | 0 | 1 | 0 | 1 | 1 | 1 | 0 | 0 | 0 | 0 | 1 | 1 | 0 |
| 234 | 0 | 0 | 0 | 0 | 1 | 1 | 1 | 0 | 0 | 0 | 0 | 1 | 1 | 0 |
| 235 | 0 | 0 | 0 | 0 | 0 | 0 | 0 | 0 | 0 | 0 | 0 | 0 | 0 | 0 |
| 236 | 0 | 0 | 0 | 0 | 0 | 0 | 0 | 0 | 0 | 0 | 0 | 0 | 0 | 0 |
| 237 | 0 | 0 | 0 | 0 | 0 | 0 | 0 | 0 | 0 | 0 | 0 | 0 | 0 | 0 |
| 238 | 0 | 0 | 0 | 0 | 0 | 0 | 0 | 0 | 0 | 0 | 0 | 0 | 0 | 0 |
| 239 | 0 | 0 | 0 | 0 | 0 | 0 | 0 | 0 | 0 | 0 | 0 | 0 | 0 | 0 |
| 240 | 0 | 0 | 0 | 0 | 0 | 0 | 0 | 0 | 0 | 0 | 0 | 0 | 0 | 0 |
| 241 | 1 | 1 | 1 | 1 | 1 | 1 | 1 | 1 | 1 | 1 | 1 | 1 | 1 | 1 |
| 242 | 1 | 1 | 1 | 1 | 1 | 1 | 1 | 0 | 1 | 0 | 1 | 1 | 1 | 1 |
| 243 | 1 | 1 | 1 | 1 | 1 | 1 | 1 | 0 | 1 | 0 | 1 | 1 | 1 | 1 |
| 244 | 0 | 0 | 0 | 0 | 0 | 0 | 0 | 0 | 1 | 0 | 0 | 0 | 0 | 0 |
| 245 | 0 | 0 | 0 | 0 | 1 | 0 | 0 | 0 | 0 | 0 | 0 | 0 | 0 | 0 |
| 246 | 0 | 0 | 0 | 0 | 0 | 0 | 0 | 0 | 0 | 0 | 0 | 0 | 0 | 0 |
| 247 | 1 | 0 | 1 | 0 | 1 | 1 | 1 | 0 | 1 | 0 | 1 | 1 | 1 | 0 |
| 248 | 1 | 1 | 1 | 1 | 1 | 1 | 1 | 1 | 1 | 1 | 1 | 1 | 1 | 1 |
| 249 | 1 | 1 | 1 | 1 | 1 | 1 | 1 | 0 | 1 | 1 | 1 | 1 | 1 | 1 |
| 250 | 0 | 0 | 0 | 0 | 0 | 0 | 0 | 0 | 0 | 0 | 0 | 0 | 0 | 0 |
| 251 | 0 | 1 | 1 | 1 | 0 | 0 | 0 | 0 | 0 | 0 | 0 | 0 | 0 | 0 |
| 252 | 0 | 0 | 0 | 0 | 0 | 0 | 0 | 0 | 0 | 0 | 0 | 0 | 0 | 0 |
| 253 | 0 | 0 | 0 | 0 | 1 | 0 | 1 | 0 | 1 | 0 | 0 | 1 | 1 | 0 |
| 254 | 0 | 0 | 0 | 0 | 1 | 0 | 1 | 0 | 1 | 0 | 0 | 1 | 1 | 0 |
| 255 | 0 | 0 | 0 | 0 | 1 | 0 | 1 | 0 | 1 | 0 | 0 | 1 | 1 | 0 |
| 256 | 0 | 0 | 0 | 0 | 0 | 0 | 0 | 0 | 0 | 0 | 0 | 0 | 0 | 0 |
| 257 | 0 | 0 | 0 | 0 | 0 | 0 | 0 | 0 | 0 | 0 | 0 | 0 | 0 | 0 |

TABLE 48-continued

| transition number | Sam131 | Sam132 | Sam133 | Sam134 | Sam135 | Sam136 | Sam137 | Sam138 | Sam139 | Sam140 | Sam141 | Sam142 | Sam143 | Sam144 |
|---|---|---|---|---|---|---|---|---|---|---|---|---|---|---|
| 258 | 0 | 0 | 0 | 0 | 0 | 0 | 0 | 0 | 0 | 0 | 0 | 0 | 0 | 0 |
| 259 | 0 | 0 | 0 | 0 | 0 | 0 | 0 | 0 | 0 | 0 | 0 | 0 | 0 | 0 |
| 260 | 0 | 0 | 0 | 0 | 0 | 0 | 0 | 0 | 0 | 0 | 0 | 0 | 0 | 0 |
| 261 | 0 | 0 | 0 | 0 | 0 | 0 | 0 | 0 | 0 | 0 | 0 | 0 | 0 | 0 |
| 262 | 0 | 0 | 0 | 0 | 0 | 0 | 0 | 0 | 0 | 0 | 0 | 1 | 1 | 0 |
| 263 | 0 | 0 | 0 | 0 | 0 | 0 | 0 | 0 | 0 | 0 | 1 | 0 | 1 | 0 |
| 264 | 0 | 0 | 0 | 0 | 0 | 0 | 0 | 0 | 0 | 0 | 0 | 1 | 0 | 0 |
| 265 | 0 | 0 | 0 | 0 | 0 | 0 | 0 | 0 | 0 | 0 | 0 | 0 | 0 | 0 |
| 266 | 0 | 0 | 0 | 0 | 0 | 0 | 0 | 0 | 0 | 0 | 0 | 0 | 0 | 0 |
| 267 | 0 | 0 | 0 | 0 | 0 | 1 | 0 | 0 | 0 | 0 | 0 | 0 | 0 | 0 |
| 268 | 0 | 0 | 0 | 0 | 0 | 0 | 0 | 0 | 0 | 0 | 0 | 0 | 0 | 0 |
| 269 | 0 | 0 | 0 | 0 | 0 | 0 | 0 | 0 | 0 | 0 | 0 | 0 | 0 | 0 |
| 270 | 0 | 0 | 0 | 0 | 0 | 0 | 0 | 0 | 0 | 0 | 0 | 0 | 0 | 0 |
| 271 | 0 | 0 | 0 | 0 | 0 | 0 | 0 | 0 | 0 | 0 | 0 | 0 | 0 | 0 |
| 272 | 0 | 0 | 0 | 0 | 0 | 0 | 0 | 0 | 0 | 1 | 0 | 0 | 0 | 0 |
| 273 | 0 | 0 | 0 | 0 | 0 | 0 | 0 | 0 | 0 | 1 | 0 | 0 | 0 | 0 |
| 274 | 0 | 0 | 0 | 0 | 0 | 0 | 0 | 0 | 0 | 0 | 0 | 0 | 0 | 0 |
| 275 | 0 | 0 | 0 | 0 | 0 | 0 | 0 | 0 | 0 | 0 | 0 | 0 | 0 | 0 |
| 276 | 0 | 0 | 0 | 0 | 0 | 0 | 0 | 0 | 0 | 0 | 0 | 0 | 0 | 0 |
| 277 | 0 | 0 | 0 | 0 | 0 | 0 | 0 | 0 | 0 | 0 | 0 | 0 | 0 | 0 |
| 278 | 0 | 0 | 0 | 0 | 0 | 0 | 0 | 0 | 0 | 0 | 0 | 0 | 0 | 0 |
| 279 | 0 | 0 | 0 | 0 | 0 | 0 | 0 | 0 | 0 | 0 | 0 | 0 | 0 | 0 |
| 280 | 0 | 0 | 0 | 0 | 1 | 0 | 0 | 0 | 0 | 0 | 0 | 0 | 0 | 0 |
| 281 | 0 | 0 | 0 | 0 | 0 | 0 | 0 | 0 | 0 | 0 | 0 | 0 | 0 | 0 |
| 282 | 0 | 0 | 0 | 0 | 1 | 0 | 0 | 0 | 0 | 0 | 0 | 0 | 0 | 0 |
| 283 | 0 | 0 | 0 | 0 | 1 | 1 | 1 | 0 | 0 | 0 | 0 | 1 | 1 | 0 |
| 284 | 0 | 1 | 1 | 0 | 0 | 1 | 1 | 0 | 0 | 0 | 0 | 1 | 1 | 0 |
| 285 | 0 | 0 | 0 | 0 | 0 | 1 | 1 | 0 | 0 | 0 | 0 | 1 | 1 | 0 |
| 286 | 0 | 0 | 0 | 0 | 0 | 0 | 0 | 0 | 0 | 0 | 0 | 0 | 0 | 0 |
| 287 | 0 | 0 | 0 | 0 | 0 | 0 | 0 | 0 | 0 | 0 | 0 | 0 | 0 | 0 |
| 288 | 0 | 0 | 0 | 0 | 0 | 0 | 0 | 0 | 0 | 0 | 0 | 0 | 0 | 0 |
| 289 | 0 | 0 | 0 | 0 | 0 | 0 | 0 | 0 | 0 | 0 | 0 | 0 | 0 | 0 |
| 290 | 0 | 0 | 0 | 0 | 0 | 0 | 0 | 0 | 0 | 0 | 0 | 0 | 0 | 0 |
| 291 | 0 | 0 | 0 | 0 | 0 | 0 | 0 | 0 | 0 | 0 | 0 | 0 | 0 | 0 |
| 292 | 0 | 0 | 0 | 0 | 0 | 0 | 0 | 0 | 0 | 0 | 0 | 0 | 0 | 0 |
| 293 | 0 | 0 | 0 | 0 | 0 | 0 | 0 | 0 | 0 | 0 | 0 | 0 | 0 | 0 |
| 294 | 0 | 0 | 0 | 0 | 0 | 0 | 0 | 0 | 0 | 0 | 0 | 0 | 0 | 0 |

Samples Sam131 to Sam144 comprise at least one peptide which is characteristic of the SHV proteins. The bacteria present in samples Sam131 to Sam144 therefore express a beta-lactamase which confers on them a resistance to penicillins.

Sample Sam142 comprises a peptide specific to phenotype 2be. Therefore sample Sam142 is resistant to penicillins, to cephalosporins and to monobactams.

No peptide specific to phenotypes 2b and 2br is observed, no sample tested is identified as belonging only to these phenotypes.

The detection methods described in examples 6 to 30 are particularly advantageous because they make it possible to assay a large number of peptides and at the same time to detect the presence of one or more resistance mechanisms induced by one or more beta-lactamases.

Furthermore, the detection is performed in a short time, less than one hour. In fact, only the part of the gradient between 3 and 34 minutes is useful to the analysis. Furthermore, the retention times of the assayed peptides are all below 34 minutes.

In addition, the detection methods described in examples 6 to 30 are more advantageous than the molecular biology methods because they detect the product of the expression of the genes, and not the genes themselves. The detection of a resistance may not have any clinical meaning if this gene is not expressed, or it if is expressed too weakly to lead to an effective resistance. The detection of a peptide characterising a protein characteristic of a resistance mechanism does not have this disadvantage.

Surprisingly, the above examples show that it is possible to attain by mass spectrometry the sensitivity necessary for the specific detection of the existence of a mechanism of resistance to at least one antimicrobial of a microorganism contained in a sample, without employing an amplification method as is usually the case when molecular biology methods are used.

BIBLIOGRAPHIC REFERENCES

[1] J. Anhalt & C. Fenselau, 1975, Anal. Chem., 47(2):219-225.
[2] A. Fox et al., ed., 1990, Analytical microbiology methods: chromatography and mass spectrometry, Plenum Press, New York, N.Y.
[3] M. Claydon et al., 1996, Nature Biotech. 14:1584-1586.
[4] T. Krishnamurthy & P. Ross, 1996, Rapid Com. Mass Spec., 10:1992-1996.
[5] P. Seng et al. 2009, Clin. Infect. Dis., 49:543-551.
[6] C. Fenselau et al., 2008, Appl. Environ. Microbiol., 904-906.
[7] S. Hofstadler et al., 2005, Int. J Mass Spectrom., 242: 23-41.
[8] D. Ecker, 2008, Nat. Rev. Microbiol., 6(7):553-558.
[9] Bush and Jacoby, 2010, Antimicrobial Agents and Chemotherapy; 54(3): 969-976
[10] W.-J. Chen et al., 2008, Anal. Chem., 80: 9612-9621
[11] D. Lopez-Ferrer et al., 2008, Anal. Chem., 80:8930-8936
[12] D. Lopez-Ferrer et al., 2005, J. Proteome res., 4(5): 1569-1574

[13] T. Fortin et al., 2009, Mol. Cell Proteomics, 8(5): 1006-1015.
[14] H. Keshishian et al., 2007, Mol. Cell Proteomics, 2212-2229.
[15] J. Stal-Zeng et al., 2007, Mol. Cell Proteomics, 1809-1817.
[16] Gaskell, Electrospray: principles and practise, 1997, J. Mass Spectrom., 32, 677-688).
[17] V. Fusaro et al., 2009, Nature Biotech. 27, 190-198.
[18] J. Mead et al., 15 Nov. 2008, Mol. Cell Proteomics, E-pub.
[19] F. Desiere et al., 2006, Nucleic Acids Res., 34(database issue): D655-8).
[20] L. Anderson & C. Hunter, 2006, Mol. Cell Proteomics, 573-588).
[21] B. Han & R. Higgs, 2008, Brief Funct Genomic Proteomic., 7(5):340-54).
[22] K.-Y. Wang et al., 2008, Anal. Chem, 80(16) 6159-6167).
[23] J. Bundy & C. Fenselau, 1999, Anal. Chem. 71: 1460-1463.
[24] K-C Ho et al., 2004, Anal. Chem. 76: 7162-7268.
[25] Y. S. Lin et al., 2005, Anal. Chem., 77: 1753-1760.
[26] S. Vaidyanathan et al., 2001, Anal. Chem., 73:4134-4144.
[27] R. Everley et al., 2009, J. Microbiol. Methods, 77:152-158.
[28] P. Seng et al., 2009, Clin. Infect. Dis., 49:543-551.
[29] Manes N. et al., 2007, Mol. & Cell. Proteomics, 6(4): 717-727.
[30] R. Nandakumar et al., 2009, Oral Microbiology Immunology, 24:347-352).
[31] L. Hernychova et al., 2008, Anal. Chem., 80:7097-7104.
[32] J.-M. Pratt et al., 2006, Nat. Protoc., 1:1029-1043.
[33] V. Brun et al., 2007, Mol. Cell Proteomics, 2139-2149.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09874570B2). An electronic copy of the "Sequence Listing" will also be available from the USPTO upon request and payment of the fee set forth in 37 CFR 1.19(b)(3).

The invention claimed is:

1. A method of detecting a TEM protein in a sample, comprising:
subjecting the sample to MS/MS spectrometry in MRM mode and detecting whether one or more TEM fragments selected from the group consisting of SEQ ID NOS: 166-230, 232-257, 259-261, 1923, 1927, and 1928 is present, wherein detection of any of the TEM fragments by the MRM mass spectrometry indicates the presence of TEM protein in the sample.

2. The detection method according to claim 1, further comprising, before performing MS/MS spectrometry in MRM mode, digesting proteins to produce peptides in the sample.

3. The detection method according to claim 2, wherein the digestion is performed by an enzyme.

4. The detection method according to claim 3, wherein the enzyme is trypsin.

5. The detection method according to claim 1, wherein the one or more TEM fragments is selected from the group consisting of SEQ ID NOS: 166-174, 180, 181, 186-203, 212-217, 219, 220, 223-230, 241-243, 250-255, 259-261, 1927, and 1928.

* * * * *